United States Patent
Lu et al.

(10) Patent No.: US 11,419,898 B2
(45) Date of Patent: Aug. 23, 2022

(54) COMBINATORIAL CANCER IMMUNOTHERAPY

(71) Applicant: Senti Biosciences, Inc., South San Francisco, CA (US)

(72) Inventors: Timothy Kuan-Ta Lu, San Francisco, CA (US); Russell Morrison Gordley, San Francisco, CA (US); Jack Tzu-Chiao Lin, Redwood City, CA (US); Brian Scott Garrison, San Jose, CA (US); Philip Janmin Lee, Alameda, CA (US); Alba Gonzalez-Junca, San Francisco, CA (US); Don-Hong Wang, South San Francisco, CA (US); Daniel Frimannsson, Alameda, CA (US)

(73) Assignee: SENTI BIOSCIENCES, INC., South San Francisco, CA (US)

( * ) Notice: Subject to any disclaimer, the term of this patent is extended or adjusted under 35 U.S.C. 154(b) by 0 days.

(21) Appl. No.: 17/219,569

(22) Filed: Mar. 31, 2021

(65) Prior Publication Data

US 2021/0228640 A1    Jul. 29, 2021

Related U.S. Application Data

(62) Division of application No. 16/656,452, filed on Oct. 17, 2019, now Pat. No. 10,993,967.

(60) Provisional application No. 62/843,180, filed on May 3, 2019, provisional application No. 62/747,114, filed on Oct. 17, 2018, provisional application No. 62/474,109, filed on Oct. 17, 2018.

(51) Int. Cl.
| | |
|---|---|
| *A61K 35/28* | (2015.01) |
| *A61P 35/00* | (2006.01) |
| *C07K 14/715* | (2006.01) |
| *C12N 5/0775* | (2010.01) |
| *C12N 15/63* | (2006.01) |
| *C07K 16/28* | (2006.01) |
| *C07K 16/30* | (2006.01) |

(52) U.S. Cl.
CPC .............. *A61K 35/28* (2013.01); *A61P 35/00* (2018.01); *C07K 14/7155* (2013.01); *C12N 5/0668* (2013.01); *C12N 15/63* (2013.01); *C07K 16/2878* (2013.01); *C07K 16/30* (2013.01)

(58) Field of Classification Search
CPC ......... A61K 35/28; A61P 35/00; C12N 15/63; C12N 5/0668; C07K 14/7155; C07K 16/2878; C07K 16/30
See application file for complete search history.

(56) References Cited

U.S. PATENT DOCUMENTS

| | | |
|---|---|---|
| 4,965,195 A | 10/1990 | Namen et al. |
| 5,328,988 A | 7/1994 | Namen et al. |
| 5,486,359 A | 1/1996 | Caplan et al. |
| 5,536,657 A | 7/1996 | Chua et al. |
| 5,554,512 A | 9/1996 | Lyman et al. |
| 5,591,625 A | 1/1997 | Gerson et al. |
| 5,674,486 A | 10/1997 | Sobol et al. |
| 5,705,149 A | 1/1998 | Namen et al. |
| 5,780,268 A | 7/1998 | Coleman et al. |
| 5,827,735 A | 10/1998 | Young et al. |
| 5,965,122 A | 10/1999 | Namen et al. |
| 5,981,724 A | 11/1999 | Armitage et al. |
| 6,153,182 A | 11/2000 | Lillard, Jr. |
| 6,156,301 A | 12/2000 | Namen et al. |
| 6,187,307 B1 | 2/2001 | Cohen |
| 6,307,024 B1 | 10/2001 | Novak et al. |
| 6,361,997 B1 | 3/2002 | Huss |
| 6,392,126 B1 | 5/2002 | Mahajan |
| 6,632,424 B1 | 10/2003 | Lyman et al. |
| 6,686,178 B2 | 2/2004 | Novak et al. |
| 6,929,932 B2 | 8/2005 | Presnell et al. |
| 7,534,867 B1 | 5/2009 | Hannum et al. |
| 7,611,699 B2 | 11/2009 | Novak et al. |
| 7,833,754 B2 | 11/2010 | Felber et al. |
| 7,993,918 B2 | 8/2011 | Paludan et al. |
| 7,998,472 B2 | 8/2011 | Huss et al. |
| 8,071,741 B2 | 12/2011 | Filpula et al. |
| 8,178,660 B2 | 5/2012 | Weiner et al. |
| 8,318,483 B2 | 11/2012 | Mistry et al. |
| 8,367,409 B2 | 2/2013 | Abbot et al. |
| 8,741,283 B2 | 6/2014 | Filpula et al. |
| 8,765,462 B2 | 7/2014 | Medin et al. |

(Continued)

FOREIGN PATENT DOCUMENTS

| | | |
|---|---|---|
| EP | 1658853 A1 | 5/2006 |
| KR | 100788930 B1 | 12/2007 |

(Continued)

OTHER PUBLICATIONS

Batra et al. "Armored Glypican-3-Specific CAR T Cells for the Immunotherapy of Hepatocellular Carcinoma." ASGCT 2018, May 2018 (May 1, 2018). Cell Technology . (Year: 2018).*

(Continued)

*Primary Examiner* — Titilayo Moloye
(74) *Attorney, Agent, or Firm* — Goodwin Procter LLP

(57) ABSTRACT

Provided herein are methods and compositions for dynamically controlling and targeting multiple immunosuppressive mechanisms in cancer. Some aspects provide cells engineered to produce multiple effector molecules, each of which modulates a different immunosuppressive mechanisms of a tumor, as well as methods of using the cells to treat cancer, such as ovarian, breast, or colon cancer.

20 Claims, 120 Drawing Sheets

Specification includes a Sequence Listing.

(56) References Cited

U.S. PATENT DOCUMENTS

| | | |
|---|---|---|
| 9,198,938 B2 | 12/2015 | Abbot et al. |
| 9,303,080 B2 | 4/2016 | Felber et al. |
| 9,434,925 B2 | 9/2016 | Nelson |
| 9,487,800 B2 | 11/2016 | Schonfeld et al. |
| 9,492,482 B2 | 11/2016 | Beech et al. |
| 9,725,492 B2 | 8/2017 | Felber et al. |
| 9,790,261 B2 | 10/2017 | Felber et al. |
| 10,022,405 B2 | 7/2018 | Medin et al. |
| 10,046,049 B2 | 8/2018 | Beech et al. |
| 10,155,024 B2 | 12/2018 | Cho et al. |
| 10,201,592 B2 | 2/2019 | Wong et al. |
| 2001/0023070 A1 | 9/2001 | Ebner et al. |
| 2003/0003545 A1 | 1/2003 | Ebner et al. |
| 2004/0033217 A1 | 2/2004 | Vanguri et al. |
| 2004/0076622 A1 | 4/2004 | Studeny et al. |
| 2005/0037218 A1 | 2/2005 | Lottes et al. |
| 2005/0037306 A1 | 2/2005 | Nakatsu |
| 2006/0035373 A1 | 2/2006 | Zhang et al. |
| 2007/0119895 A1 | 5/2007 | Pesch et al. |
| 2007/0149493 A1 | 6/2007 | Ross |
| 2008/0150368 A1 | 6/2008 | Gurcan |
| 2009/0285805 A1 | 11/2009 | Grosveld et al. |
| 2010/0135958 A1 | 6/2010 | Hwu et al. |
| 2012/0051210 A1 | 3/2012 | Komatsu |
| 2014/0011881 A1 | 1/2014 | Shin et al. |
| 2014/0050709 A1 | 2/2014 | Leen et al. |
| 2014/0255363 A1 | 9/2014 | Metelitsa et al. |
| 2015/0035235 A1 | 2/2015 | Tsuda |
| 2015/0123183 A1 | 5/2015 | Kato et al. |
| 2015/0203820 A1 | 7/2015 | Wang et al. |
| 2016/0008435 A1 | 1/2016 | Cho et al. |
| 2016/0026854 A1 | 1/2016 | Hwang et al. |
| 2016/0146819 A1 | 5/2016 | Ince |
| 2016/0220612 A1 | 8/2016 | Mazzolini et al. |
| 2016/0237407 A1 | 8/2016 | Wagner et al. |
| 2017/0044227 A1 | 2/2017 | Schonfeld et al. |
| 2017/0128569 A1 | 5/2017 | Beech et al. |
| 2017/0133175 A1 | 5/2017 | Lin et al. |
| 2017/0133633 A1 | 5/2017 | Wang et al. |
| 2017/0142367 A1 | 5/2017 | Nakano et al. |
| 2017/0209492 A1* | 7/2017 | June ............... A61K 39/001113 |
| 2017/0239297 A1 | 8/2017 | Gunther et al. |
| 2018/0044392 A1 | 2/2018 | Felber et al. |
| 2018/0071295 A1 | 3/2018 | Kuo et al. |
| 2018/0140686 A1 | 5/2018 | Varadarajan et al. |
| 2018/0160993 A9 | 6/2018 | Lee et al. |
| 2018/0161026 A1 | 6/2018 | Housman et al. |
| 2018/0161038 A1 | 6/2018 | Lorenzo |
| 2018/0162939 A1 | 6/2018 | Ma et al. |
| 2018/0170390 A1 | 6/2018 | Tatsushiro et al. |
| 2018/0191619 A1 | 7/2018 | Karthikeyan et al. |
| 2018/0213731 A1 | 8/2018 | Wykman et al. |
| 2019/0183977 A1 | 6/2019 | Wong et al. |
| 2020/0171093 A1 | 6/2020 | Lu et al. |

FOREIGN PATENT DOCUMENTS

| | | |
|---|---|---|
| WO | 1995/027722 A1 | 10/1995 |
| WO | 1998/017799 A1 | 4/1998 |
| WO | 2005/037218 A2 | 4/2005 |
| WO | 2005/037306 A1 | 4/2005 |
| WO | 2007/119895 A1 | 10/2007 |
| WO | 2007/149493 A2 | 12/2007 |
| WO | 2008/150368 A1 | 12/2008 |
| WO | 2012/051210 A2 | 4/2012 |
| WO | 2014/011881 A2 | 1/2014 |
| WO | 2015/035235 A1 | 3/2015 |
| WO | 2015/123183 A1 | 8/2015 |
| WO | 2016/026854 A2 | 2/2016 |
| WO | 2016/146819 A1 | 9/2016 |
| WO | 2017/133175 A1 | 8/2017 |
| WO | 2017/133633 A1 | 8/2017 |
| WO | 2017/141181 A1 | 8/2017 |
| WO | 2017/142367 A1 | 8/2017 |
| WO | 2017/147383 A1 | 8/2017 |
| WO | 2018/033254 A2 | 2/2018 |
| WO | 2018/071295 A1 | 4/2018 |
| WO | 2018/160993 A1 | 9/2018 |
| WO | 2018/161026 A1 | 9/2018 |
| WO | 2018/161038 A1 | 9/2018 |
| WO | 2018/170390 A1 | 9/2018 |
| WO | 2018/191619 A1 | 10/2018 |
| WO | 2018/213731 A1 | 11/2018 |
| WO | 2020/081869 A1 | 4/2020 |

OTHER PUBLICATIONS

Jayaraman et al."CAR-T design: Elements and their synergistic function." EBioMedicine. Aug. 2020;58:102931 (Year: 2020).*

Labanieh et al."Programming CAR-T cells to kill cancer." Nature Biomedical Engineering vol. 2, pp. 377-391 (2018) (Year: 2018).*

Li et al. "Strategies to improve the migration of mesenchymal stromal cells in cell therapy." Translational Neuroscience and Clinics 3.3 (2017): 159-175 (Year: 2017).*

Kimura et al. "Tumor-homing effect of human mesenchymal stem cells in a TH-MYCN mouse model of neuroblastoma." J Pediatr Surg.Dec. 2016;51(12):2068-2073. (Year: 2016).*

Uchibori et al. "Cancer gene therapy using mesenchymal stem cells," Int J Hematol. Apr. 2014;99(4):377-82 (Year: 2014).*

Bernardo et al. "Mesenchymal stromal cell therapy: a revolution in Regenerative Medicine?" Bone Marrow Transplant. Feb. 2012;47(2):164-71. (Year: 2012).*

Nayyar et al. "Overcoming Resistance to Natural Killer Cell Based Immunotherapies for Solid Tumors." Front Oncol. Feb. 11, 2019;9:51. (Year: 2019).*

Okuda et al. "Postischemic Intraventricular Administration of FGF-2-Expressing Adenoviral Vectors Improves Neurological Outcome and Reduces Infarct Volume after Permanent Focal Cerebral Ischemia in Rats." Bulletin of the Osaka Medical College 53(2):133-141, 2007 (Year: 2007).*

Patel et al.. (2020). Linkers: a synergistic way for chimeric proteins. 10.22541/au.160199719.94542802/v1. (Year: 2020).*

Lesterhuis et al. "Synergistic effect of CTLA-4 blockade and cancer chemotherapy in the induction of anti-tumor immunity." PLoS One.Apr. 23, 2013;8(4):e61895. (Year: 2013).

Zhou et al. "Expression of CD40 and growth-inhibitory activity of CD40 agonist in ovarian carcinoma cells." Cancer Immunol Immunother. Oct. 2012;61(10):1735-43 (Year: 2012).

PCT/US2019/056824—International Preliminary Report on Patentability, dated Apr. 14, 2021, 9 pages.

Reardon et al. "Glioblastoma Eradication Following Immune Checkpoint Blockade in an Orthotopic, Immunocompetent Model." Cancer Immunol Res. Feb. 2016;4(2): 124-35 (Year: 2016).

Shoji et al. "Local convection-enhanced delivery of an anti-CD40 agonistic monoclonal antibody induces antitumor effects in mouse glioma models.", Neuro-Oncology 18(8), 1120-1128, 2016.

Aalbers, C. et al., "Preclinical Potency and Biodistribution Studies on an AAV 5 Vector Expressing Human Interferon-[beta] for Local Treatment of Patients with Rheumatoid Arthritis", PLOS ONE, Jun. 24, 2015, vol. 10, No. 6, pp. 1-17.

Adams, S. et al., "Immunotherapy for ovarian cancer: what are the targets of the future?", Future Oncol. 2015;11(9):1293-1296. doi: 10.2217/fon.15.44.

Beegle, J. et al., "Preclinical evaluation of mesenchymal stem cells overexpressing VEGF to treat critical limb ischemia", Mol Ther Methods Clin Dev. Aug. 24, 2016;3:16053. doi: 10.1038/mtm.2016. 53. eCollection 2016.

Chen, F. et al., "IL10-transduced mesenchymal stem cells improve the acute graft-versus-host disease protection in a murine model", Blood (2007) 110 (11): 3242, <https://doi.org/10.1182/blood.V110. 11.3242.3242> Database Biosis, Biosciences Information Service, XP002781954, Database accession No. PREV200800218514.

Chen, X. et al., "A Tumor-selective Biotherapy With Prolonged Impact on Established Metastases Based on Cytokine Gene-engineered MSCs", Mol Ther. Apr. 2008;16(4):749-56. doi: 10.1038/mt.2008.3. Epub Feb. 5, 2008.

(56) References Cited

OTHER PUBLICATIONS

Choi, J.J. et al., "Mesenchymal stem cells overexpressing interleukin-10 attenuate collagen-induced arthritis in mice", Clinical and Experimental Immunology, Aug. 1, 2008, vol. 152, No. 2, pp. 269-276.
Cieri, N. et al., "IL-7 and IL-15 instruct the generation of human memory stem T cells from naive precursors", Blood. Jan. 24, 2013;121(4):573-84. doi: 10.1182/blood-2012-05-431718. Epub Nov. 15, 2012.
Cruz, C. et al., "Adverse Events Following Infusion of T Cells for Adoptive Immunotherapy: A 10 Year Experience", Cytotherapy. Oct. 2010;12(6):743-9. doi: 10.3109/14653241003709686.
Dembinski, J. et al., "Tumor Stroma Engraftment of Gene-Modified Mesenchymal Stem Cells as Anti-Tumor Therapy against Ovarian Cancer", Cytotherapy. Jan. 2013;15(1):20-32. doi: 10.1016/j.jcyt.2012.10.003.
Deng, P. et al., "Clinical trial perspective for adult and juvenile Huntington's disease using genetically-engineered mesenchymal stem cells",Neural Regen Res. May 2016;11(5):702-5. doi: 10.4103/1673-5374.182682.
Dominici, M. et al., "Minimal criteria for defining multipotent mesenchymal stromal cells. The International Society for Cellular Therapy position statement", Cytotherapy. 2006;8(4):315-7.
Dubinett, S. et al., "Chemokines: Can Effector Cells be Re-directed to the Site of Tumor?", Cancer J. Jul.-Aug. 2010;16(4):325-35. doi: 10.1097/PPO.0b013e3181eb33bc.
Gao, P. et al., Therapeutic potential of human mesenchymal stem cells producing IL-12 in a mouse xenograft model of renal cell carcinoma et al., Cancer Letters 290 (2010) 157-166.
Gilham, D. et al., "CAR-T cells and solid tumors: tuning T cells to challenge an inveterate foe", Trends Mol Med. Jul. 2012;18(7):377-84. doi: 10.1016/j.molmed.2012.04.009. Epub May 19, 2012.
Hamanishi J. et al., "Immune checkpoint inhibition in ovarian cancer", Int Immunol. Jul. 2016;28(7):339-48. doi: 10.1093/intimm/dxw020. Epub Apr. 7, 2016.
Hu, Y.L. et al., "Mesenchymal stem cells: A promising targeted-delivery vehicle in cancer gene therapy", J Control Release, 147 (2), 154-62 Oct. 15, 2010.
Kidd, S. et al., "Direct Evidence of Mesenchymal Stem Cell Tropism for Tumor and Wounding Microenvironments using In Vivo Bioluminescence Imaging", Stem Cells. Oct. 2009;27(10):2614-23. doi: 10.1002/stem.187.
Koneru, M. et al., "A phase I clinical trial of adoptive T cell therapy using IL-12 secreting MUC-16ecto directed chimeric antigen receptors for recurrent ovarian cancer", J Transl Med. Mar. 28, 2015;13:102. doi: 10.1186/s12967-015-0460-x.
Lengyel, E., "Ovarian Cancer Development and Metastasis", Am J Pathol. Sep. 2010;177(3):1053-64. doi: 10.2353/ajpath.2010.100105. Epub Jul. 22, 2010.
Li, S. et al., "Oncolytic virotherapy for ovarian cancer", Oncolytic Virother. Aug. 2012;1:1-21.
Li, Y.Q. et al., "Tumor Secretion of CCL22 Activates Intralumoral Treg Infiltration and Is Independent Prognostic Predictor of Breast Cancer", PLoS One. Oct. 4, 2013;8(10):e76379. doi: 10.1371/journal.pone.0076379. eCollection 2013.
Ling, X. et al., "Mesenchymal Stem Cells Overexpressing IFN-ß Inhibit Breast Cancer Growth and Metastases through Stat3 Signaling in a Syngeneic Tumor Model", Cancer Microenviron. Mar. 19, 2010;3(1):83-95. doi: 10.1007/s12307-010-0041-8.
Marofi, F. et al., "Mesenchymal Stromal/Stem Cells: A New Era in the Cell-Based Targeted Gene Therapy of Cancer", Front Immunol. Dec. 18, 2017;8:1770. doi: 10.3389/fimmu.2017.01770. eCollection 2017.
Martin, I. et al., "Challenges for mesenchymal stromal cell therapies", Sci Transl Med. Feb. 20, 2019;11(480). pii: eaat2189. doi: 10.1126/scitranslmed.aat2189.
Mirzaei, H. et al., "Application of Mesenchymal Stem Cells in Melanoma: A Potential Therapeutic Strategy for Delivery of Targeted Agents", Current Medicinal Chemistry, Jan. 1, 2016, pp. 455-463.
Mohammadi, M. et al., "Mesenchymal stem cell: a new horizon in cancer gene therapy", Cancer Gene Ther. Sep. 2016;23(9):285-6 doi: 10.1038/cgt.2016.35. Epub Aug. 19, 2016.
Nowakowski, A. et al., "Genetic Engineering of Mesenchymal Stem Cells to Induce Their Migration and Survival", Stem Cells Int. 2016;2016:4956063. doi: 10.1155/2016/4956063. Epub May 3, 2016.
Parker et al., "Antitumour actions of interferons: implications for cancer therapy." Nature Reviews Cancer 16, No. 3 (2016): 131.
PCT/US2018/027492—International Search Report and Written Opinion, dated Aug. 10, 2018, 17 pages.
PCT/US2018/022855—International Search Report, dated Jul. 2, 2018, 4 pages.
Roby et al., "Development of a syngeneic mouse model for events related to ovarian cancer." Carcinogenesis 21, No. 4 (2000): 585-591.
Schukur, L. et al., "Implantable synthetic cytokine converter cells with AND-gate logic treat experimental psoriasis", Sci Transl Med. Dec. 16, 2015;7(318):318ra201. doi: 10.1126/scitranslmed.aac4964.
Sharma, A. et al., "High Throughput Characterization of Adult Stem Cells Engineered for Delivery of Therapeutic Factors for Neuroprotective Strategies", J Vis Exp. Jan. 4, 2015;(95):e52242. doi: 10.3791/52242.
Shi, Yufang, et al., "Tumour-associated mesenchymal stem/stromal cells: emerging therapeutic targets", Nature Reviews, Drug Discovery, Nov. 4, 2016, vol. 16, No. 1, pp. 35-52.
Squillaro, T. et al., "Clinical Trials With Mesenchymal Stem Cells: An Update", Cell Transplant. 2016;25(5):829-48. doi: 10.3727/096368915X689622. Epub Sep. 29, 2015.
Studeny, M. et al., "Mesenchymal Stem Cells: Potential Precursors for Tumor Stroma and Targeted-Delivery Vehicles for Anticancer Agents", J Natl Cancer Inst. Nov. 3, 2004;96(21):1593-603.
Sun, Z. et al., "The roles of mesenchymal stem cells in tumor inflammatory microenvironment", J Hematol Oncol. Feb. 6, 2014;7:14. doi: 10.1186/1756-8722-7-14.
Wang D. et al., "Allogeneic Mesenchymal Stem Cell Transplantation in Severe and Refractory Systemic Lupus Erythematosus: 4 Years of Experience", Cell Transplant. 2013;22(12):2267-77. doi: 10.3727/096368911X582769c.
Wang, H. et al., "Genetically engineered bone marrow-derived mesenchymal stem cells co-expressing IFN-[gamma] and IL-10 inhibit hepatocellular carcinoma by modulating MAPK pathway", Journal of B.U.ON.: official journal of the Balkan Union of Oncology, Nov. 1, 2017, pp. 1517-1524.
Wang, V. et al., "The Transcriptional Specificity of NF-kappa ? Dimers is Coded within the kappa ?DNA Response Elements", Cell Reports, Oct. 2012, vol. 2, No. 4, pp. 824-839.
Waterman, R. et al., "Mesenchymal Stem Cell 1 (MSC1)-Based Therapy Attenuates Tumor Growth Whereas MSC2-Treatment Promotes Tumor Growth and Metastasis", PLoS One. 2012;7(9):e45590. doi: 10.1371/journal.pone.0045590. Epub Sep. 20, 2012.
Wiedemann, G. et al., "Cancer cell-derived IL-1 a induces CCL22 and the recruitment of regulatory T cells", Oncoimmunology. Apr. 25, 2016;5(9):e1175794. eCollection 2016.
Woo, S.R. et al., "The STING pathway and the T cell-inflamed tumor Microenvironment", (2015) Trends Immunol. Apr. 2015;36(4):250-6. doi: 10.1016/j.it.2015.02.003. Epub Mar. 7, 2015.
Xie, C. et al., "Interferon-b gene-modified human bone marrow mesenchymal stem cells attenuate hepatocellular carcinoma through inhibiting AKT/FOXO3a pathway", Br J Cancer. Sep. 3, 2013;109(5):1198-205. doi: 10.1038/bjc.2013.422. Epub Jul. 25, 2013.
Xishan, Z. et al., "Mouse Flk-1+Sca-1-Mesenchymal Stem Cells: Functional Plasticity In Vitro and Immunoregulation In Vivo", Transplantation, Mar. 15, 2014, vol. 97, No. 5, pp. 509-517.
Xu, G. et al., "Bone marrow-derived mesenchymal stem cells co-expressing interleukin-18 and interferon-[beta] exhibit potent antitumor effect against intracranial glioma in rats", Oncology Reports, Aug. 5, 2015, vol. 34, No. 4, pp. 1915-1922.

(56) References Cited

OTHER PUBLICATIONS

Zhang, Y. et al., "Gene therapy of ovarian cancer using IL-21-secreting human umbilical cord mesenchymal stem cells in nude mice", J Ovarian Res. Jan. 20, 2014;7:8. doi: 10.1186/1757-2215-7-8.

Zhao, Q. et al., "MSCs derived from iPSCs with a modified protocol are tumor-tropic but have much less potential to promote tumors than bone marrow MSCs", Proc Natl Acad Sci U S A. Jan. 13, 2015; 112(2):530-5. doi: 10.1073/pnas.1423008112. Epub Dec. 29, 2014.

Zhao, R. et al., "Mechanisms of and perspectives on the mesenchymal stem cell in immunotherapy", J Lab Clin Med. May 2004;143(5):284-91.

PCT/US2019/056824—International Search Report and Written Opinion, dated Apr. 23, 2020, 18 pages.

\* cited by examiner

Negative control

Anti-firefly luciferase (MSCs)

COMBINATORIAL CANCER IMMUNOTHERAPY

CROSS REFERENCE TO RELATED APPLICATIONS

This application is a divisional of U.S. application Ser. No. 16/656,452 filed Oct. 17, 2019, which claims the benefit of each of U.S. Provisional Application Nos. 62/747,109 filed on Oct. 17, 2018; 62/747,114 filed on Oct. 17, 2018; and 62/843,180 filed May 3, 2019, each of which is hereby incorporated in its entirety by reference.

SEQUENCE LISTING

The instant application contains a Sequence Listing which has been submitted via EFS-Web and is hereby incorporated herein by reference in its entirety. Said ASCII copy, created on Nov. 26, 2019, is named STB011_SequenceListing.txt, and is 142,504 bytes in size.

BACKGROUND

There are more than 22,000 new cases of ovarian cancer and more than 14,000 deaths each year in the United States (Siegel R L, et al. (2016) CA Cancer J Clin 66(1):7-30), with an estimated annual healthcare burden of greater than $600M (Dizon D M J (2010) Gynecol Oncol 116(3)). Conventional approaches, such as chemotherapy (e.g., carboplatin/cisplatin and/or paclitaxel), are often unable to cure ovarian cancer. Approximately 70% of patients do not achieve remission on first-line chemotherapy, and 40-50% of patients that do have a remission will relapse within three years.

Treatment of other cancers, such as breast cancer and colon cancer, is associated with five-year survival rates of 85% and 65%, respectively. Therapies often include a combination of invasive surgeries and chemotherapies.

SUMMARY

Provided herein, in some embodiments, is a combinatorial cell-based immunotherapy for the targeted treatment of cancer, such as ovarian cancer, breast cancer, colon cancer, lung cancer, and pancreatic cancer. This combinatorial immunotherapy relies on engineered cell circuits that enable multifactorial modulation within and/or near a tumor (a "tumor microenvironment (TME)"). Despite exciting advancements in combinatorial immunotherapy, its efficacy against cancer has been limited due in part to the following challenges. It is difficult to deliver multiple therapies simultaneously to achieve maximal efficacy without triggering significant side effects. It is also difficult in clinical trials to determine the appropriate dosing and timing of multiple systemically-administered and/or locally-injected therapies.

The combinatorial immunotherapy provided herein, however, is tumor-specific and effective yet limits systemic toxicity. This combinatorial immunotherapy delivers to a tumor microenvironment multiple immunomodulatory effector molecules from a single delivery vehicle. The design of the delivery vehicle is optimized to improve overall function in cancer therapy, including, but not limited to, optimization of the promoters, linkers, signal peptides, and order of the multiple immunomodulatory effector molecules.

Advantageously, cell circuits of the present disclosure are engineered in mesenchymal stem cells (MSCs), which are able to selectively home to tumors (including metastases), are able to produce a pro-inflammatory/immunostimulatory secretome and under certain conditions an anti-inflammatory secretome, and are hypoimmunogenic. These characteristics, among others, enable their use for allogenic cell therapies, for example, without significant safety issues, side effects, or rejection.

It has been increasingly recognized that tumors are a complex interplay between the tumor cells and the surrounding stroma, which includes the extracellular matrix, cancer-associated stromal cells (MSCs and fibroblasts), tumor vasculature, and the immune system. The TME suppresses anti-tumor immune responses through multiple mechanisms that target both the innate and adaptive immune system of the patient. For example, tumors can recruit and induce regulatory T cells that suppress the anti-tumor activity of conventional T cells by elaborating specific chemokines such as CCL22. Tumors can also express molecules that inhibit the activity of T cells and NK cells, such as immune checkpoints such as PD-L1. Thus, targeting a single pathway is likely insufficient for achieving robust efficacy against solid tumors.

Non-limiting examples of effector molecules encompassed by the present disclosure include cytokines, antibodies, chemokines, nucleotides, peptides, enzymes, and oncolytic viruses. For example, MSCs may be engineered to express (and typically secrete) at least one, two, three or more of the following effector molecules: IL-12, IL-16, IFN-β, IFN-γ, IL-2, IL-15, IL-7, IL-36γ, IL-18, IL-1β, IL-21, OX40-ligand, CD40L, anti-PD-1 antibodies, anti-PD-L1 antibodies, anti-CTLA-4 antibodies, anti-TGFβ antibodies, anti-TNFR2, MIP1α (CCL3), MIP1β (CCL5), CCL21, CpG oligodeoxynucleotides, and anti-tumor peptides (e.g., anti-microbial peptides having anti-tumor activity, see, e.g., Gaspar, D. et al. *Front Microbiol.* 2013; 4: 294; Chu, H. et al. PLoS One. 2015; 10(5): e0126390, and website:aps.unmc.edu/AP/main.php).

Provided for herein is an engineered cell comprising: a) a promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule. In some aspects, the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

In some aspects, the cell is a mesenchymal stem cell (MSC). In some aspects, the cell is a stem cell. In some aspects, the cell is an immune cell. In some aspects, the cell is a natural killer (NK) cell. In some aspects, the cell is a NKT cell. In some aspects, the cell is an innate lymphoid cell. In some aspects, the cell is a tumor-infiltrating lymphocyte (TIL). In some aspects, the cell is a mast cell. In some aspects, the cell is a eosinophil. In some aspects, the cell is a basophil. In some aspects, the cell is a monocyte. In some aspects, the cell is a macrophage. In some aspects, the cell is a neutrophil. In some aspects, the cell is a myeloid cell. In some aspects, the cell is a dendritic cell. In some aspects, the cell is a T cell. In some aspects, the cell is a CD8+ T cell. In some aspects, the cell is a CD4+ T cell. In some aspects, the cell is a cytotoxic T lymphocyte (CTL). In some aspects, the cell is a viral-specific T cell. In some aspects, the cell is a gamma-delta T cell. In some aspects, the cell is a T regulatory cell. In some aspects, the cell is a B cell.

In some aspects, the promoter comprises an exogenous promoter polynucleotide sequence. In some aspects, the promoter comprises an endogenous promoter. In some aspects, the promoter is operably linked to the expression cassette such that the polynucleotides are capable of being transcribed as a single polynucleotide comprising the formula S1-E1-L-S2-E2. In some aspects, the linker polynucleotide sequence is operably associated with the translation of the first effector molecule and the second effector molecule as separate polypeptides. In some aspects, the linker polynucleotide sequence encodes a 2A ribosome skipping tag. In some aspects, the 2A ribosome skipping tag is selected from the group consisting of: P2A, T2A, E2A, and F2A. In some aspects, the linker polynucleotide sequence encodes a T2A ribosome skipping tag. In some aspects, the linker polynucleotide sequence encodes an Internal Ribosome Entry Site (IRES). In some aspects, the linker polynucleotide sequence encodes a cleavable polypeptide. In some aspects, the cleavable polypeptide comprises a Furin recognition polypeptide sequence. In some aspects, the linker polynucleotide sequence further encodes a Gly-comprising. Ser-comprising, or Gly-Ser comprising polypeptide sequence, e.g., a Gly-Ser-Gly polypeptide sequence. In some aspects, the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus.

In some aspects, the linker polynucleotide sequence encodes a second promoter, wherein the promoter is operably linked to the expression cassette such that a first polynucleotide comprising the formula S1-E1 is capable of being transcribed, wherein the second promoter is operably linked to the expression cassette such that a second polynucleotide comprising the formula S2-E2 is capable of being transcribed, and wherein the first and the second polynucleotide are separate polynucleotides. In some aspects, the promoter and the second promoter are identical. In some aspects, the promoter and the second promoter are different.

In some aspects, the engineered cell is HLA-typed with reference to a subject in need of therapeutic treatment. In some aspects, the engineered cell is a human cell. In some aspects, the human cell is an isolated cell from a subject, e.g., the subject who will receive the cell. In some aspects, the isolated cell is isolated from a tissue consisting of the group of: bone marrow, adipose tissue, the umbilical cord, fetal liver, muscle, and lung tissue. In some aspects, the engineered cell is a cultured cell.

In some aspects, the engineered MSC comprises a cellular marker phenotype comprising the cellular markers CD105+, CD73+, and CD90+. In some aspects, the cellular marker phenotype further comprises a phenotype lacking or substantially lacking one or more cellular markers selected from the group consisting of: CD45, CD34, CD14, CD11b, CD79a, CD19, HLA class II, and combinations thereof. In some aspects, the engineered MSC comprises a cellular marker phenotype comprising CD105+, CD73+, CD90+, CD45−, CD34−, CD14−; a cellular marker phenotype comprising CD105+, CD73+, CD90+, CD11b−, CD79α−; a cellular marker phenotype comprising CD105+, CD73+, CD90+, CD19−, HLA class II−; or a cellular marker phenotype comprising CD73+, CD90+, CD105+, and CD166+, CD11b−, CD14−, CD19−, CD34−, CD45−, and HLA−DR−. In some aspects, the cellular marker phenotype is determined or has been determined by flow-cytometry.

In some aspects, the engineered cell comprises a T cell. In some aspects, the engineered cell comprises a NK cell. In some aspects, the engineered cell comprises a NKT cell.

In some aspects, the cellular marker phenotype further comprises a cellular marker comprising a cognate receptor or a cognate receptor ligand for the first effector molecule, the second effector molecule, or the first and second effector molecules expressed in the engineered cells. In some aspects, the receptor is selected from the group consisting of: IL12RB1, IL12RB2, CCL7, and combinations thereof.

In some aspects, the promoter and/or the second promoter comprises a constitutive promoter. In some aspects, the constitutive promoter is selected from the group consisting of: CMV, EFS, SFFV, SV40, MND, PGK, UbC, hEF1aV1, hCAGG, hEF1aV2, hACTb, heIF4A1, hGAPDH, hGRP78, hGRP94, hHSP70, hKINb, and hUBIb. In some aspects, the promoter comprises an SFFV promoter. In some aspects, the promoter and/or the second promoter comprises an inducible promoter. In some aspects, the inducible promoter is selected from the group consisting of: minP, NFkB response element, CREB response element, NFAT response element, SRF response element 1, SRF response element 2, AP1 response element, TCF-LEF response element promoter fusion, Hypoxia responsive element, SMAD binding element, STAT3 binding site, inducer molecule responsive promoters, and tandem repeats thereof.

In some aspects, the first signal peptide or the second signal peptide comprises a native signal peptide native to the first effector molecule or the second effector molecule, respectively. In some aspects, the first signal peptide or the second signal peptide comprises a non-native signal peptide non-native to the first effector molecule or the second effector molecule, respectively. In some aspects, the non-native signal peptide is selected from the group consisting of: IL12, IL2, optimized IL2, trypsiongen-2, Gaussia luciferase, CD5, human IgKVII, murine IgKVII, VSV-G, prolactin, serum albumin preprotein, azurocidin preprotein, osteonectin, CD33, IL6, IL8, CCL2, TIMP2, VEGFB, osteoprotegerin, serpin E1, GROalpha, CXCL12, and IL21.

In some aspects, the first signal peptide and the second signal peptide are identical. In some aspects, the polynucleotide sequence encoding the first signal peptide comprises a codon optimized polynucleotide sequence. In some aspects, the first secretion polypeptide is a human IL12 signal peptide.

In some aspects, the polynucleotide sequence encoding the second signal peptide comprises a codon optimized polynucleotide sequence. In some aspects, the second secretion polypeptide is a human IL21 signal peptide.

In some aspects, the first effector molecule is selected from a therapeutic class, wherein the therapeutic class is selected from the group consisting of: a cytokine, a chemokine, a growth factor, a co-activation molecule, a tumor microenvironment modifier a, a receptor, a ligand, an antibody, a polynucleotide, a peptide, and an enzyme.

In some aspects, the second effector molecule is selected from a therapeutic class, wherein the therapeutic class is selected from the group consisting of: a cytokine, a chemokine, a growth factor, a co-activation molecule, a tumor microenvironment modifier, a receptor, a ligand, an antibody, a polynucleotide, a peptide, and an enzyme. In some aspects, the therapeutic class of the first effector molecule and the second effector molecule are different.

In some aspects, the first effector molecule and/or the second effector molecule is a modified effector molecule. In some aspects, the first effector molecule and/or the second effector molecule is modified to comprises a cell membrane tethering domain. In some aspects, the cell membrane tethering domain comprises a transmembrane-intracellular domain or a transmembrane domain. In some aspects, the cell membrane tethering domain comprises a cell surface receptor, or a cell membrane-bound portion thereof. In some aspects, the modified effector molecule is a fusion protein that comprises the cell surface receptor, or a cell membrane-bound portion thereof. In some aspects, the modified effector molecule further comprises a linker between the effector molecule and the cell membrane tethering domain. In some aspects, when expressed the modified effector molecule is tethered to a cell membrane of the engineered cell.

In some aspects, the cytokine is selected from the group consisting of: IL12, IL7, IL21, IL18, IL15, Type I interferons, and Interferon-gamma. In some aspects, the IL12 cytokine is an IL12p70 fusion protein. In some aspects, the chemokine is selected from the group consisting of: CCL21a, CXCL10, CXCL11, CXCL13, CXCL10-11 fusion, CCL19, CXCL9, and XCL1. In some aspects, the growth factor is selected from the group consisting of: Flt3L and GM-CSF. In some aspects, the co-activation molecule is selected from the group consisting of: 4-1BBL and CD40L. In some aspects, the tumor microenvironment modifier is selected from the group consisting of: adenosine deaminase, TGFbeta inhibitors, immune checkpoint inhibitors, VEGF inhibitors, and HPGE2. In some aspects, the TGFbeta inhibitors are selected from the group consisting of: an anti-TGFbeta peptide, an anti-TGFbeta antibody, a TGFb-TRAP, and combinations thereof. In some aspects, the immune checkpoint inhibitors comprise anti-PD-1 antibodies. In some aspects, the VEGF inhibitors comprise anti-VEGF antibodies, anti-VEGF peptides, or combinations thereof.

In some aspects, the first effector molecule and the second effector molecule are human-derived effector molecules.

In some aspects, the first effector molecule comprises interleukin 12 (IL12), for example, p35 and p40 as a dimer that is generally referred to in the art as IL-12p70. In some aspects, the first effector molecule comprises an IL12p70 fusion protein. In some aspects, the IL12p70 fusion protein is a human IL12p70 fusion protein. In some aspects, the human IL12p70 fusion protein comprises the sequence shown in SEQ ID NO: 137. In some aspects, the human IL12 comprises the p35 subunit indicated in SEQ ID NO: 137. In some aspects, the human IL12 comprises the p40 subunit indicated in SEQ ID NO: 137.

In some aspects, the second effector molecule comprises CCL21a. In some aspects, the CCL21a is a human CCL21a. In some aspects, the second effector molecule comprises IL7. In some aspects, the IL7 is a human IL7. In some aspects, the second effector molecule comprises IL21. In some aspects, the IL21 is a human IL21.

In some aspects, the expression cassette further comprises an E3 comprising a polynucleotide sequence encoding a third effector molecule. In some aspects, the third effector molecule comprises Flt3L. In some aspects, the third effector molecule comprises anti-PD1. For example, anti-PD1 can be an anti-PD1 antibody. In some aspects, the expression cassette further comprises an E4 comprising a polynucleotide sequence encoding a fourth effector molecule. In some aspects, the fourth effector molecule comprises adenosine deaminase. In some aspects, the third effector molecule comprises adenosine deaminase. In some aspects, the third effector molecule comprises CD40L. In some aspects, the third effector molecule comprises a CXCL10-CXCL11 fusion protein. In some aspects, the third effector molecule comprises XCL1.

In some aspects, the second effector molecule comprises Flt3L. In some aspects, the second effector molecule comprises a CXCL10-CXCL11 fusion protein. In some aspects, the second effector molecule comprises anti-PD1. In some aspects, the second effector molecule comprises CD40L.

In some aspects, the first effector molecule comprises interferon-beta and the second effector molecule comprises Flt3L.

In some aspects, the polynucleotide sequence encoding the first effector molecule comprises a codon optimized polynucleotide sequence. In some aspects, the polynucleotide sequence encoding the second effector molecule comprises a codon optimized polynucleotide sequence.

In some aspects, the engineered cell comprises a polynucleotide sequence encoding the promoter and the expression cassette. In some aspects, the exogenous polynucleotide sequence comprises the sequence shown in SEQ ID NO: 144.

In some aspects, the exogenous polynucleotide sequence is integrated into the genome of the engineered cell. In some aspects, the exogenous polynucleotide sequence comprises one or more viral vector polynucleotide sequences.

In some aspects, the one or more viral vector polynucleotide sequences comprise lentiviral, retroviral, retrotransposon, or adenoviral polynucleotide sequences.

In some aspects, the expression cassette further comprises following E2, an additional exogenous polynucleotide sequence comprising a formula, oriented from 5' to 3', comprising:

$$(L-S-E)_X$$

wherein S comprises a polynucleotide sequence encoding a signal peptide, E comprises a polynucleotide sequence encoding an effector molecule, L comprises a linker polynucleotide sequence, X=1 to 20 wherein the promoter is operably linked to the expression cassette, and wherein for each X the corresponding signal peptide is operably associated with the effector molecule.

Also provided for herein is an engineered cell comprising a construct, wherein the construct comprises: a) an SFFV promoter; and b) an exogenous polynucleotide sequence comprising an expression cassette described in a formula, oriented from 5' to 3', comprising $$S1-E1-L-S2-E2$$

wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell. In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144.

Also provided for herein is an engineered cell comprising a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is a mesenchymal stem cell (MSC). In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144.

Also provided for herein is an engineered cell comprising a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is a mesenchymal stem cell (MSC), wherein the MSC comprises a cellular marker phenotype comprising CD73+, CD90+, CD105+, and CD166+, CD11b−, CD14−, CD19−, CD34−, CD45−, and HLA-DR−. In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144. In some aspects, the cellular marker phenotype is determined or has been determined by flow-cytometry.

Also provided for herein is an engineered MSC comprising a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered MSC comprises a cellular marker phenotype comprising CD73+, CD90+, CD105+, and CD166+, CD11b−, CD14−, CD19−, CD34−, CD45−, and HLA−DR−. In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144. In some aspects, the cellular marker phenotype is determined or has been determined by flow-cytometry.

Also provided for herein is an engineered cell comprising a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell. In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144. In some aspects, the cell is a mesenchymal stem cell (MSC). In some aspects, the cell is a natural killer (NK) cell. In some aspects, the cell is a NKT cell. In some aspects, the cell is an innate lymphoid cell. In some aspects, the cell is a tumor-infiltrating lymphocyte (TIL). In some aspects, the cell is a mast cell. In some aspects, the cell is a eosinophil. In some aspects, the cell is a basophil. In some aspects, the cell is a monocyte. In some aspects, the cell is a macrophage. In some aspects, the cell is a neutrophil. In some aspects, the cell is a myeloid cell. In some aspects, the cell is a dendritic cell. In some aspects, the cell is a T cell. In some aspects, the cell is a CD8+ T cell. In some aspects, the cell is a CD4+ T cell. In some aspects, the cell is a cytotoxic T lymphocyte (CTL). In some aspects, the cell is a viral-specific T cell. In some aspects, the cell is a gamma-delta T cell. In some aspects, the cell is a T regulatory cell. In some aspects, the cell is a B cell. In some aspects, the cell is a human cell.

In some aspects, the engineered cell is HLA-typed with reference to a subject in need of therapeutic treatment. In some aspects, the engineered cell is a human cell. In some aspects, the human cell is an isolated cell from a subject, e.g., the subject who will receive the cell. In some aspects, the isolated cell is isolated from a tissue consisting of the group of: bone marrow, adipose tissue, the umbilical cord, fetal liver, muscle, and lung tissue. In some aspects, the engineered cell is a cultured cell.

In some aspects, the engineered MSC comprises a cellular marker phenotype comprising the cellular markers CD105+, CD73+, and CD90+. In some aspects, the cellular marker phenotype further comprises a phenotype lacking or substantially lacking one or more cellular markers selected from the group consisting of: CD45, CD34, CD14, CD11b, CD79a, CD19, HLA class II, and combinations thereof. In some aspects, the engineered MSC comprises a cellular marker phenotype comprising CD105+, CD73+, CD90+, CD45−, CD34−, CD14−; a cellular marker phenotype comprising CD105+, CD73+, CD90+, CD11b−, CD79α−; a cellular marker phenotype comprising CD105+, CD73+, CD90+, CD19−, HLA class II−; or a cellular marker phenotype comprising CD73+, CD90+, CD105+, and CD166+, CD11b−, CD14−, CD19−, CD34−, CD45−, and HLA−DR−. In some aspects, the cellular marker phenotype is determined or has been determined by flow-cytometry.

In some aspects, the engineered cell comprises a T cell. In some aspects, the T cell is a CD8+ T cell, a CD4+ T cell, a cytotoxic T lymphocyte (CTL), a viral-specific T cell, a gamma-delta T cell, or a T regulatory cell. In some aspects, the engineered cell comprises a NK cell. In some aspects, the engineered cell comprises a NKT cell. In some aspects, the engineered cell comprises a monocyte cell. In some aspects, the engineered cell comprises a macrophage. In some aspects, the engineered cell comprises a TIL.

In some aspects, the exogenous polynucleotide sequence is integrated into the genome of the engineered cell. In some aspects, the exogenous polynucleotide sequence comprises one or more viral vector polynucleotide sequences. In some aspects, the one or more viral vector polynucleotide sequences comprise lentiviral, retroviral, retrotransposon, or adenoviral polynucleotide sequences. In some aspects, the one or more viral vector polynucleotide sequences comprise lentiviral polynucleotide sequences.

In some aspects, the cell secretes each effector molecule. In some aspects, the first effector molecule is secreted at a ratio that is 10 fold higher relative to secretion of the second effector molecule.

In some aspects, the cell further comprises an antigen recognizing receptor. In some aspects, the antigen recognizing receptor recognizes an antigen selected from the group consisting of: 5T4, ADAMS, ADGRE2, AFP, AXL, B7-H3, B7-H4, B7-H6, C4.4, CA6, Cadherin 3, Cadherin 6, CCR1, CCR4, CD117, CD123, CD131, CD133, CD138, CD142, CD166, CD25, CD244, CD30, CD300LF, CD33, CD352, CD37, CD38, CD44, CD56, CD66e, CD70, CD71, CD74, CD79b, CD80, CD93, CEA, CEACAM5, Claudin18.2, CLEC12A, cMet, CSPG4, CTLA, DLK1, DLL3, DR5, EGFR, EMB, ENPP3, EpCAM, EphA2, Ephrin A4, ETBR, FGFR2, FGFR3, FRalpha, FRb, FLT3, GAPT, GCC, GD2, GFRa4, gpA33, GPC3, gpNBM, GPRC5, HER2, IL-1RAP, IL-13R, IL-13Ra, IL-13Ra2, IL-8, IL-15, IL1RAP, Integrin aV, KIT, L1CAM, LAMP1, LAT2, Lewis Y, LeY, LILRA2, LILRB2, LIV-1, LRRC, LY6E, MCSP, Mesothelin, MLC1, MS4A3, MUC1, MUC16, MUC1C, MYADM, NaPi2B, Nectin 4, NKG2D, NOTCH3, NY ESO 1, Ovarin, P-cadherin, pan-Erb2, PIEZO1, PRAM1, PSCA, PSMA, PTK7, ROR1, S Aures, SCT, SLAMF7, SLC22A16, SLC17A9, SLITRK6, SPNS3, SSTR2, STEAP1, Survivin, TDGF1, TIM1, TROP2, VSTM1, and WT1.

In some aspects, the antigen recognizing receptor comprises an antigen-binding domain. In some aspects, the antigen-binding domain comprises an antibody, an antigen-binding fragment of an antibody, a F(ab) fragment, a F(ab') fragment, a single chain variable fragment (scFv), or a single-domain antibody (sdAb). In some aspects, the antigen-binding domain comprises a single chain variable fragment (scFv). In some aspects, the scFv comprises a heavy chain variable domain (VH) and a light chain variable domain (VL). In some aspects, the VH and VL are separated by a peptide linker. In some aspects, the scFv comprises the structure VH-L-VL or VL-L-VH, wherein VH is the heavy chain variable domain, L is the peptide linker, and VL is the light chain variable domain.

In some aspects, the antigen recognizing receptor is a chimeric antigen receptor (CAR) or T cell receptor (TCR). In some aspects, the antigen recognizing receptor is a chimeric antigen receptor (CAR). In some aspects, the CAR comprises one or more intracellular signaling domains, and the one or more intracellular signaling domains are selected from the group consisting of: a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain. In some aspects, the CAR comprises a transmembrane domain, and the transmembrane domain is selected from the group consisting of: a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain. In some aspects, the CAR comprises a spacer region between the antigen-binding domain and the transmembrane domain.

Also provided for herein is a population of cells, the population of cells comprising any of the engineered cells described herein. In some aspects, the population of cells is enriched for the engineered cells.

In some aspects, the first effector molecule, the second effector molecule, or the first and second effector molecules expressed in the engineered cells promotes increased growth, viability, or growth and viability relative to cells in the population that do not express the first effector molecule, the second effector molecule, or the first and second effector molecules. In some aspects, the first effector molecule is IL12 or an IL12p70 fusion protein. In some aspects, the population of cells enriched for the engineered cells express IL12 receptor β1 or increased levels thereof, IL12 receptor β2 or increased levels thereof, or IL12 receptor β1 and IL12 receptor β2 or increased levels thereof. In some aspects, the second effector molecule is IL21. In some aspects, the second effector molecule is CCL21. In some aspects, the population of cells enriched for the engineered cells express a CCL21 receptor or increased levels thereof. In some aspects, the CCL21 receptor is CCR7.

Also provided for herein is a method of stimulating a cell-mediated immune response to a tumor cell in a subject, the method comprising administering to a subject having a tumor a therapeutically effective dose of any of the engineered cells or the population of cells described herein.

Also provided for herein is a method of stimulating (e.g., inducing) an immune response, the method comprising administering to a subject a therapeutically effective dose of any of the engineered cells or the population of cells described herein.

Also provided for herein is a method of providing anti-tumor immunity in a subject, the method comprising administering to a subject in need thereof a therapeutically effective dose of any of the engineered cells any of the engineered cells or the population of cells described herein.

Also provided for herein is a method of treating a subject having cancer, the method comprising administering to a subject having a tumor a therapeutically effective dose of any of the engineered cells or the population of cells described herein.

Also provided for herein is a method of reducing tumor volume in a subject, the method comprising administering to a subject having a tumor a therapeutically effective dose of any of the engineered cells or the population of cells described herein.

In some aspects, the engineered cell is derived from the subject. In some aspects, the engineered cell is allogeneic with reference to the subject.

In some aspects, the tumor is selected from the group consisting of: an adenocarcinoma, an acute myeloid leukemia (AML), an acute lymphoblastic B-cell leukemia (BALL), an acute lymphoblastic T-cell leukemia (TALL), a B-cell prolymphocytic leukemia, a bladder tumor, a brain tumor, a breast tumor, a cervical tumor, a chronic lymphocytic leukemia, a chronic myeloid leukemia (CML), a colorectal tumor, an esophageal tumor, a glioma, a kidney tumor, a liver tumor, a lung tumor, a lymphoma, a melanoma, a mesothelioma, a myelodysplasia, an ovarian tumor, a pancreatic tumor, a plasma cell myeloma, a prostate tumor, a skin tumor, a thyroid tumor, and a uterine tumor. In some aspects, the tumor is an ovarian tumor. In some aspects, the tumor is a tumor located in a peritoneal space.

Also provided for herein is an engineered cell comprising: a) a promoter; and b) an exogenous polynucleotide sequence comprising an expression cassette described in a formula, oriented from 5' to 3', comprising:

$$(L\text{-}S\text{-}E)_X$$

wherein S comprises a polynucleotide sequence encoding a signal peptide, E comprises a polynucleotide sequence encoding an effector molecule, L comprises a linker polynucleotide sequence, X=2 to 20, wherein the promoter is operably linked to the expression cassette, wherein for the first iteration of the (L-S-E) unit L is absent, and wherein for each X the corresponding signal peptide is operably associated with the effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is a population of cells comprising one or more engineered cells, wherein the one or more engineered cells comprise: a) a promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is a population of cells comprising one or more engineered cells, wherein the one or more engineered cells comprise: a) a promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule, and wherein the first effector molecule, the second effector molecule, or the first and second effector molecules expressed in the engineered cells promotes increased growth, viability, or growth and viability relative to cells in the population that do not express the first effector molecule, the second effector molecule, or the first and second effector molecules, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

In some aspects, the one or more engineered cells express a cognate receptor or cognate receptor ligand for the first effector molecule, the second effector molecule, or the first and second effector molecules expressed in the engineered cells. In some aspects, the first effector molecule is IL12 or an IL12p70 fusion protein. In some aspects, the second effector molecule is IL21. In some aspects, the second effector molecule is CCL21.

Also provided for herein is a population of cells comprising one or more engineered cells, wherein the one or more engineered cells comprise a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly: T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is a population of cells comprising one or more engineered cells, wherein the one or more engineered cells comprise a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the first effector molecule, the second effector molecule, or the first and second effector molecules expressed in the engineered cells promotes increased growth, viability, or growth and viability relative to cells in the population that do not express the first effector molecule, the second effector molecule, or the first and second effector molecules, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144.

Also provided for herein is a method of producing a population of cells enriched for one or more receptors or receptor ligands, comprising culturing one or more cells under conditions where the one or more cells are contacted with a first effector molecule, a second effector molecule, or a first and a second effector molecule, wherein the contacted cells express one or more cognate receptors or cognate receptor ligands for the first effector molecule, the second effector molecule, or the first and second effector molecules, and wherein the first effector molecule, the second effector molecule, or the first and the second effector molecules increase growth, viability, or growth and viability of the contacted cells relative to cells cultured in the absence of the first effector molecule, the second effector molecule, or the first and second effector molecules.

In some aspects, the first effector molecule, the second effector molecule, or the first and second effector molecules are heterologously expressed in one or more cells, and the one or more cells are contacted with the first effector molecule, the second effector molecule, or the first and second effector molecules in an autocrine manner. In some aspects, the first effector molecule, the second effector molecule, or the first and second effector molecules are expressed in one or more additional cells, and the one or more cells are contacted with the first effector molecule, the second effector molecule, or the first and second effector molecules in an paracrine manner. In some aspects, the one or more additional cells are a feeder cells. In some aspects, the one or more cells are cultured in media.

In some aspects, the one or more cells are contacted with the first effector molecule, the second effector molecule, or the first and second effector molecules by addition of a soluble first effector molecule, a soluble second effector molecule, or a soluble first and second effector molecules to the media. In some aspects, the soluble first effector molecule and/or soluble second effector molecule is a recombinant effector molecule.

In some aspects, the one or more cells are cultured under adherent conditions. In some aspects, the one or more cells are adhered onto a surface. In some aspects, the adhered cells are contacted with the first effector molecule, the second effector molecule, or the first and second effector molecules by exposing the one or more cells to first effector molecule, the second effector molecule, or the first and second effector molecules is immobilized on the surface.

In some aspects, the first effector molecule is IL12 or an IL12p70 fusion protein. In some aspects, the population of cells is enriched for IL12 receptor β1 (IL12Rβ1), enriched for IL12 receptor β2 (IL12Rβ2), or enriched for IL12Rβ1 and IL12Rβ2. In some aspects, the population of MSCs comprises a cellular marker phenotype comprising the cellular markers CD105+, CD73+, CD90+, IL12Rβ1+, and IL12Rβ2+. In some aspects, the cellular marker phenotype further comprises a phenotype lacking or substantially lacking one or more cellular markers selected from the group consisting of: CD45, CD34, CD14, CD11b, CD79α, CD19, HLA class II, and combinations thereof.

In some aspects, the population of cells comprises a cell selected from the group consisting of: natural killer (NK) cells, NKT cells, innate lymphoid cells, mast cells, eosinophils, basophils, monocytes, macrophages, neutrophils, and dendritic cells, T cells, CD8+ T cells, CD4+ T cells, gamma-delta T cells, and T regulatory cells, and B cells. In some aspects, the population of cells comprises a T cell, a NK cell, a NKT cell, a monocyte, a macrophage, or a myeloid derived cell.

In some aspects, the second effector molecule is IL21. In some aspects, the second effector molecule is CCL21. In some aspects, the population of cells is enriched for CCR7. In some aspects, the population of MSCs comprises a cellular marker phenotype comprising the cellular markers CD105+, CD73+, CD90+, IL12Rβ1+, IL12Rβ2+, and CCR7+. In some aspects, the cellular marker phenotype further comprises a phenotype lacking or substantially lacking one or more cellular markers selected from the group consisting of: CD45, CD34, CD14, CD11b, CD79α, CD19, HLA class II, and combinations thereof.

Also provided for herein is a population of cells enriched for one or more receptors or receptor ligands produced by any of the methods described herein.

Also provided for herein is one or more proteins expressed by a polynucleotide sequence, wherein the polynucleotide sequence comprising a promoter and an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule.

Also provided for herein is one or more proteins expressed by a polynucleotide sequence, wherein the polynucleotide sequence comprises an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, the first signal peptide is operably linked to the first effector molecule, and the second signal peptide is operably linked to the second effector molecule.

Also provided for herein is an isolated polynucleotide sequence comprising a promoter and an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule.

Also provided for herein is an isolated polynucleotide sequence comprising an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, the first signal peptide is operably linked to the first effector molecule, and the second signal peptide is operably linked to the second effector molecule.

In some aspects, the promoter comprises an exogenous promoter polynucleotide sequence. In some aspects, the promoter comprises an endogenous promoter. In some aspects, the promoter is operably linked to the expression cassette such that the polynucleotides are capable of being transcribed as a single polynucleotide comprising the formula S1-E1-L-S2-E2.

In some aspects, the linker polynucleotide sequence is operably associated with the translation of the first effector molecule and the second effector molecule as separate polypeptides. In some aspects, the linker polynucleotide sequence encodes a 2A ribosome skipping tag. In some aspects, the 2A ribosome skipping tag is selected from the group consisting of: P2A, T2A, E2A, and F2A. In some aspects, the linker polynucleotide sequence encodes a T2A ribosome skipping tag. In some aspects, the linker polynucleotide sequence encodes an Internal Ribosome Entry Site (IRES).

In some aspects, the linker polynucleotide sequence encodes a cleavable polypeptide. In some aspects, the cleavable polypeptide comprises a Furin recognition polypeptide sequence. In some aspects, the linker polynucleotide sequence further encodes a Gly-comprising. Ser-comprising, or Gly-Ser comprising polypeptide sequence, e.g., a Gly-Ser-Gly polypeptide sequence. In some aspects, the linker polynucleotide sequence encodes a Furin recognition polypeptide sequence, a Gly-Ser-Gly polypeptide sequence, and a T2A ribosome skipping tag in a Furin:Gly-Ser-Gly: T2A orientation from N-terminus to C-terminus.

In some aspects, the linker polynucleotide sequence encodes a second promoter, wherein the promoter is operably linked to the expression cassette such that a first polynucleotide comprising the formula S1-E1 is capable of being transcribed, wherein the second promoter is operably linked to the expression cassette such that a second polynucleotide comprising the formula S2-E2 is capable of being transcribed, and wherein the first and the second polynucleotide are separate polynucleotides. In some aspects, the promoter and the second promoter are identical. In some aspects, the promoter and the second promoter are different.

In some aspects, the promoter and/or the second promoter comprises a constitutive promoter. In some aspects, the constitutive promoter is selected from the group consisting of: CMV, EFS, SFFV, SV40, MND, PGK, UbC, hEFIaV1, hCAGG, hEFIaV2, hACTb, heIF4A1, hGAPDH, hGRP78, hGRP94, hHSP70, hKINb, and hUBIb. In some aspects, the promoter comprises an SFFV promoter. In some aspects, the promoter and/or the second promoter comprises an inducible promoter. In some aspects, the inducible promoter is selected from the group consisting of: minP, NFkB response element, CREB response element, NFAT response element, SRF response element 1, SRF response element 2, AP1 response element, TCF-LEF response element promoter fusion, Hypoxia responsive element, SMAD binding element, STAT3 binding site, inducer molecule responsive promoters, and tandem repeats thereof.

In some aspects, the first signal peptide or the second signal peptide comprises a native signal peptide native to the first effector molecule or the second effector molecule, respectively. In some aspects, the first signal peptide or the second signal peptide comprises a non-native signal peptide non-native to the first effector molecule or the second effector molecule, respectively. In some aspects, the non-native signal peptide is selected from the group consisting of: IL12, IL2, optimized IL2, trypsiongen-2, Gaussia luciferase, CD5, human IgKVII, murine IgKVII, VSV-G, prolactin, serum albumin preprotein, azurocidin preprotein, osteonectin, CD33, IL6, IL8, CCL2, TIMP2, VEGFB, osteoprotegerin, serpin E1, GROalpha, CXCL12, and IL21. In some aspects, the first signal peptide and the second signal peptide are identical. In some aspects, the polynucleotide sequence encoding the first signal peptide comprises a codon optimized polynucleotide sequence.

In some aspects, the first secretion polypeptide is a human IL12 signal peptide. In some aspects, the polynucleotide sequence encoding the second signal peptide comprises a codon optimized polynucleotide sequence. In some aspects, the second secretion polypeptide is a human IL21 signal peptide.

In some aspects, the first effector molecule is selected from a therapeutic class, wherein the therapeutic class is selected from the group consisting of: a cytokine, a chemokine, a growth factor, a co-activation molecule, a tumor microenvironment modifier a, a receptor, a ligand, an antibody, a polynucleotide, a peptide, and an enzyme. In some aspects, the second effector molecule is selected from a therapeutic class, wherein the therapeutic class is selected from the group consisting of: a cytokine, a chemokine, a growth factor, a co-activation molecule, a tumor microenvironment modifier, a receptor, a ligand, an antibody, a polynucleotide, a peptide, and an enzyme. In some aspects, the therapeutic class of the first effector molecule and the second effector molecule are different. In some aspects, the first effector molecule and/or the second effector molecule is a modified effector molecule.

In some aspects, the first effector molecule and/or the second effector molecule is modified to comprises a cell membrane tethering domain. In some aspects, the cell membrane tethering domain comprises a transmembrane-intracellular domain or a transmembrane domain. In some aspects, the cell membrane tethering domain comprises a cell surface receptor, or a cell membrane-bound portion thereof. In some aspects, the modified effector molecule is a fusion protein that comprises the cell surface receptor, or a cell membrane-bound portion thereof. In some aspects, the modified effector molecule further comprises a linker between the effector molecule and the cell membrane tethering domain. In some aspects, when expressed in a cell, the modified effector molecule is tethered to a cell membrane of the cell.

In some aspects, the cytokine is selected from the group consisting of: IL12, IL7, IL21, IL18, IL15, Type I interferons, and Interferon-gamma. In some aspects, the IL12 cytokine is an IL12p70 fusion protein. In some aspects, the chemokine is selected from the group consisting of: CCL21a, CXCL10, CXCL11, CXCL13, CXCL10-11 fusion, CCL19, CXCL9, and XCL1. In some aspects, the growth factor is selected from the group consisting of: Flt3L and GM-CSF. In some aspects, the co-activation molecule is selected from the group consisting of: 4-1BBL and CD40L. In some aspects, the tumor microenvironment modifier is selected from the group consisting of: adenosine deaminase, TGFbeta inhibitors, immune checkpoint inhibitors, VEGF inhibitors, and HPGE2. In some aspects, the TGFbeta inhibitors are selected from the group consisting of: an anti-TGFbeta peptide, an anti-TGFbeta antibody, a TGFb-TRAP, and combinations thereof. In some aspects, the immune checkpoint inhibitors comprise anti-PD-1 antibodies. In some aspects, the VEGF inhibitors comprise anti-VEGF antibodies, anti-VEGF peptides, or combinations thereof.

In some aspects, the first effector molecule and the second effector molecule are human-derived effector molecules.

In some aspects, the first effector molecule comprises IL12. In some aspects, the first effector molecule comprises an IL12p70 fusion protein. In some aspects, the IL12p70 fusion protein is a human IL12p70 fusion protein.

In some aspects, the second effector molecule comprises CCL21a. In some aspects, the CCL21a is a human CCL21a.

In some aspects, the second effector molecule comprises IL7. In some aspects, the IL7 is a human IL7. In some aspects, the second effector molecule comprises IL21. In some aspects, the IL21 is a human IL21.

In some aspects, the expression cassette further comprises an E3 comprising a polynucleotide sequence encoding a third effector molecule. In some aspects, the third effector molecule comprises Flt3L. In some aspects, the third effector molecule comprises anti-PD1.

In some aspects, the expression cassette further comprises an E4 comprising a polynucleotide sequence encoding a fourth effector molecule. In some aspects, the fourth effector molecule comprises adenosine deaminase.

In some aspects, the third effector molecule comprises adenosine deaminase. In some aspects, the third effector molecule comprises CD40L. In some aspects, the third effector molecule comprises a CXCL10-CXCL11 fusion protein. In some aspects, the third effector molecule comprises XCL1.

In some aspects, the second effector molecule comprises Flt3L. In some aspects, the second effector molecule comprises a CXCL10-CXCL11 fusion protein. In some aspects, the second effector molecule comprises anti-PD1. In some aspects, the second effector molecule comprises CD40L.

In some aspects, the first effector molecule comprises interferon-beta and the second effector molecule comprises Flt3L.

In some aspects, the polynucleotide sequence encoding the first effector molecule comprises a codon optimized polynucleotide sequence. In some aspects, the polynucleotide sequence encoding the second effector molecule comprises a codon optimized polynucleotide sequence.

In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144.

Also provided for herein is an exogenous polynucleotide sequence comprising an SFFV promoter and an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule.

In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144.

Also provided for herein is an exogenous polynucleotide sequence comprising an SFFV promoter and an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly: T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; wherein the SFFV promoter is operably linked to the expression cassette, the first signal peptide is operably linked to the first effector molecule, and the second signal peptide is operably linked to the second effector molecule; wherein the promoter is operably linked to the expression cassette such that the polynucleotides are capable of being transcribed as a single polynucleotide comprising the formula S1-E1-L-S2-E2; and wherein the polynucleotide sequence comprises the polynucleotide sequence shown in SEQ ID NO: 144.

In some aspects, the exogenous polynucleotide sequence is encoded by a nucleic acid selected from the group consisting of: a DNA, a cDNA, an RNA, an mRNA, and a naked plasmid.

Also provided for herein is an expression vector comprising any of the exogenous polynucleotide sequences described herein. In some aspects, the expression vector is a viral vector. In some aspects, the viral vector is a lentiviral vector.

Also provided for herein is a pharmaceutical composition comprising any of the exogenous polynucleotide sequences described herein, and a pharmaceutically acceptable carrier.

Also provided for herein is a pharmaceutical composition comprising any of engineered cells described herein, and a pharmaceutically acceptable carrier.

An isolated cell comprising any of the exogenous polynucleotide sequences described herein, any of the expression vectors described herein, or any of the pharmaceutical compositions described herein.

In some aspects, the isolated cell is selected from the group consisting of: a T cell, a CD8+ T cell, a CD4+ T cell, a gamma-delta T cell, a cytotoxic T lymphocyte (CTL), a regulatory T cell, a viral-specific T cell, a Natural Killer T (NKT) cell, a Natural Killer (NK) cell, a B cell, a tumor-infiltrating lymphocyte (TIL), an innate lymphoid cell, a mast cell, an eosinophil, a basophil, a neutrophil, a myeloid cell, a macrophage, a monocyte, a dendritic cell, an erythrocyte, a platelet cell, a human embryonic stem cell (ESC), an ESC-derived cell, a pluripotent stem cell, an MSC, an induced pluripotent stem cell (iPSC), and an iPSC-derived cell.

In some aspects, the isolated cell is an MSC.

In some aspects, the exogenous polynucleotide sequence is integrated into the genome of the cell. In some aspects, the exogenous polynucleotide sequence comprises one or more viral vector polynucleotide sequences.

In some aspects, the one or more viral vector polynucleotide sequences comprise lentiviral, retroviral, retrotransposon, or adenoviral polynucleotide sequences. In some aspects, the one or more viral vector polynucleotide sequences comprise lentiviral polynucleotide sequences.

In some aspects, the engineered cell is HLA-typed with reference to a subject in need of therapeutic treatment. In some aspects, the engineered cell is a human cell. In some aspects, the human cell is an isolated cell from a subject, e.g., the subject who will receive the cell. In some aspects, the isolated cell is isolated from a tissue consisting of the group of: bone marrow, adipose tissue, the umbilical cord, fetal liver, muscle, and lung tissue. In some aspects, the cell is a cultured cell.

In some aspects, the MSC comprises a cellular marker phenotype comprising the cellular markers CD105+, CD73+, and CD90+. In some aspects, the cellular marker phenotype further comprises a phenotype lacking or substantially lacking one or more cellular markers selected from the group consisting of: CD45, CD34, CD14, CD11b, CD79α, CD19, HLA class II, and combinations thereof. In some aspects, the MSC comprises a cellular marker phenotype comprising CD105+, CD73+, CD90+, CD45−, CD34−, CD14−; a cellular marker phenotype comprising CD105+, CD73+, CD90+, CD11b−, CD79α−; a cellular marker phenotype comprising CD105+, CD73+, CD90+, CD19−, HLA class II−; or a cellular marker phenotype comprising CD73+, CD90+, CD105+, and CD166+, CD11b−, CD14−, CD19−, CD34−, CD45−, and HLA–DR−. In some aspects, the cellular marker phenotype is determined or has been determined by flow-cytometry.

In some aspects, the cellular marker phenotype further comprises a cellular marker comprising a cognate receptor or a cognate receptor ligand for the first effector molecule, the second effector molecule, or the first and second effector molecules expressed in the cell. In some aspects, the receptor is selected from the group consisting of: IL12RB1, IL12RB2, CCL7, and combinations thereof.

In some aspects, the cell secretes each effector molecule. In some aspects, the first effector molecule is secreted at a ratio that is 10 fold higher relative to secretion of the second effector molecule.

In some aspects, the cell further comprises an antigen recognizing receptor. In some aspects, the antigen recognizing receptor comprises an antigen-binding domain. In some aspects, the antigen-binding domain comprises an antibody, an antigen-binding fragment of an antibody, a F(ab) fragment, a F(ab') fragment, a single chain variable fragment (scFv), or a single-domain antibody (sdAb). In some aspects, the antigen-binding domain comprises a single chain variable fragment (scFv). In some aspects, the scFv comprises a heavy chain variable domain (VH) and a light chain variable domain (VL). In some aspects, the VH and VL are separated by a peptide linker. In some aspects, the scFv comprises the structure VH-L-VL or VL-L-VH, wherein VH is the heavy chain variable domain, L is the peptide linker, and VL is the light chain variable domain.

In some aspects, the antigen recognizing receptor is a chimeric antigen receptor (CAR) or T cell receptor (TCR). In some aspects, the antigen recognizing receptor is a chimeric antigen receptor (CAR). In some aspects, the CAR comprises one or more intracellular signaling domains, and the one or more intracellular signaling domains are selected from the group consisting of: a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain. In some aspects, the CAR comprises a transmembrane domain, and the transmembrane domain is selected from the group consisting of: a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain. In some aspects, the CAR comprises a spacer region between the antigen-binding domain and the transmembrane domain.

Also provided for herein is a virus comprising any of the exogenous polynucleotide sequences described herein or any of the expression vectors described herein. In some aspects, the virus is selected from the group consisting of: a lentivirus, a retrovirus, a retrotransposon, and an adenovirus. In some aspects, the virus is a lentivirus.

Also provided for herein is a method of reducing tumor volume in a subject, the method comprising delivering to a subject having a tumor a composition comprising cells engineered to produce multiple effector molecules that modulate tumor-mediated immunosuppressive mechanisms, in an effective amount to reduce the volume of the tumor, wherein the engineered cells comprise: a) a promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is a method of reducing tumor volume in a subject, the method comprising delivering to a subject having a tumor a composition comprising cells engineered to produce IL12 and IL21, in an effective amount to reduce the volume of the tumor, wherein the engineered cells comprise a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is a method of stimulating (e.g., inducing) an immune response, the method comprising delivering to a subject a composition comprising cells engineered to produce multiple effector molecules that modulate tumor-mediated immunosuppressive mechanisms, in an effective amount to induce an immune response, wherein the engineered cells comprise: a) a promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is a method of stimulating (e.g., inducing) an immune response in a subject, the method comprising delivering to a subject a composition comprising cells engineered to produce IL12 and IL21, in an effective amount to induce an immune response, wherein the engineered cells comprise a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144.

In some aspects, the method further comprises administering a checkpoint inhibitor. In some aspects, the checkpoint inhibitor is an anti-PD-1 antibody, anti-PD-1L antibody or an anti-CTLA-4 antibody. In some aspects, the method further comprises administering an anti-CD40 antibody.

In some aspects, the tumor is selected from the group consisting of: an adenocarcinoma, an acute myeloid leukemia (AML), an acute lymphoblastic B-cell leukemia (BALL), an acute lymphoblastic T-cell leukemia (TALL), a B-cell prolymphocytic leukemia, a bladder tumor, a brain tumor, a breast tumor, a cervical tumor, a chronic lymphocytic leukemia, a chronic myeloid leukemia (CML), a colorectal tumor, an esophageal tumor, a glioma, a kidney tumor, a liver tumor, a lung tumor, a lymphoma, a melanoma, a mesothelioma, a myelodysplasia, an ovarian tumor, a pancreatic tumor, a plasma cell myeloma, a prostate tumor, a skin tumor, a thyroid tumor, and a uterine tumor. In some aspects, the tumor is an ovarian tumor. In some aspects, the tumor is a tumor located in a peritoneal space.

In some aspects, the administering comprises systemic administration, intraperitoneal administration, or intratumoral administration.

In some aspects, the volume of the tumor is reduced by at least 25% relative to a control, optionally wherein the control is an unmodified cell. In some aspects, the volume of the tumor is reduced by at least 50% relative to a control, optionally wherein the control is an unmodified cell. In some aspects, the volume of the tumor is reduced by at least 75% relative to a control, optionally wherein the control is an unmodified cell.

Also provided for herein is a method of reducing tumor volume in a subject, the method comprising delivering to a subject having a tumor a composition capable of engineering an cell to produce multiple effector molecules that modulate tumor-mediated immunosuppressive mechanisms, in an effective amount to reduce the volume of the tumor, wherein each engineered cell comprises: a) a promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is method of reducing tumor volume in a subject, the method comprising delivering to a subject having a tumor a composition capable of engineering a cell to produce IL12 and IL21, in an effective amount to reduce the volume of the tumor, wherein the engineered cell comprises a construct, wherein the construct comprises: a)

an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly: T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is a method of stimulating (e.g., inducing) an immune response in a subject, the method comprising delivering to a subject a composition capable of engineering an cell to produce multiple effector molecules that modulate tumor-mediated immunosuppressive mechanisms, in an effective amount to induce an immune response, wherein the engineered cell comprises: a) a promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, E1 comprises a polynucleotide sequence encoding a first effector molecule, L comprises a linker polynucleotide sequence, S2 comprises a polynucleotide sequence encoding a second signal peptide, E2 comprises a polynucleotide sequence encoding a second effector molecule, and wherein the promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

Also provided for herein is method of stimulating (e.g., inducing) an immune response in a subject, the method comprising delivering to a subject a composition capable of engineering a cell to produce IL12 and IL21, in an effective amount to induce an immune response, wherein the engineered cell comprises a construct, wherein the construct comprises: a) an SFFV promoter; and b) an exogenous polynucleotide sequence comprising an expression cassette described in a formula, oriented from 5' to 3', comprising

S1-E1-L-S2-E2 wherein S1 comprises a polynucleotide sequence encoding a first signal peptide, wherein the first signal peptide is a human IL12 signal peptide; E1 comprises a polynucleotide sequence encoding a first effector molecule, wherein the first effector molecule is a human IL12p70 fusion protein; L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly: T2A orientation from N-terminus to C-terminus; S2 comprises a polynucleotide sequence encoding a second signal peptide, wherein the second signal peptide is a human IL21 signal peptide; E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

In some aspects, the human IL12p70 fusion protein comprises the sequence shown in SEQ ID NO: 137. In some aspects, the human IL12p70 fusion protein comprises the sequence shown in SEQ ID NO: 138. In some aspects, polynucleotide sequence encoding the human IL12p70 fusion protein comprises the sequence shown in SEQ ID NO: 136. In some aspects, the human IL21 comprises the sequence shown in SEQ ID NO: 142. In some aspects, the human IL21 comprises the sequence shown in SEQ ID NO: 143. In some aspects, polynucleotide sequence encoding the human IL21 comprises the sequence shown in SEQ ID NO: 141. In some aspects, the linker comprises the sequence shown in SEQ ID NO: 140. In some aspects, the linker polynucleotide sequence comprises the sequence shown in SEQ ID NO: 139. In some aspects, the construct comprises the polynucleotide sequence shown in SEQ ID NO: 144.

In some aspects, the composition comprises a delivery system selected from the group consisting of: a viral system, a transposon system, and a nuclease genomic editing system. In some aspects, the viral system is selected from the group consisting of: a lentivirus, a retrovirus, a retrotransposon, and an adenovirus. In some aspects, the nuclease genomic editing system is selected from the group consisting of: a zinc-finger system, a TALEN system, and a CRISPR system.

In some aspects, the tumor is selected from the group consisting of: an adenocarcinoma, an acute myeloid leukemia (AML), an acute lymphoblastic B-cell leukemia (BALL), an acute lymphoblastic T-cell leukemia (TALL), a B-cell prolymphocytic leukemia, a bladder tumor, a brain tumor, a breast tumor, a cervical tumor, a chronic lymphocytic leukemia, a chronic myeloid leukemia (CML), a colorectal tumor, an esophageal tumor, a glioma, a kidney tumor, a liver tumor, a lung tumor, a lymphoma, a melanoma, a mesothelioma, a myelodysplasia, an ovarian tumor, a pancreatic tumor, a plasma cell myeloma, a prostate tumor, a skin tumor, a thyroid tumor, and a uterine tumor. In some aspects, the administering comprises systemic administration, intraperitoneal administration, or intratumoral administration.

BRIEF DESCRIPTION OF THE DRAWINGS

FIG. 2A shows the treatment schematic.

FIG. 2B shows tumor free mice rejecting the tumor implant in contrast to naïve control mice where the tumor became established.

FIG. 7B shows the tumor weight for individual mice in each treatment, and the mean±SEM for each treatment group.

FIG. 9B shows the tumor weight for individual mice in each treatment, and the mean±SEM for each treatment group.

FIG. 10A shows that engineered MSCs expressing GFP do not elicit toxicity. Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 10A represents an individual mouse.

FIG. 10B shows the tumor weight for individual mice in each treatment, and the mean±SEM for each treatment group.

FIG. 11B shows the tumor weight for individual mice in each treatment, and the mean±SEM for each treatment group.

FIG. 13B shows the tumor weight for individual mice in each treatment, and the mean±SEM for each treatment group.

FIG. 17A shows the tumor volume of the individual group. Each line of FIG. 17A represents an individual mouse.

FIG. 17B shows body weight represented as mean±SEM (top left), tumor volume represented as mean±SEM (bottom left), and survival rate (right).

FIG. 18B shows the tumor weight for individual mice in each treatment, and the mean±SEM for each treatment group.

FIG. 18C is a representative graph of the infiltrating immune population within the tumor microenvironment for individual mice in each treatment, and the mean±SEM for each treatment group.

FIG. 18D shows the percentage of regulatory T cells (Treg) in the total CD3 population for individual mice in each treatment, and the mean±SEM for each treatment group. There was a significant decrease in the numbers of Tregs in the tumor microenvironment treated with engineered MSC-IL2 and CCL21a.

FIG. 18E correlates the percentage of immune infiltration with tumor weight. Samples with high lymphocytes (CD3+) were found to correlate with low tumor weight, while samples with high myeloid (CD11b+) infiltration were correlated with higher tumor burden.

FIG. 21B shows the immune profile of three (3) mice in the day 18 group to better characterize the tumor microenvironment.

FIG. 22B shows the tumor weight for individual mice in each treatment group, and the mean±SEM for each treatment group.

FIG. 23A shows a significant increase in infiltrating CD3 and CD8 cytotoxic T population in the combo group compared to the group dosed with naïve MSC.

FIG. 23B shows a significant reduction in granulocytic myeloid-derived suppressor cells (gMDSCs) and macrophage population in the combo group compared to group treated with Naïve MSC.

FIG. 24A shows that samples with more CD3+ and CD8+ T cells (top left and top center graph) correlate strongly with a decrease in tumor weight. These figures also show that samples with fewer CD11b myeloid cells, including macrophage, dendritic cells, and MDSC, display lower tumor burden (lower center and lower right graph).

FIG. 24B shows that samples with fewer CD11b myeloid cells, including macrophage, dendritic cells, and MDSC, display lower tumor burden (upper row).

FIG. 25A shows that all three lots of MSC-IL12+MSC-CCL21a can reduce tumor burden in both subcutaneous and intraperitoneal model (first 5 graphs are from the SC model and last 3 are from the IP model). Tumors from all mice were collected on day 11. Each line of FIG. 25A represents an individual mouse.

FIG. 25B shows the average tumor weight from each group, and the mean±SEM for each treatment group.

FIG. 26B shows the tumor weight for individual mice in each treatment, and the mean for each treatment group. MSC-IL12+MSC-CCL21a shows best efficacy compared to mice injected with naïve MSC. Treatment efficacy was also observed in the group treated with MSC-IFNb+MSC-CCL21a.

FIG. 27A are graphs that show immune profiles of each group treated with indicated engineered MSC. A consistent decrease in macrophage population was observed after treating with MSC-IL12+MSC-CCL21a. A general trend of increased infiltration in CD3+ population and decreased infiltration in CD11b+ population was also observed when compared to group treated with MSC-IL12+MSC-CCL21a against naïve MSC.

FIG. 27B are graphs that show immune profiles of each group treated with indicated engineered MSC. A general trend of increased infiltration in CD3+ population and decreased infiltration in CD11b+ population was also observed when compared to group treated with MSC-IL12+MSC-CCL21a against naïve MSC.

FIG. 28A shows the correlation of immune infiltration with tumor weight.

FIG. 28B shows the correlation of immune infiltration with tumor weight. Samples with low macrophage and dendritic cells have lower tumor burden (top center and top right).

FIG. 29 shows graphs combining the in vivo data from the colorectal cancer models above (FIG. 22A and FIG. 26A). The combined CT26 data from FIG. 22A and FIG. 26A capture three groups: Tumor only (PBS), treated with naïve MSC, and treated with MSC-IL12+MSC-CCL21a.

FIG. 37A shows homing in a CT26 tumor model (images shown).

FIG. 37B shows homing in a CT26 tumor model for individual mice in each treatment, and the mean±SEM for each treatment group (quantification summary of images shown in FIG. 37A).

FIG. 37C shows quantitative real time PCR for individual mice in each treatment, and the mean±SEM for each treatment group.

FIG. 37D shows fluorescence microscopy against firefly luciferase.

FIG. 37E shows homing in a B16F10 tumor model for individual mice in each treatment, and the mean±SEM for each treatment group (quantification summary of images).

FIG. 40A shows the mean tumor burden as assessed by BLI for PBS treated (circle), MSC-Flag-Myc ("Naïve MSC" square), and IL12p70/CCL21a expressing MSCs (triangle).

FIG. 40B shows the tumor burden in individual mice as assessed by BLI for PBS treated, MSC-Flag-Myc ("Naïve MSC"), and IL12p70/CCL21a expressing MSCs (left, middle, and right panels, respectively). Each line of FIG. 40B represents an individual mouse.

FIG. 52B demonstrates the BLI luciferase measurements of individual mice.

FIG. 53B shows survival curves of the treatment groups.

FIG. 57A shows naïve untreated mice.

FIG. 57B shows mice that previously received the treatment of IL12-expressing MSCs alone.

FIG. 57C shows mice that previously received the combination treatment of IL12-expressing MSCs and IL21-expressing MSCs.

FIG. 58A shows summarized BLI assessment of efficacy normalized day 17 vs day 7 for individual mice in each treatment, and the mean±SEM for each treatment group.

FIG. 58B shows BLI measurements over time for individual mice.

FIG. 58C shows BLI measurements over time for individual mice.

FIG. 58D shows survival curves of the treatment groups.

FIG. 59A shows summarized BLI assessment of efficacy normalized day 17 vs day 7 for individual mice in each treatment, and the mean±SEM for each treatment group.

FIG. 59B shows BLI measurements over time for individual mice.

FIG. 59C shows BLI measurements over time for individual mice.

FIG. 59D shows BLI measurements over time for individual mice for multiple administrations of higher doses.

FIG. 59E shows survival curves of the treatment groups.

FIG. 60A shows summarized BLI assessment of efficacy normalized day 18 vs day 9 for individual mice in each treatment, and the mean±SEM for each treatment group.

FIG. 60B shows BLI measurements over time for individual mice.

FIG. 60C shows survival curves of the treatment groups.

FIG. 61A shows summarized luciferase quantification.

FIG. 61B shows representative images of luciferase signal in organs.

FIG. 63A shows survival curves of MSC-IL12 vs rIL12.

FIG. 63B shows survival curves of MSC-IL21 vs rIL21.

FIG. 63C shows survival curves of MSC-IL12/IL21 vs rIL12+rIL21.

FIG. 63D shows BLI assessments of tumor burden for mice either treated with MSCs engineered to produce cytokines or treated with recombinant cytokine therapy.

FIG. 63E shows BLI assessments of tumor burden for mice either treated with MSCs engineered to produce cytokines or treated with recombinant cytokine therapy.

FIG. 64A shows tumor weight assessments of tumor burden for individual mice in each treatment, and the mean±SEM for each treatment group, for mice either treated with MSCs engineered to produce cytokines or treated with recombinant cytokine therapy.

FIG. 64B shows survival curves of treatment groups.

Figure 65A:
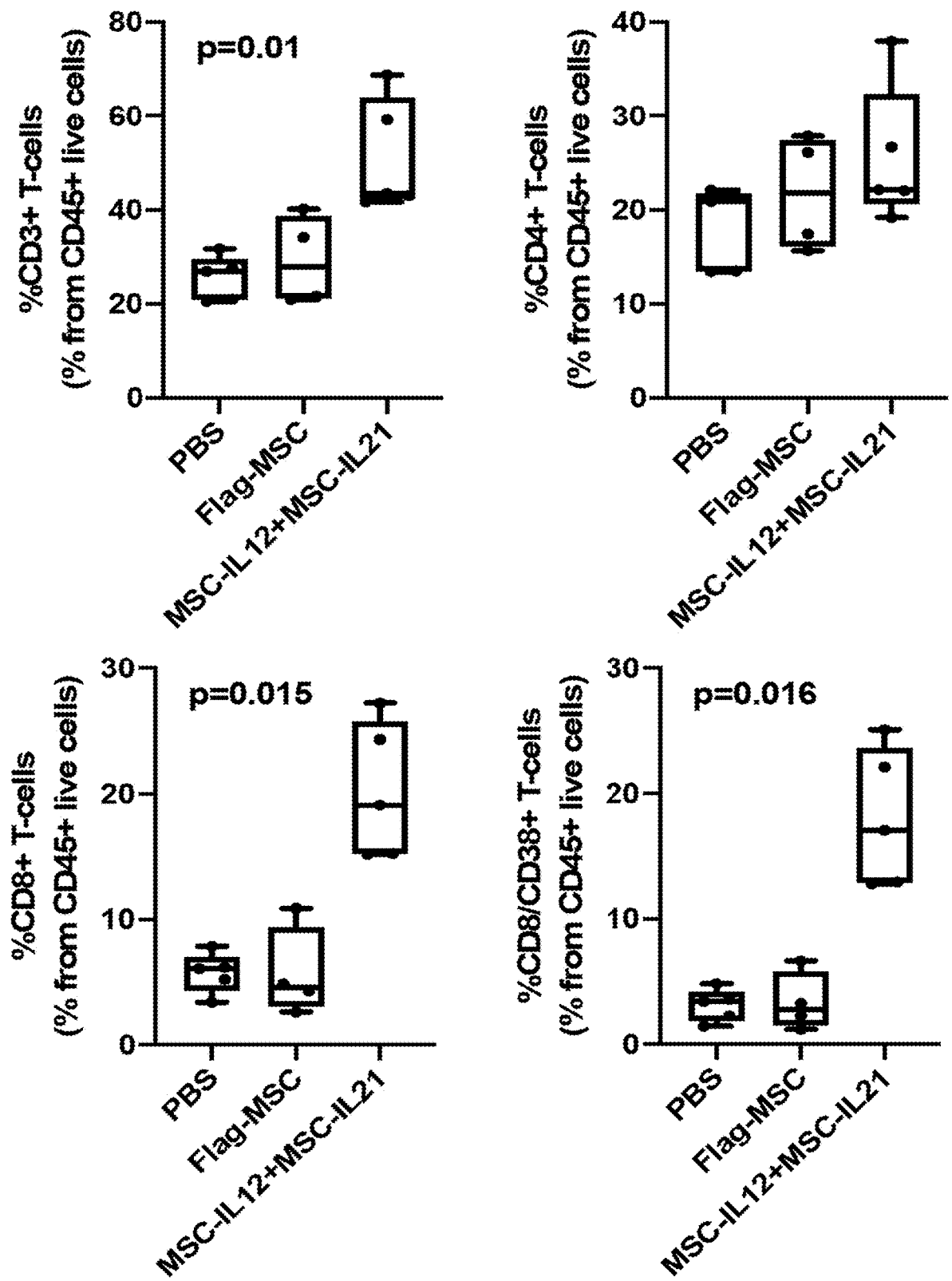

FIG. 65A shows the immune profile of mice following treatment with MSCs producing both IL12 and IL21 in a CT26 IP tumor model. Results shown are multicolor flow cytometry analysis used to characterize immune infiltrates in response to treatment. FIG. 65A shows T-cell subsets and activation markers (CD3, CD4, CD8, CD8/CD38+) for individual mice in each treatment, and the mean±SEM for each treatment group.

Figure 65B:
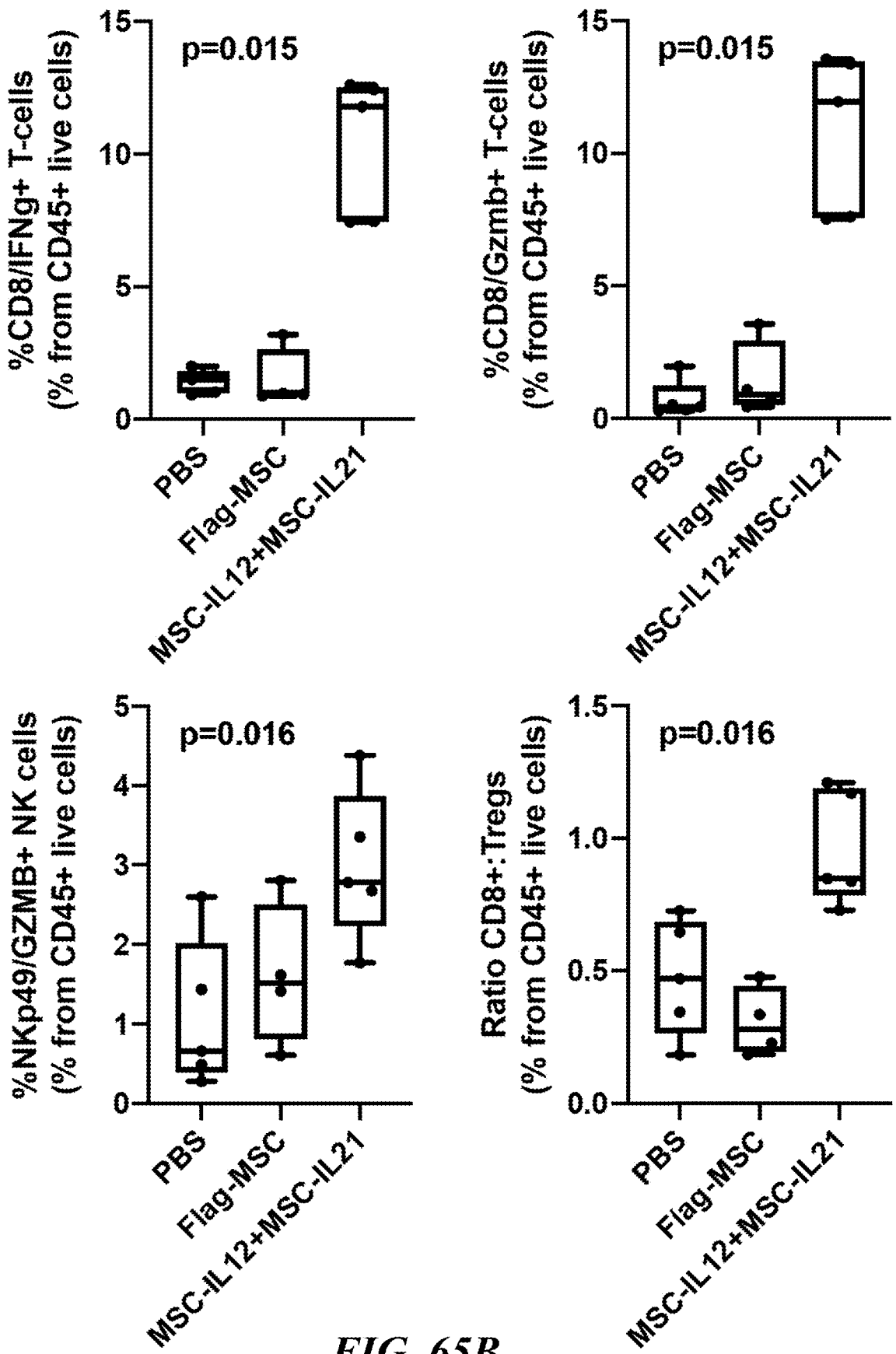

FIG. 65B shows the immune profile of mice following treatment with MSCs producing both IL12 and IL21 in a CT26 IP tumor model. Results shown are multicolor flow cytometry analysis used to characterize immune infiltrates in response to treatment. FIG. 65B shows T-cell subsets and activation markers (CD8/IFNg+, CD8/Gzmb+, NK/Gzmb+ and ratio CD8:Tregs-FoxP3) for individual mice in each treatment, and the mean±SEM for each treatment group.

Figure 65C:
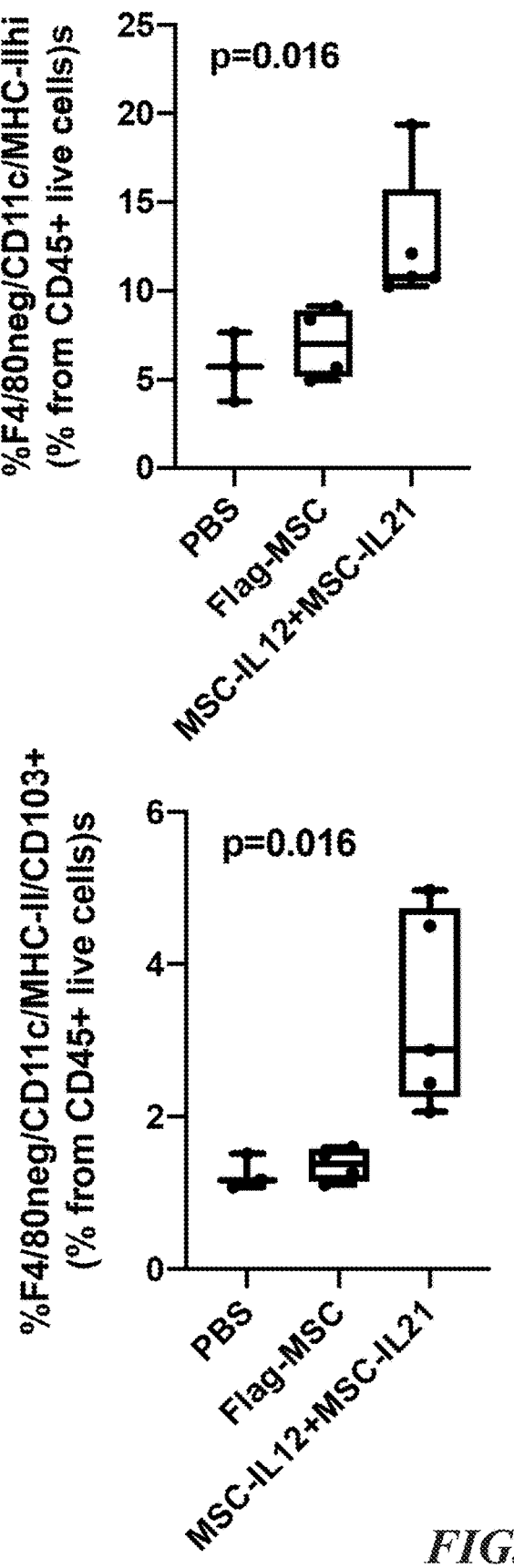
Figure 65C:
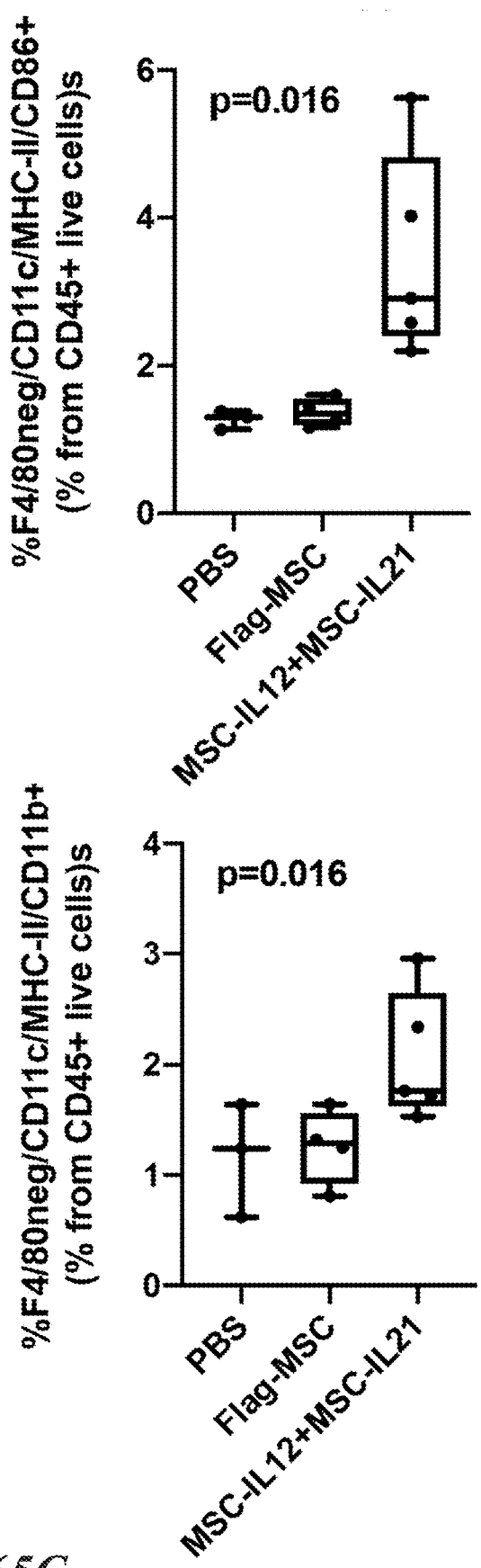

FIG. 65C shows the immune profile of mice following treatment with MSCs producing both IL12 and IL21 in a CT26 IP tumor model. Results shown are multicolor flow cytometry analysis used to characterize immune infiltrates in response to treatment. FIG. 65C shows the immune profile of antigen-presenting cells such as dendritic cells for individual mice in each treatment, and the mean±SEM for each treatment group.

DETAILED DESCRIPTION

Mesenchymal stem cells (MSCs) (also referred to as mesenchymal stromal cells, multipotent stromal cells, marrow stromal cells, or multipotent mesenchymal stromal cells) are a subset of non-hematopoietic adult stem cells that originate from the mesoderm. They possess self-renewal ability and multilineage differentiation into not only mesoderm lineages, such as chondrocytes, osteocytes and adipocytes, but also ectodermic cells and endodermic cells. MSCs, free of both ethical concerns and teratoma formation, are the major stem cell type used for cell therapy for treatment of both immune diseases and non-immune diseases. They can be easily isolated from the bone marrow, adipose tissue, the umbilical cord, fetal liver, muscle, and lung and can be successfully expanded in vitro. MSCs can be defined by cell surface marker phenotype including a cellular marker phenotype comprising CD105+, CD73+, CD90+, CD45−, CD34−, CD14−; a cellular marker phenotype comprising CD105+, CD73+, CD90+, CD11b−, CD79α−; or a cellular marker phenotype comprising CD105+, CD73+, CD90+, CD19−, HLA class II−, as discussed in greater detail in Dominici, et al. (Cytotherapy. 2006; 8(4):315-7), incorporated by reference for all purposes. Further, when MSCs are delivered exogenously and systemically to humans and animals, they tend to home to (migrate directly to) damaged tissue sites with inflammation, including tumor microenvironments and metastatic regions. The inflammation-directed MSC homing involves several important cell trafficking-related molecules, including chemokines, adhesion molecules, and matrix metalloproteinases (MMPs).

Provided herein are methods of engineering cells, such as MSCs, to produce effector molecules that modulate different tumor-mediated immunosuppressive mechanisms. These MSCs are referred to herein as "engineered MSCs." These MSCs, which typically contain engineered nucleic acid, do not occur in nature. In some embodiments, the MSCs are engineered to include a nucleic acid comprising a promoter operably linked to a nucleotide sequence encoding an effector molecule, for example, one that stimulates an immune response.

Also provided herein are methods of engineering cells such as immune cells, including, but not limited to natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell, to produce effector molecules. These cells, including both MSCs and immune cells, are referred to herein as "engineered cells." These cells, which typically contain engineered nucleic acid, do not occur in nature. In some embodiments, the cells are engineered to include a nucleic acid comprising a promoter operably linked to a nucleotide sequence encoding an effector molecule, for example, one that stimulates an immune response.

An "effector molecule," refers to a molecule (e.g., a nucleic acid such as DNA or RNA, or a protein (polypeptide) or peptide) that binds to another molecule and modulates the biological activity of that molecule to which it binds. For example, an effector molecule may act as a ligand to increase or decrease enzymatic activity, gene expression, or cell signaling. Thus, in some embodiments, an effector molecule modulates (activates or inhibits) different immunomodulatory mechanisms. By directly binding to and modulating a molecule, an effector molecule may also indirectly modulate a second, downstream molecule. In some embodiments, an effector molecule is a secreted molecule, while in other embodiments, an effector molecule is bound to the cell surface or remains intracellular. For example, effector molecules include intracellular transcription factors, microRNA, and shRNAs that modify the internal cell state to, for example, enhance immunomodulatory activity, homing properties, or persistence of the cell. Non-limiting examples of effector molecules include cytokines, chemokines, enzymes that modulate metabolite levels, antibodies or decoy molecules that modulate cytokines, homing molecules, and/or integrins.

The term "modulate" encompasses maintenance of a biological activity, inhibition (partial or complete) of a biological activity, and stimulation/activation (partial or complete) of a biological activity. The term also encompasses decreasing or increasing (e.g., enhancing) a biological activity. Two different effector molecules are considered to "modulate different tumor-mediated immunosuppressive mechanisms" when one effector molecule modulates a tumor-mediated immunosuppressive mechanism (e.g., stimulates T cell signaling) that is different from the tumor-mediated immunosuppressive mechanism modulated by the other effector molecule (e.g., stimulates antigen presentation and/or processing).

Modulation by an effector molecule may be direct or indirect. Direct modulation occurs when an effector molecule binds to another molecule and modulates activity of that molecule. Indirect modulation occurs when an effector molecule binds to another molecule, modulates activity of that molecule, and as a result of that modulation, the activity of yet another molecule (to which the effector molecule is not bound) is modulated.

In some embodiments, modulation of a tumor-mediated immunosuppressive mechanism by at least one effector molecule results in an increase in an immunostimulatory and/or anti-tumor immune response (e.g., systemically or in the tumor microenvironment) by at least 10% (e.g., 10%, 20%, 30%, 40%, 50%, 60%, 70%, 80%, 90%, 100%, or 200%). For example, modulation of a tumor-mediated immunosuppressive mechanism may result in an increase in an immunostimulatory and/or anti-tumor immune response by at least 20%, at least 30%, at least 40%, at least 50%, at least 60%, at least 70%, at least 80%, at least 90%, at least 100%. In some embodiments, modulation of a tumor-mediated immunosuppressive mechanism results in an increase in an immunostimulatory and/or anti-tumor immune response 10-20%, 10-30%, 10-40%, 10-50%, 10-60%, 10-70%, 10-80%, 10-90%, 10-100%, 10-200%, 20-30%, 20-40%, 20-50%, 20-60%, 20-70%, 20-80%, 20-90%, 20-100%, 20-200%, 50-60%, 50-70%, 50-80%, 50-90%, 50-100%, or 50-200%. It should be understood that "an increase" in an immunostimulatory and/or anti-tumor immune response, for example, systemically or in a tumor microenvironment, is relative to the immunostimulatory and/or anti-tumor immune response that would otherwise occur, in the absence of the effector molecule(s).

In some embodiments, modulation of a tumor-mediated immunosuppressive mechanism by at least one effector molecule results in an increase in an immunostimulatory and/or anti-tumor immune response (e.g., systemically or in the tumor microenvironment) by at least 2 fold (e.g., 2, 3, 4, 5, 10, 25, 20, 25, 50, or 100 fold). For example, modulation of a tumor-mediated immunosuppressive mechanism may result in an increase in an immunostimulatory and/or anti-tumor immune response by at least 3 fold, at least 5 fold, at least 10 fold, at least 20 fold, at least 50 fold, or at least 100 fold. In some embodiments, modulation of a tumor-mediated immunosuppressive mechanism results in an increase in an immunostimulatory and/or anti-tumor immune response by 2-10, 2-20, 2-30, 2-40, 2-50, 2-60, 2-70, 2-80, 2-90, or 2-100 fold.

Non-limiting examples of immunostimulatory and/or anti-tumor immune mechanisms include T cell signaling, activity and/or recruitment, antigen presentation and/or processing, natural killer cell-mediated cytotoxic signaling, activity and/or recruitment, dendritic cell differentiation and/or maturation, immune cell recruitment, pro-inflammatory macrophage signaling, activity and/or recruitment, stroma degradation, immunostimulatory metabolite production, stimulator of interferon genes (STING) signaling (which increases the secretion of IFN and Th1 polarization, promoting an anti-tumor immune response), and/or Type I interferon signaling. An effector molecule may stimulate at least one (one or more) of the foregoing immunostimulatory mechanisms, thus resulting in an increase in an immunostimulatory response. Changes in the foregoing immunostimulatory and/or anti-tumor immune mechanisms may be assessed, for example, using in vitro assays for T cell proliferation or cytotoxicity, in vitro antigen presentation assays, expression assays (e.g., of particular markers), and/ or cell secretion assays (e.g., of cytokines).

In some embodiments, modulation of a tumor-mediated immunosuppressive mechanism by at least one effector molecule results in a decrease in an immunosuppressive response (e.g., systemically or in the tumor microenvironment) by at least 10% (e.g., 10%, 20%, 30%, 40%, 50%, 60%, 70%, 80%, 90%, 100%, or 200%). For example, modulation of a tumor-mediated immunosuppressive mechanism may result in a decrease in an immunosuppressive response by at least 20%, at least 30%, at least 40%, at least 50%, at least 60%, at least 70%, at least 80%, at least 90%, at least 100%. In some embodiments, modulation of a tumor-mediated immunosuppressive mechanism results in a decrease in an immunosuppressive response 10-20%, 10-30%, 10-40%, 10-50%, 10-60%, 10-70%, 10-80%, 10-90%, 10-100%, 10-200%, 20-30%, 20-40%, 20-50%, 20-60%, 20-70%, 20-80%, 20-90%, 20-100%, 20-200%, 50-60%, 50-70%, 50-80%, 50-90%, 50-100%, or 50-200%. It should be understood that "a decrease" in an immunosuppressive response, for example, systemically or in a tumor microenvironment, is relative to the immunosuppressive response that would otherwise occur, in the absence of the effector molecule(s).

In some embodiments, modulation of a tumor-mediated immunosuppressive mechanism by at least one effector molecule results in a decrease in an immunosuppressive response (e.g., systemically or in the tumor microenvironment) by at least 2 fold (e.g., 2, 3, 4, 5, 10, 25, 20, 25, 50, or 100 fold). For example, modulation of a tumor-mediated immunosuppressive mechanism may result in a decrease in an immunosuppressive response by at least 3 fold, at least 5 fold, at least 10 fold, at least 20 fold, at least 50 fold, or at least 100 fold. In some embodiments, modulation of a tumor-mediated immunosuppressive mechanism results in a decrease in an immunosuppressive response by 2-10, 2-20, 2-30, 2-40, 2-50, 2-60, 2-70, 2-80, 2-90, or 2-100 fold.

Non-limiting examples of immunosuppressive mechanisms include negative costimulatory signaling, pro-apoptotic signaling of cytotoxic cells (e.g., T cells and/or NK cells), T regulatory (Treg) cell signaling, tumor checkpoint molecule production/maintenance, myeloid-derived suppressor cell signaling, activity and/or recruitment, immunosuppressive factor/metabolite production, and/or vascular endothelial growth factor signaling. An effector molecule may inhibit at least one (one or more) of the foregoing immunosuppressive mechanisms, thus resulting in a decrease in an immunosuppressive response. Changes in the foregoing immunosuppressive mechanisms may be assessed, for example, by assaying for an increase in T cell proliferation and/or an increase in IFNγ production (negative co-stimulatory signaling, $T_{reg}$ cell signaling and/or MDSC); Annexin V/PI flow staining (pro-apoptotic signaling); flow staining for expression, e.g., PDL1 expression (tumor checkpoint molecule production/maintenance); ELISA, LUMINEX®, RNA via qPCR, enzymatic assays, e.g., IDO tryptophan catabolism (immunosuppressive factor/metabolite production); and phosphorylation of PI3K, Akt, p38 (VEGF signaling).

In some embodiments, cells, such as MSCs, are engineered to express membrane-tethered anti-CD3 and/or anti-CD28 agonist extracellular domains.

In some embodiments, cells, such as MSCs, are engineered to produce at least two (e.g., 2, 3, 4, 5, 6, 7, 8, 9, 10 or more) effector molecules, each of which modulates a different tumor-mediated immunosuppressive mechanism. In other embodiments, cells are engineered to produce at least one effector molecule that is not natively produced by the cells. Such an effector molecule may, for example, complement the function of effector molecules natively produced by the cells In some embodiments, effector molecules function additively: the effect of two effector molecules, for example, may be equal to the sum of the effect of the two effector molecules functioning separately. In other embodiments, effector molecules function synergistically: the effect of two effector molecules, for example, may be greater than the combined function of the two effector molecules. The present disclosure also encompasses additivity and synergy between an effector molecule(s) and the immune cell (e.g., MSC) from which they are produced.

Effector molecules that modulate tumor-mediated immunosuppressive mechanisms and/or modify tumor microenvironments may be, for example, secreted factors (e.g., cytokines, chemokines, antibodies, and/or decoy receptors that modulate extracellular mechanisms involved in the immune system), inhibitors (e.g., antibodies, antibody fragments, ligand TRAP and/or small blocking peptides), intracellular factors that control cell state (e.g., microRNAs and/or transcription factors that modulate the state of cells to enhance pro-inflammatory properties), factors packaged into exosomes (e.g., microRNAs, cytosolic factors, and/or extracellular factors), surface displayed factors (e.g., checkpoint inhibitors, TRAIL), and and/or metabolic genes (e.g., enzymes that produce/modulate or degrade metabolites or amino acids).

In some embodiments, effector molecules may be selected from the following non-limiting classes of molecules: cytokines, antibodies, chemokines, nucleotides, peptides, and enzymes. Non-limiting examples of the foregoing classes of effector molecules are listed in Table 1 and specific sequences encoding exemplary effector molecules are listed in Table 6. Effector molecules can be human, such as those listed in Table 1 or Table 6 or human equivalents of murine effector molecules listed in Table 1 or Table 6. Effector molecules can be human-derived, such as the endogenous human effector molecule or an effector molecule modified and/or optimized for function, e.g., codon optimized to improve expression, modified to improve stability, or modified at its signal sequence (see below). Various programs and algorithms for optimizing function are known to those skilled in the art and can be selected based on the improvement desired, such as codon optimization for a specific species (e.g., human, mouse, bacteria, etc.).

TABLE 1

Exemplary Effector Molecules

| Effector name | Category | Function |
|---|---|---|
| anti-CD40 or CD40 Ligand | Agonist antibody | Stimulates B-cells and antigen presenting cells. |
| Flt3L | Ligand agonist | Stimulates myeloid cells and antigen presenting cells |
| CXCL10-11 fusion | Chemokine | Attracts T-cells |
| TGFb blocking peptides | Antagonist peptides | Inhibit TGFb pathway, TME modifier |
| Adenosine deaminase (ADA) | TME modifier | Degradation of suppressive adenosine in the TME |
| Kyneurinase | TME modifier | Degradation of kyneurine |
| HPGE2 | TME modifier | Degradation of PGE2 |
| CXCL13 | Chemokine | Attracts B-cells |
| anti PD-1/PD-L1 | Agonist antibody | Remove checkpoint |
| anti-CTLA-4 | Agonist antibody | Remove checkpoint |
| anti-VEGF | Antagonist antibody | Neutralizes an immunosuppressive/angiogenesis factor |
| anti-TNFa | Antagonist antibody | Neutralizes cytokine/pro-tumor factor |
| anti-IL-10 | Antagonist antibody | Neutralizes immunosuppressive cytokine |
| anti-SDF1/CXCL12 | Antagonist antibody | Neutralizes pro-tumor chemokine |
| (TβRII)2 trap | Capture trap | Neutralizes an immunosuppressive cytokine |
| CCL21 | Chemokine | Attracts leukocytes/NK |
| CCL1 | Chemokine | Attracts leukocytes/NK |
| CCL17 | Chemokine | Attracts leukocytes/NK |
| CCL19 | Chemokine | Attracts leukocytes/NK |
| CCL21 | Chemokine | Attracts leukocytes/NK |
| CCL20 | Chemokine | Attracts leukocytes/NK |
| CCL21a | Chemokine | Attracts leukocytes/NK |
| MIP1b (CCL5) | Chemokine | Attracts leukocytes/NK |
| CXCL10 | Chemokine | Attracts leukocytes/NK |
| CXCL11 | Chemokine | Attracts leukocytes/NK |
| CCL2 | Chemokine | Attracts monocytes |
| MIP-1alpha (CCL3) | Chemokine | Attracts leukocytes/NK |
| XCL1 | Chemokine | Attracts leukocytes/NK |
| IFNbeta | Cytokine | T cell response, tumor cell killing |
| IFNgamma | Cytokine | T cell response, tumor cell killing |
| IL-12 | Cytokine | T cells, NK cells |
| IL-1beta | Cytokine | T cells, NK cells |
| IL-15 | Cytokine | Stimulates T-cells and NK |
| IL-2 | Cytokine | Stimulates T-cells and NK |
| IL-21 | Cytokine | Stimulates T-cells |
| IL-24 | Cytokine | Stimulates T-cells |
| IL36-gamma | Cytokine | Stimulates T-cells |
| IL-7 | Cytokine | Stimulates T-cells |
| IL-22 | Cytokine | Stimulates T-cells |
| IL-18 | Cytokine | Stimulates T-cells |
| Granzymes/Perforin | Enzyme | Direct tumor cell killing |
| OX86 (anti-OX40) | ligand | Stimulates T-cells |
| anti-TGFbeta | Neutralizing antibody | Neutralizes an Immunosuppressive cytokine |
| TRAIL | Receptor/ligand | Direct tumor cell killing |
| FASL (CD49L) | Receptor/ligand | Direct tumor cell killing |
| OX40-L | Receptor/Ligand | Stimulates T-cells |
| cGAS | secreted molecule | Stimulates antigen-presenting cells |
| 41BBL | secreted molecule | Co-activation of T-cells |
| CD40L | secreted molecule | Stimulates T-cells |
| GM-CSF | secreted molecule | Growth factor for monocytes |
| STING | secreted molecule | Stimulates antigen-presenting cells |
| HAC-V 'microbody'_PD1 | Antagonist antibody | inhibits checkpoint |
| yCD | Pro-drug | Converts to cytotoxic molecule upon activation |
| CpG/Nucleotides | Nucleotides | STING agonist |

In some embodiments, cells, such as MSCs, comprise an engineered nucleic acid that comprises a promoter operably linked to a nucleotide sequence encoding an effector molecule. In some embodiments, an engineered nucleic acid comprises a promoter operably linked to a nucleotide sequence encoding at least 2 effector molecules. For example, the engineered nucleic acid may comprise a promoter operably linked to a nucleotide sequence encoding at least 3, at least 4, at least 5, at least 6, at least 7, at least 8, at least 8, at least 9, or at least 10 effector molecules. In some embodiments, an engineered nucleic acid comprises a promoter operably linked to a nucleotide sequence encoding 1, 2, 3, 4, 5, 6, 7, 8, 9, 10, or more effector molecules.

Engineered cells, such as engineered MSCs, in some embodiments, are engineered to include at least two engineered nucleic acids, each comprising a promoter operably linked to a nucleotide sequence encoding at least one (e.g., 1, 2 or 3) effector molecule. For example, the cells may be engineered to comprise at least 2, at least 3, at least 4, at least 5, at least 6, at least 7, at least 8, at least 8, at least 9, or at least 10, engineered nucleic acids, each comprising a promoter operably linked to a nucleotide sequence encoding at least one (e.g., 1, 2 or 3) effector molecule. In some embodiments, the cells are engineered to comprise 2, 3, 4, 5, 6, 7, 8, 9, 10, or more engineered nucleic acids, each comprising a promoter operably linked to a nucleotide sequence encoding at least one (e.g., 1, 2 or 3) effector molecule.

An "engineered nucleic acid" is a nucleic acid that does not occur in nature. It should be understood, however, that while an engineered nucleic acid as a whole is not naturally-occurring, it may include nucleotide sequences that occur in nature. In some embodiments, an engineered nucleic acid comprises nucleotide sequences from different organisms (e.g., from different species). For example, in some embodiments, an engineered nucleic acid includes a murine nucleotide sequence, a bacterial nucleotide sequence, a human nucleotide sequence, and/or a viral nucleotide sequence. The term "engineered nucleic acids" includes recombinant nucleic acids and synthetic nucleic acids. A "recombinant nucleic acid" refers to a molecule that is constructed by joining nucleic acid molecules and, in some embodiments, can replicate in a live cell. A "synthetic nucleic acid" refers to a molecule that is amplified or chemically, or by other means, synthesized. Synthetic nucleic acids include those that are chemically modified, or otherwise modified, but can base pair with naturally-occurring nucleic acid molecules. Recombinant nucleic acids and synthetic nucleic acids also include those molecules that result from the replication of either of the foregoing. Engineered nucleic acid of the present disclosure may be encoded by a single molecule (e.g., included in the same plasmid or other vector) or by multiple different molecules (e.g., multiple different independently-replicating molecules).

Engineered nucleic acid of the present disclosure may be produced using standard molecular biology methods (see, e.g., Green and Sambrook, Molecular Cloning, A Laboratory Manual, 2012, Cold Spring Harbor Press). In some embodiments, engineered nucleic acid constructs are produced using GIBSON ASSEMBLY® Cloning (see, e.g., Gibson, D. G. et al. Nature Methods, 343-345, 2009; and Gibson, D. G. et al. Nature Methods, 901-903, 2010, each of which is incorporated by reference herein). GIBSON ASSEMBLY® typically uses three enzymatic activities in a single-tube reaction: 5' exonuclease, the 'Y extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies. In some embodiments, engineered nucleic acid constructs are produced using IN-FUSION® cloning (Clontech).

A "promoter" refers to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, repressible, tissue-specific or any combination thereof. A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. Such a promoter can be referred to as "endogenous." In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see, e.g., U.S. Pat. Nos. 4,683,202 and 5,928,906).

Promoters of an engineered nucleic acid may be "inducible promoters," which refer to promoters that are characterized by regulating (e.g., initiating or activating) transcriptional activity when in the presence of, influenced by or contacted by a signal. The signal may be endogenous or a normally exogenous condition (e.g., light), compound (e.g., chemical or non-chemical compound) or protein (e.g., cytokine) that contacts an inducible promoter in such a way as to be active in regulating transcriptional activity from the inducible promoter. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter.

A promoter is "responsive to" or "modulated by" a local tumor state (e.g., inflammation or hypoxia) or signal if in the presence of that state or signal, transcription from the promoter is activated, deactivated, increased, or decreased. In some embodiments, the promoter comprises a response element. A "response element" is a short sequence of DNA within a promoter region that binds specific molecules (e.g., transcription factors) that modulate (regulate) gene expression from the promoter. Response elements that may be used in accordance with the present disclosure include, without limitation, a phloretin-adjustable control element (PEACE), a zinc-finger DNA-binding domain (DBD), an interferon-gamma-activated sequence (GAS) (Decker, T. et al. *J Interferon Cytokine Res.* 1997 March; 17(3):121-34, incorporated herein by reference), an interferon-stimulated response element (ISRE) (Han, K. J. et al. *J Biol Chem.* 2004 Apr. 9; 279(15):15652-61, incorporated herein by reference), a NF-kappaB response element (Wang, V. et al. Cell Reports. 2012; 2(4): 824-839, incorporated herein by reference), and a STAT3 response element (Zhang, D. et al. *J of Biol Chem.* 1996; 271: 9503-9509, incorporated herein by reference). Other response elements are encompassed herein. Response elements can also contain tandem repeats (e.g., consecutive repeats of the same nucleotide sequence encoding the response element) to generally increase sensitivity of the response element to its cognate binding molecule. Tandem repeats can be labeled 2×, 3×, 4×, 5×, etc. to denote the number of repeats present.

Non-limiting examples of responsive promoters (also referred to as "inducible promoters") (e.g., TGF-beta responsive promoters) are listed in Table 2, which shows the design of the promoter and transcription factor, as well as the effect of the inducer molecule towards the transcription factor (TF) and transgene transcription (T) is shown (B, binding; D, dissociation; n.d., not determined) (A, activation; DA, deactivation; DR, derepression) (see Horner, M. & Weber, W. *FEBS Letters* 586 (2012) 20784-2096m, and references cited therein). Other non-limiting examples of inducible promoters include those presented in Table 3.

TABLE 2

Examples of Responsive Promoters.

| System | Promoter and operator | Transcription factor (TF) | Inducer molecule | Response to inducer TF | T |
|---|---|---|---|---|---|
| Transcriptional activator-responsive promoters | | | | | |
| AIR | PAIR (OalcA-PhCMVmin) | AlcR | Acetaldehyde | n.d. | A |
| ART | PART (OARG-PhCMVmin) | ArgR-VP16 | 1-Arginine | B | A |
| BIT | PBIT3 (OBirA3-PhCMVmin) | BIT (BirA-VP16) | Biotin | B | A |
| Cumate-activator | PCR5 (OCuO6-PhCMVmin) | cTA (CymR-VP16) | Cumate | D | DA |

TABLE 2-continued

Examples of Responsive Promoters.

| System | Promoter and operator | Transcription factor (TF) | Inducer molecule | Response to inducer TF | Response to inducer T |
|---|---|---|---|---|---|
| Cumate-reverse activator | PCR5 (OCuO6-PhCMVmin) | rcTA (rCymR-VP16) | Cumate | B | A |
| E-OFF | PETR (OETR-PhCMVmin) | ET (E-VP16) | Erythromycin | D | DA |
| NICE-OFF | PNIC (ONIC-PhCMVmin) | NT (HdnoR-VP16) | 6-Hydroxy-nicotine | D | DA |
| PEACE | PTtgR1 (OTtgR-PhCMVmin) | TtgA1 (TtgR-VP16) | Phloretin | D | DA |
| PIP-OFF | PPIR (OPIR-Phsp70min) | PIT (PIP-VP16) | Pristinamycin I | D | DA |
| QuoRex | PSCA (OscbR-PhCMVmin)PSPA (OpapRI-PhCMVmin) | SCA (ScbR-VP16) | SCB1 | D | DA |
| Redox | PROP (OROP-PhCMVmin) | REDOX (REX-VP16) | NADH | D | DA |
| TET-OFF | PhCMV*-1 (OtetO7-PhCMVmin) | tTA (TetR-VP16) | Tetracycline | D | DA |
| TET-ON | PhCMV*-1 (OtetO7-PhCMVmin) | rtTA (rTetR-VP16) | Doxycycline | B | A |
| TIGR | PCTA (OrheO-PhCMVmin) | CTA (RheA-VP16) | Heat | D | DA |
| TraR | O7x(tra box)-PhCMVmin | p65-TraR | 3-Oxo-C8-HSL | B | A |
| VAC-OFF | P1VanO2 (OVanO2-PhCMVmin) | VanA1 (VanR-VP16) | Vanillic acid | D | DA |
| Transcriptional repressor-responsive promoters | | | | | |
| Cumate-repressor | PCuO (PCMV5-OCuO) | CymR | Cumate | D | DR |
| E-ON | PETRON8 (PSV40-OETR8) | E-KRAB | Erythromycin | D | DR |
| NICE-ON | PNIC (PSV40-ONIC8) | NS (HdnoR-KRAB) | 6-Hydroxy-nicotine | D | DR |
| PIP-ON | PPIRON (PSV40-OPIR3) | PIT3 (PIP-KRAB) | Pristinamycin I | D | DR |
| Q-ON | PSCAON8 (PSV40-OscbR8) | SCS (ScbR-KRAB) | SCB1 | D | DR |
| TET-ON<comma> repressor-based | OtetO-PHPRT | tTS-H4 (TetR-HDAC4) | Doxycycline | D | DR |
| T-REX | PTetO (PhCMV-OtetO2) | TetR | Tetracycline | D | DR |
| UREX | PUREX8 (PSV40-OhucO8) | mUTS (KRAB-HucR) | Uric acid | D | DR |
| VAC-ON | PVanON8 (PhCMV-OVanO8) | VanA4 (VanR-KRAB) | Vanillic acid | D | DR |
| Hybrid promoters | | | | | |
| QuoRexPIP-ON(NOT IF gate) | OscbR8-OPIR3-PhCMVmin | SCAPIT3 | SCB1Pristinamycin I | DD | DADR |
| QuoRexE-ON(NOT IF gate) | OscbR-OETR8-PhCMVmin | SCAE-KRAB | SCB1Erythromycin | DD | DADR |
| TET-OFFE-ON(NQT IF gate) | OtetO7-OETR8-PhCMVmin | tTAE-KRAB | TetracyclineErythromycin | DD | DADR |
| TET-OFFPIP-ONE-ON | OtetO7-OPIR3-OETR8-PhCMVmin | tTAPIT3E-KRAB | TetracyclinePristinamycin IErythromycin | DDD | DADRDR |

TABLE 3

Exemplary Inducible Promoters

| Name | DNA SEQUENCE | Source |
|---|---|---|
| minimal promoter; minP | AGAGGGTATATAATGGAAGCTCGACTTCCAG (SEQ ID NO: 1) | EU581860.1 (Promega) |
| NFkB response element protein promoter; 5x NFkB-RE | GGGAATTTCCGGGGACTTTCCGGGAATTTCCGGGGACTTTCCGGGAATTTCC (SEQ ID NO: 2) | EU581860.1 (Promega) |

TABLE 3-continued

Exemplary Inducible Promoters

| Name | DNA SEQUENCE | Source |
|---|---|---|
| CREB response element protein promoter; 4x CRE | CACCAGACAGTGACGTCAGCTGCCAGA TCCCATGGCCGTCATACTGTGACGTCTT TCAGACACCCCATTGACGTCAATGGGA GAA (SEQ ID NO: 3) | DQ904461.1 (Promega) |
| NFAT response element protein promoter; 3x NFAT binding sites | GGAGGAAAAACTGTTTCATACAGAAGG CGTGGAGGAAAAACTGTTTCATACAGA AGGCGTGGAGGAAAAACTGTTTCATAC AGAAGGCGT (SEQ ID NO: 4) | DQ904462.1 (Promega) |
| SRF response element protein promoter; 5x SRE | AGGATGTCCATATTAGGACATCTAGGA TGTCCATATTAGGACATCTAGGATGTC CATATTAGGACATCTAGGATGTCCATA TTAGGACATCTAGGATGTCCATATTAG GACATCT (SEQ ID NO: 5) | FJ773212.1 (Promega) |
| SRF response element protein promoter 2; 5x SRF-RE | AGTATGTCCATATTAGGACATCTACCA TGTCCATATTAGGACATCTACTATGTCC ATATTAGGACATCTTGTATGTCCATATT AGGACATCTAAAATGTCCATATTAGGA CATCT (SEQ ID NO: 6) | FJ773213.1 (Promega) |
| AP1 response element protein promoter; 6x API-RE | TGAGTCAGTGACTCAGTGAGTCAGTGA CTCAGTGAGTCAGTGACTCAG (SEQ ID NO: 7) | JQ858516.1 (Promega) |
| TCF-LEF response element protein promoter; 8x TCF-LEF-RE | AGATCAAAGGGTTTAAGATCAAAGGGC TTAAGATCAAAGGGTATAAGATCAAAG GGCCTAAGATCAAAGGGACTAAGATCA AAGGGTTTAAGATCAAAGGGCTTAAGA TCAAAGGGCCTA (SEQ ID NO: 8) | JX099537.1 (Promega) |
| SBEx4 | GTCTAGACGTCTAGACGTCTAGACGTC TAGAC (SEQ ID NO: 9) | Addgene Cat No: 16495 |
| SMAD2/3-CAGACA x4 | CAGACACAGACACAGACACAGACA (SEQ ID NO: 10) | Jonk et al. (J Biol Chem. 1998 August 14;273(33):21145-52. |
| STAT3 binding site | Ggatccggtactcgagatctgcgatctaagtaagcttggcattc cggtactgttggtaaagccac (SEQ ID NO: 11) | Addgene Sequencing Result #211335 |

Other non-limiting examples of promoters include the cytomegalovirus (CMV) promoter, the elongation factor 1-alpha (EF1a) promoter, the elongation factor (EFS) promoter, the MND promoter (a synthetic promoter that contains the U3 region of a modified MoMuLV LTR with myeloproliferative sarcoma virus enhancer), the phosphoglycerate kinase (PGK) promoter, the spleen focus-forming virus (SFFV) promoter, the simian virus 40 (SV40) promoter, and the ubiquitin C (UbC) promoter (see Table 4).

TABLE 4

Exemplary Constitutive Promoters

| Name | DNA SEQUENCE |
|---|---|
| CMV | GTTGACATTGATTATTGACTAGTTATTAATAGTAATCAATTACGGGGTCATT AGTTCATAGCCCATATATGGAGTTCCGCGTTACATAACTTACGGTAAATGG CCCGCCTGGCTGACCGCCCAACGACCCCCGCCCATTGACGTCAATAATGAC GTATGTTCCCATAGTAACGCCAATAGGGACTTTCCATTGACGTCAATGGGT GGAGTATTTACGGTAAACTGCCCACTTGGCAGTACATCAAGTGTATCATAT GCCAAGTACGCCCCCTATTGACGTCAATGACGGTAAATGGCCCGCCTGGCA TTATGCCCAGTACATGACCTTATGGGACTTTCCTACTTGGCAGTACATCTAC GTATTAGTCATCGCTATTACCATGGTGATGCGGTTTTGGCAGTACATCAATG GGCGTGGATAGCGGTTTGACTCACGGGGATTTCCAAGTCTCCACCCCATTG ACGTCAATGGGAGTTTGTTTTGGCACCAAAATCAACGGGACTTTCCAAAAT GTCGTAACAACTCCGCCCCATTGACGCAAATGGGCGGTAGGCGTGTACGGT GGGAGGTCTATATAAGCAGAGCTC (SEQ ID NO: 12) |
| EF1a | GGCTCCGGTGCCCGTCAGTGGGCAGAGCGCACATCGCCCACAGTCCCCGA GAAGTTGGGGGGAGGGGTCGGCAATTGAACCGGTGCCTAGAGAAGGTGGC GCGGGGTAAACTGGGAAAGTGATGCCGTGTACTGGCTCCGCCTTTTTCCCG AGGGTGGGGGAGAACCGTATATAAGTGCAGTAGTCGCCGTGAACGTTCTTT TTCGCAACGGGTTTGCCGCCAGAACACAGGTAAGTGCCGTGTGTGGTTCCC |

TABLE 4-continued

Exemplary Constitutive Promoters

| Name | DNA SEQUENCE |
|---|---|
| | GCGGGCCTGGCCTCTTTACGGGTTATGGCCCTTGCGTGCCTTGAATTACTTC<br>CACCTGGCTGCAGTACGTGATTCTTGATCCCGAGCTTCGGGTTGGAAGTGG<br>GTGGGAGAGTTCGAGGCCTTGCGCTTAAGGAGCCCCTTCGCCTCGTGCTTG<br>AGTTGAGGCCTGGCCTGGGCGCTGGGGCCGCCGCGTGCGAATCTGGTGGC<br>ACCTTCGCGCCTGTCTCGCTGCTTTCGATAAGTCTCTAGCCATTTAAAATTT<br>TTGATGACCTGCTGCGACGCTTTTTTTCTGGCAAGATAGTCTTGTAAATGCG<br>GGCCAAGATCTGCACACTGGTATTTCGGTTTTTGGGGCCGCGGGCGGCGAC<br>GGGGCCCGTGCGTCCCAGCGCACATGTTCGGCGAGGCGGGGCCTGCGAGC<br>GCGACCACCGAGAATCGGACGGGGGTAGTCTCAAGCTGGCCGGCCTGCTC<br>TGGTGCCTGTCCTCGCGCCGCCGTGTATCGCCCCGCCCCGGGCGGCAAGGC<br>TGGCCCGGTCGGCACCAGTTGCGTGAGCGGAAAGATGGCCGCTTCCCGGTC<br>CTGCTGCAGGGAGCTCAAAATGGAGGACGCGGCGCTCGGGAGAGCGGGCG<br>GGTGAGTCACCCACACAAAGGAAAAGGGCCTTTCCGTCCTCAGCCGTCGCT<br>TCATGTGACTCCACGGAGTACCGGGCGCCGTCCAGGCACCTCGATTAGTTC<br>TCGAGCTTTTGGAGTACGTCGTCTTTAGGTTGGGGGGAGGGGTTTTATGCG<br>ATGGAGTTTCCCCACACTGAGTGGGTGGAGACTGAAGTTAGGCCAGCTTGG<br>CACTTGATGTAATTCTCCTTGGAATTTGCCCTTTTTGAGTTTGGATCTTGGT<br>TCATTCTCAAGCCTCAGACAGTGGTTCAAAGTTTTTTTCTTCCATTTCAGGT<br>GTCGTGA (SEQ ID NO: 13) |
| EFS | GGATCTGCGATCGCTCCGGTGCCCGTCAGTGGGCAGAGCGCACATCGCCCA<br>CAGTCCCCGAGAAGTTGGGGGGAGGGGTCGGCAATTGAACCGGTGCCTAG<br>AGAAGGTGGCGCGGGGTAAACTGGGAAAGTGATGTCGTGTACTGGCTCCG<br>CCTTTTTCCCGAGGGTGGGGGAGAACCGTATATAAGTGCAGTAGTCGCCGT<br>GAACGTTCTTTTTCGCAACGGGTTTGCCGCCAGAACACAGCTGAAGCTTCG<br>AGGGGCTCGCATCTCTCCTTCACGCGCCCGCCGCCCTACCTGAGGCCGCCA<br>TCCACGCCGGTTGAGTCGCGTTCTGCCGCCTCCCGCCTGTGGTGCCTCCTGA<br>ACTGCGTCCGCCGTCTAGGTAAGTTTAAAGCTCAGGTCGAGACCGGGCCTT<br>TGTCCGGCGCTCCCTTGGAGCCTACCTAGACTCAGCCGGCTCTCCACGCTTT<br>GCCTGACCCTGCTTGCTCAACTCTACGTCTTTGTTTCGTTTTCTGTTCTGCGC<br>CGTTACAGATCCAAGCTGTGACCGGCGCCTAC (SEQ ID NO: 14) |
| MND | TTTATTTAGTCTCCAGAAAAAGGGGGGAATGAAAGACCCCACCTGTAGGTT<br>TGGCAAGCTAGGATCAAGGTTAGGAACAGAGAGACAGCAGAATATGGGCC<br>AAACAGGATATCTGTGGTAAGCAGTTCCTGCCCCGGCTCAGGGCCAAGAA<br>CAGTTGGAACAGCAGAATATGGGCCAAACAGGATATCTGTGGTAAGCAGT<br>TCCTGCCCCGGCTCAGGGCCAAGAACAGATGGTCCCCAGATGCGGTCCCGC<br>CCTCAGCAGTTTCTAGAGAACCATCAGATGTTTCCAGGGTGCCCCAAGGAC<br>CTGAAATGACCCTGTGCCTTATTTGAACTAACCAATCAGTTCGCTTCTCGCT<br>TCTGTTCGCGCGCTTCTGCTCCCCGAGCTCAATAAAAGAGCCCA (SEQ ID<br>NO: 15) |
| PGK | GGGGTTGGGGTTGCGCCTTTTCCAAGGCAGCCCTGGGTTTGCGCAGGGACG<br>CGGCTGCTCTGGGCGTGGTTCCGGGAAACGCAGCGGCGCCGACCCTGGGT<br>CTCGCACATTCTTCACGTCCGTTCGCAGCGTCACCCGGATCTTCGCCGCTAC<br>CCTTGTGGGCCCCCCGGCGACGCTTCCTGCTCCGCCCCTAAGTCGGGAAGG<br>TTCCTTGCGGTTCGCGGCGTGCCGGACGTGACAAACGGAAGCCGCACGTCT<br>CACTAGTACCCTCGCAGACGGACAGCGCCAGGGAGCAATGGCAGCGCGCC<br>GACCGCGATGGGCTGTGGCCAATAGCGGCTGCTCAGCGGGGCGCGCCGAG<br>AGCAGCGGCCGGGAAGGGGCGGTGCGGGAGGCGGGGTGTGGGCGGTAG<br>TGTGGGCCCTGTTCCTGCCCGCGCGGTGTTCCGCATTCTGCAAGCCTCCGG<br>AGCGCACGTCGGCAGTCGGCTCCCTCGTTGACCGAATCACCGACCTCTCTC<br>CCCAG (SEQ ID NO: 16) |
| SFFV | GTAACGCCATTTTGCAAGGCATGGAAAAATACCAAACCAAGAATAGAGAA<br>GTTCAGATCAAGGGCGGGTACATGAAAATAGCTAACGTTGGGCCAAACAG<br>GATATCTGCGGTGAGCAGTTTCGGCCCCGGCCCGGGGCCAAGAACAGATG<br>GTCACCGCAGTTTCGGCCCCGGCCCGAGGCCAAGAACAGATGGTCCCCAG<br>ATATGGCCCAACCCTCAGCAGTTTCTTAAGACCCATCAGATGTTTCCAGGC<br>TCCCCCAAGGACCTGAAATGACCCTGCGCCTTATTTGAATTAACCAATCAG<br>CCTGCTTCTCGCTTCTGTTCGCGCGCTTCTGCTTCCCGAGCTCTATAAAAGA<br>GCTCACAACCCCTCACTCGGCGCGCCAGTCCTCCGACAGACTGAGTCGCCC<br>GGG (SEQ ID NO: 17) |
| SV40 | CTGTGGAATGTGTGTCAGTTAGGGTGTGGAAAGTCCCCAGGCTCCCCAGCA<br>GGCAGAAGTATGCAAAGCATGCATCTCAATTAGTCAGCAACCAGGTGTGG<br>AAAGTCCCCAGGCTCCCCAGCAGGCAGAAGTATGCAAAGCATGCATCTCA<br>ATTAGTCAGCAACCATAGTCCCGCCCCTAACTCCGCCCATCCCGCCCCTAA<br>CTCCGCCCAGTTCCGCCCATTCTCCGCCCCATGGCTGACTAATTTTTTTTAT<br>TTATGCAGAGGCCGAGGCCGCCTCTGCCTCTGAGCTATTCCAGAAGTAGTG<br>AGGAGGCTTTTTTGGAGGCCTAGGCTTTTGCAAAAAGCT (SEQ ID NO: 18) |
| UbC | GCGCCGGGTTTGGCGCCTCCCGCGGGCGCCCCCCTCCTCACGGCGAGCGC<br>TGCCACGTCAGACGAAGGGCGCAGGAGCGTTCCTGATCCTTCCGCCCGGAC<br>GCTCAGGACAGCGGCCCGCTGCTCATAAGACTCGGCCTTAGAACCCCAGTA<br>TCAGCAGAAGGACATTTTAGGACGGGACTTGGGTGACTCTAGGGCACTGG |

TABLE 4-continued

Exemplary Constitutive Promoters

| Name | DNA SEQUENCE |
|---|---|
| | TTTTCTTTCCAGAGAGCGGAACAGGCGAGGAAAAGTAGTCCCTTCTCGGCG
ATTCTGCGGAGGGATCTCCGTGGGGCGGTGAACGCCGATGATTATATAAG
GACGCGCCGGGTGTGGCACAGCTAGTTCCGTCGCAGCCGGGATTTGGGTCG
CGGTTCTTGTTTGTGGATCGCTGTGATCGTCACTTGGTGAGTTGCGGGCTGC
TGGGCTGGCCGGGGCTTTCGTGGCCGCCGGGCCGCTCGGTGGGACGGAAG
CGTGTGGAGAGACCGCCAAGGGCTGTAGTCTGGGTCCGCGAGCAAGGTTG
CCCTGAACTGGGGGTTGGGGGGAGCGCACAAAATGGCGGCTGTTCCCGAG
TCTTGAATGGAAGACGCTTGTAAGGCGGGCTGTGAGGTCGTTGAAACAAG
GTGGGGGGCATGGTGGGCGGCAAGAACCCAAGGTCTTGAGGCCTTCGCTA
ATGCGGGAAAGCTCTTATTCGGGTGAGATGGGCTGGGGCACCATCTGGGG
ACCCTGACGTGAAGTTTGTCACTGACTGGAGAACTCGGGTTTGTCGTCTGG
TTGCGGGGGCGGCAGTTATGCGGTGCCGTTGGGCAGTGCACCCGTACCTTT
GGGAGCGCGCGCCTCGTCGTGTCGTGACGTCACCCGTTCTGTTGGCTTATA
ATGCAGGGTGGGGCCACCTGCCGGTAGGTGTGCGGTAGGCTTTTCTCCGTC
GCAGGACGCAGGGTTCGGGCCTAGGGTAGGCTCTCCTGAATCGACAGGCG
CCGGACCTCTGGTGAGGGGAGGGATAAGTGAGGCGTCAGTTTCTTTGGTCG
GTTTTATGTACCTATCTTCTTAAGTAGCTGAAGCTCCGGTTTTGAACTATGC
GCTCGGGGTTGGCGAGTGTGTTTTGTGAAGTTTTTTAGGCACCTTTTGAAAT
GTAATCATTTGGGTCAATATGTAATTTTCAGTGTTAGACTAGTAAAGCTTCT
GCAGGTCGACTCTAGAAAATTGTCCGCTAAATTCTGGCCGTTTTGGCTTTT
TTGTTAGAC (SEQ ID NO: 19) |
| hEF1aV1 | GGCTCCGGTGCCCGTCAGTGGGCAGAGCGCACATCGCCCACAGTCCCC
GAGAAGTTGGGGGGAGGGGTCGGCAATTGAACCGGTGCCTAGAGAAGG
TGGCGCGGGGTAAACTGGGAAAGTGATGTCGTGTACTGGCTCCGCCTTT
TTCCCGAGGGTGGGGGAGAACCGTATATAAGTGCAGTAGTCGCCGTGAA
CGTTCTTTTTCGCAACGGGTTTGCCGCCAGAACACAGGTAAGTGCCGTGT
GTGGTTCCCGCGGGCCTGGCCTCTTTACGGGTTATGGCCCTTGCGTGCC
TTGAATTACTTCCACCTGGCTGCAGTACGTGATTCTTGATCCCGAGCTTC
GGGTTGGAAGTGGGTGGGAGAGTTCGAGGCCTTGCGCTTAAGGAGCCC
CTTCGCCTCGTGCTTGAGTTGAGGCCTGGCCTGGGCGCTGGGGCCGCC
GCGTGCGAATCTGGTGGCACCTTCGCGCCTGTCTCGCTGCTTTCGATAA
GTCTCTAGCCATTTAAAATTTTTGATGACCTGCTGCGACGCTTTTTTTCTG
GCAAGATAGTCTTGTAAATGCGGGCCAAGATCTGCACACTGGTATTTCGG
TTTTTGGGGCCGCGGGCGGCGACGGGGCCCGTGCGTCCCAGCGCACAT
GTTCGGCGAGGCGGGGCCTGCGAGCGCGGCCACCGAGAATCGGACGG
GGGTAGTCTCAAGCTGGCCGGCCTGCTCTGGTGCCTGGTCTCGCGCCG
CCGTGTATCGCCCCGCCCTGGGCGGCAAGGCTGGCCCGGTCGGCACCA
GTTGCGTGAGCGGAAAGATGGCCGCTTCCCGGCCCTGCTGCAGGGAGC
TCAAAATGGAGGACGCGGCGCTCGGGAGAGCGGGCGGGTGAGTCACCC
ACACAAAGGAAAAGGGCCTTTCCGTCCTCAGCCGTCGCTTCATGTGACTC
CACGGAGTACCGGGCGCCGTCCAGGCACCTCGATTAGTTCTCGAGCTTT
TGGAGTACGTCGTCTTTAGGTTGGGGGGAGGGGTTTTATGCGATGGAGT
TTCCCCACACTGAGTGGGTGGAGACTGAAGTTAGGCCAGCTTGGCACTT
GATGTAATTCTCCTTGGAATTTGCCCTTTTTGAGTTTGGATCTTGGTTCATT
CTCAAGCCTCAGACAGTGGTTCAAAGTTTTTTTCTTCCATTTCAGGTGTCG
TGA (SEQ ID NO: 20) |
| hCAGG | ACTAGTTATTAATAGTAATCAATTACGGGGTCATTAGTTCATAGCCCATAT
ATGGAGTTCCGCGTTACATAACTTACGGTAAATGGCCCGCCTGGCTGACC
GCCCAACGACCCCCGCCCATTGACGTCAATAATGACGTATGTTCCCATAG
TAACGCCAATAGGGACTTTCCATTGACGTCAATGGGTGGAGTATTTACGG
TAAACTGCCCACTTGGCAGTACATCAAGTGTATCATATGCCAAGTACGCC
CCCTATTGACGTCAATGACGGTAAATGGCCCGCCTGGCATTATGCCCAGT
ACATGACCTTATGGGACTTTCCTACTTGGCAGTACATCTACGTATTAGTCA
TCGCTATTACCATGGTCGAGGTGAGCCCCACGTTCTGCTTCACTCTCCCC
ATCTCCCCCCCCTCCCCACCCCCAATTTTGTATTTATTTATTTTTTAATTAT
TTTGTGCAGCGATGGGGGCGGGGGGGGGGGGGGGCGCGCGCCAGGC
GGGGCGGGCGGGGCGAGGGGCGGGGCGGGGCGAGGCGGAGAGGTG
CGGCGGCAGCCAATCAGAGCGGCGCGCTCCGAAAGTTTCCTTTTATGGC
GAGGCGGCGGCGGCGGCGGCCCTATAAAAAGCGAAGCGCGCGGCGGG
CGGGGAGTCGCTGCGACGCTGCCTTCGCCCCGTGCCCGCTCCGCCGC
CGCCTCGCGCCGCCCGCCCCGGCTCTGACTGACCGCGTTACTCCCACA
GGTGAGCGGGCGGGACGGCCCTTCTCCTCCGGGCTGTAATTAGCGCTTG
GTTTAATGACGGCTTGTTTCTTTTCTGTGGCTGCGTGAAAGCCTTGAGGG
GCTCCGGGAGGGCCCTTTGTGCGGGGGAGCGGCTCGGGGGTGCGT
GCGTGTGTGTGCGTGGGGAGCGCCGCGTGCGGCTCCGCGCTGCCCG
GCGGCTGTGAGCGCTGCGGGCGCGGCGCGGGGCTTTGTGCGCTCCGCA
GTGTGCGCGAGGGGAGCGCGGCCGGGGCGGTGCCCCGCGGTGCGGG
GGGGGCTGCGAGGGGAACAAAGGCTGCGTGCGGGGTGTGTGCGTGGG
GGGGTGAGCAGGGGGTGTGGGCGCGTCGGTCGGGCTGCAACCCCCCT
GCACCCCCCTCCCCGAGTTGCTGAGCACGGCCCGGCTTCGGGTGCGGG
GCTCCGTACGGGGCGTGGCGCGGGGCTCGCCGTGCCGGGCGGGGGT
GGCGGCAGGTGGGGGTGCCGGGCGGGGCGGGGCCGCCTCGGGCCGG
GGAGGGCTCGGGGAGGGGCGCGGCGGCCCCCGGAGCGCCGGCGGC
TGTCGAGGCGCGGCGAGCCGCAGCCATTGCCTTTTATGGTAATCGTGCG |

TABLE 4-continued

Exemplary Constitutive Promoters

| Name | DNA SEQUENCE |
|---|---|
| | AGAGGGCGCAGGGACTTCCTTTGTCCCAAATCTGTGCGGAGCCGAAATC<br>TGGGAGGCGCCGCCGCACCCCCTCTAGCGGGCGCGGGGCGAAGCGGT<br>GCGGCGCCGGCAGGAAGGAAATGGGCGGGGAGGGCCTTCGTGCGTCG<br>CCGCGCCGCCGTCCCCTTCTCCCTCTCCAGCCTCGGGGCTGTCCGCGG<br>GGGGACGGCTGCCTTCGGGGGGACGGGGCAGGGCGGGGTTCGGCTT<br>CTGGCGTGTGACCGGCGGCTCTAGAGCCTCTGCTAACCATGTTCATGCC<br>TTCTTCTTTTTCCTACAGCTCCTGGGCAACGTGCTGGTTATTGTGCTGTCT<br>CATCATTTTGGCAAAGAATTC (SEQ ID NO: 21) |
| hEF1aV2 | Gggcagagcgcacatcgcccacagtccccgagaagttgggggggaggggtcggcaattgaaccggtgcc<br>tagagaaggtggcgaggggtaaactgggaaagtgatgtcgtgtactggctccgccttttcccgagggtggg<br>ggagaaccgtatataagtgcagtagtcgccgtgaacgttcttttcgcaacgggtttgccgccagaacacag<br>(SEQ ID NO: 22) |
| hACTb | CCACTAGTTCCATGTCCTTATATGGACTCATCTTTGCCTATTGCGACACAC<br>ACTCAATGAACACCTACTACGCGCTGCAAAGAGCCCCGCAGGCCTGAGG<br>TGCCCCCACCTCACCACTCTTCCTATTTTTGTGTAAAAATCCAGCTTCTTG<br>TCACCACCTCCAAGGAGGGGGAGGAGGAGGAAGGCAGGTTCCTCTAGG<br>CTGAGCCGAATGCCCCTCTGTGGTCCCACGCCACTGATCGCTGCATGCC<br>CACCACCTGGGTACACACAGTCTGTGATTCCCGGAGCAGAACGGACCCT<br>GCCCACCCGGTCTTGTGTGCTACTCAGTGGACAGACCCAAGGCAAGAA<br>GGGTGACAAGGACAGGGTCTTCCCAGGCTGGCTTTGAGTTCCTAGCACC<br>GCCCCGCCCCAATCCTCTGTGGCACATGGAGTCTTGGTCCCCAGAGTC<br>CCCCAGCGGCCTCCAGATGGTCTGGGAGGGCAGTTCAGCTGTGGCTGC<br>GCATAGCAGACATACAACGGACGGTGGGCCCAGACCCAGGCTGTGTAGA<br>CCCAGCCCCCCGCCCCGCAGTGCCTAGGTCACCCACTAACGCCCCAG<br>GCCTGGTCTTGGCTGGGCGTGACTGTTACCCTCAAAAGCAGGCAGCTCC<br>AGGGTAAAAGGTGCCCTGCCCTGTAGAGCCCACCTTCCTTCCCAGGGCT<br>GCGGCTGGGTAGGTTTGTAGCCTTCATCACGGGCCACCTCCAGCCACTG<br>GACCGCTGGCCCCTGCCCTGTCCTGGGGAGTGTGGTCCTGCGACTTCTA<br>AGTGGCCGCAAGCCACCTGACTCCCCAACACCACACTCTACCTCTCAA<br>GCCCAGGTCTCTCCCTAGTGACCCACCCAGCACATTTAGCTAGCTGAGC<br>CCCACAGCCAGAGGTCCTCAGGCCCTGCTTTCAGGGCAGTTGCTCTGAA<br>GTCGGCAAGGGGGAGTGACTGCCTGGCCACTCCATGCCCTCCAAGAGCT<br>CCTTCTGCAGGAGCGTACAGAACCCAGGGCCCTGGCACCCGTGCAGACC<br>CTGGCCCACCCCACCTGGGCGCTCAGTGCCCAAGAGATGTCCACACCTA<br>GGATGTCCCGCGGTGGGTGGGGGGCCCGAGAGACGGGCAGGCCGGGG<br>GCAGGCCTGGCCATGCGGGGCCGAACCGGGCACTGCCCAGCGTGGGG<br>CGCGGGGGCCACGCGCGCGCCCCCAGCCCCGGGCCCAGCACCCCA<br>AGGCGGCCAACGCCAAAACTCTCCCTCCTCCTCTTCCTCAATCTCGCTCT<br>CGCTCTTTTTTTTTTCGCAAAAGGAGGGGAGAGGGGGTAAAAAAATGCT<br>GCACTGTGCGGCGAAGCCGGTGAGTGAGCGGCGCGGGGCCAATCAGCG<br>TGCGCCGTTCCGAAAGTTGCCTTTTATGGCTCGAGCGGCCGCGGCGGCG<br>CCCTATAAAACCCAGCGGCGCGACGCGCCACCACCGCCGAGACCGCGT<br>CCGCCCCGCGAGCACAGAGCCTCGCCTTTGCCGATCCGCCGCCCGTCC<br>ACACCCGCCGCCAGgtaagcccggccagccgaccggggcaggcggctcacggcccggccgc<br>aggcggccgcgccccttcgcccgtgcagagccgccgtctgggccgcagcgggggggcgcatggggggg<br>gaaccggaccgccgtgggggggcgcgggagaagcccctgggcctccggagatgggggacaccccacgc<br>cagttcggaggcgcgaggccgcgctcgggaggcgcgctccggggtgccgctctcggggcggggcaa<br>ccggcggggtctttgtctgagccgggctcttgccaatgggatcgcagggtgggcgcggcggagccccgc<br>caggcccggtgggggctggggcgccattgcgcgtgcgcgctggtccttgggcgctaactgcgtgcgcgctg<br>ggaattggcgctaattgcgcgtgcgcgctgggactcaaggcgctaactgcgcgtgcgttctggggcccggg<br>gtgccgcggcctgggctggggcgaaggcgggctcggccggaaggggtggggtcgccgcggctcccggg<br>cgcttgcgcgcacttcctgcccgagccgctggccgcccgagggtgtggccgctgcgtgcgcgcgcgcga<br>cccggcgctgtttgaaccgggcggaggcggggctggcgcccggttgggaggggggttggggcctggcttcct<br>gccgcgcgccgcggggacgcctccgaccagtgttttgccttttatggtaataacgcggccggcccggcttcctttt<br>gtccccaatctgggcgcgcgccggcgcccctggcggcctaaggactcggcgcgccggaagtggccagg<br>gcgggggcgacctcggctcacagcgcgcccggctat (SEQ ID NO: 23) |
| heIF4A1 | GTTGATTTCCTTCATCCCTGGCACACGTCCAGGCAGTGTCGAATCCATCT<br>CTGCTACAGGGGAAAACAAATAACATTTGAGTCCAGTGGAGACCGGGAG<br>CAGAAGTAAAGGGAAGTGATAACCCCCAGAGCCCGGAAGCCTCTGGAGG<br>CTGAGACCTCGCCCCCCTTGCGTGATAGGGCCTACGAGCCACATGACC<br>AAGGCACTGTCGCCTCCGCACGTGTGAGAGTGCAGGGCCCCAAGATGG<br>CTGCCAGGCCTCGAGGCCTGACTCTTCTATGTCACTTCCGTACCGGCGA<br>GAAAGGCGGGCCCTCCAGCCAATGAGGCTGCGGGCGGGCCTTCACCT<br>TGATAGGCACTCGAGTTATCCAATGGTGCCTGCGGGCCGGAGCGACTAG<br>GAACTAACGTCATGCCGAGTTGCTGAGCGCCGGCAGGCGGGGCCGGGG<br>CGGCCAAACCAATGCGATGGCCGGGCGGAGTCGGGCGCTCTATAAGTT<br>GTCGATAGGCGGGCACTCCGCCCTAGTTTCTAAGGACCATG (SEQ ID NO: 24) |
| hGAPDH | AGTTCCCCAACTTTCCCGCCTCTCAGCCTTTGAAAGAAAGAAAGGGGAGG<br>GGGCAGGCCGCGTGCAGTCGCGAGCGGTGCTGGGCTCCGGCTCCAATT<br>CCCCATCTCAGTCGCTCCCAAAGTGCTTCTGTTTCATCCAAGCGTGTAAG<br>GGTCCCCGTCCTTGACTCCCTAGTGTCCTGCTGCCCACAGTCCAGTCCT |

TABLE 4-continued

Exemplary Constitutive Promoters

| Name | DNA SEQUENCE |
|---|---|
| | GGGAACCAGCACCGATCACCTCCCATCGGGCCAATCTCAGTCCCTTCCC<br>CCCTACGTCGGGGCCCACACGCTCGGTGCGTGCCCAGTTGAACCAGGC<br>GGCTGCGGAAAAAAAAAAGCGGGGAGAAAGTAGGGCCCGGCTACTAGC<br>GGTTTTACGGGCGCACGTAGCTCAGGCCTCAAGACCTTGGGCTGGGACT<br>GGCTGAGCCTGGCGGGAGGCGGGGTCCGAGTCACCGCCTGCCGCCGC<br>GCCCCCGGTTTCTATAAATTGAGCCCGCAGCCTCCCGCTTCGCTCTCTGC<br>TCCTCCTGTTCGACAGTCAGCCGCATCTTCTTTTGCGTCGCCAGgtgaagac<br>gggcggagagaaacccgggaggctagggacggcctgaaggcggcagggggcgggcgcaggccggat<br>gtgttcgcgccgctgcggggtgggcccgggcggcctccgcattgcaggggcgggcggaggacgtgatgc<br>ggcgcgggctgggcatggaggcctggtggggagggaggggaggcgtgggtgtcggccggggccact<br>aggcgctcactgttctctccctccgcgcagCCGAGCCACATCGCTGAGACAC (SEQ ID<br>NO: 25) |
| hGRP78 | AGTGCGGTTACCAGCGGAAATGCCTCGGGGTCAGAAGTCGCAGGAGAGA<br>TAGACAGCTGCTGAACCAATGGGACCAGCGGATGGGGCGGATGTTATCT<br>ACCATTGGTGAACGTTAGAAACGAATAGCAGCCAATGAATCAGCTGGGG<br>GGGCGGAGCAGTGACGTTTATTGCGGAGGGGGCCGCTTCGAATCGGCG<br>GCGGCCAGCTTGGTGGCCTGGGCCAATGAACGGCCTCCAACGAGCAGG<br>GCCTTCACCAATCGGCGGCCTCCACGACGGGGCTGGGGGAGGGTATAT<br>AAGCCGAGTAGGCGACGGTGAGGTCGACGCCGGCCAAGACAGCACAGA<br>CAGATTGACCTATTGGGGTGTTTCGCGAGTGTGAGAGGGAAGCGCCGCG<br>GCCTGTATTTCTAGACCTGCCCTTCGCCTGGTTCGTGGCGCCTTGTGACC<br>CCGGGCCCCTGCCGCCTGCAAGTCGGAAATTGCGCTGTGCTCCTGTGCT<br>ACGGCCTGTGGCTGGACTGCCTGCTGCTGCCCAACTGGCTGGCAC (SEQ<br>ID NO: 26) |
| hGRP94 | TAGTTTCATCACCACCGCCACCCCCCCGCCCCCCCGCCATCTGAAAGGG<br>TTCTAGGGGATTTGCAACCTCTCTCGTGTGTTTCTTCTTTCCGAGAAGCG<br>CCGCCACACGAGAAAGCTGGCCGCGAAAGTCGTGCTGGAATCACTTCCA<br>ACGAAACCCCAGGCATAGATGGGAAAGGGTGAAGAACACGTTGCCATGG<br>CTACCGTTTCCCCGGTCACGGAATAAACGCTCTCTAGGATCCGGAAGTAG<br>TTCCGCCGCGACCTCTCTAAAAGGATGGATGTGTTCTCTGCTTACATTCAT<br>TGGACGTTTTCCCTTAGAGGCCAAGGCCGCCCAGGCAAAGGGGCGGTCC<br>CACGCGTGAGGGGCCCGCGGAGCCATTTGATTGGAGAAAAGCTGCAAAC<br>CCTGACCAATCGGAAGGAGCCACGCTTCGGGCATCGGTCACCGCACCTG<br>GACAGCTCCGATTGGTGGACTTTCCGCCCCCCCTCACGAATCCTCATTGG<br>GTGCCGTGGGTGCGTGGTGCGGCGCGATTGGTGGGTTCATGTTTCCCGT<br>CCCCCGCCCGCGAGAAGTGGGGGTGAAAAGCGGCCCGACCTGCTTGGG<br>GTGTAGTGGGCGGACCGCGCGGCTGGAGGTGTGAGGATCCGAACCCAG<br>GGGTGGGGGTGGAGGCGGCTCCTGCGATCGAAGGGGACTTGAGACTC<br>ACCGGCCGCACGTC (SEQ ID NO: 27) |
| hHSP70 | GGGCCGCCCACTCCCCCTTCCTCTCAGGGTCCCTGTCCCCTCCAGTGAA<br>TCCCAGAAGACTCTGGAGAGTTCTGAGCAGGGGGCGGCACTCTGGCCTC<br>TGATTGGTCCAAGGAAGGCTGGGGGGCAGGACGGGAGGCGAAAACCCT<br>GGAATATTCCCGACCTGGCAGCCTCATCGAGCTCGGTGATTGGCTCAGA<br>AGGGAAAAGGCGGGTCTCCGTGACGACTTATAAAAGCCCAGGGGCAAGC<br>GGTCCGGATAACGGCTAGCCTGAGGAGCTGCTGCGACAGTCCACTACCT<br>TTTTCGAGAGTGACTCCCGTTGTCCCAAGGCTTCCCAGAGCGAACCTGTG<br>CGGCTGCAGGCACCGGCGCGTCGAGTTTCCGGCGTCCGGAAGGACCGA<br>GCTCTTCTCGCGGATCCAGTGTTCCGTTTCCAGCCCCCAATCTCAGAGCG<br>GAGCCGACAGAGAGCAGGGAACCC (SEQ ID NO: 28) |
| hKINb | GCCCCACCCCCGTCCGCGTTACAACCGGGAGGCCCGCTGGGTCCTGCA<br>CCGTCACCCTCCTCCCTGTGACCGCCCACCTGATACCCAAACAACTTTCT<br>CGCCCCTCCAGTCCCCAGCTCGCCGAGCGCTTGCGGGGAGCCACCCAG<br>CCTCAGTTTCCCCAGCCCCGGGCGGGGCGAGGGGCGATGACGTCATGC<br>CGGCGCGCGGCATTGTGGGGCGGGGCGAGGCGGGGCGCCGGGGGGA<br>GCAACACTGAGACGCCATTTTCGGCGGCGGGGAGCGGCGCAGGCGGCCG<br>AGCGGGACTGGCTGGGTCGGCTGGGCTGCTGGTGCGAGGAGCCGCGG<br>GGCTGTGCTCGGCGGCCAAGGGGACAGCGCGTGGGTGGCCGAGGATG<br>CTGCGGGGCGGTAGCTCCGGCGCCCCTCGCTGGTGACTGCTGCGCCGT<br>GCCTCACACAGCCGAGGCGGGCTCGGCGCACAGTCGCTGCTCCGCGCT<br>CGCGCCCGGCGGCGCTCCAGGTGCTGACAGCGCGAGAGAGCGCGGCC<br>TCAGGAGCAACAC (SEQ ID NO: 29) |
| hUBIb | TTCCAGAGCTTTCGAGGAAGGTTTCTTCAACTCAAATTCATCCGCCTGATA<br>ATTTTCTTATATTTTCCTAAAGAAGGAAGAGAAGCGCATAGAGGAGAAGG<br>GAAATAATTTTTTAGGAGCCTTTCTTACGGCTATGAGGAATTTGGGGCTCA<br>GTTGAAAAGCCTAAACTGCCTCTCGGGAGGTTGGGCGCGGCGAACTACT<br>TTCAGCGGCGCACGGAGACGGCGTCTACGTGAGGGGTGATAAGTGACG<br>CAACACTCGTTGCATAAATTTGCGCTCCGCCAGCCCGGAGCATTTAGGG<br>GCGGTTGGCTTTGTTGGGTGAGCTTGTTTGTGTCCCTGTGGGTGGACGT<br>GGTTGGTGATTGGCAGGATCCTGGTATCCGCTAACAGgtactggcccacagccgt<br>aaagacctgcggggggcgtgagagggggaatgggtgaggtcaagctggaggcttcttgggggttgggtggg<br>ccgctgaggggaggggagggcgaggtgacgcgacacccgcctttctgggagagtgggccttgttgacct |

TABLE 4-continued

Exemplary Constitutive Promoters

| Name | DNA SEQUENCE |
|---|---|
| | aaggggggcgagggcagttggcacgcgcacgcgccgacagaaactaacagacattaaccaacagcga<br>ttccgtcgcgtttacttgggaggaaggcggaaaagaggtagtttgtgtggcttctggaaaccctaaatttggaat<br>cccagtatgagaatggtgtcccttcttgtgtttcaatgggattttttacttcgcgagtcttgtgggtttggttttgtttt<br>cagtttgcctaacaccgtgcttaggtttgaggcagattggagttcggtcgggggagtttgaatatccggaacagttag<br>tggggaaagctgtggacgcttggtaagagagcgctctggattttccgctgttgacgttgaaaccttgaatgacg<br>aatttcgtattaagtgacttagccttgtaaaattgaggggaggcttgcggaatattaacgtatttaaggcattttga<br>aggaatagttgctaattttgaagaatattaggtgtaaaagcaagaaatacaatgatcctgaggtgacacgctt<br>atgttttacttttaaactagGTCACC (SEQ ID NO: 30) |

In some embodiments, a promoter of the present disclosure is modulated by signals within a tumor microenvironment. A tumor microenvironment is considered to modulate a promoter if, in the presence of the tumor microenvironment, the activity of the promoter is increased or decreased by at least 10%, relative to activity of the promoter in the absence of the tumor microenvironment. In some embodiments, the activity of the promoter is increased or decreased by at least 20%, at least 30%, at least 40%, at least 50%, at least 60%, at least 70%, at least 80%, at least 90%, at least 100%, relative to activity of the promoter in the absence of the tumor microenvironment. For example, the activity of the promoter is increased or decreased by 10-20%, 10-30%, 10-40%, 10-50%, 10-60%, 10-70%, 10-80%, 10-90%, 10-100%, 10-200%, 20-30%, 20-40%, 20-50%, 20-60%, 20-70%, 20-80%, 20-90%, 20-100%, 20-200%, 50-60%, 50-70%, 50-80%, 50-90%, 50-100%, or 50-200%, relative to activity of the promoter in the absence of the tumor microenvironment.

In some embodiments, the activity of the promoter is increased or decreased by at least 2 fold (e.g., 2, 3, 4, 5, 10, 25, 20, 25, 50, or 100 fold), relative to activity of the promoter in the absence of the tumor microenvironment. For example, the activity of the promoter is increased or decreased by at least 3 fold, at least 5 fold, at least 10 fold, at least 20 fold, at least 50 fold, or at least 100 fold, relative to activity of the promoter in the absence of the tumor microenvironment. In some embodiments, the activity of the promoter is increased or decreased by 2-10, 2-20, 2-30, 2-40, 2-50, 2-60, 2-70, 2-80, 2-90, or 2-100 fold, relative to activity of the promoter in the absence of the tumor microenvironment.

In some embodiments, a promoter of the present disclosure is activated under a hypoxic condition. A "hypoxic condition" is a condition where the body or a region of the body is deprived of adequate oxygen supply at the tissue level. Hypoxic conditions can cause inflammation (e.g., the level of inflammatory cytokines increase under hypoxic conditions). In some embodiments, the promoter that is activated under hypoxic condition is operably linked to a nucleotide encoding an effector molecule that decreases the expression of activity of inflammatory cytokines, thus reducing the inflammation caused by the hypoxic condition. In some embodiments, the promoter that is activated under hypoxic conditions comprises a hypoxia responsive element (HRE). A "hypoxia responsive element (HRE)" is a response element that responds to hypoxia-inducible factor (HIF). The HRE, in some embodiments, comprises a consensus motif NCGTG (where N is either A or G).

In some embodiments, engineered cells produce multiple effector molecules. For example, cells may be engineered to produce 2-20 different effector molecules. In some embodiments, Cells engineered to produce 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-20, 3-19, 3-18, 3-17, 3-16, 3-15, 3-14, 3-13, 3-12, 3-11, 3-10, 3-9, 3-8, 3-7, 3-6, 3-5, 3-4, 4-20, 4-19, 4-18, 4-17, 4-16, 4-15, 4-14, 4-13, 4-12, 4-11, 4-10, 4-9, 4-8, 4-7, 4-6, 4-5, 5-20, 5-19, 5-18, 5-17, 5-16, 5-15, 5-14, 5-13, 5-12, 5-11, 5-10, 5-9, 5-8, 5-7, 5-6, 6-20, 6-19, 6-18, 6-17, 6-16, 6-15, 6-14, 6-13, 6-12, 6-11, 6-10, 6-9, 6-8, 6-7, 7-20, 7-19, 7-18, 7-17, 7-16, 7-15, 7-14, 7-13, 7-12, 7-11, 7-10, 7-9, 7-8, 8-20, 8-19, 8-18, 8-17, 8-16, 8-15, 8-14, 8-13, 8-12, 8-11, 8-10, 8-9, 9-20, 9-19, 9-18, 9-17, 9-16, 9-15, 9-14, 9-13, 9-12, 9-11, 9-10, 10-20, 10-19, 10-18, 10-17, 10-16, 10-15, 10-14, 10-13, 10-12, 10-11, 11-20, 11-19, 11-18, 11-17, 11-16, 11-15, 11-14, 11-13, 11-12, 12-20, 12-19, 12-18, 12-17, 12-16, 12-15, 12-14, 12-13, 13-20, 13-19, 13-18, 13-17, 13-16, 13-15, 13-14, 14-20, 14-19, 14-18, 14-17, 14-16, 14-15, 15-20, 15-19, 15-18, 15-17, 15-16, 16-20, 16-19, 16-18, 16-17, 17-20, 17-19, 17-18, 18-20, 18-19, or 19-20 effector molecules. In some embodiments, cells are engineered to produce 1, 2, 3, 4, 5, 6, 7, 8, 9, 10, 11, 12, 13, 14, 15, 16, 17, 18, 19, or 20 effector molecules.

In some embodiments, exogenous sequences can be multicistronic, i.e., more than one separate polypeptide (e.g., multiple effector molecules) can be produced from a single mRNA transcript. Exogenous sequences can be multicistronic through the use of various linkers, e.g., a polynucleotide sequence encoding a first effector molecule can be linked to a nucleotide sequence encoding a second effector molecule, such as in a first gene:linker:second gene 5' to 3' orientation. A linker can encode a 2A ribosome skipping element, such as T2A. Other 2A ribosome skipping elements include, but are not limited to, E2A, P2A, and F2A. 2A ribosome skipping elements allow production of separate polypeptides encoded by the first and second genes are produced during translation. A linker can encode a cleavable linker polypeptide sequence, such as a Furin cleavage site or a TEV cleavage site, wherein following expression the cleavable linker polypeptide is cleaved such that separate polypeptides encoded by the first and second genes are produced. A cleavable linker can include a polypeptide sequence, such as such a flexible linker (e.g., a Gly-Ser-Gly sequence), that further promotes cleavage.

A linker can encode an Internal Ribosome Entry Site (IRES), such that separate polypeptides encoded by the first and second genes are produced during translation. A linker can encode a splice acceptor, such as a viral splice acceptor.

A linker can be a combination of linkers, such as a Furin-2A linker that can produce separate polypeptides through 2A ribosome skipping followed by further cleavage of the Furin site to allow for complete removal of 2A residues. In some embodiments, a combination of linkers can include a Furin sequence, a flexible linker, and 2A linker. Accordingly, in some embodiments, the linker is a Furin- Gly-Ser-Gly-2A fusion polypeptide. In some embodiments, a linker of the present disclosure is a Furin-Gly-Ser-Gly-T2A fusion polypeptide.

In general, a multicistronic system can use any number or combination of linkers, to express any number of genes or portions thereof (e.g., an exogenous sequence can encode a first, a second, and a third effector molecule, each separated by linkers such that separate polypeptides encoded by the first, second, and third effector molecules are produced).

Exogenous sequences can use multiple promoters to express genes from multiple ORFs, i.e., more than one separate mRNA transcript can be produced from the exogenous sequence. For example, a first promoter can be operably linked to a polynucleotide sequence encoding a first effector molecule, and a second promoter can be operably linked to a polynucleotide sequence encoding a second effector molecule.

"Linkers," as used herein can refer to polypeptides that link a first polypeptide sequence and a second polypeptide sequence, the multicistronic linkers described above, or the additional promoters that are operably linked to additional ORFs described above.

Engineered cells, such as MSCs, of the present disclosure typically produce multiple effector molecules, at least two of which modulate different tumor-mediated immunosuppressive mechanisms. In some embodiments, at least one of the effector molecules stimulates an inflammatory pathway in the tumor microenvironment, and at least one of the effector molecules inhibits a negative regulator of inflammation in the tumor microenvironment.

A "tumor microenvironment" is the cellular environment in which a tumor exists, including surrounding blood vessels, immune cells, fibroblasts, bone marrow-derived inflammatory cells, lymphocytes, signaling molecules and the extracellular matrix (ECM) (see, e.g., Pattabiraman, D. R. & Weinberg, R. A. *Nature Reviews Drug Discovery* 13, 497-512 (2014); Balkwill, F. R. et al. *J Cell Sci* 125, 5591-5596, 2012; and Li, H. et al. *J Cell Biochem* 101(4), 805-15, 2007).

In some embodiments, cells are engineered to produce at least one homing molecule. "Homing," refers to active navigation (migration) of a cell to a target site (e.g., a cell, tissue (e.g., tumor), or organ). A "homing molecule" refers to a molecule that directs cells to a target site. In some embodiments, a homing molecule functions to recognize and/or initiate interaction of a cell to a target site. Non-limiting examples of homing molecules include CXCR1, CCR9, CXCR2, CXCR3, CXCR4, CCR2, CCR4, FPR2, VEGFR, IL6R, CXCR1, CSCR7, and PDGFR.

In some embodiments, a homing molecule is a chemokine receptor (cell surface molecule that binds to a chemokine). Chemokines are small cytokines or signaling proteins secreted by cells that can induce directed chemotaxis in cells. Chemokines can be classified into four main subfamilies: CXC, CC, CX3C and XC, all of which exert biological effects by binding selectively to chemokine receptors located on the surface of target cells. In some embodiments, cells are engineered to produce CXCR4, a chemokine receptor which allows cells to home along a chemokine gradient towards a stromal cell-derived factor 1 (also known as SDF1, C-X-C motif chemokine 12, and CXCL12)—expressing cell, tissue, or tumor. Non-limiting examples of chemokine receptors that may be produced by the engineered cells of the present disclosure include: CXC chemokine receptors (e.g., CXCR1, CXCR2, CXCR3, CXCR4, CXCR5, CXCR6, and CXCR7), CC chemokine receptors (CCR1, CCR2, CCR3, CCR4, CCR5, CCR6, CCR7, CCR8, CCR9, CCR10, and CCR11), CX3C chemokine receptors (e.g., CX3CR1, which binds to CX3CL1), and XC chemokine receptors (e.g., XCR1). In some embodiments, a chemokine receptor is a G protein-linked transmembrane receptor, or a member of the tumor necrosis factor (TNF) receptor superfamily (including but not limited to TNFRSF1A, TNFRSF1B). In some embodiments, cells are engineered to produce CXCL8, CXCL9, and/or CXCL10, 11 or a fusion protein that encompass CXCL10 and CXCL11 (promote T-cell recruitment), CCL3 and/or CXCL5, CCL21 (Th1 recruitment and polarization). In some embodiments cells are engineered to produce CXCL13 to promote B-cell recruitment.

In some embodiments, cells are engineered to produce G-protein coupled receptors (GPCRs) that detect N-formylated-containing oligopeptides (including but not limited to FPR2 and FPRL1).

In some embodiments, cells are engineered to produce receptors that detect interleukins (including but not limited to IL6R).

In some embodiments, cells are engineered to produce receptors that detect growth factors secreted from other cells, tissues, or tumors (including but not limited to FGFR, PDGFR, EGFR, and receptors of the VEGF family, including but not limited to VEGF-C and VEGF-D).

In some embodiments, a homing molecule is an integrin. Integrins are transmembrane receptors that facilitate cell-extracellular matrix (ECM) adhesion. Integrins are obligate heterodimers having two subunits: α (alpha) and β (beta). The a subunit of an integrin may be, without limitation: ITGA1, ITGA2, ITGA3, ITGA4, ITGA5, ITGA6, IGTA7, ITGA8, ITGA9, IGTA10, IGTA11, ITGAD, ITGAE, ITGAL, ITGAM, ITGAV, ITGA2B, ITGAX. The 13 subunit of an integrin may be, without limitation: ITGB1, ITGB2, ITGB3, ITGB4, ITGB5, ITGB6, ITGB7, and ITGB8. Cells of the present disclosure may be engineered to produce any combination of the integrin α and β subunits.

In some embodiments, a homing molecule is a matrix metalloproteinase (MMP). MMPs are enzymes that cleave components of the basement membrane underlying the endothelial cell wall. Non-limiting examples of MMPs include MMP-2, MMP-9, and MMP. In some embodiments, cells are engineered to produce an inhibitor of a molecule (e.g., protein) that inhibits MMPs. For example, cells may be engineered to express an inhibitor (e.g., an RNAi molecule) of membrane type 1 MMP (MT1-MMP) or TIMP metallopeptidase inhibitor 1 (TIMP-1).

In some embodiments, a homing molecule is a ligand that binds to selectin (e.g., hematopoietic cell E-/L-selectin ligand (HCELL), Dykstra et al., Stem Cells. 2016 October; 34(10):2501-2511) on the endothelium of a target tissue, for example.

The term "homing molecule" also encompasses transcription factors that regulate the production of molecules that improve/enhance homing of cells.

In some embodiments, cell homing is increased by locally irradiating a tumor/cancer cells in a subject. Radiological tissue damage aids in cell homing, as well as endogenous T cell homing to that damaged tissue.

Examples of Engineered Cells

Cells (e.g., MSCs) as provided herein are engineered to produce multiple effector molecules, at least two of which modulate different tumor-mediated immunosuppressive mechanisms. In some embodiments, at least one (e.g., 1, 2, 3, 4, 5, or more) effector molecule stimulates at least one immunostimulatory mechanism in the tumor microenvironment, or inhibits at least one immunosuppressive mechanism in the tumor microenvironment. In some embodiments, at least one (e.g., 1, 2, 3, 4, 5, or more) effector molecule inhibits at least one immunosuppressive mechanism in the tumor microenvironment, and at least one effector molecule (e.g., 1, 2, 3, 4, 5, or more) inhibits at least one immunosuppressive mechanism in the tumor microenvironment. In yet other embodiments, at least two (e.g., 2, 3, 4, 5, or more) effector molecules stimulate at least one immunostimulatory mechanism in the tumor microenvironment. In still other embodiments, at least two (e.g., 1, 2, 3, 4, 5, or more) effector molecules inhibit at least one immunosuppressive mechanism in the tumor microenvironment.

In some embodiments, a cell (e.g., MSC) is engineered to produce at least one effector molecule that stimulates T cell signaling, activity and/or recruitment. In some embodiments, a cell (e.g., MSC) is engineered to produce at least one effector molecule that stimulates antigen presentation and/or processing. In some embodiments, a cell (e.g., MSC) is engineered to produce at least one effector molecule that stimulates natural killer cell-mediated cytotoxic signaling, activity and/or recruitment. In some embodiments, a cell (e.g., MSC) is engineered to produce at least one effector molecule that stimulates dendritic cell differentiation and/or maturation. In some embodiments, a cell (e.g., MSC) is engineered to produce at least one effector molecule that stimulates immune cell recruitment. In some embodiments, a cell (e.g., MSC) is engineered to produce at least one effector molecule that stimulates M1 macrophage signaling, activity and/or recruitment. In some embodiments, a cell (e.g., MSC) is engineered to produce at least one effector molecule that stimulates Th1 polarization. In some embodiments, a cell (e.g., MSC) is engineered to produce at least one effector molecule that stimulates stroma degradation. In some embodiments, a cell (e.g., MSC) is engineered to produce at least one effector molecule that stimulates immunostimulatory metabolite production. In some embodiments, a cell (e.g., MSC) is engineered to produce at least one effector molecule that stimulates Type I interferon signaling. In some embodiments, a cell (e.g., MSC) is engineered to produce at least one effector molecule that inhibits negative costimulatory signaling. In some embodiments, a cell (e.g., MSC) is engineered to produce at least one effector molecule that inhibits pro-apoptotic signaling (e.g., via TRAIL) of anti-tumor immune cells. In some embodiments, a cell (e.g., MSC) is engineered to produce at least one effector molecule that inhibits T regulatory ($T_{reg}$) cell signaling, activity and/or recruitment. In some embodiments, a cell (e.g., MSC) is engineered to produce at least one effector molecule that inhibits tumor checkpoint molecules. In some embodiments, a cell (e.g., MSC) is engineered to produce at least one effector molecule that activates stimulator of interferon genes (STING) signaling. In some embodiments, a cell (e.g., MSC) is engineered to produce at least one effector molecule that inhibits myeloid-derived suppressor cell signaling, activity and/or recruitment. In some embodiments, a cell (e.g., MSC) is engineered to produce at least one effector molecule that degrades immunosuppressive factors/metabolites. In some embodiments, a cell (e.g., MSC) is engineered to produce at least one effector molecule that inhibits vascular endothelial growth factor signaling. In some embodiments, a cell (e.g., MSC) is engineered to produce at least one effector molecule that directly kills tumor cells (e.g., granzyme, perforin, oncolytic viruses, cytolytic peptides and enzymes, anti-tumor antibodies, e.g., that trigger ADCC).

In some embodiments, at least one effector molecule: stimulates T cell signaling, activity and/or recruitment, stimulates antigen presentation and/or processing, stimulates natural killer cell-mediated cytotoxic signaling, activity and/or recruitment, stimulates dendritic cell differentiation and/or maturation, stimulates immune cell recruitment, stimulates macrophage signaling, stimulates stroma degradation, stimulates immunostimulatory metabolite production, or stimulates Type I interferon signaling; and at least one effector molecule inhibits negative costimulatory signaling, inhibits pro-apoptotic signaling of anti-tumor immune cells, inhibits T regulatory (Treg) cell signaling, activity and/or recruitment, inhibits tumor checkpoint molecules, activates stimulator of interferon genes (STING) signaling, inhibits myeloid-derived suppressor cell signaling, activity and/or recruitment, degrades immunosuppressive factors/metabolites, inhibits vascular endothelial growth factor signaling, or directly kills tumor cells.

In some embodiments, a cell (e.g., MSC) is engineered to produce at least one effector molecule selected from IL-12, IFN-β, IFN-γ, IL-2, IL-15, IL-7, IL-36γ, IL-18, IL-1β, OX40-ligand, and CD40L; and/or at least one effector molecule selected from anti-PD-1 antibodies, anti-PD-L1 antibodies, anti-CTLA-4 antibodies, and anti-IL-35 antibodies; and/or at least one effector molecule selected from MIP1α (CCL3), MIP1β (CCLS), and CCL21; and/or at least one effector molecule selected from CpG oligodeoxynucleotides; and/or at least one effector molecule selected from microbial peptides.

In some embodiments, a cell (e.g., MSC) is engineered to produce IFN-β and at least one effector molecule selected from cytokines, antibodies, chemokines, nucleotides, peptides, enzymes, and stimulators of interferon genes (STINGs). In some embodiments, a cell (e.g., MSC) is engineered to produce IFN-β and at least one cytokine or receptor/ligand (e.g., IL-12, IFN-γ, IL-2, IL-15, IL-7, IL-36γ, IL-18, IL-1β, OX40-ligand, and/or CD40L).

In some embodiments, a cell (e.g., MSC) is engineered to produce IFN-β and at least one cytokine or receptor/ligand (e.g., IL-12, IFN-γ, IL-2, IL-15, IL-7, IL-36γ, IL-18, IL-1β, OX40-ligand, and/or CD40L).

In some embodiments the cytokine is produced as an engineered fusion protein with an antibody, antibody-fragment, or receptor that self-binds to the cytokine to induce cell-specific targeted binding such as with IL-2 fused to an antibody fragment preventing it from binding to Treg cells and preferentially binding to CD8 and NK cells. In some embodiments, a cell (e.g., MSC) is engineered to produce IFN-β and at least one antibody (e.g., anti-PD-1 antibody, anti-PD-L1 antibody, anti-CTLA-4 antibody, anti-VEGF, anti-TGF-β, anti-IL-10, anti-TNF-α, and/or anti-IL-35 antibody). In some embodiments, a cell (e.g., MSC) is engineered to produce IFN-β and at least one chemokine (MIP1α (CCL3), MIP1β (CCLS), and/or CCL21). In some embodiments, a cell (e.g., MSC) is engineered to produce IFN-β and at least one nucleotide (e.g., a CpG oligodeoxynucleotide). In some embodiments, a cell (e.g., MSC) is engineered to produce IFN-β and at least one peptide (e.g., an anti-tumor peptide). In some embodiments, a cell (e.g., MSC) is engineered to produce IFN-β and at least one enzyme. In some embodiments, a cell (e.g., MSC) is engineered to produce IFN-β and at least one STING activator. In some embodiments, a cell (e.g., MSC) is engineered to produce IFN-β and at least one effector with direct anti-tumor activity (e.g., oncolytic virus).

In some embodiments, a cell (e.g., MSC) is engineered to produce IFN-α and MIP1-α. In some embodiments, a cell (e.g., MSC) is engineered to produce IFN-α and MIP1-β. In some embodiments, a cell (e.g., MSC) is engineered to produce IFN-α and CXCL9. In some embodiments, a cell (e.g., MSC) is engineered to produce IFN-α and CXCL10. In some embodiments, a cell (e.g., MSC) is engineered to produce IFN-α and CXCL11. In some embodiments, a cell (e.g., MSC) is engineered to produce IFN-α and CCL21. In some embodiments, the cell is engineered to further produce IL-12, IFN-γ, IL-2, IL-7, IL-15, IL36-γ, IL-18, CD40L and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce IFN-β and MIP1-α. In some embodiments, a cell (e.g., MSC) is engineered to produce IFN-β and MIP1-β. In some embodiments, a cell (e.g., MSC) is engineered to produce IFN-β and CXCL9. In some embodiments, a cell (e.g., MSC) is engineered to produce IFN-β and CXCL10. In some embodiments, a cell (e.g., MSC) is engineered to produce IFN-β and CXCL11. In some embodiments, a cell (e.g., MSC) is engineered to produce IFN-β and CCL21. In some embodiments, the cell is engineered to further produce IL-12, IFN-γ, IL-2, IL-7, IL-15, IL36-γ, IL-18, CD40L and/or 41BB-L. In some embodiments, the cell is engineered to further produce anti-CD40 antibody, anti-CTLA4 antibody, anti-PD-L1 antibody, and/or OX40L. In some embodiments, a cell (e.g., MSC) is engineered to produce IL-12 and MIP1-α.

In some embodiments, a cell (e.g., MSC) is engineered to produce IL-12 and MIP1-β. In some embodiments, a cell (e.g., MSC) is engineered to produce IL-12 and CXCL9. In some embodiments, a cell (e.g., MSC) is engineered to produce IL-12 and CXCL10. In some embodiments, a cell (e.g., MSC) is engineered to produce IL-12 and CXCL11. In some embodiments, a cell (e.g., MSC) is engineered to produce IL-12 and CCL21. In some embodiments, the cell is engineered to further produce IFN-β, IFN-γ, IL-2, IL-7, IL-15, IL36-γ, IL-18, CD40L and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce TNF-related apoptosis-inducing ligand (TRAIL) and MIP1-α. In some embodiments, a cell (e.g., MSC) is engineered to produce TRAIL and MIP1-β. In some embodiments, a cell (e.g., MSC) is engineered to produce TRAIL and CXCL9. In some embodiments, a cell (e.g., MSC) is engineered to produce TRAIL and CXCL10. In some embodiments, a cell (e.g., MSC) is engineered to produce TRAIL and CXCL11. In some embodiments, a cell (e.g., MSC) is engineered to produce TRAIL and CCL21. In some embodiments, the cell is engineered to further produce IL-12, IFN-γ, IL-2, IL-7, IL-15, IL36-γ, IL-18, CD40L and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce a stimulator of interferon gene (STING) and MIP1-α. In some embodiments, a cell (e.g., MSC) is engineered to produce STING and MIP1-β. In some embodiments, a cell (e.g., MSC) is engineered to produce STING and CXCL9. In some embodiments, a cell (e.g., MSC) is engineered to produce STING and CXCL10. In some embodiments, a cell (e.g., MSC) is engineered to produce STING and CXCL11. In some embodiments, a cell (e.g., MSC) is engineered to produce STING and CCL21. In some embodiments, the cell is engineered to further produce IL-12, IFN-γ, IL-2, IL-7, IL-15, IL36-γ, IL-18, CD40L and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce CD40L and MIP1-α. In some embodiments, a cell (e.g., MSC) is engineered to produce CD40L and MIP1-β. In some embodiments, a cell (e.g., MSC) is engineered to produce CD40L and CXCL9. In some embodiments, a cell (e.g., MSC) is engineered to produce CD40L and CXCL10. In some embodiments, a cell (e.g., MSC) is engineered to produce CD40L and CXCL11. In some embodiments, a cell (e.g., MSC) is engineered to produce CD40L and CCL21. In some embodiments, the cell is engineered to further produce IL-12, IFN-γ, IL-2, IL-7, IL-15, IL36-γ, IL-18, and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce cytosine deaminase and MIP1-α. In some embodiments, a cell (e.g., MSC) is engineered to produce cytosine deaminase and MIP1-β. In some embodiments, a cell (e.g., MSC) is engineered to produce cytosine deaminase and CXCL9. In some embodiments, a cell (e.g., MSC) is engineered to produce cytosine deaminase and CXCL10. In some embodiments, a cell (e.g., MSC) is engineered to produce cytosine deaminase and CXCL11. In some embodiments, a cell (e.g., MSC) is engineered to produce cytosine deaminase and CCL21. In some embodiments, the cell is engineered to further produce IL-12, IFN-γ, IL-2, IL-7, IL-15, IL36-γ, IL-18, CD40L, and/or 41BB-L. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce IFN-α and IL-12. In some embodiments, a cell (e.g., MSC) is engineered to produce IFN-α and IFN-γ. In some embodiments, a cell (e.g., MSC) is engineered to produce IFN-α and IL-2. In some embodiments, a cell (e.g., MSC) is engineered to produce IFN-α and IL-7. In some embodiments, a cell (e.g., MSC) is engineered to produce IFN-α and IL-15. In some embodiments, a cell (e.g., MSC) is engineered to produce IFN-α and IL-36γ. In some embodiments, a cell (e.g., MSC) is engineered to produce IFN-α and IL-18. In some embodiments, a cell (e.g., MSC) is engineered to produce IFN-α and CD40L. In some embodiments, a cell (e.g., MSC) is engineered to produce IFN-α and 41BB-L. In some embodiments, the cell is engineered to further produce MIP1-α, MIP1-β, CXCL9, CXCL10, CXCL11, CXCL10-11 fusion, CXCL13 and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce IFN-β and IL-12. In some embodiments, a cell (e.g., MSC) is engineered to produce IFN-β and IFN-γ. In some embodiments, a cell (e.g., MSC) is engineered to produce IFN-β and IL-2. In some embodiments, a cell (e.g., MSC) is engineered to produce IFN-β and IL-7. In some embodiments, a cell (e.g., MSC) is engineered to produce IFN-β and IL-15. In some embodiments, a cell (e.g., MSC) is engineered to produce IFN-β and IL-36γ. In some embodiments, a cell (e.g., MSC) is engineered to produce IFN-β and IL-18. In some embodiments, a cell (e.g., MSC) is engineered to produce IFN-β and CD40L. In some embodiments, a cell (e.g., MSC) is engineered to produce IFN-β and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce TNF-related apoptosis-inducing ligand (TRAIL) and IL-12. In some embodiments, a cell (e.g., MSC) is engineered to produce TRAIL and IFN-γ. In some embodiments, a cell (e.g., MSC) is engineered to produce TRAIL and IL-2. In some embodiments, a cell (e.g., MSC) is engineered to produce TRAIL and IL-7. In some embodiments, a cell (e.g., MSC) is engineered to produce TRAIL and IL-15. In some embodiments, a cell (e.g., MSC) is engineered to produce TRAIL and IL-36γ. In some embodiments, a cell (e.g., MSC) is engineered to produce TRAIL and IL-18. In some embodiments, a cell (e.g., MSC) is engineered to produce TRAIL and CD40L. In some embodiments, a cell (e.g., MSC) is engineered to produce TRAIL and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce a stimulator of interferon gene (STING) and IL-12. In some embodiments, a cell (e.g., MSC) is engineered to produce STING and IFN-γ. In some embodiments, a cell (e.g., MSC) is engineered to produce STING and IL-2. In some embodiments, a cell (e.g., MSC) is engineered to produce STING and IL-7. In some embodiments, a cell (e.g., MSC) is engineered to produce STING and IL-15. In some embodiments, a cell (e.g., MSC) is engineered to produce STING and IL-36γ. In some embodiments, a cell (e.g., MSC) is engineered to produce STING and IL-18. In some embodiments, a cell (e.g., MSC) is engineered to produce STING and CD40L. In some embodiments, a cell (e.g., MSC) is engineered to produce STING and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce CD40L and IL-12. In some embodiments, a cell (e.g., MSC) is engineered to produce CD40L and IFN-γ. In some embodiments, a cell (e.g., MSC) is engineered to produce CD40L and IL-2. In some embodiments, a cell (e.g., MSC) is engineered to produce CD40L and IL-7. In some embodiments, a cell (e.g., MSC) is engineered to produce CD40L and IL-15. In some embodiments, a cell (e.g., MSC) is engineered to produce CD40L and IL-36γ. In some embodiments, a cell (e.g., MSC) is engineered to produce CD40L and IL-18. In some embodiments, a cell (e.g., MSC) is engineered to produce CD40L and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce cytosine deaminase and IL-12. In some embodiments, a cell (e.g., MSC) is engineered to produce cytosine deaminase and IFN-γ. In some embodiments, a cell (e.g., MSC) is engineered to produce cytosine deaminase and IL-2. In some embodiments, a cell (e.g., MSC) is engineered to produce cytosine deaminase and IL-7. In some embodiments, a cell (e.g., MSC) is engineered to produce cytosine deaminase and IL-15. In some embodiments, a cell (e.g., MSC) is engineered to produce cytosine deaminase and IL-36γ. In some embodiments, a cell (e.g., MSC) is engineered to produce cytosine deaminase and IL-18. In some embodiments, a cell (e.g., MSC) is engineered to produce cytosine deaminase and CD40L. In some embodiments, a cell (e.g., MSC) is engineered to produce cytosine deaminase and 41BB-L. In some embodiments, the cell is engineered to further produce MIP1-α, MIP1-β, CXCL9, CXCL10, CXCL11, and/or CCL21. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce MIP1-α and IL-12. In some embodiments, a cell (e.g., MSC) is engineered to produce MIP1-α and MIP1-γ. In some embodiments, a cell (e.g., MSC) is engineered to produce MIP1-α and IL-2. In some embodiments, a cell (e.g., MSC) is engineered to produce MIP1-α and IL-7. In some embodiments, a cell (e.g., MSC) is engineered to produce MIP1-α and IL-15. In some embodiments, a cell (e.g., MSC) is engineered to produce MIP1-α and IL-36γ. In some embodiments, a cell (e.g., MSC) is engineered to produce MIP1-α and IL-18. In some embodiments, a cell (e.g., MSC) is engineered to produce MIP1-α and CD40L. In some embodiments, a cell (e.g., MSC) is engineered to produce MIP1-α and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce MIP1-β and IL-12. In some embodiments, a cell (e.g., MSC) is engineered to produce MIP1-β and MIP1-γ. In some embodiments, a cell (e.g., MSC) is engineered to produce MIP1-β and IL-2. In some embodiments, a cell (e.g., MSC) is engineered to produce MIP1-β and IL-7. In some embodiments, a cell (e.g., MSC) is engineered to produce MIP1-β and IL-15. In some embodiments, a cell (e.g., MSC) is engineered to produce MIP1-β and IL-36γ. In some embodiments, a cell (e.g., MSC) is engineered to produce MIP1-β and IL-18. In some embodiments, a cell (e.g., MSC) is engineered to produce MIP1-β and CD40L. In some embodiments, a cell (e.g., MSC) is engineered to produce MIP1-β and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce CXCL9 and IL-12. In some embodiments, a cell (e.g., MSC) is engineered to produce CXCL9 and IFN-γ. In some embodiments, a cell (e.g., MSC) is engineered to produce CXCL9 and IL-2. In some embodiments, a cell (e.g., MSC) is engineered to produce CXCL9 and IL-7. In some embodiments, a cell (e.g., MSC) is engineered to produce CXCL9 and IL-15. In some embodiments, a cell (e.g., MSC) is engineered to produce CXCL9 and IL-36γ. In some embodiments, a cell (e.g., MSC) is engineered to produce CXCL9 and IL-18. In some embodiments, a cell (e.g., MSC) is engineered to produce CXCL9 and CD40L. In some embodiments, a cell (e.g., MSC) is engineered to produce CXCL9 and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce a CXCL10 and IL-12. In some embodiments, a cell (e.g., MSC) is engineered to produce CXCL10 and IFN-γ. In some embodiments, a cell (e.g., MSC) is engineered to produce CXCL10 and IL-2. In some embodiments, a cell (e.g., MSC) is engineered to produce CXCL10 and IL-7. In some embodiments, a cell (e.g., MSC) is engineered to produce CXCL10 and IL-15. In some embodiments, a cell (e.g., MSC) is engineered to produce CXCL10 and IL-36γ. In some embodiments, a cell (e.g., MSC) is engineered to produce CXCL10 and IL-18. In some embodiments, a cell (e.g., MSC) is engineered to produce CXCL10 and CD40L. In some embodiments, a cell (e.g., MSC) is engineered to produce CXCL10 and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce CXCL11 and IL-12. In some embodiments, a cell (e.g., MSC) is engineered to produce CXCL11 and IFN-γ. In some embodiments, a cell (e.g., MSC) is engineered to produce CXCL11 and IL-2. In some embodiments, a cell (e.g., MSC) is engineered to produce CXCL11 and IL-7. In some embodiments, a cell (e.g., MSC) is engineered to produce CXCL11 and IL-15. In some embodiments, a cell (e.g., MSC) is engineered to produce CXCL11 and IL-36γ. In some embodiments, a cell (e.g., MSC) is engineered to produce CXCL11 and IL-18. In some embodiments, a cell (e.g., MSC) is engineered to produce CXCL11 and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce CCL21 and IL-12. In some embodiments, a cell (e.g., MSC) is engineered to produce CCL21 and IFN-γ. In some embodiments, a cell (e.g., MSC) is engineered to produce CCL21 and IL-2. In some embodiments, a cell (e.g., MSC) is engineered to produce CCL21 and IL-7. In some embodiments, a cell (e.g., MSC) is engineered to produce CCL21 and IL-15. In some embodiments, a cell (e.g., MSC) is engineered to produce CCL21 and IL-36γ. In some embodiments, a cell (e.g., MSC) is engineered to produce CCL21 and IL-18. In some embodiments, a cell (e.g., MSC) is engineered to produce CCL21 and CD40L. In some embodiments, a cell (e.g., MSC) is engineered to produce CCL21 and 41BB-L. In some embodiments, the cell is engineered to further produce IFN-α, IFN-β, TRAIL, STING, CD40L, and/or cytosine deaminase. In some embodiments, the cell is engineered to further produce anti-CD40 antibody, anti-CTLA4 antibody, anti-PD-L1 antibody, and/or OX40L.

In some embodiments, a cell (e.g., MSC) is engineered to produce IFN-α and anti-PD-L1 antibody. In some embodiments, a cell (e.g., MSC) is engineered to produce IFN-α and OX40L. In some embodiments, a cell (e.g., MSC) is engineered to produce IFN-α and anti-CTLA4 antibody. In some embodiments, a cell (e.g., MSC) is engineered to produce IFN-α and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce IFN-β and anti-PD-L1 antibody. In some embodiments, a cell (e.g., MSC) is engineered to produce IFN-β and OX40L. In some embodiments, a cell (e.g., MSC) is engineered to produce IFN-β and anti-CTLA4 antibody. In some embodiments, a cell (e.g., MSC) is engineered to produce IFN-β and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce TRAIL and anti-PD-L1 antibody. In some embodiments, a cell (e.g., MSC) is engineered to produce TRAIL and OX40L. In some embodiments, a cell (e.g., MSC) is engineered to produce TRAIL and anti-CTLA4 antibody. In some embodiments, a cell (e.g., MSC) is engineered to produce TRAIL and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce STING and anti-PD-L1 antibody. In some embodiments, a cell (e.g., MSC) is engineered to produce STING and OX40L. In some embodiments, a cell (e.g., MSC) is engineered to produce STING and anti-CTLA4 antibody. In some embodiments, a cell (e.g., MSC) is engineered to produce STING and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CD40L and anti-PD-L1 antibody. In some embodiments, a cell (e.g., MSC) is engineered to produce CD40L and OX40L. In some embodiments, a cell (e.g., MSC) is engineered to produce CD40L and anti-CTLA4 antibody. In some embodiments, a cell (e.g., MSC) is engineered to produce CD40L and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce cytosine deaminase and anti-PD-L1 antibody. In some embodiments, a cell (e.g., MSC) is engineered to produce cytosine deaminase and OX40L. In some embodiments, a cell (e.g., MSC) is engineered to produce cytosine deaminase and anti-CTLA4 antibody. In some embodiments, a cell (e.g., MSC) is engineered to produce cytosine deaminase and anti-CD47 antibody. In some embodiments, the cell is engineered to further produce MIP1-α, MIP1-β, CXCL9, CXCL10, CXCL11, and/or CXCL21. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce MIP1-α and anti-PD-L1 antibody. In some embodiments, a cell (e.g., MSC) is engineered to produce MIP1-α and OX40L. In some embodiments, a cell (e.g., MSC) is engineered to produce MIP1-α and anti-CTLA4 antibody. In some embodiments, a cell (e.g., MSC) is engineered to produce MIP1-α and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce MIP1-β and anti-PD-L1 antibody. In some embodiments, a cell (e.g., MSC) is engineered to produce MIP1-β and OX40L. In some embodiments, a cell (e.g., MSC) is engineered to produce MIP1-β and anti-CTLA4 antibody. In some embodiments, a cell (e.g., MSC) is engineered to produce MIP1-β and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CXCL9 and anti-PD-L1 antibody. In some embodiments, a cell (e.g., MSC) is engineered to produce CXCL9 and OX40L. In some embodiments, a cell (e.g., MSC) is engineered to produce CXCL9 and anti-CTLA4 antibody. In some embodiments, a cell (e.g., MSC) is engineered to produce CXCL9 and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CXCL10 and anti-PD-L1 antibody. In some embodiments, a cell (e.g., MSC) is engineered to produce CXCL10 and OX40L. In some embodiments, a cell (e.g., MSC) is engineered to produce CXCL10 and anti-CTLA4 antibody. In some embodiments, a cell (e.g., MSC) is engineered to produce CXCL10 and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CXCL11 and anti-PD-L1 antibody. In some embodiments, a cell (e.g., MSC) is engineered to produce CXCL11 and OX40L. In some embodiments, a cell (e.g., MSC) is engineered to produce CXCL11 and anti-CTLA4 antibody. In some embodiments, a cell (e.g., MSC) is engineered to produce CXCL11 and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce CCL21 and anti-PD-L1 antibody. In some embodiments, a cell (e.g., MSC) is engineered to produce CCL21 and OX40L. In some embodiments, a cell (e.g., MSC) is engineered to produce CCL21 and anti-CTLA4 antibody. In some embodiments, a cell (e.g., MSC) is engineered to produce CCL21 and anti-CD47 antibody. In some embodiments, the cell is engineered to further produce IFN-α, IFN-β, TRAIL, STING, CD40L, and/or cytosine deaminase. In some embodiments, the cell is engineered to further produce IL-12, IFN-γ, IL-2, IL-7, IL-15, IL-36γ, IL-18, CD40L, and/or 41BB-L.

In some embodiments, a cell (e.g., MSC) is engineered to produce IL-12 and anti-PD-L1 antibody. In some embodiments, a cell (e.g., MSC) is engineered to produce IL-12 and OX40L. In some embodiments, a cell (e.g., MSC) is engineered to produce IL-12 and anti-CTLA4 antibody. In some embodiments, a cell (e.g., MSC) is engineered to produce IL-12 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IFN-γ and anti-PD-L1 antibody. In some embodiments, a cell (e.g., MSC) is engineered to produce IFN-γ and OX40L. In some embodiments, a cell (e.g., MSC) is engineered to produce IFN-γ and anti-CTLA4 antibody. In some embodiments, a cell (e.g., MSC) is engineered to produce IFN-γ and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IL-2 and anti-PD-L1 antibody. In some embodiments, a cell (e.g., MSC) is engineered to produce IL-2 and OX40L. In some embodiments, a cell (e.g., MSC) is engineered to produce IL-2 and anti-CTLA4 antibody. In some embodiments, a cell (e.g., MSC) is engineered to produce IL-2 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IL-7 and anti-PD-L1 antibody. In some embodiments, a cell (e.g., MSC) is engineered to produce IL-7 and OX40L. In some embodiments, a cell (e.g., MSC) is engineered to produce IL-7 and anti-CTLA4 antibody. In some embodiments, a cell (e.g., MSC) is engineered to produce IL-7 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IL-15 and anti-PD-L1 antibody. In some embodiments, a cell (e.g., MSC) is engineered to produce IL-15 and OX40L. In some embodiments, a cell (e.g., MSC) is engineered to produce IL-15 and anti-CTLA4 antibody. In some embodiments, a cell (e.g., MSC) is engineered to produce IL-15 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IL-36-γ and anti-PD-L1 antibody. In some embodiments, a cell (e.g., MSC) is engineered to produce IL-36-γ and OX40L. In some embodiments, a cell (e.g., MSC) is engineered to produce IL-36-γ and anti-CTLA4 antibody. In some embodiments, a cell (e.g., MSC) is engineered to produce IL-36-γ and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce IL-18 and anti-PD-L1 antibody. In some embodiments, a cell (e.g., MSC) is engineered to produce IL-18 and OX40L. In some embodiments, a cell (e.g., MSC) is engineered to produce IL-18 and anti-CTLA4 antibody. In some embodiments, a cell (e.g., MSC) is engineered to produce IL-18 and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce CD40L and anti-PD-L1 antibody. In some embodiments, a cell (e.g., MSC) is engineered to produce CD40L and OX40L. In some embodiments, a cell (e.g., MSC) is engineered to produce CD40L and anti-CTLA4 antibody. In some embodiments, a cell (e.g., MSC) is engineered to produce CD40L and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

In some embodiments, a cell (e.g., MSC) is engineered to produce 41BB-L and anti-PD-L1 antibody. In some embodiments, a cell (e.g., MSC) is engineered to produce 41BB-L and OX40L. In some embodiments, a cell (e.g., MSC) is engineered to produce 41BB-L and anti-CTLA4 antibody. In some embodiments, a cell (e.g., MSC) is engineered to produce 41BB-L and anti-CD47 antibody. In some embodiments, the cell is engineered to further produce IFN-α, IFN-β, TRAIL, STING, CD40L, and/or cytosine deaminase. In some embodiments, the cell is engineered to further produce MIP1-α, MIP1-β, CXCL9, CXCL10, CXCL11, and/or CCL21.

Secretion Signals

In general, the one or more effector molecules comprise a secretion signal peptide (also referred to as a signal peptide or signal sequence) at the effector molecule's N-terminus that direct newly synthesized proteins destined for secretion or membrane insertion to the proper protein processing pathways. The secretion signal peptide operably associated with a effector molecule can be a native secretion signal peptide native secretion signal peptide (e.g., the secretion signal peptide generally endogenously associated with the given effector molecule). The secretion signal peptide operably associated with a effector molecule can be a non-native secretion signal peptide native secretion signal peptide. Non-native secretion signal peptides can promote improved expression and function, such as maintained secretion, in particular environments, such as tumor microenvironments. Non-limiting examples of non-native secretion signal peptide are shown in Table 5.

TABLE 5

Exemplary Signal Secretion Peptides

| Name | Protein SEQUENCE | Source (Uniprot) | DNA SEQUENCE |
|---|---|---|---|
| IL-12 | MCHQQLV ISWFSLV FLASPLVA (SEQ ID NO: 112) | P29460 | ATGTGTCACCAGC AGCTCGTTATAT CCTGGTTTAGTTT GGTGTTTCTCGCT TCACCCCTGGTGG CA (SEQ ID NO: 31) |
| IL-12 (Codon Optimized) | MCHQQLV ISWFSL VFLASPL VA (SEQ ID NO: 112) | — | ATGTGCCATCAG CAACTCGTCATCT CCTGGTTCTCCCT TGTGTTCCTCGCT TCCCCTCTGGTCG CC (SEQ ID NO: 32) |
| IL-2 (Optimized) | MQLLSCI ALILALV (SEQ ID NO: 113) | — | ATGCAACTGCTGT CATGTATCGCAC TCATCCTGGCGCT GGTA (SEQ ID NO: 33) |
| IL-2 (Native) | MYRMQLL SCIALS LALVTNS (SEQ ID NO: 114) | P60568 | ATGTATCGGATGCA ACTTTTGAGCTGCA TCGCATTGTCTCTG GCGCTGGT GACAAATTCC (SEQ ID NO: 34) |
| Trypsinogen-2 | MNLLLIL TFVAAA VA (SEQ ID NO: 115) | P07478 | ATGAATCTCTTGC TCATACTTACGT TTGTCGCTGCTGC CGTTGCG (SEQ ID NO: 35) |
| Gaussia Luciferase | MGVKVLF ALICIA VAEA (SEQ ID NO: 116) | — | ATGGGCGTGAAGG TCTTGTTTGCCC TTATCTGCATAGC TGTTGCGGAGGC G (SEQ ID NO: 36) |
| CD5 | MPMGSL QPLATLY LLGMLVA SCLG (SEQ ID NO: 117) | P06127 | ATGCCGATGGG GAGCCTTCAAC CTTTGGCAACG CTTTATCTTCT GGGGATGTTGG TTGCTAGTTGC CTTGGG (SEQ ID NO: 37) |
| IgKVII (mouse) | METDTLL LWVLLL WVPGSTGD (SEQ ID NO: 118) | | ATGGAAACTGA CACGTTGTTGC TGTGGGTATTG CTCTTGTGGGT CCCAGGATCTA CGGGCGAC (SEQ ID NO: 38) |
| IgKVII (human) | MDMRVPA QLLGL LLLWLRG ARC (SEQ ID NO: 119) | P01597 | ATGGATATGAGG GTTCCCGCCCAG CTTTTGGGGCTG CTTTTGTTGTGG CTTCGAGGGGCT CGGTGT (SEQ ID NO: 39) |

TABLE 5-continued

Exemplary Signal Secretion Peptides

| Name | Protein SEQUENCE | Source (Uniprot) | DNA SEQUENCE |
|---|---|---|---|
| VSV-G | MKCLLYLAFLFIGVNC (SEQ ID NO: 120) | — | ATGAAGTGTCTGTTGTACCTGGCGTTTCTGTTCATTGGTGTAAACTGT (SEQ ID NO: 40) |
| Prolactin | MNIKGSPWKGSLLLLLVSNLLLCQSVAP (SEQ ID NO: 121) | P01236 | ATGAATATCAAAGGAAGTCCGTGGAAGGGTAGTCTCCTGCTGCTCCTCGTATCTAACCTTCTCCTTTGTCAATCCGTGGCACCC (SEQ ID NO: 41) |
| Serum albumin pre-proprotein | MKWVTFISLLFLFSSAYS (SEQ ID NO: 122) | P02768 | ATGAAATGGGTAACATTCATATCACTTCTCTTTCTGTTCAGCTCTGCGTATTCT (SEQ ID NO: 42) |
| Azurocidin Pre-proprotein | MTRLTVLALLAGLLASSRA (SEQ ID NO: 123) | 20160 | ATGACAAGGCTTACTGTTTTGGCTCTCCTGCTGGACTCTTGGCTTCCTCCCGAGCA (SEQ ID NO: 43) |
| Osteonectin (BM40) | MRAWIFFLLCLAGRALA (SEQ ID NO: 124) | P09486 | ATGAGGGCTTGGATTTTTTTTCTGCTCTGCCTTGCCGGTCGAGCCCTGGCG (SEQ ID NO: 44) |
| CD33 | MPLLLLLPLLWAGALA (SEQ ID NO: 125) | P20138 | ATGCCTCTTCTGCTTTTGCTTCCTCTTTTGTGGGCAGGTGCCCTCGCA (SEQ ID NO: 45) |
| IL-6 | MNSFSTSAFGPVAFSLGLLLVLPAAFPAP (SEQ ID NO: 126) | P05231 | ATGAACTCTTTCTCAACCTCTGCGTTTGGTCCGGTCGCTTTCTCCCTTGGGCTCCTGCTTGTCTTGCCAGCAGCGTTTCCTGCGCCA (SEQ ID NO: 46) |
| IL-8 | MTSKLAVALLAAFLISAALC (SEQ ID NO: 127) | P10145 | ATGACAAGTAAACTGGCGGTAGCCTTGCTCGCGGCCTTTTTGATTTCCGCAGCCCTTGT (SEQ ID NO: 47) |
| CCL2 | MKVSAALLCLLLIAATFIPQGLA (SEQ ID NO: 128) | P13500 | ATGAAGGTAAGTGCAGGTTGCTTTGCCTTCTCCTCATTGCAGCGACCTTTATTCCTCAAGGGCTGGCC (SEQ ID NO: 48) |
| TIMP2 | MGAAARTLRLALGLLLLATLLRPADA (SEQ ID NO: 129) | P16035 | ATGGGAGCGGCAGCTAGAACACTTCGACTTGCCCTTGGGCTCTTGCTCCTTGCAACCCTCCTTAGACCTGCCGACGCA (SEQ ID NO: 49) |
| VEGFB | MSPLLRRLLLAALLQLAPAQA (SEQ ID NO: 130) | P49765 | ATGTCACCGTTGTTGCGGAGATTGCTGTTGGCCGCACTTTTGCAACTGGCTCCTGCTCAAGCC (SEQ ID NO: 50) |
| Osteo-protegerin | MNNLLCCALVFLDISIKWTTQ (SEQ ID NO: 131) | O00300 | ATGAATAACCTGCTCTGTTGTGCGCTCGTGTTCCTGGACATTTCTATAAAATGGACAACGCAA (SEQ ID NO: 51) |
| Serpin E1 | MQMSPALTCLVLGLALVFGEGSA (SEQ ID NO: 132) | P05121 | ATGCAAATGTCTCCTGCCCTTACCTGTCTCGTACTTGGTCTTGCGCTCGTATTTGGAGAGGGATCAGCC (SEQ ID NO: 52) |
| GROalpha | MARAALSAAPSNPRLLRVALLLLLLVAAGRRAAG (SEQ ID NO: 133) | P09341 | ATGGCAAGGGCTGCACTCAGTGCTGCCCCGTCTAATCCCAGATTGCTTCGAGTTGCATTGCTTCTGCAGCTGGTAGGAGAGCAGCGGGT (SEQ ID NO: 53) |
| CXCL12 | MNAKVVVVLVLVLTALCLSDG (SEQ ID NO: 134) | P48061 | ATGAATGCAAAAGTCGTGGTCGTGCTGGTTTTGGTTCTGACGGCGTTGTGTCTTAGTGATGGG (SEQ ID NO: 54) |
| IL-21 (Codon Optimized) | MERIVICLMVIFLGTLVHKSSS (SEQ ID NO: 135) | Q9HBE4 | ATGGAACGCATTGTGATCTGCCTGATGGTCATCTTCCTGGGCACCTTAGTGCACAAGTCGAGCAGC (SEQ ID NO: 55) |

Cell Types

The present disclosure refers to mesenchymal stem cells (MSCs) (e.g., human MSCs) engineered to produce multiple effector molecules. An engineered cell (engineered to produce effector molecules), as provided herein, may also be selected from natural killer (NK) cells, NKT cells, innate lymphoid cells, mast cells, eosinophils, basophils, macrophages, neutrophils, and dendritic cells, T cells (e.g., CD8+ T cells, CD4+ T cells, gamma-delta T cells, and T regulatory cells (CD4$^+$, FOXP3$^+$, CD25$^+$)) and B cells. It should be understood, however, that any reference to MSC engineering can also be applied to other cell types (e.g., cell types of the immune system).

In some embodiments, an engineered cell (e.g., MSC) is from (e.g., obtained from or derived from) bone marrow. In some embodiments, an engineered mesenchymal stem cell is from (e.g., obtained from or derived from) adipose tissue. In some embodiments, an engineered mesenchymal stem cell is from (e.g., obtained from or derived from) an umbilical cord. In some embodiments, engineered mesenchymal stem cell is from a pluripotent stem cell (e.g., an embryonic stem cell or an induced pluripotent stem cell).

Thus, the present disclosure provides a T cell (e.g., CD8+ T cell, CD4+ T cell, gamma-delta T cell, or T regulatory cell (CD4$^+$, FOXP3$^+$, CD25$^+$)) engineered to produce multiple effector molecules, at least two of which modulate different tumor-mediated immunosuppressive mechanisms. In some embodiments, a B cell is engineered to produce multiple effector molecules, at least two of which modulate different tumor-mediated immunosuppressive mechanisms. In some embodiments, a NK cell is engineered to produce multiple effector molecules, at least two of which modulate different tumor-mediated immunosuppressive mechanisms. In some embodiments, a NKT cell is engineered to produce multiple effector molecules, at least two of which modulate different tumor-mediated immunosuppressive mechanisms. In some embodiments, an innate lymphoid cell is engineered to produce multiple effector molecules, at least two of which modulate different tumor-mediated immunosuppressive mechanisms. In some embodiments, a mast cell is engineered to produce multiple effector molecules, at least two of which modulate different tumor-mediated immunosuppressive mechanisms. In some embodiments, an eosinophil is engineered to produce multiple effector molecules, at least two of which modulate different tumor-mediated immunosuppressive mechanisms. In some embodiments, a basophil is engineered to produce multiple effector molecules, at least two of which modulate different tumor-mediated immunosuppressive mechanisms. In some embodiments, a macrophage is engineered to produce multiple effector molecules, at least two of which modulate different tumor-mediated immunosuppressive mechanisms. In some embodiments, a neutrophil is engineered to produce multiple effector molecules, at least two of which modulate different tumor-mediated immunosuppressive mechanisms. In some embodiments, a dendritic cell is engineered to produce multiple effector molecules, at least two of which modulate different tumor-mediated immunosuppressive mechanisms.

In some embodiments, at least one of the effector molecules stimulates an immunostimulatory mechanism in the tumor microenvironment and/or inhibits an immunosuppressive mechanism in the tumor microenvironment.

In some embodiments, at least one of the effector molecules (a) stimulates T cell signaling, activity and/or recruitment, (b) stimulates antigen presentation and/or processing, (c) stimulates natural killer cell-mediated cytotoxic signaling, activity and/or recruitment, (d) stimulates dendritic cell differentiation and/or maturation, (e) stimulates immune cell recruitment, (f) stimulates pro-inflammatory macrophage signaling, activity and/or recruitment or inhibits anti-inflammatory macrophage signaling, activity and/or recruitment, (g) stimulates stroma degradation, (h) stimulates immunostimulatory metabolite production, (i) stimulates Type I interferon signaling, (j) inhibits negative costimulatory signaling, (k) inhibits pro-apoptotic signaling of anti-tumor immune cells, (l) inhibits T regulatory (T$_{reg}$) cell signaling, activity and/or recruitment, (m) inhibits tumor checkpoint molecules, (n) stimulates stimulator of interferon genes (STING) signaling, (o) inhibits myeloid-derived suppressor cell signaling, activity and/or recruitment, (p) degrades immunosuppressive factors/metabolites, (q) inhibits vascular endothelial growth factor signaling, and/or (r) directly kills tumor cells.

Methods

Also provided herein are methods that include culturing the engineered MSCs (or other engineered immune cell) of the present disclosure. Methods of culturing MSCs are known. In some embodiments, MSCs are culture in growth medium (e.g., MSCGM human Mesenchymal Stem Cell Growth BULLETKIT™ Medium (serum containing), THERAPEAK™ MSCGM-CD™ Mesenchymal Stem Cell Chemically Defined Medium (serum free), or RoosterBio xeno-free MSC media). Methods of culturing other cells, such as immune cells, are known to those skilled in the art.

Further provided herein are methods that include delivering, or administering, to a subject (e.g., a human subject) engineered cells as provided herein to produce in vivo at least one effector molecule produced by the cells. In some embodiments, the cells are administered via intravenous, intraperitoneal, intratracheal, subcutaneous, intratumoral, oral, anal, intranasal (e.g., packed in a delivery particle), or arterial (e.g., internal carotid artery) routes. Thus, the cells may be administered systemically or locally (e.g., to a TME). The engineered cells or polynucleotides described herein can be in a composition containing a pharmaceutically acceptable carrier, e.g., an aqueous carrier. A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Some methods comprise selecting a subject (or patient population) having a tumor (or cancer) and treating that subject with engineered cells.

The engineered cells of the present disclosure may be used, in some instances, to treat cancer, such as ovarian cancer. Other cancers are described herein. For example, the engineered cells may be used to treat bladder tumors, brain tumors, breast tumors, cervical tumors, colorectal tumors, esophageal tumors, gliomas, kidney tumors, liver tumors, lung tumors, melanomas, ovarian tumors, pancreatic tumors, prostate tumors, skin tumors, thyroid tumors, and/or uterine tumors.

The methods provided herein also include delivering a preparation of engineered cells, such as engineered cells. A preparation, in some embodiments, is a substantially pure preparation, containing, for example, less than 5% (e.g., less than 4%, 3%, 2%, or 1%) of cells other than cells. A preparation may comprise $1\times10^5$ cells/kg to $1\times10^7$ cells/kg, such as engineered cells.

The methods provided herein also include delivering a composition in vivo capable of producing the engineered cells described herein, such as delivering a lentivirus in vivo. Other in vivo delivery mechanisms and systems can also be used, including those known for use in human therapy, such as viral delivery systems (e.g., retroviral or adenoviral systems), transposons (e.g., Sleeping Beauty and PiggyBac transposon systems), integrated using PhiC31 into genomic pseudosites, or using nucleases, such as zinc fingers (ZFs), clustered regularly interspaced short palindromic repeats (CRISPR), or transcription activator-like effector nucleases (TALENs).

TABLE 6

Sequences encoding exemplary effector molecules

IL12 (Human) (SEQ ID NO: 56)
ATGTGCCATCAGCAGCTTGTCATATCTTGGTTTTCACTTGTATTCC
TGGCCAGCCCTTTGGTTGCGATCTGGGAGCTCAAGAAGGATGTGTA
CGTTGTAGAGCTGGACTGGTACCCCGATGCTCCCGGTGAGATGGTC
GTTTTGACATGTGACACTCCAGAAGAGGACGGTATTACGTGGACTC
TGGACCAGTCCTCCGAAGTTCTTGGTTCTGGTAAGACTCTGACTAT
CCAGGTGAAAGAATTTGGGGATGCGGGACAATACACATGCCACAAG
GGAGGCGAGGTGTTGTCTCATAGTTTGCTGCTTCTCCACAAGAAAG
AGGATGGAATCTGGAGCACCGACATACTCAAGGATCAAAAGGAACC
CAAAAATAAGACATTTCTGCGATGTGAGGCTAAGAACTATAGTGGC
CGCTTCACTTGTTGGTGGCTGACTACCATCAGCACAGATCTCACGT
TTTCAGTAAAAAGTAGTAGAGGTTCAAGTGATCCTCAAGGGGTAAC
GTGCGGTGCTGCAACACTGTCTGCTGAACGCGTAAGAGGAGATAAT
AAGGAGTACGAGTATTCCGTAGAATGCCAAGAGGACAGTGCTTGTC
CTGCGGCCGAGGAGTCTCTCCCAATAGAAGTGATGGTGGACGCGGT
GCATAAACTGAAATATGAGAACTACACAAGCAGTTTTTTTATAAGA
GATATCATCAAGCCCGATCCGCCGAAGAATTTGCAACTTAAACCGC
TTAAAAACTCACGCCAGGTTGAAGTATCCTGGGAGTATCCGGATAC
ATGGTCAACACCACACAGCTATTTTTCCCTTACCTTCTGTGTGCAG
GTCCAAGGGAAGAGCAAAAGGGAGAAGAAGGACAGGGTATTCACTG
ATAAAACTTCCGCGACGGTCATCTGCCGAAAAAACGCTAGTATATC
TGTACGGGCGCAGGATAGGTACTATAGTTCTTCTTGGTCTGAGTGG
GCCTCAGTTCCGTGCTCTGGGGGAGGAAGTGGAGGAGGGTCCGGCG
GTGGAAGCGGGGGAGGGAGTCGCAACTTGCCAGTGGCTACACCAGA
TCCAGGCATGTTTCCATGTCTGCATCATTCCCAGAATCTCCTGAGA
GCGGTGTCAAATATGCTCAAAAAGCGAGACAAACACTGGAATTTT
ACCCGTGTACCAGTGAGGAGATTGATCACGAGGACATAACCAAGGA
CAAGACCTCAACTGTAGAAGCGTGTTTGCCGCTGGAGATTGACAAG
AATGAGTCCTGCCTCAATTCCAGAGAAACTTCATTCATTACTAACG
GCAGTTGTCTTGCATCCCGGAAAACGTCCTTTATGATGGCCCTTTG
CCTTAGTTCAATTTACGAGGATCTTAAAATGTATCAAGTGGAGTTT
AAAACCATGAATGCTAAACTTCTTATGGACCCCAAACGACAAATTT
TTCTGGATCAGAATATGCTTGCCGTGATAGACGAACTCATGCAGGC
GCTTAATTTTAACTCCGAAACAGTTCCACAAAAATCTAGCCTTGAA
GAACCTGATTTTTATAAAACGAAGATTAAACTGTGTATCCTGCTGC
ATGCCTTTCGCATCCGAGCTGTCACAATCGATAGGGTTATGTCCTA
CCTTAACGCGAGCtaG IL12p70 (Human; codon optimized;
bold denotes signal sequence)
(SEQ ID NO: 57)
**ATGTGCCATCAGCAACTCGTCATCTCCTGGTTCTCCCTTGTGTTCC
TCGCTTCCCCTCTGGTCGCC**ATTTGGGAACTGAAGAAGGACGTCTA
CGTGGTCGAGCTGGATTGGTACCCGGACGCCCCTGGAGAAATGGTC
GTGCTGACTTGCGATACGCCAGAAGAGGACGGCATAACCTGGACCC
TGGATCAGAGCTCCGAGGTGCTCGGAAGCGGAAAGACCCTGACCAT
TCAAGTCAAGGAGTTCGGCGACGCGGGCCAGTACACTTGCCACAAG
GGTGGCGAAGTGCTGTCCCACTCCCTGCTGCTGCTGCACAAGAAAG
AGGATGGAATCTGGTCCACTGACATCCTCAAGGACCAAAAGGAACC
GAAGAACAAGACCTTCCTCCGCTGCGAAGCCAAGAACTACAGCGGT
CGGTTCACCTGTTGGTGGCTGACGACAATCTCCACCGACCTGACTT
TCTCCGTGAAGTCGTCACGGGGATCAAGCGATCCTCAGGGCGTGAC
CTGTGGAGCCGCCACTCTGCTCCGCCGAGAGAGTCAGGGGAGACAA
AAGGAATATGAGTACTCCGTGGAATGCCAGGAGGACAGCGCCTGCC
CTGCCGCGAAGAGTCCCTGCCTATCGAGGTCATGGTCGATGCCGT
GCATAAGCTGAAATACGAGAACTACACTTCCTCCTTCTTTATCCGC
GACATCATCAAGCCCTGACCCCCCAAGAACTTGCAGCTGAAGCCAC
TCAAGAACTCCCGCCAAGTGGAAGTGTCTTGGGAATATCCAGACAC
TTGGAGCACCCCGCCACTCATACTTCTCGCTCACTTTCTGTGTGCAA
GTGCAGGGAAAGTCCAAACGGGAGAAGAAAGACCGGGTGTTCACCG
ACAAACCTCCGCCACTGTGATTTGTCGGAAGAACGCGTCAATCAC
CGTCCGGGCGCAGGATAGATACTACTCGTCCTCCTGGAGCGAATGG
GCCAGCGTGCCTTGTTCCGGTGGCGGATCAGGCGGAGGTTCAGGAG
GAGGCTCCGGAGGAGGTTCCCGGAACCTCCCTGTGGCAACCCCCGA
CCCTGGAATGTTCCCGTGCCTACACCACTCCCAAAACCTCCTGAGG
GCTGTGTCGAACATGTTGCAGAAGGCCCGCCAGACCCTTGAGTTCT TABLE 6-continued Sequences encoding exemplary effector molecules ACCCCTGCACCTCGGAAGAAATTGATCACGAGGACATCACCAAGGA
CAAGACCTCGACCGTGGAAGCCTGCCTGCCGCTGGAACTGACCAAG
AACGAATCGTGTCTGAACTCCCGCGAGACAAGCTTTATCACTAACG
GCAGCTGCCTGGCGTCGAGAAAGACCTCATTCATGATGGCGCTCTG
TCTTTCCTCGATCTACGAAGATCTGAAGATGTATCAGGTCGAGTTC
AAGACCATGAACGCCAAGCTGCTCATGGACCCGAAGCGGCAGATCT
TCCTGGACCAGAATATGCTCGCCGTGATTGATGAACTGATGCAGGC
CCTGAATTTCAACTCCGAGACTGTGCCTCAAAAGTCCAGCCTGGAA
GAACCGGACTTCTACAAGACCAAGATCAAGCTGTGCATCCTGTTGC
ACGCTTTCCGCATTCGAGCCGTGACCATTGACCGCGTGATGTCCTA
CCTGAACGCCAGT IL12 (Mouse) (SEQ ID NO: 58)
ATGTGTCCACAGAAGCTGACAATAAGTTGGTTTGCCATTGTCCTCC
TGGTGAGCCCACTCATGGCAATGTGGGAACTCGAAAAGGATGTCTA
CGTGGTAGAAGTAGATTGGACTCCAGACGCGCCAGGGGAGACAGTG
AATTTGACATGTGACACACCAGAAGAAGATGACATTACATGGACAT
CTGACCAACGCCATGGCGTAATAGGGAGTGGGAAAACATTCACGAT
CACAGTTAAAGAGTTCTTGGATGCTGGTCAATATACTTGCCATAAA
GGCGGCGAGACACTCAGCCACTCACATTTGCTTTTGCATAAAAAAG
AGAATGGCATTTGGAGCACTGAAATACTTAAGAACTTTAAGAACAA
GACATTTCTCAAGTGTGAGGCCCCTAATTACAGCGGCAGGTTCACG
TGCTCATGGCTGGTCCAGCGACAACATGGACCTCAAGTTTAACATAA
AATCTTCTTCCTCTTCACCTGACTCCAGAGCTGTTACTTGCGGCAT
GGCTTCTCTGAGCGCAGAAAAAGTAACGTTGGATCAAAGAGACTAC
GAAAAGTACTCTGTTTCTTGTCAAGAGGATGTTACGTGCCCGACGG
CCGAAGAAACGCTTCCAATTGAACTCGCGTTGGAAGCTCGCCAACA
AAACAAGTATGAAAACTACAGTACAAGCTTCTTTATCGGGATATA
ATTAAACCCGATCCCCCCAAGAACTTGCAAATGAAACCACTTAAGA
ACAGCCAGGTGGAAGTTTCCTGGGAGTATCCAGACTCATGGAGTAC
TCCTCACAGCTATTTTTCTCTGAAATTCTTTGTAAGGATACAACGG
AAGAAAGAGAAGATGAAAGAGACCGAGGAGGGTTGTAATCAGAAGG
GAGCGTTTCTCGTGGAGAAAACGTCTACCGAAGTCCAATGTAAAGG
TGGCAATGTGTGCGTCCAAGCTCAGGATAGATACTATAATTCAAGT
TGCTCCAAGTGGGCCTGTGTTCCATGCCGCGTTCGGAGCGGGGGAG
GTAGCGGAGGAGGTAGTGGGGGTGGGTCAGGAGGAGGGAGTCGAGT
TATCCCGGTGTCAGGCCCCGCACGCTGCTTGAGCCAGAGTCGCAAC
CTCCTTAAGCAACAGATGACATGGTGAAAACAGCACGCGAAAAGC
TTAAACACTACTCTTGTACGCGGAGGATATTGATCACGAGGATAT
TACCCGAGACCAAACTAGCACTTTGAAAACCTGTCTGCCCCTTGAA
CTTCATAAAAATGAGAGCTGTCTGGCTACACGAGAGACGTCAAGTA
CGACTAGGGGCAGCTGTCTCCCGCCGCAAAAGACAAGCCTCATGAT
GACGCTCTGTTTGGGTTCCATTTACGAGGACTTGAAAATGTATCAA
ACGGAGTTCCAGGCTATAAATGCGGCGTTGCAGAACCATAACCATC
AACAAATTATACTTGATAAAGGCATGTTGGTGGCGATTGATGAACT
CATGCAGAGTCTCAATCACAACGGGGAAACGTTGAGACAGAAACCC
CCAGTCGGTGAAGCGGACCCATATCGAGTAAAAATGAAGCTCTGCA
TTCTGCTTCACGCATTCAGCACTAGAGTTGTTACCATCAACCGGGT
AATGGGATATCTCTCCAGTGCGtaG IL21 (Human; codon optimized; bold denotes
signal sequence)
(SEQ ID NO: 59)
**ATGGAACGCATTGTGATCTGCCTGATGGTCATCTTCCTGGGCACCT
TAGTGCACAAGTCGAGCAGCC**AGGGACAGGACAGGCACATGATTAG
AATGCGCCAGCTCATCGATATCGTGGACCAGTTGAAGAACTACGTG
AACGACCTGGTGCCCGAGTTCCTGCCGGCCCCCGAAGATGTGGAAA
CCAATTGCGAATGGTCGGCATTTTCCTGCTTTCAAAAGGCACAGCT
CAAGTCCGCTAACACCGGGAACAACGAACGGATCATCAACGTGTCC
ATCAAAAAGCTGAAGCGGAAGCCTCCCTCCACCAACGCCGGACGGA
GGCAGAAGCATAGGCTGACTTGCCCGTCATGCGACTCCTACGAGAA
GAAGCCGCCAAGGAGTTCCTGGAGCGGTTCAAGTCGCTCCTGCAA
AAGATGATTCATCAGCACCTGTCCTCCCGGACTCATGGGTCTGAGG
ATTCA IL12p70_T2A_IL21
(Human; codon optimized; bold denotes
signal sequences) (SEQ ID NO: 60)
**ATGTGCCATCAGCAACTCGTCATCTCCTGGTTCTCCCTTGTGTTCC
TCGCTTCCCCTCTGGTCGCC**ATTTGGGAACTGAAGAAGGACGTCTA
CGTGGTCGAGCTGGATTGGTACCCGGACGCCCCTGGAGAAATGGTC
GTGCTGACTTGCGATACGCCAGAAGAGGACGGCATAACCTGGACCC
TGGATCAGAGCTCCGAGGTGCTCGGAAGCGGAAAGACCCTGACCAT
TCAAGTCAAGGAGTTCGGCGACGCGGGCCAGTACACTTGCCACAAG
GGTGGCGAAGTGCTGTCCCACTCCCTGCTGCTGCTGCACAAGAAAG
AGGATGGAATCTGGTCCACTGACATCCTCAAGGACCAAAAGGAACC
GAAGAACAAGACCTTCCTCCGCTGCGAAGCCAAGAACTACAGCGGT TABLE 6-continued Sequences encoding exemplary
effector molecules CGGTTCACCTGTTGGTGGCTGACGACAATCTCCACCGACCTGACTT
TCTCCGTGAAGTCGTCACGGGGATCAAGCGATCCTCAGGGCGTGAC
CTGTGGAGCCGCCACTCTGTCCGCCGAGAGAGTCAGGGGAGACAAC
AAGGAATATGAGTACTCCGTGGAATGCCAGGAGGACAGCGCCTGCC
CTGCCGCGGAAGAGTCCCTGCCTATCGAGGTCATGGTCGATGCCGT
GCATAAGCTGAAATACGAGAACTACACTTCCTCCTTCTTTATCCGC
GACATCATCAAGCCTGACCCCCCAAGAACTTGCAGCTGAAGCCAC
TCAAGAACTCCCGCCAAGTGGAAGTGTCTTGGGAATATCCAGACAC
TTGGAGCACCCCGCACTCATACTTCTCGCTCACTTTCTGTGTGCAA
GTGCAGGGAAAGTCCAAACGGGAGAAGAAAGACCGGGTGTTCACCG
ACAAAACCTCCGCCACTGTGATTTGTCGGAAGAACGCGTCAATCAG
CGTCCGGGCGCAGGATAGATACTACTCGTCCTCCTGGAGCGAATGG
GCCAGCGTGCCTTGTTCCGGTGGCGGATCAGGCGGAGGTTCAGGAG
GAGGCTCCGGAGGAGGTTCCCGGAACCTCCCTGTGGCAACCCCCGA
CCCTGGAATGTTCCCGTGCCTACACCACTCCCAAAACCTCCTGAGG
GCTGTGTCGAACATGTTGCAGAAGGCCCGCCAGACCCTTGAGTTCT
ACCCCTGCACCTCGGAAGAAATTGATCACGAGGACATCACCAAGGA
CAAGACCTCGACCGTGGAAGCCTGCCTGCCGCTGGAACTGACCAAG
AACGAATCGTGTCTGAACTCCCGCGAGACAAGCTTTATCACTAACG
GCAGCTGCCTGGCGTCGAGAAAGACCTCATTCATGATGGCGCTCTG
TCTTTCCTCGATCTACGAAGATCTGAAGATGTATCAGGTCGAGTTC
AAGACCATGAACGCCAAGCTGCTCATGGACCCGAAGCGGCAGATCT
TCCTGGACCAGAATATGCTCGCCGTGATTGATGAACTGATGCAGGC
CCTGAATTTCAACTCCGAGACTGTGCCTCAAAAGTCCAGCCTGGAA
GAACCGGACTTCTACAAGACCAAGATCAAGCTGTGCATCCTGTTGC
ACGCCTTTCGCATTCGAGCCGTGACCATTGACCGCGTGATGTCCTA
CCTGAACGCCAGTAGACGGAAACGCGGAAGCGGAGAGGGCAGAGGC
TCGCTGCTTACATGCGGGGACGTGGAAGAGAACCCCGGTCCG**ATGG
AACGCATTGTGATCTGCCTGATGGTCATCTTCCTGGGCACCTTAGT
GCACAAGTCGAGCAGC**CAGGGACAGGACAGGACAGCACATGATTAGAATG
CGCCAGCTCATCGATATCGTGGACCAGTTGAAGAACTACGTGAACG
ACCTGGTGCCCGAGTTCCTGCCGGCCCCGAAGATGTGGAAACCAA
TTGCGAATGGTCGGCATTTTCCTGCTTTCAAAAGGCACAGCTCAAG
TCCGCTAACACCGGGAACAACGAACGGATCATCAACGTGTCCATCA
AAAAGCTGAAGCGGAAGCCTCCCTCCACCAACGCCGGACGGAGGCA
GAAGCATAGGCTGACTTGCCCGTCATGCGACTCCTACGAGAAGAAG
CCGCCGAAGGAGTTCCTGGAGCGGTTCAAGTCGCTCCTGCAAAAGA
TGATTCATCAGCACCTGTCCTCCCGGACTCATGGGTCTGAGGATTC
A IL-12 2A CCL21a (Human) (SEQ ID NO: 61)
ATGTGCCATCAGCAGCTTGTCATATCTTGGTTTTCACTTGTATTCC
TGGCCAGCCCTTTGTTGCGATCTGGGAGCTCAAGAAGGATGTGTA
CGTTGTAGAGCTGGACTGGTACCCCGATGCTCCCGGTGAGATGGTC
GTTTTGACATGTGACACTCCAGAAGAGGACGGTATTACGTGGACTG
TGGACCAGTCCTCCGAAGTTCTTGGTTCTGGTAAGACTCTGACTAT
CCAGGTGAAAGAATTTGGGGATGCGGGACAATACAATATCAAGGCG
GGAGGCGAGGTGTTGTCTCATAGTTTGCTGCTTCTCCACAAGAAAG
AGGATGGAATCTGGAGCACCGACATACTCAAGGATCAAAAGGAACC
CAAAAATAAGACATTTCTGCGATGTGAGGCTAAGAACTATAGTGGC
CGCTTCACTTGTTGGTGGCTGACTACCATCAGCACAGATCTCACGT
TTTCAGTAAAAAGTAGTAGAGGTTCAAGTGATCCTCAAGGGGTAAC
GTGCGGTGCTGCAACACTGTCTGCTGAACGCGTAAGAGGAGATAAT
AAGGAGTACGAGTATTCCGTAGAATGCCAAGAGGACAGTGCTTGTC
CTGCGGCCGAGGAGTCTCTCCCAATAGAAGTGGTGGCGAGGCTTG
GCATAAACTGAAATATGAGAACTACACAAGCAGTTTTTTTATAAGA
GATATCATCAAGCCCGATCCGCCGAAGAATTTGCAACTTAAACGC
TTAAAAACTCACGCCAGGTTGAAGTATCCTGGGAGTATCCGGATAC
ATGGTCAACACCACACGCTATTTTCCCTTACCTTCTGTGTGCAG
GTCCAGGGAAGAGCAAAAGGGAGAGAAGGACAGGTATTCACTG
ATAAAACTTCCGCGACGGTCATCTGCCGAAAAAAGCTAGTATATC
TGTACGGGCGCAGGATAGGTACTATAGTTCTTCTTGGTCTGAGTGG
GCCTCAGTTCCGTGCTCTGGGGAGGAAGTGGAGGAGGGTCCGGCG
GTGGAGCGGGGAGGGAGTGCATCTGCCAGTGGCTGCACAGGA
TCCAGGCATGTTTCATGTCTGCATCATTCCCAGAATCTCCTGAGA
GCGGTGTCAAATATGCTCAAAAAGCGAGACAAACACTGGAATTTT
ACCCGTGTACCAGTGAGGAGATTGATCACGAGGACATAACCAAGGA
CAAGACCTCAACTGTAGAAGCGTGTTTGCCGCTGGAGTTGACTAAG
AATGAGTTCCTGCCTCAATTCCAGAGAAACTTCATTCATTACTAACG
GCAGTTGTCTTGCATCCCGGAAAACGTCTTTATGATGGCCCTTTG
CCTTAGTTCAATTTACGAGGATCTTAAAATGTATCAAGTGGAGTTT
AAAACCATGAATGCTAAACTTCTTATGGACCCCAAACGACAAATTT
TTCTGGATCAGAATATGCTTGCCGTGATAGACGAACTCATGCAGGC
GCTTAATTTTAACTCCGAAACAGTTCCACAAAATCTAGCCTTGAA
GAACCTGATTTTATAAAACGAAGATTAAACTGTGTATCCTGCTGC
ATGCCTTTCGCATCCGAGCTGTCACAATCGATAGGGTTATGTCCTA
CCTTAACGCGAGCCGGCGCAAGAGGGGTTCCGGAGAGGGAAGGGGT AGTCTGCTCACCTGCGGCGATGTTGAAGAAAATCCTGGTCCCATGG
CGCAAAGTCTGGCTCTTTCACTCCTGATCCTGGTCTTGGCCTTCGG
GATTCCGAGGACCCAAGGAAGTGATGGTGGCGCCCAAGATTGTTGC
CTTAAATACAGCCAGCGGAAAATACCCGCGAAAGTGGTCAGGAGTT
ATAGAAACACAGGAGCCTTCCCTGGGTTGTAGTATCCCCGCCATACT
TTTCCTCCCGAGAAAACGGAGCCAGGCCGAACTGTGCGCTGACCCT
AAGGAACTTTGGGTGCAACAACTTATGCAACACCTGGATAAGACAC
CTTCTCCTCAAAAGCCAGCTCAGGGCTGCCGAAAAGATAGAGGCGC
CTCAAAAACCGGAAAAAGGGCAAAGGTTCTAAAGGATGTAAGCGG
ACTGAACGCTCTCAAACGCCTAAAGGGCCGtaG IL-12 2A CCL21a (Mouse) (SEQ ID NO: 62)
ATGTGTCCACAGAAGCTGACAATAAGTTGGTTTGCCATTGTCCTCC
TGGTGAGCCCACTCATGGCAATGTGGGAACTCGAAAAGGATGTCTA
CGTGGTAGAAGTAGATTGGACTCCAGACGCGCCAGGGGAGACAGTG
AATTTGACATGTGACACACCAGAAGAAGATGACATTACATGGACAT
CTGACCAACGCCATGGCGTAATAGGGAGTGGGAAAACACTCACGAT
CACAGTTAAAGATTTCTTGGATGCTGGTCAATATACTTGCCATAAA
GGCGGCGAGACACTCAGCCACTCACATTTGCTTTTGCATAAAAAAG
AGAATGGCATTTGGAGCACTGAAATACTTAAGAACTTTAAGAACAA
GACATTTCTCAAGTGTGAGGCCCCTAATTACAGCGGCAGGTTCACG
TGCTCATGGCTGTCCAGCGCAACATGGACCTCAAGTTTAACATAA
AATCTTCTTCCTCTTCACCTGACTCCAGAGCTGTTACTTGCGGCAT
GGCTTCTCTGAGCGCAGAAAAGTAACGTTGGATCAAAGAGACTAC
GAAAAGTACTCTGTTTCTTGTCAAGAGGATGTTACGTGCCCGACGG
CCGAAGAACGCTTCCAATTGAACTCGCGTTGGAAGCTCGCCAACA
AAACAAGTATGAAAACTACAGTACAAGCTTCTTTATACGGGATATA
ATTAAACCCGATCCCCCAAGAACTTGCAAATGAAACCACTTAAGA
ACAGCCAGGTGGAAGTTTCCTGGGAGTATCCAGACTCATGGAGTAC
TCCTCACACGTCATTTTTCTCTGAAATTCTTTGTAAGGATACAACGG
AAGAAAGAGAAGATGAAAGAGACCGAGGAGGGTTGTAATCAGAAGG
GAGCGTTTCTCGTGGAGAAAACGTCTACCGAAGTCCAATGTAAGG
TGGCAATGTGTGCGTCCAAGCTCAGGATAGATACTATAATTCAAGT
TGCTCCAAGTGGGCCTGTGTTCCATGCCGCGTTCGGAGCGGGGGAG
GTAGCGGAGGAGGTAGTGGGGGTGGGTCAGGAGGAGGGAGTCGAGT
TATCCCGGTGTCAGGCCCCGCACGCTGCTTGAGCCAGAGTCGCAAC
CTCCTTAAGCAACAGATGACATGGTGAAAACAGCACGCGAAAAGC
TTAAACACTACTCTTGTACGGCGGAGGATATTGACACGAGGATAT
TACCCGAGACCAAACTAGCACTTTGAAAACCTGTCTGCCCCTTGAA
CTTCATAAAAATGAGAGCTGTCTGGCTACACGAGAGACGTCAAGTA
CGACTAGGGGCAGCTGTCTCCCGCCGCAAAAGACAAGCCTCATGAT
GACGCTCTGTTTGGGTTCCATTTACGAGGACTTGAAATGTATCAA
ACGGAGTTCCAGGCTATAAATGCGGCGTTGCAGAACCATAACCATC
AACAATTATACTTATAAAGGCATGTTGGTGGCGATTGATGAACT
CATGCAGAGTCTCAATCACAACGGGAAACGTTGAGACAGAAACCC
CCAGTCGGTGAAGCGGACCCATATCGAGTAAAATGAAGCTCTGCA
TTCTGCTTCACGCATTCAGCACTAGAGTTGTTACCATCAACCGGT
AATGGGATATCTCTCCAGTGCGCGGCCAAGAGGGTTCCGGAGAG
GGAAGGGGTAGTCTGCTCACCTGCGGCGATGTTGAAGAAAATCCTG
GTCCCATGGCGCAAATGATGACCCTTTCCCTGCTGAGTCTTGTCCT
CGCGCTCTGCATCCCGTGGACGCAGGGGTCTGATGGGGGGGCCAA
GACTGTTGCCTGAAGTATTCACAAAAAAAGATACCGTACTCTATTG
TCAGAGGGTACAGGAAGCAAGAACCCTCCTTGGGTTGCCCTATACC
AGCAATTCTTTTCTCCCCACGCAAGCATTCCAAACCAGAACTGTGT
GCGAACCCCGAGGAGGGTTGGGTACAGAACTTGATGCGAAGGCTTG
ACCAGCCCCCAGCCCCTCGGCAAGCAGTCACCTGGGTGCAGAAAAA
CAGAGGTACTTCAAAGAGCGGCAAGAAAGGCAAAGGGAGTAAAGGA
TGTAAAAGAACGGAGCAGACCCAGCCTTCACGAGGCtaG CCL21a 2A IL-12 (Mouse) (SEQ ID NO: 63)
ATGGCGCAAATGATGACCCTTTCCCTGCTGAGTCTTGTCCTCGCGC
TCTGCATCCCGTGGACGCAGGGGTCTGATGGGGGGGCCAAGACTG
TTGCCTGAAGTATTCACAAAAAAAGATACCGTACTCTATTGTCAGA
GGGTACAGGAAGCAAGAACCCTCCTTGGGTTGCCCTATACCAGCAA
TTCTTTTCTCCCCACGCAAGCATTCCAAACCAGAACTGTGTGCGAA
CCCCGAGGAGGGTTGGGTACAGAACTTGATGCGAAGGCTTGACCAG
CCCCCAGCCCCTGGCAAGCAGTCACCTGGGTGCAGAAAAAACAGAG
GTACTTCAAAGAGCGGCAAGAAAGGCAAAGGGAGTAAAGGATGTAA
AGAACGGAGCAGACCCAGCCTTCACGAGGCGGCGCAAGAGGGGT
TCCGGAGAGGGAAGGGGTAGTCTGCTCACCTGCGGCGATGTTGAAG
AAAATCCTGGTCCCATGTGTCCACAGAAGCTGACAATAAGTTGGTT
TGCCATTGTCCTCCTGGTGAGCCCACTCATGGCAATGTGGGAACTC
GAAAAGGATGTCTACGTGGTAGAAGTAGATTGGACTCCAGACGCGC
CAGGGGAGACAGTGAATTTGACATGTGACACACCAGAAGAAGATGA
CATTACATGGACATCTGACCAACGCCATGGCGTAATAGGGAGTGGG
AAAACACTCACGATCACAGTTAAAGAGTTCTTGGATGCTGGTCAAT
ATACTTGCCATAAAGGCGGCGAGACACTCAGCCACTCACATTTGCT TABLE 6-continued Sequences encoding exemplary
effector molecules TTTGCATAAAAAAGAGAATGGCATTTGGAGCACTGAAATACTTAAG
AACTTTAAGAACAAGACATTTCTCAAGTGTGAGGCCCCTAATTACA
GCGGCAGGTTCACGTGCTCATGGCTGGTCCAGCGCAACATGGACCT
CAAGTTTAACATAAAATCTTCTTCCTCTTCACCTGACTCCAGAGCT
GTTACTTGCGGCATGGCTTCTCTGAGCGCAGAAAAAGTAACGTTGG
ATCAAAGAGACTACGAAAAGTACTCTGTTTCTTGTCAAGAGGATGT
TACGTGCCCGACGGCCGAAGAAACGCTTCCAATTGAACTCGCGTTG
GAAGCTCGCCAACAAAACAAGTATGAAAACTACAGTACAAGCTTCT
TTATACGGGATATAATTAAACCCGATCCCCCCAAGAACTTGCAAAT
GAAACCACTTAAGAACAGCCAGGTGGAAGTTTCCTGGGAGTATCCA
GACTCATGGAGTACTCCTCACAGCTATTTTTCTCTGAAATTCTTTG
TAAGGATACAACGGAAGAAAGAGAAGATGAAAGAGACCGAGGAGGG
TTGTAATCAGAAGGGAGCGTTTCTCGTGGAGAAAACGTCTACCGAA
GTCCAATGTAAAGGTGGCAATGTGTCGCGTCCAAGCTCAGGATAGAT
ACTATAATTCAAGTTGCTCCAAGTGGGCCTGTGTTCCATGCCGCGT
TCGGAGCGGGGGAGGTAGCGGAGGAGGTAGTGGGGGTGGGTCAGGA
GGAGGGAGTCGAGTTATCCCGGTGTCAGGCCCCGCACGCTGCTTGA
GCCAGAGTCGCAACCTCCTTAAGACAACAGATGACATGGTGAAAAC
AGCACGCGAAAAGCTTAAACACTACTCTTGTACGGCGGAGGATATT
GATCACGAGGATATTACCCGAGACCAAACTAGCACTTTGAAAACCT
GTCTGCCCCTTGAACTTCATAAAAATGAGAGCTGTCTGGCTACACG
AGAGACGTCAAGTACGACTAGGGGCAGCTGTCTCCCGCCGCAAAAG
ACAAGCCTCATGATGACGCTCTGTTTGGGTTCCATTTACGAGGACT
TGAAAATGTATCAAACGGAGTTCCAGGCTATAAATGCGGCGTTGCA
GAACCATAACCATCAACAAATTATACTTGATAAAGGCATGTTGGTG
GCGATTGATGAACTCATGCGAGTCTCAATCACAACGGGGAAACGT
TGAGACAGAAACCCCCAGTCGGTGAAGCGGACCCATATCGAGTAAA
AATGAAGCTCTGCATTCTGCTTCACGCATTCAGCACTAGAGTTGTT
ACCATCAACCGGGTAATGGGATATCTCTCCAGTGCGtaG IL7 (Mouse) (SEQ ID NO: 64)
ATGTTTCATGTGTCCTTCAGGTACATATTTGGTATCCCACCACTTA
TATTGGTGCTCTTGCCTGTAACCAGCTCTGAATGTCATATAAAAGA
CAAGGAGGGCAAAGACATACGAGTCCGTATTGATGATCTCAATCGAT
GAACTTGACAAGATGACAGGGACCGATTCTAATTGTCCAAATAACG
AGCCAAACTTCTTTCGGAAACACGTGTGTGATGATACAAAAGAAGC
TGCTTTTCTTAACAGAGCTGCCAGAAAACTCAAGCAGTTCCTCAAG
ATGAATATATCCGAGGAATTTAACGTGCATCTCCTCACAGTATCTC
AGGGAACTCAAACCCTTGTAAACTGCACTTCTAAGGAGGAGAAGAA
TGTCAAAGAGCAGAAGAAAAATGATGCATGTTTTTTGAAACGGCTG
TTGAGGGAGATCAAACATGCTGGAATAAAATCCTCAAGGGCTCAA
TTtaG IL15 (Human) (SEQ ID NO: 65)
ATGGAAACAGACACATTGCTGCTTTGGGTATTGTTGCTCTGGGTGC
CTGGATCAACAGGAAACTGGGTAAACGTAATTTCAGATCTGAAGAA
GATCGAGGACCTTATTCAATCCATGCACATCGATGCCACTCTCTAC
ACCGAAAAGCGACGTTCACCCATCTTGCAAGGTGACCGCTATGAAAT
GTGAATTGTTGGAACTTCAGGTAATTTCTCTGGAGAGCGGCGATGC
CTCAATACATGACACCGTTGAAAATCTTATCATCCTTGCTAATGAT
TCACTCTCTAGTAATGGGAACGTAACAGAGAGCGGGTGTAAGGAGT
GTGAAGAACTGGAGGAGAAAAACATTAAGGAATTTTTGCAGTCATT
CGTCCATATAGTGCAAATGTTCATAAACACTTCCAGAAGAAAGCGA
GGCTCTGGGGAGGGGCGAGGCTCTCTGCTGACCTGTGGGGATGTAG
AAGAGAATCCAGGTCCCATGGACCGGCTGACCAGCTCATTCCTGCT
TCTGATTGTGCCAGCCTACGTGCTCTCCATCACATGTCCTCCCCCA
ATGAGCGTCGAGCATGCTGACATCTGGGTGAAGTCATACTCCTTGT
ACAGCAGAGAGAGATACATTTGTAATTCCGGATTCAAGCGCAAGGC
CGGCACCTCCTCTCTGACAGAGTGCGTCCTTAACAAAGCAACCAAC
GTAGCACATTGGACACAACCATCCTTGAAGTGCATACGAGAACCTA
AATCTTGCGATAAGCATCATACTTGTCCACCTTGTCCAGCCCCAGA
ACTGCTTGGCGGACCCTCAGTATTTTGTTCCCACCAAAGCCAAAA
GACACACTCATGATATCCAGAACTCCTGAGGTGACCTGTGTCGTTG
TAGACGTTTCCCACGAAGATCCTGAAGTAAAATTCAACTGGTACGT
GGATGGGGTCGAAGTCCATAACGCCAAGACTAAACCAAGGGAGGAA
CAGTATAACTCTACTTACCGAGTAGTTTCTGTGTTGACCGTGCTGC
ACCAGGACTGGTTGAACGGGAAGGAGTACAAATGCAAGGTGAGCAA
TAAAGCTCTGCCCGCCACCAATCGAAAAGACAATATCTAAGGCCAAG
GGGCAGCCACGAGAGCCCCAGGTATACACACTGCCACCCTCACGCG
ATGAATTGACTAAGAACCAGGTTTCCCTGACCTGTCTTGTAAAAGG
TTTCTACCCTTCCGACATAGCTGTTGAGTGGGAAAGTAACGGGCAG
CCAGAGAACAATTACAAGACAACTCCACCCGTTCTTGACTCAGACG
GATCATTTTTCTGTATTCCAAACTCACTGTCGATAAAAGTCGCTG
GCAGCAAGGCAATGTTTTAGCTGCTCAGTCATGCACGAAGCACTG
CATAATCACTACACACAAAAAAGTTTGTCCCTTAGCCCTGGTAAGt
aG IL15 (Human) (SEQ ID NO: 66)
ATGTACTCAATGCAGTTGGCCTCCTGTGTAACATTGACCTTGGTCC
TCTTGGTCAACAGCAATTGGATCGATGTACGCTACGACTTGGAGAA
GATTGAGTCCCTTATACAGAGTATACACATAGATACAACCTTGTAT
ACTGACAGTGACTTCCATCCCAGCTGTAAAGTGACTGCAATGAACT
GTTTTTTGTTGGAGTTGCAAGTAATTCTGCATGAATACAGCAACAT
GACCCTCAATGAAACCGTTAGGAATGTCCTTTATCTCGCAAATTCT
ACTCTGAGTAGCAATAAGAATGTTGCCGAAAGCGGCTGCAAGGAGT
GCGAAGAACTGGAGGAAAAAACTTTCACCGAGTTTCTCCAGAGTTT
CATCAGAATTGTCCAAATGTTCATTAATACAAGTAGTGGTGGTGGG
AGCGGGGGTGGAGGCAGTGGGGGAGGTGGGAGCGGAGGTGGAGGGT
CCGGAGGGGGAGCCTTCAAGGCACTACTTGTCCTCCACCCGTATC
CATCGAGCACGCCGATATTCGAGTTAAAAATTATAGTGTTAATAGC
AGAGAACGATACGTCTGCAACTCAGGGTTTAAGAGAAGTGGCCGGAA
CTTCAACTCTCATAGAATGCGTGATTAATAAGAATACTAACGTCGC
ACATTGGACTACTCCCAGTCTCAAGTGCATACGCGATCCATCTCTC
GCTCATTACTCACCAGTACCTACAGTGGTTACTCCTAAGGTGACCT
CTCAGCCCCGAATCACCATCTCCCAGCGCAAAAGAGCCTGAGGCCTT
TTCTCCTAAATCAGACACTGCTCATGACTACAGAAACAGCCATAATG
CCAGGAAGCCGGCTGACACCATCTCAAACTACCAGCGCAGGCACAA
CTGGGACTGGCTCCCACAAAAGCTCACGCGCACCAAGTCTCGCCGC
AACAATGACATTGACGCCTACAGCCAGCACATCTCTTAGAATCACA
GAAATTTCTCCCCACAGTAGCAAGATGACCAAGGTGGCAATTAGTA
CCAGCGTCCTTCTTGTAGGAGCTGGAGTTGTGATGGCATTTTTGGC
ATGGTATATCAAAAGCAGGtaG IL15 (Mouse) (SEQ ID NO: 67)
ATGAAGATCCTCAAGCCATACATGCGAAACACTAGTATTAGCTGTT
ACTTGTGTTTTCTGCTGAATAGTCATTTTTTGACTGAAGCAGGAAT
CCATGTATTTATACTCGGTTGTGTGTCTGTAGGTCTGCCAAAGCAT
GAGGCTAATTGGATTGACGTGCGCTATGATCTTGAAAAAATAGAGT
CCTTGATTCAATCAATACACATCGATACCACTCTCTACACCGACAG
TGATTTCCATCCTTCCTGCAAGGTAACAGCTATGAATTGCTTCCTC
CTGGAGCTCCAAGTCATTCTCCATGAGTACTCCAACATGACTTTGA
ACGAAACTGTAAGAAACGTATTGTATCTGGCTAATAGCACCTTGTC
TAGTAACAAAAATGTGGCAGAGAGCGGCTGCAAAGAATGTGAAGAA
TTGGAAGAGAAAACATTTACAGATTCCTGCAATCCTTTATTCGCA
TCGTCCAAATGTTTATCAATACCTCTtaG IL15 (Mouse) (SEQ ID NO: 68)
ATGTATTCCATGCAACTTGCCAGTTGTGTAACCCTTACTCTCGTC
CTGCTCGTTAATTCCGCTGGTGCTAACTGGATAGATGTTCGATAC
GATCTGGAAAAGATTGAGTCCCTTATCCAATCCATTCATATAGAT
ACCACCCTTTATACTGACAGCGACTTCCATCCTTCTTGCAAGGTG
ACCGCTATGAATTGTTCCTGCTGGAACTCCAAGTTATTCTGCAT
GAATACTCTAATATGACACTTAACGAGACCGTAAGAAATGTTCTC
TATCTCGCTAATAGTACTTTGAGCTCAATAAGAACGTGGCCGAG
TCTGGGTGTAAGGAATGCGAAGAGCTGGAAGAAAAAGACATTCACC
GAGTTTCTCCAGTCTTTCATACGGATTGTGCAGATGTTTATCAAC
ACATCAGATTACAAAGACGACGATGATAAGtaG IL18 (Mouse) (SEQ ID NO: 69)
ATGGCAGCCATGTCTGAGGACTCTTGTGTGAACTTTAAAGAAATG
ATGTTCATAGACAATACACTCTACTTTATACCTGAGGAGAATGGA
GATTTGGAATCTGACAACTTTGCAGGCTGCATTGCACTACCGCA
GTTATCCGAAACATCAACGATCAGGTACTGTTTGTTGATAAAAGA
CAACCTGTATTCGAGGACATGACCGACATAGATCAGTCTGCCTCA
GAGCCCCAGACTAGGCTTATCATCTATATGTACAAGGACAGCGAA
GTACAGGCCTGGCTGTTACACTCTCAGTCAAAGACTCTAAGATG
AGCACCCTGTCATGCAAGAACAAAATTATCAGTTTTGAGGAGATG
GACCCACCTGAAACATAGATGACATTCAGTCAGACCTCATTTTT
TTTCAAAAGCGGGTACCAGGACACAACAAATGGAATTTGAATCA
TCACTCTACGAAGGACATTTCCTTGCATGCCAGAAAGAGGATGAC
GCATTCAAATTCTCTGAAAAAAAGACGAAAATGGTGATAAA
TCAGTCATGTTTACATTGACCAATCTTCACCAAAGTtaG IL18 (Mouse) (SEQ ID NO: 70)
ATGGCTGCAATGTCTGAAGATAGCTGTGTCAACTTTAAGGAGATG
ATGTTCATTGATAATACTTTGTACTTTATACCTGAAGAAAATGGA
GACTTGAGTCAGACAACTTTCGGGAGACTGCACTGCACAACTGCC
GTTATCCGAAACATAAATGATCAAGTATTGTTCGTGGACAAAAGA
CAACCAGTCTTTGAGGATATGACAGACATCGACCAATCCGCATCT
GAACCTCAGACTCGTCTGATCATCTATATGTACGCCGACTCCGAA
GTAAGAGGCCTTGCTGTGACACTTAGTGTTAAGGATAGTAAGATG
AGCACACTGTCCTGTAAGAATAAGATTATATCTTTTGAAGAGATG
GACCCTCCCGAGAACATAGATGACATCCAGAGCGACTTGATCTTC
TTTCAGAAGCGAGTGCCAGGCCATAACAAGATGGAATTTGAATCA
TCTCTTTATGAAGGCCATTTCCTCGCATGTCAAAAGGAGGACGAT TABLE 6-continued Sequences encoding exemplary effector molecules GCCTTCAAGCTCATTCTGAAAAAAAAAGACGAGAACGGTGATAAG
AGCGTGATGTTCACTCTGACAAATCTGCACCAGTCAtaG IL18 (Human) (SEQ ID NO: 71)
ATGTATCGCATGCAACTCCTGTCCTGCATTGCTCTGAGCTTGGCT
TTGGTAACCAACTCATACTTCGGGAAACTGGAGAGTAAACTCTCC
GTAATCAGGAATCTTAATGACCAAGTATTGTTTATTGACCAGGGC
AACCGCCCGTTGTTCGAGGATATGACTGATTCTGACTGTCGGGAT
AACGCTCCGAGAACTATCTTTATCATTTCAATGTACAAGGACAGC
CAACCGCGGGGTATGGCTGCTGACAATCAGTGTCAAATGTGAGAAG
ATTTCCACGCTGTCCTGCGAAAACAAGTAATTTCTTTCAAAGAA
ATGAACCCCCTGACAATATAAAGGATACAAAGAGTGATATCATC
TTCCTTTCAGAGGTCCGTGCCCGGCCACGATAATAAGATGCAATTT
GAAAGTTCATCTTTATGAGGGGTACTTTTTGGCATGCGAGAAAA
AGGGATCTCTTCAAGTTGATCCTGAAGAAGGAGGACGAATTGGGC
GACCGCTCCATCATGTTCACAGTCCAGAACGAGGACtaG IL18 (Human) (SEQ ID NO: 72)
ATGTACCGCATGCAGCTCCTGAGTTGTATTGCCCTTTCCCTCGCT
CTCGTTACCAATTCTTACTTCGGTAAGCTTGCCTCTAAACTCTCT
GTTATTAGGAACTTGAACGACCAAGTCCTTTTCATAGACCAAGGG
AACAGACCACTGTTTGAAGATATGACGGATAGCGATTGCCAGAT
AATGCCCCTAGGACGATTTTTATCATTAGTATGTATGCGGACTCT
CAACCGAGGGGGATGGCCGTTACTATAAGTGTGAAATGCGAGAAA
ATATCAACGCTCAGTTGTGAGAACAAAATCATAAGTTTCAAGGAG
ATGAATCCACCTGATAACATCAAAGACACTAAGTCTGATTATTA
TTTTTCCAACGAAGTGTTCCGGGACACGATAACAAAATGCAATTT
GAGAGCTCCTCATACGAGGGCTACTTCCTCGCGTGTGAGAAGAA
AGGGATTTGTTTAAGCTTATCCTCAAGAAAGAGGACGAGTTGGGG
GATCGGAGCATAATGTTTACCGTACAGAATGAGGACtaG IL21 (Mouse) (SEQ ID NO: 73)
ATGGAGCGGACACTCGTGTGTCTTGTCGTAATTTTTCTCGGGACA
GTCGCACACAAGTCCTCACCCCAGGGTCCTGATCGCCTTCTCATA
CGCCTCCGACATTTGATCGACATTGTAGAGCAGCTCAAAATTTAC
GAGAATGACCTCGATCCCGAGCTTTTGAGTGCTCCCCAAGACGTT
AAGGGTCATTGCGAGCACGCAGCTTTTGCTTGCTTCCAGAAGGCC
AAGTTGAAACCAAGCAACCCTGGTAATAATAAGACTTTCATCATC
GACTTGGTCGCCCAACTCCGAAGGAGGCTGCCTGCCCGGCGCGGA
GGAAAAAAACAAAAGCATATTGCAAAGTGTCCTTCATGTGATTCA
TACGAAAAGCGGACTCCCAAAGAGTTCTTGGAAAGGTTGAAATGG
CTTCTTCAGAAGATGATTCATCAACATTTGTCAtaG IFN-beta (Human) (SEQ ID NO: 74)
ATGACCAACAAATGCCTTTTGCAAATTGCCCTGCTTTTGTGTTTT
AGCACTACCGCATTGAGCATGTCATATAACCTCCTCGGCTTCCTT
CAGAGATCATCAAACTTTCAGTGTCAGAAACTGCTTTGGCAACTT
AATGGCAGGCTCGAATATTGTCTGAAAGATCGGATGAATTTCGAC
ATTCCAGAAGAAATAAAACAGCTTCAACAATTCCAGAAAGAGGAC
GCCGCCCTGACTATTTACGAGATGCTCCAGAATATCTTCGCCATT
TTCCGGCAGGACAGCTCATCCACGGGGTGGAATGAGACTATTGTA
GAAAATCTTCTGGCTAATGTGTACCATCAAATTAATCACCTCAAA
ACGGTGCTTGAGGAAAAACTTGAAAAGGAAGATTTCACACGGGGC
AAGTTGATGTCCTCCCTGCACCTTAAACGATACTACGGCAGGATT
CTTCATTACTTGAAGGCTAAGGAGTATAGCCATTGCGCGTGGACA
ATTGTACGGGTAGAAATACTGCGAAACTTTTATTTCATCAACCGG
CTCACTGGATACCTTAGAAATtaG IFN-beta (Mouse) (SEQ ID NO: 75)
ATGAACAATCGGTGGATACTCCACGCCGCATTTCTCCTCTGCTTT
AGCACGACGGCCCTGTCCATCAACTACAAACAGCTTCAGTTGCAG
GAGCGGACTAACATAAGGAAGTGCCAGGAACTGCTGGAACAGCTT
AATGGTAAAATTAATCTTACATACCGAGCTGACTTCAAAATTCCT
ATGGAAATGACCGAGAAGATGCAGAAATCCTACACGGCATTCGCC
ATCCAGGAAATGCTCCAGAACGTATTTCGTGTTCCGAATAAT
TTCTCTTCTACGGGTTGGAACGAAACCATTGTTGTTAGACTGCTT
GACGAACTGCATCAGCAAACCGTGTTCCTTAAACCGTGCTTGAG
GAGAGCAGGAGGAGCGCCTGACTTGGGAGTGTCTAGTACCGCA
CTTCACTTGAAATCCTACTACTGGCGCGTTCAGCGGTATCCGAAG
CTGATGAAGTATAACTCATACGCCTGGATGGTAGTGCGCGCAGAG
ATCTTCAGAAACTTTCTTATCATCCGGCGACTGACCCGAAACTTT
CAGAATtaG IFN-gamma (Human) (SEQ ID NO: 76)
ATGAAGTACACTAGCTATATATTGGCCTTCCAGCTTTGCATCGTA
TTGGGTAGCCTCGGATGCTATTGCCAAGACCCGTATGTCAAAGAA
GCCGAAAATCTCAAAAAGTATTTCAATGCCGGACACTCAGACGTC TABLE 6-continued Sequences encoding exemplary effector molecules GCGGATAACGGTACACTGTTTCTTGGCATCCTGAAAAATTGGAAG
GAAGAGAGTGACAGAAAATAATGCAGTCACAAATAGTGTCCTTT
TACTTTAAGCTGTTCAAAAATTTCAAGGATGACCAAAGTATCCAG
AAGAGTGTTGAAACTATCAAAGAGGACATGAATGTGAAATTCTTT
AACAGTAATAAGAAGAAGCGCGATGACTTTCAGAAACTCACTAAT
TACAGCGTAACGGATCTTAACGTCCAACGCAAGGCAATCCACGAG
CTTATACAGGTAATGGCTGAGCTTAGTCCCGCAGCCAAGACAGGG
AAGAGAAAAAGGTCTCAAATGCTTTTTCGGGGCCGGCGAGCTTCA
CAAtaG IFN-gamma (Mouse) (SEQ ID NO: 77)
ATGAACGCTACGCATTGCATCCTCGCACTCCAATTGTTCCTCATG
GCTGTGTCAGGGTGTTACTGTCACGGTACTGTCATAGAAAGCCTC
GAATCCCTGAATAACTATTTTAACAGTAGCGGTTATAGATGTAGAA
GAAAAGTCTCTCTTTCTTGACATCTGGAGGAATTGGCAAAAGGAT
GGAGACATGAAGATTCTCCAATCTCAGATTATATCATTTTACTTG
AGGCTTTTTGAGGTTCTGAAGGATAACCAGGCGATCAGCAATAAT
ATCAGCGTAATTGAATCTCACCTTATTACAACATTTTTCTCAAAT
TCCAAGGCAAAGAAAGATGCTTTCATGTCTATCGCGAAATTTGAG
GTGAACAATCCTCAGGTACAAAGGCAAGCCTTTAACGAGCTGATT
AGAGTTGTACATCAGTTGTTGCCCGAAAGTAGTCTTAGAAAACGC
AAACGGAGCCGATGCtaG IFN-alpha (Mouse) (SEQ ID NO: 78)
ATGGCAAGGTTGTGCGCTTTTCTCATGGTACTGGCTGTGCTCTCC
TATTGGCCTACTTGTTCTCTGGGATGCGACTTGCCACAGACCCAC
AATCTGCGGAATAAGAGGGCTCTGACTCTGCTGGTGCAAATGAGA
CGGCTCTCTCCACTTAGCTGTTTGAAAGATAGAAAGGATTTCGGG
TTCCCCCAGGAGAAGGTGGATGCCCAGCAGATCAAGAAGGCACAG
GCTATCCCCGTCCTTTCCGAGCTGACCCAGCAAATTTTGAACATC
TTTACAAGTAAGGATAGTTCAGCTGCATGGAATACCACACTTTTG
GATTCTTTTTGTAACGATCTGCATCAGCAGCTGAACGATCTCCAG
GGATGCCTGATGCAGCAAGTCGGCGTGCAAGAATTTCCACTCACC
CAGGAGGACGCTCTGCTCGCAGTGCGAAAGTATTTCACCGAATT
ACCGTGCTACCTCCGGGAGAAAAGACATTCACCCTGCGCTTGGGAA
GTAGTCAGGGCCGAAGTATGGAGAGCCCTTAGTAGCTCCGCTAAT
GTACTGGGCCGGTTGCGGGAAGAGAAAtaG CCL21 (Human) (SEQ ID NO: 79)
ATGGCGCAAAGTCTGGCTCTTTCACTCCTGATCCTGGTCTTGGCC
TTCGGGATTCCGAGGACCCAAGGAAGTGATGGTGGCGCCCAAGAT
TGTTGCCTTAAATACAGCCAGCGGAAAATACCCGCGAAAGTGGTC
AGGAGTTATAGAAAACAGGAGCCTTCCCTGGGTTGTAGTATCCC
GCCATACTTTTCCTCCCGAGAAAACGGAGCCAGGCCGAACTGTGC
GCTGACCCTAAGGAACTTTGGGTGCAACAACTTATGCAACACCTG
GATAAGACACCTTCTCCTCAAAAGCCAGCTCAGGGCTGCCGAAAA
GATAGAGGCGCCTCAAAAACCGGAAAAAAGGGCAAAGGTTCTAAA
GGATGTAAGCGGACTGAACGCTCTCAAACGCCTAAAGGGCCGtaG CCL21a (Mouse) (SEQ ID NO: 80)
ATGGCGCAAATGATGACCCTTTCCTGCTGAGTCTTGTCCTCGCG
CTCTGCATCCCGTGGACGCAGGGGTCTGATGGGGGGCCAAGAC
TGTTGCCTGAAGTATTCACAAAAAAAGATACCGTACTCTATTGTC
AGAGGGTACAGGAAGCAAGAACCCTCCTTGGGTTGCCCTATACCA
GCAATTCTTTTCTCCCCACGCAAGCATTCCAAACCAGAACTGTGT
GCGAACCCCGAGGAGGTTGGGTACAGAACTTGATGCGAAGGCTT
GACCAGCCCCCAGCCCCTGGCAAGCAGTCACCTGGGTGCAGAAAA
AACAGAGGTACTTCAAAGAGCGGCAAGAAAGGCAAAGGGAGTAAA
GGATGTAAAGAACGGAGCAGACCCAGCCTTCACGAGGCtaG Tail-less CCL21 (Human) (SEQ ID NO: 81)
ATGGCGCAAAGTCTGGCTCTTTCACTCCTGATCCTGGTCTTGGCC
TTCGGGATTCCGAGGACCCAAGGAAGTGATGGTGGCGCCCAAGAT
TGTTGCCTTAAATACAGCCAGCGGAAAATACCCGCGAAAGTGGTC
AGGAGTTATAGAAAACAGGAGCCTTCCCTGGGTTGTAGTATCCC
GCCATACTTTTCCTCCCGAGAAAACGGAGCCAGGCCGAACTGTGC
GCTGACCCTAAGGAACTTTGGGTGCAACAACTTATGCAACACCTG
GATAAGACACCTTCTCCTCAAAAGCCAGCTCAGGGCtaG Tail-less CCL21 (Mouse) (SEQ ID NO: 82)
ATGGCGCAAATGATGACCCTTTCCTGCTGAGTCTTGTCCTCGCG
CTCTGCATCCCGTGGACGCAGGGGTCTGATGGGGGGCCAAGAC
TGTTGCCTGAAGTATTCACAAAAAAAGATACCGTACTCTATTGTC
AGAGGGTACAGGAAGCAAGAACCCTCCTTGGGTTGCCCTATACCA
GCAATTCTTTTCTCCCCACGCAAGCATTCCAAACCAGAACTGTGT
GCGAACCCCGAGGAGGTTGGGTACAGAACTTGATGCGAAGGCTT
GACCAGCCCCCAGCCCCTGGCAAGCAGTCACCTGGGtaG TABLE 6-continued Sequences encoding exemplary effector molecules CCL19 (Mouse) (SEQ ID NO: 83)
ATGGCACCCCGCGTCACACCCTTGCTTGCTTTTTCTCTGCTTGTC
CTCTGGACCTTCCCCGCTCCTACCCTTGGAGGAGCCAATGATGCC
GAGGATTGCTGCCTGAGTGTTACACAAAGGCCAATACCAGGGAAT
ATAGTGAAGGCATTCCGGTATCTGCTCAATGAAGATGGGTGCAGA
GTCCCCGCAGTTGTCTTTACAACATTGCGAGGTTACCAGCTTTGT
GCTCCCCCAGACCAGCCTTGGGTAGATCGCATTATTCGCCGGTTG
AAGAAGAGCTCAGCAAAGAATAAGGGCAATTCCACACGGAGAAGC
CCCGTCTCCtaG CCL19 (Mouse) (SEQ ID NO: 84)
ATGAAAATCAGCAGTCCTTTTCTTGCTCGGGATTATTTTTCTGGAA
CAATGTGGAGTGAGGGGAACACTCGTAATAAGAAACGCTCAGTTG
TCATGCATATCAACATCACGGGGCACTATCCACTACAAATCCCTG
AAGGATCTGAAGCAGTTCGCCCCAAGCCCTAACTGTAACAAGACC
GAAATTATCGCAACTCTCAAAAATGGAGATCAGACTTGTCTTGAC
CCAGATTCAGCAAATGTCAAGAAGCTGATGAAAGAGTGGGAAAAG
AAGATTTCACAAAAAAAAAGCAAAAACGCGGCAAGAAACATCAA
AAGAACATGAAAAACAGGAAACCTAAGACTCCCCAGTCAAGGAGA
AGATCCCGCAAGCAACCtaG CXCL11 (Mouse) (SEQ ID NO: 85)
ATGAACAGAAAAGTTACCGCTATAGCACTTGCTGCCATAATATGG
GCCACCGCAGCTCAAGGGTTCCTGATGTTCAAGCAGGGCCGATGC
CTCTGCATTGGCCCTGGAATGAAGGCCGTGAAAATGGCCGAAATA
GAAAAAGCTAGTGTCATATACCCCTCTAACGGTTGCGATAAAGTC
GAGGTTATAGTCACAATGAAAGCTCATAAACGCCAACGCTGCCTC
GACCCCCGGTCTAAGCAGGCTAGGCTCATAATGCAAGCAATCGAG
AAGAAAAACTTTCTTAGACGGCAAAACATGtaG CXCL10 (Mouse) (SEQ ID NO: 86)
ATGAACCCATCTGCCGCCGTTATTTTCTGTCTGATACTCCTTGGG
CTGAGTGGCACACAAGGCATACCCCTCGCCCGCACAGTCCGGTGT
AATTGTATACATATTGACGACGGCCCTGTTAGAATGCGGGCCATC
GGTAAGCTGGAGATTATACCAGCAAGCCTTAGTTGTCCCAGGGTT
GAAATCATAGCAACTATGAAAAAAAACGACGAACAAAGATGTTTG
AATCCCGAGAGCAAGACAATCAAAAACCTTATGAAAGCATTTAGT
CAAAAACGCTCTAAACGCGCTCCAtaG CXCL10 (Human) (SEQ ID NO: 87)
ATGAATCAGACGGCAATCCTTATATGCTGCCTTATATTCCTTACT
CTCTCAGGGATACAAGGGGTACCACTTTCTGCACGTGTTCGCTGC
ACTTGCATTTCAATATCTAACCAACCTGTAAATCCGCGGAGCCTG
GAAAAAATTGGAGATTATACCTGCTTCTCAATTCTGCCCTCGGGTG
GAAATCATCGCCACTATGAAGAAGAAGGGCGAGAAAAGGTGTCTG
AATCCAGAGTCAAAGGCAATCAAAAACCTGCTGAAAGCGGTGTCA
AAGGAACGGTCCAAGAGATCACCCtaG CXCL11-CXCL 10 (Mouse) (SEQ ID NO: 88)
ATGAACAGGAAAGTAACAGCCATTGCATTGGCTGCCATAATCTGG
GCCACCGCAGCACAGGGTTTTCTGATGTTTAAGCAAGGGCGCTGT
CTCTGTATAGGCCCAGGCATGAAGGCCGTGAAGATGGCAGAGATT
GAGAAGGCATCTGTGATTTATCCTTCTAACGGGTGCGATAAAGTC
GAAGTTATTGTGACAATGAAGGCACACAAACGCCAACGGTGTTG
GACCCACGATCTAAACAGGCAAGATTGATTATGCAAGCCATCGAG
AAAAAGAACTTTCTCCGAAGGCAAAATATGATCCCTTTGGCTCGG
ACAGTGCGGTGTAACTGTATTCACATCGACGATGGGCCAGTACGG
ATGAGAGCAATAGGAAAGCTCGAAATCATACCCGCCTCATTGTCT
TGTCCCAGGGTGGAAATAATCGCCACTATGAAAAAGAACGATGAA
CAGAGGTGTCTCAACCCAGAGAGTAAGACTATCAAGAACCTTATG
AAGGCATTCAGTCAGAAGAGGTCAAAGCGAGCACCAtaG XCL 1 (Human) (SEQ ID NO: 89)
ATGAGACTTCTCTCATATTGGCGCTTCTCGGGATATGTTCTCTTACG
GCATACATAGTTGAGGGGTGGGATCTGAGGTTAGCGATAAACGA
ACTTGTGTTAGTCTTACAACACAGAGGCTTCCAGTCTCCAGGATA
AAAACATATACGAACTAATGAGGGATCTCTCAGACGGTCATCTTC
ATAACGAAGAGGGCCTGAAGGTCTGTGCTGACCCACAAGCGACT
TGGGTAAGGGACGTTGTCGGAGCATGGACAGGAAGAGCAATACT
CGCAACAACATGATCCAAACCAAACCTACGGGCACCCAACAGTCA
ACCAATACTGCGGTAACATTGACGGGGtaG XCL 1 (Mouse) (SEQ ID NO: 90)
ATGCGCCTCCTTCTGCTGACTTTTCTGGGTGTATGTTGCCTGACA
CCCTGGGTCGTAGAAGGAGTAGGAACCGAGGTTCTGGAAGAGTCC
TCATGTGTAAACTTGCAGACACAACGACTCCCCGTCAAAAAATC
AAGACCTATATAATCTGGGAGGGGGCAATGCGGGCCGTCATTTTC
GTGACTAAACGAGGTCTCAAAATCTGCGCCGACCCCGAGGCTAAG
TGGGTGAAGGCAGCCATTAAGACCGTGGATGGGAGAGCCAGCACC
AGAAAGAACATGGCCGAAACAGTACCTACTGGCGCACAGCGGTCA
ACCTCAACTGCTATAACCTTGACAGGAtaG m sCD40L #1 (SEQ ID NO: 91)
ATGGAGACTGACACTCTGCTTCTGTGGGTGTTGCTGCTGTGGGTG
CCTGGCAGTACAGGCGATATGCAACGAGGTGACGAGGACCCTCAA
ATCGCCGCCCATGTAGTCTCTGAAGCTAATAGCAACGCTGCATCC
GTCTTGCAGTGGGCAAAGAAAGGCTACTATACTATGAAGTCCAAC
TTGGTAATGCTTGAAAACGGCAAGCAGTTGACTGTCAAGAGAGAG
GGACTTTATTACGTCTATACCCAAGTCACATTCTGTAGCAATCGA
GAACCCTCCTCACAGAGGCCTTTTATAGTGGGACTCTGGCTTAAA
CCAAGTAGCGGCTCTGAGCGCATACTGTTGAAAGCCGCAAACACA
CACAGCTCTTCCCAACTCTGCGAGCAGCAATCCGTGCATCTCGGT
GGAGTATTTGAGCTTCAAGCCGGTGCCTCAGTGTTTGTGAACGTC
ACTGAGGCCTCCAGTCCATCATCGAGTTGGGTTCAGCTCCTTC
GGCTTGCTCAAGCTctaG m sCD40L #2 (SEQ ID NO: 92)
ATGGAAACTGATACATTGCTGCTCTGGGTTTTGCTGCTCTGGGTG
CCTGGGAGTACAGGCGACATGAGGAGGCAGTTCGAGGATCTCGTT
AAGGATATTACCCTTAATAAGGAGGAGAAGAAAGAAACTCTTTT
GAGATGCAACGAGGGGACGAAGATCCTCAGATCGCTGCTCACGTG
GTCTCTGAAGCTAACAGCAACGCCGCTTCTGCCTCCAGTGGGCC
AAGAAAGGTTATTACACCATGAAATCAAACCTTGTAATGCTTGAA
AACGGGAAACAGCTTACAGTGAAGAGGGAAGGTCTTTACTACGTC
TATACCCAGGTAACCTTCTGCTCAAACAGAGAACCATCAAGCCAG
AGGCCATTCATAGTGGGGCCTTGGCTCAAACCTTCCAGTGGCAGC
GAGAGAATCTTGTTGAAAGCTGCTAATACACATAGTAGTAGCCAG
CTTTTGCGAGCAACAGTCAGTCCACCTCGGGGGGTGTTTGAGTTG
CAAGCAGGGGCCTCAGTATTCGTGAATGTCACTGAGGCTTCCCAG
GTAATTCACAGGGTAGGCTTTAGTTCATTCGGTTTGCTGAAGCTT
taG m sCD40L #3 (SEQ ID NO: 93)
ATGCGAAGAATGCAGCTTCTGCTCCTTATTGCTCTGAGTCTCGCC
CTTGTCACCAACTCCGGGGACAGAATGAAACAAATCGAGGACAA
ATTGAAGAAATACTGAGTAAAATATATCACATCGAAAACGAAATT
GCACGCATTAAGAAATTGATTGGCGAACGCACCAGTGGCGGCTCT
GGTGGCACCGGAGGTTCAGGCGGGACCGGGGGCTCTGACAAAGTC
GAAGAGGAGGTTAACCTTCATGAGGCTTCTGTTCATCAAGAAG
CTGAAACGGTGCAATAAAGGAGAAGGTTCTTTGAGCCTCCTTAAT
TGCAAGAGATGCGACGACAGTTCGAGGATCTGGTTAAGGACATT
ACACTTAATAAGGAAGAGAAAAGGAGAACTCTTTCGAAATGCAG
CGCGGCGATGAAGATCCCCAGATAGCCGCCCATGTCGTCTCTGAG
GCCAACTCTAACGCAGCATCCGTCCTCCAGTGGGCTAAGAAAGGA
TATTACTATGAAAAGCAATTTGGTCATGCTCGAAAACGGTAAA
CAGCTCACTGTTAAGAGAGAAGGCCTCTATTACGTATATACTCAA
GTAACTTTCTGTTCTAATAGGGAACCCTCCTCTCAAAGACCTTTT
ATCGTAGGACTCTGGTTGAAACCAAGTAGCGGTAGTGAAAGGATT
CTGCTCAAAGCAGCTAATACTCACTCCAGCAGTCAACTGTGCGAA
CAACAAAGCGTTCACCTCGGGGCGTCTTTGAACTTCAGGCAGGT
GCCAGTGTTTTCGTCAACGTAACAGAAGCATCCCAGGTAATTCAT
CGAGTAGGGTTTTCTAGCTTTGGITTGCTGAAGCTGtaG anti-CD40_FGK4.5 (SEQ ID NO: 94)
ATGGAAACTGATCGCCTGTTGCTCTGGGTACTTCTTCTGTGGGTG
CCTGGGTCCACTGGTGACACTGTACTTACACAATCACCCGCTTTG
GCCGTTTCTCCTGGTGAACGGGTCACAATTAGTTGCCGAGCTTCC
GATTCTGTATCTACTCTTATGCATTGGTATCAACAAAAACCTGGT
CAGCAGCCAAAATTGCTCATTTATCTTGCTAGTCACTTGGAGTCC
GGCGTACCTGCTCGATTCAGTGGTTCAGGCAGTGGCACAGATTTC
ACTTTGACCATAGATCCCGTGGAGGCCGATGACACTGCAACCTAC
TATTGCCAGCAATCCTGAACGACCCTTGGACTTTCGGCGGCGGC
ACCAAGCTGGAACTCAAGCGAGCAGATGCTGCCCCAACCGTTAGT
ATATTCCCACCTTCACCAGAACAGCTGCACAGGAGGGCGTAGT
GTCGTGTGTCTTATGAACAATTTCTATCCACGAGACATTAGCGTC
AAGTGGAAAATTGATGGGACAGAAAGGCGAGATGGAGTTTTGGAT
TCAGTAACAGACCAGGATTCAAAGGATTCTACCTATAGCATGAGC
TCCACCTTGACCCTGACCAAAGCTGATTATGAATCTCATAACCTG
TATACTTGTGAAGTGGTGCATAAGACTTCTAGCTCACCAGTGGTT
AAATCTTTTAACCGCAACGAATGTCGGCGCAAGAGGGTTCCGGA
GAGGGAAGGGGTAGTCTGCTCACCTGCGGCGATGTTGAAGAAAAT
CCTGGTCCCATGGACATTCGGCTCTCTTTGGTATTCCTGGTACTT
TTTATAAAGGGGGTGCAATGTGAAGTCCAGCTCGTGGAAAGCGGT TABLE 6-continued Sequences encoding exemplary effector molecules GGGGGCCTGGTTCAGCCCGGTCGCAGCCTTAAACTTAGTTGCGCA
GCATCCGGATTTACATTTTCTGACTATAACATGGCCTGGGTTCGA
CAGGCACCCAAAAAAGGGCTGGAGTGGGTCGCAACTATCATATAC
GATGGTTCCCGGACATACTATAGAGATTCAGTGAAGGGGCGCTTT
ACAATAAGCAGGGACAATGCTAAGTCTACCTTGTATCTTCAGATG
GACTCCCTGAGGAGCGAAGATACAGCAACATATTATTGTGCTACA
AACCGCTGGTTGCTGCTTCATTATTTCGACTACTGGGGTCAGGGC
GTCATGGTAACTGTATCAAGCGCCGAGACCACAGCCCCTTCTGTA
TATCCATTGGCACCAGGTACTGCTCTGAAATCCAACTCAATGGTA
ACCCTTGGATGTCTGGTTAAGGGTTATTTTCCCGAGCCCGTCACA
GTTACTTGGAACTCTGGGGCCTTTCTAGCGGAGTCCATACCTTT
CCCGCCGTTTTGCAGAGTGGTCTGTACACCCTTACCTCAAGCGTC
ACAGTTCCATCTAGCACATGGAGCTCCCAGGCAGTAACTTGTAAT
GTGGCCCATCCAGCCTCCTCAACTAAGGTAGATAAAAAGATCGTT
CCCAGAGAATGCAATCCATGTGGATGCACCGGGTCTGAGGTCAGC
AGTGTGTTCATTTTCCCACCCAAGACTAAAGATGTATTGACTATT
ACTCTTACACCCAAAGTAACCTGCGTGGTGGTTGATATTAGTCAA
AATGATCCCGAGGTACGGTTCTCTTGGTTTATCGACGACGTCGAA
GTACATACAGCTCAGACACACGCTCCCGAGAAACAAAGCAATTCC
ACTCTTAGGAGCGTGTCCGAGTTGCCAATCGTACATAGGGATTGG
CTTAATGGCAAGACCTTTAAGTGTAAGGTCAATTCAGGGGCATTC
CCCGCACAATAGAAGAGTATAAGCAAACCCGAGGGGACACCC
AGAGGTCCACAGGTCTATACAATGGCTCCCCCCAAGGAAGAGATG
ACCCAAAGTCAAGTCTCAATTACATGTATGGTGAAGGGCTTTAT
CCACCCGACATATACACTGAGTGGAAGATGAATGGACAGCCCCAA
GAGAATTATAAAAACACTCCCCCTACCATGGACACCGACGGGTCC
TATTTTCTTTATAGTAAATTGAACGTGAAAAAGGAGACCTGGCA
CAAGGCAACACTTTCACCTGCTCCGTTCTTCACGAGGGCCTGCAT
AATCATCATACCGAAAAGTCTCTCAGTCATTCTCCAGGTAAGtaG CD40L 2 (Human) (SEQ ID NO: 95)
ATGGAAACAGATACGTTGCTGTTGTGGGTACTTCTCCTTTGGGTC
CCTGGCAGCACAGGGGACGAGAATAGTTTCGAAATGCAGAAGGGC
GACCAGAACCCACAGATCGCGGCTCACGTTATATCAGAAGCAAGT
AGTAAGACCACTTCCGTACTTCAGTGGGCTGAAAAAGGAATATTAC
ACCATGTCCAACAATCTCGTGACACTGGAGAACGGTAAACAACTT
ACGGTGAAACGACAGGGCCTCTATTACATCTACGCTCAGGTGACA
TTCTGCTCAAATAGGGAGGCTTCTAGTCAAGCGCCCTTCATCGCC
AGCCTGTGCCTCAAATCTCCCGGCCGGTTCGAACGAATCCTGTT
CGAGCGGCCAATACCCATAGCTCAGCTAAACCTTGCGGCCAGCAG
AGTATTCATCTTGGTGGTGTGTTGAACTTCAGCGGGAGCATCT
GTGTTCGTCAACGTAACGGACCCTAGCCAAGTGTCTCATGGGACA
GGTTTTACATCCTTCGGACTCCTCAAGTTGtaG Flt3L (Human) (SEQ ID NO: 96)
ATGACAGTTCTCGCGCCAGCTTGGAGTCCCACCACATACTTGCTT
TTGCTTCTGCTTCTGTCCCTCTGGCCTGAGTGGGACCCAAGATTGT
TCCTTTCAACATTCCCCAATTAGTTCTGATTTTGCAGTGAAGATT
AGAGAGCTCTCAGACTATCTGCTGCAAGATTATCCTGTCACAGTC
GCTTCAAACCTGCAAGACGAAGAGCTCTGCGGTGCCTTGTGGCGG
TTGGTCTTGGCTCAAAGATGGATGGAGAGACTGAAAACCGTACGA
GGCAGCAAGATGCAGGGTTCCTGGAAAGGGTGAACACGGAAATC
CATTTTGTGACCAAGTGCGCGTTCCAGCCCCACCGAGTTGTCTC
CGGTTTGTTCAAACGAATATATCCCGGTTGCTCCAGGAAACCTCA
GAACAACTGGTGGCTTTGAAACCCTGGATCACAAGACAAAACTTT
AGTCGGTGCCTCGAACTCCAGTGCCAACCAGATTCTTCTACACTT
CCCCCCCCGTGGTCCCCGCGCCCGTTGGAAGCAACGGCCCCATaG TGFb TRAP (Human) (SEQ ID NO: 97)
ATGGCCTGGAGTCCTCTGTTTCTGACTCTTATAACTCACTGTGCC
GGCAGTTGGGCTATACCCCCTCATGTACAGAAGTCTGTAAACAAC
GACATGATTGTAACCGACAATAATGGCGCAGTGAAATTCCCACAA
CTGTGTAAGTTCTGTGATGTACGGTTAGTACATGCGACAATCAA
AAAAGCTGTATGTCTAACTGCTCTATTACATCCAATATGTGAAAA
CCTCAGGAGGTGTGTGTTGCCGTTTGGCGAAAAAATGATGAGAAT
ATCACACTGGAGACAGTATGTCATGACCCTAAACTGCCATACCAT
GATTTCATACTGGAGGACGCCGCCAGTCCTAAGTGCATTATGAAA
GAGAAAAAGAAACCGGTGAAACATTCTTTATGTCTCTTGTAAG
TCTGACGAGTGTAACGACAACATTATATTCAGCGAGGAGTACAAT
ACAAGCAACCCCGATATACCACCTCACGTACAAAAAAGTGTCAAC
AACGATATGATTGTTACCGACAATAACGGAGCTGTTAAGTTTCCT
CAGTTGTGCAAGTTCTGCGATGTGACGTTCTCTACCTGCGACAAC
CAAAAGTCATGTATGTCTAACTGTTCCATAACCTCCATCTGCGAG
AAGCCCCAGGAAGTCTGCGTCGCCGTGTGGCGGAAAAACGACGAG
AATATCACTCTTGAAACCGTTTGTCATGATCCTAAACTGCCCTAT
CACGACTTTATTCTGGAAGATGCTGCTTCCCCTAAGTGTATCATG
AAAGAAAAGAAGAAACCTGGGGAGACATTCTTTATGTGTTCATGC TABLE 6-continued Sequences encoding exemplary effector molecules TCCTCCGATGAGTGTAACGACAATATCATCTTCTCTGAGGAATAC
AACACTTCTAACCCTGATtaG Fresolimumab (Human) (SEQ ID NO: 98)
ATGGCCTGGTCCCCTCTTTTCTGACCCTCATCACACACTGTGCA
GGCTCATGGGCTGAGACCGTCTTGACCCAGTCCCCAGGAACTTTG
TCTCTGTCTCCTGGTGAAAGAGCTACCCTTAGTTGTCGAGCCTCT
CAGTCCCTTGGTTCTAGCTATCTCGCTTGGTACCAGCAAAAGCCA
GGCCAGGCCCCACGACTGCTGATCTACGGAGCATCTTCACGGGCT
CCCGGCATTCCCGATCGATTTTCCGGATCTGGTAGTGGTACAGAT
TTCACACTGACCATATCTGCCTGGAGCCCGAGGACTTTGCTGTT
TATTATTGTCAGCAGTACGCCGATTCTCCTATCACTTTTGGACAG
GGAACCCGCCTGGAGATTAAGCGACAGTAGCAGCTCCATCCGTC
TTTATCTTTCCACCATCAGATGAACAGCTCAAGAGTGGGACCGCA
AGTGTAGTATGCCTGCTGAACAATTTTTACCCTAGAGAGGCCAAA
GTGCAGTGGAAGGTGGATAACGCCCTCCAGAGTGGCAATAGTCAA
GAAAGTGTTACTGAGCAAGATAGTAAGGACTCTACATACTCTTTG
AGTTCTACTTTGACCCTGTCAAAGCAGATTATGAAAAACATAAG
GTGTATGCATGTGAAGTTACACACCAAGGGTTGTCCTCTCCAGTT
ACAAAATCTTTTAATAGGGAGAGTGCCGCCGCAAACGCGGTAGT
GGAGAAGGTCGAGGCTCACTCTTGACCTGTGGCGACGTGGAAGAA
AATCCCGGTCCTATGGATTGGACTTGGAGGGTATTTTGTCTTTTG
GCAGTAACACCTGGAGCTCACCCCCAAGTACAGCTCGTCCAATCT
GGTGCCGAGGTTAAAAGCCTGGAAGTTCAGTGAAGGTCTCTTGC
AAGGCATCTGGATACACCTTTTCATCTAACGTCATATCCTGGGTA
CGGCAAGCCCCAGGACAGGGATTGGAGTGGATGGGAGGGGTCATC
CCCATCGTGGACATTGCTAATTACGCTCAGCGATTCAAAGGGCGG
GTTACTATAACTGCCGACGAGTCTACCTCAACTACTACATGGAG
TTGTCCTCTCTCCGCTCCGAGGACACTGCTGTATATTACTGTGCC
AGCACTCTCGGGTTGGTGTTGGATGCCATGGACTATTGGGGACAA
GGAACCCTGGTGACAGTTAGCTCCGCAAGCACTAAAGGCCCTTCT
GTTTTTCCCTTGGCACCTTGTAGTAGGTCTACCTCTGAGTCTACA
GCAGCACTTGGATGCTTGGTTAAGGACTATTTTCCCGAGCCAGTT
ACAGTCTCTTGGAACAGTGGTGCCCTCACAAGTGGGGTTCATACC
TTCCCCGCAGTCCTCCAGAGTAGTGGCCTTTACAGCCTCTCATCA
GTTGTGACTGTTCCTAGTTCATCACTCGGTACTCAAGACATATACA
TGTAACGTAGACCACAAGCCAAGCAACACAAAAGTAGACAAACGA
GTCGAATCTAAGTATGGACCCCCTTGTCCCTCCTGTCCTGCTCCC
GAGTTCCTTGGGGGCCCTTCCGTGTTCTTGTTTCCTCCCAAGCCC
AAGGATACCCTCATGATCTCACGAACCCCAGAGGTAACATGTGTG
GTTGTTGACGTAAGTCAGGAAGATCCCGAAGTGCAATTTAATTGG
TACGTGGATGGCGTCGAAGTCCATAACGCTAAAACAAAACCCCGA
GAGGAACAATTCAATTCCACATATCGGGTGGTGAGTGTATTGACC
GTTCTTCACCAAGATTGGCTGAACGGCAAGGAGTATAAGTGTAAA
GTAAGCAACAAAGGTCTGCCAAGTAGCATAGAAAAACAATATCT
AAAGCTAAGGGCCAACCAAGGGAACCACAAGTATATACATTGCCC
CCCTCTCAGGAAGAGATGACAAAGAACCAAGTCAGTTAGCCTGACCTGT
TTGGTAAAGGGTTCTATCCCTCAGATATAGCAGTCGAGTGGGAA
TCTAACGGCCAGCCCGAGAATAATTATAAAACAACCCCCCCTGTG
TTGGACTCAGACGGCAGCTTCTTTCTCTATTCACGGCTCACTGTT
GATAAGTCCCGATGGCAGGAGGGGAATGTTTTCAGCTGTAGCGTG
ATGCACGAAGCTCTCCACAACCACTATACACAGAAAAGTTTGTCT
TTGTCCCTTGGAAAAtaG TGFb neutralizing peptide (Human) (SEQ ID NO: 99)
ATGAGTACATCCTTTCCAGAGCTGGATCTGGAGAATTTTGAGTAT
GACGACAGTGCCGAAGCCTGCTACCTCGGGGACATAGTCGCATTC
GGGACAATCTTTTTGTCTGTATTTTACGCCCTGGTGTTTACATTT
GGCCTGGTTGGAAATCTGTTGGTCGTACTCGCTCTCACCAATTCC
CGAAAATCCAAAAGTATAACAGACATATACCTGTTGAATCTGCA
CTGAGTGACCTTTGTTCGTCGCCACCCTTCCTTTTGGACACAC
TACCTTATCAGTCACGAGGGCTTCATAATGCTATGTGCAAGCTC
ACTACTGCCTTCTTTTATCGGATTCTTCGGGGGTATCTTTTTT
ATCACAGTTATTAGCATTGACCGATACCTTGCCATAGTGCTTCGCA
GCCAACTCAATGAACAACCGCACCGTGCAGCATGGAGTGACTATT
CCTTGGGTGTGTGGGCCGCTGCTATACTTGTCGCCAGCCCTCAA
TTCATGTTCCAAAGGAAAGACCAATGAGTGCCTCCGGAGATTAC
CCTGAGGTGTTCAAGAATGTGGCCTGTACTTCGAAATAGCGAA
GTGAATATACTCGGCTTTGCTCTTCCTCTGCTCATCATGTCATTC
TGTTATTTTCGAATAATCCAAACATTGTTCAGCTGTAAGAACCGA
AAGAAGCCTCGGCTACGCCTGCTTCGGCTCGTTGTCGTTGCC
TTTTTCTGTTTGGACTCCTTACAACATAATGATATTCTGGAG
ACTCTCAAATTCTATAACTTTTTCCCTCCTGTGATATGAAAGG
GACCTTAGATTGGCTCTCAGTGTCACTGAAACAGTAGCCTTTAGC
CATTGTTGTCTCAACCCTTTCATATATGCATTTGCAGGGGAAAAG
TTCCGGCGGTATCTCGGACATTTGTATCGGAAGTGCTTGGCCGTG TABLE 6-continued Sequences encoding exemplary effector molecules TTGTGTGGTCATCCTGTCCATACCGGATTCTCTCCTGAGAGTCAA
CGGAGCCGCCAAGATTCAATCCTGTCCAGTTTCACTCACTATACT
TCAGAGGGGGATGGCAGCCTTCTGCTC Kynureinase #1 (SEQ ID NO: 100)
ATGGAGACCGACACTTTGTTGCTGTGGGTACTTTTGTTGTGGGTC
CCAGGATCTACCGGGGATATGGAACCCTCTCCTCTTGAACTGCCA
GTAGACGCCGTGCGCCGCATTGCAGCCGAGTTGAATTGCGATCCA
ACAGATGAACGTTGCCCTGAGGCTCGACGAAGAGGATAAATTG
TCACATTTCAGGAACTGCTTTTACATTCCAAAGATGAGGGATCTT
CCATCCATAGATCTTAGCCTCGTGTCCGAGGATGACGATGCCATA
TATTTTCTTGGGAACAGTCTTGGGTTGCAGCCAAAAATGGTACGG
ACATATCTCGAAGAGGAGCTGGACAAATGGGCTAAAATGGGTGCT
TACGGCCACGACGTGGGAAACGCCCCTGGATAGTTGGCGACGAA
TCTATCGTGAGTCTTATGAAAGATATAGTTGGAGCACATGAGAAA
GAAATTGCACTGATGAATGCCCTTACTATCAATCTGCATCTCCTC
TTGCTTTCATTCTTTAAGCCCACTCCTAAACGCCACAAAATACTT
TTGGAAGCAAAAGCCTTTCCAAGCGACCACTACGCTATTGAGTCA
CAAATACAACTCCATGGACTTGATGTGGAAAAGTCTATGCGGATG
GTAAAACCACGCGAAGGCGAGGAGACCCTTCGAATGGAGGACATA
CTTGAGGTCATCGAAGAAGAAGGAGATAGTATAGCAGTTATCCTT
TTCAGCGGGCTGCACTTCTACACAGGTCAACTCTTTAACATTCCA
GCTATTACTAAGGCAGGCCACGCTAAAGGATGCTTCGTGGGCTTT
GACCTTGCACACGCAGTAGGAAACGTAGAGCTCCGCTTGCACGAT
TGGGGCGTTGATTTCGCCTGCTGGTGTTCATATAAGTATCTTAAC
TCAGGAGCTGGTGGGTTGGCAGGCGCATTCGTACACGAGAACAC
GCTCATACCGTAAAGCTGCACTGGTAGGGTGGTTCGGACACGAT
CTCTCTACCCGCTTCAATATGGATAATAAACTCCAGCTTATACCT
GGCGCCAATGGATTCAGGATCTCAAATCCTCCTATTTTGCTCGTT
TGCAGTTTGCACGCATCTCTTGAGGTGTTCCAGCAGGCTACCATG
ACTGCACTCCGCCGGAAGTCAATCCTTTTGACCGGATACTTGGAG
TATATGCTGAAACATTATCACTCAAAAGATAACACTGAGAATAAG
GGCCCCATAGTAAACATTATCACTCCATCTCGGGCTGAAGAGCGC
GGCTGCCAACTCACATTGACTTTTTCCATTCCCAAGAAGTCAGTG
TTCAAAGAGTTGGAGAAACGGGGGGTTGTATGTGATAAGCGGGAG
CCAGATGGAATCCGCGTTGCCCCAGTCCCCCTCTATAATTCTTTT
CACGATGTATACAAGTTTATTAGACTGCTGACAAGTATCTTGGAC
TCATCTGAGCGATCTtaG Kynureinase #2 (SEQ ID NO: 101)
ATGGAACCCTCTCCTCTTGAACTGCCAGTAGACGCCGTGCGCCGC
ATTGCAGCCGAGTTGAATTGCGATCCAACAGATGAACGCGTTGCC
CTGAGGCTCGACGAAGAGGATAAATTGTCACATTTCAGGAACTGC
TTTTACATTCCAAAGATGAGGGATCTTCCATCCATAGATCTTAGC
CTCGTGTCCGAGGATGACGATGCCATATATTTTCTTGGGAACAGT
CTTGGGTTGCAGCCAAAAATGGTACGGACATATCTCGAAGAGGAG
CTGGACAAATGGGCTAAAATGGGTGCTTACGGCCACGACGTGGGA
AAACGCCCCTGGATAGTTGGCGACGAATCTATCGTGAGTCTTATG
AAAGATATAGTTGGAGCACATGAGAAAGAAATTGCACTGATGAAT
GCCCTTACTATCAATCTGCATCTCCTCTTGCTTTCATTCTTTAAG
CCCACTCCTAAACGCCACAAAATACTTTTGGAAGCAAAATACTTTT
CCAAGCGACCACTACGCTATTGAGTCACAAATACAACTCCATGGA
CTTGATGTGGAAAAGTCTATGCGGATGGTAAAACCACGCGAAGGC
GAGGAGACCCTTCGAATGGAGGACATACTTGAGGTCATCGAAGAA
GAAGGAGATAGTATAGCAGTTATCCTTTTCAGCGGGCTGCACTTC
TACACAGGTCAACTCTTTAACATTCCAGCTATTACTAAGGCAGGC
CACGCTAAAGGATGCTTCGTGGGCTTTGACCTTGCACACGCAGTA
GGAAACGTAGAGCTCCGCTTGCACGATTGGGGCGTTGATTTCGCC
TGCTGGTGTTCATATAAGTATCTTAACTCAGGAGCTGGTGGGTTG
GCAGGCGCATTCGTACACGAGAAACACGCTCATACCGTAAAGCCT
GCACTGGTAGGGTGGTTCGGACACGATCTCTCTACCCGCTTCAAT
ATGGATAATAAACTCCAGCTTATACCTGGCGCCAATGGATTCAGG
ATCTCAAATCCTCCTATTTTGCTCGTTTGCAGTTTGCACGCATCT
CTTGAGGTGTTCCAGCAGGCTACCATGACTGCACTCCGCCGGAAG
TCAATCCTTTTGACCGGATACTTGGAGTATATGCTGAAACATTAT
CACTCAAAAGATAACACTGAGAATAAGGGCCCCATAGTAAACATT
ATCACTCCATCTCGGGCTGAAGAGCGCGGCTGCCAACTCACATTG
ACTTTTTCCATTCCCAAGAAGTCAGTTCGGGGGGTTGTATGTGATAAG
CGGGGGGTTGTATGTGATAAGCGGGAGCCAGATGGAATCCGCGTT
GCCCCAGTCCCCCTCTATAATTCTTTTCACGATGTATACAAGTTT
ATTAGACTGCTGACAAGTATCTTGGACTCATCTGAGCGATCTtaG VEGF (SEQ ID NO: 102)
ATGAATTTCTTGCTGAGCTGGGTGCATTGGACACTCGCATTGTTG
CTGTACTTGCACCATGCCAAGTGGTCCCAGGCTGCACCCACTACT
GAGGGCGAGCAAAAGTCTCATGAGGTGATTAAATTTATGGACGTT
TACCAACGATCATACTGTCGGCCAATCGAAACCCTCGTAGATATA TTCCAGGAGTACCCAGACGAGATCGAATACATTTTCAAGCCCTCA
TGTGTCCCATTGATGCGATGTGCTGGGTGCTGTAACGACGAAGCA
CTTGAATGTGTCCCCACCTCCGAGAGTAACATCACAATGCAAATA
ATGAGAATCAAGCCCCACCAATCCCAACATATCGGTGAAATGTCA
TTCCTTCAGCATTCCCGCTGCGAGTGCCGGCCTAAGAAGGACCGC
ACCAAACCAGAGAACCATTGTGAACCCTGTTCTGAGAGACGGAAG
CACTTGTTCGTACAGGACCCTCAAACATGCAAGTGCAGCTGTAAG
AATACCGACTCACGGTGTAAAGCTAGGCAACTGGAGCTTAATGAA
AGGACCTGCCGATGCGATAAACCCAGGAGGtaa GM-CSF (SEQ ID NO: 103)
ATGTGGTTGCAGAATTTGCTCTTCCTGGGGATTGTGGTCTACAGC
CTCTCCGCACCTACCCGCTCTCCTATCACAGTTACAAGACCCTGG
AAACATGTGGAGGCCATTAAAGAAGCATTGAATTTGTTGGACGAT
ATGCCCGTCACCCTGAATGAAGAAGTAGAAGTTGTTTCTAATGAG
TTCAGCTTTAAAAAATTGACCTGTGTGCAGACACGGCTTAAAATT
TTTGAACAGGGACTTAGAGGAAACTTTACTAAGCTGAAGGGGCA
CTTAACATGACAGCTTCTTATTATCAGACCTATTGTCCTCCAACA
CCTGAAACCGACTGTGAAACACAGGTAACCACTTACGCCGATTTT
ATTGATTCTTTGAAAACATTCCTCACCGATATACCATTTGAGTGT
AAGAAGCCAGGCCAAAAGtaG Anti-PD1 (SEQ ID NO: 104)
ATGGAAACTGACACACTTCTTCTGTGGGTCTTGCTCCTGTGGGTC
CCAGGCTCTACTGGTGACAGTCCTGATAGGCCATGGAACCCACCT
ACCTTTAGTCCAGCCTTGCTCGTCGTAACCGAAGGGGACAACGCT
ACATTCACCTGCTCTTTTAGCAATACTTCTGAGAGTTTTCATGTA
GTCTGGCATCGGGAGAGTCCATCCGGACAAAGATACTTTGGCC
GCTTTTCCAGAGGATAGGTCTCAACCTGGGCAAGACGCAAGGTTT
CGAGTCACACAGCTTCCTAACGGGAGAGATTTTCACATGTCTGTA
GTTCGGGCACCGCGAAATGATTCTGGCACATATGTTTGCGGTGTG
ATCTCACTTGCTCCAAAGATTCAAATAAAGGAGAGCCTTCGCGCC
GAGTTGCGGGTGACTGAGCGGGAGCCCAAGTCCTGCGACAAAACC
CATACTTGTCCACCCTGTGGCCGCGGGTCATCCGGTGGCGGGTCT
GGGGGGCAACCAAGAGAGCCACAGGTATATACTCTTCCCCCCAGC
AGAGAAGAAATGACAAAAAACCAAGTGTCCCTGACATGTCTGGTT
AAAGGATTTTATCCCAGTGACATTGCTGTAGAATGGGAATCCAAT
GGTCAACCCGAGAATAACTACAAAACCACTCCTCCAGTATTGGAC
AGTGACGGTTCCTTCTTCCTCTATTCCAAACTTACAGTGGATAAA
TCCCGCTGGCAGCAAGGGAATGTATTCAGCTGTAGTGTCATGCAC
GAAGCTCTTCATAACCATTATACACAGAAATCTCTTTCCCTGAGC
CCAGGTAAAtaG Adenosine Deaminase (ADA) #1 (Mouse)
(SEQ ID NO: 105)
ATGGAGACTGATACACTTTTGCTCTGGGTTTTGCTCTTGTGGGT
ACCAGGGTCTACTGGAGATGCACAAACTCCTGCATTCAACAAGC
CTAAGGTAGAGCTTCATGTCCATTTGGACGGAGCCATAAAACCT
GAAACCATACTCTATTTCGGCAAGAAACGGGGTATAGCACTTCC
CGCTGATACCGTGGAAGAGTTGAGAAATATCATTGGCATGGACA
AACCTCTTAGCCTGCCTGGCTTTCTGGCAAAGTTCGACTACTAT
ATGCCAGTTATAGCAGGGTGTAGAGAAGCAATAAAGCGAATCGC
CTATGAGTTCGTTGAGATGAAGGCTAAAGAAGGAGTTGTTTACG
TGGAAGTCCGGTACTCACCTCATCTGCTTGCTAATAGCAAGGTG
GACCCAATGCCATGGAATCAAACTGAAGGTGATGTAACCCCTGA
CGATGTGGTCGATTTGGTCAATCAAGGTCTCCAAGAAGGCGAGC
AGGCTTTCGGCATTAAGGTAAGAAGTATATTGTGCTGTATGCGA
CATCAACCTTCATGGTCCCTGGAGGTCCTCGAATTGTGCAAAAA
GTACAATCAAAAAACGGTGTCGCAATGGATCTCGCTGGAGATG
AGACCATAGAAGGTTCCTCTCTTTTTCCCCGGTCATGTCGAAGCA
TATGAAGGGGCTGTCAAAATGGTATCACCGCACCGTCCACGC
AGGGGAAGTAGGGTCCCCAGAAGTAGTCAGGGAAGCCGTTGACA
TTTGAAAACAGAAAGAGTCGGGCATGGCTACCATACAATAGAG
GACGAAGCCTCTACCGACTTTTGAAAGAAAATATGCACTT
CGAGGTCGTCCCTGGAGTTCATATCTCACCGGAGCATGGGACC
CCAAAACAACCCACGCCGTCGTACGCTTCAAGAATGATAAGGCA
AACTACAGTTTGAATACAGATGATCCACTGATATTCAAGTCAAC
ACTTGACACTGACTACCAGATGCAACCTGAAGGATATGGGTTTCA
CCGAAGAAGAGTTCAAGAGATTGAACATTAACGCAGCAAAAGC
TCCTTCCTGCCAGAGGAAGAGAAAAAGAATTGCTTGAAAGGTT
GTATCGAGAATACCAA Adenosine Deaminase (ADA) #2 (Mouse)
(SEQ ID NO: 106)
ATGGCACAAACTCCAGCTTTTAATAAGCCCAAAGTGGAACTTCA
TGTTCATCTGGATGGGGCAATTAAGCCCGAAACTATATTGTACT
TTGGCAAAAAGAGGGGTATTGCCCTGCCAGCAGATACCGTTGAG

TABLE 6-continued

Sequences encoding exemplary effector molecules

```
GAGCTTCGCAACATCATTGGGATGGACAAGCCCCTCTCTCTGCC
AGGTTTTCTCGCTAAATTCGATTATTATATGCCTGTTATTGCTG
GTTGCCGGGAGGCCATCAAGAGGATAGCCTACGAGTTTGTTGAG
ATGAAGGCCAAAGAGGGCGTGGTGTACGTAGAGGTCAGATACAG
CCCTCACCTGCTTGCCAACAGCAAGGTGGACCCAATGCCCTGGA
ACCAAACCGAGGGGGATGTCACTCCCGACGACGTTGTAGACCTC
GTAAATCAGGGCCTTCAAGAGGGCGAGCAGGCATTTGGCATAAA
AGTCCGGTCTATACTCTGCTGTATGAGGCACCAACCCTCCTGGT
CTTTGGAGGTACTTGAGTTGTGTAAGAAATACAATCAAAAGACT
GTAGTCGCCATGGATCTTGCAGGCGATGAAACCATCGAGGGTAG
CTCCTTGTTCCCTGGACATGTTGAAGCCTACGAGGGGGCCGTAA
AAAATGGGATACACAGGACTGTCCACGCTGGTGAAGTCGGAAGC
CCAGAGGTGGTAAGGGAGGCAGTTGACATACTCAAGACAGAGCG
GGTTGGACACGGATACCACACAATTGAGGACGAGGCCCTGTATA
ACCGCCTCCTCAAAGAGAACATGCATTTTGAGGTGTGTCCTTGG
TCCAGCTACCTGACTGGTGCTTGGGACCCTAAAACAACTCACGC
CGTGGTCCGGTTCAAGAACGATAAAGCCAATTACTCTTTGAATA
CCGACGACCCCCTCATATTCAAATCAACATTGGATACCGACTAC
CAAATGACCAAAAAGGATATGGGGTTTACTGAAGAGGAGTTCAA
GAGGCTCAACATAAATGCCGCTAAATCCTCCTTTCTCCCCGAGG
AAGAAAAAAAAGAACTCCTTGAGCGGCTGTATAGGGAGTATCAA 4-1BBL #1 (Mouse) (SEQ ID NO: 107)
ATGGAAACAGATACACTCTTGCTCTGGGTACTGCTTCTGTGGGT
CCCCGGCTCTACTGGGGATGAAGATGATGTAACTACTACAGAAG
AACTCGCTCCCGCTCTTGTCCCCCACCCAAGGGTACCTGCGCC
GGTTGGATGGCTGGCATCCCAGGACATCCAGGTCACAACGGTAC
CCCCGGAAGAGATGGTCGGGATGAACTCCCGGCGAGAAGGGCG
AAAAAGGGGATGCAGGGCTTCTGGGACCTAAAGGTGAAACAGGG
GACGTTGGAATGACTGGTGCAGAAGGGCCTCGCGGCTTTCCTGG
CACCCCTGGGAGGAAAGGAGAGCCCGGAGAGCTCCAGAGAACTG
AACCTCGGCCTGCACTCACTATAACTACTTCCCTAATCTTGGG
ACCCGCGAGAACAACGCCGATCAGGTTACACCTGTAAGCCATAT
CGGGTGCCCCAATACTACCCAGCAAGGGAGTCCCGTGTTCGCAA
AGCTTTTGGCTAAAAACCAAGCATCCCTGTGTAACACTACTCTT
AATTGGCATTCACAAGACGGTGCTGGTAGCTCTTATCTTTCTCA
GGGGCTGCGGTACGAAGAAGATAAGAAGGAATTGGTTGTGGATT
CTCCAGGACTCTATTATGTCTTTCTCGAATTGAAGCTCAGTCCC
ACCTTCACAAACACTGGACACAAAGTCCAGGGCTGGGTAAGTCT
GGTACTCCAAGCAAAGCCCCAGGTTGACGATTTCGACAATTTGG
CACTCACCGTAGAGCTTTTCCCATGCTCCATGGAAAATAAACTT
GTTGATCGGTCATGGTCACAGCTCTTGCTGCTTAAGGCAGGGCA
TCGCCTCTCAGTGGGTCTGAGAGCTTATTTGCATGGTGCACAAG
ATGCTTACAGGGATTGGGAATTGTCCTACCCAAACACTACAAGT
TTCGGGTTGTTCCTTGTCAAACCTGATAACCCATGGGAGtaG 4-1BBL #2 (Mouse) (SEQ ID NO: 108)
ATGGAAACTGATACACTCCTCCTGTGGGTCCTTCTTTTGTGGGT
GCCCGGATCAACCGGCGATGGCTGGATGGCAGGCATCCCAGGAC
ACCCAGGACACAACGGTACTCCAGGTCGAGACGGTCGGGATGGG
ACTCCTGGGGAGAAAGGCGAGAAAGGGGACGCTGGTTTGCTCGG
TCCTAAGGGGGAAACCGGGGATGTAGGAATGACAGGGGCTGAAG
GGCCTCGGGGATTTCCTGGGACACCAGGCAGGAAGGGTGAACCA
GGGGAGGCCCTCCAGCGCACCGAGCCACGGCCAGCTCTGACCAT
AACAACAAGTCCAAACCTGGGCACACGCGAAAACAATGCTGACC
AGGTGACTCCTGTAAGCTCACATCGGATGCCCTAACACTACACAA
CAGGGCTCTCCTGTATTTGCAAAGCTTCTCGCAAAAAATCAAGC
ATCACTTTGTAATACAACCCTGAACTGGCATTCTCAGGACGGAG
CAGGGTCCTCTTATTTGTCTCAAGGGCTCCGCTACGAAGAAGAT
AAAAAGGAATTGGTTGTTGACAGTCCAGGTTTGTATTATGTGTT
TTTGGAACTTAAGCTGTCACCAACCTTCACTAACACCGGCCACA
AGGTCCAAGCTGGGTTAGTCTTGTTTTGCAAGCCAAACCTCAA
GTGGATGATTTTGACAATCTGGCTTTGACTGTTGAGCTTTTTCC
ATGCAGTATGGAGAATAAACTGGTTGATCGGTCATGGTCACAGC
TCCTTCTGCTCAAGGCCGGACATAGGCTGAGTGTGGGACTTCGG
GCCTACTTGCACGGCGCCCAGGACGCATACCGAGACTGGGAACT
CAGCTACCCTAACACAACTTCTTTTGGGTTGTTCCTTGTCAAAC
CCGATAATCCTTGGGAAtaG HPGE2 #1 (Mouse) (SEQ ID NO: 109)
ATGGAGACTGATACTTTGCTCCTGTGGGTTCTTCTCCTGTGGGT
TCCTGGTTCCACAGGGGATATGCATGTCAATGGCAAGGTAGCAC
TCGTGACTGGGGCTGCACAGGGTATCGGGAAAGCTTTTGCCGAG
GCCCTGTTGCTGCATGGCGCCAAGGTCGCTTTGGTAGATTGGAA
CTTGGAGGCTGGAGTTAAATGCAAAGCTGCACTCGACGAACAAT
TTGAGCCTCAAAAAACCCTCTTTGTGCAGTGTGACGTTGCTGAC
CAAAAGCAACTCAGGGACACATTCAGGAAGGTCGTAGACCATTT
CGGACGCCTCGATATACTCGTTAATAATGCCGGGGTAAACAACG
AAAAGAACTGGGAACAAACATTGCAAATCAACCTGGTAAGTGTC
ATTAGCGGAACTTATCTGGGTCTTGATTATATGAGCAAGCAGAA
CGGGGGCGAGGGCGGGATCATTATCAACATGTCAAGTCTTGCCG
GATTGATGCCAGTTGCTCAGCAGCCTGTTTACTGTGCCAGCAAG
CACGGTATTATTGGGTTTACCCGGAGTGCCGCCATGGCCGCAAA
TCTTATGAAGAGTGGGGTAAGACTGAATGTTATCTGCCCAGGTT
TCGTAGATACCCCAATCCTGGAGAGCATCGAGAAGGAGGAAAAT
ATGGGACAATACATTGAATATAAAGATCAAATCAAGGCTATGAT
GAAGTTCTACGGGGTTCTGCATCCATCCACAATTGCCAACGGGC
TCATTAATCTGATTGAGGACGACGCCTTGAACGGAGCTATAATG
AAAATCACAGCTTCCAAAGGCATTCACTTCCAAGATTATGATAT
ATCACCCTTGCTTGTCAAGGCTCCTCTGACAAGT HPGE2 #2 (Mouse) (SEQ ID NO: 110)
ATGCATGTCAATGGCAAGGTAGCACTCGTGACTGGGGCTGCACA
GGGTATCGGGAAAGCTTTTGCCGAGGCCCTGTTGCTGCATGGCG
CCAAGGTCGCTTTGGTAGATTGGAACTTGGAGGCTGGAGTTAAA
TGCAAAGCTGCACTCGACGAACAATTTGAGCCTCAAAAAACCCT
CTTTGTGCAGTGTGACGTTGCTGACCAAAAGCAACTCAGGGACA
CATTCAGGAAGGTCGTAGACCATTTCGGACGCCTCGATATACTC
GTTAATAATGCCGGGGTAAACAACGAAAAGAACTGGGAACAAAC
ATTGCAAATCAACCTGGTAAGTGTCATTAGCGGAACTTATCTGG
GTCTTGATTATATGAGCAAGCAGAACGGGGGCGAGGGCGGGATC
ATTATCAACATGTCAAGTCTTGCCGGATTGATGCCAGTTGCTCA
GCAGCCTGTTTACTGTGCCAGCAAGCACGGTATTATTGGGTTTA
CCCGGAGTGCCGCCATGGCCGCAAATCTTATGAAGAGTGGGGTA
AGACTGAATGTTATCTGCCCAGGTTTCGTAGATACCCCAATCCT
GGAGAGCATCGAGAAGGAGGAAAATATGGGACAATACATTGAAT
ATAAAGATCAAATCAAGGCTATGATGAAGTTCTACGGGTTCTG
CATCCATCCACAATTGCCAACGGGCTCATTAATCTGATTGAGGA
CGACGCCTTGAACGGAGCTATAATGAAAATCACAGCTTCCAAAG
GCATTCACTTCCAAGATTATGATATATCACCCTTGCTTGTCAAG
GCTCCTCTGACAAGT
```

Additional Embodiments

Provided below are enumerated paragraphs describing specific embodiments:

1. An engineered cell comprising:
   a) a promoter; and
   b) an exogenous polynucleotide sequence comprising an expression cassette described in a formula, oriented from 5' to 3', comprising

S1-E1-L-S2-E2 wherein
   S1 comprises a polynucleotide sequence encoding a first signal peptide,
   E1 comprises a polynucleotide sequence encoding a first effector molecule,
   L comprises a linker polynucleotide sequence,
   S2 comprises a polynucleotide sequence encoding a second signal peptide,
   E2 comprises a polynucleotide sequence encoding a second effector molecule, and
   wherein the promoter is operably linked to the expression cassette, the first signal peptide is operably linked to the first effector molecule, and the second signal peptide is operably linked to the second effector molecule, and
   wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.
2. The engineered cell of paragraph 1, wherein the promoter comprises an exogenous promoter polynucleotide sequence.
3. The engineered cell of paragraph 1, wherein the promoter comprises an endogenous promoter.
4. The engineered cell of any one of paragraphs 1-3, wherein the promoter is operably linked to the expression cassette such that the polynucleotides are capable of being transcribed as a single polynucleotide comprising the formula S1-E1-L-S2-E2.
5. The engineered cell of paragraph 4, wherein the linker polynucleotide sequence is operably associated with the translation of the first effector molecule and the second effector molecule as separate polypeptides.
6. The engineered cell of paragraph 5, wherein the linker polynucleotide sequence encodes a 2A ribosome skipping tag.
7. The engineered cell of paragraph 6, wherein the 2A ribosome skipping tag is selected from the group consisting of: P2A, T2A, E2A, and F2A.
8. The engineered cell of paragraph 5, wherein the linker polynucleotide sequence encodes a T2A ribosome skipping tag.
9. The engineered cell of paragraph 5, the linker polynucleotide sequence encodes an Internal Ribosome Entry Site (IRES).
10. The engineered cell of any one of paragraphs 5-9, wherein the linker polynucleotide sequence encodes a cleavable polypeptide.
11. The engineered cell of paragraph 10, wherein the cleavable polypeptide comprises a Furin recognition polypeptide sequence.
12. The engineered cell of any one of paragraphs 5-9, wherein the linker polynucleotide sequence further encodes a Gly-Ser-Gly polypeptide sequence.
13. The engineered cell of any one of paragraphs 1-5, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus.
14. The engineered cell of any one of paragraphs 1-3, wherein the linker polynucleotide sequence encodes a second promoter,
wherein the promoter is operably linked to the expression cassette such that a first polynucleotide comprising the formula S1-E1 is capable of being transcribed,
wherein the second promoter is operably linked to the expression cassette such that a second polynucleotide comprising the formula S2-E2 is capable of being transcribed, and wherein the first and the second polynucleotide are separate polynucleotides.
15. The engineered cell of paragraph 14, wherein the promoter and the second promoter are identical.
16. The engineered cell of paragraph 14, wherein the promoter and the second promoter are different.
17. The engineered cell of any one of paragraphs 1-16, wherein the engineered cell is HLA-typed with reference to a subject in need of therapeutic treatment.
18. The engineered cell of any one of paragraphs 1-17, wherein the engineered cell is a human cell.
19. The engineered cell of paragraph 18, wherein the human cell is an isolated cell from a subject.
20. The engineered cell of paragraph 19, wherein the isolated cell is isolated from a tissue consisting of the group of: bone marrow, adipose tissue, the umbilical cord, fetal liver, muscle, and lung tissue.
21. The engineered cell of any one of paragraphs 1-20, wherein the engineered cell is a cultured cell.
22. The engineered cell of any one of paragraphs 1-21, wherein the engineered MSC comprises a cellular marker phenotype comprising the cellular markers CD105+, CD73+, and CD90+.
23. The engineered cell of paragraph 22, wherein the cellular marker phenotype further comprises a phenotype lacking or substantially lacking one or more cellular markers selected from the group consisting of: CD45, CD34, CD14, CD11b, CD79α, CD19, HLA class II, and combinations thereof.
24. The engineered cell of any one of paragraphs 1-21, wherein the engineered MSC comprises a cellular marker phenotype comprising CD105+, CD73+, CD90+, CD45−, CD34−, CD14−; a cellular marker phenotype comprising CD105+, CD73+, CD90+, CD11b−, CD79α−; a cellular marker phenotype comprising CD105+, CD73+, CD90+, CD19−, HLA class II−; or a cellular marker phenotype comprising CD73+, CD90+, CD105+, and CD166+, CD11b−, CD14−, CD19−, CD34−, CD45−, and HLA-DR−.
25. The engineered cell of any one of paragraphs 22-24, wherein the cellular marker phenotype is determined or has been determined by flow-cytometry.
26. The engineered cell of any one of paragraphs 1-21, wherein the engineered cell comprises a T cell.
27. The engineered cell of any one of paragraphs 1-21, wherein the engineered cell comprises a NK cell.
28. The engineered cell of any one of paragraphs 1-21, wherein the engineered cell comprises a NKT cell.
29. The engineered cell of any of paragraphs 22-28, wherein the cellular marker phenotype further comprises a cellular marker comprising a cognate receptor or a cognate receptor ligand for the first effector molecule, the second effector molecule, or the first and second effector molecules expressed in the engineered cells.
30. The engineered cell of paragraph 29, wherein the receptor is selected from the group consisting of: IL12RB1, IL12RB2, CCL7, and combinations thereof
31. The engineered cell of any one of paragraphs 1-30, wherein the promoter and/or the second promoter comprises a constitutive promoter.
32. The engineered cell of paragraph 31, wherein the constitutive promoter is selected from the group consisting of: CMV, EFS, SFFV, SV40, MND, PGK, UbC, hEF1aV1, hCAGG, hEF1aV2, hACTb, heIF4A1, hGAPDH, hGRP78, hGRP94, hHSP70, hKINb, and hUBIb.
33. The engineered cell of any one of paragraphs 1-30, wherein the promoter comprises an SFFV promoter.
34. The engineered cell of any one of paragraphs 1-30, wherein the promoter and/or the second promoter comprises an inducible promoter.
35. The engineered cell of paragraph 34, wherein the inducible promoter is selected from the group consisting of: minP, NFkB response element, CREB response element, NFAT response element, SRF response element 1, SRF response element 2, AP1 response element, TCF-LEF response element promoter fusion, Hypoxia responsive element, SMAD binding element, STAT3 binding site, inducer molecule responsive promoters, and tandem repeats thereof
36. The engineered cell of any one of paragraphs 1-35, wherein the first signal peptide or the second signal peptide comprises a native signal peptide native to the first effector molecule or the second effector molecule, respectively.
37. The engineered cell of any one of paragraphs 1-36, wherein the first signal peptide or the second signal peptide comprises a non-native signal peptide non-native to the first effector molecule or the second effector molecule, respectively.
38. The engineered cell of paragraph 37, wherein the non-native signal peptide is selected from the group consisting of: IL12, IL2, optimized IL2, trypsiongen-2, *Gaussia* luciferase, CD5, human IgKVII, murine IgKVII, VSV-G, prolactin, serum albumin preprotein, azurocidin preprotein, osteonectin, CD33, IL6, IL8, CCL2, TIMP2, VEGFB, osteoprotegerin, serpin E1, GROalpha, CXCL12, and IL21.
39. The engineered cell of any one of paragraphs 1-38, wherein the first signal peptide and the second signal peptide are identical.
40. The engineered cell of any one of paragraphs 1-39, wherein the polynucleotide sequence encoding the first signal peptide comprises a codon optimized polynucleotide sequence.
41. The engineered cell of any one of paragraphs 1-40, wherein the first secretion polypeptide is a human IL12 signal peptide.
42. The engineered cell of any one of paragraphs 1-40, wherein the polynucleotide sequence encoding the second signal peptide comprises a codon optimized polynucleotide sequence.
43. The engineered cell of any one of paragraphs 1-42, wherein the second secretion polypeptide is a human IL21 signal peptide.
44. The engineered cell of any one of paragraphs 1-42, wherein the first effector molecule is selected from a therapeutic class, wherein the therapeutic class is selected from the group consisting of: a cytokine, a chemokine, a growth factor, a co-activation molecule, a tumor microenvironment modifier a, a receptor, a ligand, an antibody, a polynucleotide, a peptide, and an enzyme.
45. The engineered cell of any one of paragraphs 1-44, wherein the second effector molecule is selected from a therapeutic class, wherein the therapeutic class is selected from the group consisting of: a cytokine, a chemokine, a growth factor, a co-activation molecule, a tumor microenvironment modifier, a receptor, a ligand, an antibody, a polynucleotide, a peptide, and an enzyme.
46. The engineered cell of paragraph 45, wherein the therapeutic class of the first effector molecule and the second effector molecule are different.
47. The engineered cell of any one of paragraphs 1-46, wherein the first effector molecule and/or the second effector molecule is a modified effector molecule.
48. The engineered cell of paragraph 47, wherein the first effector molecule and/or the second effector molecule is modified to comprises a cell membrane tethering domain.
49. The engineered cell of paragraph 48, wherein the cell membrane tethering domain comprises a transmembrane-intracellular domain or a transmembrane domain.
50. The engineered cell of paragraph 48, wherein the cell membrane tethering domain comprises a cell surface receptor, or a cell membrane-bound portion thereof
51. The engineered cell of paragraph 50, wherein the modified effector molecule is a fusion protein that comprises the cell surface receptor, or a cell membrane-bound portion thereof
52. The engineered cell of any one of paragraphs 48-51, wherein the modified effector molecule further comprises a linker between the effector molecule and the cell membrane tethering domain.
53. The engineered cell of any one of paragraphs 47-52, wherein when expressed the modified effector molecule is tethered to a cell membrane of the engineered cell.
54. The engineered cell of any one of paragraphs 44-53, wherein the cytokine is selected from the group consisting of: IL12, IL7, IL21, IL18, IL15, Type I interferons, and Interferon-gamma.
55. The engineered cell of paragraph 54, wherein the IL12 cytokine is an IL12p70 fusion protein.
56. The engineered cell of any one of paragraphs 44-55, wherein the chemokine is selected from the group consisting of: CCL21a, CXCL10, CXCL11, CXCL13, CXCL10-11 fusion, CCL19, CXCL9, and XCL1.
57. The engineered cell of any one of paragraphs 44-56, wherein the growth factor is selected from the group consisting of: Flt3L and GM-CSF.
58. The engineered cell of any one of paragraphs 44-57, wherein the co-activation molecule is selected from the group consisting of: 4-1BBL and CD40L.
59. The engineered cell of any one of paragraphs 34-41, wherein the tumor microenvironment modifier is selected from the group consisting of: adenosine deaminase, TGF-beta inhibitors, immune checkpoint inhibitors, VEGF inhibitors, and HPGE2.
60. The engineered cell of paragraph 59, wherein the TGF-beta inhibitors are selected from the group consisting of: an anti-TGFbeta peptide, an anti-TGFbeta antibody, a TGFb-TRAP, and combinations thereof
61. The engineered cell of paragraph 59, wherein the immune checkpoint inhibitors comprise anti-PD-1 antibodies.
62. The engineered cell of paragraph 59, wherein the VEGF inhibitors comprise anti-VEGF antibodies, anti-VEGF peptides, or combinations thereof
63. The engineered cell of any one of paragraphs 1-59, wherein the first effector molecule and the second effector molecule are human-derived effector molecules.
64. The engineered cell of any one of paragraphs 1-63, wherein the first effector molecule comprises IL12.
65. The engineered cell of any one of paragraphs 1-63, wherein the first effector molecule comprises an IL12p70 fusion protein.
66. The engineered cell of paragraph 65, wherein the IL12p70 fusion protein is a human IL12p70 fusion protein.
67. The engineered cell of any one of paragraphs 64-66, wherein the second effector molecule comprises CCL21a.
68. The engineered cell of paragraph 67, wherein the CCL21a is a human CCL21a.
69. The engineered cell of any one of paragraphs 64-66, wherein the second effector molecule comprises IL7.
70. The engineered cell of paragraph 69, wherein the IL7 is a human IL7.
71. The engineered cell of any one of paragraphs 64-66, wherein the second effector molecule comprises IL21.
72. The engineered cell of paragraph 71, wherein the IL21 is a human IL21.
73. The engineered cell of any one of paragraphs 1-72, wherein the expression cassette further comprises an E3 comprising a polynucleotide sequence encoding a third effector molecule.
74. The engineered cell of paragraph 73, wherein the third effector molecule comprises Flt3L.

75. The engineered cell of paragraph 73, wherein the third effector molecule comprises anti-PD1.
76. The engineered cell of paragraph 75, wherein the expression cassette further comprises an E4 comprising a polynucleotide sequence encoding a fourth effector molecule.
77. The engineered cell of paragraph 76, wherein the fourth effector molecule comprises adenosine deaminase.
78. The engineered cell of paragraph 73, wherein the third effector molecule comprises adenosine deaminase.
79. The engineered cell of paragraph 73, wherein the third effector molecule comprises CD40L.
80. The engineered cell of paragraph 73, wherein the third effector molecule comprises a CXCL10-CXCL11 fusion protein.
81. The engineered cell of paragraph 73, wherein the third effector molecule comprises XCL1.
82. The engineered cell of paragraph 64, wherein the second effector molecule comprises Flt3L.
83. The engineered cell of paragraph 64, wherein the second effector molecule comprises a CXCL10-CXCL11 fusion protein.
84. The engineered cell of paragraph 64, wherein the second effector molecule comprises anti-PD1.
85. The engineered cell of paragraph 64, wherein the second effector molecule comprises CD40L.
86. The engineered cell of any one of paragraphs 1-63, wherein the first effector molecule comprises interferon-beta and the second effector molecule comprises Flt3L.
87. The engineered cell of any one of paragraphs 1-86, wherein the polynucleotide sequence encoding the first effector molecule comprises a codon optimized polynucleotide sequence.
88. The engineered cell of any one of paragraphs 1-87, wherein the polynucleotide sequence encoding the second effector molecule comprises a codon optimized polynucleotide sequence.
89. The engineered cell of any one of paragraphs 1-88, wherein the engineered cell comprises a polynucleotide sequence encoding the promoter and the expression cassette.
90. The engineered cell of paragraph 89, wherein the exogenous polynucleotide sequence comprises the sequence shown in SEQ ID NO: 144.
91. The engineered cell of any one of paragraphs 1-90, wherein the exogenous polynucleotide sequence is integrated into the genome of the engineered cell.
92. The engineered cell of any one of paragraphs 1-91, wherein the exogenous polynucleotide sequence comprises one or more viral vector polynucleotide sequences.
93. The engineered cell of paragraph 92, wherein the one or more viral vector polynucleotide sequences comprise lentiviral, retroviral, retrotransposon, or adenoviral polynucleotide sequences.
94. The engineered cell of any one of paragraphs 1-93, wherein the expression cassette further comprises following E2, an additional exogenous polynucleotide sequence comprising a formula, oriented from 5' to 3', comprising:

(L-S-E)$_X$ wherein
S comprises a polynucleotide sequence encoding a signal peptide,
E comprises a polynucleotide sequence encoding an effector molecule,
L comprises a linker polynucleotide sequence,
X=1 to 20
wherein the promoter is operably linked to the expression cassette, and wherein for each X the corresponding signal peptide is operably associated with the effector molecule.
95. An engineered cell comprising a construct, wherein the construct comprises:
a) an SFFV promoter; and
b) an exogenous polynucleotide sequence comprising an expression cassette described in a formula, oriented from 5' to 3', comprising

S1-E1-L-S2-E2 wherein
S1 comprises a polynucleotide sequence encoding a first signal peptide, wherein the first signal peptide is a human IL12 signal peptide;
E1 comprises a polynucleotide sequence encoding a first effector molecule, wherein the first effector molecule is a human IL12p70 fusion protein;
L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus;
S2 comprises a polynucleotide sequence encoding a second signal peptide, wherein the second signal peptide is a human IL21 signal peptide;
E2 comprises a polynucleotide sequence encoding a second effector molecule, wherein the second effector molecule is human IL21; and
wherein the SFFV promoter is operably linked to the expression cassette, the first signal peptide is operably linked to the first effector molecule, and the second signal peptide is operably linked to the second effector molecule, and
wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.
96. The engineered cell of paragraph 95, wherein the construct comprises the polynucleotide sequence shown in SEQ ID NO: 144.
97. The engineered cell of paragraph 95 or paragraph 96, wherein the engineered cell is HLA-typed with reference to a subject in need of therapeutic treatment.
98. The engineered cell of any one of paragraphs 95-97, wherein the engineered cell is a human cell.
99. The engineered cell of paragraph 98, wherein the human cell is an isolated cell from a subject.
100. The engineered cell of paragraph 99, wherein the isolated cell is isolated from a tissue consisting of the group of: bone marrow, adipose tissue, the umbilical cord, fetal liver, muscle, and lung tissue.
101. The engineered cell of any one of paragraphs 95-100, wherein the engineered cell is a cultured cell.
102. The engineered cell of any one of paragraphs 95-101, wherein the engineered MSC comprises a cellular marker phenotype comprising the cellular markers CD105+, CD73+, and CD90+.
103. The engineered cell of paragraph 102, wherein the cellular marker phenotype further comprises a phenotype lacking or substantially lacking one or more cellular markers selected from the group consisting of: CD45, CD34, CD14, CD11b, CD79α, CD19, HLA class II, and combinations thereof 104. The engineered cell of any one of paragraphs 95-101, wherein the engineered MSC comprises a cellular marker phenotype comprising CD105+, CD73+, CD90+, CD45−, CD34−, CD14−; a cellular marker phenotype comprising CD105+, CD73+, CD90+, CD11b−, CD79α−; a cellular marker phenotype comprising CD105+, CD73+, CD90+, CD19−, HLA class II−; or a cellular marker phenotype comprising CD73+, CD90+, CD105+, and CD166+, CD11b−, CD14−, CD19−, CD34−, CD45−, and HLA-DR−.
105. The engineered cell of any one of paragraphs 95-101, wherein the engineered cell comprises a T cell.
106. The engineered cell of paragraph 105, wherein the T cell is a CD8+ T cell, a CD4+ T cell, a cytotoxic T lymphocyte (CTL), a viral-specific T cell, a gamma-delta T cell, or a T regulatory cell.
107. The engineered cell of any one of paragraphs 95-101, wherein the engineered cell comprises a NK cell.
108. The engineered cell of any one of paragraphs 95-101, wherein the engineered cell comprises a NKT cell.
109. The engineered cell of any one of paragraphs 95-101, wherein the engineered cell comprises a monocyte cell.
110. The engineered cell of any one of paragraphs 95-101, wherein the engineered cell comprises a macrophage.
111. The engineered cell of any one of paragraphs 95-101, wherein the engineered cell comprises a TIL.
112. The engineered cell of any one of paragraphs 95-111, wherein the exogenous polynucleotide sequence is integrated into the genome of the engineered cell.
113. The engineered cell of any one of paragraphs 95-112, wherein the exogenous polynucleotide sequence comprises one or more viral vector polynucleotide sequences.
114. The engineered cell of paragraph 113, wherein the one or more viral vector polynucleotide sequences comprise lentiviral, retroviral, retrotransposon, or adenoviral polynucleotide sequences.
115. The engineered cell of paragraph 113, wherein the one or more viral vector polynucleotide sequences comprise lentiviral polynucleotide sequences.
116. The engineered cell of any one of paragraphs 1-115, wherein the cell secretes each effector molecule.
117. The engineered cell of paragraph 116, wherein the first effector molecule is secreted at a ratio that is 10 fold higher relative to secretion of the second effector molecule.
118. The engineered cell of any one of paragraphs 1-117, wherein the cell further comprises an antigen recognizing receptor.
119. The engineered cell of paragraph 118, wherein the antigen recognizing receptor recognizes an antigen selected from the group consisting of: 5T4, ADAM9, ADGRE2, AFP, AXL, B7-H3, B7-H4, B7-H6, C4.4, CA6, Cadherin 3, Cadherin 6, CCR1, CCR4, CD117, CD123, CD131, CD133, CD138, CD142, CD166, CD25, CD244, CD30, CD300LF, CD33, CD352, CD37, CD38, CD44, CD56, CD66e, CD70, CD71, CD74, CD79b, CD80, CD93, CEA, CEACAM5, Claudin18.2, CLEC12A, cMet, CSPG4, CTLA, DLK1, DLL3, DR5, EGFR, EMB, ENPP3, EpCAM, EphA2, Ephrin A4, ETBR, FGFR2, FGFR3, FRalpha, FRb, FLT3, GAPT, GCC, GD2, GFRa4, gpA33, GPC3, gpNBM, GPRC5, HER2, IL-1RAP, IL-13R, IL-13Ra, IL-13Ra2, IL-8, IL-15, IL1RAP, Integrin aV, KIT, L1CAM, LAMP1, LAT2, Lewis Y, LeY, LILRA2, LILRB2, LIV-1, LRRC, LY6E, MCSP, Mesothelin, MLC1, MS4A3, MUC1, MUC16, MUC1C, MYADM, NaPi2B, Nectin 4, NKG2D, NOTCH3, NY ESO 1, Ovarin, P-cadherin, pan-Erb2, PIEZO1, PRAM1, PSCA, PSMA, PTK7, ROR1, S Aures, SCT, SLAMF7, SLC22A16, SLC17A9, SLITRK6, SPNS3, SSTR2, STEAP1, Survivin, TDGF1, TIM1, TROP2, VSTM1, and WT1
120. The engineered cell of paragraph 118 or paragraph 119, wherein the antigen recognizing receptor comprises an antigen-binding domain.
121. The engineered cell of paragraph 120, wherein the antigen-binding domain comprises an antibody, an antigen-binding fragment of an antibody, a F(ab) fragment, a F(ab') fragment, a single chain variable fragment (scFv), or a single-domain antibody (sdAb).
122. The engineered cell of paragraph 120, wherein the antigen-binding domain comprises a single chain variable fragment (scFv).
123. The engineered cell of paragraph 122, wherein the scFv comprises a heavy chain variable domain (VH) and a light chain variable domain (VL).
124. The engineered cell of paragraph 123, wherein the VH and VL are separated by a peptide linker.
125. The engineered cell of paragraph 124, wherein the scFv comprises the structure VH-L-VL or VL-L-VH, wherein VH is the heavy chain variable domain, L is the peptide linker, and VL is the light chain variable domain.
126. The engineered cell of any one of paragraphs 118-125, the antigen recognizing receptor is a chimeric antigen receptor (CAR) or T cell receptor (TCR).
127. The engineered cell of any one of paragraphs 118-125, the antigen recognizing receptor is a chimeric antigen receptor (CAR).
128. The engineered cell of paragraph 127, wherein the CAR comprises one or more intracellular signaling domains, and the one or more intracellular signaling domains are selected from the group consisting of: a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain.
129. The engineered cell of paragraph 127 or paragraph 128, wherein the CAR comprises a transmembrane domain, and the transmembrane domain is selected from the group consisting of: a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.
130. The engineered cell of any one of paragraphs 127-129, wherein the CAR comprises a spacer region between the antigen-binding domain and the transmembrane domain.

131. A population of cells, the population of cells comprising any of the engineered cells of any one of paragraphs 1-130.
132. The population of cells of paragraph 131, wherein the population of cells is enriched for the engineered cells.
133. The population of cells of paragraph 131 or paragraph 132, wherein the first effector molecule, the second effector molecule, or the first and second effector molecules expressed in the engineered cells promotes increased growth, viability, or growth and viability relative to cells in the population that do not express the first effector molecule, the second effector molecule, or the first and second effector molecules.
134. The population of cells of paragraph 133, wherein the first effector molecule is IL12 or an IL12p70 fusion protein.
135. The population of cells of paragraph 134, wherein the population of cells enriched for the engineered cells express IL12 receptor β1 or increased levels thereof, IL12 receptor β2 or increased levels thereof, or IL12 receptor β1 and IL12 receptor β2 or increased levels thereof
136. The population of cells of any of paragraphs 133-135, wherein the second effector molecule is IL21.
137. The population of cells of any of paragraphs 133-135, wherein the second effector molecule is CCL21.
138. The population of cells of paragraph 137, wherein the population of cells enriched for the engineered cells express a CCL21 receptor or increased levels thereof
139. The population of cells of paragraph 138, wherein the CCL21 receptor is CCR7.
140. A method of stimulating a cell-mediated immune response to a tumor cell in a subject, the method comprising administering to a subject having a tumor a therapeutically effective dose of any of the engineered cells of any one of paragraphs 1-114 or the population of cells of any of paragraphs 131-139.
141. A method of providing an anti-tumor immunity in a subject, the method comprising administering to a subject in need thereof a therapeutically effective dose of any of the engineered cells of any one of paragraphs 1-114 or the population of cells of any of paragraphs 131-139.
142. A method of treating a subject having cancer, the method comprising administering to a subject having a tumor a therapeutically effective dose of any of the engineered cell of any one of paragraphs 1-114 or the population of cells of any of paragraphs 131-139.
143. A method of reducing tumor volume in a subject, the method comprising administering to a subject having a tumor a therapeutically effective dose of any of the engineered cells of any one of paragraphs 1-114 or the population of cells of any of paragraphs 131-139.
144. The method of any one of paragraphs 140-143, wherein the engineered cell is derived from the subject.
145. The method of any one of paragraphs 140-143, wherein the engineered cell is allogeneic with reference to the subject.
146. The method of any one of paragraphs 140-145, wherein the tumor is selected from the group consisting of: an adenocarcinoma, an acute myeloid leukemia (AML), an acute lymphoblastic B-cell leukemia (BALL), an acute lymphoblastic T-cell leukemia (TALL), a B-cell prolymphocytic leukemia, a bladder tumor, a brain tumor, a breast tumor, a cervical tumor, a chronic lymphocytic leukemia, a chronic myeloid leukemia (CML), a colorectal tumor, an esophageal tumor, a glioma, a kidney tumor, a liver tumor, a lung tumor, a lymphoma, a melanoma, a mesothelioma, a myelodysplasia, an ovarian tumor, a pancreatic tumor, a plasma cell myeloma, a prostate tumor, a skin tumor, a thyroid tumor, and a uterine tumor.
147. The method of any one of paragraphs 140-145, wherein the tumor is an ovarian tumor.
148. The method of any one of paragraphs 140-147, wherein the tumor is a tumor located in a peritoneal space.
149. An engineered cell comprising:
a) a promoter; and
b) an exogenous polynucleotide sequence comprising an expression cassette described in a formula, oriented from 5' to 3', comprising:

$$(L\text{-}S\text{-}E)_X$$

wherein
S comprises a polynucleotide sequence encoding a signal peptide,
E comprises a polynucleotide sequence encoding an effector molecule,
L comprises a linker polynucleotide sequence,
X=2 to 20,
wherein the promoter is operably linked to the expression cassette, wherein for the first iteration of the (L-S-E) unit L is absent, and wherein for each X the corresponding signal peptide is operably associated with the effector molecule, and
wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.
150. A population of cells comprising one or more engineered cells, wherein the one or more engineered cells comprise:
a) a promoter; and
b) an exogenous polynucleotide sequence comprising an expression cassette described in a formula, oriented from 5' to 3', comprising $$S1\text{-}E1\text{-}L\text{-}S2\text{-}E2$$

wherein
S1 comprises a polynucleotide sequence encoding a first signal peptide,
E1 comprises a polynucleotide sequence encoding a first effector molecule,
L comprises a linker polynucleotide sequence,
S2 comprises a polynucleotide sequence encoding a second signal peptide,
E2 comprises a polynucleotide sequence encoding a second effector molecule, and
wherein the promoter is operably linked to the expression cassette, the first signal peptide is operably linked to the first effector molecule, and the second signal peptide is operably linked to the second effector molecule, and
wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

151. A population of cells comprising one or more engineered cells, wherein the one or more engineered cells comprise:
a) a promoter; and
b) an exogenous polynucleotide sequence comprising an expression cassette described in a formula, oriented from 5' to 3', comprising

S1-E1-L-S2-E2 wherein
S1 comprises a polynucleotide sequence encoding a first signal peptide,
E1 comprises a polynucleotide sequence encoding a first effector molecule,
L comprises a linker polynucleotide sequence,
S2 comprises a polynucleotide sequence encoding a second signal peptide,
E2 comprises a polynucleotide sequence encoding a second effector molecule, and
wherein the promoter is operably linked to the expression cassette, the first signal peptide is operably linked to the first effector molecule, and the second signal peptide is operably linked to the second effector molecule, and
wherein the first effector molecule, the second effector molecule, or the first and second effector molecules expressed in the engineered cells promotes increased growth, viability, or growth and viability relative to cells in the population that do not express the first effector molecule, the second effector molecule, or the first and second effector molecules, and
wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

152. The population of cells of paragraph 151, wherein the one or more engineered cells express a cognate receptor or cognate receptor ligand for the first effector molecule, the second effector molecule, or the first and second effector molecules expressed in the engineered cells.

153. The population of cells of paragraph 151 or paragraph 152, wherein the first effector molecule is IL12 or an IL12p70 fusion protein.

154. The population of cells of any of paragraphs 151-153, wherein the second effector molecule is IL21.

155. The population of cells of any of paragraphs 151-153, wherein the second effector molecule is CCL21.

156. A population of cells comprising one or more engineered cells, wherein the one or more engineered cells comprise a construct, wherein the construct comprises:
a) an SFFV promoter; and
b) an exogenous polynucleotide sequence comprising an expression cassette described in a formula, oriented from 5' to 3', comprising

S1-E1-L-S2-E2 wherein
S1 comprises a polynucleotide sequence encoding a first signal peptide, wherein the first signal peptide is a human IL12 signal peptide;
E1 comprises a polynucleotide sequence encoding a first effector molecule, wherein the first effector molecule is a human IL12p70 fusion protein;
L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus;
S2 comprises a polynucleotide sequence encoding a second signal peptide, wherein the second signal peptide is a human IL21 signal peptide;
E2 comprises a polynucleotide sequence encoding a second effector molecule, wherein the second effector molecule is human IL21; and
wherein the SFFV promoter is operably linked to the expression cassette, the first signal peptide is operably linked to the first effector molecule, and the second signal peptide is operably linked to the second effector molecule, and
wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

157. A population of cells comprising one or more engineered cells, wherein the one or more engineered cells comprise a construct, wherein the construct comprises:
a) an SFFV promoter; and
b) an exogenous polynucleotide sequence comprising an expression cassette described in a formula, oriented from 5' to 3', comprising

S1-E1-L-S2-E2 wherein
S1 comprises a polynucleotide sequence encoding a first signal peptide, wherein the first signal peptide is a human IL12 signal peptide;
E1 comprises a polynucleotide sequence encoding a first effector molecule, wherein the first effector molecule is a human IL12p70 fusion protein;
L comprises a linker polynucleotide sequence, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus;
S2 comprises a polynucleotide sequence encoding a second signal peptide, wherein the second signal peptide is a human IL21 signal peptide;
E2 comprises a polynucleotide sequence encoding a second effector molecule, wherein the second effector molecule is human IL21; and
wherein the SFFV promoter is operably linked to the expression cassette, the first signal peptide is operably linked to the first effector molecule, and the second signal peptide is operably linked to the second effector molecule, and
wherein the first effector molecule, the second effector molecule, or the first and second effector molecules expressed in the engineered cells promotes increased growth, viability, or growth and viability relative to cells in the population that do not express the first effector molecule, the second effector molecule, or the first and second effector molecules, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

158. The population of cells of paragraph 156 or paragraph 157, wherein the construct comprises the polynucleotide sequence shown in SEQ ID NO: 144.

159. A method of producing a population of cells enriched for one or more receptors or receptor ligands, comprising culturing one or more cells under conditions where the one or more cells are contacted with a first effector molecule, a second effector molecule, or a first and a second effector molecule, wherein the contacted cells express one or more cognate receptors or cognate receptor ligands for the first effector molecule, the second effector molecule, or the first and second effector molecules, and wherein the first effector molecule, the second effector molecule, or the first and the second effector molecules increase growth, viability, or growth and viability of the contacted cells relative to cells cultured in the absence of the first effector molecule, the second effector molecule, or the first and second effector molecules.

160. The method of paragraph 159, wherein the first effector molecule, the second effector molecule, or the first and second effector molecules are heterologously expressed in one or more cells, and the one or more cells are contacted with the first effector molecule, the second effector molecule, or the first and second effector molecules in an autocrine manner.

161. The method of paragraph 159, wherein the first effector molecule, the second effector molecule, or the first and second effector molecules are expressed in one or more additional cells, and the one or more cells are contacted with the first effector molecule, the second effector molecule, or the first and second effector molecules in an paracrine manner.

162. The method of paragraph 161, wherein the one or more additional cells are a feeder cells.

163. The method of paragraph 159, wherein the one or more cells are cultured in media.

164. The method of paragraph 163, wherein the one or more cells are contacted with the first effector molecule, the second effector molecule, or the first and second effector molecules by addition of a soluble first effector molecule, a soluble second effector molecule, or a soluble first and second effector molecules to the media.

165. The method of paragraph 163 or paragraph 164, wherein the soluble first effector molecule and/or soluble second effector molecule is a recombinant effector molecule.

166. The method of paragraph 159, wherein the one or more cells are cultured under adherent conditions.

167. The method of paragraph 166, wherein the one or more cells are adhered onto a surface.

168. The method of paragraph 167, wherein the adhered cells are contacted with the first effector molecule, the second effector molecule, or the first and second effector molecules by exposing the one or more cells to first effector molecule, the second effector molecule, or the first and second effector molecules is immobilized on the surface.

169. The method of any one of paragraphs 159-168, wherein the first effector molecule is IL12 or an IL12p70 fusion protein.

170. The method of paragraph 169, wherein the population of cells is enriched for IL12 receptor β1 (IL12Rβ1), enriched for IL12 receptor β2 (IL12Rβ2), or enriched for IL12Rβ1 and IL12Rβ2.

171. The method of paragraph 170, wherein the population of MSCs comprises a cellular marker phenotype comprising the cellular markers CD105+, CD73+, CD90+, IL12Rβ1+, and IL12Rβ2+.

172. The method of paragraph 171, wherein the cellular marker phenotype further comprises a phenotype lacking or substantially lacking one or more cellular markers selected from the group consisting of: CD45, CD34, CD14, CD11b, CD79α, CD19, HLA class II, and combinations thereof 173. The method of paragraph 159, wherein the population of cells comprises a cell selected from the group consisting of: natural killer (NK) cells, NKT cells, innate lymphoid cells, mast cells, eosinophils, basophils, monocytes, macrophages, neutrophils, and dendritic cells, T cells, CD8+ T cells, CD4+ T cells, gamma-delta T cells, and T regulatory cells, and B cells.

174. The method of paragraph 173, wherein the population of cells comprises a T cell, a NK cell, a NKT cell, a monocyte, a macrophage, or a myeloid derived cell.

175. The method of any one of paragraphs 159-174, wherein the second effector molecule is IL21.

176. The method of any one of paragraphs 159-174, wherein the second effector molecule is CCL21.

177. The method of paragraph 176, wherein the population of cells is enriched for CCR7.

178. The method of paragraph 177, wherein the population of MSCs comprises a cellular marker phenotype comprising the cellular markers CD105+, CD73+, CD90+, IL12Rβ1+, IL12Rβ2+, and CCR7+.

179. The method of paragraph 178, wherein the cellular marker phenotype further comprises a phenotype lacking or substantially lacking one or more cellular markers selected from the group consisting of: CD45, CD34, CD14, CD11b, CD79α, CD19, HLA class II, and combinations thereof 180. A population of cells enriched for one or more receptors or receptor ligands produced by the method of any one of paragraphs 159-179.

181. An exogenous polynucleotide sequence comprising a promoter and an expression cassette described in a formula, oriented from 5' to 3', comprising

S1-E1-L-S2-E2 wherein
S1 comprises a polynucleotide sequence encoding a first signal peptide,
E1 comprises a polynucleotide sequence encoding a first effector molecule,
L comprises a linker polynucleotide sequence,
S2 comprises a polynucleotide sequence encoding a second signal peptide,
E2 comprises a polynucleotide sequence encoding a second effector molecule, and
wherein the promoter is operably linked to the expression cassette, the first signal peptide is operably linked to the first effector molecule, and the second signal peptide is operably linked to the second effector molecule.
182. The exogenous polynucleotide sequence of paragraph 181, wherein the promoter comprises an exogenous promoter polynucleotide sequence.
183. The exogenous polynucleotide sequence of paragraph 181, wherein the promoter comprises an endogenous promoter.
184. The exogenous polynucleotide sequence of any one of paragraphs 181-183, wherein the promoter is operably linked to the expression cassette such that the polynucleotides are capable of being transcribed as a single polynucleotide comprising the formula S1-E1-L-S2-E2.
185. The exogenous polynucleotide sequence of paragraph 184, wherein the linker polynucleotide sequence is operably associated with the translation of the first effector molecule and the second effector molecule as separate polypeptides.
186. The exogenous polynucleotide sequence of paragraph 185, wherein the linker polynucleotide sequence encodes a 2A ribosome skipping tag.
187. The exogenous polynucleotide sequence of paragraph 186, wherein the 2A ribosome skipping tag is selected from the group consisting of: P2A, T2A, E2A, and F2A.
188. The exogenous polynucleotide sequence of paragraph 185, wherein the linker polynucleotide sequence encodes a T2A ribosome skipping tag.
189. The exogenous polynucleotide sequence of paragraph 185, the linker polynucleotide sequence encodes an Internal Ribosome Entry Site (IRES).
190. The exogenous polynucleotide sequence of any one of paragraphs 185-189, wherein the linker polynucleotide sequence encodes a cleavable polypeptide.
191. The exogenous polynucleotide sequence of paragraph 190, wherein the cleavable polypeptide comprises a Furin recognition polypeptide sequence.
192. The exogenous polynucleotide sequence of any one of paragraphs 185-191, wherein the linker polynucleotide sequence further encodes a Gly-Ser-Gly polypeptide sequence.
193. The exogenous polynucleotide sequence of any one of paragraphs 181-185, wherein the linker polynucleotide sequence encodes a Furin recognition polypeptide sequence, a Gly-Ser-Gly polypeptide sequence, and a T2A ribosome skipping tag in a Furin:Gly-Ser-Gly:T2A orientation from N-terminus to C-terminus.
194. The exogenous polynucleotide sequence of any one of paragraphs 181-183, wherein the linker polynucleotide sequence encodes a second promoter,
wherein the promoter is operably linked to the expression cassette such that a first polynucleotide comprising the formula S1-E1 is capable of being transcribed,
wherein the second promoter is operably linked to the expression cassette such that a second polynucleotide comprising the formula S2-E2 is capable of being transcribed, and wherein the first and the second polynucleotide are separate polynucleotides.
195. The exogenous polynucleotide sequence of paragraph 194, wherein the promoter and the second promoter are identical.
196. The exogenous polynucleotide sequence of paragraph 194, wherein the promoter and the second promoter are different.
197. The exogenous polynucleotide sequence of any one of paragraphs 181-196, wherein the promoter and/or the second promoter comprises a constitutive promoter.
198. The exogenous polynucleotide sequence of paragraph 197, wherein the constitutive promoter is selected from the group consisting of: CMV, EFS, SFFV, SV40, MND, PGK, UbC, hEF1aV1, hCAGG, hEF1aV2, hACTb, heIF4A1, hGAPDH, hGRP78, hGRP94, hHSP70, hKINb, and hUBIb.
199. The exogenous polynucleotide sequence of any one of paragraphs 181-196, wherein the promoter comprises an SFFV promoter.
200. The exogenous polynucleotide sequence of any one of paragraphs 181-196, wherein the promoter and/or the second promoter comprises an inducible promoter.
201. The exogenous polynucleotide sequence of paragraph 200, wherein the inducible promoter is selected from the group consisting of: minP, NFkB response element, CREB response element, NFAT response element, SRF response element 1, SRF response element 2, AP1 response element, TCF-LEF response element promoter fusion, Hypoxia responsive element, SMAD binding element, STAT3 binding site, inducer molecule responsive promoters, and tandem repeats thereof
202. The exogenous polynucleotide sequence of any one of paragraphs 181-201, wherein the first signal peptide or the second signal peptide comprises a native signal peptide native to the first effector molecule or the second effector molecule, respectively.
203. The exogenous polynucleotide sequence of any one of paragraphs 181-202, wherein the first signal peptide or the second signal peptide comprises a non-native signal peptide non-native to the first effector molecule or the second effector molecule, respectively.
204. The exogenous polynucleotide sequence of paragraph 203, wherein the non-native signal peptide is selected from the group consisting of: IL12, IL2, optimized IL2, trypsiongen-2, Gaussia luciferase, CD5, human IgKVII, murine IgKVII, VSV-G, prolactin, serum albumin preprotein, azurocidin preprotein, osteonectin, CD33, IL6, IL8, CCL2, TIMP2, VEGFB, osteoprotegerin, serpin E1, GROalpha, CXCL12, and IL21.
205. The exogenous polynucleotide sequence of any one of paragraphs 181-204, wherein the first signal peptide and the second signal peptide are identical.
206. The exogenous polynucleotide sequence of any one of paragraphs 181-205, wherein the polynucleotide sequence encoding the first signal peptide comprises a codon optimized polynucleotide sequence.
207. The exogenous polynucleotide sequence of any one of paragraphs 181-206, wherein the first secretion polypeptide is a human IL12 signal peptide.
208. The exogenous polynucleotide sequence of any one of paragraphs 181-206, wherein the polynucleotide sequence encoding the second signal peptide comprises a codon optimized polynucleotide sequence.
209. The exogenous polynucleotide sequence of any one of paragraphs 181-208, wherein the second secretion polypeptide is a human IL21 signal peptide.
210. The exogenous polynucleotide sequence of any one of paragraphs 181-208, wherein the first effector molecule is selected from a therapeutic class, wherein the therapeutic class is selected from the group consisting of: a cytokine, a chemokine, a growth factor, a co-activation molecule, a tumor microenvironment modifier a, a receptor, a ligand, an antibody, a polynucleotide, a peptide, and an enzyme.
211. The exogenous polynucleotide sequence of any one of paragraphs 181-210, wherein the second effector molecule is selected from a therapeutic class, wherein the therapeutic class is selected from the group consisting of:

a cytokine, a chemokine, a growth factor, a co-activation molecule, a tumor microenvironment modifier, a receptor, a ligand, an antibody, a polynucleotide, a peptide, and an enzyme.

212. The exogenous polynucleotide sequence of paragraph 211, wherein the therapeutic class of the first effector molecule and the second effector molecule are different.

213. The exogenous polynucleotide sequence of any one of paragraphs 181-212, wherein the first effector molecule and/or the second effector molecule is a modified effector molecule.

214. The exogenous polynucleotide sequence of paragraph 213, wherein the first effector molecule and/or the second effector molecule is modified to comprises a cell membrane tethering domain.

215. The exogenous polynucleotide sequence of paragraph 214, wherein the cell membrane tethering domain comprises a transmembrane-intracellular domain or a transmembrane domain.

216. The exogenous polynucleotide sequence of paragraph 214, wherein the cell membrane tethering domain comprises a cell surface receptor, or a cell membrane-bound portion thereof 217. The exogenous polynucleotide sequence of paragraph 216, wherein the modified effector molecule is a fusion protein that comprises the cell surface receptor, or a cell membrane-bound portion thereof 218. The exogenous polynucleotide sequence of any one of paragraphs 214-217, wherein the modified effector molecule further comprises a linker between the effector molecule and the cell membrane tethering domain.

219. The exogenous polynucleotide sequence of any one of paragraphs 213-218, wherein when expressed in a cell, the modified effector molecule is tethered to a cell membrane of the cell.

220. The exogenous polynucleotide sequence of any one of paragraphs 210-219 wherein the cytokine is selected from the group consisting of: IL12, IL7, IL21, IL18, IL15, Type I interferons, and Interferon-gamma.

221. The exogenous polynucleotide sequence of paragraph 220, wherein the IL12 cytokine is an IL12p70 fusion protein.

222. The exogenous polynucleotide sequence of any one of paragraphs 210-221, wherein the chemokine is selected from the group consisting of: CCL21a, CXCL10, CXCL11, CXCL13, CXCL10-11 fusion, CCL19, CXCL9, and XCL1.

223. The exogenous polynucleotide sequence of any one of paragraphs 210-222, wherein the growth factor is selected from the group consisting of: Flt3L and GM-CSF.

224. The exogenous polynucleotide sequence of any one of paragraphs 210-223, wherein the co-activation molecule is selected from the group consisting of: 4-1BBL and CD40L.

225. The exogenous polynucleotide sequence of any one of paragraphs 210-224, wherein the tumor microenvironment modifier is selected from the group consisting of: adenosine deaminase, TGFbeta inhibitors, immune checkpoint inhibitors, VEGF inhibitors, and HPGE2.

226. The exogenous polynucleotide sequence of paragraph 225, wherein the TGFbeta inhibitors are selected from the group consisting of: an anti-TGFbeta peptide, an anti-TGFbeta antibody, a TGFb-TRAP, and combinations thereof 227. The exogenous polynucleotide sequence of paragraph 225, wherein the immune checkpoint inhibitors comprise anti-PD-1 antibodies.

228. The exogenous polynucleotide sequence of paragraph 225, wherein the VEGF inhibitors comprise anti-VEGF antibodies, anti-VEGF peptides, or combinations thereof 229. The exogenous polynucleotide sequence of any one of paragraphs 181-225, wherein the first effector molecule and the second effector molecule are human-derived effector molecules.

230. The exogenous polynucleotide sequence of any one of paragraphs 181-229, wherein the first effector molecule comprises IL12.

231. The exogenous polynucleotide sequence of any one of paragraphs 181-229, wherein the first effector molecule comprises an IL12p70 fusion protein.

232. The exogenous polynucleotide sequence of paragraph 231, wherein the IL12p70 fusion protein is a human IL12p70 fusion protein.

233. The exogenous polynucleotide sequence of any one of paragraphs 230-232, wherein the second effector molecule comprises CCL21a.

234. The exogenous polynucleotide sequence of paragraph 233, wherein the CCL21a is a human CCL21a.

235. The exogenous polynucleotide sequence of any one of paragraphs 230-232, wherein the second effector molecule comprises IL7.

236. The exogenous polynucleotide sequence of paragraph 235, wherein the IL7 is a human IL7.

237. The exogenous polynucleotide sequence of any one of paragraphs 230-232, wherein the second effector molecule comprises IL21.

238. The exogenous polynucleotide sequence of paragraph 237, wherein the IL21 is a human IL21.

239. The exogenous polynucleotide sequence of any one of paragraphs 181-238, wherein the expression cassette further comprises an E3 comprising a polynucleotide sequence encoding a third effector molecule.

240. The exogenous polynucleotide sequence of paragraph 239, wherein the third effector molecule comprises Flt3L.

241. The exogenous polynucleotide sequence of paragraph 239, wherein the third effector molecule comprises anti-PD1.

242. The exogenous polynucleotide sequence of paragraph 241, wherein the expression cassette further comprises an E4 comprising a polynucleotide sequence encoding a fourth effector molecule.

243. The exogenous polynucleotide sequence of paragraph 242, wherein the fourth effector molecule comprises adenosine deaminase.

244. The exogenous polynucleotide sequence of paragraph 239, wherein the third effector molecule comprises adenosine deaminase.

245. The exogenous polynucleotide sequence of paragraph 239, wherein the third effector molecule comprises CD40L.

246. The exogenous polynucleotide sequence of paragraph 239, wherein the third effector molecule comprises a CXCL10-CXCL11 fusion protein.

247. The exogenous polynucleotide sequence of paragraph 239, wherein the third effector molecule comprises XCL1.

248. The exogenous polynucleotide sequence of paragraph 230, wherein the second effector molecule comprises Flt3L.

249. The exogenous polynucleotide sequence of paragraph 230, wherein the second effector molecule comprises a CXCL10-CXCL11 fusion protein.

250. The exogenous polynucleotide sequence of paragraph 230, wherein the second effector molecule comprises anti-PD1.

251. The exogenous polynucleotide sequence of paragraph 230, wherein the second effector molecule comprises CD40L.

252. The exogenous polynucleotide sequence of any one of paragraphs 181-229, wherein the first effector molecule comprises interferon-beta and the second effector molecule comprises Flt3L.

253. The exogenous polynucleotide sequence of any one of paragraphs 181-252, wherein the polynucleotide sequence encoding the first effector molecule comprises a codon optimized polynucleotide sequence.

254. The exogenous polynucleotide sequence of any one of paragraphs 181-253, wherein the polynucleotide sequence encoding the second effector molecule comprises a codon optimized polynucleotide sequence.

255. The exogenous polynucleotide sequence of any one of paragraphs 181-254, wherein the exogenous polynucleotide sequence comprises the polynucleotide sequence shown in SEQ ID NO: 144.

256. An exogenous polynucleotide sequence comprising an SFFV promoter and an expression cassette described in a formula, oriented from 5' to 3', comprising

S1-E1-L-S2-E2 wherein

S1 comprises a polynucleotide sequence encoding a first signal peptide, wherein the first signal peptide is a human IL12 signal peptide;

E1 comprises a polynucleotide sequence encoding a first effector molecule, wherein the first effector molecule is a human IL12p70 fusion protein;

L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus;

S2 comprises a polynucleotide sequence encoding a second signal peptide, wherein the second signal peptide is a human IL21 signal peptide;

E2 comprises a polynucleotide sequence encoding a second effector molecule, wherein the second effector molecule is human IL21; and wherein the SFFV promoter is operably linked to the expression cassette, the first signal peptide is operably linked to the first effector molecule, and the second signal peptide is operably linked to the second effector molecule.

257. The exogenous polynucleotide sequence of paragraph 256, wherein the polynucleotide sequence comprises the polynucleotide sequence shown in SEQ ID NO: 144.

258. An exogenous polynucleotide sequence comprising an SFFV promoter and an expression cassette described in a formula, oriented from 5' to 3', comprising

S1-E1-L-S2-E2 wherein

S1 comprises a polynucleotide sequence encoding a first signal peptide, wherein the first signal peptide is a human IL12 signal peptide;

E1 comprises a polynucleotide sequence encoding a first effector molecule, wherein the first effector molecule is a human IL12p70 fusion protein;

L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus;

S2 comprises a polynucleotide sequence encoding a second signal peptide, wherein the second signal peptide is a human IL21 signal peptide;

E2 comprises a polynucleotide sequence encoding a second effector molecule, wherein the second effector molecule is human IL21;

wherein the SFFV promoter is operably linked to the expression cassette, the first signal peptide is operably linked to the first effector molecule, and the second signal peptide is operably linked to the second effector molecule;

wherein the promoter is operably linked to the expression cassette such that the polynucleotides are capable of being transcribed as a single polynucleotide comprising the formula S1-E1-L-S2-E2; and wherein the polynucleotide sequence comprises the polynucleotide sequence shown in SEQ ID NO: 144.

259. The exogenous polynucleotide sequence of any one of paragraphs 181-258, wherein the exogenous polynucleotide sequence is encoded by a nucleic acid selected from the group consisting of: a DNA, a cDNA, an RNA, an mRNA, and a naked plasmid.

260. An expression vector comprising the exogenous polynucleotide sequence of any one of paragraphs 181-259.

261. The expression vector of paragraph 260, wherein the expression vector is a viral vector.

262. The expression vector of paragraph 261, wherein the viral vector is a lentiviral vector.

263. A composition comprising the exogenous polynucleotide sequence of any one of paragraphs 181-259, and a pharmaceutically acceptable carrier.

264. An isolated cell comprising the exogenous polynucleotide sequence of any one of paragraphs 181-259, the expression vector of any one of paragraphs 260-262, or the composition of paragraph 263.

265. The isolated cell of paragraph 264, wherein the isolated cell is selected from the group consisting of: a T cell, a CD8+ T cell, a CD4+ T cell, a gamma-delta T cell, a cytotoxic T lymphocyte (CTL), a regulatory T cell, a viral-specific T cell, a Natural Killer T (NKT) cell, a Natural Killer (NK) cell, a B cell, a tumor-infiltrating lymphocyte (TIL), an innate lymphoid cell, a mast cell, an eosinophil, a basophil, a neutrophil, a myeloid cell, a macrophage, a monocyte, a dendritic cell, an erythrocyte, a platelet cell, a human embryonic stem cell (ESC), an ESC-derived cell, a pluripotent stem cell, an MSC, an induced pluripotent stem cell (iPSC), and an iPSC-derived cell.

266. The isolated cell of paragraph 264, wherein the isolated cell is an MSC.

267. The isolated cell of any one of paragraphs 264-266, wherein the exogenous polynucleotide sequence is integrated into the genome of the cell.

268. The isolated cell of any one of paragraphs 264-267, wherein the exogenous polynucleotide sequence comprises one or more viral vector polynucleotide sequences.

269. The isolated cell of paragraph 268, wherein the one or more viral vector polynucleotide sequences comprise lentiviral, retroviral, retrotransposon, or adenoviral polynucleotide sequences.

270. The isolated cell of paragraph 268, wherein the one or more viral vector polynucleotide sequences comprise lentiviral polynucleotide sequences.

271. The isolated cell of any one of paragraphs 264-270, wherein the engineered cell is HLA-typed with reference to a subject in need of therapeutic treatment.
272. The isolated cell of any one of paragraphs 264-271, wherein the engineered cell is a human cell.
273. The isolated cell of paragraph 272, wherein the human cell is an isolated cell from a subject.
274. The isolated cell of paragraph 273, wherein the isolated cell is isolated from a tissue consisting of the group of: bone marrow, adipose tissue, the umbilical cord, fetal liver, muscle, and lung tissue.
275. The isolated cell of any one of paragraphs 264-272, wherein the cell is a cultured cell.
276. The isolated cell of any one of paragraphs 264-275, wherein the cell comprises a cellular marker phenotype comprising the cellular markers CD105+, CD73+, and CD90+.
277. The isolated cell of paragraph 276, wherein the cellular marker phenotype further comprises a phenotype lacking or substantially lacking one or more cellular markers selected from the group consisting of: CD45, CD34, CD14, CD11b, CD79α, CD19, HLA class II, and combinations thereof
278. The isolated cell of any one of paragraphs 264-275, wherein the cell comprises a cellular marker phenotype comprising CD105+, CD73+, CD90+, CD45−, CD34−, CD14−; a cellular marker phenotype comprising CD105+, CD73+, CD90+, CD11b−, CD79α−; a cellular marker phenotype comprising CD105+, CD73+, CD90+, CD19−, HLA class II−; or a cellular marker phenotype comprising CD73+, CD90+, CD105+, and CD166+, CD11b−, CD14−, CD19−, CD34−, CD45−, and HLA-DR−.
279. The isolated cell of any one of paragraphs 264-278, wherein the cellular marker phenotype further comprises a cellular marker comprising a cognate receptor or a cognate receptor ligand for the first effector molecule, the second effector molecule, or the first and second effector molecules expressed in the cell.
280. The isolated cell of paragraph 279, wherein the receptor is selected from the group consisting of: IL12RB1, IL12RB2, CCL7, and combinations thereof
281. The isolated cell of any one of paragraphs 264-280, wherein the cell secretes each effector molecule.
282. The isolated cell of paragraph 281, wherein the first effector molecule is secreted at a ratio that is 10 fold higher relative to secretion of the second effector molecule.
283. The isolated cell of any one of paragraphs 264-282, wherein the cell further comprises an antigen recognizing receptor.
284. The isolated cell of paragraph 283, wherein the antigen recognizing receptor comprises an antigen-binding domain.
285. The isolated cell of paragraph 284, wherein the antigen-binding domain comprises an antibody, an antigen-binding fragment of an antibody, a F(ab) fragment, a F(ab') fragment, a single chain variable fragment (scFv), or a single-domain antibody (sdAb).
286. The isolated cell of paragraph 284, wherein the antigen-binding domain comprises a single chain variable fragment (scFv).
287. The isolated cell of paragraph 286, wherein the scFv comprises a heavy chain variable domain (VH) and a light chain variable domain (VL).
288. The isolated cell of paragraph 287, wherein the VH and VL are separated by a peptide linker.
289. The isolated cell of paragraph 288, wherein the scFv comprises the structure VH-L-VL or VL-L-VH, wherein VH is the heavy chain variable domain, L is the peptide linker, and VL is the light chain variable domain.
290. The isolated cell of any one of paragraphs 283-289, the antigen recognizing receptor is a chimeric antigen receptor (CAR) or T cell receptor (TCR).
291. The isolated cell of any one of paragraphs 283-289, the antigen recognizing receptor is a chimeric antigen receptor (CAR).
292. The isolated cell of paragraph 291, wherein the CAR comprises one or more intracellular signaling domains, and the one or more intracellular signaling domains are selected from the group consisting of: a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain.
293. The isolated cell of paragraph 291 or paragraph 292, wherein the CAR comprises a transmembrane domain, and the transmembrane domain is selected from the group consisting of: a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.
294. The isolated cell of any one of paragraphs 291-293, wherein the CAR comprises a spacer region between the antigen-binding domain and the transmembrane domain.
295. A virus comprising the exogenous polynucleotide sequence of any one of paragraphs 181-259 or the expression vector of any one of paragraphs 260-262.
296. The virus of paragraph 295, wherein the virus is selected from the group consisting of: a lentivirus, a retrovirus, a retrotransposon, and an adenovirus.
297. The virus of paragraph 295, wherein the virus is a lentivirus.
298. A method of reducing tumor volume in a subject, the method comprising delivering to a subject having a tumor a composition comprising cells engineered to produce multiple effector molecules that modulate tumor-mediated immunosuppressive mechanisms, in an effective amount to reduce the volume of the tumor, wherein the engineered cells comprise:

a) a promoter; and b) an exogenous polynucleotide sequence comprising an expression cassette described in a formula, oriented from 5' to 3', comprising

S1-E1-L-S2-E2 wherein

S1 comprises a polynucleotide sequence encoding a first signal peptide,

E1 comprises a polynucleotide sequence encoding a first effector molecule,

L comprises a linker polynucleotide sequence,
S2 comprises a polynucleotide sequence encoding a second signal peptide,
E2 comprises a polynucleotide sequence encoding a second effector molecule, and
wherein the promoter is operably linked to the expression cassette, the first signal peptide is operably linked to the first effector molecule, and the second signal peptide is operably linked to the second effector molecule, and
wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

299. A method of reducing tumor volume in a subject, the method comprising delivering to a subject having a tumor a composition comprising cells engineered to produce IL12 and IL21, in an effective amount to reduce the volume of the tumor, wherein the engineered cells comprise a construct, wherein the construct comprises:
a) an SFFV promoter; and
b) an exogenous polynucleotide sequence comprising an expression cassette described in a formula, oriented from 5' to 3', comprising

S1-E1-L-S2-E2 wherein
S1 comprises a polynucleotide sequence encoding a first signal peptide, wherein the first signal peptide is a human IL12 signal peptide;
E1 comprises a polynucleotide sequence encoding a first effector molecule, wherein the first effector molecule is a human IL12p70 fusion protein;
L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus;
S2 comprises a polynucleotide sequence encoding a second signal peptide, wherein the second signal peptide is a human IL21 signal peptide;
E2 comprises a polynucleotide sequence encoding a second effector molecule, wherein the second effector molecule is human IL21; and
wherein the SFFV promoter is operably linked to the expression cassette, the first signal peptide is operably linked to the first effector molecule, and the second signal peptide is operably linked to the second effector molecule, and
wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

300. The method of paragraph 299, wherein the construct comprises the polynucleotide sequence shown in SEQ ID NO: 144.

301. The method of any one of paragraphs 298-300, wherein the method further comprises administering a checkpoint inhibitor.

302. The method of paragraph 301, wherein the checkpoint inhibitor is an anti-PD-1 antibody, anti-PD-1L antibody or an anti-CTLA-4 antibody.

303. The method of any one of paragraphs 298-302, wherein the method further comprises administering an anti-CD40 antibody.

304. The method of any one of paragraphs 298-303, wherein the tumor is selected from the group consisting of: an adenocarcinoma, an acute myeloid leukemia (AML), an acute lymphoblastic B-cell leukemia (BALL), an acute lymphoblastic T-cell leukemia (TALL), a B-cell prolymphocytic leukemia, a bladder tumor, a brain tumor, a breast tumor, a cervical tumor, a chronic lymphocytic leukemia, a chronic myeloid leukemia (CML), a colorectal tumor, an esophageal tumor, a glioma, a kidney tumor, a liver tumor, a lung tumor, a lymphoma, a melanoma, a mesothelioma, a myelodysplasia, an ovarian tumor, a pancreatic tumor, a plasma cell myeloma, a prostate tumor, a skin tumor, a thyroid tumor, and a uterine tumor.

305. The method of any one of paragraphs 298-303, wherein the tumor is an ovarian tumor.

306. The method of any one of paragraphs 298-303, wherein the tumor is a tumor located in a peritoneal space.

307. The method of any one of paragraphs 298-306, wherein the administering comprises systemic administration, intraperitoneal administration, or intratumoral administration.

308. The method of any one of paragraphs 298-307, wherein the volume of the tumor is reduced by at least 25% relative to a control, optionally wherein the control is an unmodified cell.

309. The method of paragraph 307, wherein the volume of the tumor is reduced by at least 50% relative to a control, optionally wherein the control is an unmodified cell.

310. The method of paragraph 309, wherein the volume of the tumor is reduced by at least 75% relative to a control, optionally wherein the control is an unmodified cell.

311. A method of reducing tumor volume in a subject, the method comprising delivering to a subject having a tumor a composition capable of engineering an cell to produce multiple effector molecules that modulate tumor-mediated immunosuppressive mechanisms, in an effective amount to reduce the volume of the tumor, wherein each engineered cell comprises:
a) a promoter; and
b) an exogenous polynucleotide sequence comprising an expression cassette described in a formula, oriented from 5' to 3', comprising

S1-E1-L-S2-E2 wherein
S1 comprises a polynucleotide sequence encoding a first signal peptide,
E1 comprises a polynucleotide sequence encoding a first effector molecule,
L comprises a linker polynucleotide sequence,
S2 comprises a polynucleotide sequence encoding a second signal peptide,
E2 comprises a polynucleotide sequence encoding a second effector molecule, and
wherein the promoter is operably linked to the expression cassette, the first signal peptide is operably linked to the first effector molecule, and the second signal peptide is operably linked to the second effector molecule, and wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

312. A method of reducing tumor volume in a subject, the method comprising delivering to a subject having a tumor a composition capable of engineering a cell to produce IL12 and IL21, in an effective amount to reduce the volume of the tumor, wherein the engineered cell comprises a construct, wherein the construct comprises:
a) an SFFV promoter; and
b) an exogenous polynucleotide sequence comprising an expression cassette described in a formula, oriented from 5' to 3', comprising

S1-E1-L-S2-E2 wherein
S1 comprises a polynucleotide sequence encoding a first signal peptide, wherein the first signal peptide is a human IL12 signal peptide;
E1 comprises a polynucleotide sequence encoding a first effector molecule, wherein the first effector molecule is a human IL12p70 fusion protein;
L comprises a linker polynucleotide sequence, wherein the linker polynucleotide sequence encodes Furin recognition polypeptide sequence, a Gly-Ser-Gly polypeptide sequence, and a T2A ribosome skipping tag in a Furin:Gly-Ser-Gly:T2A orientation from N-terminus to C-terminus;
S2 comprises a polynucleotide sequence encoding a second signal peptide, wherein the second signal peptide is a human IL21 signal peptide;
E2 comprises a polynucleotide sequence encoding a second effector molecule, wherein the second effector molecule is human IL21; and
wherein the SFFV promoter is operably linked to the expression cassette, the first signal peptide is operably linked to the first effector molecule, and the second signal peptide is operably linked to the second effector molecule, and
wherein the engineered cell is selected from the group consisting of: a mesenchymal stem cell (MSC), stem cell, immune cell, natural killer (NK) cell, NKT cell, innate lymphoid cell, tumor-infiltrating lymphocyte (TIL), mast cell, eosinophil, basophil, monocyte, macrophage, neutrophil, myeloid cell, dendritic cell, T cell, CD8+ T cell, CD4+ T cell, cytotoxic T lymphocyte (CTL), viral-specific T cell, gamma-delta T cell, T regulatory cell, and B cell.

313. The method of paragraph 312, wherein the construct comprises the polynucleotide sequence shown in SEQ ID NO: 144.

314. The method of any one of paragraphs 311-313, wherein the composition comprises a delivery system selected from the group consisting of: a viral system, a transposon system, and a nuclease genomic editing system.

315. The method of paragraph 314, wherein the viral system is selected from the group consisting of: a lentivirus, a retrovirus, a retrotransposon, and an adenovirus.

316. The method of paragraph 314, wherein the nuclease genomic editing system is selected from the group consisting of: a zinc-finger system, a TALEN system, and a CRISPR system.

317. The method of any one of paragraphs 311-316, wherein the tumor is selected from the group consisting of: an adenocarcinoma, an acute myeloid leukemia (AML), an acute lymphoblastic B-cell leukemia (BALL), an acute lymphoblastic T-cell leukemia (TALL), a B-cell prolymphocytic leukemia, a bladder tumor, a brain tumor, a breast tumor, a cervical tumor, a chronic lymphocytic leukemia, a chronic myeloid leukemia (CML), a colorectal tumor, an esophageal tumor, a glioma, a kidney tumor, a liver tumor, a lung tumor, a lymphoma, a melanoma, a mesothelioma, a myelodysplasia, an ovarian tumor, a pancreatic tumor, a plasma cell myeloma, a prostate tumor, a skin tumor, a thyroid tumor, and a uterine tumor.

318. The method of any one of paragraphs 311-317, wherein the administering comprises systemic administration, intraperitoneal administration, or intratumoral administration.

EXAMPLES

Example 1

This Example describes the in vitro characterization of MSCs with individual and combination immunotherapy payloads. Direct anti-cancer effects of immunotherapy-expressing MSCs on cancer cells are first measured. Next, the effects of immunotherapy-expressing MSCs on co-cultures with primary immune cells (focusing on T cells) and cancer cells are measured. The immuno-stimulatory properties of immunotherapy-expressing MSCs are rank-ordered based on inflammatory biomarker panels in both mouse and human cell systems. Immunotherapy-expressing MSCs that significantly enhance cancer cell killing either on their own or together with T cells are identified, and the top candidates to advance to in vivo testing are selected.

Methods: Immunotherapy-expressing MSCs are engineered to express the effector molecules listed in Table 1 are evaluated for their functional effects using in vitro models relevant to cancer therapy. Human ovarian cancer cells (e.g., OVCAR8 and SKOV3) and human immune cells isolated from circulating PBMCs are used to test the hMSCs expressing hITs. Mouse ovarian cancer cells (e.g., ID8) and mouse immune cells are used to test the mMSCs expressing mITs.

Checkpoint inhibitors. Cell-binding assays are used to verify the activity of the expressed antibodies. The targets of the antibodies, CTLA4 and PD1, both negatively regulate T cells, but they are upregulated at different stages of T-cell activation (Boutros C, et al. (2016) *Nat Rev Clin Oncol* 13(8):473-486; Valsecchi M E (2015) *New Engl J Med* 373(13):1270-1270). CTLA4 is briefly upregulated in the priming phase, whereas PD1 is consistently expressed in the effector phase of T cell activation (Pardoll D M (2012) *Nat Rev Cancer* 12(4):252-264; Legat A, et al. (2013) *Front Immunol* 4:455). Anti-CTLA4 antibody binds to CTLA4 on the T-cell surface, blocking CTLA4 from shutting down T-cell activation in the early stage, and the human anti-PD1 antibody binds to PD1, preventing tumor cells from inhibiting T-cell activity.

T cells are isolated from PBMC by negative selection using EASYSEP™ magnetic bead (STEMCELL Technologies). The isolated T cells are activated by Human T-Activator CD3/28 Dynabeads (Thermo Fisher) and expression of CTLA-4 and PD-1 is monitored over 5 days to select for optimal timing of expression for each surface marker. On the appropriate days, conditioned media from the MSCs expressing antibodies for CTLA-4 or PD-1, or control conditioned media from non-expressing MSCs, are applied to the activated T cells to validate direct cell-surface-receptor binding of these antibodies. Fluorochrome-labeled secondary detection antibodies together with flow cytometry should confirm binding.

Chemokines. CCL21 chemokine functionality is confirmed using cell migration assays and isolated naïve T cells, which express chemokine receptor CCR7 that is responsive to CCL21 chemotaxis. Specifically, CCL21-expressing or control MSCs are added to one compartment of a trans-well and then cell migration is assessed by isolated naïve T cells from the other compartment, followed by enumeration of numbers of migrated T cells (Justus C R, et al. (2014) *J Vis Exp* (88)).

Cytokines. The activity of IL2, IL12, and IL15 is measured. ELISA assays specific to IL2, IL12, and IL15 are used to detect levels of these cytokines in MSC supernatants. Functional bioactivity assays employ the CTLL-2 cell line to assess of IL2 or IL15-mediated proliferation, or the NKG cell line to assess IL12-mediated IFN-gamma production by MSC supernatants. Multiplexed cytokine profiling assays using LUMINEX® technology may also be used to assess cytokine expression and effects on immune cells.

STING pathway. STING pathway activation is measured with the constitutive STING mutant payload. Using LUMINEX® beads, the secretion of Type I interferons (e.g. IFN-alpha2 and IFN-beta) with expression of the STING mutant are profiled in MSCs.

Direct effects of immunotherapy-expressing MSCs on ovarian cancer cells. Any direct effects of MSCs on ovarian cancer cell growth and viability are tested in vitro. For example, mMSC or hMSC candidates are co-cultured with the mouse ovarian cancer cell line (ID8) or human ovarian cancer cell lines (OVCAR8 and SKOV3) and cancer cell cytotoxicity is measured by the well-characterized lactate dehydrogenase (LDH) assay. After 24 hours of co-culture, the supernatants are collected and measured for LDH levels correlated to cellular death via an enzymatic reaction that is subsequently quantified by specific absorbance on a plate reader. Additionally, cancer cell numbers are assessed by counting live versus dead cells by Trypan Blue exclusion and live versus apoptotic/dead cells by flow cytometric measurement using Annexin-V and propidium iodide staining.

Effects of immunotherapy-expressing MSCs on T cell and ovarian cancer cell co-culture systems. Tests determine whether immunotherapy-expressing MSCs can stimulate immune cells, such as T cells, to have improved anti-cancer activity against ovarian cancer cells in vitro. Specifically, mMSC-mIT candidates are co-cultured with mouse splenocytes and the ID8 cancer cell line, or hMSC-hIT candidates are co-cultured with human PBMCs and the OVCAR8 or SKOV3 cell lines. The co-culture assays entail using PBMCs/splenocytes with the ovarian cancer cells, with or without the MSCs, and stimulation with anti-CD3/28 beads. To assess cancer cell death, 16 hour killing assays are performed using techniques such as LDH cytotoxicity measurements, combining dye-labeled ovarian cancer cells with non-labeled effector PBMCs/splenocytes at fixed ratios and assaying killing by flow cytometry (Jedema I, et al. (2004) *Blood* 103(7):2677-2682), and apoptosis readouts by flow cytometry using Annexin-V with propidium iodide. T cell activation/proliferation is specifically assay by CFSE cell division at 3-5 days and cytokine production of IFN-gamma at 1-3 days.

An alternative strategy to generate T cells expressing CTLA-4 and PD1 is to activate with phytohaemagglutinin (PHA) to express the cell surface receptors PD1 and CTLA4. On Day 3, ~99% of the activated T cells should express PD1 while ~15% of them should express CTLA4 (Pardoll D M (2012) *Nat Rev Cancer* 12(4):252-264; Legat A, et al. (2013) *Front Immunol* 4:455). On Day 10, the activated T cells should be in the effector phase, when CTLA4 expression is downregulated but PD1 expression is maintained. Direct cell-surface-receptor binding of these antibodies is evaluated. On Day 3 and Day 10 post-induction, MSCs with the respective checkpoint inhibitor antibody expression constructs are applied to the T cell cultures. Labeled detection antibodies are used together with flow cytometry to confirm binding. Commercial antibodies are used as controls.

Example 2

This Example describes the in vivo characterization of MSCs expressing immunotherapy payloads in a syngeneic ovarian cancer model. The anti-tumor efficacy of immunotherapy-expressing MSCs is characterized using syngeneic mouse models of ovarian cancer (mMSC-mIT with mouse immune system). Tumor homing of engineered MSCs and expression of individual and combinatorial immunotherapies in a syngeneic ovarian mouse model are measured. Ovarian tumor burden and mouse survival with engineered MSC treatments are also measured. This Example should demonstrate selective homing of engineered MSCs to the TME and localized production of immunotherapy factors in ovarian tumors versus other body sites. This Example should also demonstrate significant reductions in tumor burden and extension of mouse survival with immunotherapy-expressing engineered MSCs.

Methods: The mouse ID8 cell line originated from spontaneous transformation of mouse ovarian epithelial surface cells (MOSE), is used to create a syngeneic ovarian tumor model (Roby K F, et al. (2000) Carcinogenesis 21(4):585-591). Derivatives of the ID8 cell line are also used (e.g., ID8-VEGF (ID8-Defb29/Vegf-a), ID8-P53DN, ID8-P53KO-PTEN KO, ID8-P53KO-BRCA2 KO, ID8-P53KO-BRCA1 KO, ID8-PD53KO-Nf1KO). The ID8 cell line is infected with a lentivirus expressing *Renilla* luciferase (rLuc) to allow for in vivo bioluminescence imaging that is orthogonal to MSCs expressing Firefly luciferase (ffLuc). Successful rLuc expression is confirmed in ID8 in vitro prior to establishing the syngeneic ovarian cancer model in mice. For the syngeneic model, $5 \times 10^5$ ID8 cells are injected into the peritoneal cavity of C57BL/6 mice between 6 to 8 weeks old (36, 54). MSCs are engineered as in Example 1, along with an ffLuc-expressing plasmid.

mMSC-mIT candidates are introduced into the syngeneic mouse model starting on day 25 (after tumor cell injection) at a dose of $10^6$ MSC per animal once per week for 5 weeks (Dembinski J L, et al. (2013) *Cytotherapy* 15(1):20-32). The ovarian tumor load and mMSC-mIT candidates are visualized over time through rLuc and ffLuc bioluminescence imaging, respectively, as well as histological analyses following terminal time points. Mice are euthanized when they develop signs of distress, such as body-weight loss, ruffled fur, poor body posture, distended abdomen, and jaundice. Survival curves for the mice are measured. Distal metastasis of tumor cells is quantified by bioluminescence imaging (BLI) and by necropsy at time of euthanasia. Immune system profiling and activity is measured at different time points as biomarkers of response to the therapy.

To assess for variability in the expected anti-tumor effects of the MSCs, the dose of ID8 cells used to establish the model is varied (e.g., increase the number of cells to 5×10$^6$), the dose of MSCs used is changed, and the time when MSCs are delivered after tumor establishment is modulated.

Even though mMSCs have been shown to home to ovarian tumors in mouse models, it is possible that some payloads disrupt this homing activity. In these instances, expression of these payloads may be engineered to be inducible. This can be achieved, for example, with a phloretin-inducible system (Gitzinger M, et al. (2009) *Proc Natl Acad Sci USA* 106(26):10638-10643). Alternatively, the Dimerizer system may be used to link a synthetic zinc-finger DNA-binding domain with a transactivator domain using a small molecule (Clackson T, et al. (1998) *Proc Natl Acad Sci USA* 95(18):10437-10442). Alternatively or additionally, inducible payload expression constructs that are triggered in the tumor microenvironment based on signals such as low O$_2$ may be constructed.

Lentiviral ffLuc constructs may also be used to infect MSCs.

Example 3

This Example describes the in vivo characterization of the efficacy of MSCs expressing immunotherapy payloads in xenograft models of human ovarian cancer in mice with human immune cells. The activity of engineered MSCs in human ovarian cancer models in immunodeficient mice that are engrafted with human immune cells via CD34+ cell transplants (hMSC-hIT with humanized immune system) is tested. Homing of engineered MSCs and expression of individual and combinatorial immunotherapies in human xenograft ovarian tumors in mice with human immune cells are measured. Ovarian tumor burden and mouse survival with engineered MSC treatments are also tested. This Example should demonstrate elevated homing of engineered MSCs and localized production of immunotherapy factors into human xenograft ovarian tumors versus other body sites in mice. This Example should also demonstrate significant reductions in tumor burden and extension of mouse survival with immunotherapy-expressing engineered MSCs correlating with changes in the immune system composition.

Methods. To enable translation of engineered MSCs into human clinical trials, hMSC-hIT constructs are tested in humanized mouse models of human cancers. The effects of the immunotherapy-expressing hMSCs in mice are modeled by using xenografts of human ovarian cancer cell lines in immuno-deficient mice (NSG) engrafted with CD34$^+$ hematopoietic stem cells (HSCs).

For human ovarian cancer cells, OVCAR8 and SKOV3 cell lines are used. Similar assays as described in Example 3 are used to investigate tumor load and mouse survival over time.

Two alternative approaches may also be used. (1) Human T cells can be infused into the mice. (2) Human PBMCs can be infused into the mice.

```
Expression Vector: pL + MCS
                                     (SEQ ID NO: 111)
ACGCGTGTAGTCTTATGCAATACTCTTGTAGTCTTGCAACATGG

TAACGATGAGTTAGCAACATGCCTTACAAGGAGAGAAAAGCAC
```

-continued

```
CGTGCATGCCGATTGGTGGAAGTAAGGTGGTACGATCGTGCCTT

ATTAGGAAGGCAACAGACGGGTCTGACATGGATTGGACGAACCA

CTGAATTGCCGCATTGCAGAGATATTGTATTTAAGTGCCTAGCT

CGATACAATAAACGGGTCTCTCTGGTTAGACCAGATCTGAGCCT

GGGAGCTCTCTGGCTAACTAGGGAACCCACTGCTTAAGCCTCAA

TAAAGCTTGCCTTGAGTGCTTCAAGTAGTGTGTGCCCGTCTGTT

GTGTGACTCTGGTAACTAGAGATCCCTCAGACCCTTTTAGTCAG

TGTGGAAAATCTCTAGCAGTGGCGCCCGAACAGGGACCTGAAAG

CGAAAGGGAAACCAGAGCTCTCTCGACGCAGGACTCGGCTTGCT

GAAGCGCGCACGGCAAGAGGCGAGGGGCGGCGACTGGTGAGTAC

GCCAAAAATTTTGACTAGCGGAGGCTAGAAGGAGAGAGATGGGT

GCGAGAGCGTCAGTATTAAGCGGGGGAGAATTAGATCGCGATGG

GAAAAAATTCGGTTAAGGCCAGGGGGAAAGAAAAAATATAAATT

AAAACATATAGTATGGGCAAGCAGGGAGCTAGAACGATTCGCAG

TTAATCCTGGCCTGTTAGAAACATCAGAAGGCTGTAGACAAATA

CTGGGACAGCTACAACCATCCCTTCAGACAGGATCAGAAGAACT

TAGATCATTATATAATACAGTAGCAACCCTCTATTGTGTGCATC

AAAGGATAGAGATAAAAGACACCAAGGAAGCTTTAGACAAGATA

GAGGAAGAGCAAAACAAAAGTAAGACCACCGCACAGCAAGCGGC

CACTGATCTTCAGACCTGGAGGAGGAGATATGAGGGACAATTGG

AGAAGTGAATTATATAAATATAAAGTAGTAAAAATTGAACCATT

AGGAGTAGCACCCACCAAGGCAAAGAGAAGAGTGGTGCAGAGAG

AAAAAAGAGCAGTGGGAATAGGAGCTTTGTTCCTTGGGTTCTTG

GGAGCAGCAGGAAGCACTATGGGCGCAGCCTCAATGACGCTGAC

GGTACAGGCCAGACAATTATTGTCTGGTATAGTGCAGCAGCAGA

ACAATTTGCTGAGGGCTATTGAGGCGCAACAGCATCTGTTGCAA

CTCACAGTCTGGGGCATCAAGCAGCTCCAGGCAAGAATCCTGGC

TGTGGAAAGATACCTAAAGGATCAACAGCTCCTGGGGATTTGGG

GTTGCTCTGGAAAACTCATTTGCACCACTGCTGTGCCTTGGAAT

GCTAGTTGGAGTAATAAATCTCTGGAACAGATTGGAATCACACG

ACCTGGATGGAGTGGGACAGAGAAATTAACAATTACACAAGCTT

AATACACTCCTTAATTGAAGAATCGCAAAACCAGCAAGAAAAGA

ATGAACAAGAATTATTGGAATTAGATAAATGGGCAAGTTTGTGG

AATTGGTTTAACATAACAAATTGGCTGTGGTATATAAAATTATT

CATAATGATAGTAGGAGGCTTGGTAGGTTTAAGAATAGTTTTTG

CTGTACTTTCTATAGTGAATAGAGTTAGGCAGGGATATTCACCA

TTATCGTTTCAGACCCACCTCCCAACCCCGAGGGGACCCGACAG

GCCCGAAGGAATAGAAGAAGAAGGTGGAGAGAGAGACAGAGACA

GATCCATTCGATTAGTGAACGGATCTCGACGGTATCGGTTAACT

TTTAAAAGAAAAGGGGGGATTGGGGGGTACAGTGCAGGGGAAAG
```

```
AATAGTAGACATAATAGCAACAGACATACAAACTAAAGAATTAC
AAAAACAAATTACAAAAATCAAAATTTTATCTCGACATGGTGGC
GACCGGTAGCGCTAGCGGATCGATAAGCTTGATATCGCCTGCAG
CCGAATTCCTTGACTTGGGATCCGCGTCAAGTGGAGCAAGGCAG
GTGGACAGTCCTGCAGGCATGCGTGACTGACTGAGGCCGCGACT
CTAGTTTAAACTGCGTGACTGACTCTAGAAGATCCGGCAGTGCG
GCCGCGTCGACAATCAACCTCTGGATTACAAAATTTGTGAAAGA
TTGACTGGTATTCTTAACTATGTTGCTCCTTTTACGCTATGTGG
ATACGCTGCTTTAATGCCTTTGTATCATGCTATTGCTTCCCGTA
TGGCTTTCATTTTCTCCTCCTTGTATAAATCCTGGTTGCTGTCT
CTTTATGAGGAGTTGTGGCCCGTTGTCAGGCAACGTGGCGTGGT
GTGCACTGTGTTTGCTGACGCAACCCCCACTGGTTGGGGCATTG
CCACCACCTGTCAGCTCCTTTCCGGGACTTTCGCTTTCCCCCTC
CCTATTGCCACGCGGAACTCATCGCCGCCTGCCTTGCCCGCTG
CTGGACAGGGGCTCGGCTGTTGGGCACTGACAATTCCGTGGTGT
TGTCGGGAAATCATCGTCCTTTCCTTGGCTGCTCGCCTGTGTT
GCCACCTGGATTCTGCGCGGGACGTCCTTCTGCTACGTCCCTTC
GGCCCTCAATCCAGCGGACCTTCCTTCCCGCGGCCTGCTGCCGG
CTCTGCGGCCTCTTCCGCGTCTTCGCCTTCGCCCTCAGACGAGT
CGGATCTCCCTTTGGGCCGCCTCCCCGCCTGGTACCTTTAAGAC
CAATGACTTACAAGGCAGCTGTAGATCTTAGCCACTTTTTAAAA
GAAAAGGGGGACTGGAAGGGCTAATTCACTCCCAACGAAAATA
AGATCTGCTTTTTGCTTGTACTGGGTCTCTCTGGTTAGACCAGA
TCTGAGCCTGGGAGCTCTCTGGCTAACTAGGGAACCCACTGCTT
AAGCCTCAATAAAGCTTGCCTTGAGTGCTTCAAGTAGTGTGTGC
CCGTCTGTTGTGTGACTCTGGTAACTAGAGATCCCTCAGACCCT
TTTAGTCAGTGTGGAAAATCTCTAGCAGTAGTAGTTCATGTCAT
CTTATTATTCAGTATTTATAACTTGCAAAGAAATGAATATCAGA
GAGTGAGAGGAACTTGTTTATTGCAGCTTATAATGGTTACAAAT
AAAGCAATAGCATCACAAATTTCACAAATAAAGCATTTTTTCA
CTGCATTCTAGTTGTGGTTTGTCCAAACTCATCAATGTATCTTA
TCATGTCTGGCTCTAGCTATCCCGCCCCTAACTCCGCCCAGTTC
CGCCCATTCTCCGCCCCATGGCTGACTAATTTTTTTATTTATG
CAGAGGCCGAGGCCGCCTCGGCCTCTGAGCTATTCCAGAAGTAG
TGAGGAGGCTTTTTGGAGGCCTAGACTTTTGCAGAGACGGCCC
AAATTCGTAATCATGGTCATAGCTGTTTCCTGTGTGAAATTGTT
ATCCGCTCACAATTCCACACAACATACGAGCCGGAAGCATAAAG
TGTAAAGCCTGGGGTGCCTAATGAGTGAGCTAACTCACATTAAT
TGCGTTGCGCTCACTGCCCGCTTTCCAGTCGGGAAACCTGTCGT
GCCAGCTGCATTAATGAATCGGCCAACGCGCGGGGAGAGGCGGT
TTGCGTATTGGGCGCTCTTCCGCTTCCTCGCTCACTGACTCGCT

GCGCTCGGTCGTTCGGCTGCGGCGAGCGGTATCAGCTCACTCAA
AGGCGGTAATACGGTTATCCACAGAATCAGGGGATAACGCAGGA
AAGAACATGTGAGCAAAAGGCCAGCAAAAGGCCAGGAACCGTAA
AAAGGCCGCGTTGCTGGCGTTTTTCCATAGGCTCCGCCCCCCTG
ACGAGCATCACAAAAATCGACGCTCAAGTCAGAGGTGGCGAAAC
CCGACAGGACTATAAAGATACCAGGCGTTTCCCCCTGGAAGCTC
CCTCGTGCGCTCTCCTGTTCCGACCCTGCCGCTTACCGGATACC
TGTCCGCCTTTCTCCCTTCGGGAAGCGTGGCGCTTTCTCATAGC
TCACGCTGTAGGTATCTCAGTTCGGTGTAGGTCGTTCGCTCCAA
GCTGGGCTGTGTGCACGAACCCCCCGTTCAGCCCGACCGCTGCG
CCTTATCCGGTAACTATCGTCTTGAGTCCAACCCGGTAAGACAC
GACTTATCGCCACTGGCAGCAGCCACTGGTAACAGGATTAGCAG
AGCGAGGTATGTAGGCGGTGCTACAGAGTTCTTGAAGTGGTGGC
CTAACTACGGCTACACTAGAAGGACAGTATTTGGTATCTGCGCT
CTGCTGAAGCCAGTTACCTTCGGAAAAAGAGTTGGTAGCTCTTG
ATCCGGCAAACAAACCACCGCTGGTAGCGGTGGTTTTTTTGTTT
GCAAGCAGCAGATTACGCGCAGAAAAAAAGGATCTCAAGAAGAT
CCTTTGATCTTTTCTACGGGGTCTGACGCTCAGTGGAACGAAAA
CTCACGTTAAGGGATTTTGGTCATGAGATTATCAAAAAGGATCT
TCACCTAGATCCTTTTAAATTAAAAATGAAGTTTTAAATCAATC
TAAAGTATATATGAGTAAACTTGGTCTGACAGTTACCAATGCTT
AATCAGTGAGGCACCTATCTCAGCGATCTGTCTATTTCGTTCAT
CCATAGTTGCCTGACTCCCCGTCGTGTAGATAACTACGATACGG
GAGGGCTTACCATCTGGCCCCAGTGCTGCAATGATACCGCGAGA
CCCACGCTCACCGGCTCCAGATTTATCAGCAATAAACCAGCCAG
CCGGAAGGGCCGAGCGCAGAAGTGGTCCTGCAACTTTATCCGCC
TCCATCCAGTCTATTAATTGTTGCCGGGAAGCTAGAGTAAGTAG
TTCGCCAGTTAATAGTTTGCGCAACGTTGTTGCCATTGCTACAG
GCATCGTGGTGTCACGCTCGTCGTTTGGTATGGCTTCATTCAGC
TCCGGTTCCCAACGATCAAGGCGAGTTACATGATCCCCCATGTT
GTGCAAAAAAGCGGTTAGCTCCTTCGGTCCTCCGATCGTTGTCA
GAAGTAAGTTGGCCGCAGTGTTATCACTCATGGTTATGGCAGCA
CTGCATAATTCTCTTACTGTCATGCCATCCGTAAGATGCTTTTC
TGTGACTGGTGAGTACTCAACCAAGTCATTCTGAGAATAGTGTA
TGCGGCGACCGAGTTGCTCTTGCCCGGCGTCAATACGGGATAAT
ACCGCGCCACATAGCAGAACTTTAAAAGTGCTCATCATTGGAAA
ACGTTCTTCGGGGCGAAAACTCTCAAGGATCTTACCGCTGTTGA
GATCCAGTTCGATGTAACCCACTCGTGCACCCAACTGATCTTCA
GCATCTTTTACTTTCACCAGCGTTTCTGGGTGAGCAAAAACAGG
AAGGCAAAATGCCGCAAAAAAGGGAATAAGGGCGACACGGAAAT
```

-continued
```
GTTGAATACTCATACTCTTCCTTTTTCAATATTATTGAAGCATT

TATCAGGGTTATTGTCTCATGAGCGGATACATATTTGAATGTAT

TTAGAAAAATAAACAAATAGGGGTTCCGCGCACATTTCCCCGAA

AAGTGCCACCTGACGTCTAAGAAACCATTATTATCATGACATTA

ACCTATAAAATAGGCGTATCACGAGGCCCTTTCGTCTCGCGCG

TTTCGGTGATGACGGTGAAAACCTCTGACACATGCAGCTCCCGG

AGACGGTCACAGCTTGTCTGTAAGCGGATGCCGGGAGCAGACAA

GCCCGTCAGGGCGCGTCAGCGGGTGTTGGCGGGTGTCGGGGCTG

GCTTAACTATGCGGCATCAGAGCAGATTGTACTGAGAGTGCACC

ATATGCGGTGTGAAATACCGCACAGATGCGTAAGGAGAAAATAC

CGCATCAGGCGCCATTCGCCATTCAGGCTGCGCAACTGTTGGGA

AGGGCGATCGGTGCGGGCCTCTTCGCTATTACGCCAGCTGGCGA

AAGGGGGATGTGCTGCAAGGCGATTAAGTTGGGTAACGCCAGGG

TTTTCCCAGTCACGACGTTGTAAAACGACGGCCAGTGCCAAGCTG
```

Example 4: 4T1 Triple Negative Breast Carcinoma

In the following experiments, MSCs were engineered to express one of the following effector molecules, then administered, alone or in combinations, to an orthotopic breast cancer mouse model: IFNβ, IFNγ, IL12, IL15, IL36γ, IL7, TRAIL, cGAS, CCL21a, OX40L, CD40L, or HACv-PD1. In some examples, a checkpoint inhibitor (anti-CD40, anti-PD1, or anti-CTLA-4 antibody) was injected in combination with administration with the engineered MSCs.

MSC Homing

Figure 3:
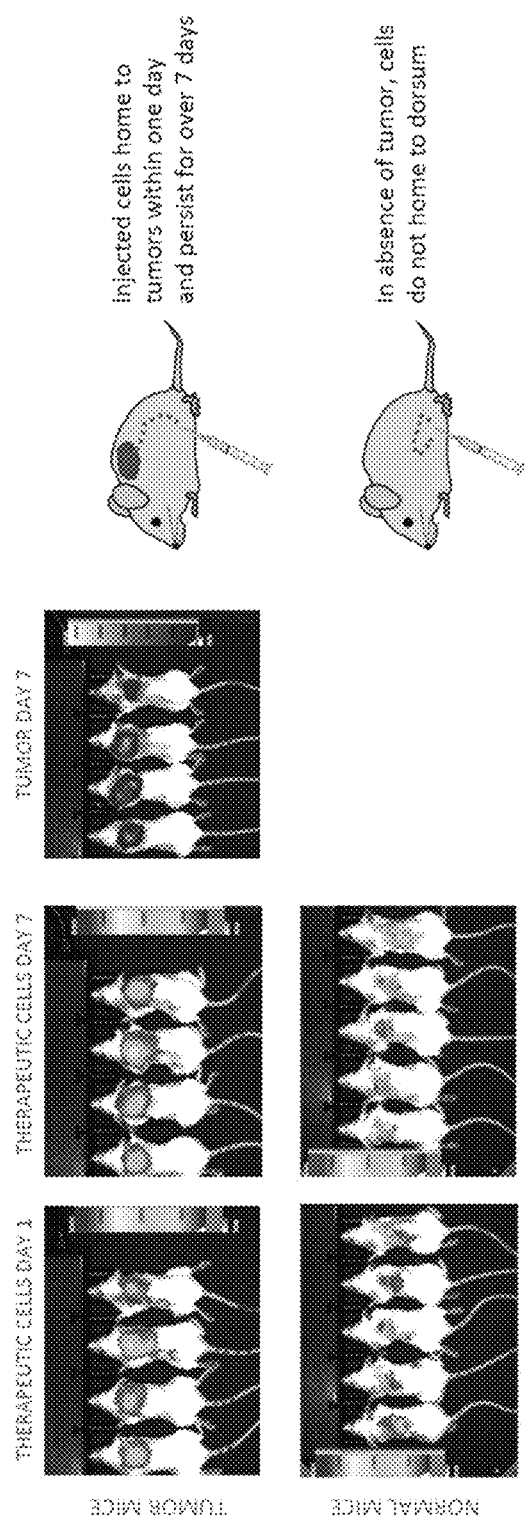
FIG. 3 shows data indicating that intraperitoneally injected murine BM-derived MSCs (BM-MSCs) home to the tumor site of 4T1 breast cancer cells in vivo. Fluorescently labeled BM-MSCs (therapeutic cells) were injected into mice bearing 4T1 breast tumor cells. The breast tumor cells express a luciferase reporter. The first top two panels on the left show imaging of therapeutic cells (BM-MSCs) in mice bearing tumors on day 1 and on day 7 after injection as indicated. The third top panel on the left shows imaging of tumor cells in mice bearing tumors on day 7 after injection. The bottom two panels on the left show imaging of therapeutic cells in normal mice not bearing tumors on day 1 and on day 7 after injection as indicated. A schematic showing the effect of tumors on homing of therapeutic cells is provided on the far right.

The following experiments demonstrate that murine MSCs home to tumors in an orthotopic mouse model of breast cancer. Luciferase-expressing 4T1 breast tumor cells ($5 \times 10^5$) were orthotopically implanted into the dorsal fat pad of female BALB/cJ mice. After 5 days, mice were intraperitoneally injected with 1 million fluorescently-labeled (with XenoLight DiR (Caliper Life Sciences)) murine BM-derived MSCs (BM-MSCs, therapeutic cells). At days 1 and 7 after MSC injection, fluorescence analysis was used to determine MSC localization using the Ami HT live animal imager (Spectral Instruments). On day 7, tumor localization and size was determined through the 4T1 cell's luciferase bioluminescence reporter using the Ami HT imager. As shown in FIG. 3, the injected MSCs co-localized to the site of the tumor, indicating that these cells do in fact specifically home in vivo to sites of 4T1 breast tumors. The injected MSCs home to tumors within one day and persist for over 7 days. In contrast, injected MSCs do not home to the dorsum in the absence of tumor in normal mice. These results suggest that MSCs can be used as a delivery vehicle for anti-cancer molecules, proteins or compounds.

Figure 11A:
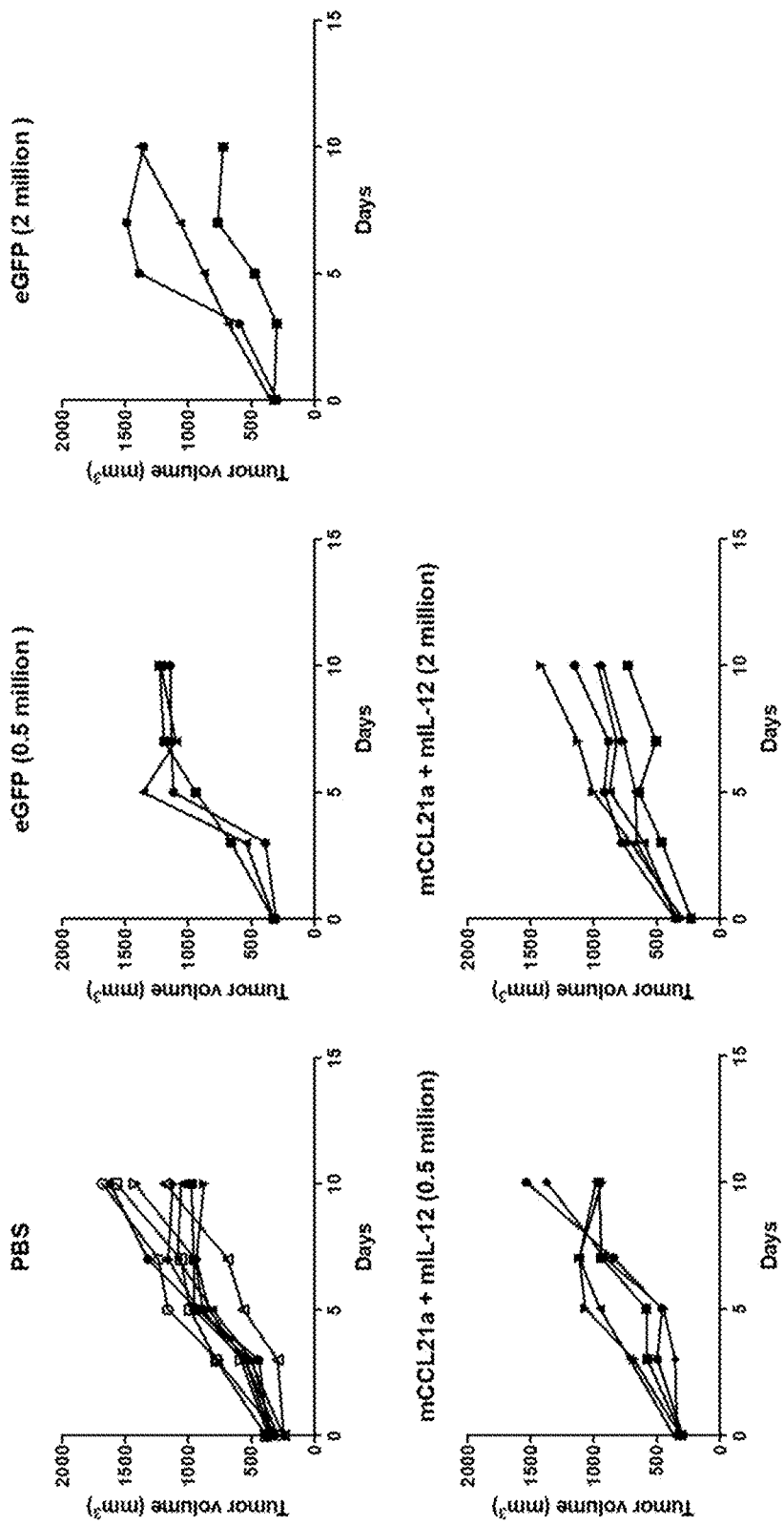
FIG. 11A shows that engineered human MSCs do not home to mouse 4T1 tumors. Each line of FIG. 11A represents an individual mouse.
Figure 11B:
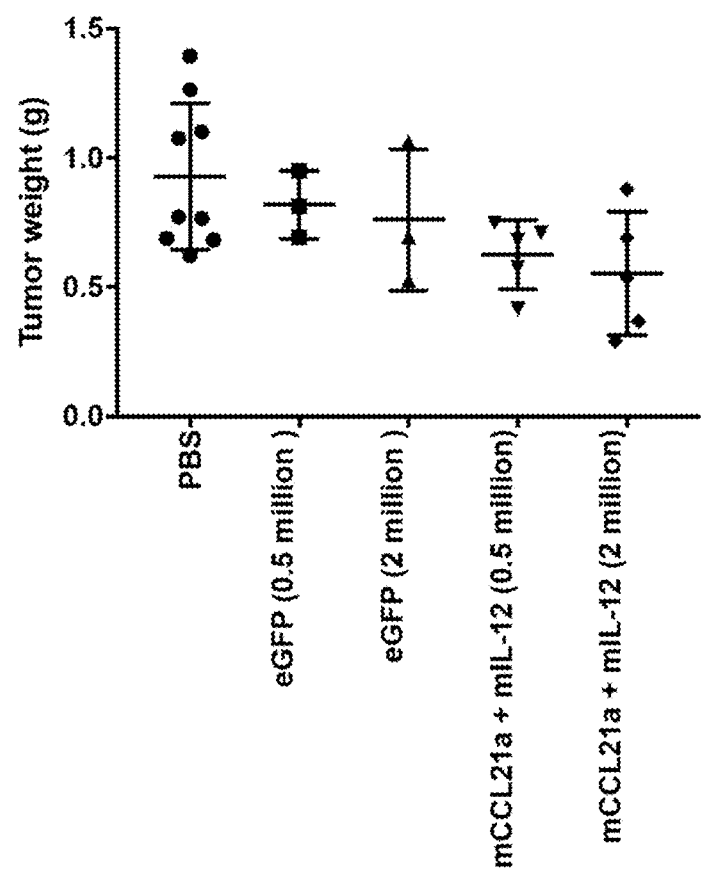
FIG. 11B shows that engineered human MSCs do not home to mouse 4T1 tumors.

To determine whether engineered human MSCs can home toward mouse tumors, different lines of engineered human MSC expressing either GFP, IL2 or CCL21a were injected into BALB/c mice with 4T1 tumors. Efficacy was determined by tumor volume from caliper measurement every other day. FIGS. 11A-11B show that human MSCs do not home to mouse 4T1 tumors.

In Vivo Efficacy

The following experiments demonstrate the in vivo efficacy of MSCs expressing immunotherapy effectors (payloads) in the orthotopic model of breast cancer. 4T1-Neo-Fluc mouse breast tumor cells (Imanis Life Sciences, $5 \times 10^5$ cells) were implanted orthotopically into the dorsal fat pad of female BALB/cJ mice (The Jackson Laboratory). Mice were then randomized into the treatment groups 5 days after tumor implantation. Mice received intraperitoneal injection of either control MSC growth media or engineered MSCs ($2 \times 10^6$ cells) expressing different immunotherapy effectors (payloads) once a week for two weeks. Each immunotherapy was expressed by a different MSC, and MSCs were combined (1:1 ratio) for combinatorial treatment. Tumor growth was monitored by caliper measurements every other day, and mouse weights were recorded twice weekly. Mice were euthanized 14 days after first MSC treatment and tissues were collected for further analysis.

Figure 4:
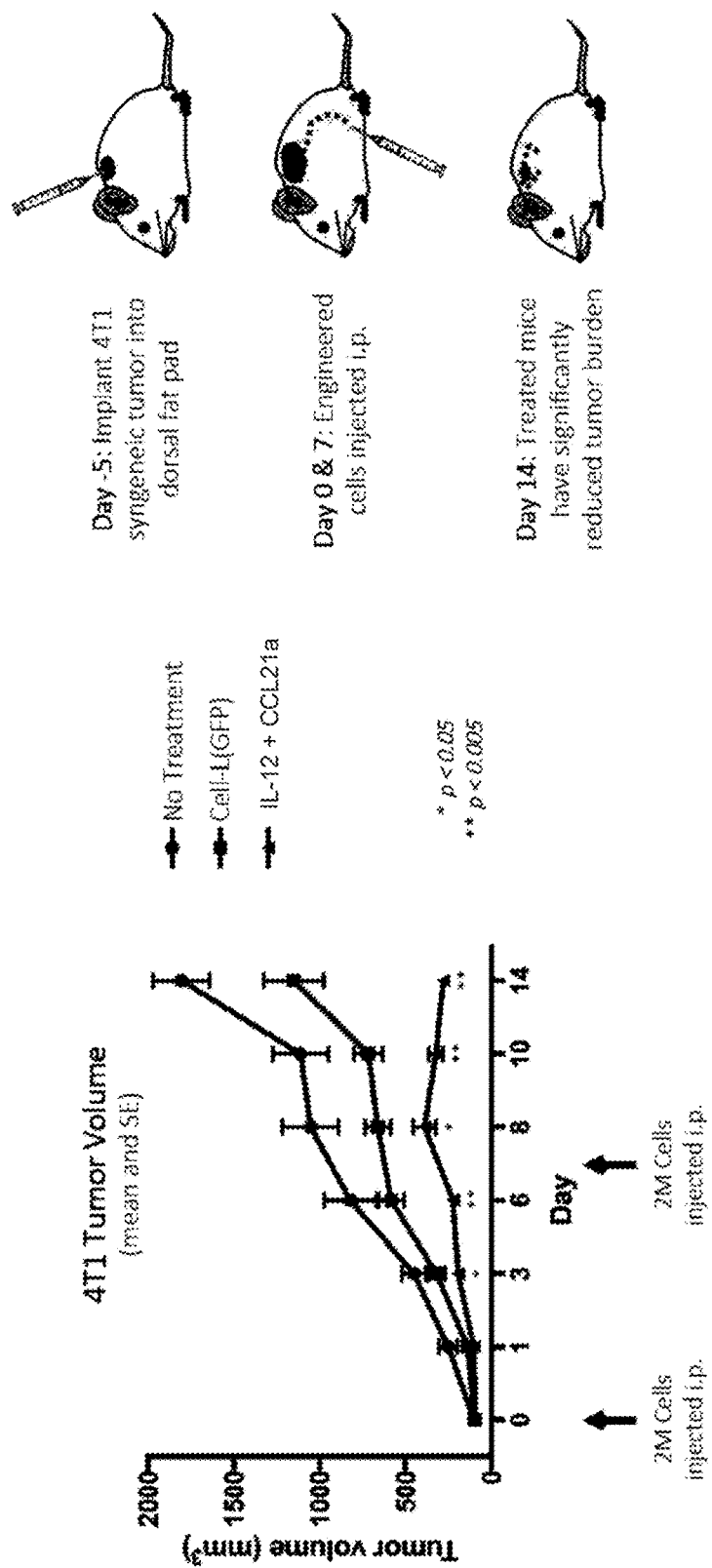
FIG. 4 shows data indicating that engineered MSCs expressing IL-12 and CCL21a induced significant tumor growth delay in an orthotopic mouse model of breast cancer. The chart on the left shows the effects of engineered MSCs on 4T1 breast tumor growth in mice (n=8). Each line in the chart represents tumor volume in mice receiving intraperitoneal injection of either control MSC growth media or engineered MSCs on day 0 and day 7. Mice received intraperitoneal injection of engineered MSCs expressing IL-12 and engineered MSCs expressing CCL21a. Tumor volume was determined by caliper measurements every other day. Data represent mean±SEM. *p<0.05, **p<0.005 as compared to control media group. The schematic on the right shows a timeline of treatment and the effect of engineered MSCs expressed combinatorial genes IL-12 and CCL21a on tumor burden in treated mice.

FIG. 4 shows that tumor growth was delayed in mice treated with engineered MSCs expressed combinatorial genes IL-12 and CCL21a compared to controls treated with media.

Figure 5A:
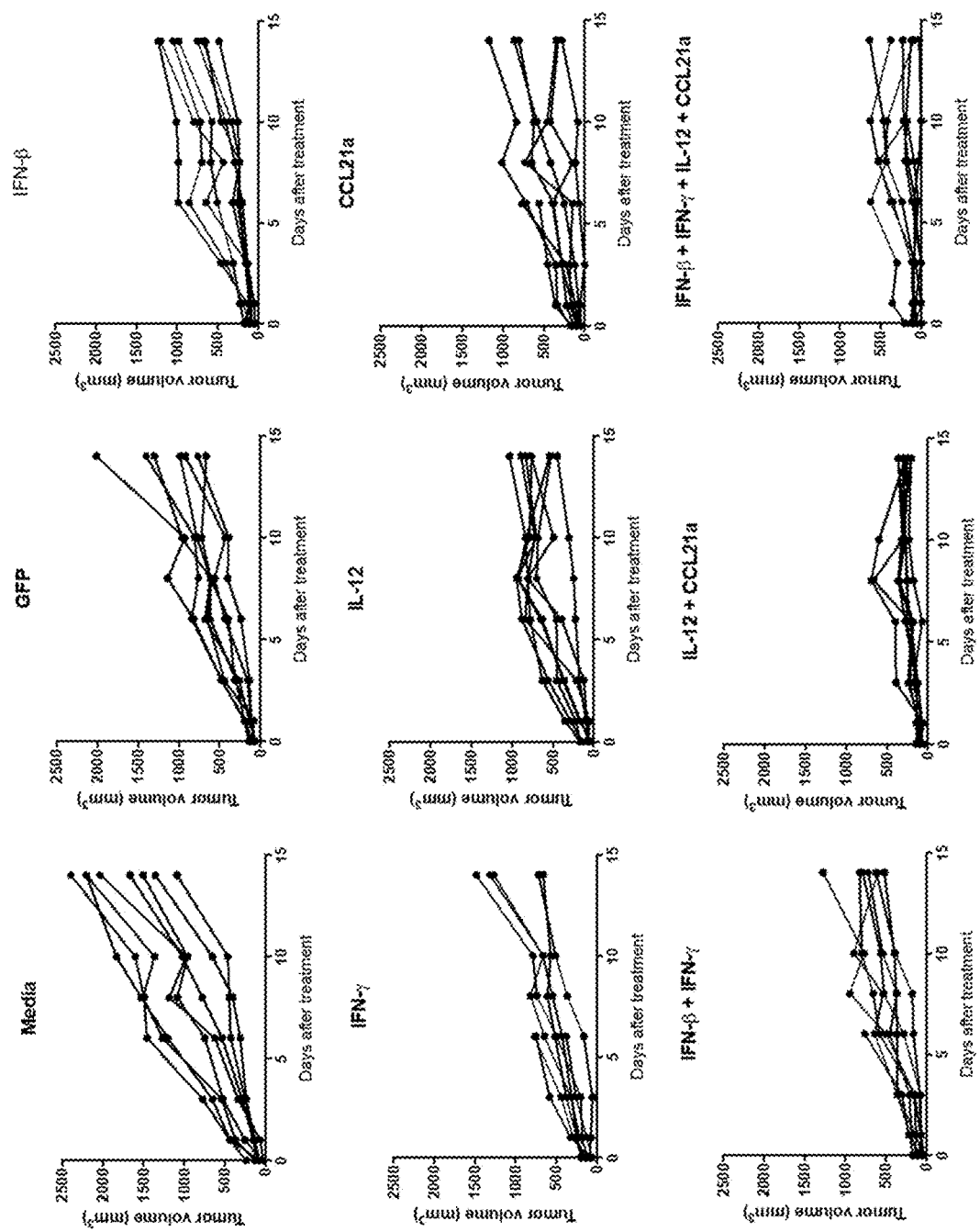
FIG. 5A includes data indicating that engineered MSCs expressing IFN-β, IFN-γ, IL-12, CCL21a, or combinations thereof inhibit tumor growth in an orthotopic mouse model of breast cancer (4T1 triple negative breast carcinoma). Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 5A represents an individual mouse.
Figure 5B:
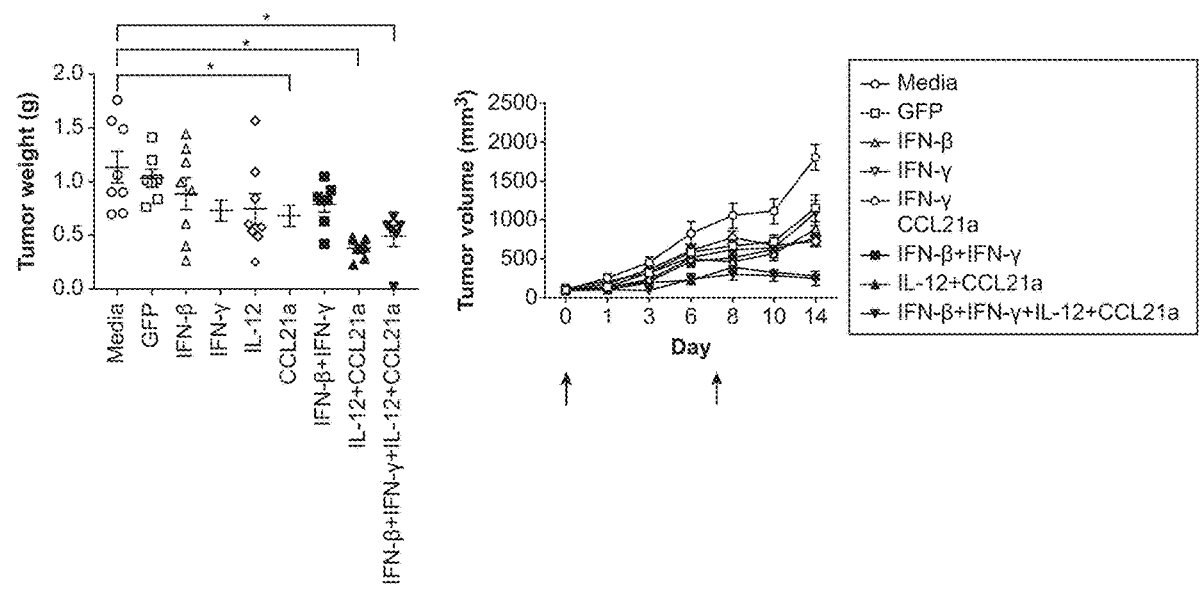
FIG. 5B includes data indicating that engineered MSCs expressing IFN-β, IFN-γ, IL-12, CCL21a, or combinations thereof inhibit tumor growth in an orthotopic mouse model of breast cancer (4T1 triple negative breast carcinoma). Each effector was expressed by a different MSC, and the MSCs were combined (at a 1:1 ratio) for combinatorial treatment. The left graph of FIG. 5B shows the tumor weight for individual mice in each treatment on day 14, and the mean±SEM for each treatment group. The right graph of FIG. 5B shows the tumor volume represented as mean±SEM for mice receiving each treatment over time.

FIGS. 5A-5C show that engineered MSCs that express single immunotherapy effectors (e.g., IFN-β, IFN-γ, IL-12 or CCL21a) inhibited growth of syngeneic 4T1 mouse tumors compared to media-treated mice. Surprisingly, a synergistic effect on tumor growth was observed when the immunotherapy effectors were combined, particularly the combination of IL-12 and CCL21a, and the combination of IFN-β, IFN-γ, IL-12 and CCL21a (FIGS. 5A-5C).

Figure 6A:
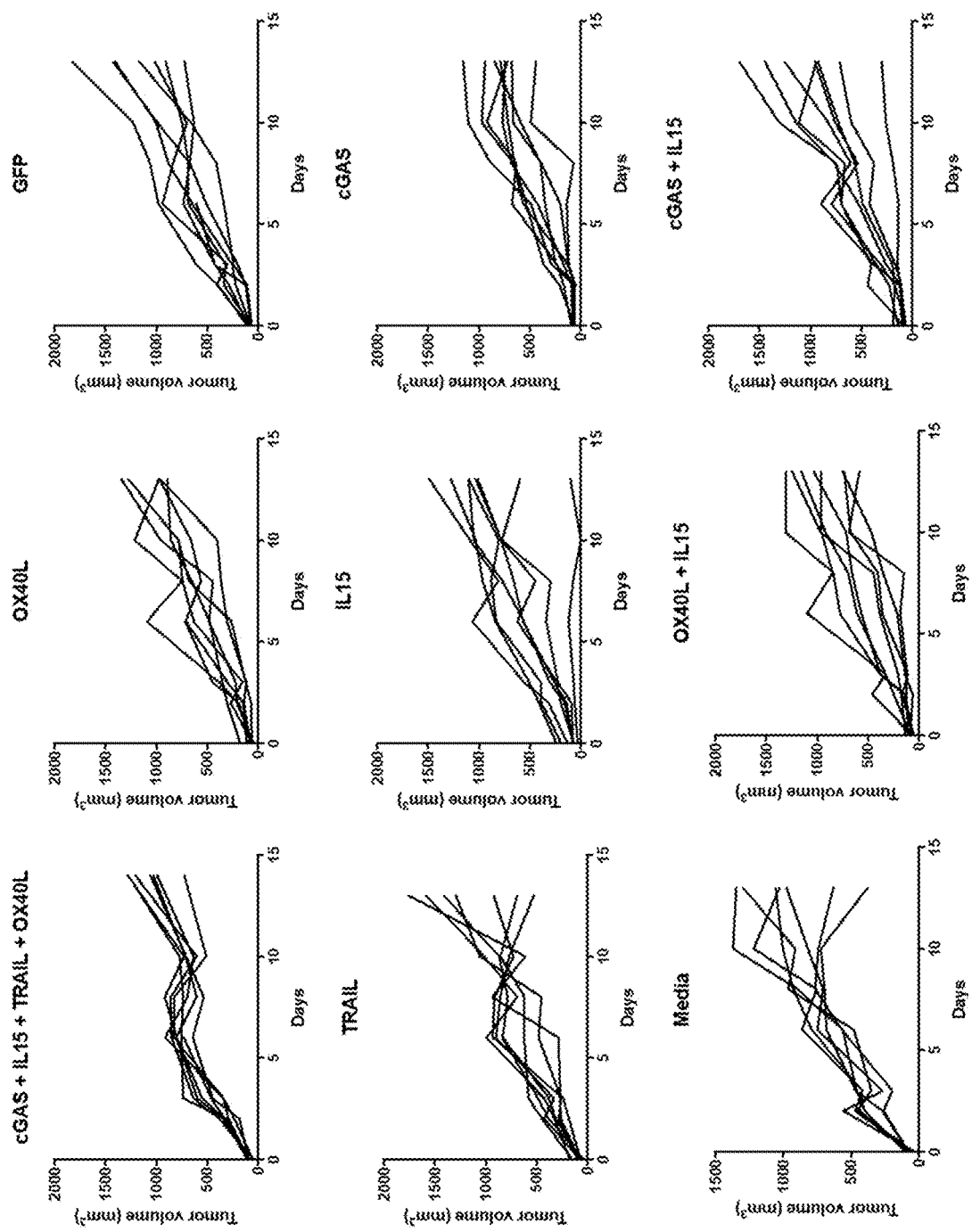
FIG. 6A includes data indicating that engineered MSCs expressing OX40L, TRAIL, IL15, cGAS, or combinations thereof do not inhibit tumor growth significantly in an orthotopic mouse model of breast cancer (4T1 triple negative breast carcinoma). Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 6A represents an individual mouse.
Figure 6B:
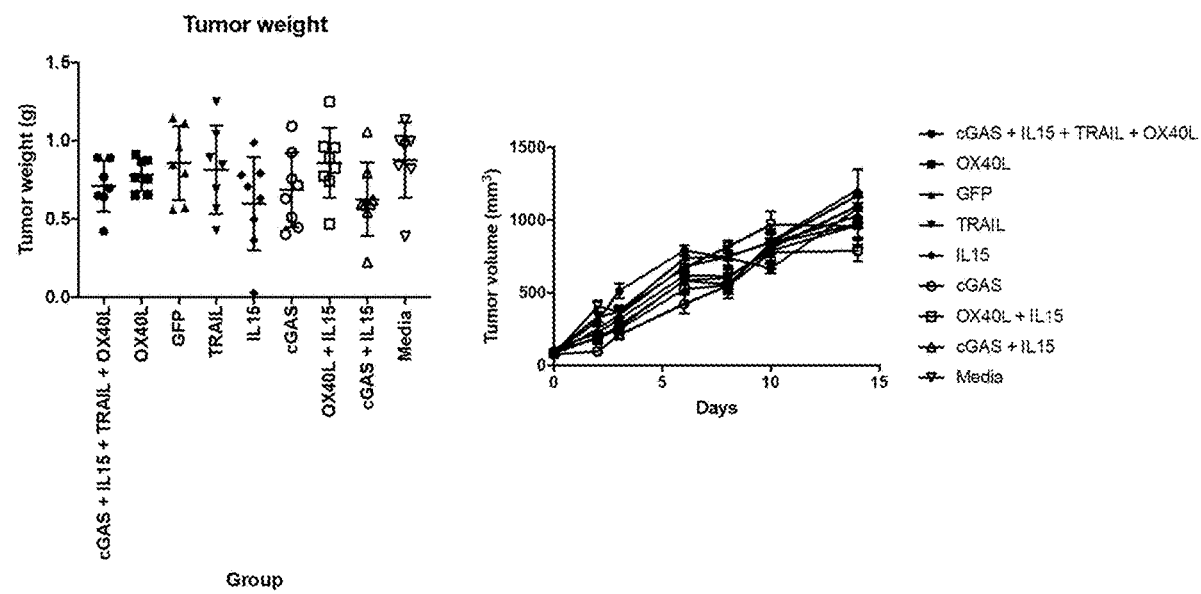
FIG. 6B includes data indicating that engineered MSCs expressing OX40L, TRAIL, IL15, cGAS, or combinations thereof do not inhibit tumor growth significantly in an orthotopic mouse model of breast cancer (4T1 triple negative breast carcinoma). Each effector was expressed by a different MSC, and the MSCs were combined (at a 1:1 ratio) for combinatorial treatment. The left graph of FIG. 6B shows the tumor weight for individual mice in each treatment, and the mean±SEM for each treatment group. The right graph of FIG. 6B shows tumor volume represented as mean±SEM for mice receiving each treatment over time.

FIGS. 6A-6B show that engineered MSCs expressing OX40L, TRAIL, IL15, cGAS, or combinations thereof do not inhibit tumor growth.

Figure 7A:
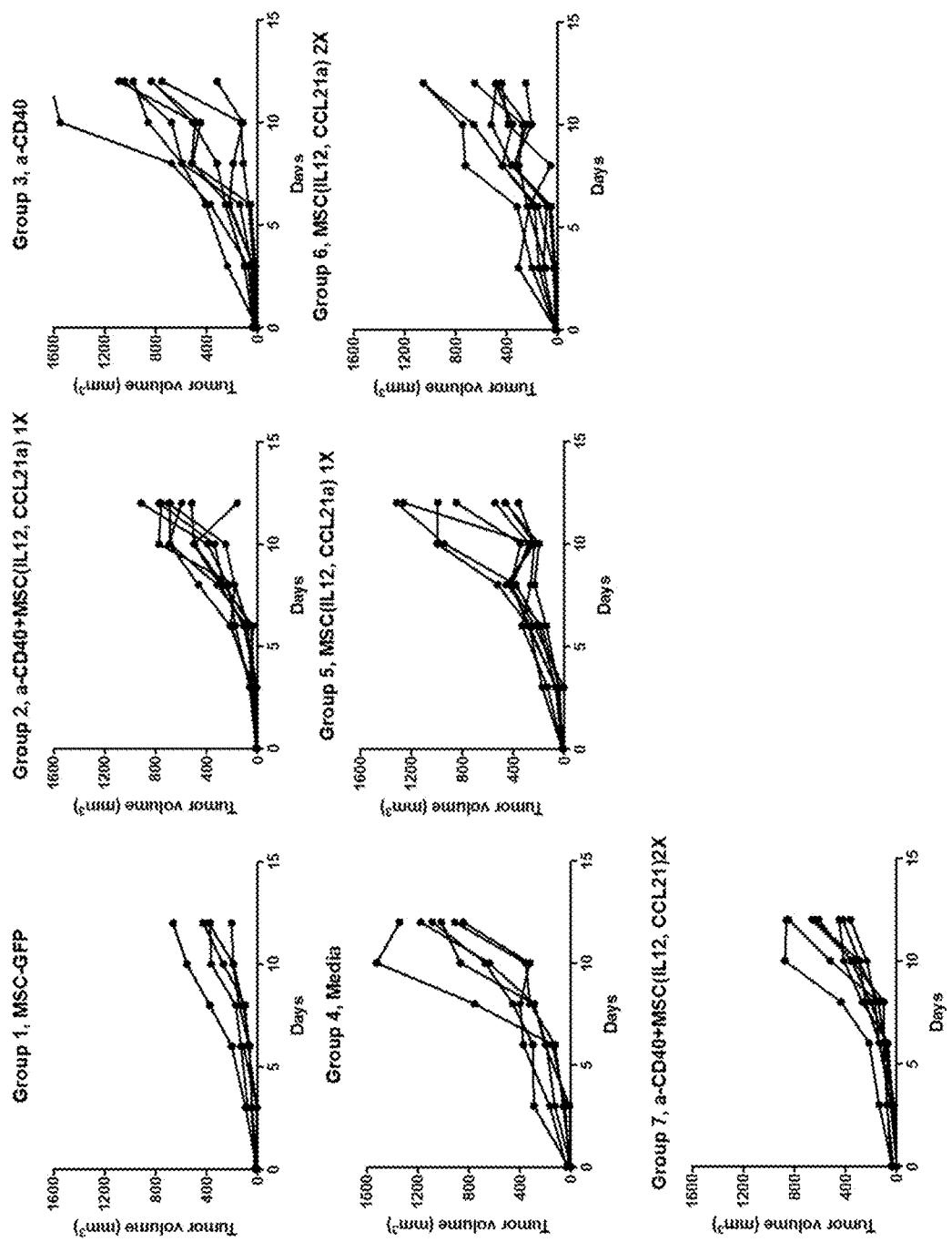
FIG. 7A includes data indicating that engineered MSCs expressing IL-12 and CCL21a inhibit tumor growth in an orthotopic mouse model of breast cancer (4T1 triple negative breast carcinoma); however the addition of anti-CD40 antibody does not reduce tumor growth. Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 7A represents an individual mouse.
Figure 7B:
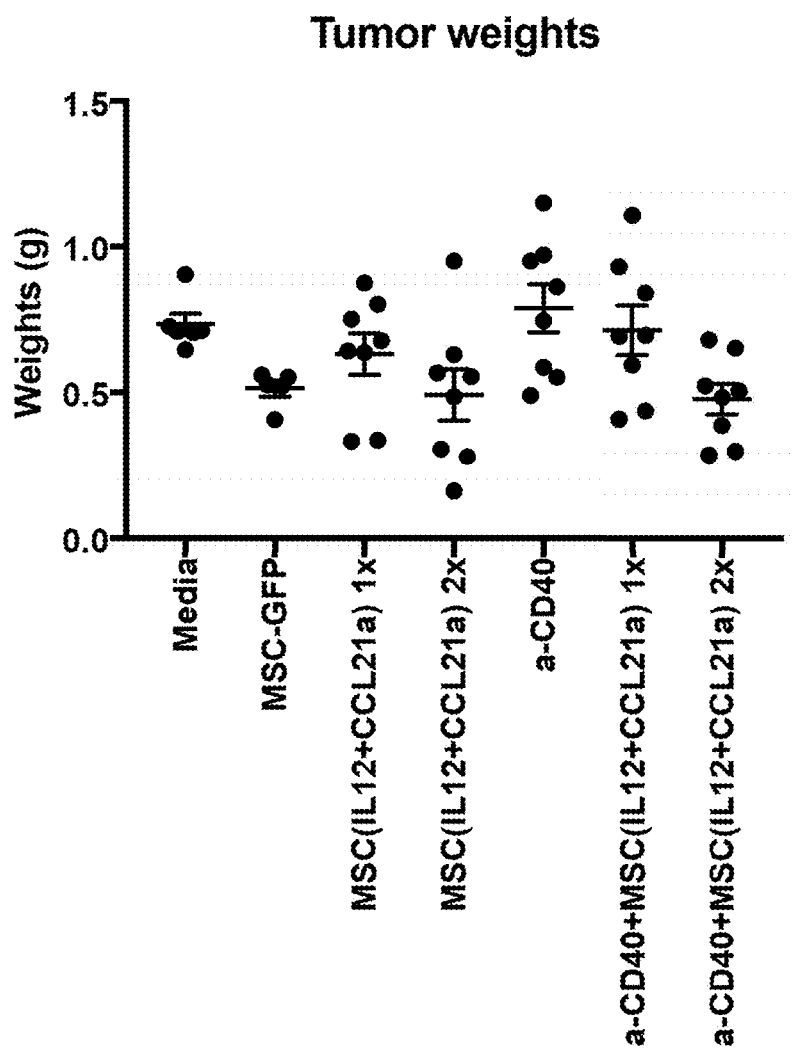
FIG. 7B includes data indicating that engineered MSCs expressing IL-12 and CCL21a inhibit tumor growth in an orthotopic mouse model of breast cancer (4T1 triple negative breast carcinoma); however the addition of anti-CD40 antibody does not reduce tumor growth. Each effector was expressed by a different MSC, and the MSCs were combined (at a 1:1 ratio) for combinatorial treatment.

FIGS. 7A-7B show that engineered MSCs expressing IL-12 and CCL21a inhibit tumor growth; however the addition of anti-CD40 antibody does not reduce tumor growth.

Figure 8A:
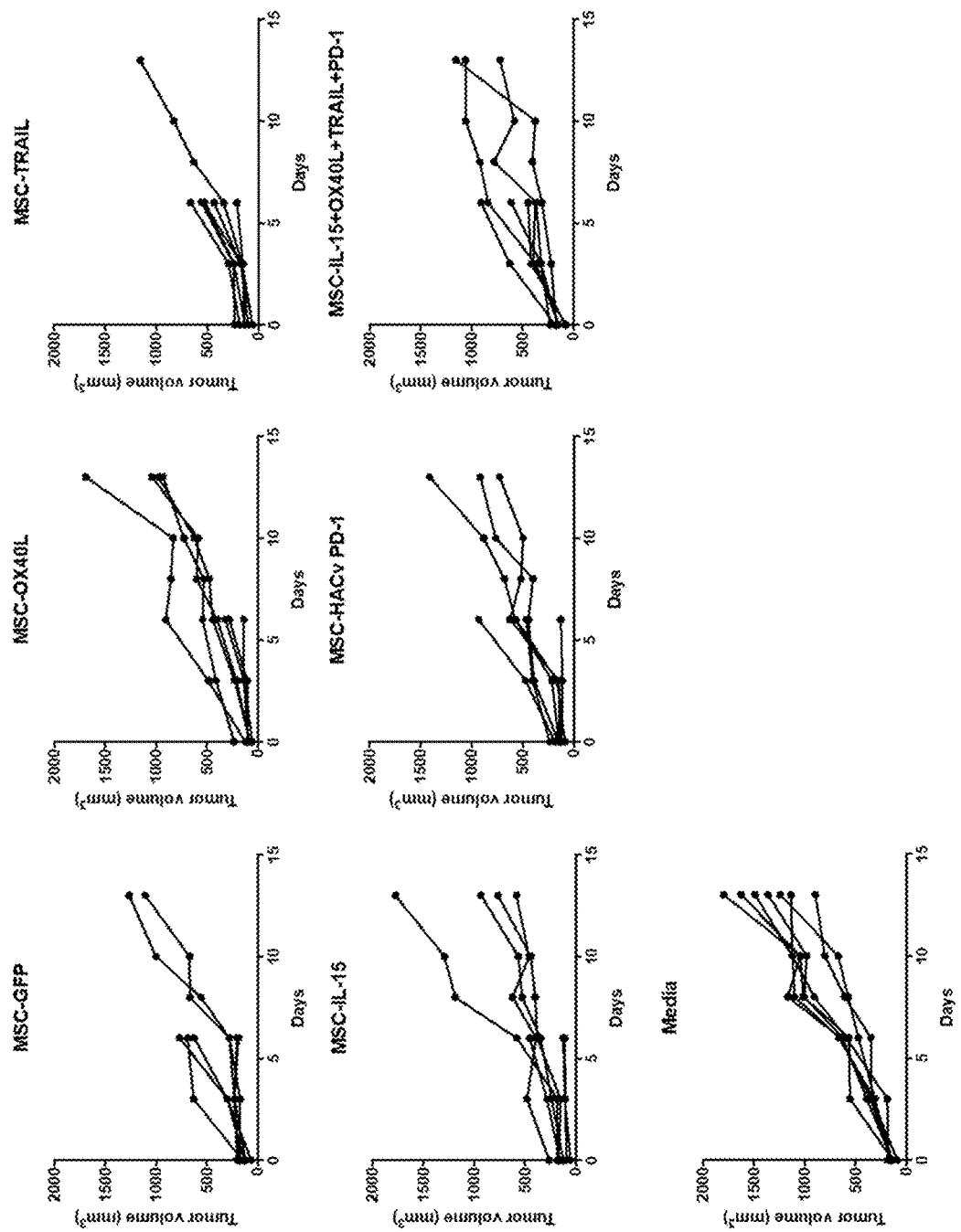
FIG. 8A includes data indicating that engineered MSCs expressing OX40L, TRAIL, IL15, HACvPD-1, or combinations thereof do not inhibit tumor growth significantly in an subcutaneous mouse model of breast cancer (4T1 triple negative breast carcinoma). Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 8A represents an individual mouse.
Figure 8B:
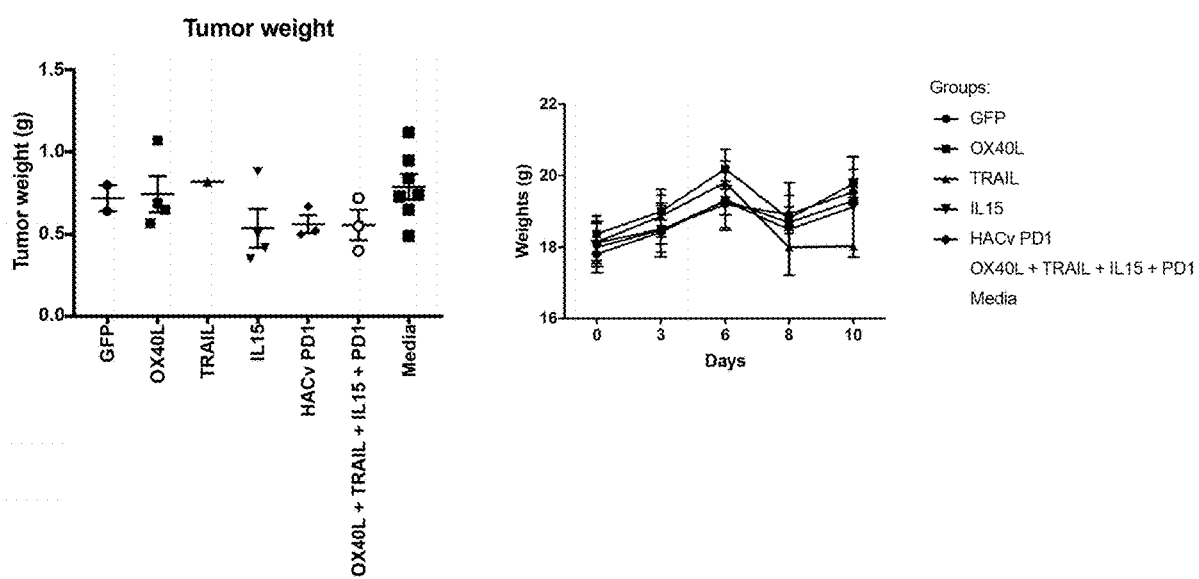
FIG. 8B includes data indicating that engineered MSCs expressing OX40L, TRAIL, IL15, HACvPD-1, or combinations thereof do not inhibit tumor growth significantly in an subcutaneous mouse model of breast cancer (4T1 triple negative breast carcinoma). Each effector was expressed by a different MSC, and the MSCs were combined (at a 1:1 ratio) for combinatorial treatment. The left graph of FIG. 8B shows the tumor weight for individual mice in each treatment, and the mean±SEM for each treatment group. The right graph of FIG. 8B shows body weight represented as mean±SEM for mice receiving each treatment over time.

FIGS. 8A-8B show that engineered MSCs expressing OX40L, TRAIL, IL15, HACvPD-1, or combinations thereof do not inhibit tumor growth significantly in a subcutaneous breast cancer model.

Figure 9A:
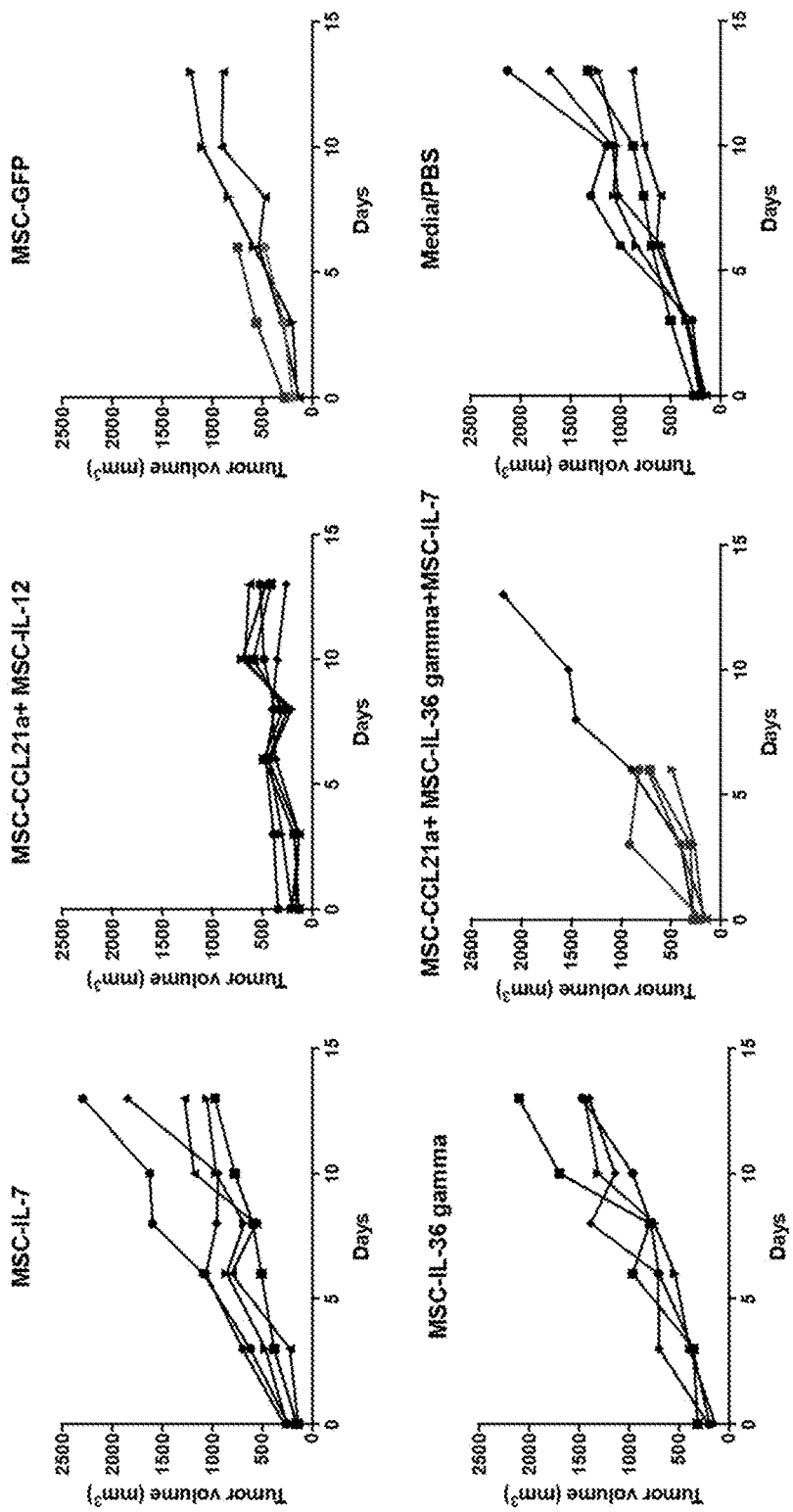
FIG. 9A includes data indicating that engineered MSCs expressing IL-12 and CCL21a inhibit tumor growth in an orthotopic mouse model of breast cancer (4T1 triple negative breast carcinoma); however the combination of MSCs expressing CCL21a, IL-36 gamma and IL-7 does not reduce tumor growth. Some of the effector combinations tested, however, may cause toxicity. Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 9A represents an individual mouse.
Figure 9B:
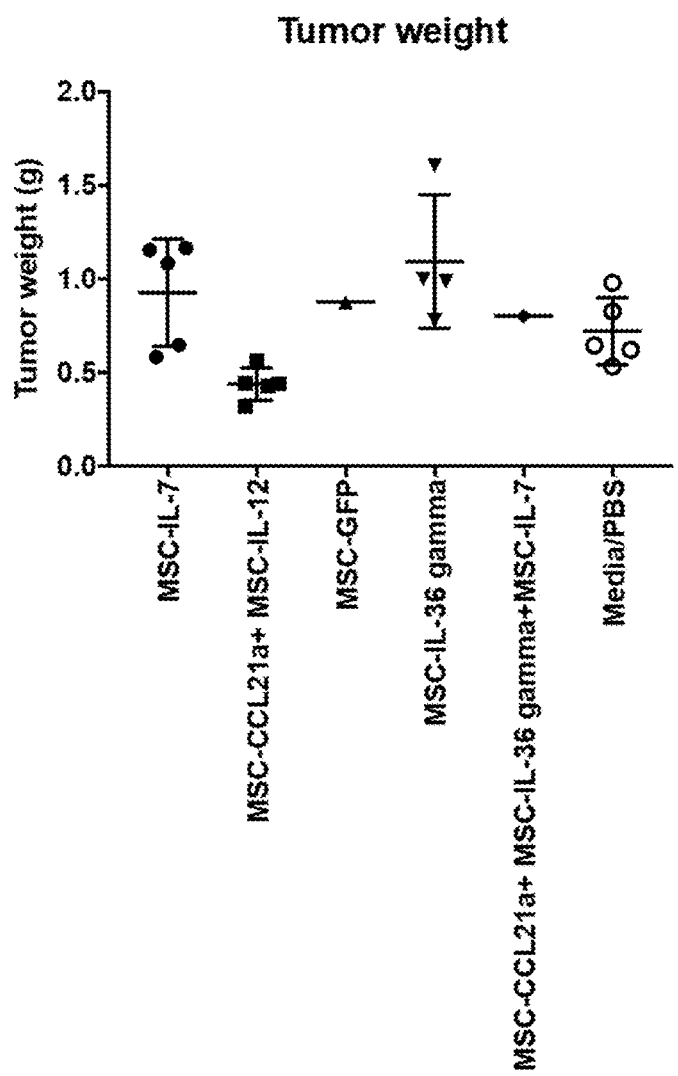
FIG. 9B includes data indicating that engineered MSCs expressing IL-12 and CCL21a inhibit tumor growth in an orthotopic mouse model of breast cancer (4T1 triple negative breast carcinoma); however the combination of MSCs expressing CCL21a, IL-36 gamma and IL-7 does not reduce tumor growth. Some of the effector combinations tested, however, may cause toxicity. Each effector was expressed by a different MSC, and the MSCs were combined (at a 1:1 ratio) for combinatorial treatment.

FIGS. 9A-9B show that engineered MSCs expressing IL-12 and CCL21a inhibit tumor growth; however the combination of MSCs expressing CCL21a, IL-36 gamma and IL-7 does not reduce tumor growth. Some of the effector combinations tested, however, may cause toxicity.

Dose Escalation

Figure 10A:
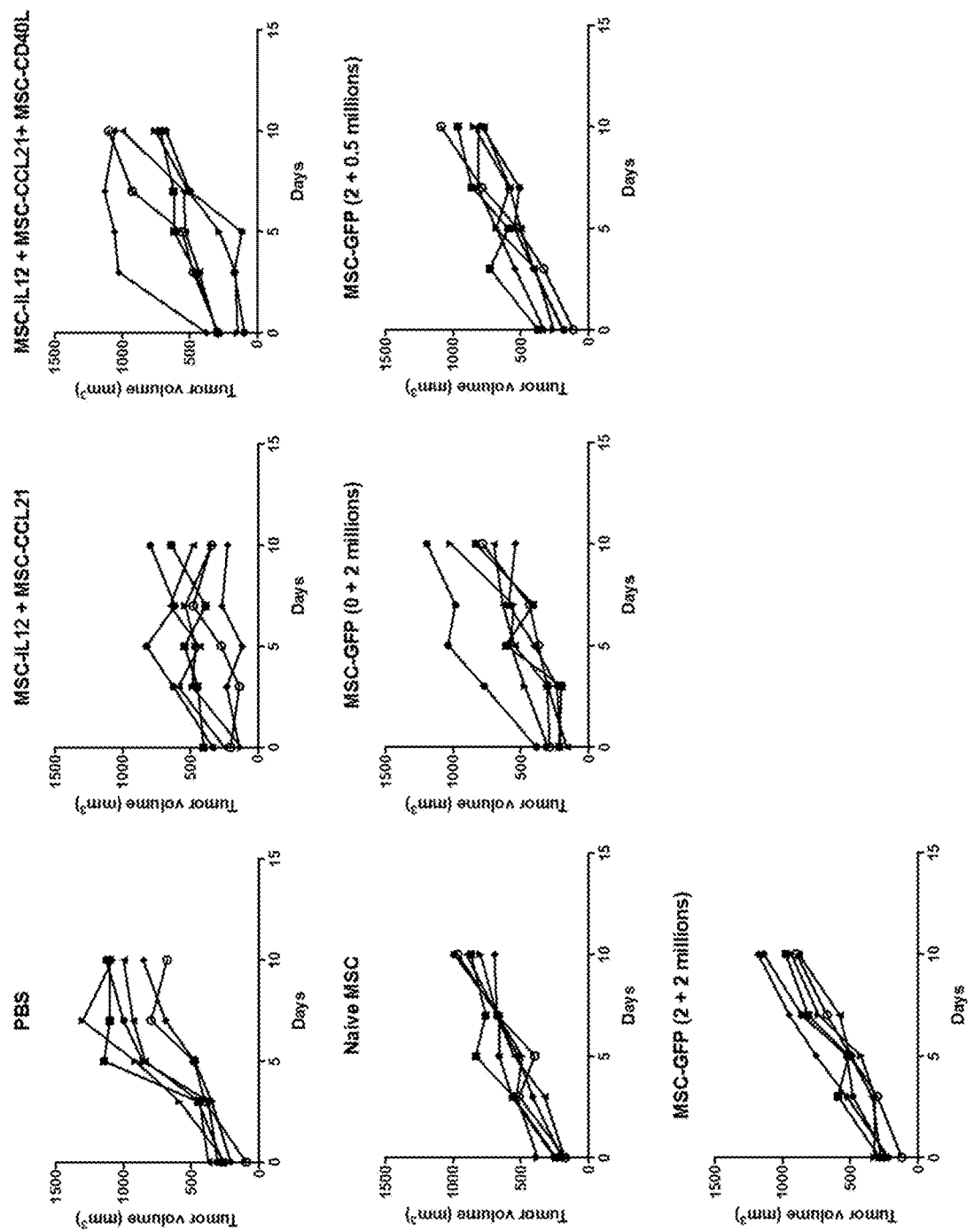
FIG. 10A includes data from a GFP dose escalation study for toxicity and screening.
Figure 10B:
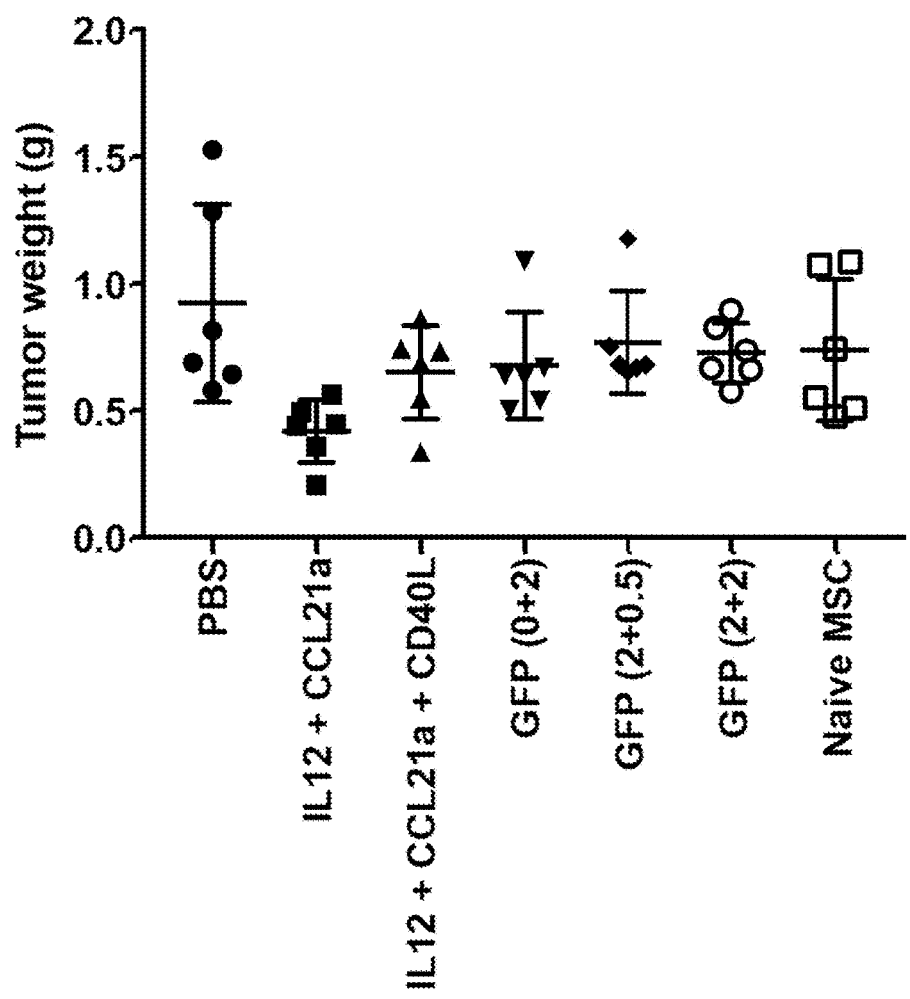
FIG. 10B includes data from a GFP dose escalation study for toxicity and screening. Each effector was expressed by a different MSC, and the MSCs were combined (at a 1:1 ratio) for combinatorial treatment.

A dose escalation study was performed. This experiment determined that engineered MSC cell expression GFP does not elicit toxicity (FIGS. 10A-10B).

Effect on Large Tumors

Figure 12:
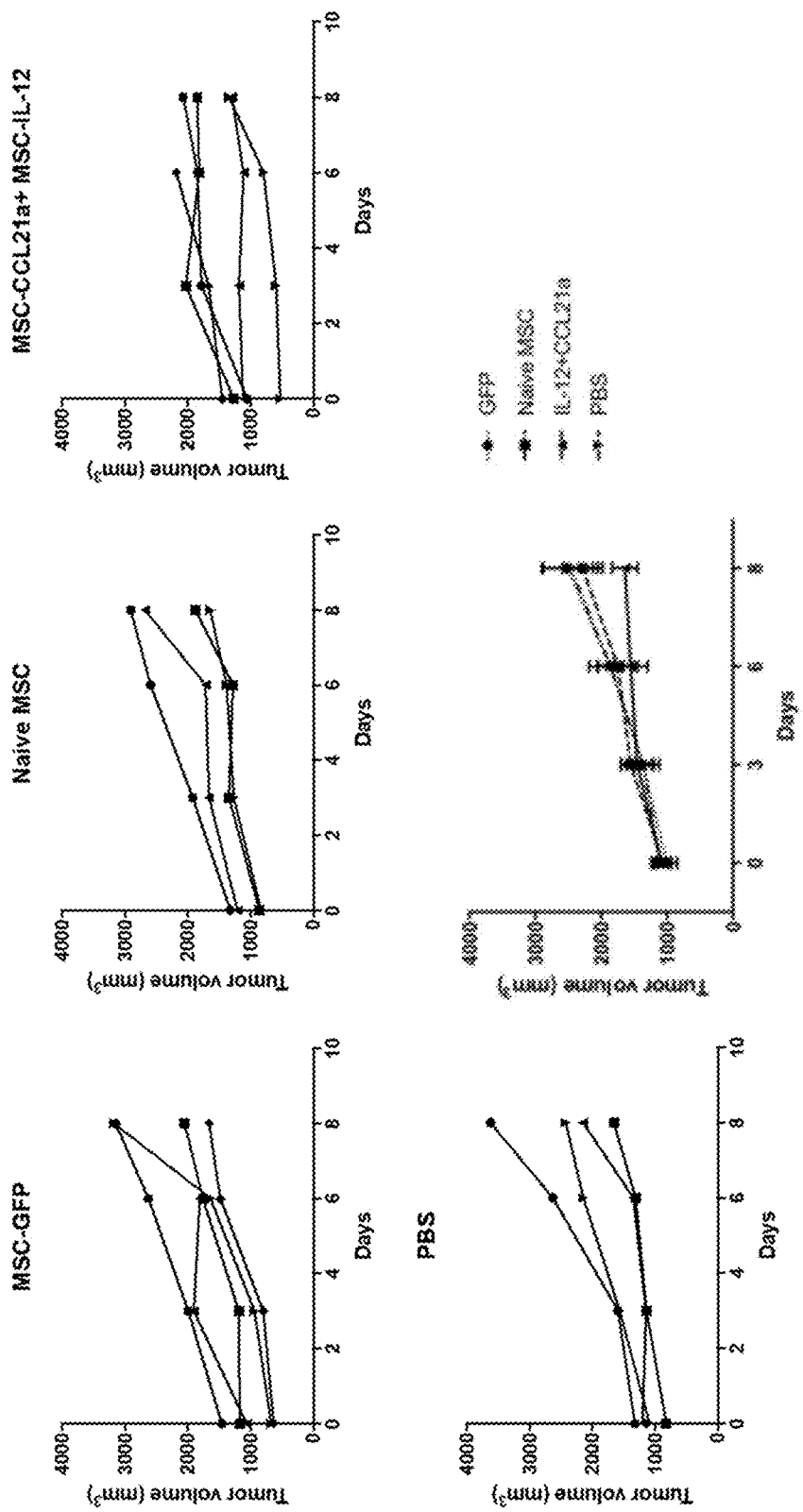
FIG. 12 includes data showing that IL-12 and CCL21a can reduce tumor expansion. Each line of FIG. 12 represents an individual mouse.

This experiment tested whether engineered mouse MSCs expressing IL12 and CCL21a can reduce tumor burden from larger tumor (>800 mm³). Larger tumor are more difficult to treat than small tumor, and this experiment demonstrates this effector combination can reduce tumor expansion (FIGS. 12A-12B).

Checkpoint Inhibitors

Figure 13A:
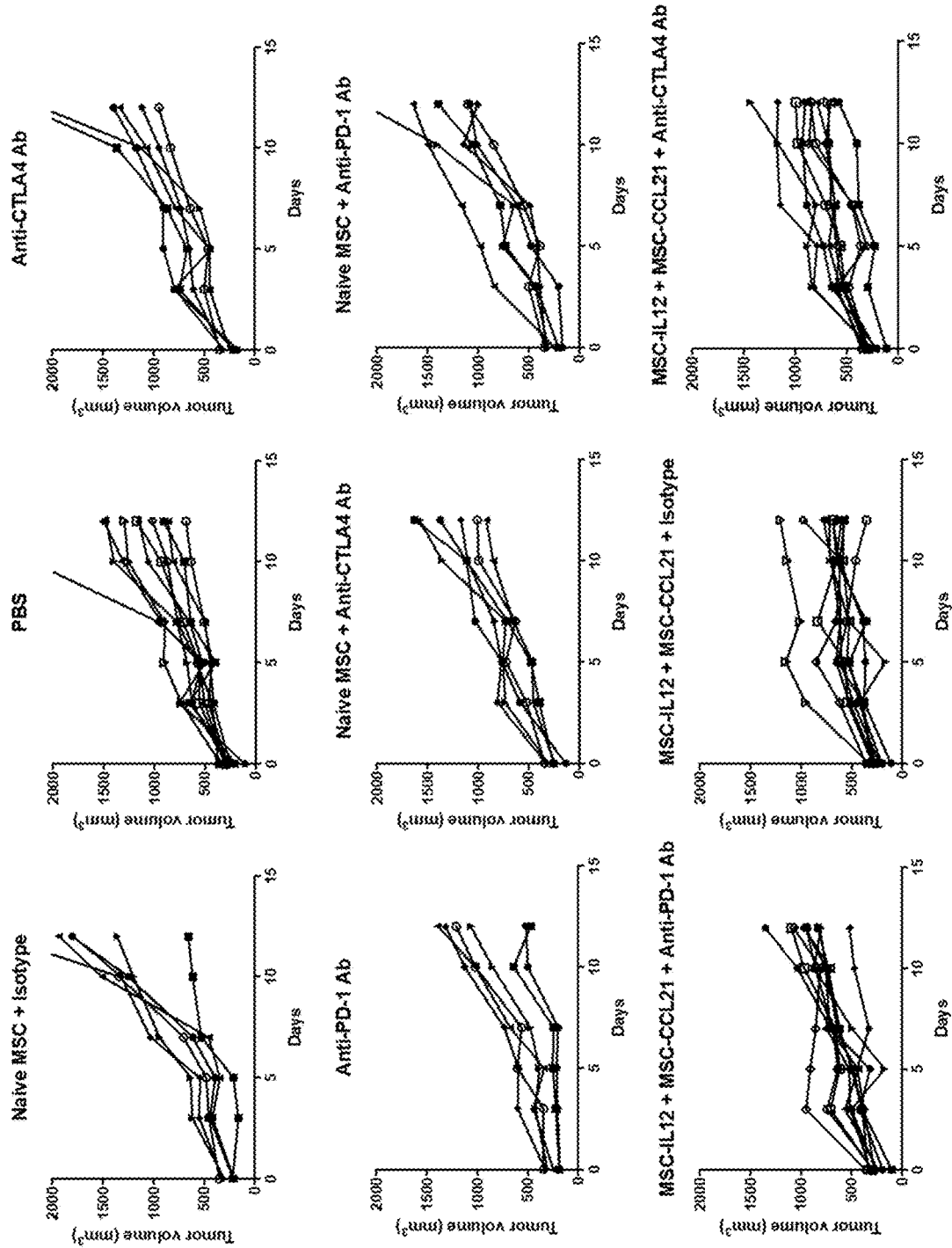
FIG. 13A includes data indicating that engineered MSCs expressing IL-12 and CCL21 are sufficient to inhibit tumor growth in an orthotopic mouse model of breast cancer (4T1 triple negative breast carcinoma), and the addition of a checkpoint inhibitor (anti-PD-1 antibody or anti-CTLA-4 antibody) did not increase efficacy. Each effector was expressed by a different MSC, and the MSCs were combined (at a 1:1 ratio) for combinatorial treatment, and the checkpoint inhibitor was injected separately. Each chart shows the effect of engineered MSCs expressing the indicated immunotherapies alone or in combination on the growth of 4T1 breast tumors in mice (n=6-8). Each line of FIG. 13A represents an individual mouse.
Figure 13B:
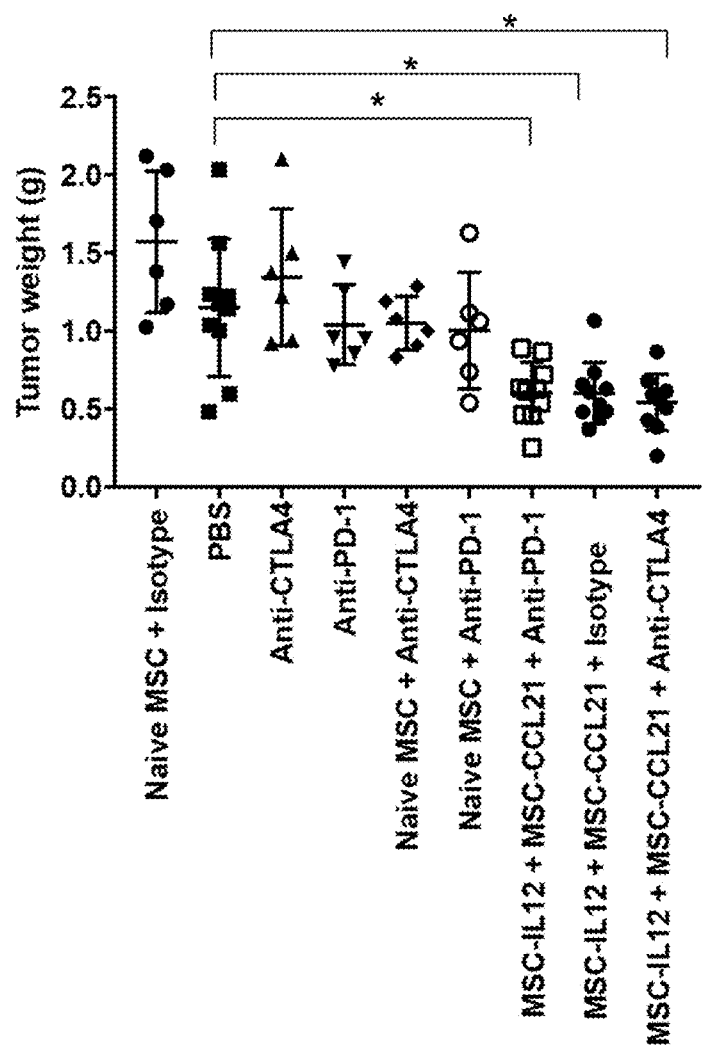
FIG. 13B includes data indicating that engineered MSCs expressing IL-12 and CCL21 are sufficient to inhibit tumor growth in an orthotopic mouse model of breast cancer (4T1 triple negative breast carcinoma), and the addition of a checkpoint inhibitor (anti-PD-1 antibody or anti-CTLA-4 antibody) did not increase efficacy. Each effector was expressed by a different MSC, and the MSCs were combined (at a 1:1 ratio) for combinatorial treatment, and the checkpoint inhibitor was injected separately.

FIG. 13A shows that engineered MSCs expressing IL-12 and CCL21 are sufficient to inhibit tumor growth, although the addition of a checkpoint inhibitor (anti-PD-1 antibody or anti-CTLA-4 antibody) by injection did not increase efficacy in a subcutaneous tumor model.

Example 5: CT26 Colorectal Carcinoma

In the following experiments, MSCs were engineered to express one of the following effector molecules, then administered, alone or in combinations, to a colorectal carcinoma mouse model: IFNβ, IL12, IL15, IL36γ, IL7, CCL21a, HACv-PD1, or 41BB. In some examples, a checkpoint inhibitor (anti-CD40 or anti-CTLA-4 antibody) was injected in combination with administration with the engineered MSCs.

Figure 14:
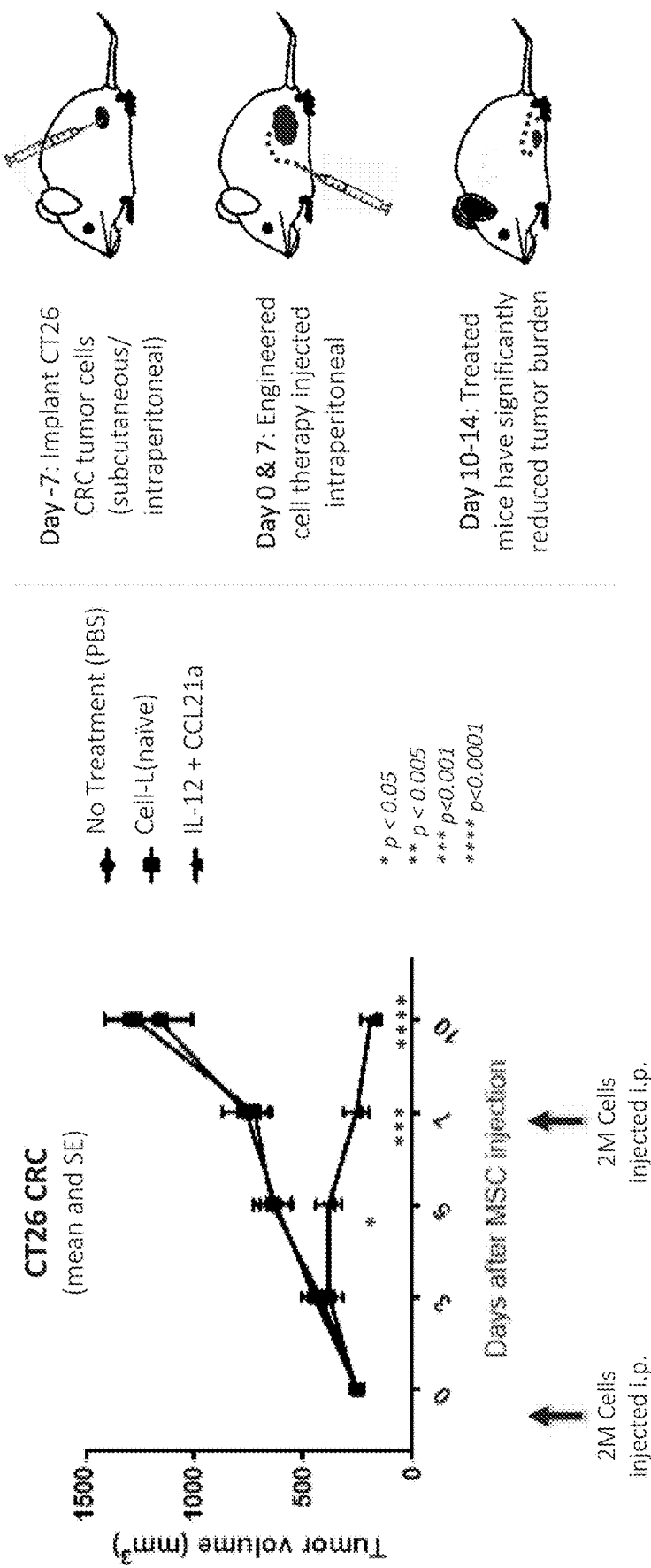
FIG. 14 shows data indicating that engineered MSCs expressing IL-12 and CCL21a induced significant tumor growth delay in a mouse model of colorectal cancer. The graph on the left shows the effects of engineered MSCs on CT26 colorectal tumor growth in mice (n=8). Each line in the chart represents tumor volume in mice receiving intraperitoneal injection of either control MSC growth media or engineered MSCs on day 0 and day 7. Mice received intraperitoneal injection of engineered MSCs expressing IL-12 and engineered MSCs expressing CCL21a. Tumor volume was determined by caliper measurements every other day. Data represent mean±SEM. *p<0.05, **p<0.005 as compared to control media group. The schematic on the right shows a timeline of treatment and the effect of engineered MSCs expressed combinatorial genes IL-12 and CCL21a on tumor burden in treated mice.

FIG. 14 shows that engineered MSCs expressing IL-12 and CCL21a induced significant tumor growth delay.

Figure 15:
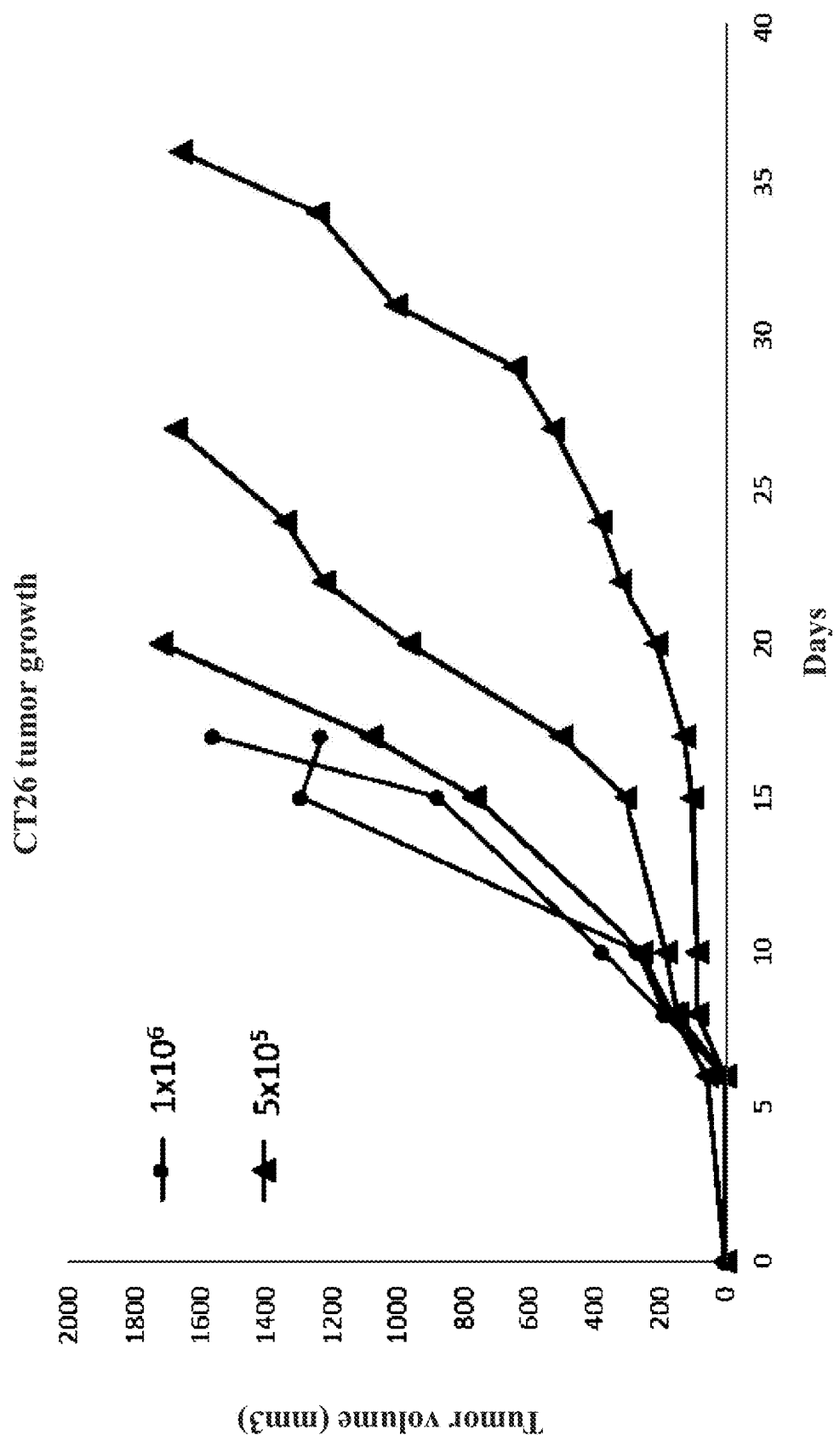
FIG. 15 is a graph showing tumor growth kinetics in the CT26 mouse model to determine optimal time for dosing the engineered MSC cells.

FIG. 15 shows tumor growth kinetics in the CT26 mouse model to determine optimal time for dosing the engineered MSC cells.

In Vivo Efficacy

Figure 16A:
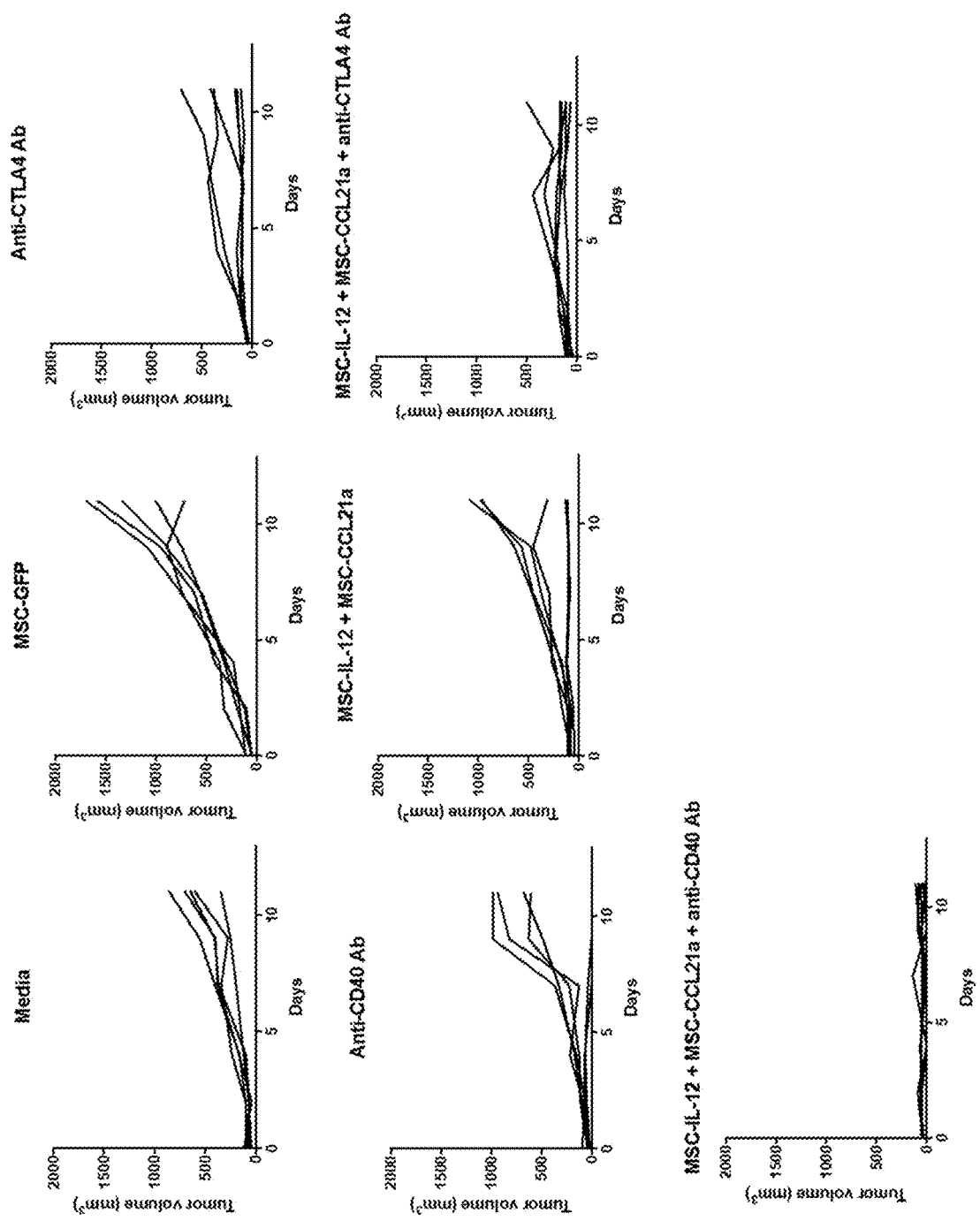
FIG. 16A includes data indicating the effects of engineered MSCs expressing IL-12 and CCL21a combined with anti-CD40 or anti-CTLA4 antibodies on average tumor growth in a syngeneic mouse model of colon cancer. Mice bearing CT26 colon tumors were treated with one of seven treatments (n=5-6 per treatment group). MSC-IL-12+MSC-CCL21a indicates treatment with engineered cells expressing IL-12 and with engineered cells expressing CCL21a (at a 1:1 ratio) for combinatorial treatment. Each line of FIG. 16A represents an individual mouse.
Figure 16B:
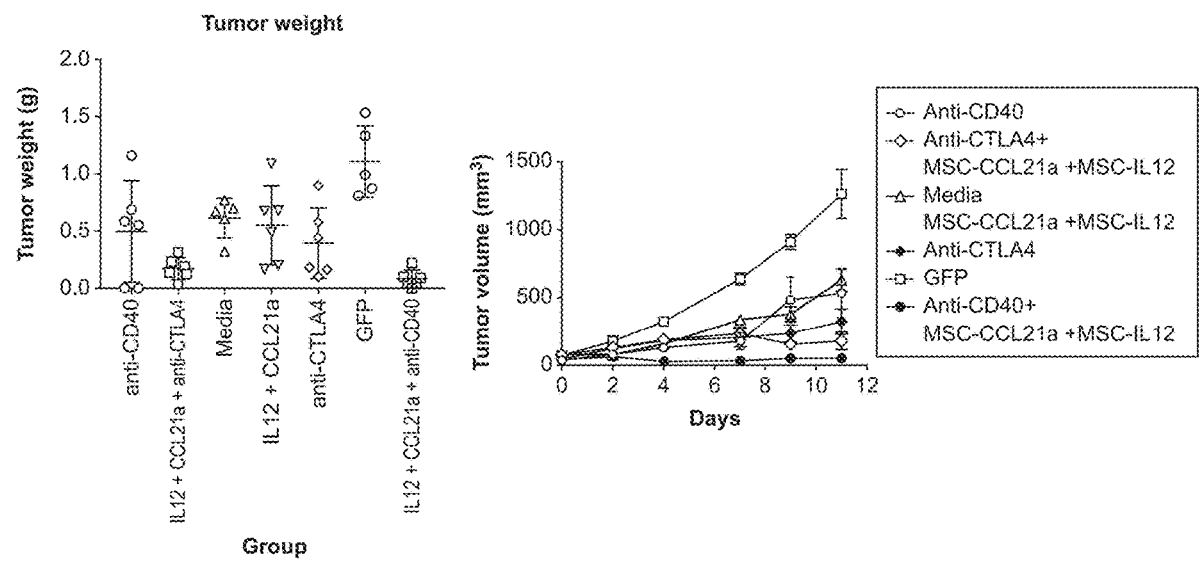
FIG. 16B includes data indicating the effects of engineered MSCs expressing IL-12 and CCL21a combined with anti-CD40 or anti-CTLA4 antibodies on average tumor growth in a syngeneic mouse model of colon cancer. Mice bearing CT26 colon tumors were treated with one of seven treatments (n=5-6 per treatment group). MSC-IL-12+MSC-CCL21a indicates treatment with engineered cells expressing IL-12 and with engineered cells expressing CCL21a (at a 1:1 ratio) for combinatorial treatment. The left graph of FIG. 16B shows the tumor weight for individual mice in each treatment, and the mean±SEM for each treatment group. The right graph of FIG. 16B shows the tumor volume represented as mean±SEM for mice receiving each treatment over time.

The following experiments demonstrate the in vivo efficacy of MSCs expressing immunotherapy effectors (payloads) in the subcutaneous mouse model of colon (colorectal) cancer. CT26-Neo-Fluc mouse colon cancer cells (Imanis Life Sciences, $5 \times 10^5$) were injected subcutaneously into the flanks of female BALB/cJ mice (The Jackson Laboratory). Seven days after tumor implantation, mice were then randomized into the following treatment groups: control MSC growth media, engineered MSCs (MSC-12+CCL21a), anti-CD40 antibody, anti-CTLA4 antibody (Bio X cell), MSC-12+CCL21a in combination with anti-CD40 antibody or MSC-12+CCL21a in combination with anti-CTLA4 antibody. Engineered MSCs ($2 \times 10^6$ cells) were injected intraperitoneally (ip) once a week for two weeks (Day 0 and 7). Anti-CD40 antibodies were injected ip (100 μg) on Days 0 and 3. Anti-CTLA4 antibodies were injected ip (100 μg) on Days 0, 3 and 7. Tumor growth was monitored by caliper measurements every other day, and mouse weights were recorded twice weekly. Mice were euthanized 11 days after first MSC treatment and tumors were collected and weighed. The tumor weight of individual mice in each treatment group was measured and the results are shown in the bottom left of FIG. 16B (left graph). The average tumor volume of each treatment group was monitored over time (FIG. 16B, right graph). Treatment Groups 2 (IL-12+CCL21a+ anti-CTLA4 antibody), 4 (IL-12+CCL21a) and 7 (IL-12+CCL21a+ anti-CD40 antibody) inhibited the average growth of CT26 colon tumors compared to GFP-treated mice (FIG. 16B, right graph). Similar results were observed when the tumor volume of individual mice in each treatment group was measured over time (FIG. 16A). Therefore, combinatorial treatment with MSCs expressing immunotherapies inhibited the growth of colon cancer cells in vivo.

Figure 18A:
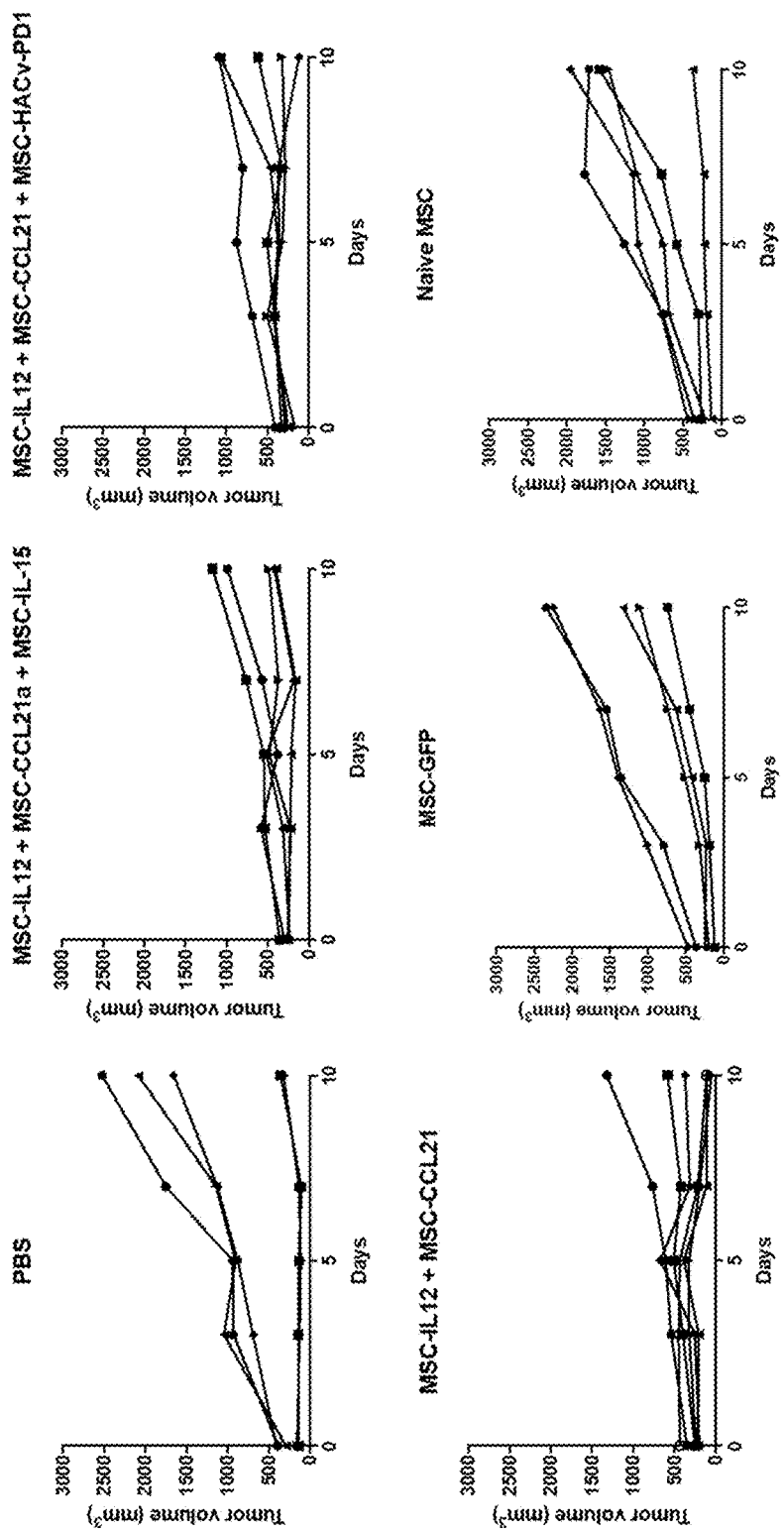
FIG. 18A includes data indicating that engineered MSCs expressing IL-12, CCL21a, and either IL15 or HACvPD-1 inhibit tumor growth significantly in a mouse model of colorectal cancer. Each effector was expressed by a different MSC, and the MSCs were combined (at a 1:1 ratio) for combinatorial treatment. Each chart shows the effect of engineered MSCs expressing the indicated immunotherapies alone or in combination on the growth of CT26 colorectal tumors in mice (n=6-8). Each line of FIG. 18A represents an individual mouse.
Figure 18B:
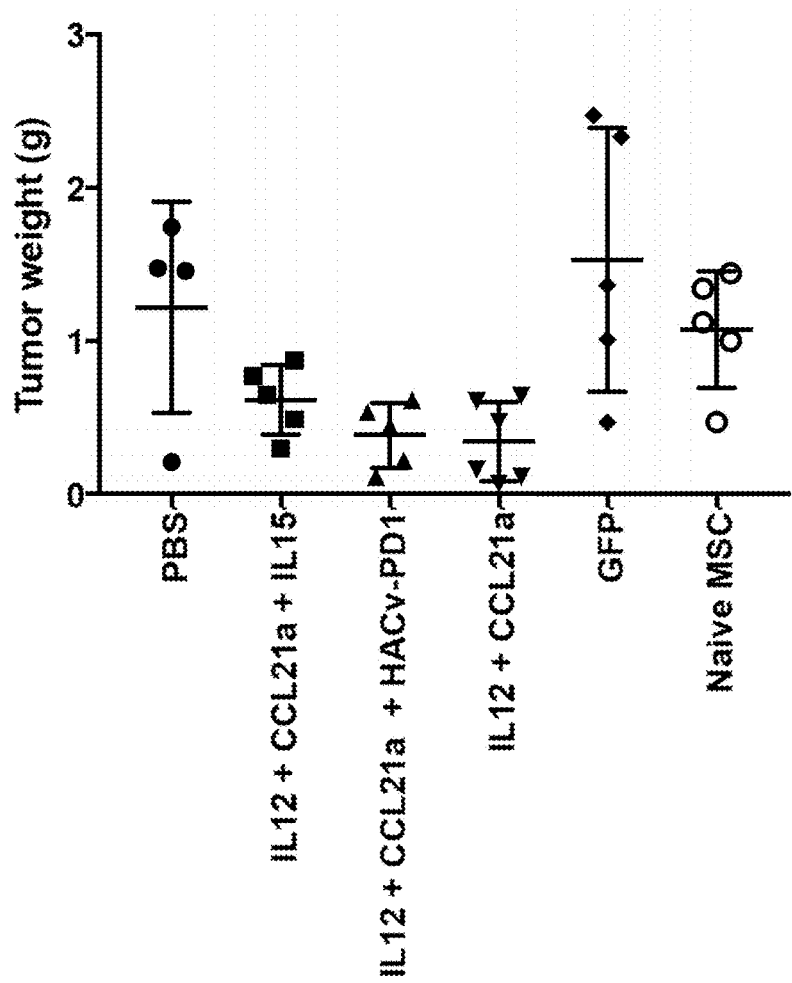
FIG. 18B includes data indicating that engineered MSCs expressing IL-12, CCL21a, and either IL15 or HACvPD-1 inhibit tumor growth significantly in a mouse model of colorectal cancer. Each effector was expressed by a different MSC, and the MSCs were combined (at a 1:1 ratio) for combinatorial treatment.
Figure 18C:
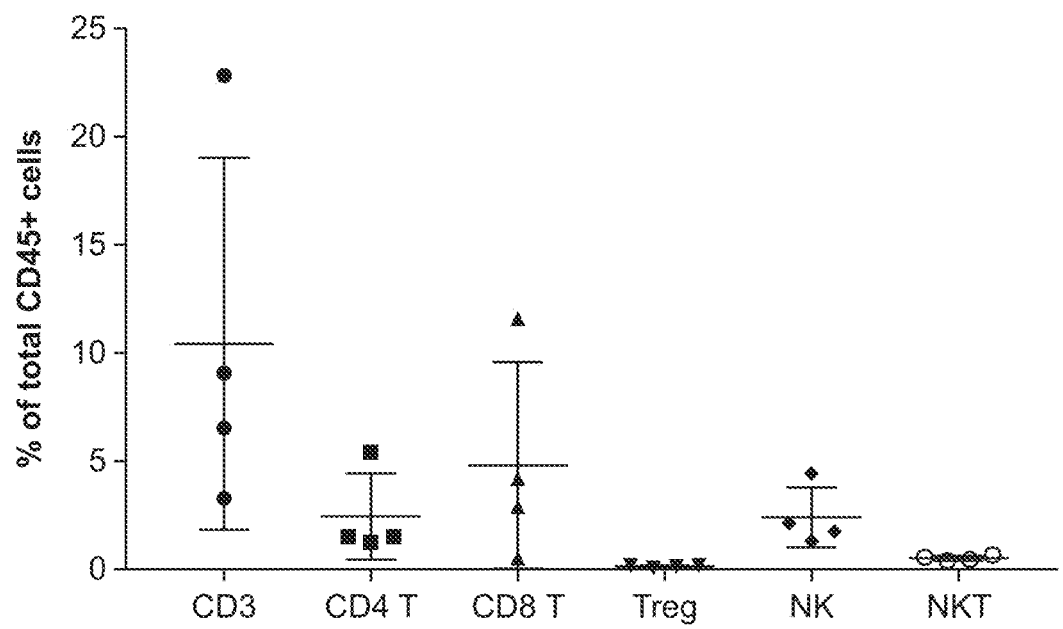
FIG. 18C includes data indicating that engineered MSCs expressing IL-12, CCL21a, and either IL15 or HACvPD-1 inhibit tumor growth significantly in a mouse model of colorectal cancer. Each effector was expressed by a different MSC, and the MSCs were combined (at a 1:1 ratio) for combinatorial treatment.
Figure 18C:
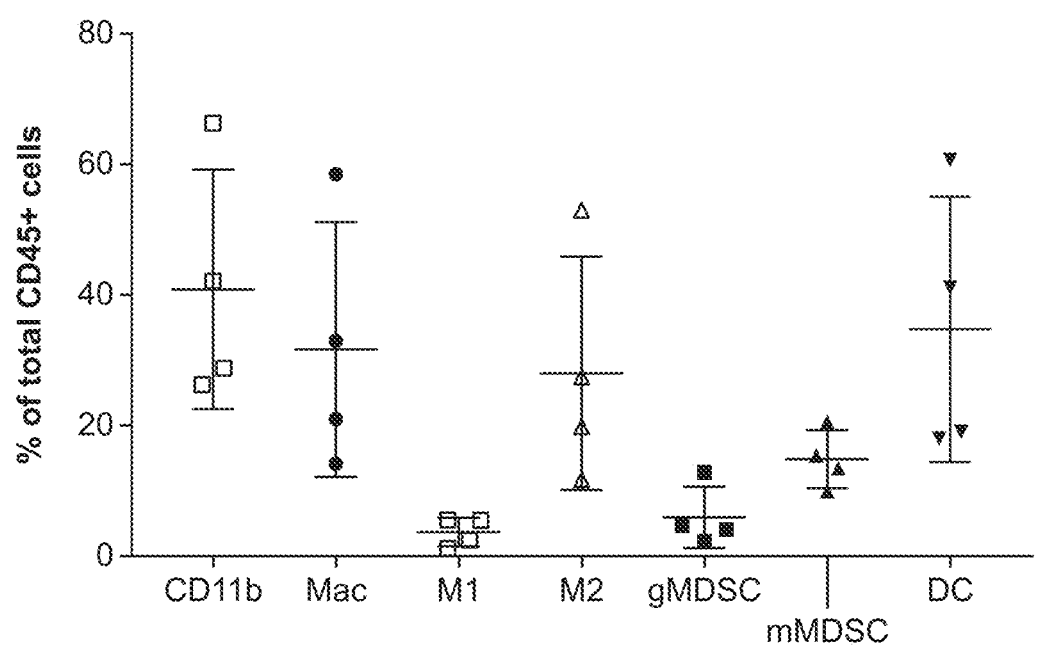
Figure 18D:
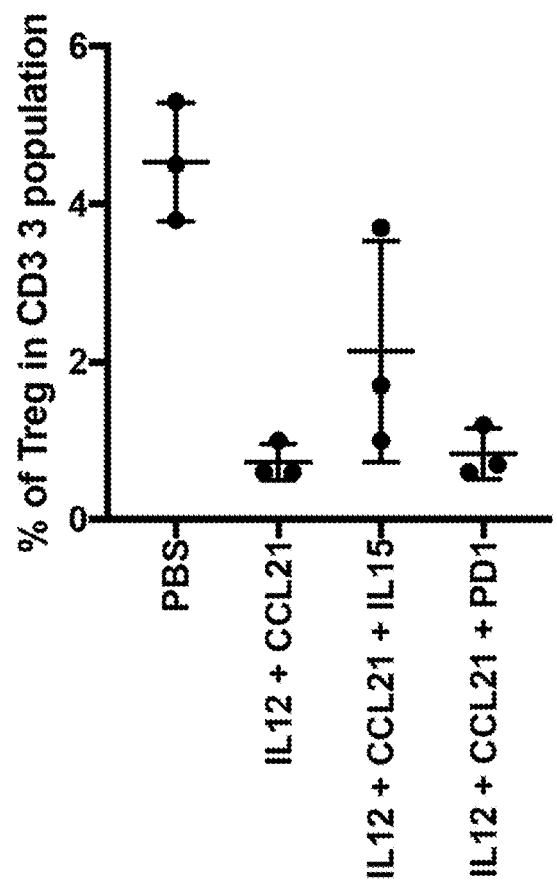
FIG. 18D includes data indicating that engineered MSCs expressing IL-12, CCL21a, and either IL15 or HACvPD-1 inhibit tumor growth significantly in a mouse model of colorectal cancer. Each effector was expressed by a different MSC, and the MSCs were combined (at a 1:1 ratio) for combinatorial treatment.
Figure 18E:
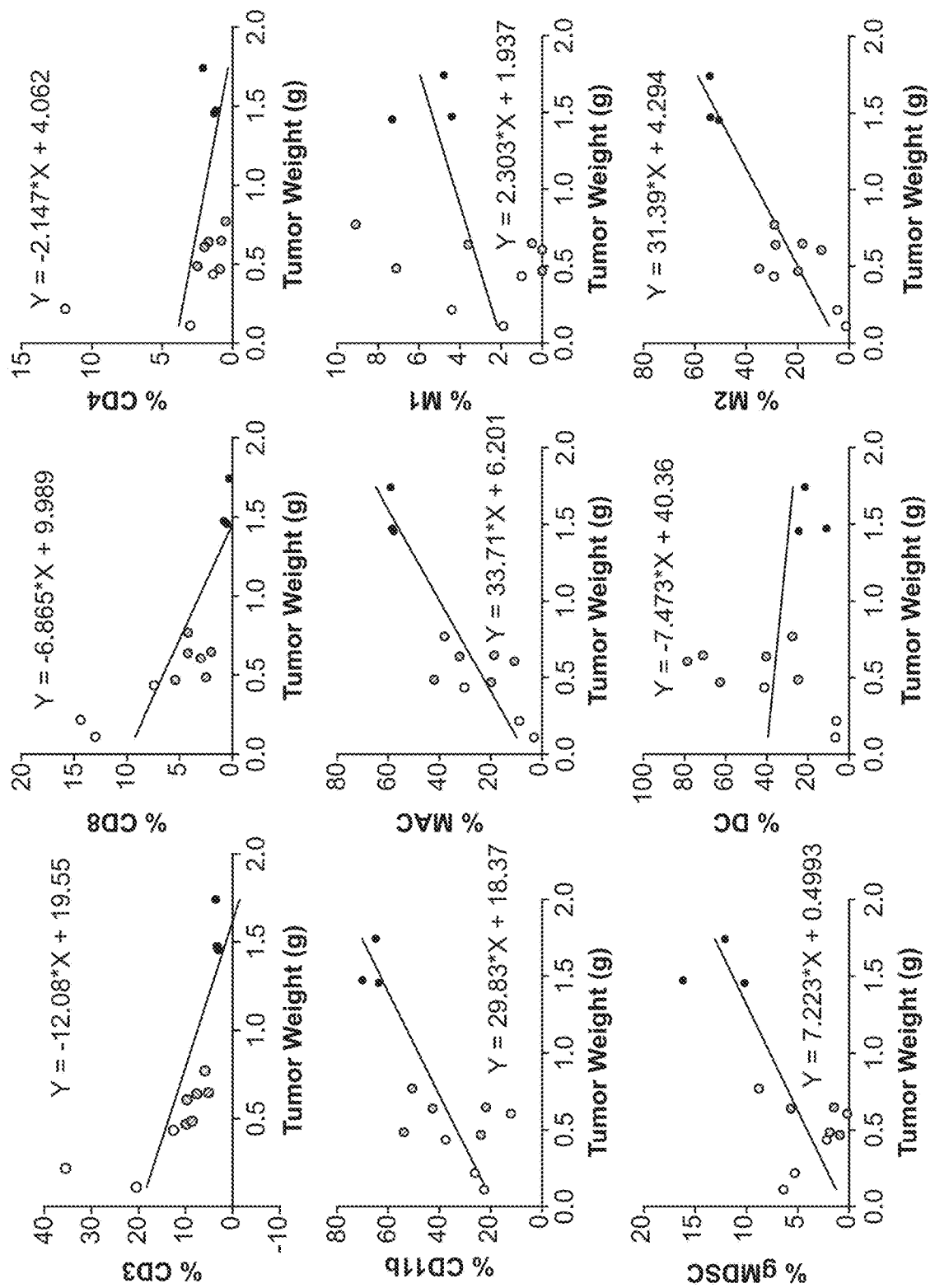
FIG. 18E includes data indicating that engineered MSCs expressing IL-12, CCL21a, and either IL15 or HACvPD-1 inhibit tumor growth significantly in a mouse model of colorectal cancer. Each effector was expressed by a different MSC, and the MSCs were combined (at a 1:1 ratio) for combinatorial treatment.
Figure 19:
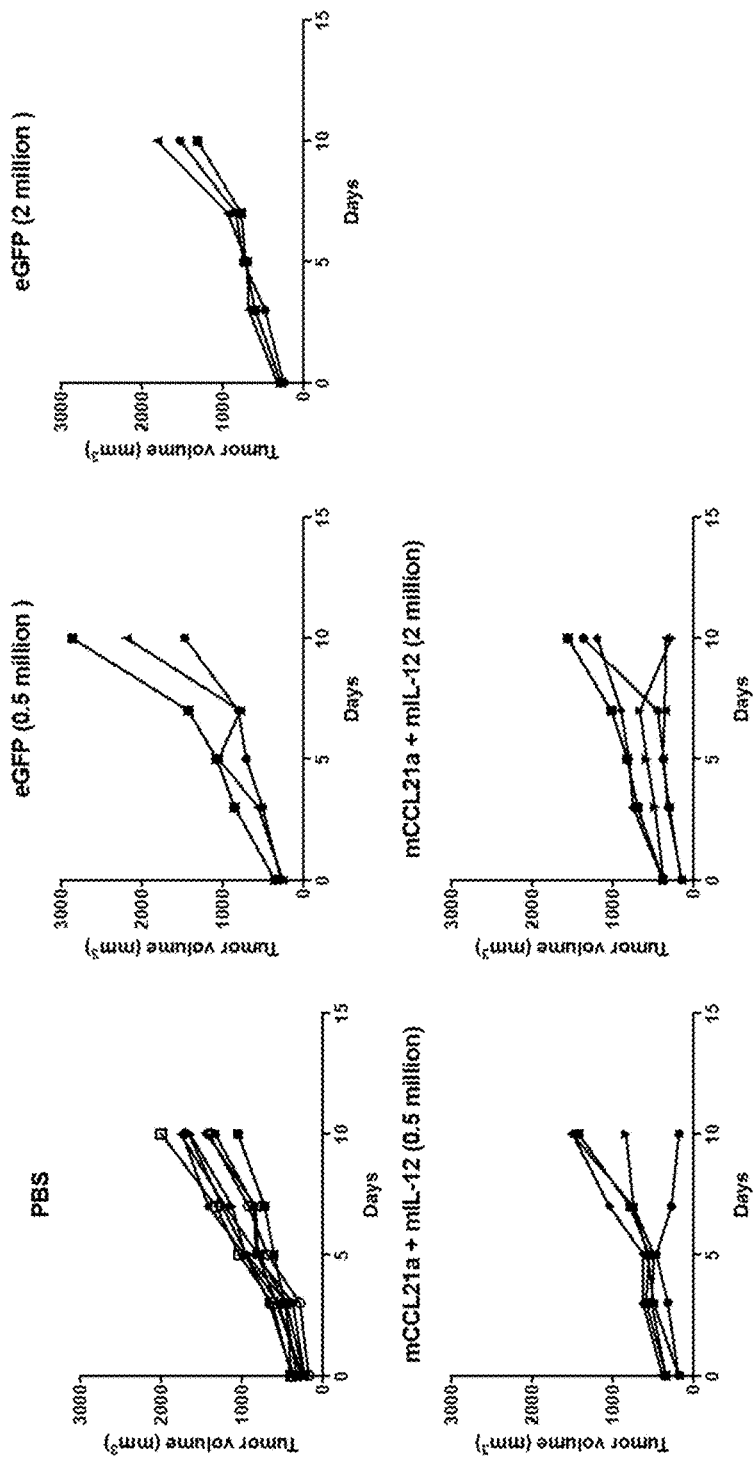
FIG. 19 shows the tumor volume for individual mice in each treatment. Efficacy was determined by tumor volume from caliper measurement every other day.

FIG. 18A shows that engineered MSCs expressing IL-12, CCL21a, and either IL15 or HACvPD-1 inhibit tumor growth significantly in a mouse model of colorectal cancer. FIG. 18B shows the tumor weight for individual mice in each treatment. FIG. 18C is a representative graph of the infiltrating immune population within the tumor microenvironment. FIG. 18D shows the percentage of regulatory T cells (Treg) in the total CD3 population. There was a significant decrease in the numbers of Tregs in the tumor microenvironment treated with engineered MSC-IL2 and CCL21a. FIG. 18E correlates the percentage of immune infiltration with tumor weight. Samples with increase in lymphocytes (CD3+) were found to correlate with low tumor weight, while samples with high myeloid (CD11b+) infiltration were correlated with higher tumor burden.

Long-Term Survival

Figure 17A:
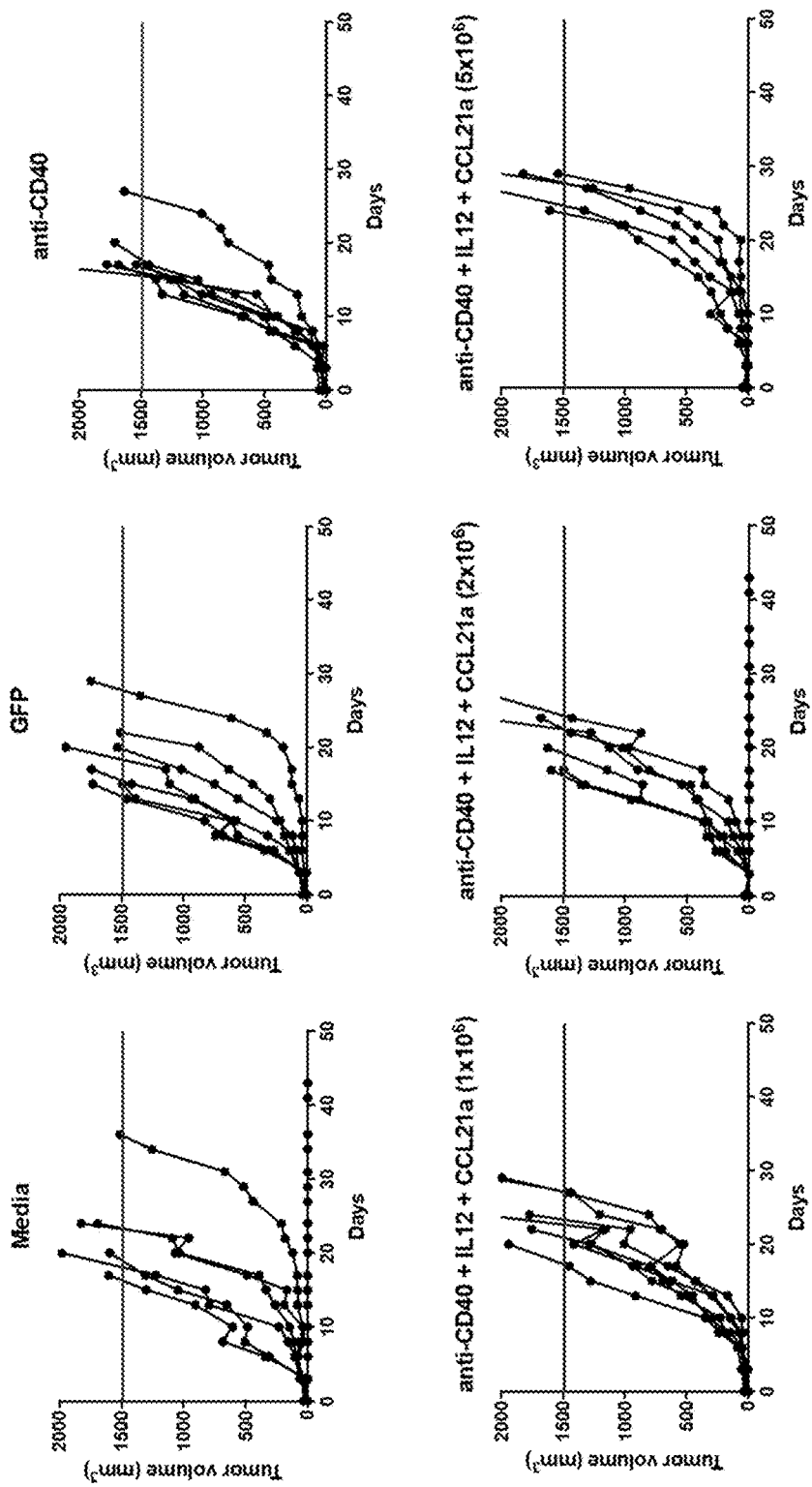
FIG. 17A includes data from a dose-dependent long-term survival study.
Figure 17B:
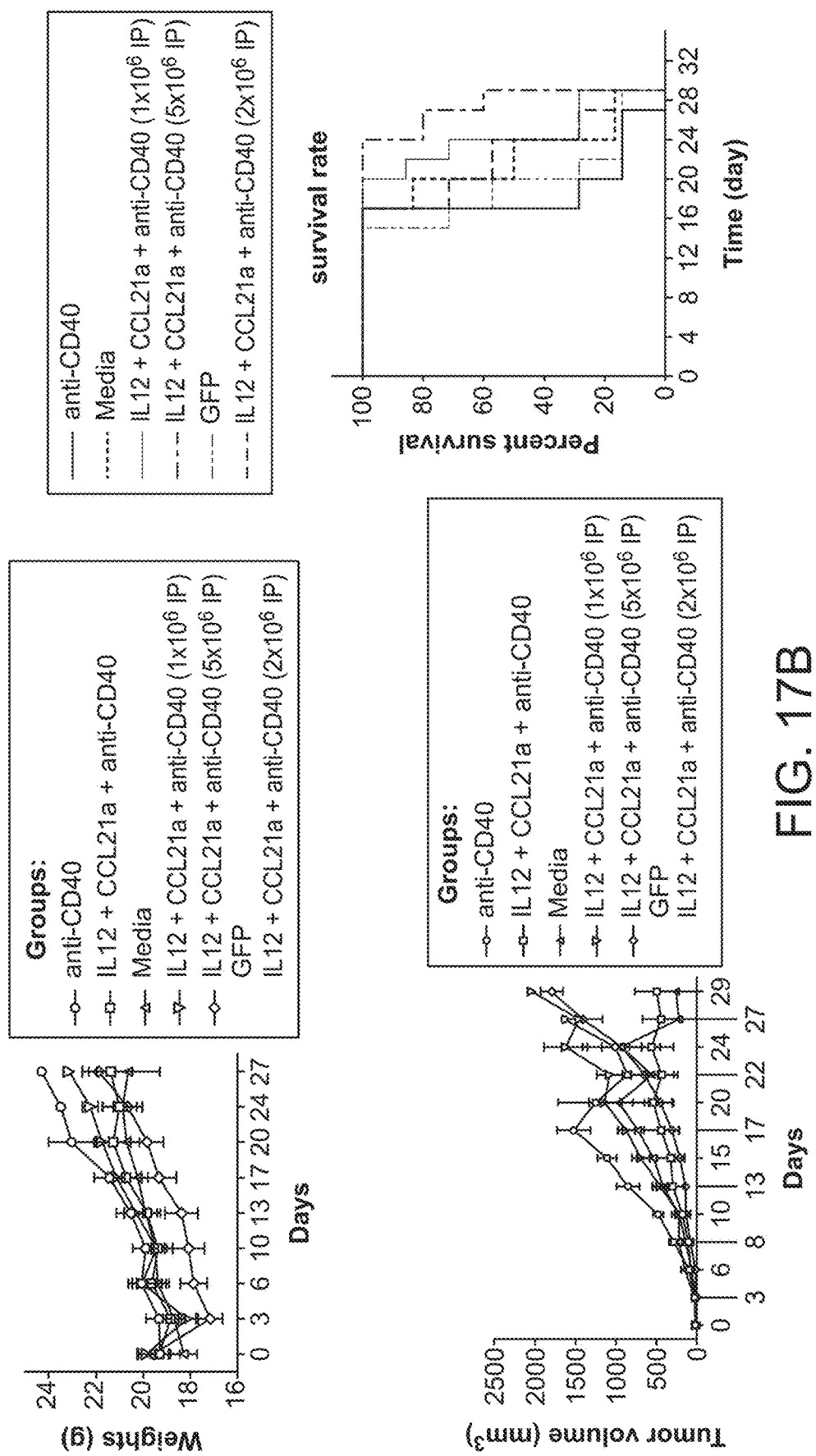
FIG. 17B includes data from a dose-dependent long-term survival study.

Mice were dosed twice with different concentration of engineered MSC-IL12 and CCL21a therapy in combination with injected anti-CD40 antibody. After the second dose, tumor volume was monitored twice a week until tumor burden is greater than 1500 mm³ and the mice were sacrificed. FIG. 17A shows the tumor volume of the individual group. FIG. 17B, left graph, tracks the mice weight and tumor volume from individual group over time. FIG. 17B, right graph, shows the survival plot of the different groups.

MSC Efficacy

Figure 20:
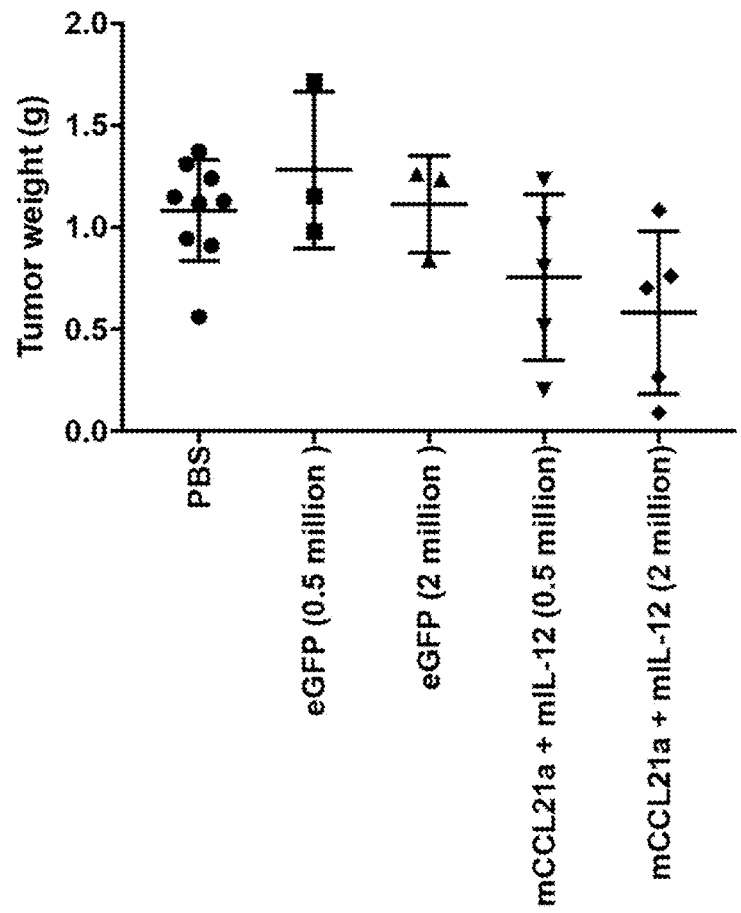
FIG. 20 shows the tumor weight for individual mice in each treatment, and the mean±SEM for each treatment group. Efficacy was determined by tumor weight.

FIG. 20A shows the tumor volume for individual mice in each treatment. FIG. 20B shows the tumor weight for individual mice in each treatment. Efficacy was determined by tumor volume from caliper measurement every other day.

Tumor Growth Kinetics

Figure 21A:
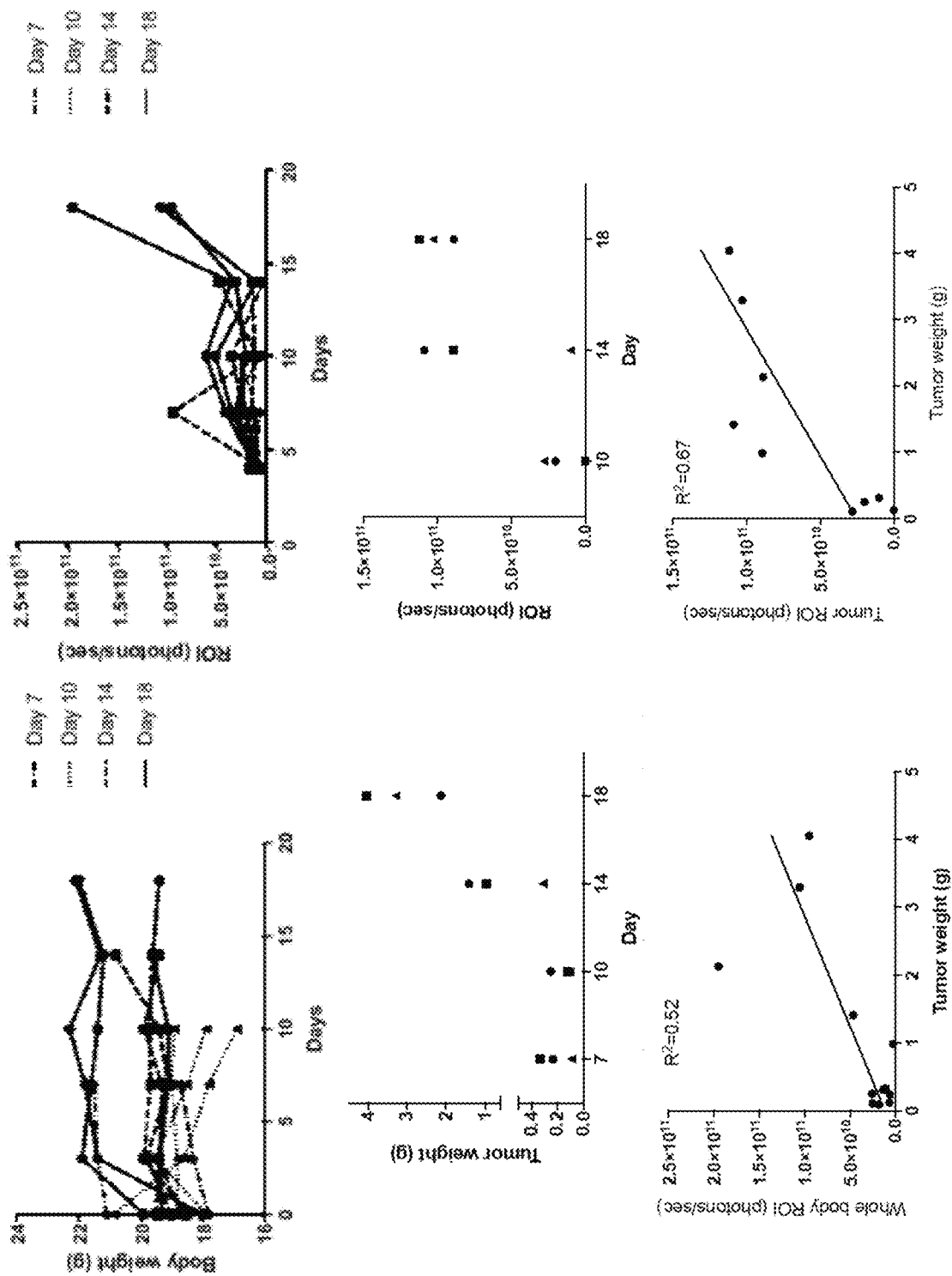
FIG. 21A shows the kinetics of CT26-LUC (luciferase) tumor growth in the intraperitoneal space. A CT26 cell line was injected at day 0 and three (3) mice were harvested at day 7, day 10, day 14, and day 18 to determine the kinetics of tumor growth. The first row of FIG. 21A measures the mice body weight (left panel) and ROI (right panel) with an IVIS imager to monitor tumor burden. The second row monitors the tumor weight (left panel) and the ROI (right panel) of the tumor of individual mice in each group. The third row correlates the tumor weight with either whole body ROI (left panel) or tumor ROI (right panel).
Figure 21B:
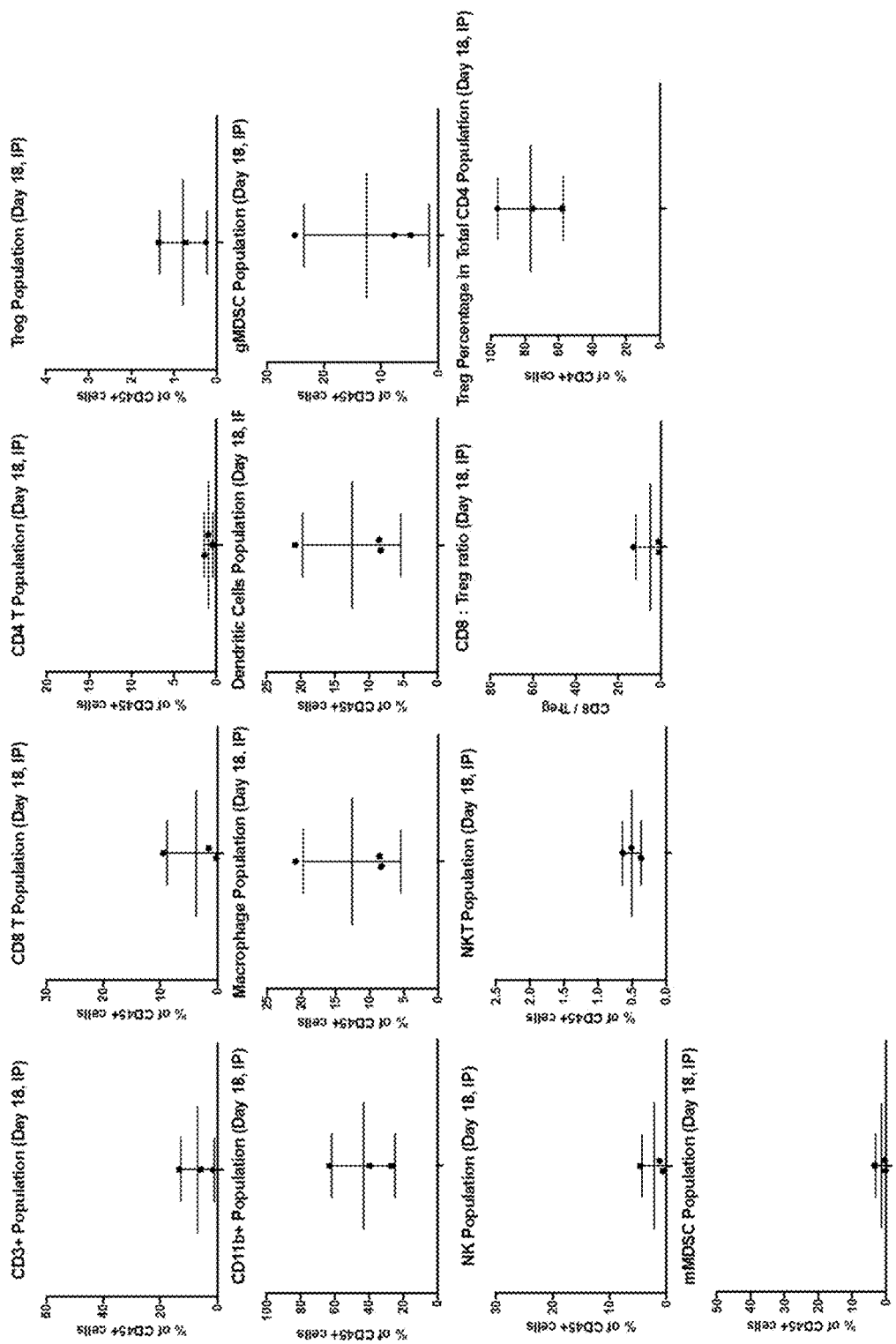
FIG. 21B shows the kinetics of CT26-LUC (luciferase) tumor growth in the intraperitoneal space. A CT26 cell line was injected at day 0 and three (3) mice were harvested at day 7, day 10, day 14, and day 18 to determine the kinetics of tumor growth.

FIGS. 21A-21B show the kinetics of CT26-LUC (luciferase) tumor growth in the intraperitoneal space. A CT26 cell line was injected at day 0 and three (3) mice were harvested at day 7, day 10, day 14, and day 18 to determine the kinetics of tumor growth. The first row of FIG. 21A measures the mice body weight and ROI with an IVIS imager to monitor tumor burden. The second row monitors the tumor weight and the ROI of the tumor of individual mice in each group. The third row correlates the tumor weight with either whole body ROI or tumor ROI. FIG. 21B shows the immune profile of three (3) mice in the day 18 group to better understand the tumor microenvironment.

Tumor Infiltrate Statistics/Immune Percentage/Tumor Weight

Subcutaneous Mouse Model

Figure 22A:
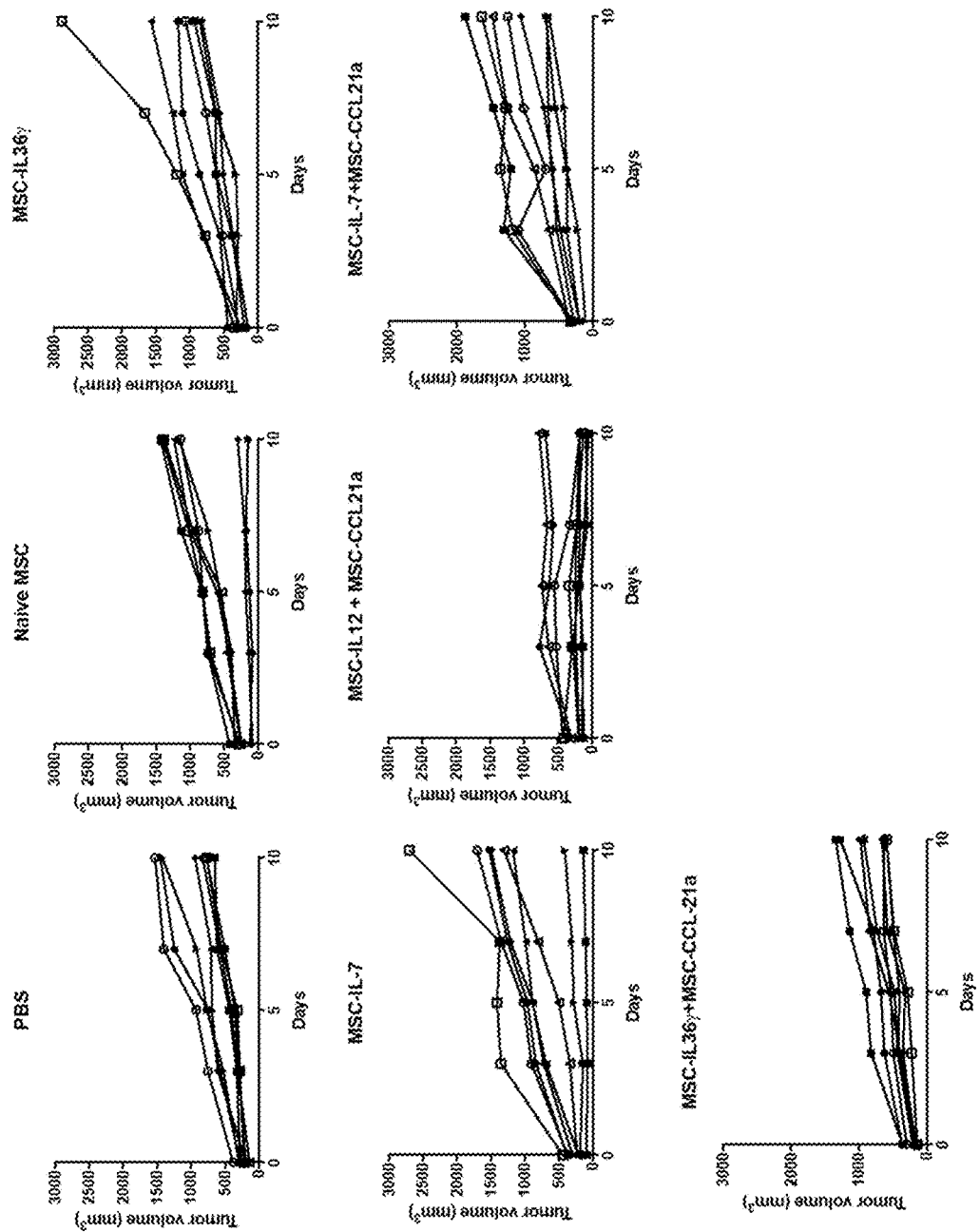
FIG. 22A includes data indicating that engineered MSCs expressing IL-12 and CCL21a inhibit tumor growth in a subcutaneous mouse model of colorectal cancer; however the combination of MSCs expressing CCL21a and IL-36 gamma or IL-7 does not reduce tumor growth. Each effector was expressed by a different MSC, and the MSCs were combined (at a 1:1 ratio) for combinatorial treatment. Each chart shows the effect of engineered MSCs expressing the indicated immunotherapies alone or in combination on the growth of CT26 colon tumors in mice (n=6-8). Each line of FIG. 22A represents an individual mouse.
Figure 22B:
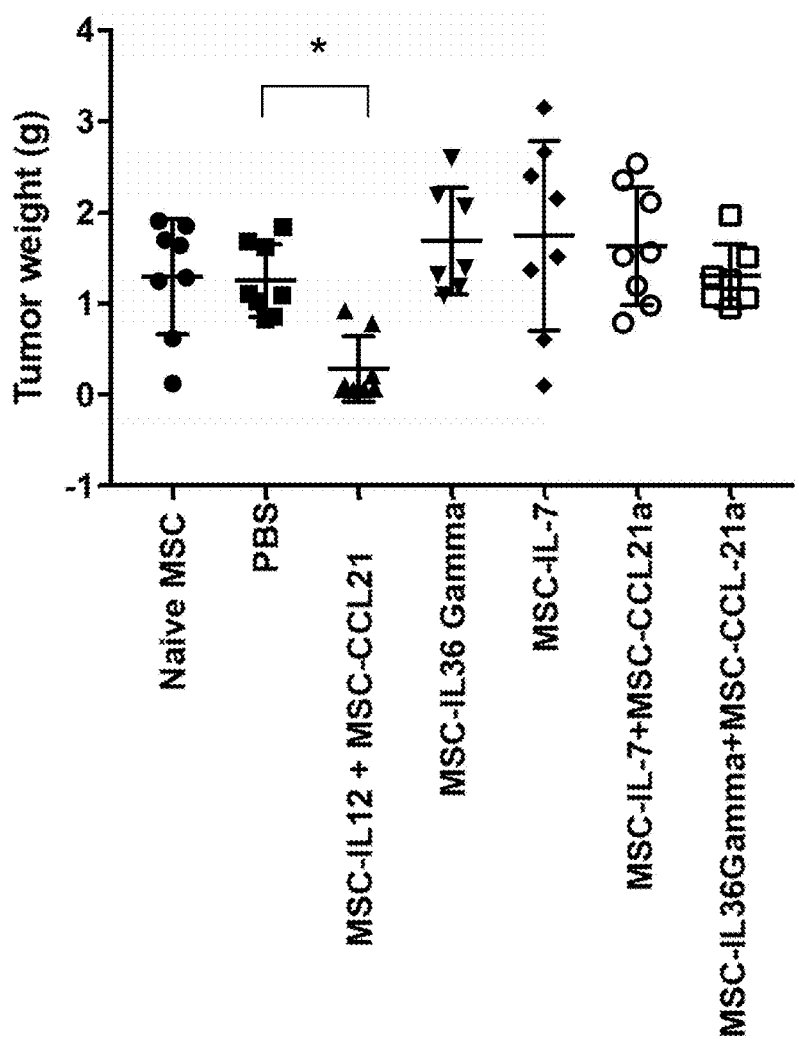
FIG. 22B includes data indicating that engineered MSCs expressing IL-12 and CCL21a inhibit tumor growth in a subcutaneous mouse model of colorectal cancer; however the combination of MSCs expressing CCL21a and IL-36 gamma or IL-7 does not reduce tumor growth. Each effector was expressed by a different MSC, and the MSCs were combined (at a 1:1 ratio) for combinatorial treatment.
Figure 23A:
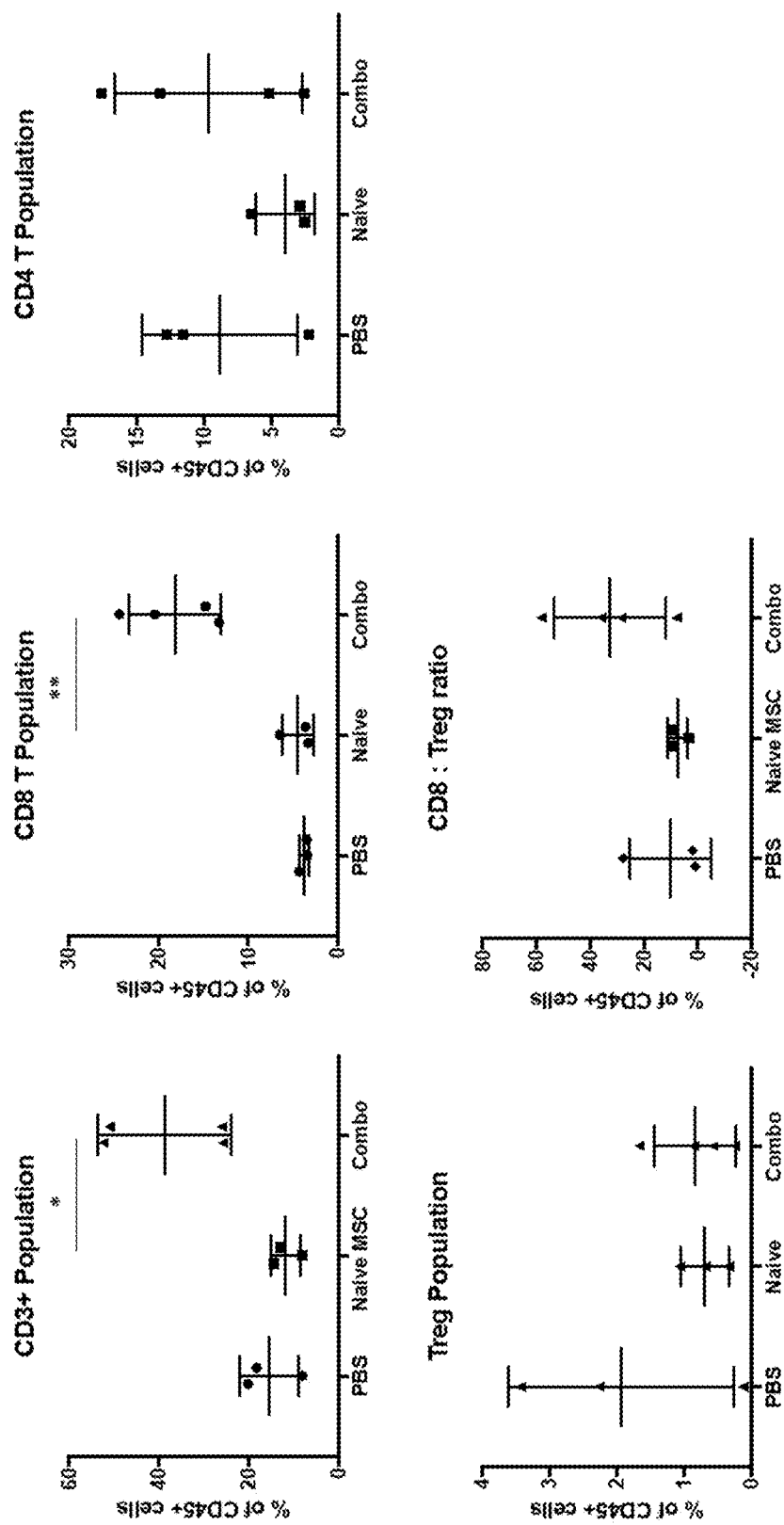
FIG. 23A includes tumor immune infiltrate statistics from the experiment represented by FIGS. 22A-22B. Three mice were selected from PBS, Naïve MSC, and MSC-IL12+ MSC-CCL21a (combo) group to run flow cytometry to immune profile tumor microenvironment.
Figure 23B:
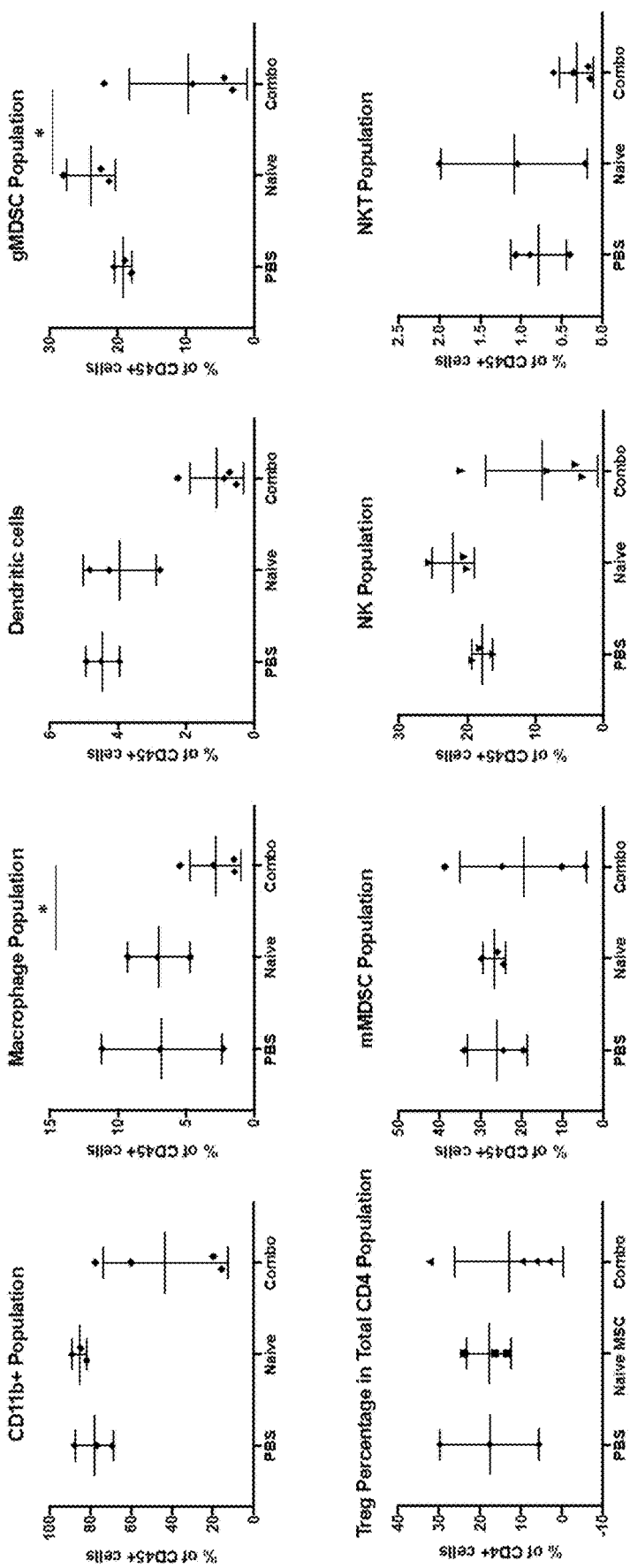
FIG. 23B includes tumor immune infiltrate statistics from the experiment represented by FIGS. 22A-22B. Three mice were selected from PBS, Naïve MSC, and MSC-IL12+ MSC-CCL21a (combo) group to run flow cytometry to immune profile tumor microenvironment.

FIG. 22A includes data indicating that engineered MSCs expressing IL-12 and CCL21a inhibit tumor growth in an subcutaneous mouse model of colorectal cancer; however the combination of MSCs expressing CCL21a and IL-36 gamma or IL-7 does not reduce tumor growth. FIGS. 23A-23B include the tumor immune infiltrate statistics. Three mice were selected from PBS, Naïve MSC, and MSC-IL12+MSC-CCL21a (combo) group to run flow cytometry to immune profile tumor microenvironment. FIG. 23A shows a significant increase in infiltrating CD3 and CD8 cytotoxic T population in the combo group compared to the group dosed with naïve MSC. FIG. 23B shows a significant reduction in granulocytic myeloid-derived suppressor cells (gMDSCs) and macrophage population in the combo group compared to group treated with Naïve MSC.

Figure 24A:
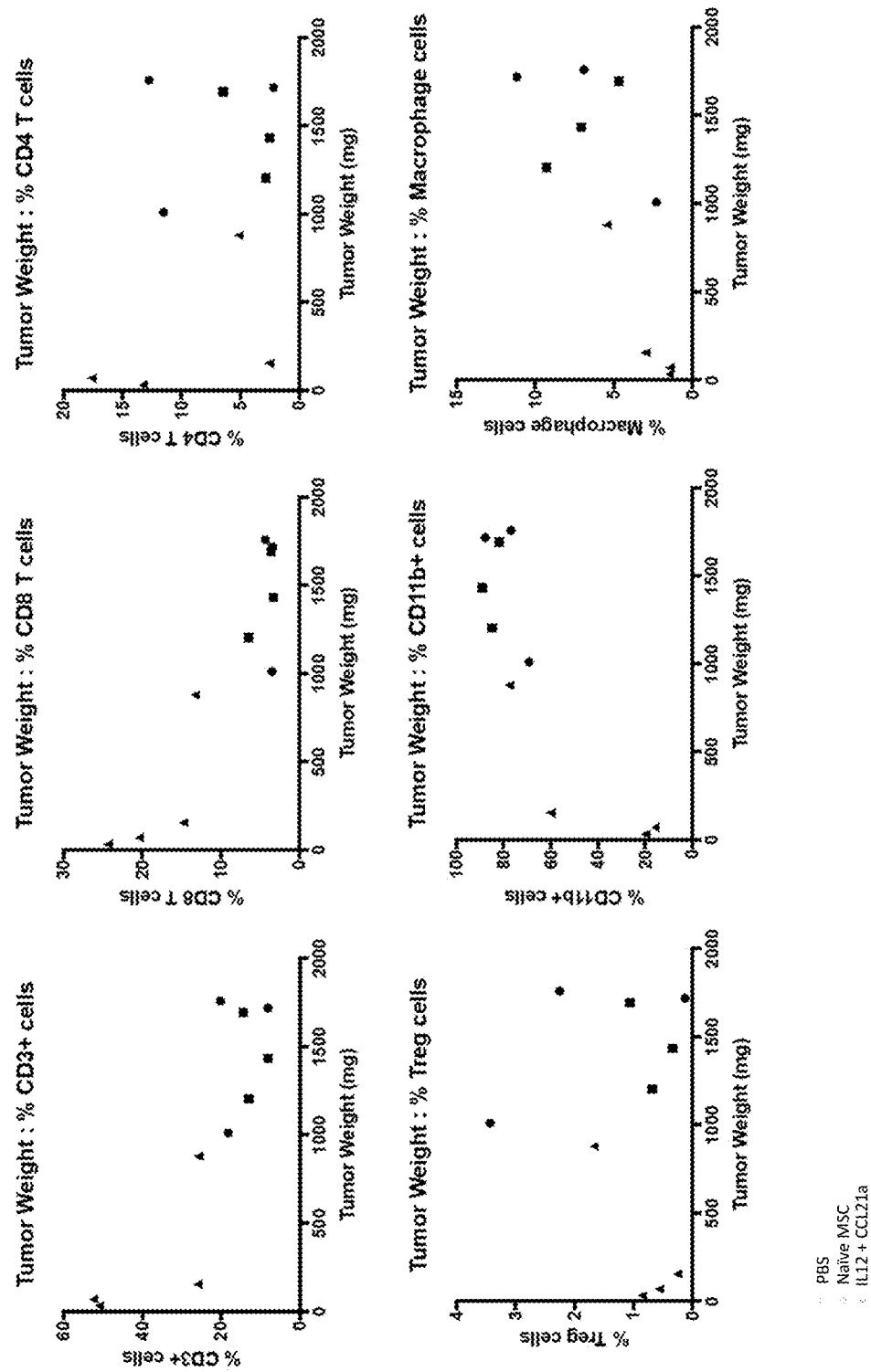
FIG. 24A includes data relating to immune percentage and tumor weight, relating to the experiments represented by FIGS. 22A-22B.
Figure 24B:
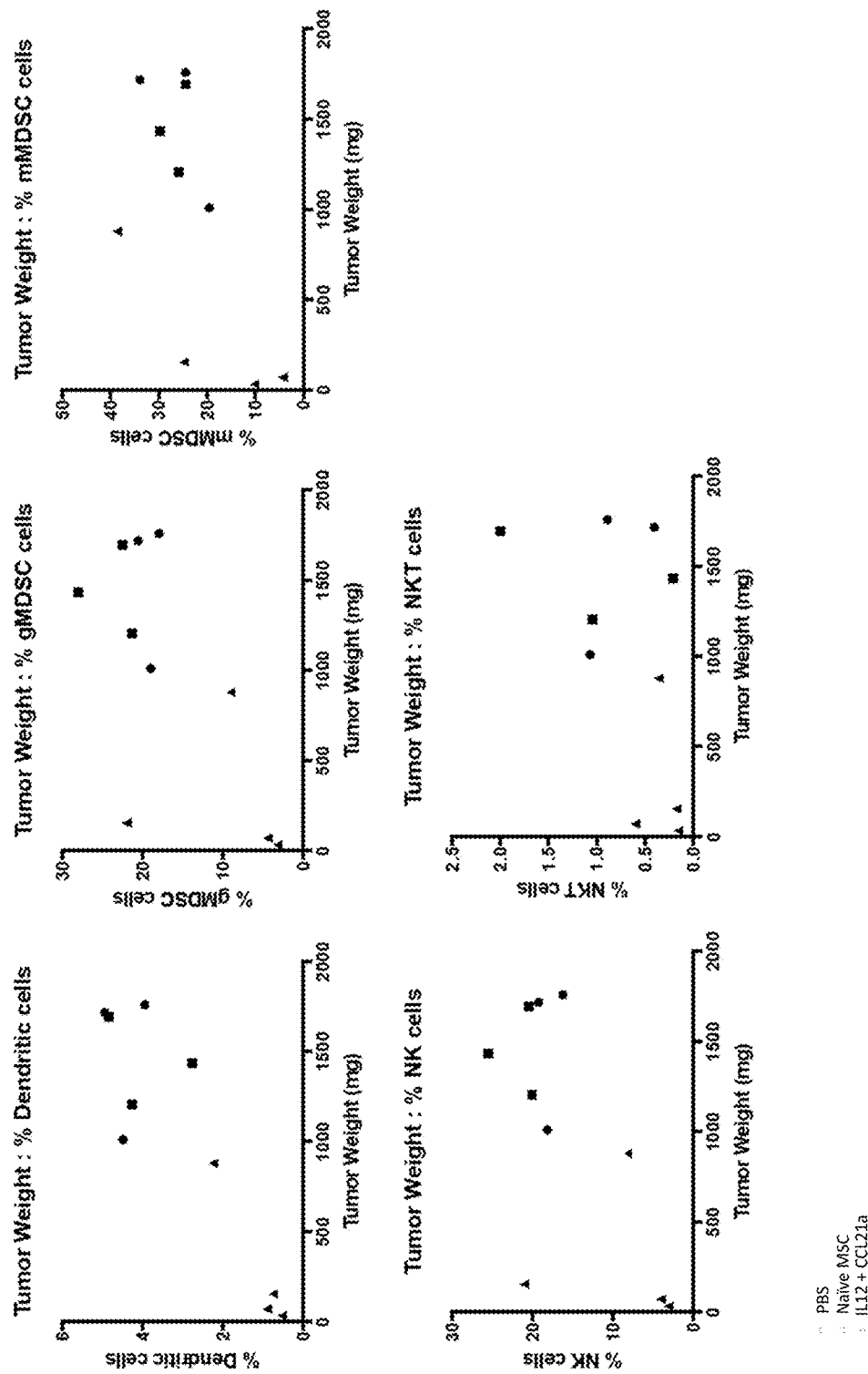
FIG. 24B includes data relating to immune percentage and tumor weight, relating to the experiments represented by FIGS. 22A-22B.

FIGS. 24A-24B include data relating to immune percentage and tumor weight, showing that samples with more CD3+ and CD8+ T cells (top left and center graph) correlate strongly with a decrease in tumor weight. These figures also show that samples with fewer CD11b myeloid cells, including macrophage, dendritic cells, and MDSC, display lower tumor burden (lower center and right graph of FIG. 24A and upper row of FIG. 24B).

Orthotopic Mouse Model

Figure 26A:
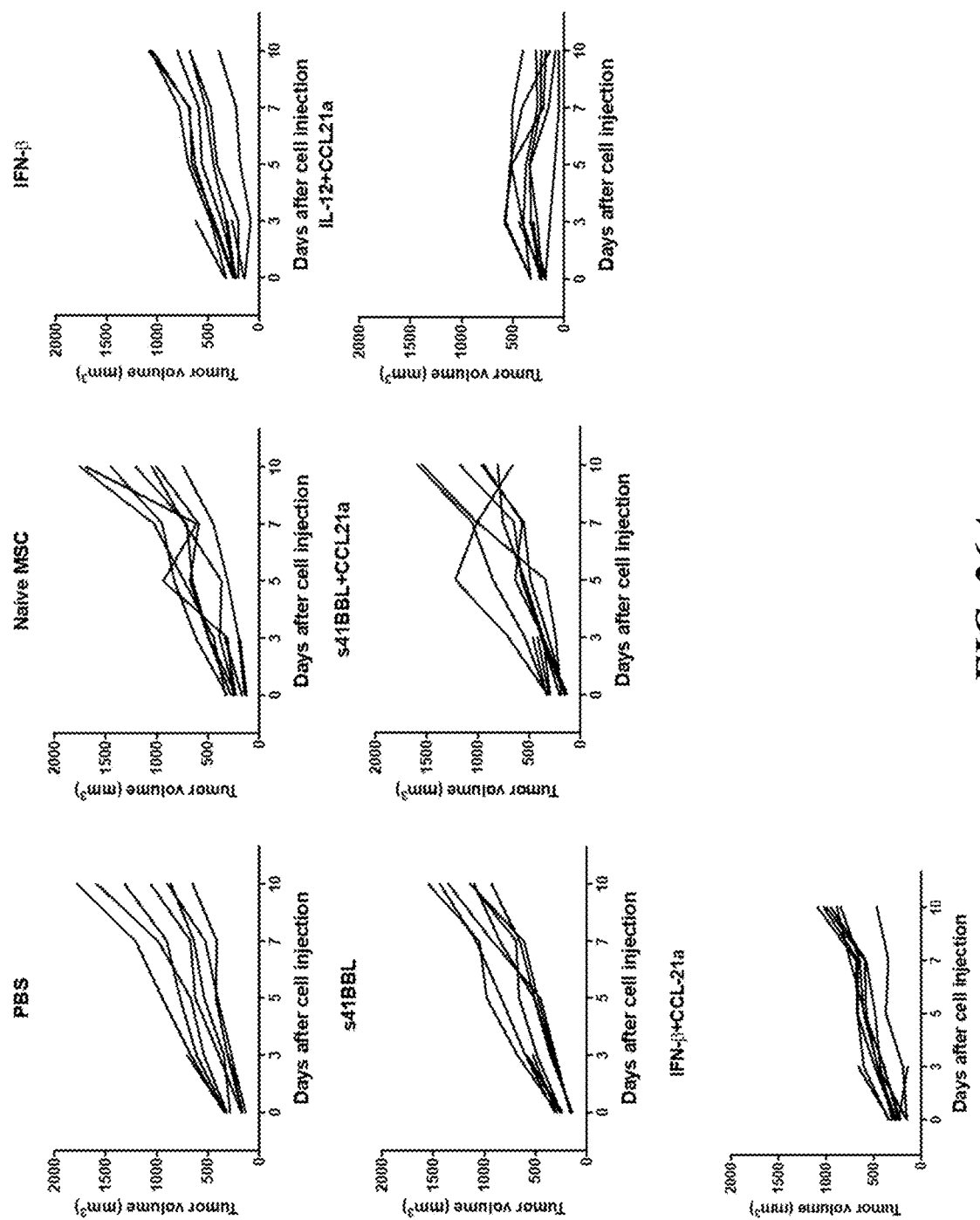
FIG. 26A includes data indicating that engineered combination treatment MSC-IL-12+MSC-CCL21a, or MSC-CCL21a+MSC-IFN-β, inhibit tumor growth in a subcutaneous mouse model of colorectal cancer; however the combination of MSCs expressing CCL21a and s41BBL does not reduce tumor growth. Each effector was expressed by a different MSC, and the MSCs were combined (at a 1:1 ratio) for combinatorial treatment. Each chart shows the effect of engineered MSCs expressing the indicated immunotherapies alone or in combination on the growth of CT26 tumors in mice (n=6-8). Each line of FIG. 26A represents an individual mouse.
Figure 26B:
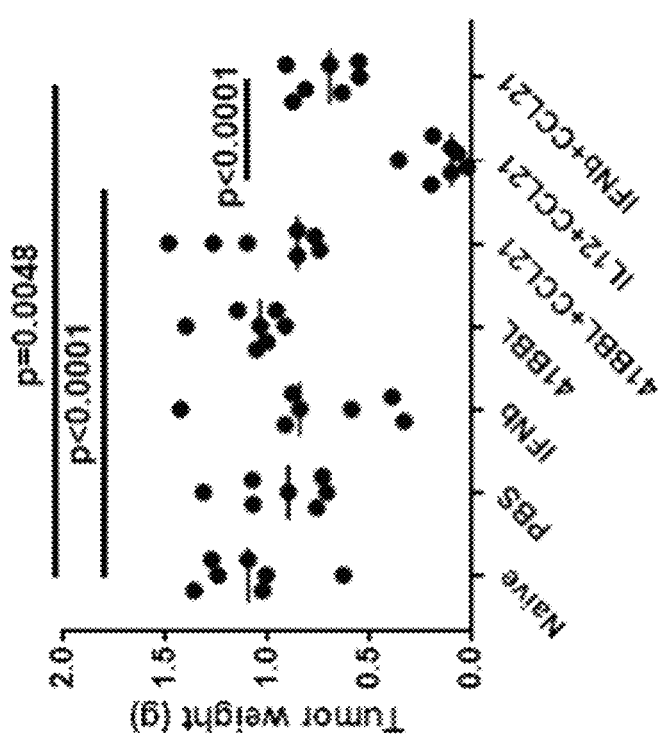
FIG. 26B includes data indicating that engineered combination treatment MSC-IL-12+MSC-CCL21a, or MSC-CCL21a+MSC-IFN-β, inhibit tumor growth in a subcutaneous mouse model of colorectal cancer; however the combination of MSCs expressing CCL21a and s41BBL does not reduce tumor growth. Each effector was expressed by a different MSC, and the MSCs were combined (at a 1:1 ratio) for combinatorial treatment.

FIG. 26A shows that engineered MSCs expressing IL-12 and CCL21a, or CCL21a and IFN-β, inhibit tumor growth in an orthotopic mouse model of colorectal cancer; however the combination of MSCs expressing CCL21a and s41BBL does not reduce tumor growth. Each effector was expressed by a different MSC, and the MSCs were combined (at a 1:1 ratio) for combinatorial treatment. Each chart shows the effect of engineered MSCs expressing the indicated immunotherapies alone or in combination on the growth of 4T1 breast tumors in mice (n=6-8). Each line of FIG. 26A represents an individual mouse. FIG. 26B shows the tumor weight for individual mice in each treatment. MSC-IL12+MSC-CCL21a shows best efficacy compared to mice injected with naïve MSC. Treatment efficacy was also observed in the group treated with MSC-IFNb+MSC-CCL21a.

Figure 27A:
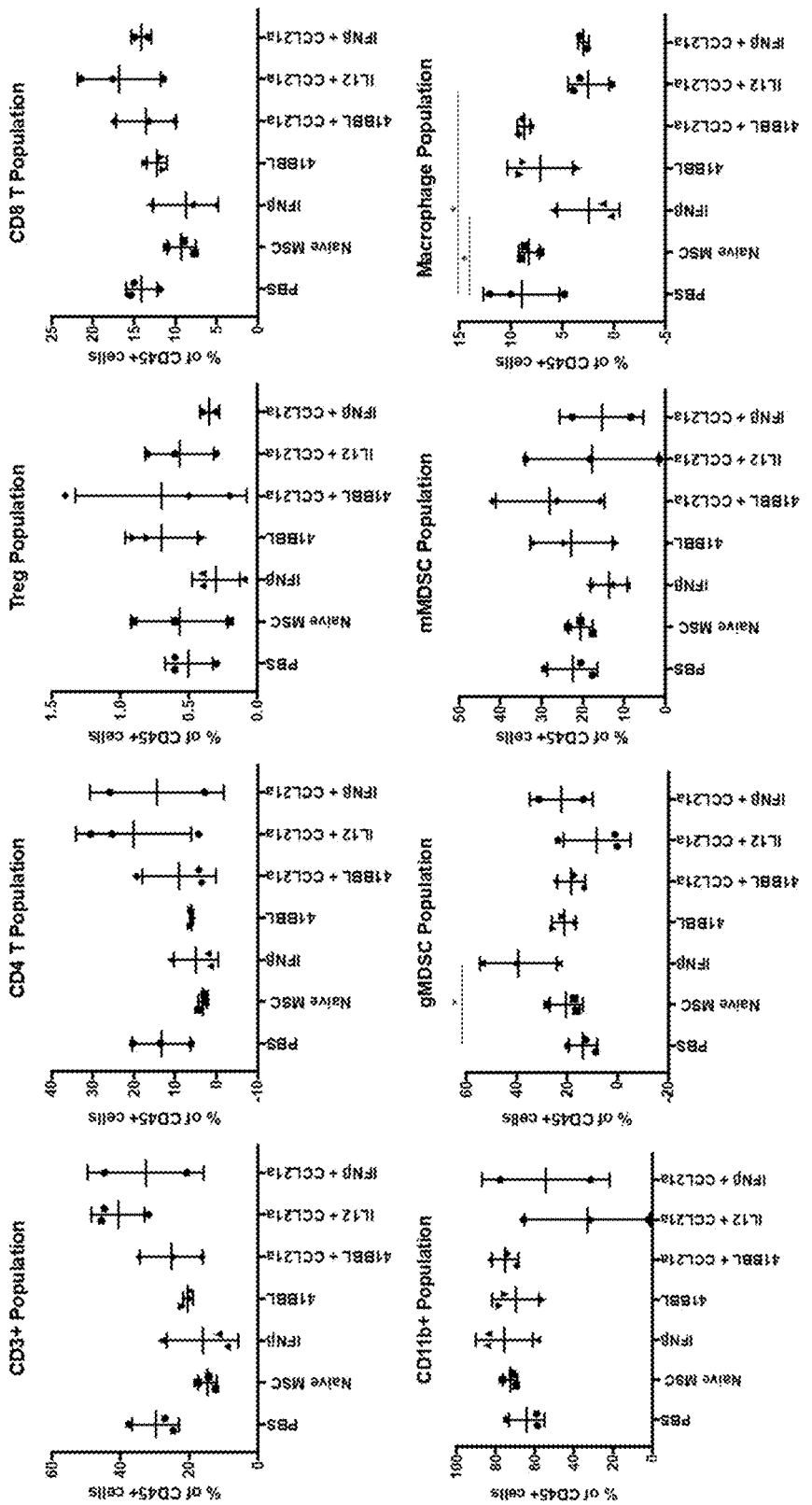
FIG. 27A provides additional data from the experiment represented by FIGS. 26A-26B.
Figure 27B:
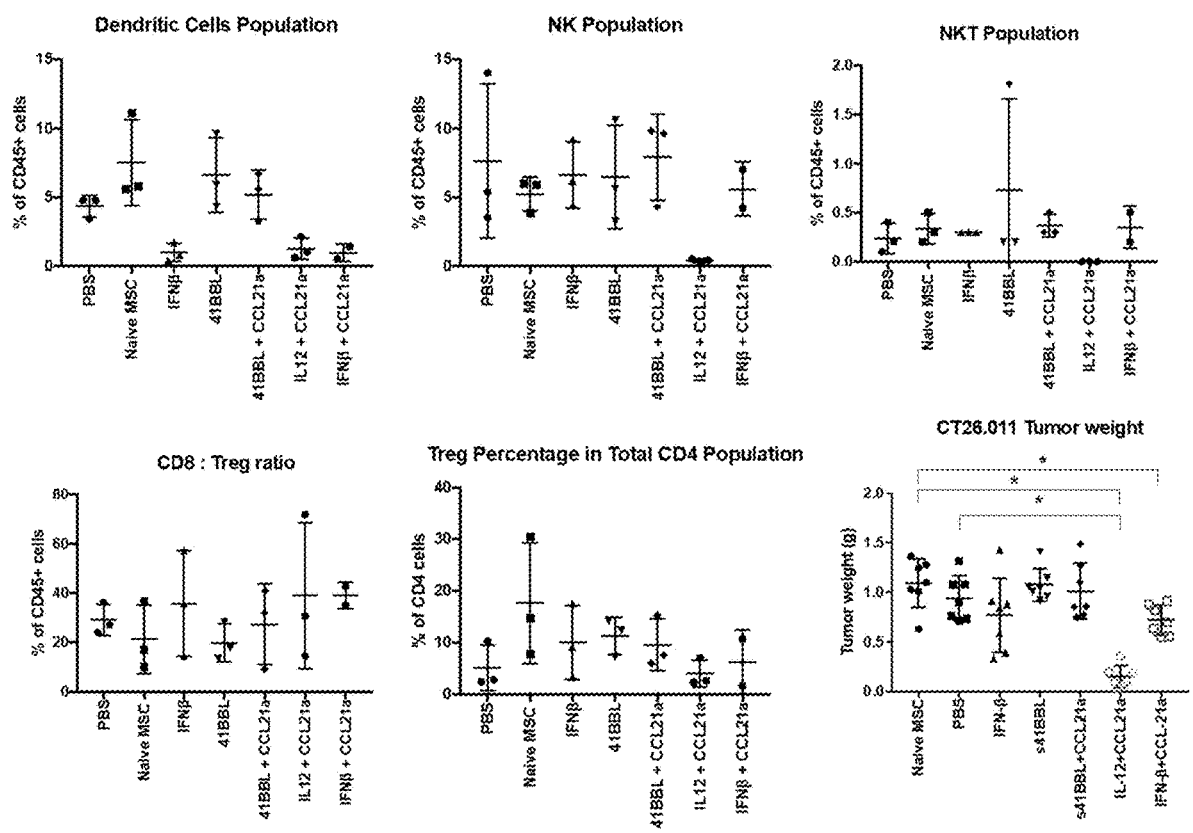
FIG. 27B provides additional data from the experiment represented by FIGS. 26A-26B.

FIGS. 27A-27B are graphs that show immune profiles of each group treated with indicated engineered MSC. A consistent decrease in macrophage population was observed after treating with MSC-IL12+MSC-CCL21a (FIG. 27A). A general trend of increased infiltration in CD3+ population and decreased infiltration in CD11b+ population was also observed when compared to group treated with MSC-IL12+MSC-CCL21a against naïve MSC (FIG. 27A and FIG. 27B).

Figure 28A:
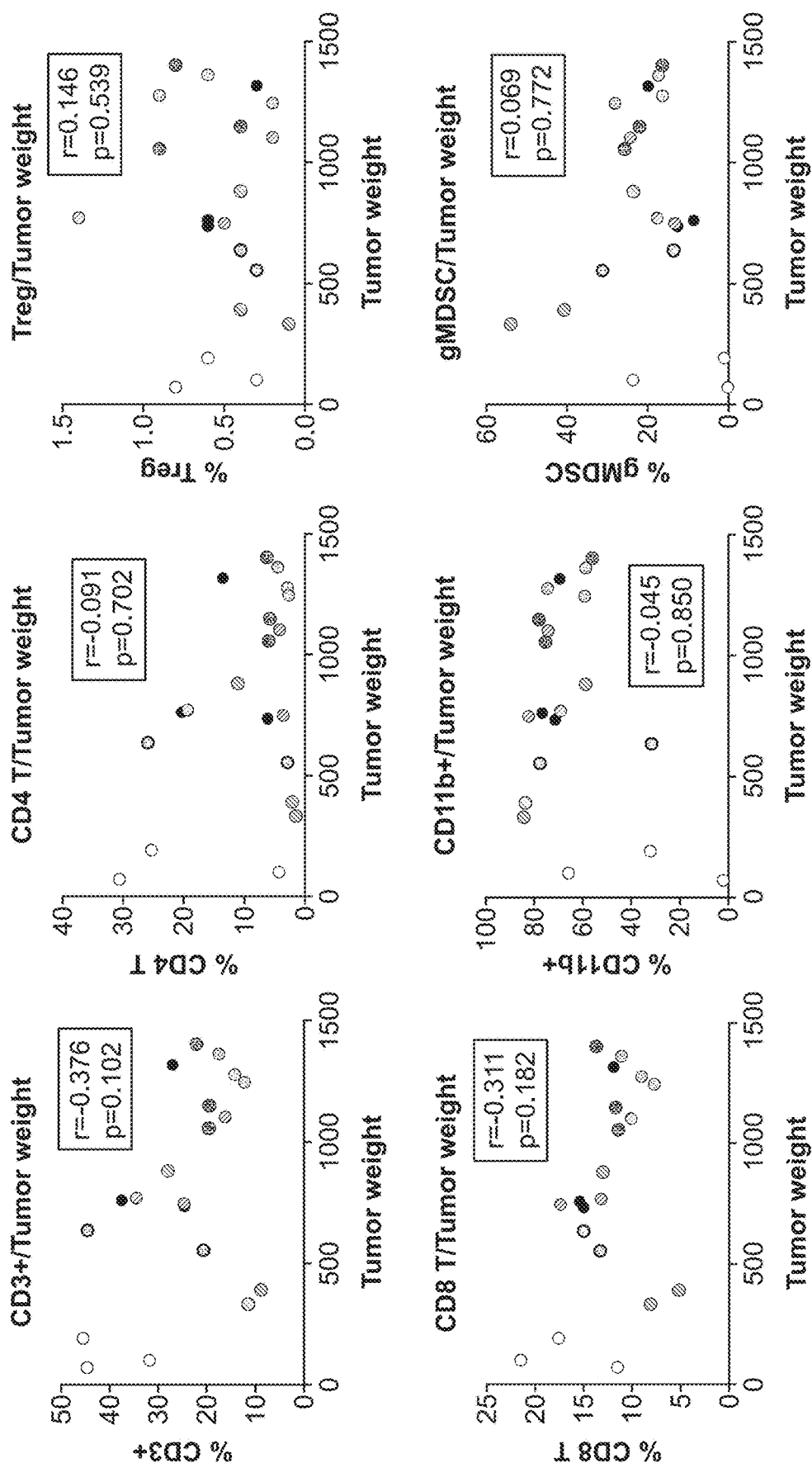
FIG. 28A also provides additional data from the experiment represented by FIGS. 26A-26B.
Figure 28B:
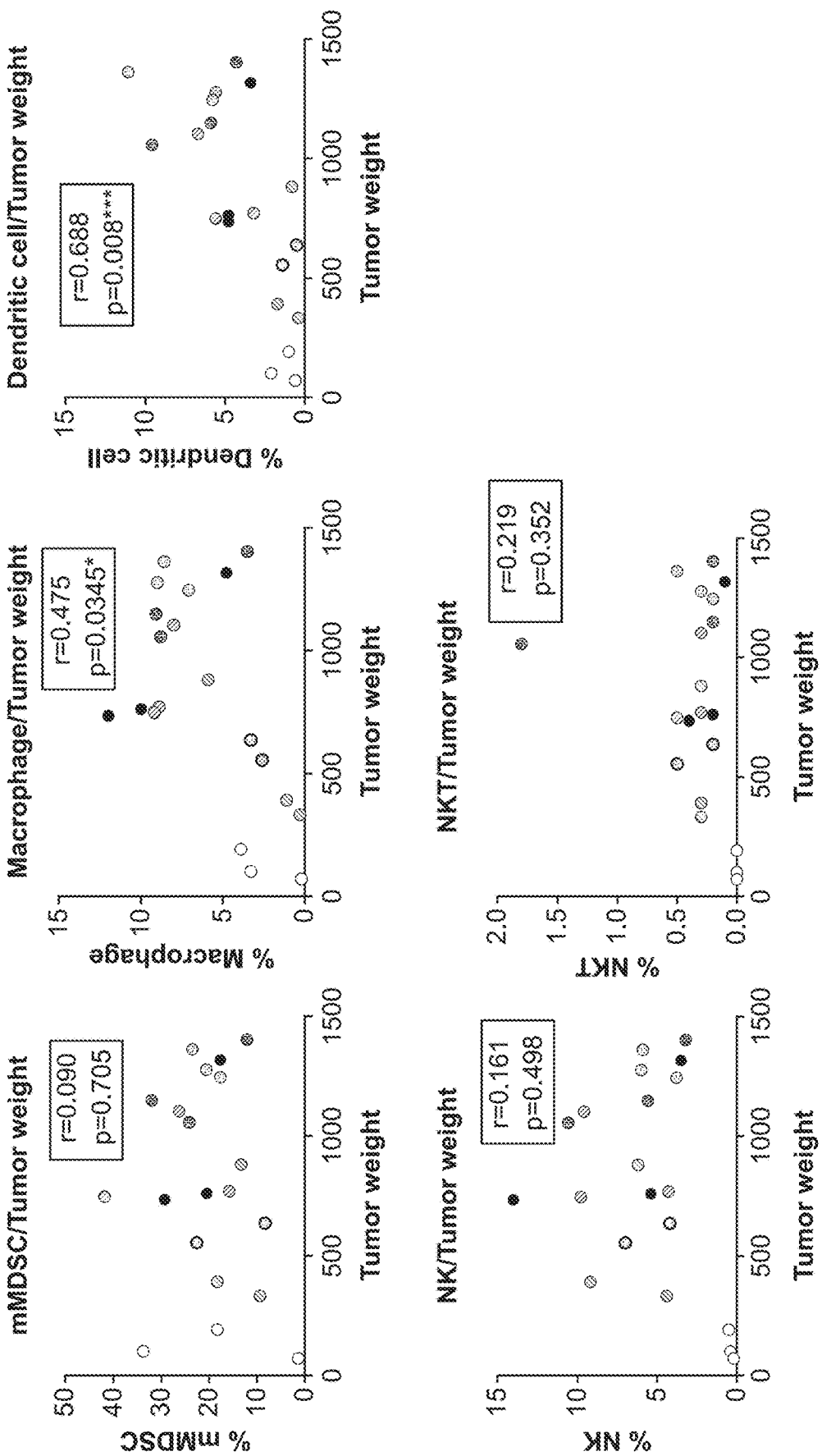
FIG. 28B also provides additional data from the experiment represented by FIGS. 26A-26B.

FIG. 28A-28B show the correlation of immune infiltration with tumor weight. Samples with low macrophage and dendritic cells have lower tumor burden (FIG. 28B, top center and top right). FIG. 28C shows the average tumor weight from each group. Statistical significance was observed with both MSC-IL12+MSC-CCL21a, or MSC-IFNb+MSC-CCL21a compared with naïve MSC.

Figure 29:
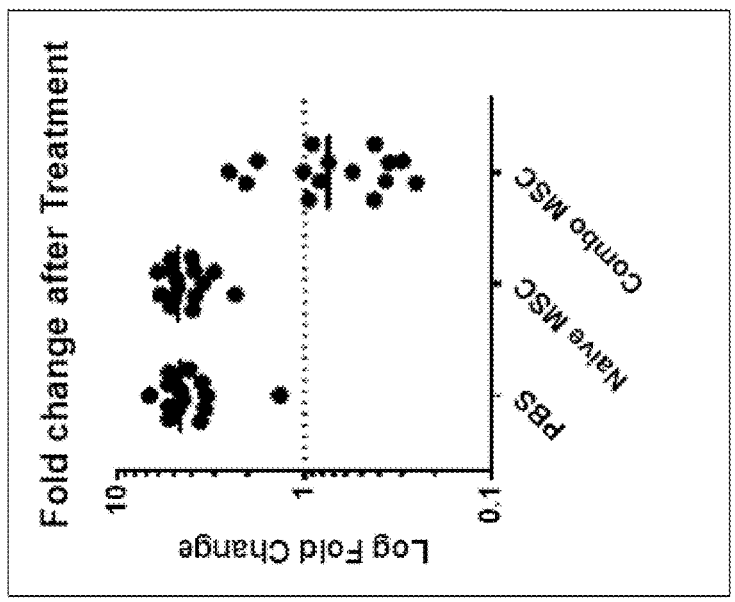
Figure 29:
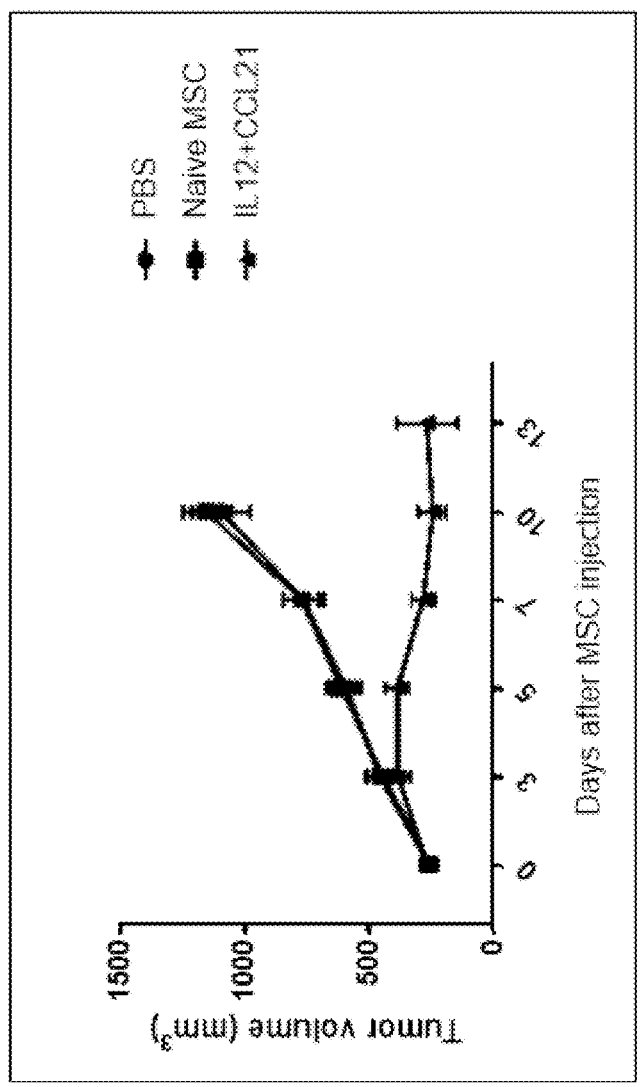

FIG. 29 shows graphs combining the in vivo data from the colorectal cancer models above (FIG. 22A and FIG. 26A). The combined CT26 data from FIG. 22A and FIG. 26A capture three groups: tumor only (PBS), treated with naïve MSC, and treated with MSC-IL12+MSC-CCL21a.

Figure 30A:
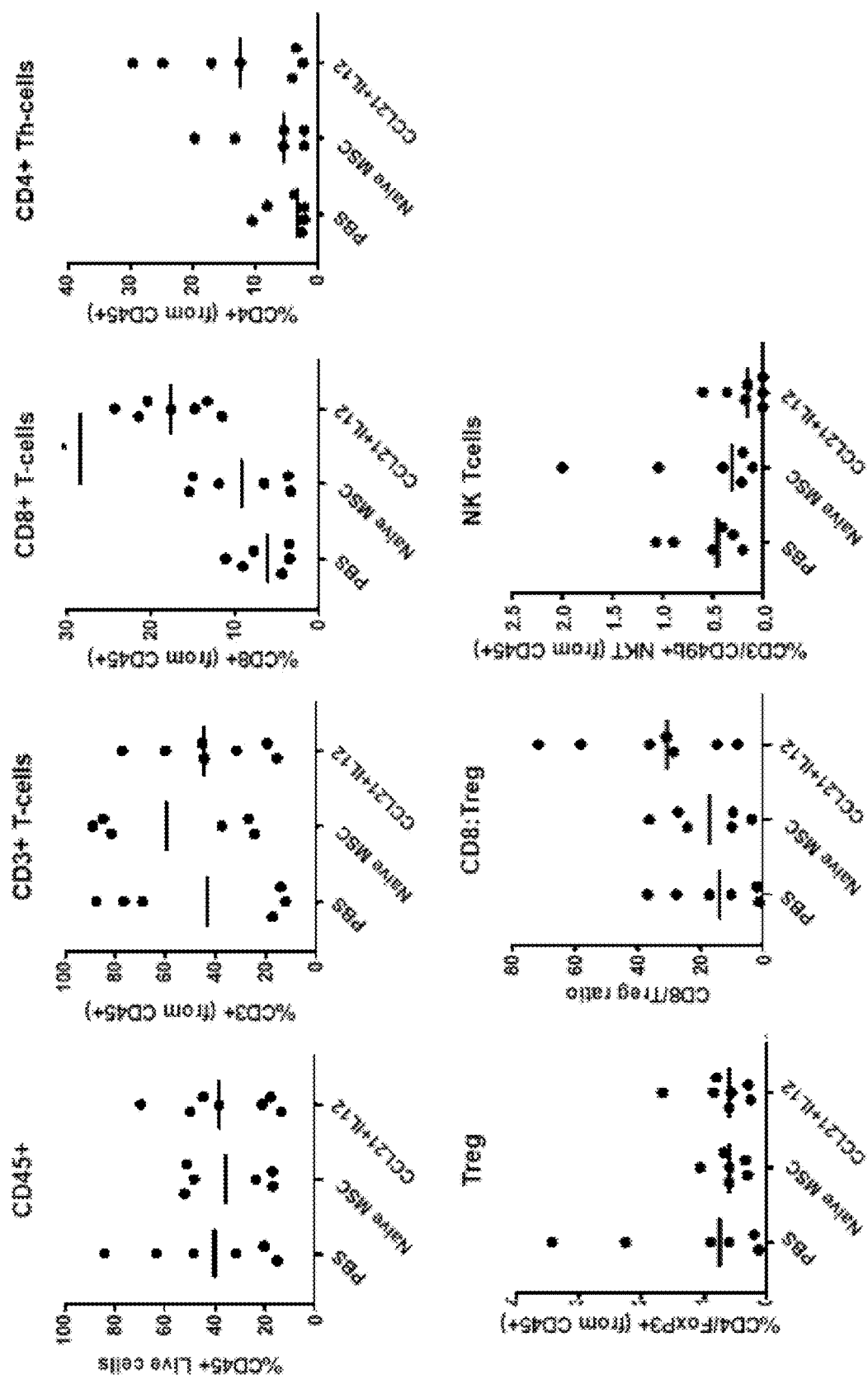
FIG. 30A also shows combined data from FIG. 22A and FIG. 26A. The graphs show the average number of immune infiltration from the flow cytometry experiment data. Statistical significance was observed in CD8+T, demonstrating the ability of MSC-IL12+MSC-CCL21a to repolarize tumor microenvironment and allow more cytotoxic T cell infiltration.
Figure 30B:
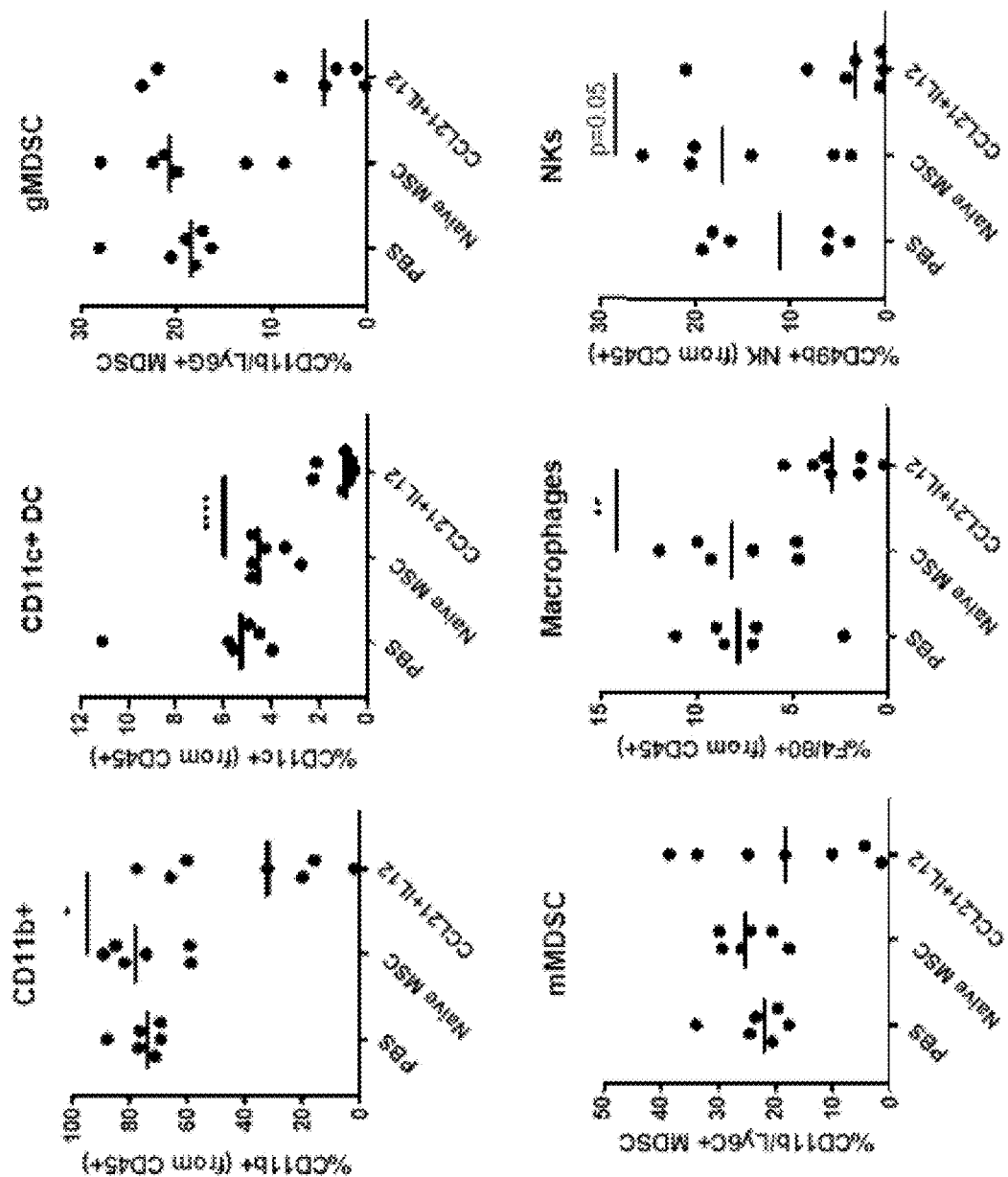
FIG. 30B also shows combined data from FIG. 22A and FIG. 26A. The graphs show the average number of immune infiltration from the flow cytometry experiment data. There was a reduction in CD11b+ myeloid population infiltration in the groups that were treated by MSC-IL12+MSC-CCL21a. The data collected show that the dendritic cells and the macrophage population was statistical significance.

FIGS. 30A-30C also show combined data from FIG. 22A and FIG. 26A. The graphs show the average number of immune infiltration from the flow cytometry experiment data. Statistical significance was observed in CD8+T from FIG. 30A, demonstrating the ability of MSC-IL12+MSC-CCL21a to repolarize tumor microenvironment and allow more cytotoxic T cell infiltration. Furthermore, there was a reduction in CD11b+ myeloid population infiltration in the groups that were treated by MSC-IL12+MSC-CCL21a (FIG. 30B). The data collected using dendritic cells and the macrophage population was statistical significance.

Figure 25A:
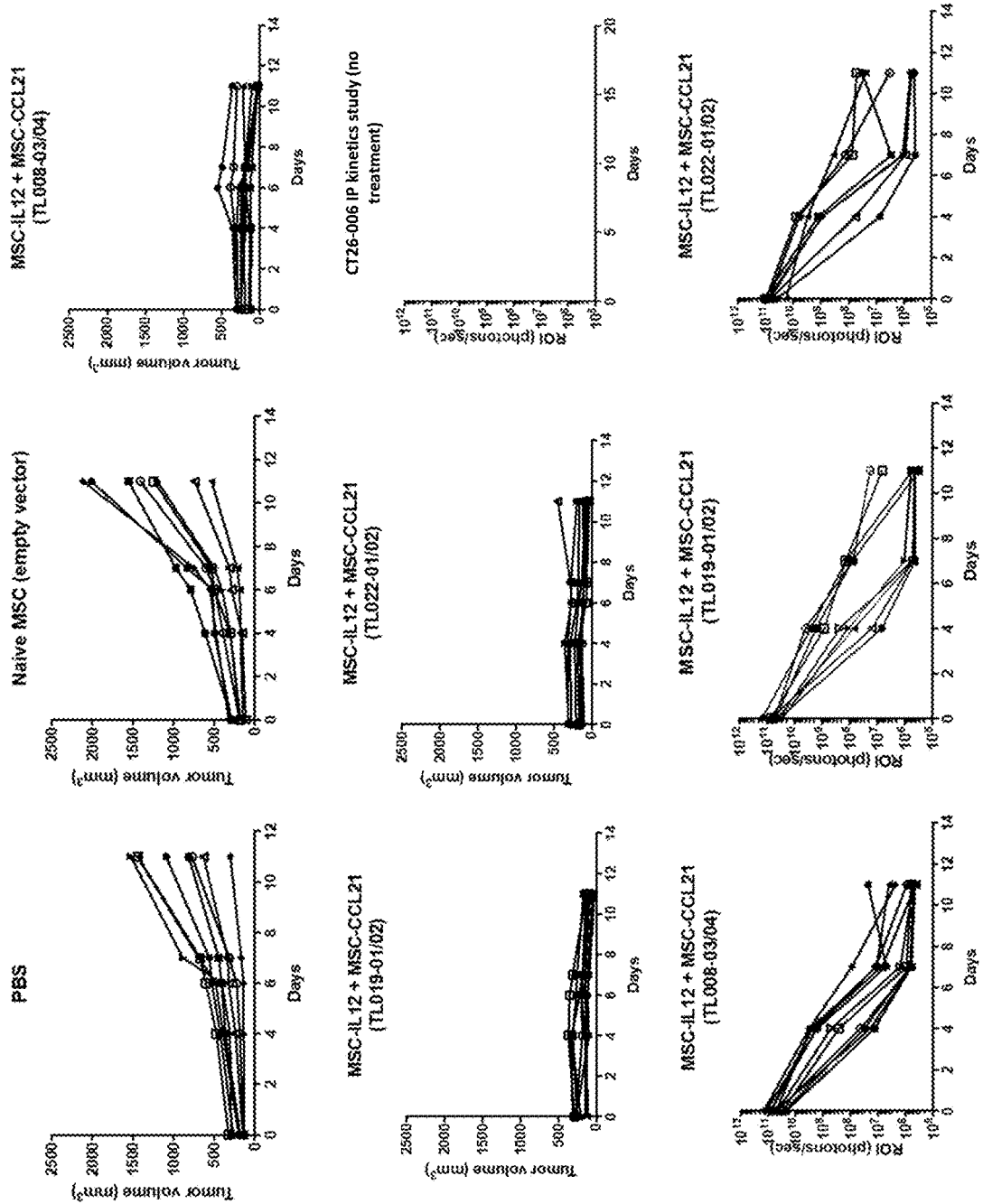
FIG. 25A includes data from MSC-IL-12+CCL21a therapy in intraperitoneal and subcutaneous colorectal cancer mouse models. Three different lots of a lentiviral transduced line was tested for MSC-IL12 and CCL21a (TLOO8-3/4, TL019-01/02, and TL022-01/02; each TL number represents one lot).
Figure 25B:
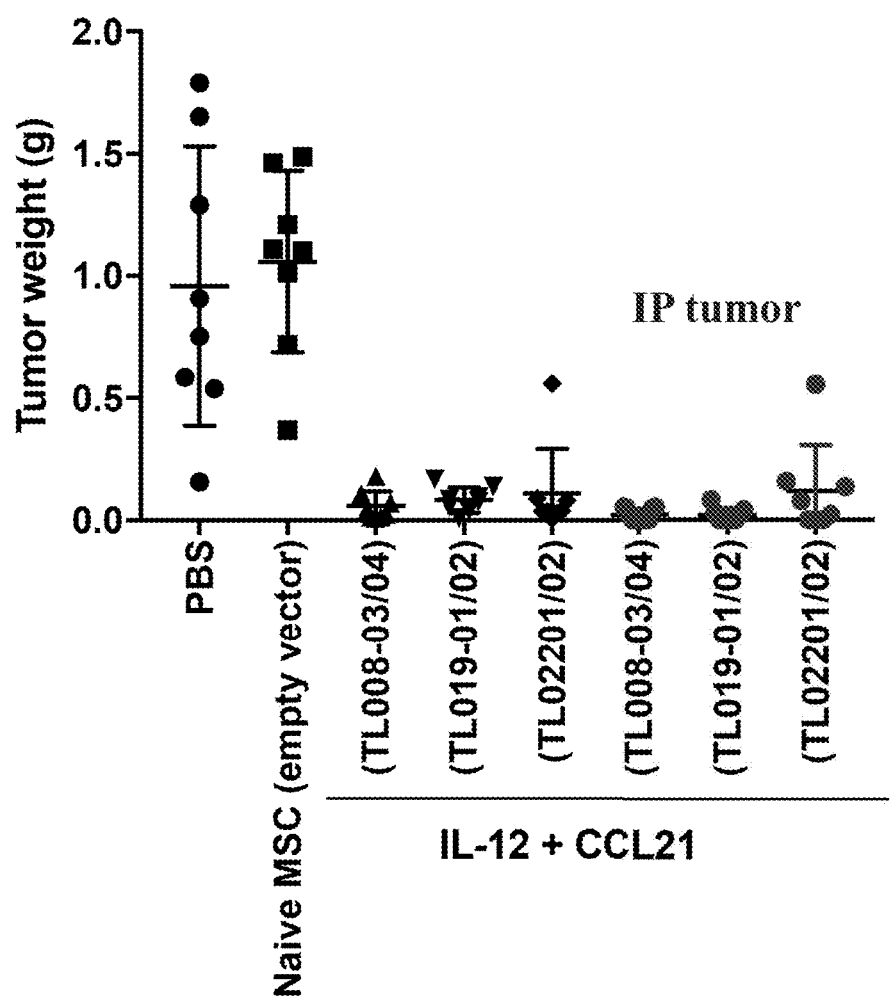
FIG. 25B includes data from MSC-IL-12+CCL21a therapy in intraperitoneal and subcutaneous colorectal cancer mouse models. Three different lots of a lentiviral transduced line was tested for MSC-IL12 and CCL21a (TLOO8-3/4, TL019-01/02, and TL022-01/02; each TL number represents one lot).

IL12 and CCL21a Therapy in Intraperitoneal and Subcutaneous Mouse Models of Colorectal Cancer FIGS. 25A-25B include data from MSC-IL-12+CCL21a therapy in intraperitoneal and subcutaneous colorectal cancer mouse models. Three different lots of a lentiviral transduced line was tested for MSC-IL12 and CCL21a (TLOO8-3/4, TL019-01/02, and TL022-01/02; each TL number represents one lot). FIG. 25A shows that all three lots of MSC-IL12+MSC-CCL21a can reduce tumor burden in both subcutaneous and intraperitoneal model (first 5 graphs are from the SC model and last 3 are from the IP model). Tumors from all mice were collected on day 11. FIG. 25B shows the average tumor weight from each group.

Example 6: MSC Combination Cytokine Therapy Methods

The following methods were used in experiments, as indicated.
Methods:
MSC Culturing
Bone-marrow derived C57BL/6 and Balb/C murine MSCs (mMSCs) were purchased from Cyagen (Cat. No. MUBMX-01001 and MUCMX-01001, respectively). mMSC culturing media was composed of: MEM Corning Cat #10-022-CV (500 ml)+MSC FBS Gibco Cat #12662-029 (final conc 10%)+L-Glut (200 mM) Stem cell 07100 (Final conc 2 mM)+PenStrep 100×VWR Cat #97063-708 (Final conc 1×)+murine FGF Peprotech Cat #450-33-100uG (Final conc-1:10,000 dilution). TrypLE Express was purchased (ThermoFisher—#12604021). PBS did not contain magnesium, calcium, or phenol red. mMSCs were passaged according to the protocol below:
1. mMSCs should be passaged at 70-90% confluency.
2. Aspirate media from dish/flask.
3. Rinse plate with PBS (e.g. 2 mL for 10 cm dish, 3 ml for 15 cm dish).
4. Add TrypLE Express (e.g. 2 mL for 10 cm dish, 3 ml for 15 cm dish)
5. Incubate for 3-4 minutes at 37 degrees.
6. Knock plate on side to dislodge cells. Confirm by microscopy that most cells have been dislodged.
7. Wash cells off plate using media (e.g. 8 mL for 10 cm dish).
8. Place cells in 15 conical and centrifuge 400×g for 5 min.
9. Aspirate media.
10. Resuspend cells in appropriate media and plate cells into fresh plates/flasks.
Note: 70% confluent cells can be
split 1:3. 90% confluent cells can be split 1:4. Alternatively, cells can be plated at 3000-5000 cells/cm2.

Bone-marrow derived human MSCs were purchased (RoosterBank-hBM-1M-XF, RoosterBio). Various hMSC culturing media were purchased: Xeno-free hMSC media—(RoosterBio—#KT-016); +FBS (serum-containing) hMSC media (Lonza—MSCGM media—#PT-3001). TrypLE Express was purchased (ThermoFisher—#12604021). PBS did not contain magnesium, calcium, or phenol red.

hMSCs were passaged according to the exemplary protocol below:
1. hMSCs should be passaged at 70-90% confluency.
2. Aspirate media from dish/flask.
3. Rinse plate with PBS (e.g. 2 mL for 10 cm dish).
4. Add TrypLE Express (e.g. 2 mL for 10 cm dish)
5. Incubate for 3-4 minutes at 37 degrees or 5 minutes RT.
6. Knock plate on side to dislodge cells. Confirm by microscopy that most cells have been dislodged.
7. Wash cells off plate using Lonza MSCGM media (e.g. 8 mL for 10 cm dish).
8. Place cells in 15 conical and centrifuge 400×g for 5 min.
9. Aspirate media.
10. Resuspend cells in Rooster xeno-free media and plate cells into fresh plates/flasks. Note: 70% confluent cells can be split 1:3. 90% confluent cells can be split 1:4. Alternatively, cells can be plated at 3000-5000 cells/cm2.

hMSCs were thawed according to the exemplary protocol below:
1. Pre-warm hMSC media to 37°.
2. Remove hMSC aliquot from liquid nitrogen.
3. Thaw by holding the tube ½ submerged in 37° bath for 60-90 seconds, until ⅔ of the frozen sample has thawed.
4. Wipe the tube with 70% ethanol to sterilize tube.
5. Add 0.5 mL media to the cryotube, gently pipette 2-3 times, and then transfer cells into 9 mL media (10 mL total) in 15 mL conical tube.
6. Centrifuge 400×g for 5 min.
7. Aspirate media, and then gently resuspend pellet in appropriate volume of Rooster xeno-free media. Plate cells at a concentration of 3000-5000 cells/cm2.

Lentiviral Production

Lentivirus was produced using: Lenti-X 293T packaging cell line (Clontech, Cat #632180); LX293T Complete growth medium, without antibiotics; DMEM, hi-glucose; 1 mM Sodium Pyruvate; 10% FBS, heat-inactivated; Opti-Mem I Reduced Serum Media (Gibco/Thermo Fisher; Cat #31985); FuGene HD (Promega, Cat #E2311); Envelope, Packaging, and Transfer Vector plasmids; VSV-G-pseudotyped envelope vector (pMD2.G); Packaging vector that contains Gag, Pol, Rev, and Tat that can be used with 2nd and 3rd generation transfer vectors (psMAX2). 293T(FT) cells from 90% confluent 10 cm dishes were lifted and dispensed at 1:3 dilution late in the afternoon the day before transfection and incubated cells as normal overnight at 37° C., 5% CO2 (cells should be 60-85% confluent the next day at time of transfection).

A transfection reaction was prepped for each 10 cm dish according to the protocol below:
1. Prep transfection reaction for each 10 cm dish in a separate 1.7 mL tube.
2. Add 900 uL Opti-Mem I at RT.
3. Add 9 ug vector backbone (containing gene of interest) per reaction.
4. Add Bug packaging vector per reaction.
5. Add 1 ug envelope vector per reaction (pMD2.G).
6. Mix thoroughly by quickly vortexing for 3 seconds.
7. Add 55 uL Fugene HD per reaction.
8. Mix by quickly pipetting up and down 20-30 times.
9. Let sit at RT for 10 min (allowing DNA complexes to form).
10. Slowly add mixture in dropwise manner around the dish, then mix by gently rocking back-forth and up-down for 5-10 seconds (do not swirl).
11. Place dish into virus incubator.

Viral supernatants were harvested on days 2 and 3 using a serological pipette. Cellular debris was removed using a Millipore steriflip 0.45 um filters. A Lenti-X Concentrator (Cat. Nos. 631231 & 631232) was used according to the protocol: 1) Combine 1 volume of Lenti-X Concentrator with 3 volumes of clarified supernatant. Mix by gentle inversion; 2) Incubate mixture on ice or at 4° C. for 30 minutes to overnight; (3) Centrifuge sample at 1,500×g for 45 minutes at 4° C.; (4) Carefully remove and discard supernatant, taking care not to disturb the pellet; (5) Gently resuspend the pellet in 1/10 to 1/100th of the original volume using sterile PBS+0.1% BSA.

Vectors

Figure 31:
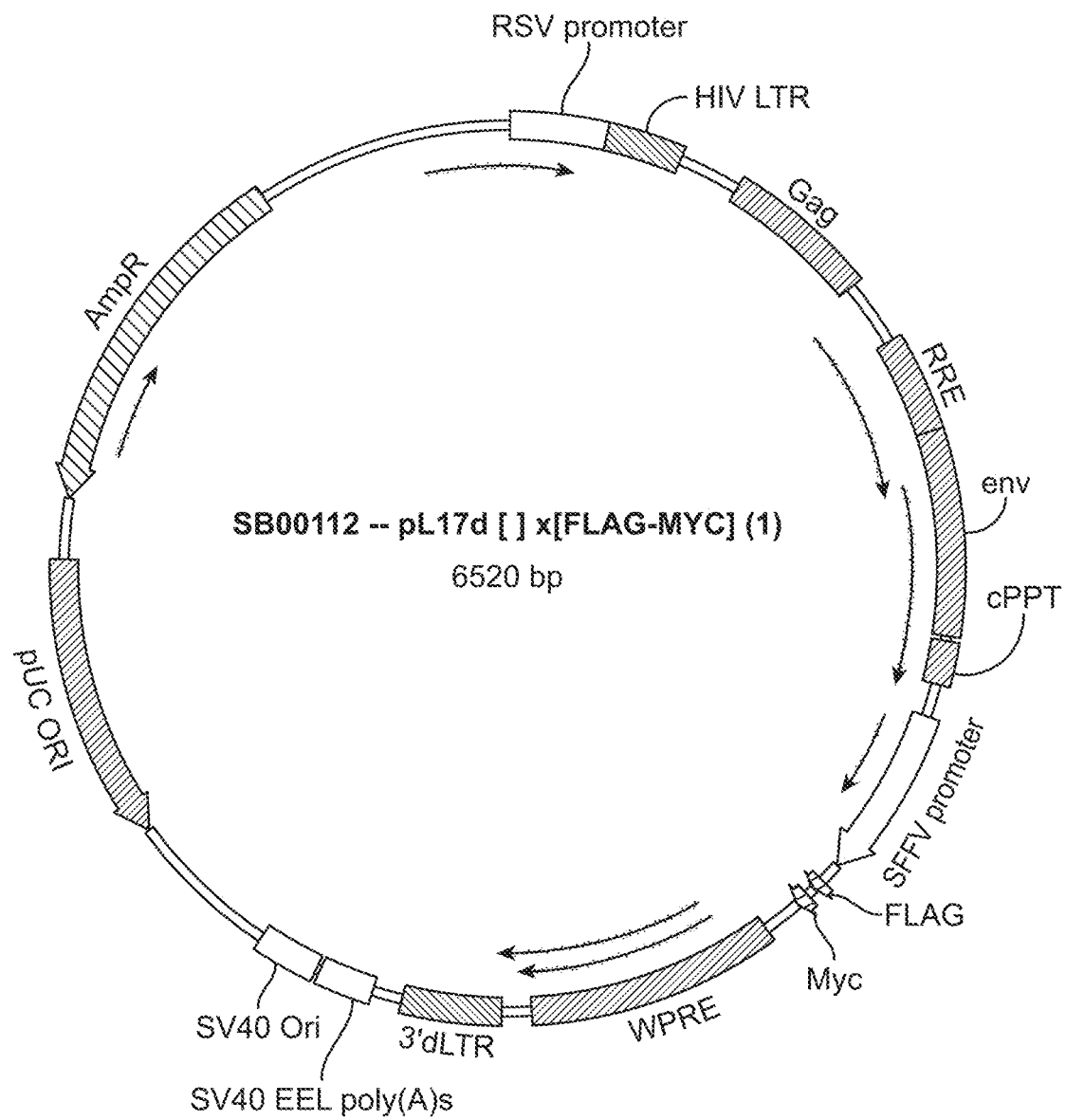
FIG. 31 shows the vector map of pL17D.

Cytokine expression cassettes were cloned into a pL17D, the vector map of which is shown in FIG. 31 with salient features annotated; e.g., a SFFV promoter; a FLAG and MYC epitope tag; LTRs; etc.

Lentiviral Transduction

Murine MSCs were seeded in 6-well plates and infected when cells were 50% confluent. Virus was added at the appropriate MOI and incubated for 3 hours to transduce cells. Following infection, fresh media was added to the cells.

Human MSCs were transduced following the exemplary protocol below:
1. 200,000 human MSCs were plated in each well of 6-well plate, in 2 mL xeno-free human MSC media.
2. After 2 hours, the media was removed and replaced with 1 mL of PBS.
3. Appropriate amount of virus was added to each well, as indicate by MOI below, and cells were incubated with virus for 3 hours with occasional rocking, at 37 degrees and 5% CO2.
4. Virus was removed after 3 hours, plates were washed with media, and then the MSCs were cultured normally (as noted above) until cells reached senescence. Cells were counted at each passage, so that total cell numbers could be determined.

Example 7: MSC Combination Cytokine Therapy (CT26)

In the following example, balb/c mMSCs were engineered to express various cytokines using the lentiviral transduction method described in Example 6.

Figure 32:
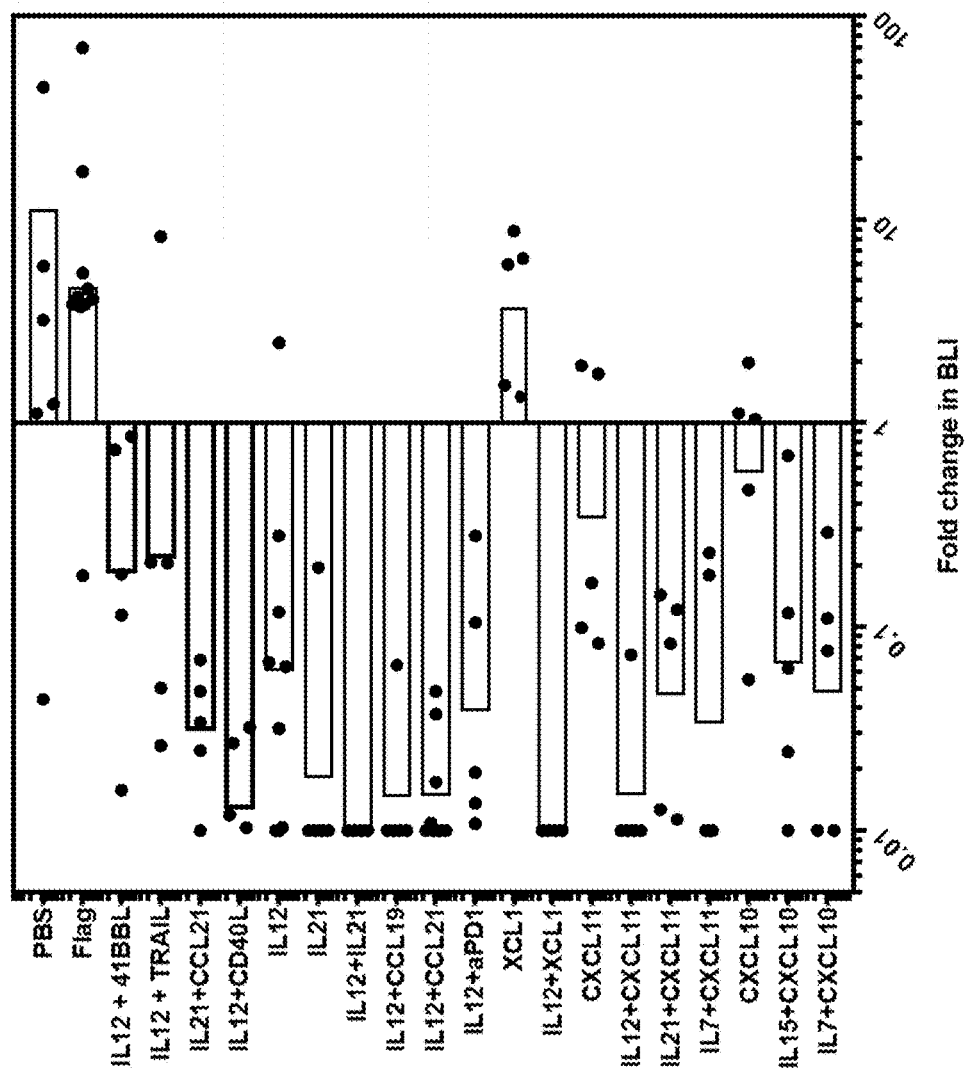
FIG. 32 shows MSCs engineered to express different effector molecules either alone or in combination and their efficacy in reducing CT26 tumor burden in an IP tumor model as assessed by BLI levels.

CT26 tumor cells ($5 \times 10^4$ cells in 100 µl) modified to constitutively express luciferase enzyme (Cat no: CL043, Lot no: CL-IM147 Imanis Life Sciences) were injected into the peritoneal space of immunocompetent balb/c (age 6-8 weeks). One week after tumor implantation, tumor burden was measured by luciferase imaging (BLI) using an AMI imager. Mice were randomized into treatment groups and treated with intraperitoneally delivered mMSCs ($1 \times 10^6$) expressing effector molecules as single agent or as a combination of mMSCs to deliver a combination of agents. MSC-Flag-Myc and PBS were used as a negative control. Tumor burden was assessed at day 12 and 17. Bioluminescent signal (photons/second) was normalized for each individual mouse relative to the initial signal (pre-treatment). Reduction of BLI signal by more than 100 fold (0.01) was equivalent to a complete cure (no tumor was evident at the time of necropsy). As shown in FIG. 32, MSCs engineered to express different effector molecules either alone or in combination demonstrated efficacy in reducing CT26 tumor burden in an IP tumor model as assessed by BLI levels.

Example 8: MSC Combination Cytokine Therapy (B16F10)

In the following example, C57BL/6 mMSCs were engineered to express various cytokines using the lentiviral transduction method described in Example 6.

Figure 33:
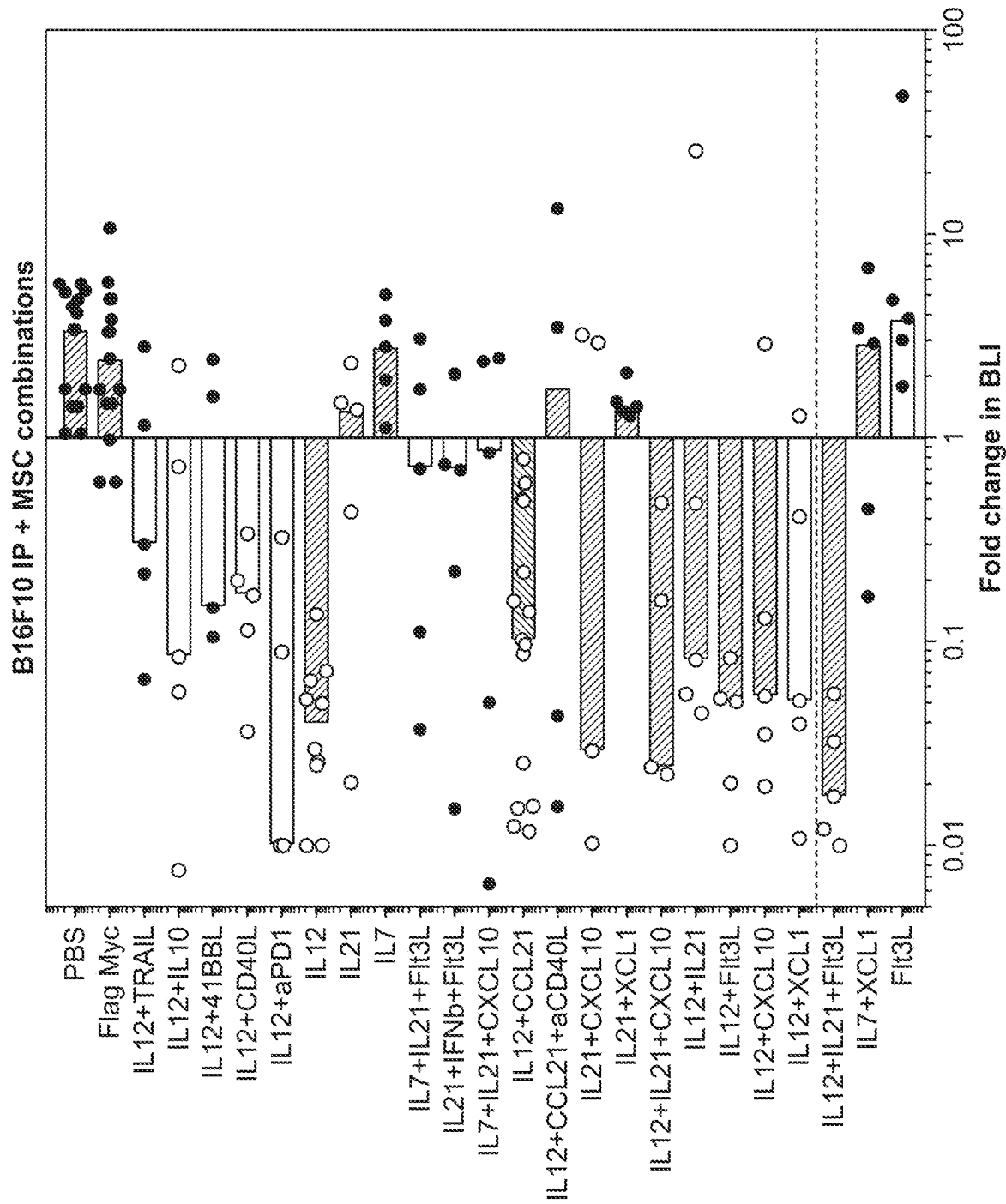
FIG. 33 shows MSCs engineered to express different effector molecules either alone or in combination and their efficacy in reducing B16F10 tumor burden in an IP tumor model as assessed by BLI levels.

B16F10 tumor cells ($5 \times 10^4$ cells in 100 µl) modified to constitutively express luciferase enzyme (B16F10-Fluc-Puro Cat #:CL052, lot #: CL-IM150 Imanis Life Sciences) were injected into the peritoneal space of immunocompetent C57BL/6 (age 6-8 weeks). One week after tumor implantation, tumor burden was measured by luciferase imaging (BLI) using an AMI imager. Mice were randomized into treatment groups and treated with intraperitoneally delivered mMSCs ($1 \times 10^6$) expressing effector molecules as single agent or as a combination of mMSCs to deliver a combination of agents. MSC-Flag-Myc and PBS were used as a negative control. Tumor burden was assessed at day 12 and 17. Bioluminescent signal (photons/second) was normalized for each individual mouse relative to the initial signal (pre-treatment). Reduction of BLI signal by more than 100 fold (0.01) was equivalent to a complete cure (no tumor was evident at the time of necropsy). As shown in FIG. 33, MSCs engineered to express different effector molecules either alone or in combination demonstrated efficacy in reducing B16F10 tumor burden in an IP tumor model as assessed by BLI levels.

Example 9: Engineered Human MSC Cytokine Production

Figure 34:
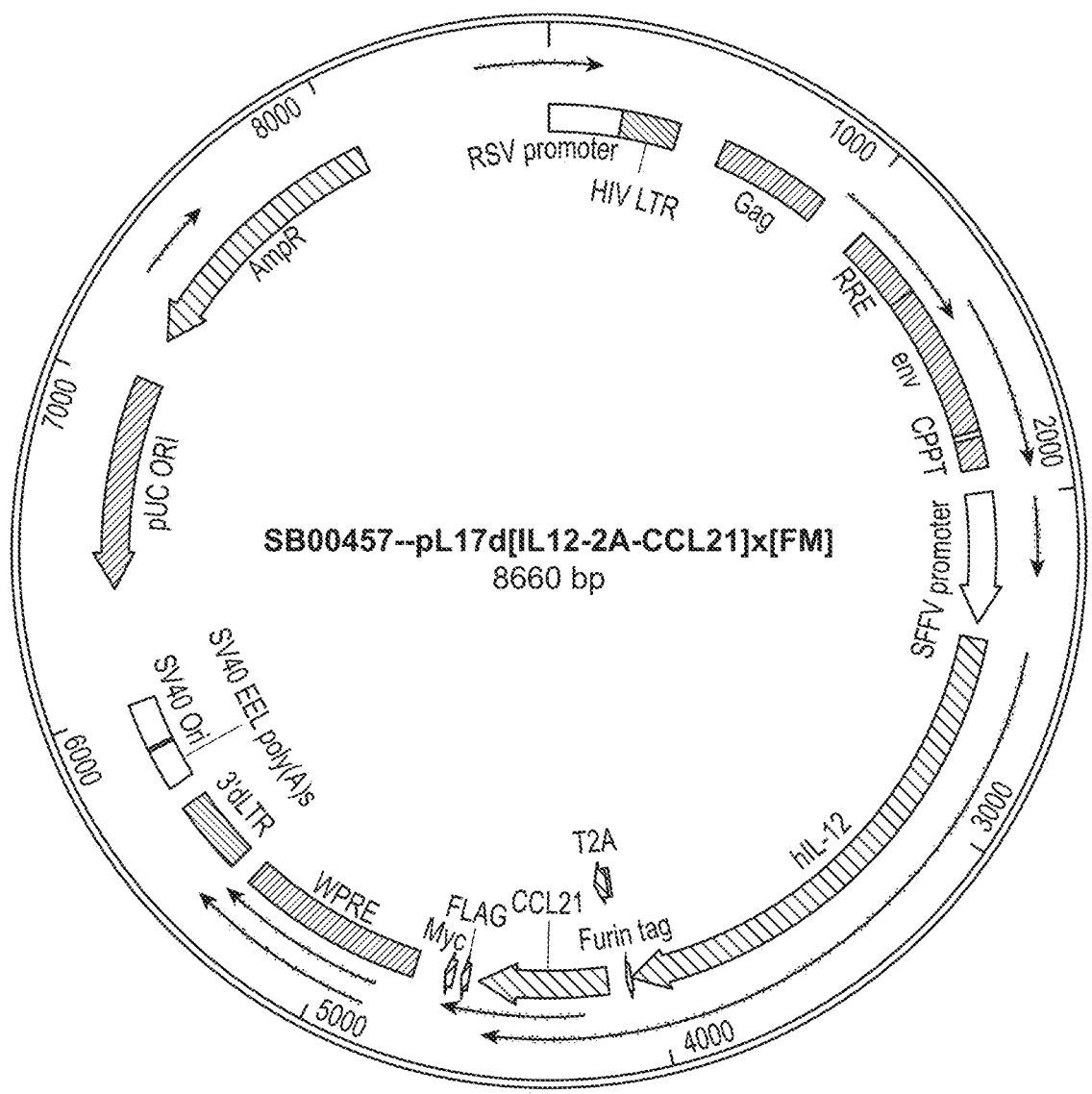
FIG. 34 shows the lentiviral expression vector map for expression of human IL12 (p70) and human CCL21a from a single lentiviral expression vector.

In the following example, bone-marrow derived hMSCs (derived from 3 human volunteer healthy donors) were engineered to express human IL12 (p70) and human CCL21a from a single lentiviral expression vector using the lentiviral transduction method described in Example 6. The lentiviral expression vector (schematic vector map of which is shown in FIG. 34) used a 2A ribosome skipping elements to express both cytokines from a single transcript.

Figure 35A:
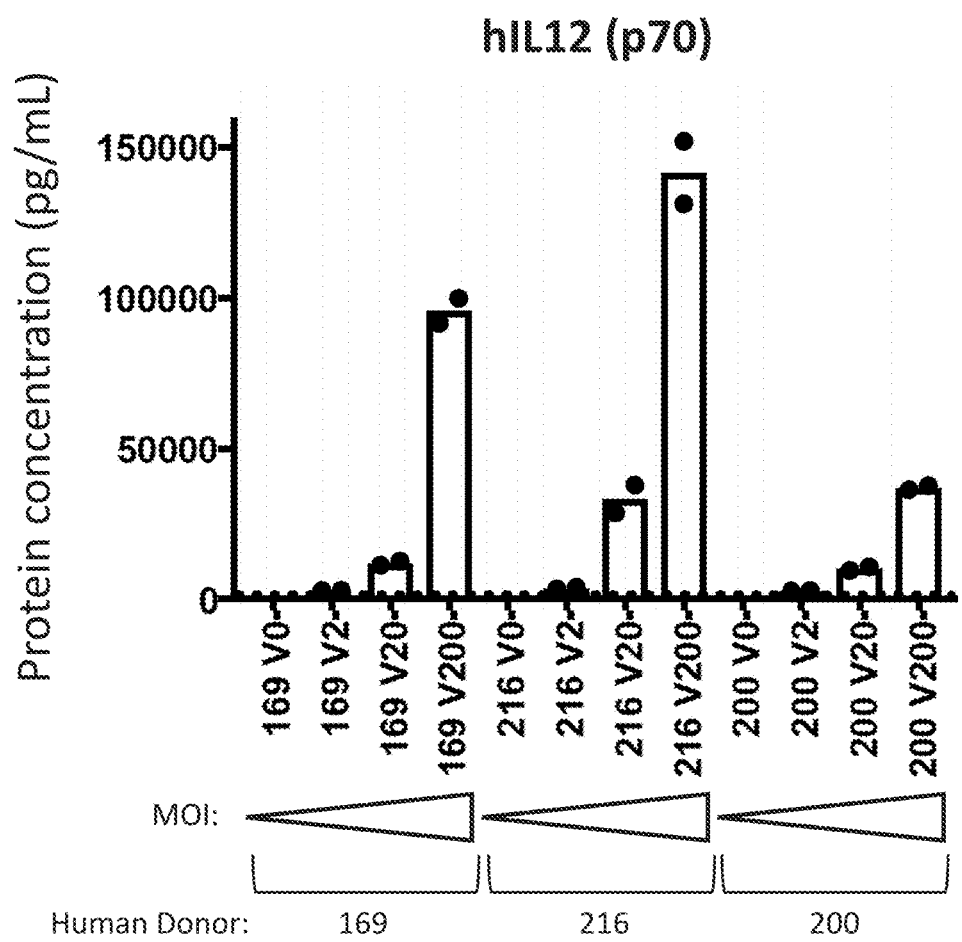
FIG. 35A shows production by engineered hMSCs of hIL12, as assessed by cytokine ELISA.
Figure 35B:
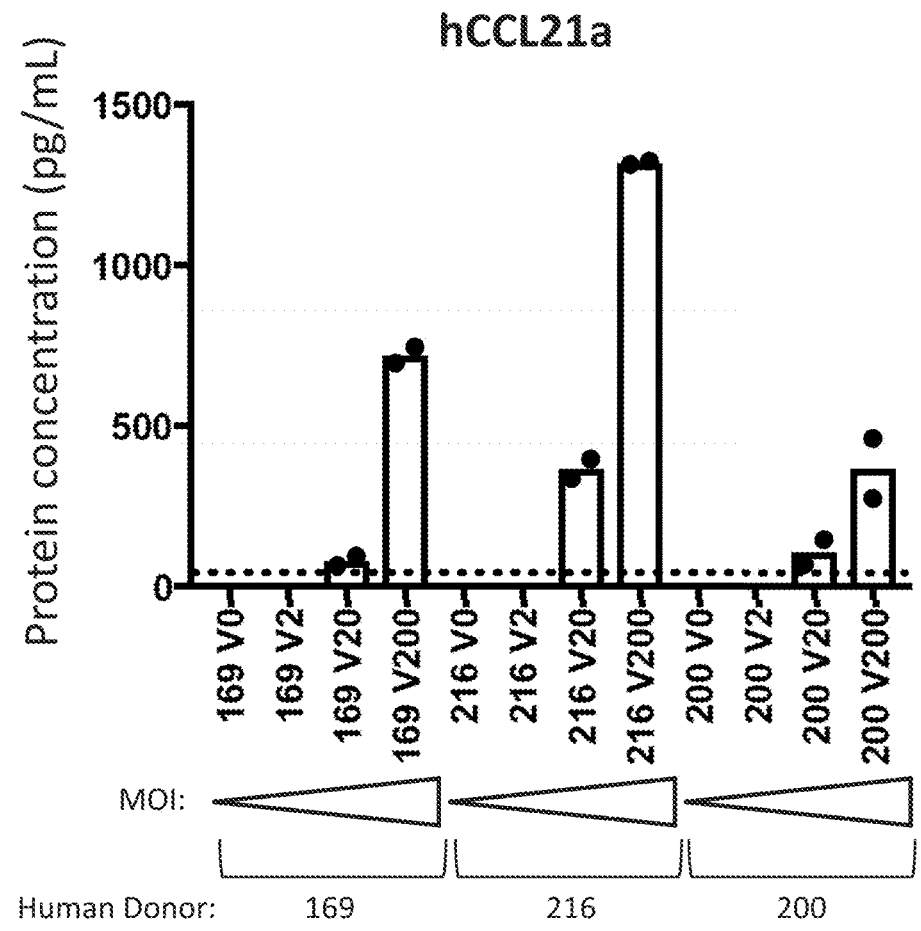
FIG. 35B shows production by engineered hMSCs of hCCL21a, as assessed by cytokine ELISA.

As shown in FIG. 35, engineered hMSCs were able to produce both hIL12 (FIG. 35A) and hCCL21a (FIG. 35B), as assessed by cytokine ELISA. Notably, protein secretion was correlated with the amount of viral particles (MOI) used during the transduction of MSCs.

Example 10: Engineered Human MSC Functional Assessment

Figure 36A:
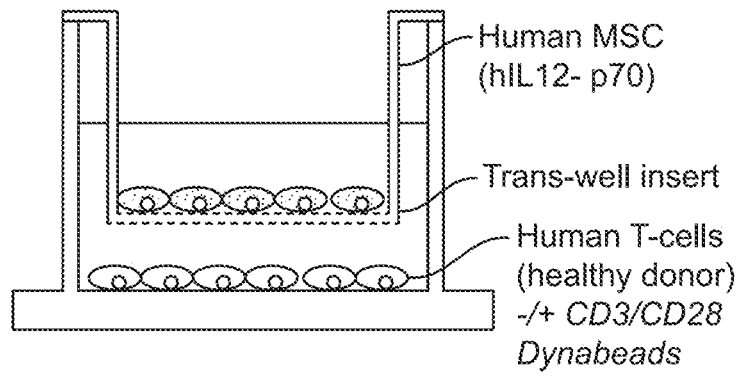
FIG. 36A shows a schematic of a transwell assay for assessing functional T cell modulation by hIL12 produced from MSCs.
Figure 36B:
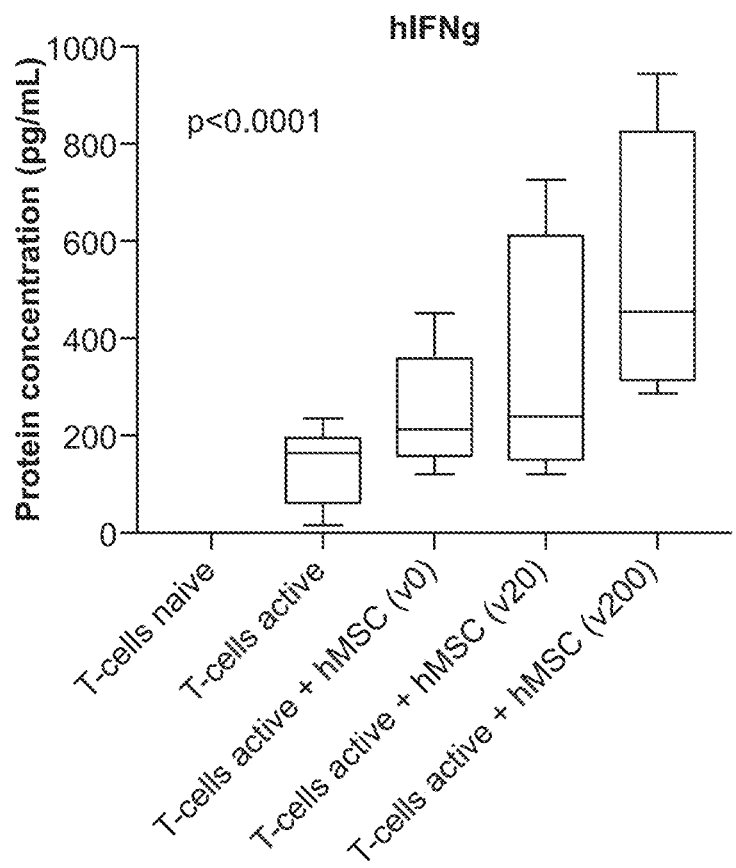
FIG. 36B shows a transwell assay demonstrating functional T cell modulation by hIL12 produced from MSCs as assessed by IFNγ production.

In the following example, bone-marrow derived hMSCs were engineered to express human IL12 (p70) using the lentiviral transduction method described in Example 6. Engineered hMSCs were co-cultured into 0.4 μm transwell inserts with human T-cells isolated from healthy blood donors (a schematic representation of the transwell assay is shown in FIG. 36A). To assess IL12 induced Th1 polarization on activated naïve T-cells, IFNγ production by T-cells was measured by ELISA on the supernatant collected from the lower compartment (T-cells). As shown in FIG. 36B, IFNγ production was increased in a MOI dose-dependent manner by co-culturing CD3 T-cells with hMSCs expressing IL12p70.

Example 11: MSCs Home to Tumors in an IP Model

Figure 37A:
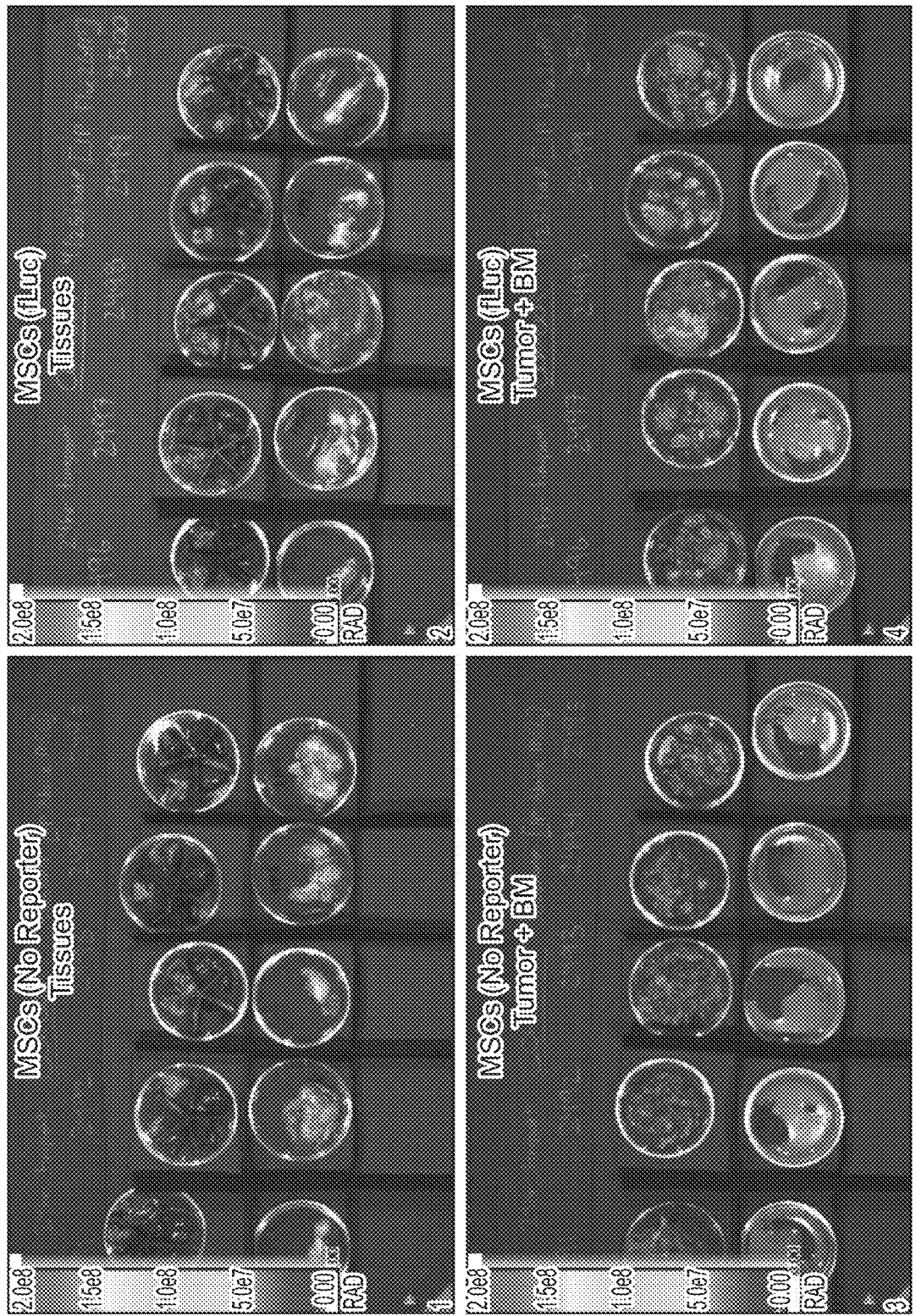
FIG. 37A shows homing to tumors by MSCs in IP tumor-bearing mice tumors as assessed by bioluminescence imaging.
Figure 37B:
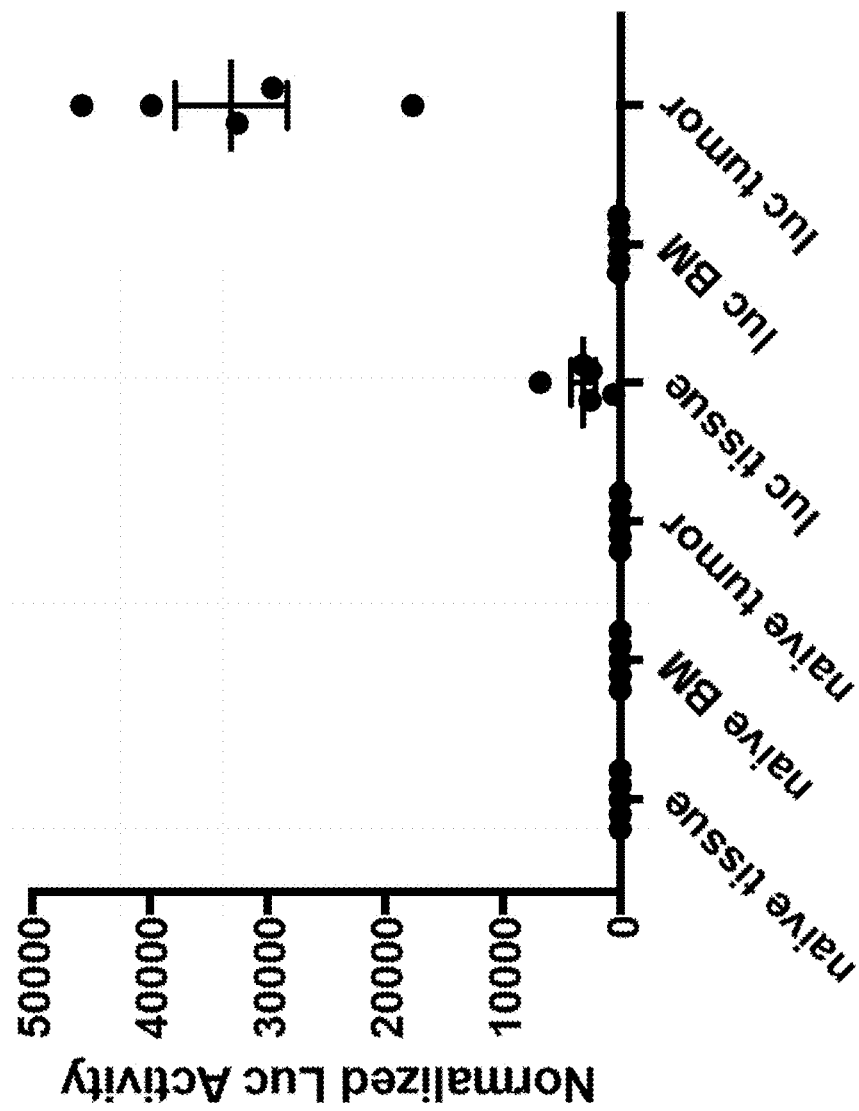
FIG. 37B shows homing to tumors by MSCs in IP tumor-bearing mice tumors as assessed by bioluminescence imaging.
Figure 37C:
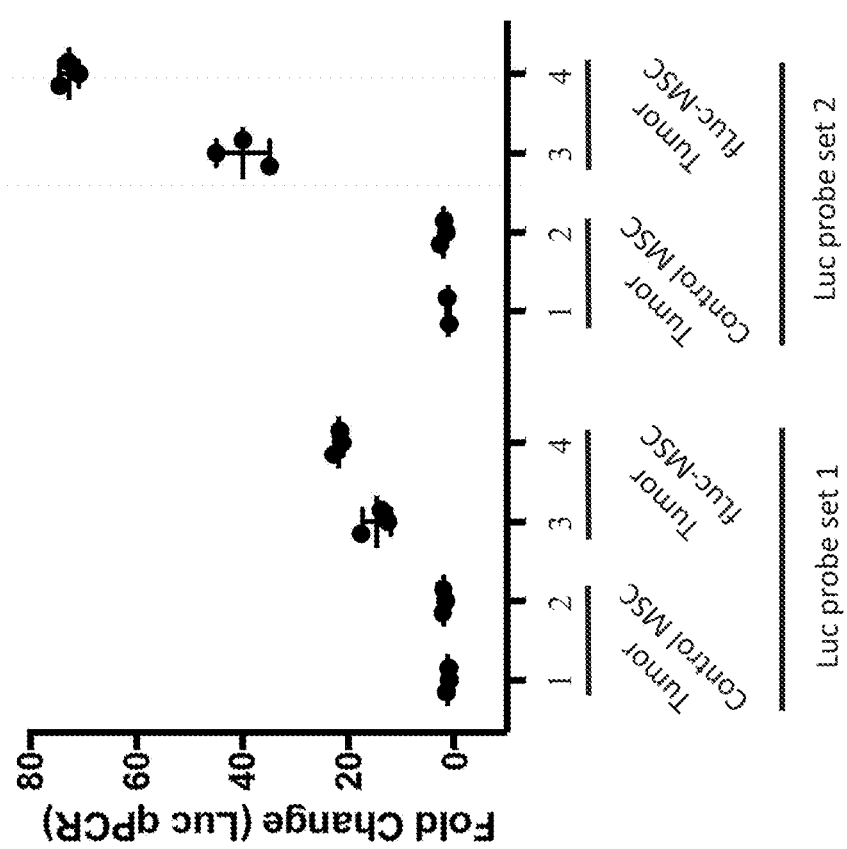
FIG. 37C shows homing to tumors by MSCs in IP tumor-bearing mice tumors as assessed by bioluminescence imaging.
Figure 37D:
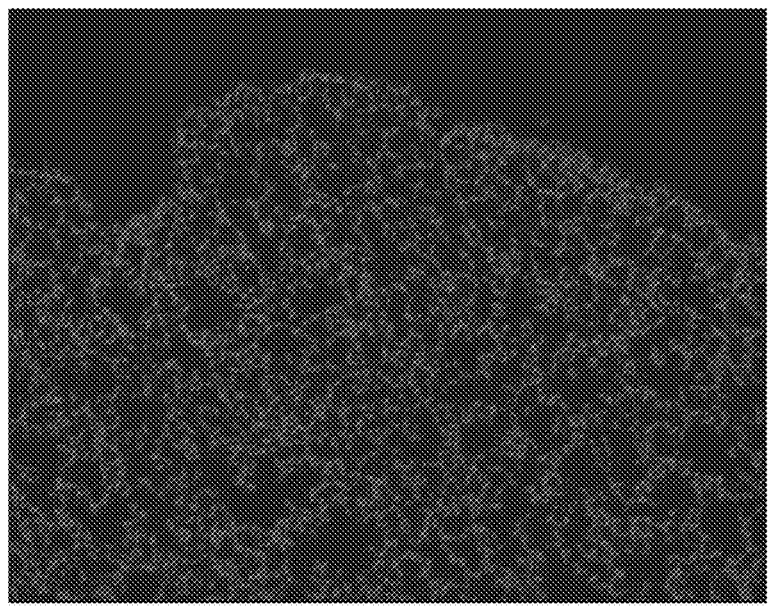
FIG. 37D shows homing to tumors by MSCs in IP tumor-bearing mice tumors as assessed by bioluminescence imaging.
Figure 37D:
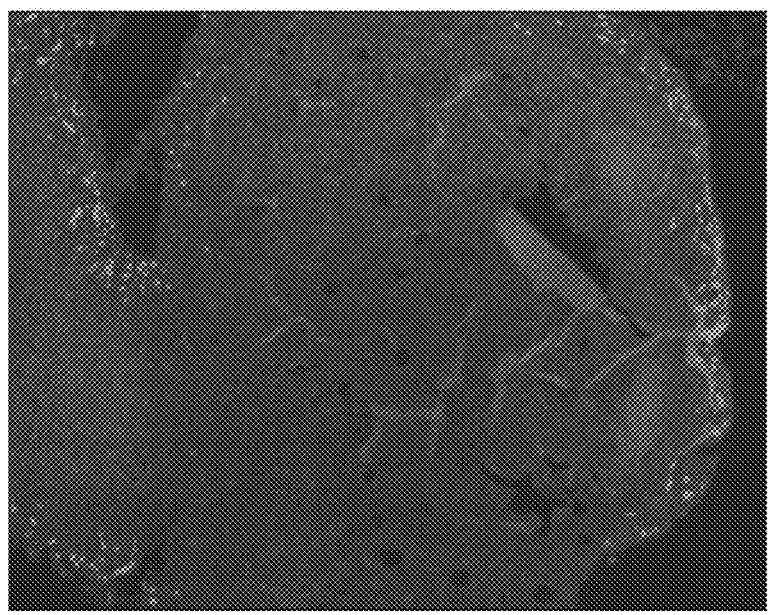

In the following example, balb/c MSCs ($2 \times 10^6$ cells) expressing fLUC were injected IP into CT-26 IP tumor-bearing mice. Mice were euthanized and tissues were collected 24 hours after injection. As shown in FIG. 37, fLUC-MSCs were significantly enriched in the tumors as detected by bioluminescence imaging (images shown in FIG. 37A, quantification of images in FIG. 37B), quantitative real time PCR (FIG. 37C), and fluorescence microscopy against firefly luciferase (FIG. 37D).

Figure 37E:
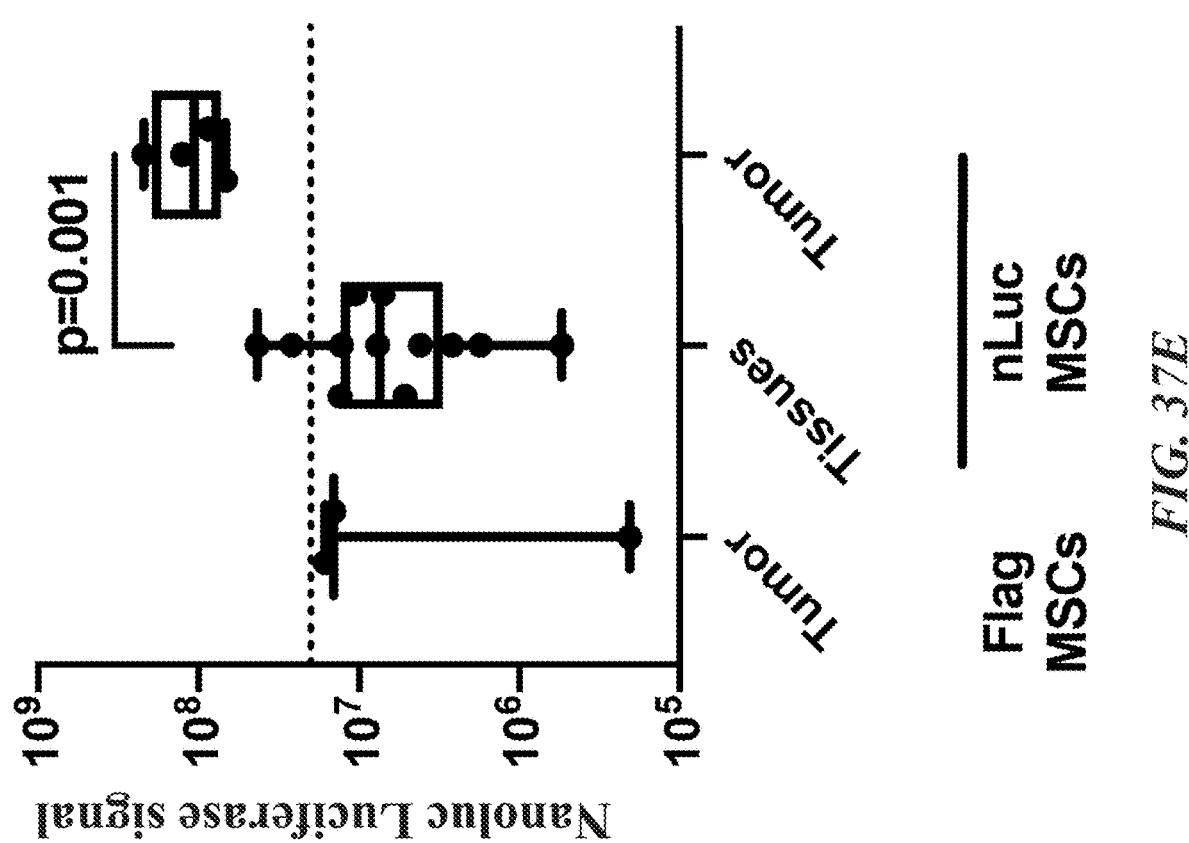
FIG. 37E shows homing to tumors by MSCs in IP tumor-bearing mice tumors as assessed by bioluminescence imaging.

Additionally, C57Bl/6 mice were implanted with $5 \times 10^4$ B16F10-fLUC cells IP. 7 days after tumor implantation, $1 \times 10^6$ C57Bl/6 murine BM-MSCs engineered to express Nanoluc-EGFP were injected IP. Mice were euthanized at 24 hours post injection of MSCs and peritoneal organs (stomach, kidney, liver, colon, spleen, pancreas, omentum/tumor, ovaries and Fallopian tubes) were imaged ex-vivo for nano-luc signaling (NanoGlo Substrate Kit, Vendor: Promega, Catalog No.: N1110). As shown in FIG. 37E, murine MSC nanoluc signal was preferentially enriched in the tumor compared to the other organs in the peritoneal cavity in a B16F10 tumor model.

Example 12: IL12 Producing MSCs Reduce CT26 Tumor Burden in an IP Model

In the following example, balb/c mMSCs were engineered to express murine IL12p70 using the lentiviral transduction method described in Example 6.

Figure 38:
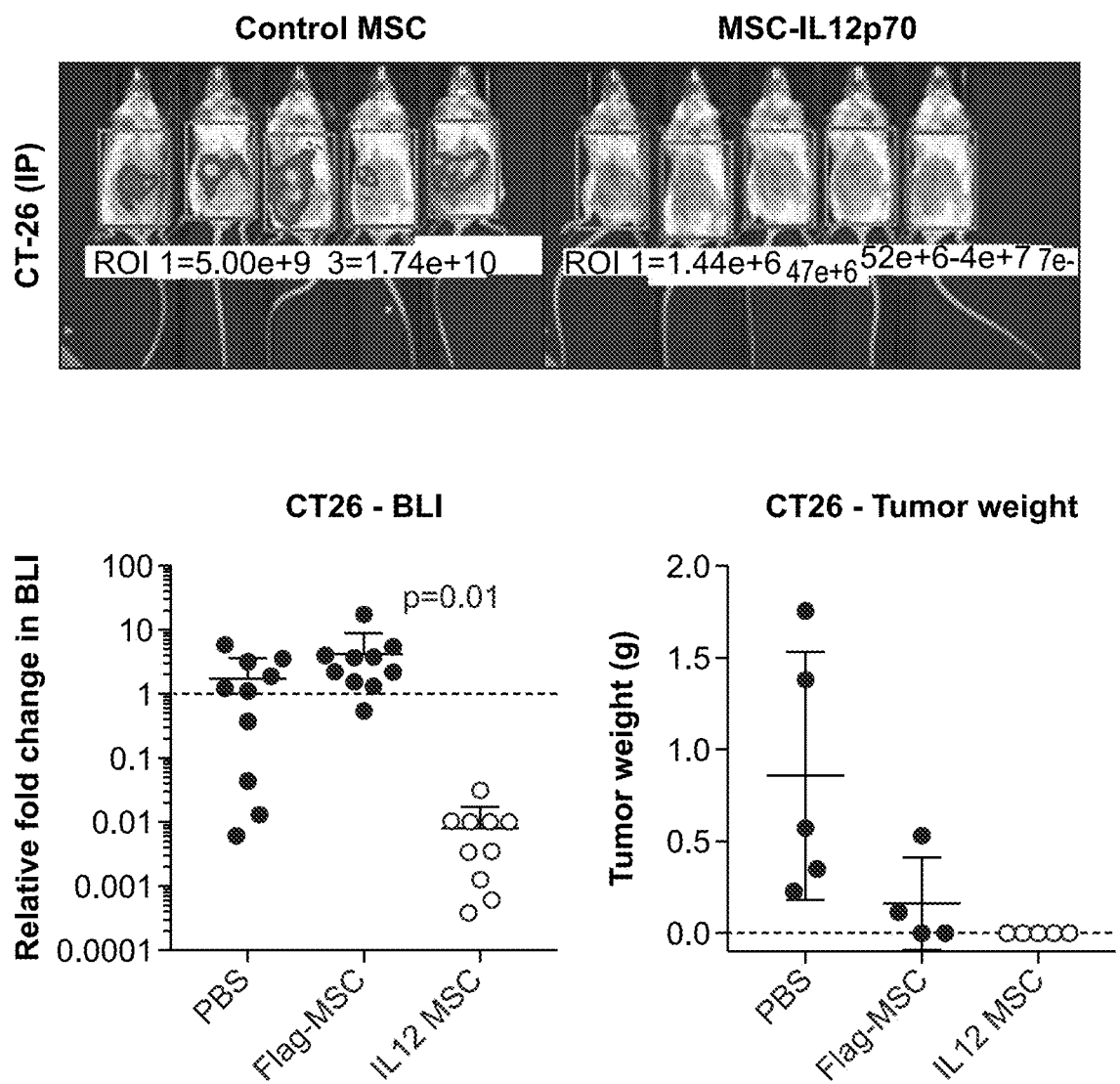
FIG. 38 shows IL12p70 expressing MSCs leading to reduction in tumor burden as assessed by BLI (top panels—images; and bottom left panel—individual mice in each treatment and the mean±SEM for each treatment group) and a complete elimination of detectable intraperitoneal tumors by tumor weight for individual mice in each treatment, and the mean±SEM for each treatment group (bottom right panel) in a CT26 IP model.

CT26 tumor cells ($5 \times 10^4$ cells in 100 μl) modified to constitutively express luciferase enzyme (Cat no: CL043, Lot no: CL-IM147 Imanis Life Sciences) were injected into the peritoneal space of immunocompetent balb/c (age 6-8 weeks). One week after tumor implantation, tumor burden was measured by luciferase imaging (BLI) using an AMI imager. Mice were randomized into treatment groups and treated with intraperitoneally delivered mMSCs ($1 \times 10^6$ cells) expressing IL12p70. MSC-Flag-Myc and PBS were used as a negative control. As shown in FIG. 38, IL12p70 expressing MSCs led to reduction in tumor burden as assessed by BLI (top panels and bottom left panel) and a complete elimination of detectable intraperitoneal tumors by tumor weight (bottom right panel) in a CT26 model.

Example 13: IL12 Producing MSCs Reduce B16F10 Tumor Burden in an IP Model

In the following example, C57BL/6 mMSCs were engineered to express murine IL12p70 using the lentiviral transduction method described in Example 6.

Figure 39:
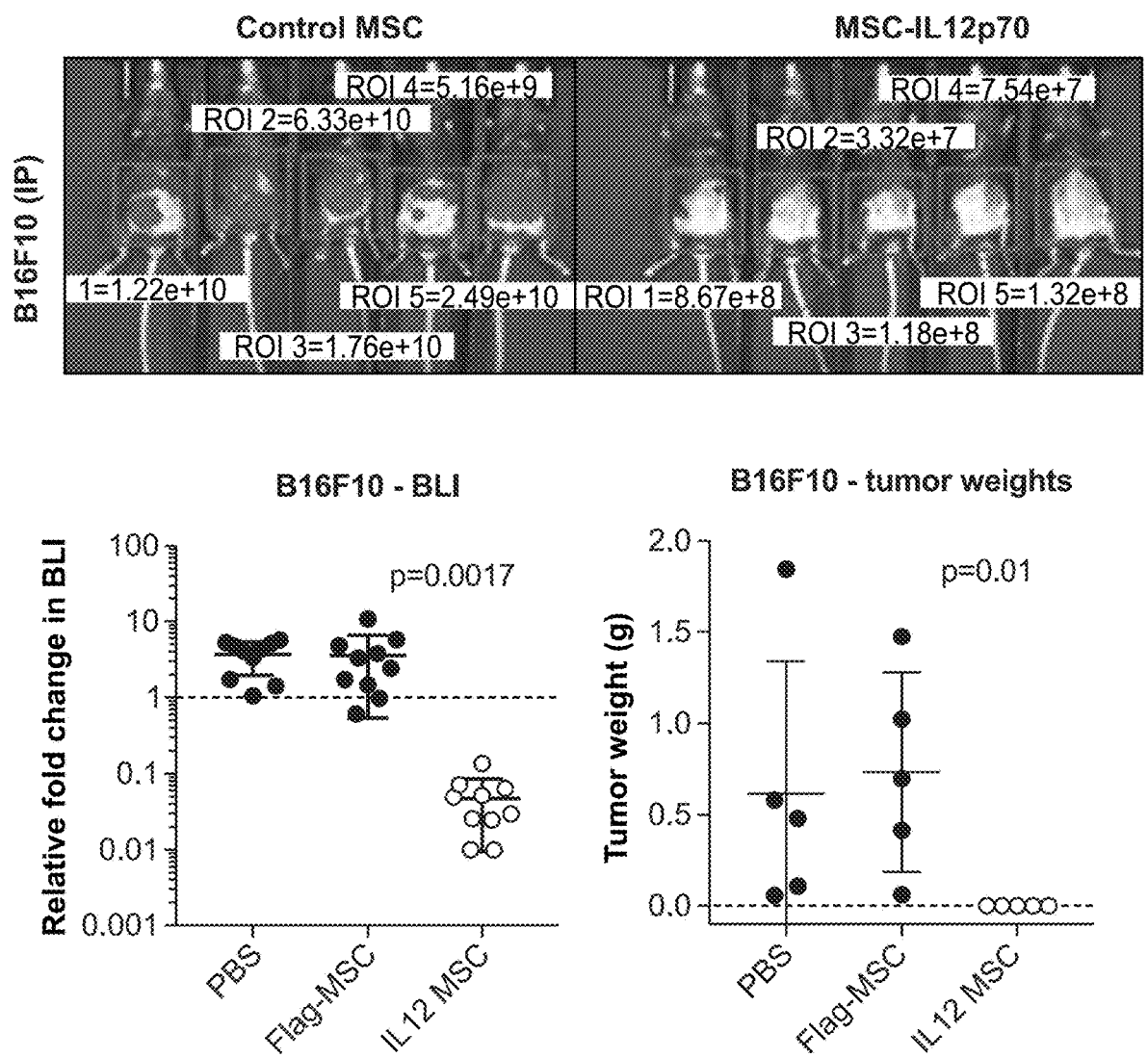
FIG. 39 shows IL12p70 expressing MSCs leading to reduction in tumor burden as assessed by BLI (top panels—images; and bottom left panel—individual mice in each treatment and the mean±SEM for each treatment group) and a complete elimination of detectable intraperitoneal tumors by tumor weight for individual mice in each treatment, and the mean±SEM for each treatment group (bottom right panel) in a B16F10 IP model.

B16F10 tumor cells ($5 \times 10^4$ cells in 100 μl) modified to constitutively express luciferase enzyme (B16F10-Fluc-Puro Cat #:CL052, lot #: CL-IM150 Imanis Life Sciences) were injected into the peritoneal space of immunocompetent C57BL/6 (age 6-8 weeks). One week after tumor implantation, tumor burden was measured by luciferase imaging (BLI) using an AMI imager. Mice were randomized into treatment groups and treated with intraperitoneally delivered mMSCs $1 \times 10^6$ expressing IL12p70. MSC-Flag-Myc and PBS were used as a negative control. As shown in FIG. 39, IL12p70 expressing MSCs led to reduction in tumor burden as assessed by BLI (top panels and bottom left panel) and a complete elimination of detectable intraperitoneal tumors by tumor weight (bottom right panel) in a B16F10 model.

Example 14: MSCs Producing IL12 and CCL21a Reduce Tumor Burden and Prolong Survival in a CT26 IP Tumor Model In the following example, balb/c mMSCs were engineered to express murine IL12 (p70) and murine CCL21a from a single lentiviral expression vector. The lentiviral expression vector used a 2A ribosome skipping elements to express both cytokines from a single transcript using the lentiviral transduction method described in Example 6.

Figure 40A:
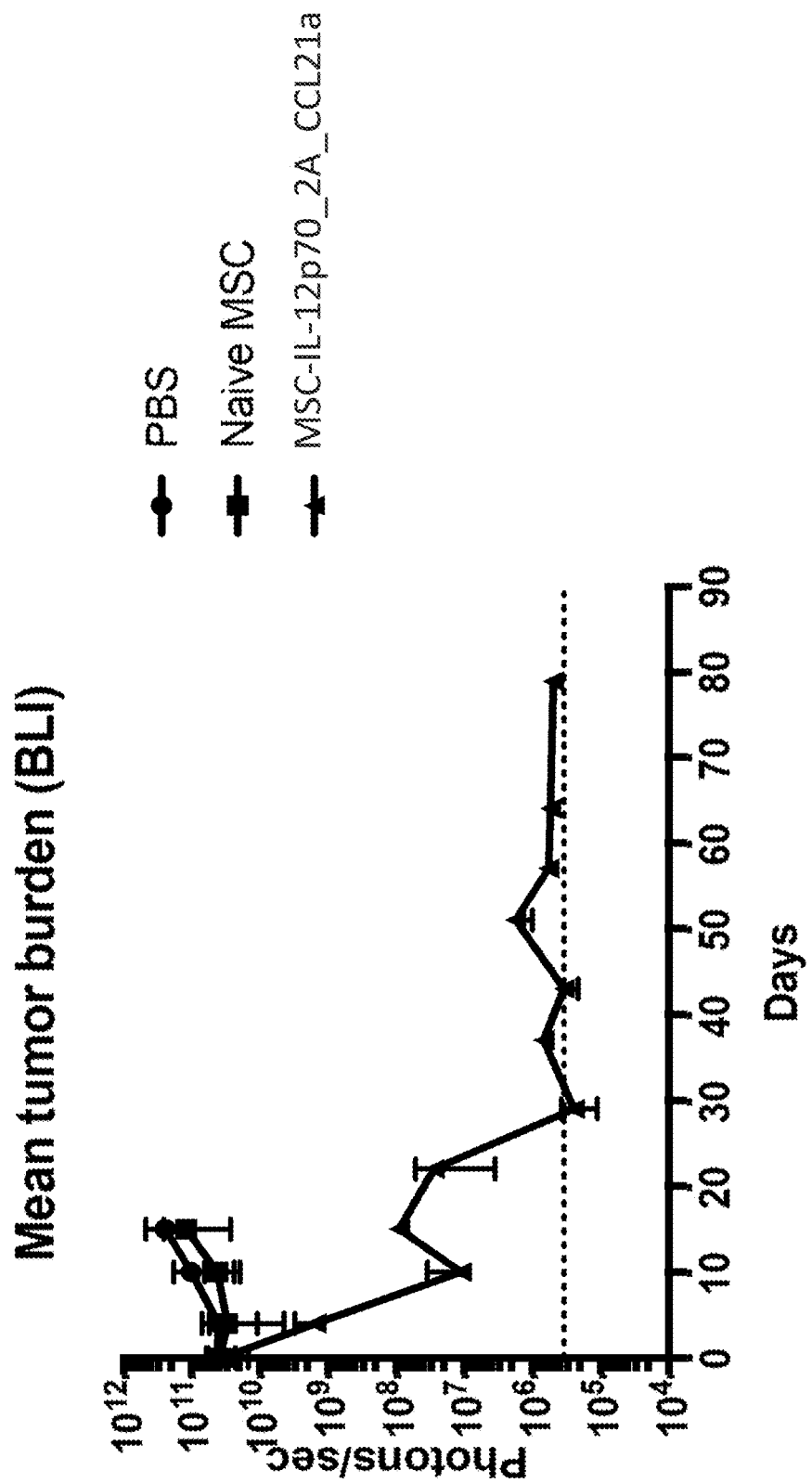
FIG. 40A shows IL12p70/CCL21a expressing MSCs leading to reduction in tumor burden as assessed by BLI in a CT26 IP model.
Figure 40B:
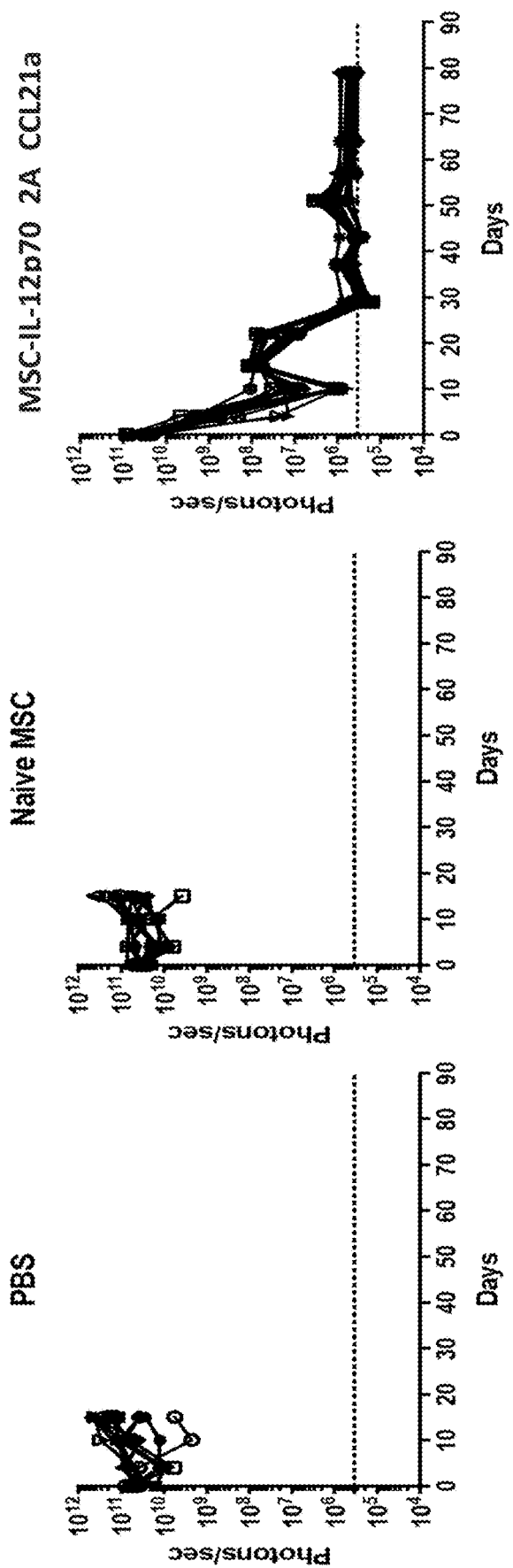
FIG. 40B shows IL12p70/CCL21a expressing MSCs leading to reduction in tumor burden as assessed by BLI in a CT26 IP model.
Figure 40C:
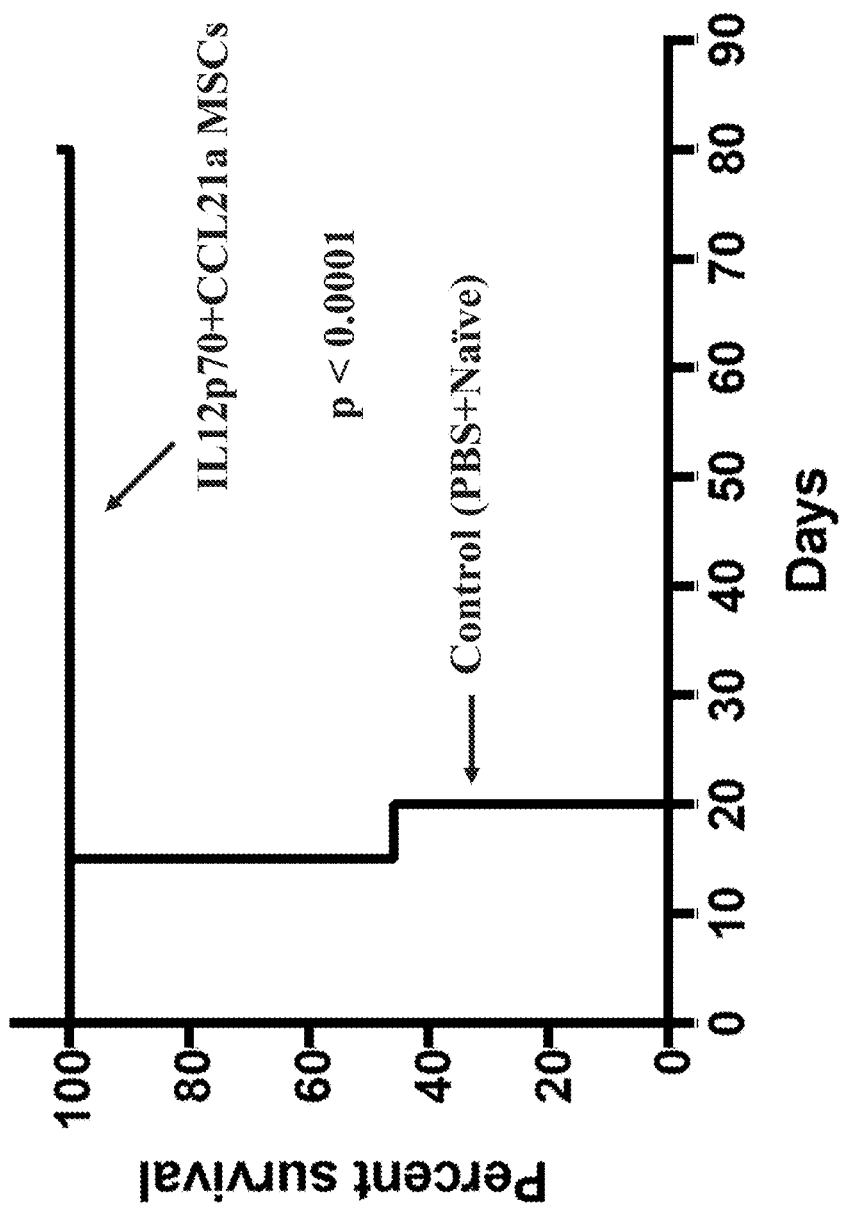
FIG. 40C shows treatment with IL12p70/CCL21a expressing MSCs led to prolonged survival (100% survival greater than 90 days), while control treated mice all died or were euthanized by Day 20.

CT26 tumor cells ($1 \times 10^6$ cells) modified to constitutively express luciferase enzyme (Cat no: CL043, Lot no: CL-IM147 Imanis Life Sciences) were injected into the peritoneal space of immunocompetent balb/c mice (age 6-8 weeks). One week after tumor implantation, tumor burden was measured by luciferase imaging (BLI) using an AMI imager. Mice were randomized into treatment groups and treated with intraperitoneally delivered mMSCs $1 \times 10^6$ expressing IL12p70 and CCL21a by the same MSC ("MSC-IL-12p70_2A_CCL21a"). MSC-Flag-Myc and PBS were used as a negative control. As shown in FIG. 40, IL12p70/CCL21a expressing MSCs led to reduction in tumor burden as assessed by BLI (top panels and bottom left panel) and a complete elimination of detectable intraperitoneal tumors by tumor weight (bottom right panel) in a CT26 model. FIG. 40A demonstrates the mean tumor burden as assessed by BLI for PBS treated (circle), MSC-Flag-Myc ("Naïve MSC" square), and IL12p70/CCL21a expressing MSCs (triangle). FIG. 40B demonstrates the tumor burden in individual mice as assessed by BLI for PBS treated, MSC-Flag-Myc ("Naïve MSC"), and IL12p70/CCL21a expressing MSCs (left, middle, and right panels, respectively). Notably, as shown in FIG. 40C, treatment with IL12p70/CCL21a expressing MSCs led to prolonged survival (100% survival greater than 90 days), while control treated mice all died or were euthanized by Day 20.

Example 15: MSCs Producing IL12 and IL21 Reduce Tumor Burden and Prolong Survival in a B16F10 IP Tumor Model In the following example, C57BL/6 mMSCs were engineered to express murine IL12 (p70) or murine IL21 (i.e., each MSC engineered to express only a single agent) using the lentiviral transduction method described in Example 6.

Figure 41:
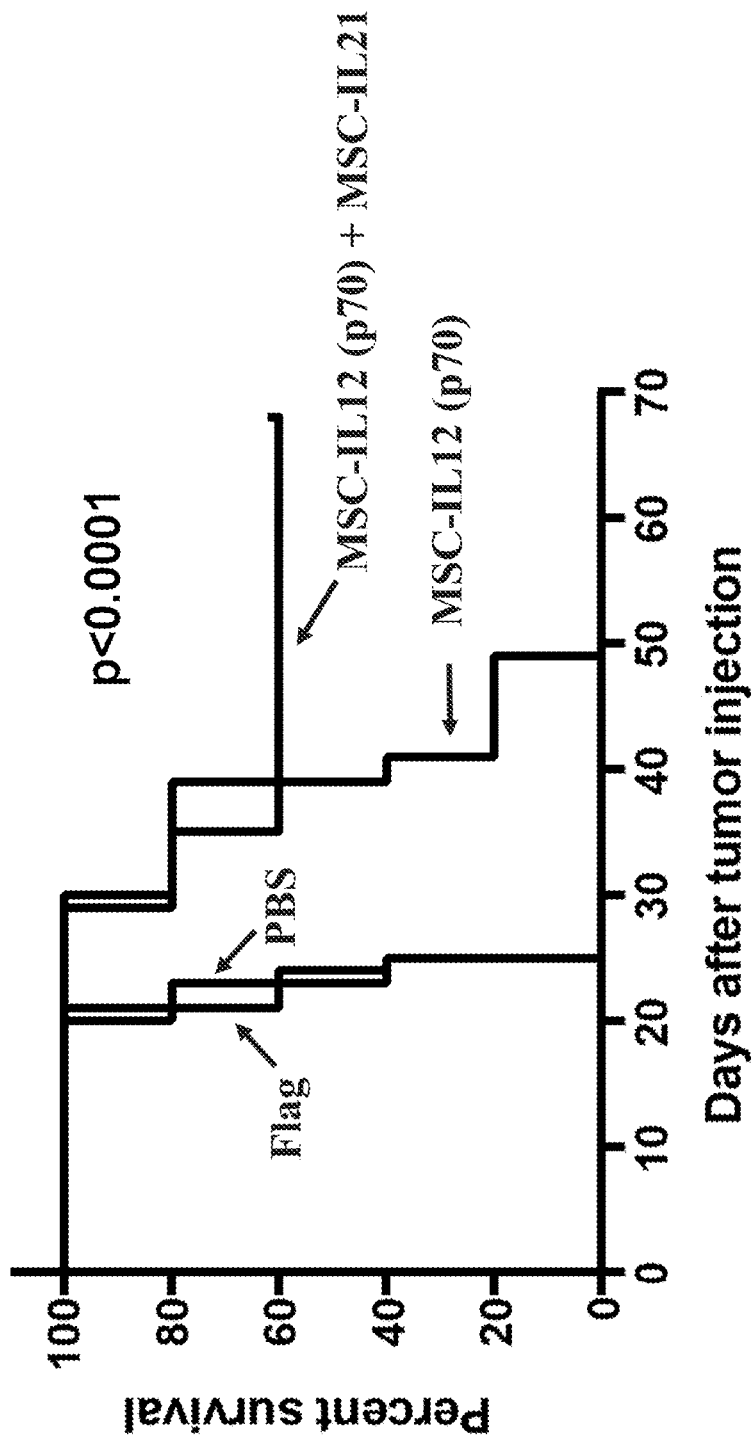
FIG. 41 shows treatment with IL12p70 expressing MSCs led to prolonged survival.

B16F10 tumor cells ($5 \times 10^4$ cells in 100 μl) modified to constitutively express luciferase enzyme (B16F10-Fluc-Puro Cat #:CL052, lot #: CL-IM150 Imanis Life Sciences) were injected into the peritoneal space of immunocompetent C57BL/6 (age 6-8 weeks). One week after tumor implantation, tumor burden was measured by luciferase imaging (BLI) using an AMI imager. Mice were randomized into treatment groups and treated with intraperitoneally delivered mMSCs (1×10⁶ cells) expressing IL12p70 in combination with mMSCs (1×10⁶ cells) expressing IL21, or mMSCs (1×10⁶ cells) expressing IL12p70 alone. MSC-Flag-Myc and PBS were used as a negative control. As shown in FIG. 41, treatment with IL12p70 expressing MSCs led to prolonged survival relative to control treated mice but all mice still all died or were euthanized by Day 50. In contrast, treatment with IL12p70 expressing MSCs in combination with IL21 expressing MSCs led to prolonged survival relative to treatment with IL12p70 expressing MSCs (60% survival past 60 days). Thus, IL21 expression by MSCs enhanced the efficacy of IL12p70 expressing MSCs.

Example 16: Allogeneic MSCs Producing IL12 and CCL21a Reduce Tumor Burden and Prolong Survival in a CT26 IP Tumor Model In the following example, balb/c mMSCs (syngeneic) and C57BL/6 mMSCs (allogeneic) were engineered to express murine IL12 (p70) and murine CCL21a from a single lentiviral expression vector. The lentiviral expression vector used a 2A ribosome skipping elements to express both cytokines from a single transcript using the lentiviral transduction method described in Example 6.

Figure 1:
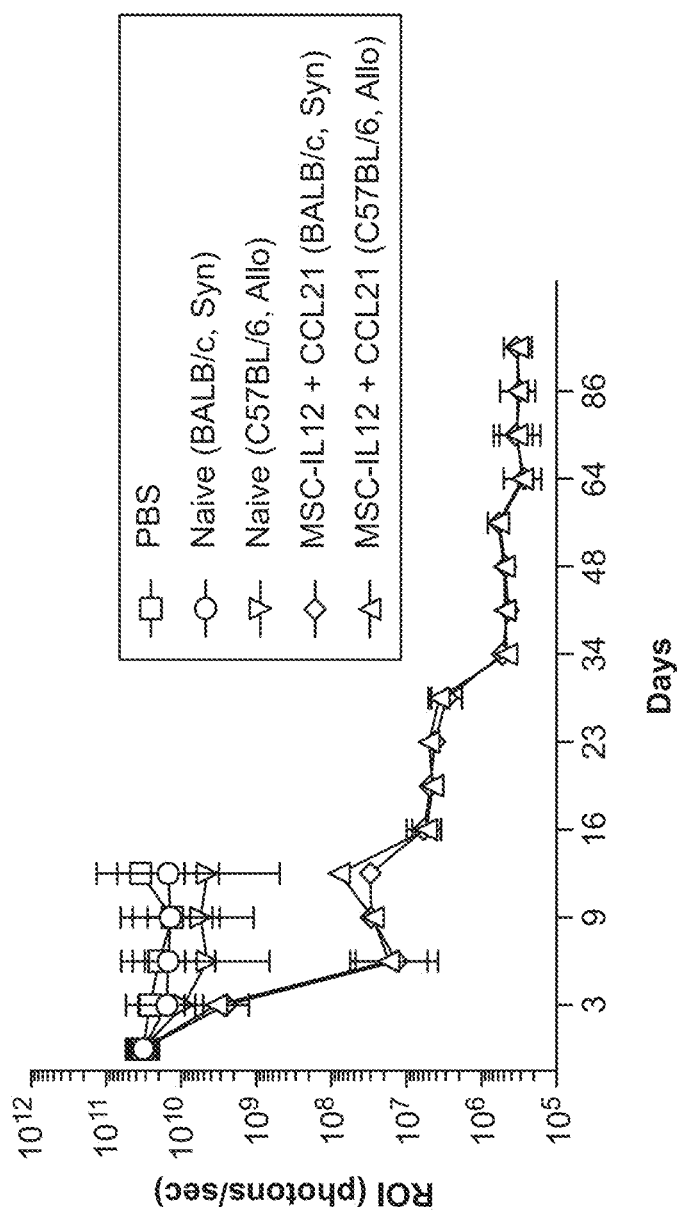
FIG. 1 shows treatment using syngeneic and allogeneic MSCs expressing IL12p70/CCL21a in a CT26 model.
Figure 2A:
FIG. 2A shows rechallenge of tumor free mice with CT26 tumors previously treated using syngeneic and allogeneic MSCs expressing IL12p70/CCL21a in a CT26 model.
Figure 2B:
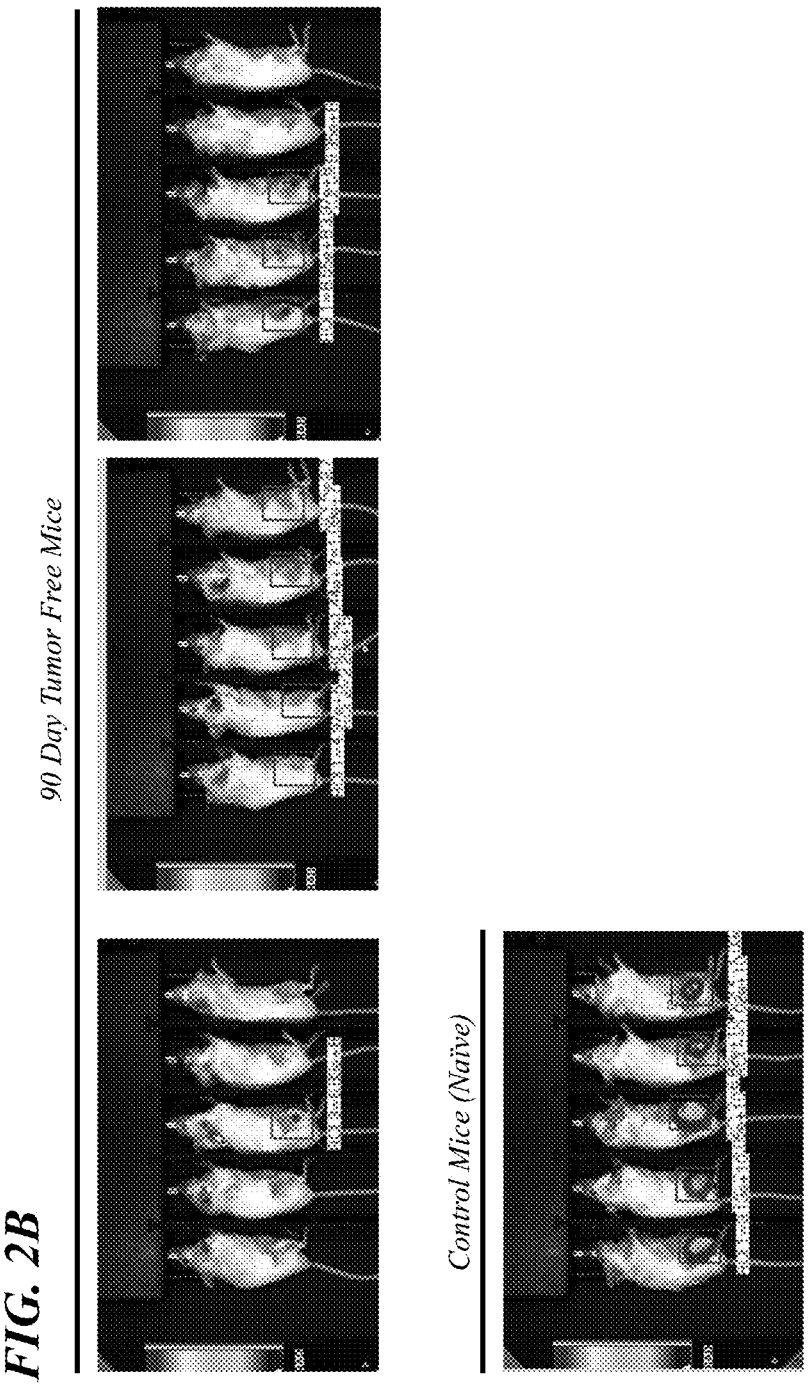
FIG. 2B shows rechallenge of tumor free mice with CT26 tumors previously treated using syngeneic and allogeneic MSCs expressing IL12p70/CCL21a in a CT26 model.

CT26 tumor cells (1×10⁶ cells) modified to constitutively express luciferase enzyme (Cat no: CL043, Lot no: CL-IM147 Imanis Life Sciences) were injected into the peritoneal space of immunocompetent balb/c mice (age 6-8 weeks). One week after tumor implantation, tumor burden was measured by luciferase imaging (BLI) using an AMI imager. Mice were randomized into treatment groups and treated with intraperitoneally delivered mMSCs (1×10⁶ cells) expressing IL12p70 and CCL21a by the same MSC ("MSC-IL12+CCL21"). Both balb/c control mMSCs (syngeneic) and C57BL/6 control mMSCs (allogeneic) were engineered to express MSC-Flag-Myc ("Naïve"). PBS was also used as a negative control. As shown in FIG. 1, both syngeneic and allogeneic MSCs expressing IL12p70/CCL21a led to reduction in tumor burden as assessed by BLI in a CT26 model, while control treatments did not. Additionally, mice that were previously treated with mMSCs expressing IL12p70 and CCL21a in both syngeneic and allogeneic models and were determined to be tumor free for 90 days were subsequently challenged with CT26 tumor cells (0.5×10⁶ cells in 100 µl PBS) implanted subcutaneously in the thigh, as schematized in FIG. 2A. As shown in FIG. 2B, tumor free mice rejected the tumor implant in contrast to naïve control mice where the tumor became established. Thus, treatment with MSCs expressing IL12p70/CCL21a led to prolonged tumor burden reduction as well as immunological memory.

Example 17: MSCs Producing IL12 and CCL21a Demonstrate Enhanced Growth Relative to Unmodified Cells In the following example, human MSCs from 3 different donors were engineered at different multiplicity of infections (MOIs) to express and secrete human IL-12 and human CCL21a from a single lentiviral expression vector. The lentiviral expression vector used a 2A ribosome skipping elements to express both cytokines from a single transcript using the lentiviral transduction method described in Example 6.

Figure 42A:
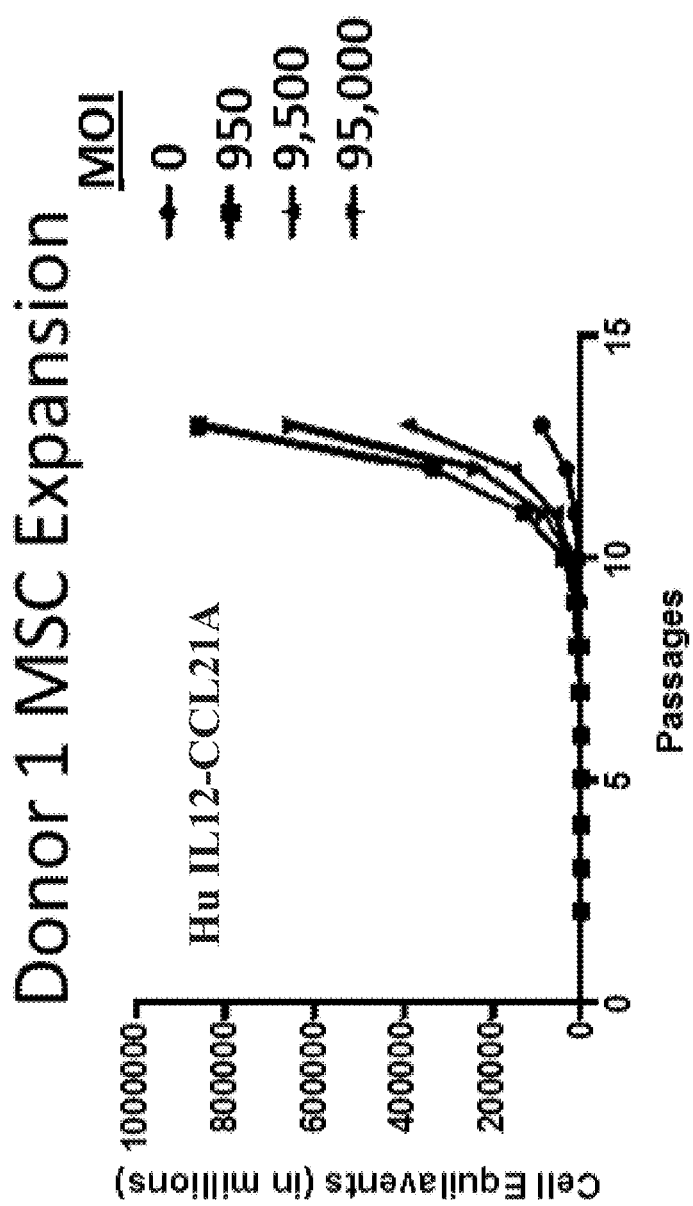
FIG. 42A shows relative growth of genetically engineered MSCs across different MOIs (95000, 9500, 950, or uninfected) in Donor 1.
Figure 42B:
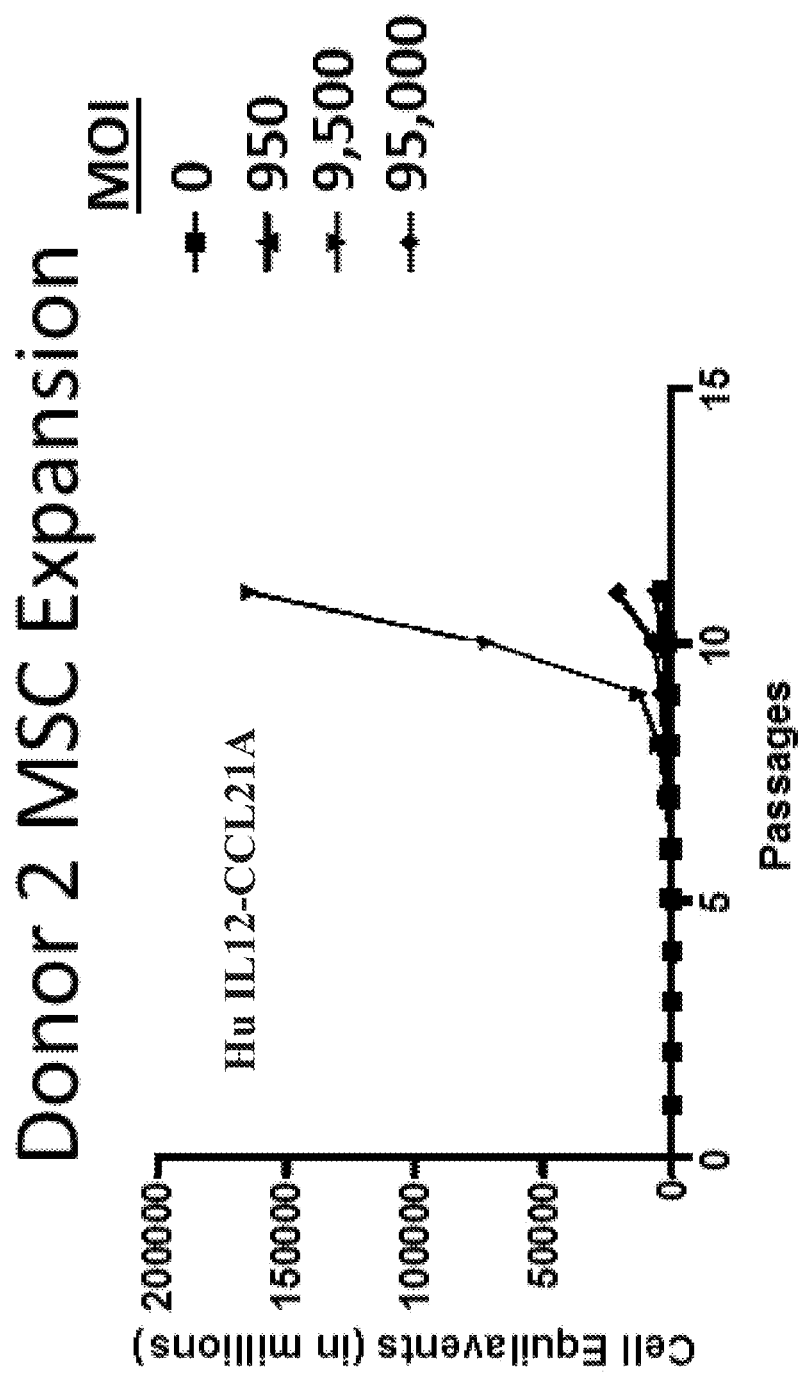
FIG. 42B shows relative growth of genetically engineered MSCs across different MOIs (95000, 9500, 950, or uninfected) in Donor 2.
Figure 42C:
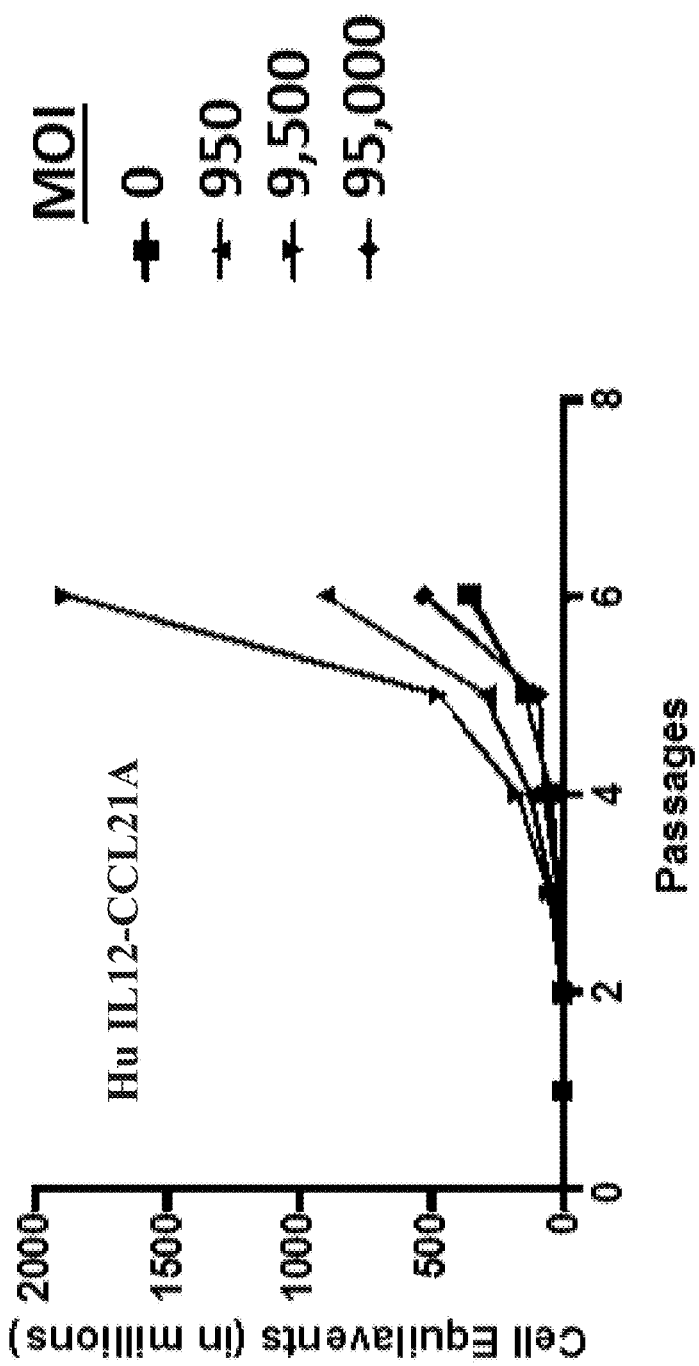
FIG. 42C shows relative growth of genetically engineered MSCs across different MOIs (95000, 9500, 950, or uninfected) in Donor 3.

As shown in FIG. 42, the genetically engineered MSCs (MOI=95000, 9500, or 950) exhibited enhanced cell expansion and growth compared to the non-genetically engineered human MSCs (MOI=0) in the three donors tested (FIG. 42A, Donor 1; FIG. 42B, Donor 2; FIG. 42C, Donor 3). Human MSCs genetically engineered with lentivirus to express GFP did not show a similar enhanced cell expansion or growth phenotype (data not shown).

Example 18: Selection of Promoter for Sustained Protein Expression in Human Bone-Marrow MSCs (BM-MSCs)

In the following example, various promoters were tested for driving expression of a reporter EGFP construct in human MSCs. Promoters tested were CMV, SFFV, EF1a, EF1a-LTR, EFS, MND, PGK, UbC (see Table 4). Cells were transduced using equivalent MOI (multiplicity of infection) using the lentiviral transduction method described in Example. EGFP percentage and Median Fluorescence Intensity (MFI) were quantified over serial passages using flow cytometry.

Figure 43:
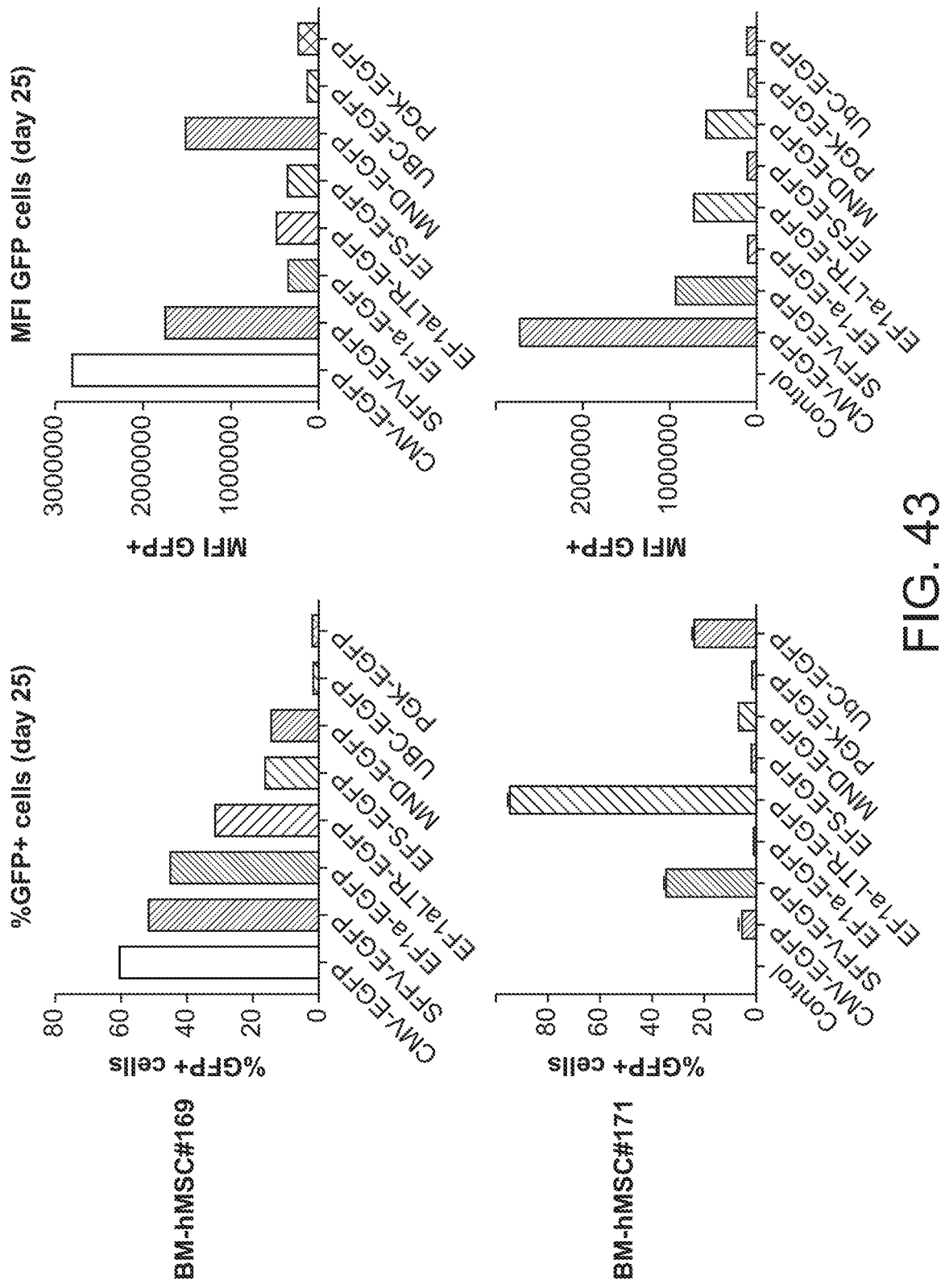
FIG. 43 shows two independent human BM-MSC cell lines from 2 different donors (top and bottom row, respectively) that were transduced with constructs containing various promoters driving EGFP expression. Percent GFP (left panels) and MFI (right panels) of engineered cells at day 25 post transduction is shown.

As shown in FIG. 43, two independent human BM-MSC cell lines from 2 different donors (top and bottom row, respectively were engineered and percent GFP (left panels) and MFI (right panels) of engineered cells was assessed at day 25 post transduction. The SFFV promoter demonstrated GFP expression in both cell lines by both GFP percentage and MFI.

Figure 44:
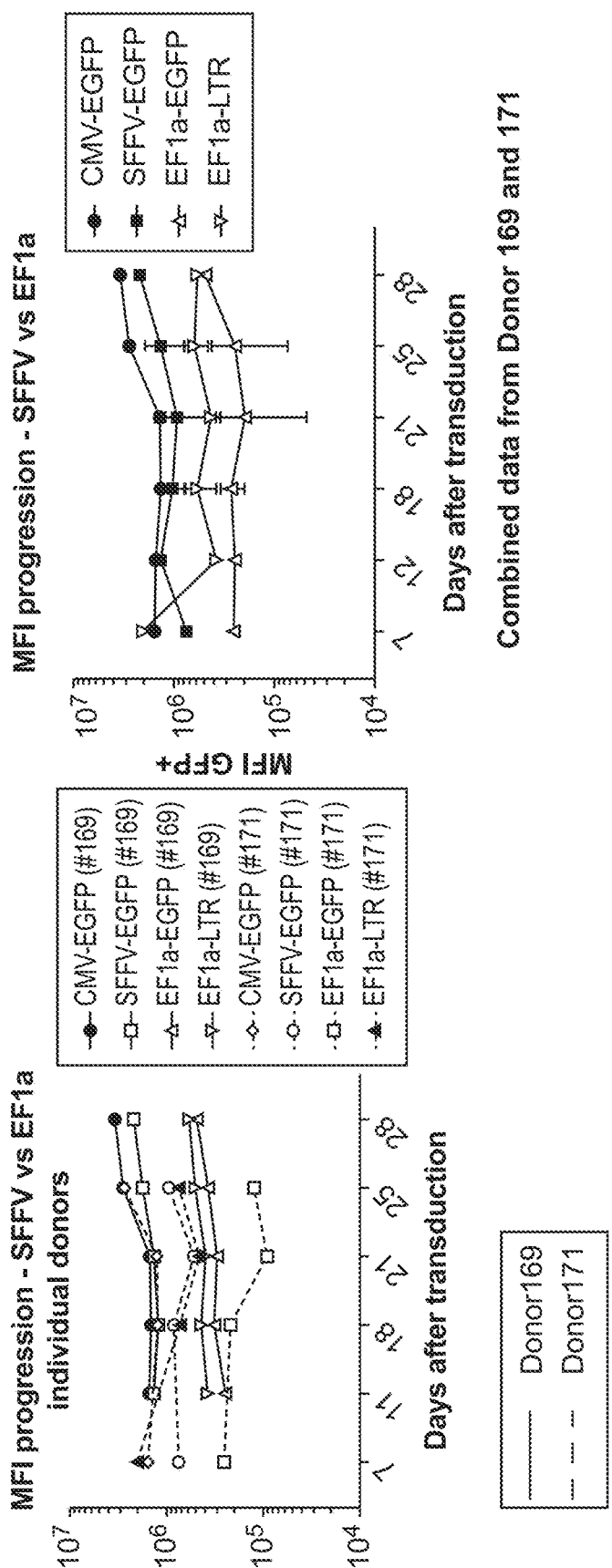
FIG. 44 shows two independent human BM-MSC cell lines from 2 different donors that were transduced with constructs containing various promoters driving EGFP expression. Shown is EGFP MFI tracked over time (day 7 to day 28 post-transduction) for either the two independent human BM-MSC cell lines individually (left panel) or with data from the two independent human BM-MSC cell lines combined (right panel).

As shown in FIG. 44, EGFP MFI was tracked over time (day 7 to day 28 post-transduction) for either the two independent human BM-MSC cell lines individually (left panel) or with data from the two independent human BM-MSC cell lines combined (right panel). Protein expression was stable over time during more than 28 days. Additionally, in comparison to EF1a promoters, SFFV promoter consistently drove almost ten-fold more protein expression as quantified by MFI.

Example 19: Engineering Human MSCs to Produce IL12 and IL21

In the following example, human bone-marrow MSCs were stably transduced to express IL12p70 and IL21 from various constructs using the lentiviral transduction method described in Example 6. Cells were expanded for 3 to 4 passages post-transduction and 0.2×10⁶ cells were seeded in 6-well plates in 4 mL of media. Conditioned media was collected after 24 hours and ELISAs were performed to determine the IL-12 and IL-21 concentrations produced.

Various constructs were tested with different combinations and/or arrangements of promoter-signal sequence 1-cytokine 1-2A linker-signal sequence 2-cytokine 2. The combinations tested are described below in Table 7. Specific details of construct SB00880 are presented below in Table 8.

TABLE 7

IL-12 and IL-21 Expression Constructs

| Construct Name (SB#) | Promoter | Insert | Backbone | Codon Optimization |
|---|---|---|---|---|
| SB00743 | SFFV_1 | IL12ss-IL12 | pL23d | None |
| SB00763 | EFa1 (pEF6) | IL12ss-IL12-fT2A*-IL21ss-IL21 | pL40g | None |
| SB00765 | EFa1 (pEF6) | IL12ss-IL12-fT2A-IL21ss-IL21 | pL40g | None |

TABLE 7-continued

IL-12 and IL-21 Expression Constructs

| Construct Name (SB#) | Promoter | Insert | Back-bone | Codon Opti-mi-zation |
|---|---|---|---|---|
| SB00766 | EFa1 (pEF6) | IL12ss-IL12-fT2A-IL8ss-IL21 | pL40g | None |
| SB00767 | EF1a (pEF6) | IL12ss-IL12-fT2A-IL21 | pL40g | None |
| SB00768 | EFa1 (pEF6) | IL21ss-IL21-fT2A-IL12ss-IL12 | pL40g | None |
| SB00769 | EFa1 (pEF6) | IL12ss-IL21-fT2A-IL12ss-IL12 | pL40g | None |
| SB00770 | EFa1 (pEF6) | IL6ss-IL21-fT2A-IL12ss-IL12 | pL40g | None |
| SB00771 | EF1a (pEF6) | IL8ss-IL21-fT2A-IL12ss-IL12 | pL40g | None |
| SB00772 | EF1a (pEF6) | IL21ss-IL21-fT2A-IL12 | pL40g | None |
| SB00773 | EF1a (pEF6) | IL12ss-IL21-fT2A-IL12 | pL40g | None |
| SB00774 | EF1a (pEF6) | IL6ss-IL21-fT2A-IL12 | pL40g | None |
| SB00775 | EF1a (pEF6) | IL8ss-IL21-fT2A-IL12 | pL40g | None |
| SB00772 | EF1a (pEF6) | IL21ss-IL21-fT2A-IL12 | pL40g | None |
| SB00620 | SFFV_1 | IL2ss-IL21 | pL17d | None |
| SB00838 | SFFV_1 | IL12ss-IL12-fT2A-IL21ss-IL21 | pL41g | None |
| SB00839 | SFFV_1 | IL12ss-IL12-fT2A-IL8ss-IL21 | pL41g | None |
| SB00840 | SFFV_1 | IL12ss-IL12-fT2A-IL21 | pL41g | None |
| SB00841 | SFFV_1 | IL21ss-IL21-fT2A-IL12ss-IL12 | pL41g | None |
| SB00843 | SFFV_1 | IL21ss-IL21-fT2A-IL12 | pL41g | None |
| SB00844 | SFFV_1 | IL8ss-IL21-fT2A-IL12 | pL41g | None |
| SB00868 | SFFV_1 | IL12ss-IL12 | pL41g | Yes |
| SB00870 | EF1a (pEF6) | IL12ss-IL12-fT2A-IL21ss-IL21 | pL40g | Yes |
| SB00872 | EF1a (pEF6) | IL12ss-IL12-fT2A-IL21 | pL40g | Yes |
| SB00869 | EF1a (pEF6) | IL21ss-IL21-fT2A-IL12ss-IL12 | pL40g | Yes |
| SB00871 | EF1a (pEF6) | IL21ss-IL21-fT2A-IL12 | pL40g | Yes |
| SB00879 | SFFV_1 | IL21ss-IL21-fT2A-IL12ss-IL12 | pL41g | Yes |
| SB00880 | SFFV_1 | IL12ss-IL12-fT2A-IL21ss-IL21 | pL41g | Yes |
| SB00881 | SFFV_1 | IL21ss-IL21-fT2A-IL12 | pL41g | Yes |
| SB00882 | SFFV_1 | IL12ss-IL12-fT2A-IL21 | pL41g | Yes |
| SB00862 | SFFV_1 | IL21ss-IL21 | pL23d | None |
| SB00863 | SFFV_1 | IL2ss-IL21 | pL41g | Yes |
| SB00968 | SFFV_1 | IL2ss-IL21-fT2A-IL12ss-IL12 | pL41g | Yes |
| SB00969 | SFFV_1 | IL8ss-IL21-fT2A-IL12ss-IL12 | pL41g | Yes |
| SB00970 | SFFV_1 | IL12ss-IL12-fT2A-IL2ss-IL21 | pL41g | Yes |
| SB00971 | SFFV_1 | IL12ss-IL12-fT2A-IL8ss-IL21 | pL41g | Yes |
| SB00862 + SB00743 | SFFV_1 | Co-transduction IL12 + IL21 | pL41g | None |
| SB00868 + 863 | SFFV_1 | Co-transduction IL12 + IL21 (IL2ssIL21) | pL41g | Yes |

*fT2A refers to Furin-T2A

TABLE 8

SB00880 Expression Construct Sequences

SFFV promoter (SEQ ID NO: 17)
GTAACGCCATTTTGCAAGGCATGGAAAATACCAAACCAAGAATAGA
GAAGTTCAGATCAAGGGCGGGTACATGAAAATAGCTAACGTTGGGCC
AAACAGGATATCTGCGGTGAGCAGTTTCGGCCCCGGCCCGGGGCCAA
GAACAGATGGTCACCGCAGTTTCGGCCCCCGGCCCGAGGCCAAGAACA
GATGGTCCCCAGATATGGCCCAACCCTCAGCAGTTTCTTAAGACCCA
TCAGATGTTTCCAGGCTCCCCAAGGACCTGAAATGACCCTGCGCCT
TATTTGAATTAACCAATCAGCCTGCTTCTCGCTTCTGTTCGCGCGCT
TCTGCTTCCCGAGCTCTATAAAAGAGCTCACAACCCCTCACTCGGCGC
CGCCAGTCCTCCGACAGACTGAGTCGCCCGGG Human IL-12 signal sequence; codon optimized
(nucleic acid) (SEQ ID NO: 32)
ATGTGCCATCAGCAACTCGTCATCTCCTGGTTCTCCCTTGTGTTCCT
CGCTTCCCCTCTGGTCGCC Human IL-12 signal sequence (amino acid)
(SEQ ID NO: 112)
MCHQQLVISWFSLVFLASPLVA Human IL-12 protein without signal sequence;
codon optimized (nucleic acid) (SEQ ID NO: 136)
ATTTGGGAACTGAAGAAGGACGTCTACGTGGTCGAGCTGGATTGGTA
CCCGGACGCCCCTGGAGAAATGGTCGTGCTGACTTGCGATACGCCAG
AAGAGGACGGCATAACCTGGACCCTGGATCAGAGCTCCGAGGTGCTC
GGAAGCGGAAAGACCCTGACCATTCAAGTCAAGGAGTTCGGCGACGC
GGGCCAGTACACTTGCCACAAGGGTGGCGAAGTGCTGTCCCACTCCC
TGCTGCTGCTGCACAAGAAAGAGGATGGAATCTGGTCCACTGACATC
CTCAAGGACCAAAAAGAACCGAAGAACAAGACCTTCCTCCGCTGCGA
AGCCAAGAACTACAGCGGTCGGTTCACCTGTTGGTGGCTGACGACAA
TCTCCACCGACCTGACTTTCTCCGTGAAGTCGTCACGGGGATCAAGC
GATCCTCAGGGCGTGACCTGTGGAGCCGCCACTCTGTCCGCCGAGAG
AGTCAGGGGAGACAACAAGGAATATGAGTACTCCGTGGAATGCCAGG
AGGACAGCGCCTGCCCTGCCGCGGAAGAGTCCCTGCCTATCGAGGTC
ATGGTCGATGCCGTGCATAAGCTGAAATACGAGAACTACACTTCCTC
CTTCTTTATCCGCGACATCATCAAGCCTGACCCCCCCAAGAACTTGC
AGCTGAAGCCACTCAAGAACTCCCGCCAAGTGGAAGTGTCTTGGGAA
TATCCAGACACTTGGAGCACCCCGCACTCATACTTCTCGCTCACTTT
CTGTGTGCAAGTCAGGGAAAGTCCAAACGGGAGAAGAAAGACCGGG
TGTTCACCGACAAAACCTCCGCCACTGTGATTTGTCGGAAGAACGCG
TCAATCAGCGTCCGGGCGCAGGATAGATACTACTCGTCCTCCTGGAA
CGAATGGCCAGCGTGCCTTGTTCCGGTGGCGGATCAGGCCGGAGGTT
CAGGAGGAGGCTCCGGAGGAGGTTCCCGGAACCTCCCTGTGGCAACC
CCCGACCCTGGAATGTTCCCGTGCCTACACCACTCCCAAAACCTCCT
GAGGGCTGTGTCGAACATGTTGCAGAAGGCCCGCCAGACCCTTGAGT
TCTACCCCTGCACCTCGGAAGAATTGATCACGAGGACATCACCAAG
GACAAGACCTCGACCGTGGAAGCCTGCCTGCCGCTGGAACTGACCAA
GAACGAATCGTGTCTGAACTCCCGCGAGACAAGCTTTATCACTAACG
GCAGCTGCCTGGCGTCGAGAAAGACCTCATTCATGATGGCGCTCTGT
CTTTCCTCGACTATGAAGATCTGAAAATGTATCAGGTCGAGTTCAA
GACCATGAACGCCAAGCTGCTCATGGACCCGAAGCGGCAGATCTTCC
TGGACCAGAATATGCTCGCCGTGATTGATGAACTGATGCAGGCCCTG
AATTTCAACTCCGAGACTGTGCCTCAAAAGTCCAGCCTGGAAGAACC
GGACTTCTACAAGACCAAGATCAAGCTGTGCATCCTGTTGCACGCTT
TCCGCATTCGAGCCGTGACCATTGACCGCGTGATGTCCTACCTGAAC
GCCAGT Human IL-12 protein without signal sequence
(amino acid) (SEQ ID NO: 137); p35 subunit
in bold; p40 subunit in italics
*IWELKKDVYVVELDWYPDAPGLTCDTPEEDGITWTLDQSSEVLGSGK*
*TLTIQVKEFGDAGQYTCHKGGEVLSHSLLLLHKKEDGIWSTDILKDQ*
*KEPKNKTFLRCEAKNYSGRFTCWWLTTISTDLTFSVKSSRGSSDPQG*
*VTCGAATLSAERVRGDNKEYEYSVECQEDSACPAAEESLPIEVMVDA*
*VHKLKYENYTSSFFIRDIIKPDPPKNLQLKPLKNSRQVEVSWEYPDT*
*WSTPHSYFSLTFCVQVQGKSKREKKDRVETDKTSATVICRKNASISV*
*RAQDRYYSSSWSEWASVPCS*GGGSGGGGSGGGSGGGGSRNLPVATPDPG
MFPCLHHSQNLLRAVSNMLQKARQTLEFYPCTSEEIDHEDITKDKTS
TVEACLPLELTKNESCLNSRETSFITNGSCLASRKTSFMMALCLSSI
YEDLKMYQVEFKTMNAKLLMDPKRQIFLDQNMLAVIDELMQALNENS
ETVPQKSSLEEPDFYKTKIKLCILLHAFRIRAVTIDRVMSYLNAS

Human IL-12 protein with signal sequence (amino
acid) (SEQ ID NO: 138); p35 subunit in bold;
p40 subunit in italics
MCHQQLVISWFSLVFLASPLVA*IWELKLDVYVVELDWYPDAPGLTCD*
*TPEEDGITWTLDQSSEVLGSGKTLTIQVKEFGDAGQYTCHKGGEVLS*
*HSLLLLHKKEDGIWSTDILKDQKEPKNKTFLRCE4KNYSGRFTCWWL*
*TTISTDLTFSVKSSRGSSDPQGVTCGAATLSAERVRGDNKEYEYSVE*
*CQEDSACPAAEESLPIEVMVDAVHKLKYENYTSSFFIRDIIKPDPPK*
*NLQLKPLKNSRQVEVSWEYPDTWSTPHSYFSLTFCVQVQGKSKREKK*
*DRVETDKTSATVICRKNASISVRAQDRYYSSSWSEWASVPCSGGGSG*
*GGSGGGGS*RNLPVATPDPGMFPCLHHSQNLLRAVSNMLQKARQT
LEFYPCTSEEIDHEDITKDKTSTVEACLPLELTKNESCLNSRETSFI
TNGSCLASRKTSFMMALCLSSIYEDLKMYQVEFKTMNAKLLMDPKRQ
IFLDQNMLAVIDELMQALNFNSETVPQKSSLEEPDFYKTKIKLCILL
HAFRIRAVTIDRVMSYLNAS

TABLE 8-continued

SB00880 Expression Construct Sequences

Furin-T2A Linker (nucleic acid) (SEQ ID NO: 139)
AGACGGAAACGCGGAAGCGGAGAGGGCAGAGGCTCGCTGCTTACATG
CGGGGACGTGGAAGAGAACCCCGGTCCG Furin-T2A Linker (amino acid) (SEQ ID NO: 140)
RRKRGSGEGRGSLLTCGDVEENPGP Human IL-21 signal sequence; codon optimized
(nucleic acid) (SEQ ID NO: 55)
ATGGAACGCATTGTGATCTGCCTGATGGTCATCTTCCTGGGCACCTT
AGTGCACAAGTCGAGCAGC Human IL-21 signal sequence (amino acid)
(SEQ ID NO: 135)
MERIVICLMVIFLGTLVHKSSS Human IL-21 protein without signal sequence;
codon optimized (nucleic acid) (SEQ ID NO: 141)
CAGGGACAGGACAGGCACATGATTAGAATGCGCCAGCTCATCGATATC
GTGGACCAGTTGAAGAACTACGTGAACGACCTGGTGCCCGAGTTCCTG
CCGGCCCCCGAAGATGTGGAAACCAATTGCGAATGGTCGGCATTTTCC
TGCTTTCAAAAGGCACAGCTCAAGTCCGCTAACACCGGGAACAACGAA
CGGATCATCAACGTGTCCATCAAAAAGCTGAAGCGGAAGCCTCCCTCC
ACCAACGCCGGACGGAGGCAGAAGCATAGGCTGACTTGCCCGTCATGC
GACTCCTACGAGAAGAAGCCGCCGAAGGAGTTCCTGGAGCGGTTCAAG
TCGCTCCTGCAAAAGATGATTCATCAGCACCTGTCCTCCCGGACTCAT
GGGTCTGAGGATTCA Human IL-21 protein without signal sequence
(amino acid) (SEQ ID NO: 142)
QGQDRHMIRMRQLIDIVDQLKNYVNDLVPEFLPAPEDVETNCEWSAFS
CFQKAQLKSANTGNNERIINVSIKKLKRKPPSTNAGRRQKHRLTCPSC
DSYEKKPPKEFLERFKSLLQKMIHQHLSSRTHGSEDS Human IL-21 protein with signal sequence
(amino acid) (SEQ ID NO: 143)
MERIVICLMVIFLGTLVHKSSSQGQDRHMIRMRQLIDIVDQLKNYVND
LVPEFLPAPEDVETNCEWSAFSCFQKAQLKSANTGNNERIINVSIKKL
KRKPPSTNAGRRQKHRLTCPSCDSYEKKPPKEFLERFKSLLQKMIHQH
LSSRTHGSEDS SB00880 Cassette (SFFV-IL12ss-IL12-fT2A-
IL21ss-IL21)
(SEQ ID NO: 144)
GTAACGCCATTTTGCAAGGCATGGAAAAATACCCAAACCAAGAATAGAGA
AGTTCAGATCAAGGGCGGGTACATGAAAATAGCTAACGTTGGGCAAAC
AGGATATCTGCGGTGAGCAGTTCGGCCCCGGCCCGGGGCCAAGAACAG
ATGGTCACCGCAGTTTCGGCCCCGGGCCCGAGGCCAAGAACAGATGGTCC
CCAGATATGGCCCAACCCTCAGCAGTTTCTTAAGACCCATCAGATGTTT
CCAGGCTCCCCCAAGGACCTGAAATGACCCTGCGCCTTATTTGAATTAA
CCAATCAGCCTGCTTCTCGCTTCTGTTCGCGCGCTTCTGCTTCCCGAGC
TCTATAAAAGAGCTCACAACCCCTCACTCGGCGCGCCAGTCTTCCGCATCA
GACTGAGTCGCCCGGGGATCCGCGGAATTCGCCGCCACCATGTGCCAT
CAGCAACTCGTCATCTCCTGGTTCTCCCTTGTGTTCCTCGCTTCCCCTC
TGGTCGCCATTTGGGAACTGAAGAAGGACGTCTACGTGGTCGAGCTGGA
TTGGTACCCGGACGCCCCTGGGAATAGGTCGTGCTGACTTGCGATACG
CCAGAAGAGGACGGCATAACCTGGACCTGGATCAGAGCTCCGAGGTGC
TCGGAAGCGGAAAGACCCTGACCATTCAAGTCAAGGAGTTCGGCGACGC
GGGCCAGTACACTTGCCACAAGGGTGGCGAAGTGCTGTCCCACTCCCTG
CTGCTGCTGCACAAGAAAGAGGATGGAATCTGGTCCACTGACATCCTCA
AGGACCAAAAAGAACAAGAAGCCTTCCTCCGCTGCGAAGCCAA
GAACTACAGCGGTCGGTTCACCTGTTGGTGGCTGACGACAATCTCCACC
GACCTGACTTTCTCCGTGAAGTCGTCACGGGGATCAAGCGATCCTCAGG
GCGTGACCTGTGGAGCCGCCACTCTGTCCGCCGAGAGAGTCAGGGGAGA
CAACAAGGAATATGAGTACTCCGTGGAATGCCAGGAGGACAGCGCCTGCC
CCTGCCGCGGAAGAGTCCCTGCCTATCGAGGTCATGGTCGATGCCGTGC
ATAAGCTGAAATACGAGAACTACACTTCCTCCTTCTTTATCCGGACAT
CATCAAGCCTGACCCCCCAAGAACTTGCAGCTGAAGCCACTCAAGAAC
TCCCGCCAAGTGGAAGTGCTTTGGGAATATCAGCACTTGGAGCACCC
CGCACTCATACTTCTCGCTCACTTTCTGTGTGCAAGTGCAGGGAAAGTC
CAAACGGGAGAAGAAAGACCGGGTGTTCACCGACAAACCTCCGCCACT
GTGATTTGTCGGAAGAACGCGTCAATCAGCGTCCGGGCGCAGGATAGAT
ACTACCTCGTCCTGGAGCGAATGGGCCAGCGTGCCTTGTTCCGGTGG
CGGATCAGGCGGAGGTTCAGGAGGAGGCTCCGGAGGAGGTTCCGGAAC
CTCCCTGTGGCAACCCCGACCCTGGAATGTTCCCGTGCCTACACACT
CCCAAAACCTCCTGAGGGCTGTGTCGAACATGTTGCAGAAGGCCCGCCA
GACCCTTGAGTTCTACCCCTGCACCTCGGAAGAAATTGATCACGAGGAC
ATCACCAAGGACAAGACCTCGACCGTGGAAGCCTGCCTGCCGCTGGAAC TGACCAAGAACGAATCGTGTCTGAACTCCCGCGAGACAAGCTTTATCAC
TAACGGCAGCTGCCTGGCGTCGAGAAAGACCTCATTCATGATGGCGTC
TGTCITTCCTCGATCTACGAAGATCTGAAGATGTATCAGGTCGAGTTCA
AGACCATGAACGCCAAGCTGCTCATGGACCCGAAGCGGCAGATCTTCCT
GGACCAGAATATGCTCGCCGTGATTGATGAACTGATGCAGGCCCTGAAT
TTCAACTCCGAGACTGTGCCTCAAAAGTCCAGCCTGGAAGAACCGGACT
TCTACAAGACCAAGATCAAGCTGTGCATCCTCCTTGTGCACGCTTTCCGCAT
TCGAGCCGTGACCATTGACCGCGTGATGTCCTACCTGAACGCCAGTAGA
CGGAAACGCGGAAGCGGAGAGGGCAGAGGCTCGCTGCTTACATGCGGGG
ACGTGGAAGAGAACCCCGGTCCGATGGAACGCATTGTGATCTGCCTGAT
GGTCATCTTCCTGGGCACCTTAGTGCACAAGTCGAGCAGCCAGGGACAG
GACAGGCACATGATTAGAATGCGCCAGCTCATCGATATCGTGGACCAGT
TGAAGAACTACGTGAACGACCTGGTGCCCGAGTTCCTGCCGGCCCCCGA
AGATGTGGAAACCAATTGCGAATGGTCGGCATTTTCCTGCTTTCAAAAG
GCACAGCTCAAGTCCGCTAACACCGGGAACAACGAACGGATCATCAACG
TGTCCATCAAAAAGCTGAAGCGGAAGCCTCCCTCCACCAACGCCGGACG
GAGGCAGAAGCATAGGCTGACTTGCCCGTCATGCGACTCCTACGAGAAG
AAGCCGCCGAAGGAGTTCCTGGAGCGGTTCAAGTCGCTCCTGCAAAAGA
TGATTCATCAGCACCTGTCCTCCCGGACTCATGGGTCTGAGGATTCATG
A SB00880 Full Vector (PL41g + SB00880 Cassette)
(SEQ ID NO: 145)
TGACTCCTGCGCAGTCCAAAAAAAAAGGCTCCAAAAGGAGCCTTTAATT
GTATCGGTGGGCCCTTAGAAAAACTCATCGAGCATCAAATGAAACTGCA
ATTTATTCATATCAGGATTATCAATACCATATTTTTGAAAAAGCCGTTT
CTGTAATGAAGGAGAAAACTCACCGAGGCAGTTCCATAGGATGGCAAGA
TCCTGGTATCGGTCTGCGATTCCGACTCGTCCAACATCAATACAACCTA
TTAATTTCCCCTCGTCAAAAATAAGGTTATCAAGTGAGAAATCACCATG
AGTGACGACTGAATCCGGTGAGAATGGCAAAAGCTTATGCATTTCTTTC
CAGACTTGTTCAACAGGCCAGCCATTACGCTCGTCATCAAAATCACTCG
CATCAACCAAACCGTTATTCATTCGTGATTGCGCCTGAGCGAGACGAAA
TACGCGATCGCTGTTAAAAGGACAATTACAAACAGGAATCGAATGCAAC
CGGCGCAGGAACACTGCCAGCGCATCAACAATATTTTCACCTGAATCAG
GATATTCTTCTAATACCTGGAATGCTGTTTTCCCGGGGATCGCAGTGGT
GAGTAACCATGCATCATCAGGAGTACGGATAAAATGCTTGATGGTCGGA
AGAGGCATAAATTCCGTCAGCCAGTTTAGTCTGACCATCTCATCTGTAA
CATCATTGGCAACGCTACCTTTGCCATGTTTCAGAAACAACTCTGGCGC
ATCGGGCTTCCCATACAATCGATAGATTGTCGCACCTGATTGCCCGACA
TTATCGCGAGCCCATTTATACCCATATAAATCAGCATCCATGTTGGAAT
TTAATCGCGGCCTCGAGCAAGACGTTTCCCGTTGAATATGGCTCATAAC
ACCCCTTGTATTACTGTTTATGTAAGCAGACAGTTTTATTGTTCATGAT
GATATATTTTTATCTTGTGCAATGTAACATCAGAGATTTTGAGACACAA
CGTGGTTTCAACAAATAGTCAAAAGCCTCCGGCGACTAGTCGGGGTCAT
TAGTTCATAGCCCATATATGGAGTTCCGCGTTACATAACTTACGGTAAA
TGGCCCGCCTGGCTGACCGCCCAACGACCCCCGCCCATTGACGTCAATA
ATGACGTATGTTCCCATAGTAACGCCAATAGGGACTTTCCATTGACGTC
AATGGGTGGAGTATTTACGGTAAACTGCCCACTTGGCAGTACATCAAGA
GTATCATATGCCAAGTACGCCCCCTATTGACGTCAATGACGGTAAATGG
CCCGCCTGGCATTATGCCCAGTACATGACCTTATGGGACTTTCCTACTT
GGCAGTACATCTACGTATTAGTCATCGCTATTACCATGGTGATGCGGTT
TTGGCAGTACATCAATGGGCGTGGATAGCGGTTTGACTCACGGGGATTT
CCAAGTCTCCACCCCATTGACGTCAATGGGAGTTTGTTTTGGCACCAAA
ATCAACGGGACTTTCCAAAATGTCGTAACAACTCCGCCCCATTGACGCA
AATGGGCGGTAGGCGTGTACGGTGGGAGGTCTATATAAGCAGAGCTGGT
TTAGTGAACCGTCTCTCTGGTTAGACCAGATTTGAGCCTGGGAGCTC
TCTGGCTAACTAGGGAACCCACTGCTTAAGCCTCAATAAAGCTTGCCTT
GAGTGCTTCAAGTAGTGTGTGCCCGTCTGTTGTGTGACTCTGGTAACTA
GAGATCCCTCAGACCCTTTTAGTCAGTGTGGAAAATCTCTAGCAGTGGC
GCCCGAACAGGGACCTGAAAGCGAAAGGGAAACCAGAGGAGCTCTCTCG
ACGCAGGACTCGGCTTGCTGAAGCGCGCACGGCAAGAGGCGAGGGGCGG
CGACTGCAGAGTACGCCAAAATTTTGACTAGCGGAGGCTAGAAGGAGAG
AGATGGGTGCGAGAGCGTCAGTATTAAGCGGGGGAAAATTAGATGCGCC
ACAATTTTAAAAGAAAAGGGGGGATTGGGGGGTACAGTGCAGGGGAAAG
AATAGTAGACATAATAGCAACAGACATACAAACTAAAGAATTACAAAAA
CAAATTACAAAAATTCAAAATTTTCGGGGTTCCTGTAACGCCATTTTGCA
AGGCATGGAAAATACCAAACCAAGAATAGAGAAGTTCAGATCAAGGGC
GGGTACATGAAAATAGCTAACGTTGGGCCAAACAGGATATCTGCGGTGA
GCAGTTTCGGCCCCGGCCCGGGGCCAAGAACAGATGGTCACCGCAGTTT
CGGCCCCGGCCCGAGGCCAAGAACAGATGGTCCCCAGATATGGCCCAAC
CCTCAGCAGTTTCTTAAGACCCATCAGATGTTTCCAGGCTCCCCCAAGG
ACCTGAAATGACCCTGCGCCTTATTTGAATTAACCAATCAGCCTGCTTC
TCGCTTCTGTTCGCGCGCTTCTGCTTCCCGAGCTCTATAAAGAGCTCA
CAACCCCTCACTCGGCGCGCCAGTCCTCCGACAGACTGAGTCGCCCGGG
GGATCCGCGGAATTCGCCGCCACCATGTGCCATCAGCAACTCGTCATCT
CCTGGTTCTCCCTTGTGTTCCTCGCTTCCCCTCTGGTCGCCATTTGGGA
ACTGAAGAAGGACGTCTACGTGGTCGAGCTGGATTGGTACCCGGACGCC
CCTGGAGAAATGGTCGTGCTGACTTGCGATACGCCAGAAGAGGACGGCA TABLE 8-continued SB00880 Expression Construct Sequences

```
TAACCTGGACCCTGGATCAGAGCTCCGAGGTGCTCGGAAGCGGAAAGAC
CCTGACCATTCAAGTCAAGGAGTTCGGCGACGCGGGCCAGTACACTTGC
CACAAGGGTGGCGAAGTGCTGTCCCACTCCCTGCTGCTGCTGCACAAGA
AAGAGGATGGAATCTGGTCCACTGACATCCTCAAGGACCAAAAGAACC
GAAGAACAAGACCTTCCTCCGCTGCGAAGCCAAGAACTACAGCGGTCGG
TTCACCTGTTGGTGGCTGACGACAATCTCCACCGACCTGACTTTCTCG
TGAAGTCGTCACGGGGATCAAGCGATCCTCAGGGCGTGACCTGTGGAGC
CGCCACTCTGTCCGCCGAGAGAGTCAGGGGAGACAACAAGGAATATGAG
TACTCCGTGGAATGCCAGGAGGACAGCGCCTGCCCTGCCGCGGAAGAGT
CCCTGCCTATCGAGGTCATGGTCGATGCCGTGCATAAGCTGAAATACGA
GAACTACACTTCCTCCTTCTTTATCCGCGACATCATCAAGCCTGACCCC
CCCAAGAACTTGCAGCTGAAGCCACTCAAGAACTCCCGCCAAGTGGAAG
TGTCTTGGGAATATCCAGACACTTGGAGCACCCCGCACTCATACTTCTC
GCTCACTTTCTGTGTGCAAGTGCAGGGAAAGTCCAAACGGGAGAAGAAA
GACCGGGTGTTCACCGACAAAACCTCCGCCACTGTGATTTGTCGGAAGA
ACGCGTCAATCAGCGTCCGGGCGCAGGATAGATACTACTCGTCCTCCTG
GAGCGAATGGGCCAGCGTGCCTTGTTCCGGTGGCGGATCAGGCGGAGGT
TCAGGAGGAGGCTCCGGAGGAGGTTCCCGGAACCTCCCTGTGGCAACCC
CCGACCCTGGAATGTTCCCGTGCCTACACCACTCCCAAAACCTCCTGAG
GGCTGTGTCGAACATGTTGCAGAAGGCCCGCCAGACCCTTGAGTTCTAC
CCCTGCACCTCGGAAGAAATTGATCACGAGGACATCACCAAGGACAAGA
CCTCGACCGTGGAAGCCTGCCTGCCGCTGGAACTGACCAAGAACGAATC
GTGTCTGAACTCCCGCGAGACAAGCTTTATCACTAACGGCAGCTGCCTG
GCGTCGAGAAAGACCTCATTCATGATGGCGCTCTGTCTTTCCTCGATCT
ACGAAGATCTGAAGATGTATCAGGTCGAGTTCAAGACCATGAACGCCAA
GCTGCTCATGGACCCGAAGCGGCAGATCTTCCTGGACCAGAATATGCTC
GCCGTGATTGATGAACTGATGCAGGCCCTGAATTTCAACTCCGAGACTG
TGCCTCAAAAGTCCAGCCTGGAAGAACCGGACTTCTACAAGACCAAGAT
CAAGCTGTGCATCCTGTTGCACGCTTTCCGCATTCGAGCCGTGACCATT
GACCGCGTGATGTCCTACCTGAACGCCAGTAGACGGAAACGCGGAAGCG
GAGAGGGCAGAGGCTCGCTGCTTACATGCGGGGACGTGGAAGAGAACCC
CGGTCCGATGGAACGCATTGTGATCTGCCTGATGGTCATCTTCCTGGGC
ACCTTAGTGCACAAGTCGAGCAGCCAGGGACAGGACAGGCACATGATTA
GAATGCGCCAGCTCATCGATATCGTGGACCAGTTGAAGAACTACGTGAA
CGACCTGGTGCCCGAGTTCCTGCCGGCCCCCGAAGATGTGGAAACCAAT
TGCGAATGGTCGGCATTTTCCTGCTTTCAAAAGGCACAGCTCAAGTCCG
CTAACACCGGGAACAACGAACGGATCATCAACGTGTCCATCAAAAAGCT
GAAGCGGAAGCCTCCCTCCACCAACGCCGGACGGAGGCAGAAGCATAGG
CTGACTTGCCCGTCATGCGACTCCTACGAGAAGAAGCCGCCGAAGGAGT
TCCTGGAGCGGTTCAAGTCGCTCCTGCAAAAGATGATTCATCAGCACCT
GTCCTCCCGGACTCATGGGTCTGAGGATTCATGAGGTTAGTCGACAATC
AACCTCTGGATTACAAAATTTGTGAAAGATTGACTGGTATTCTTAACTA
TGTTGCTCCTTTTACGCTATGTGGATACGCTGCTTTAATGCCTTTGTAT
CATGCTATTGCTTCCCGTATGGCTTTCATTTTCTCCTCTGTATAAAT
CCTGGTTGCTGTCTCTTTATGAGGAGTTGTGGCCCGTTGTCAGGCAACG
TGGCGTGGTGTGCACTGTGTTTGCTGACGCAACCCCCACTGGTTGGGGC
ATTGCCACCACCTGTCAGCTCCTTTCCGGGACTTTCGCTTTCCCCCTCC
CTATTGCCACGGCGGAACTCATCGCCGCCTGCCTTGCCCGCTGCTGGAC
AGGGGCTCGGCTGTTGGGCACTGACAATTCCGTGGTGTTGTCGGGGAAA
TCATCGTCCTTTCCTTGGCTGCTCGCCTGTGTTGCCACCTGGATTCTGC
GCGGGACGTCCTTCTGCTACGTCCCTTCGGCCCTCAATCCAGCGGACCT
TCCTTCCCCGACCTGCTGCCGGCCTCTGCGGCCTCTTCCGCGTCTTCGC
CTTCGCCCTCCAGACGAGTCGGATCTCCCTTTGGGCCGCCTCCCCGCTTA
GTACTGGTACCTTTAAGACCAATGACTTACAAGGCAGCTGTAGATCTTA
GCCACTTTTTAAAAGAAAAGGGGGGACTGGAAGGGCTAATTCACTCCCA
ACGAAGACAAGATTCCGGAATTTATTTGTGAAATTTGTGATGCTATTGC
TTTATTTGTAAACCGGTGCAGCTGCTTTTTGCCTGTACTGGGTCTCTCT
GGTTAGACCAGATCTGAGCCTGGGAGCTCTCTGGCTAACTAGGGAACCC
ACTGCTTAAGCCTCAATAAAGCTTGCCTTGAGTGCTTCAAGTAGTGTGT
GCCCGTCTGTTGTGTGACTCTGGTAACTAGAGATCCCTCAGACCCTTTT
AGTCAGTGTGGAAAATCTCTAGCATCTAGAGTATGCAAAGCATGCATCT
CAATTAGTCAGCAACCAGGTGTGGAAAGTCCCCAGGCTCCCCAGCAGGC
AGAAGTATGCAAAGCATGCATCTCAATTAGTCAGCAACCATAGTCCCGC
CCCTAACTCCGCCCATCCCGCCCCTAACTCCGCCCAGTTCCGCCCATTC
TCCGCCCCATGGCTGACTAATTTTTTTATTTATGCAGAGGCCGAGGCC
GCCTCGGCCTCTGAGCTATTCCAGAAGTAGTGAGGAGGCTTTTTTGGAG
GCCTAGGCTAGAGATCATAATCAGCCATACCACATTTGTAGAGGTTTTA
CTTGCTTTAAAAAACCTCCCACACCTCCCCCTGAACCTGAAACATAAAA
TGAATGCAATTGTTGTTGTTAACTTGTTTATTGCAGCTTATAATGGTTA
CAAATAAAGCAATAGCATCACAAATTTCACAAATAAAGCATTTTTTTCA
CTGCATTCTAGTTGTGGTTTGTCCAAACTCATCAATGTATCTTATCATG
TCTGCTAGCCGGGCTTTTTTTCTTAGGCCTTCTTCCGCTTCCTCGCTC
ACTGACTCGCTGCGCTCGGTCGTTCGGCTGCGGCGAGCGGTATCAGCTC
ACTCAAAGGCGGTAATACGGTTATCCACAGAATCAGGGGATAACGCAGG
AAAGAACATGTGAGCAAAAGGCCAGCAAAAGGCCAGGAACCGTAAAAAG
GCCGCGTTGCTGGCGTTTTTCCATAGGCTCCGCCCCCCTGACGAGCATC
ACAAAAATCGACGCTCAAGTCAGAGGTGGCGAAACCCGACAGGACTATA
AAGATACCAGGCGTTTCCCCCTGGAAGCTCCCTCGTGCGCTCTCCTGTT
CCGACCCTGCCGCTTACCGGATACCTGTCCGCCTTTCTCCCTTCGGGAA
GCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAA
GACACGACTTATCGCCACTGGCAGCAGCCACTGGTAACAGGATTAGCAG
AGCGAGGTATGTAGGCGGTGCTACAGAGTTCTTGAAGTGGTGGCCTAAC
TACGGCTACACTAGAAGAACAGTATTTGGTATCTGCGCTCTGCTGAAGC
CAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGC
AGAAAAAAAGGATCTCAAGAAGATCCTTTGATCTTTTCTACGGGGTCTG
ACGCTCAGTGGAACGAAAACTCACGTTAAGGGATTTTGGTCATGAGATT
ATCAAAAAGGATCTTCACCTAGATCCTTTTAAATTAAAAATGAAGTTTT
AAATCAATCTAAAGTATATATGAGTAAACTTGGTCTGACAGTTACCAAT
GCTTAATCAGTGAGGCACCTATCTCAGCGATCTGTCTATTTCGTTCATC
CATAGTTGCC
```

Figure 45:
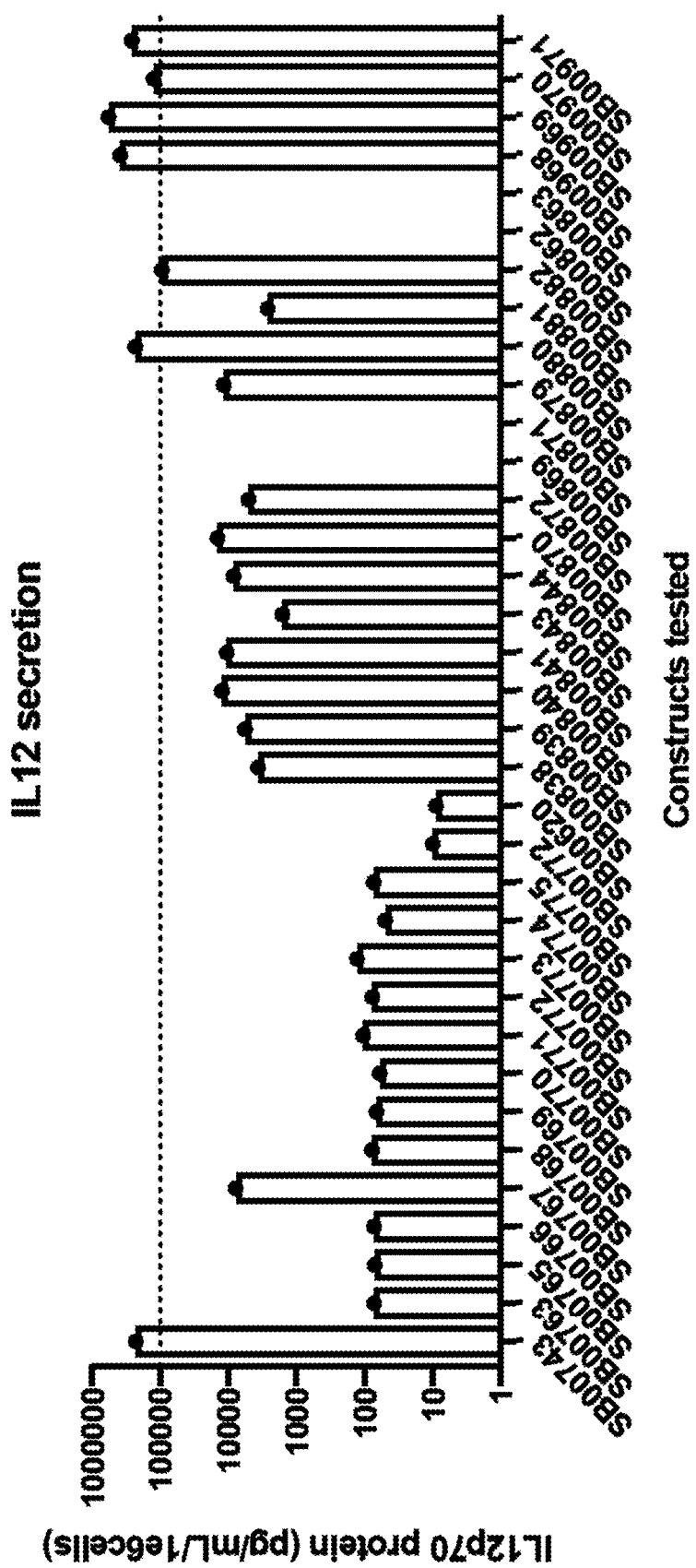
FIG. 45 shows secretion of IL-12p70 by engineered MSCs as assessed by ELISA.
Figure 46:
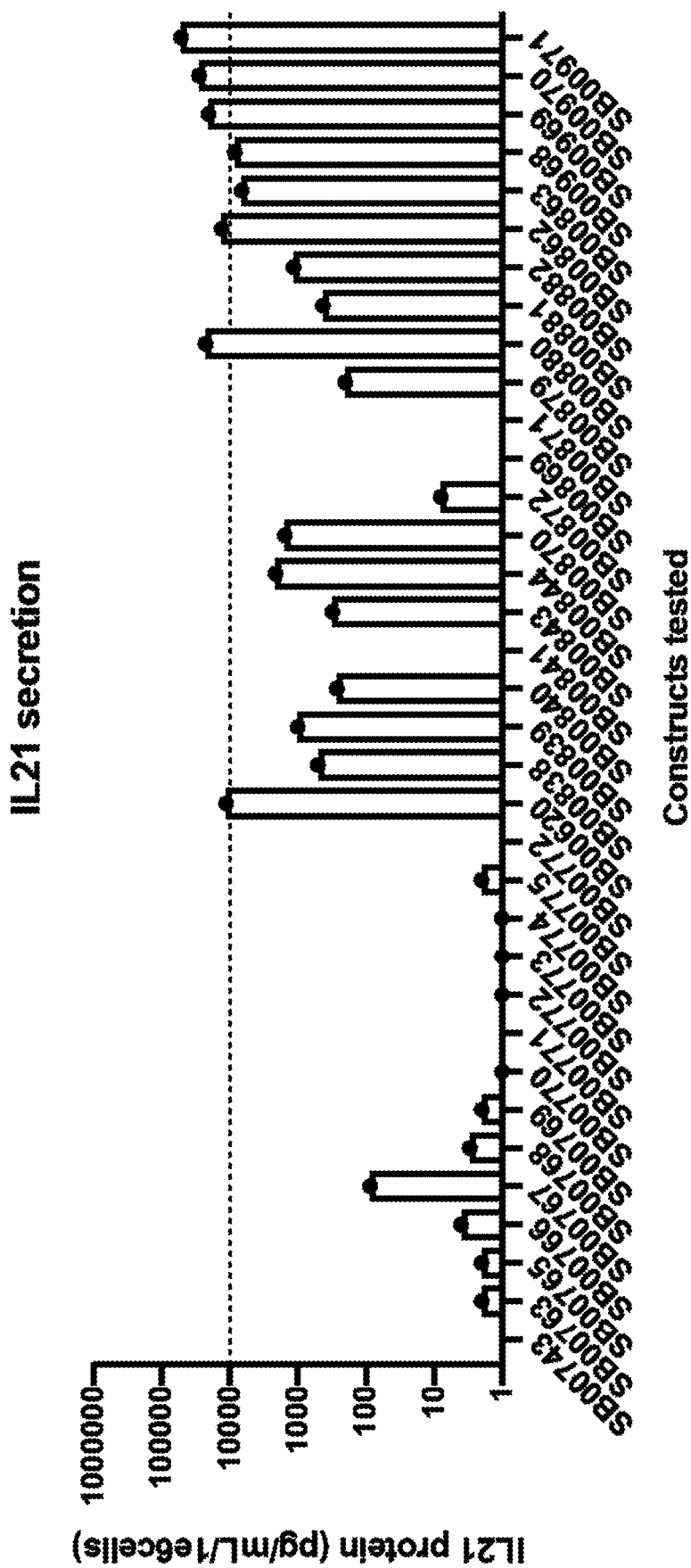
FIG. 46 shows secretion of IL-21 by engineered MSCs as assessed by ELISA.
Figure 47:
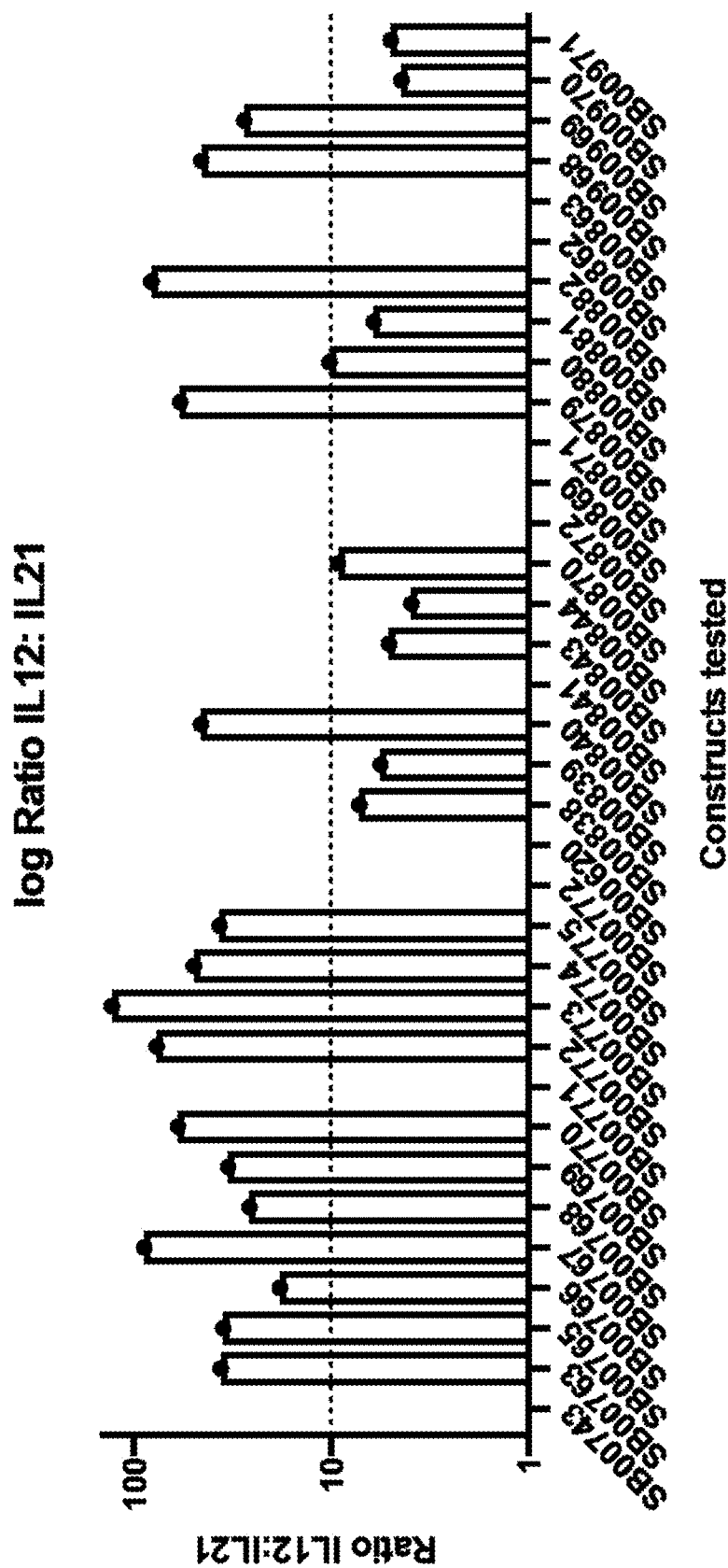
FIG. 47 shows the ratio of secreted IL-12p70 to IL-21 by engineered MSCs as assessed by ELISA.

Secretion of IL-12p70 and IL-21 by engineered MSCs are shown in FIG. 45 and FIG. 46, respectively, as assessed by ELISA. SB00880 demonstrated expression of both cytokines by engineered MSCs at higher levels than the majority of constructs tested. Additionally, the ratio of IL-12 to IL-21 was determined, as assessed by ELISA and shown in FIG. 47. MSCs engineered using SB00880 demonstrated a 10 fold higher ratio of IL-12p70 relative to IL-21. Notably, a ratio of 10:1 has demonstrated pre-clinical efficacy (data not shown).

Figure 48:
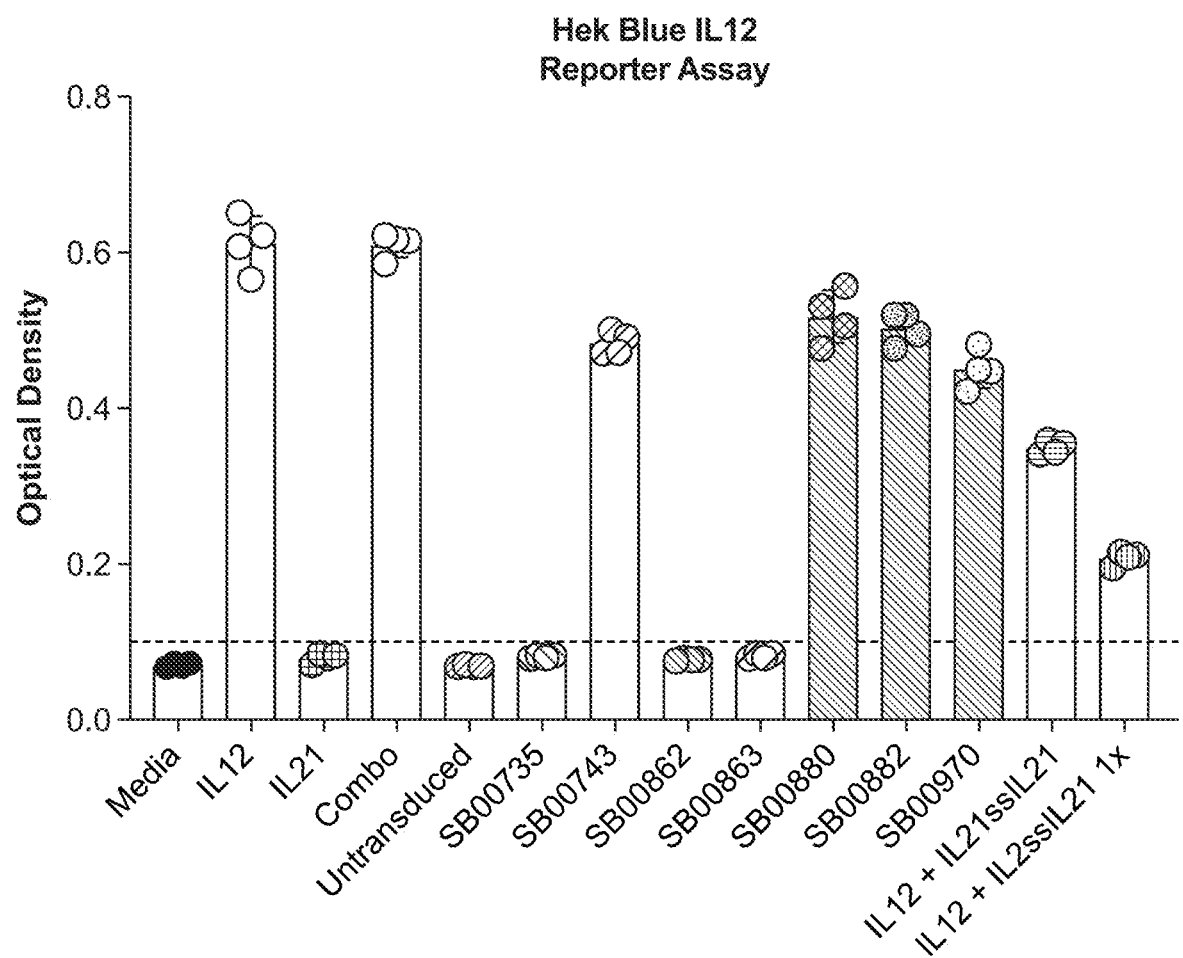
FIG. 48 shows results of a functional reporter assay for IL-12p70 using HEK-293T cells with a STAT4-SEAP reporter to assess cytokine production and secretion by engineered MSCs.

Functional assays demonstrating expression of IL-12p70 by engineered MSCs were performed. HEK-293T cells with a STAT4-SEAP reporter, which reports IL12p70 binding to its receptor and signaling through the JAK-STAT4 pathway, were used to determine potency and activity of IL12p70 produced by engineered hMSCs. Engineered MSCs were cultured for 24 hours and media was collected and incubated with HEK-293T STAT4-SEAP reporter cells. SEAP production was determined with spectrophotometer. As shown in FIG. 48, all constructs that encode IL-12 demonstrated reporter activity indicating functional IL12p70 signaling.

Figure 49:
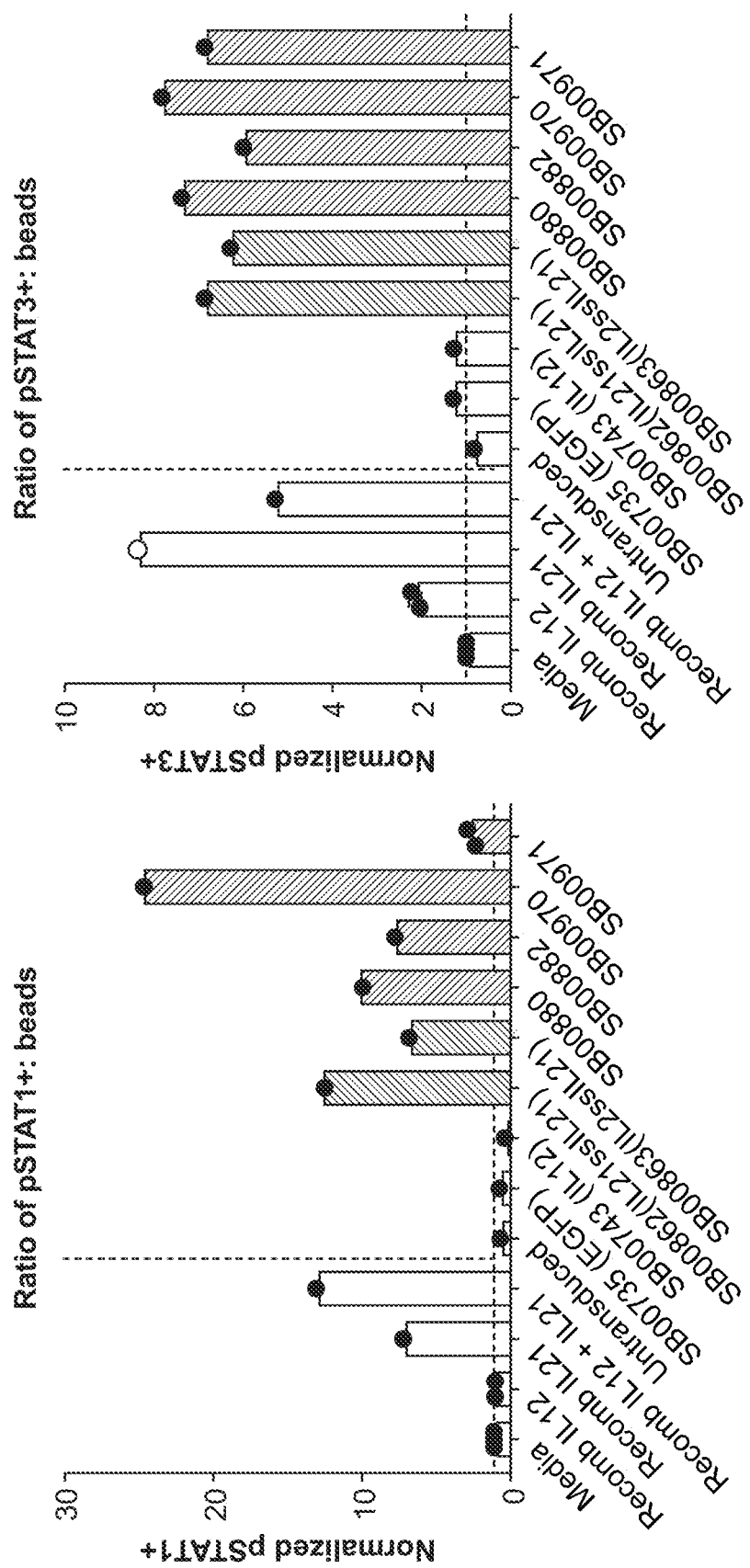
FIG. 49 shows a results of a functional reporter assay for IL-21 using intracellular phospho-flow to quantify phospho-STAT1 (left panel) and phospho-STAT3 (right panel) in NK-92 human natural killer cells to assess cytokine production and secretion by engineered MSCs.

Functional assays demonstrating expression of IL-21 by engineered MSCs were performed. NK-92 human natural killer cells were used to determine function of IL-21 produced by engineered hMSCs. Engineered hMSCs were cultured for 24 hours and conditioned media was collected and used to treat NK-92 cells that were deprived from IL-2. Intracellular phospho-flow was performed to quantify phospho-STAT1 and phospho-STAT3 activation as a readout for IL-21 activity. As shown in FIG. 49, all constructs that encode IL-21 demonstrated STAT1 (left panel) and STAT3 (right panel) phosphorylation indicating functional IL-21 signaling.

Figure 50:
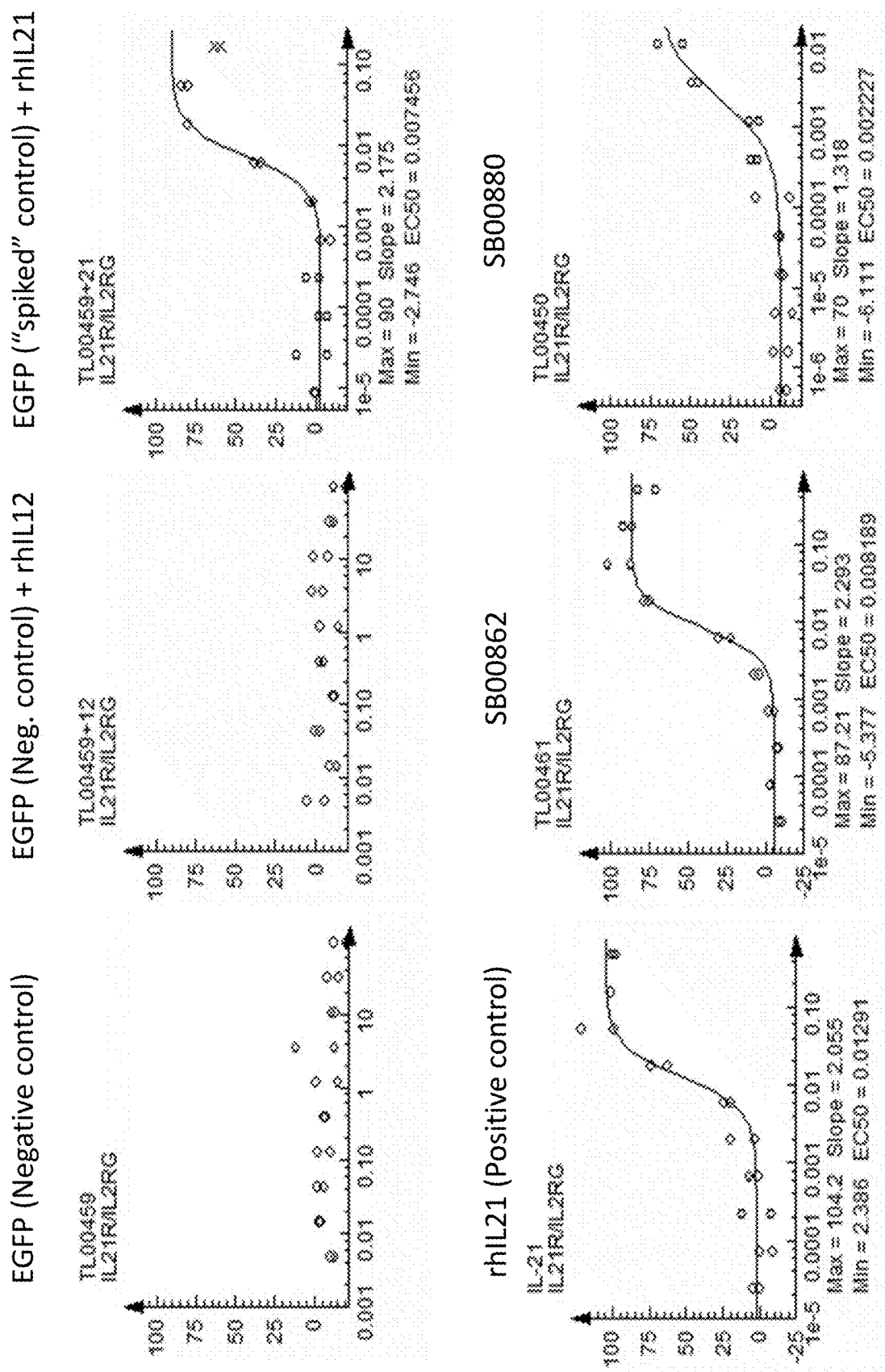
FIG. 50 shows results of a functional reporter assay for IL-12 using a IL21R-U2OS IL21R/IL2RG dimerization reporter to assess cytokine production and secretion by engineered MSCs.

Functional assays for IL-21 was also performed using a IL21R-U2OS IL21R/IL2RG dimerization reporter (Path-Hunter® U2OS IL21R/IL2RG Dimerization Cell Line, DiscoverX Cat. No: 93-1035C3). Reporter cells were incubated with conditioned media from engineered human MSCs or the appropriate positive (recombinant cytokine) or negative controls. As shown in FIG. 50, all constructs that encode IL-21 demonstrated dimerization.

Example 20: Engineered MSC Efficacy in CT26 Tumor Model

In the following example, balb/c mMSCs were engineered to express each of the various murine immune effectors shown in FIG. 51A using the lentiviral transduction method described in Example 6. Each MSC was engineered to express only a single agent. CT26 tumor cells ($5 \times 10^4$ cells in 100 μl) modified to constitutively express luciferase enzyme (Cat no: CL043, Lot no: CL-IM147 Imanis Life Sciences) were injected into the peritoneal space of immunocompetent balb/c female mice (age 6-8 weeks). One week after tumor implantation, tumor burden was measured by luciferase imaging (BLI) using an AMI imager. Mice were randomized into treatment groups and treated with intraperitoneally delivered engineered mMSCs ($1\times10^6$ cells). MSC-Flag-Myc and PBS were used as a negative control.

Figure 51A:
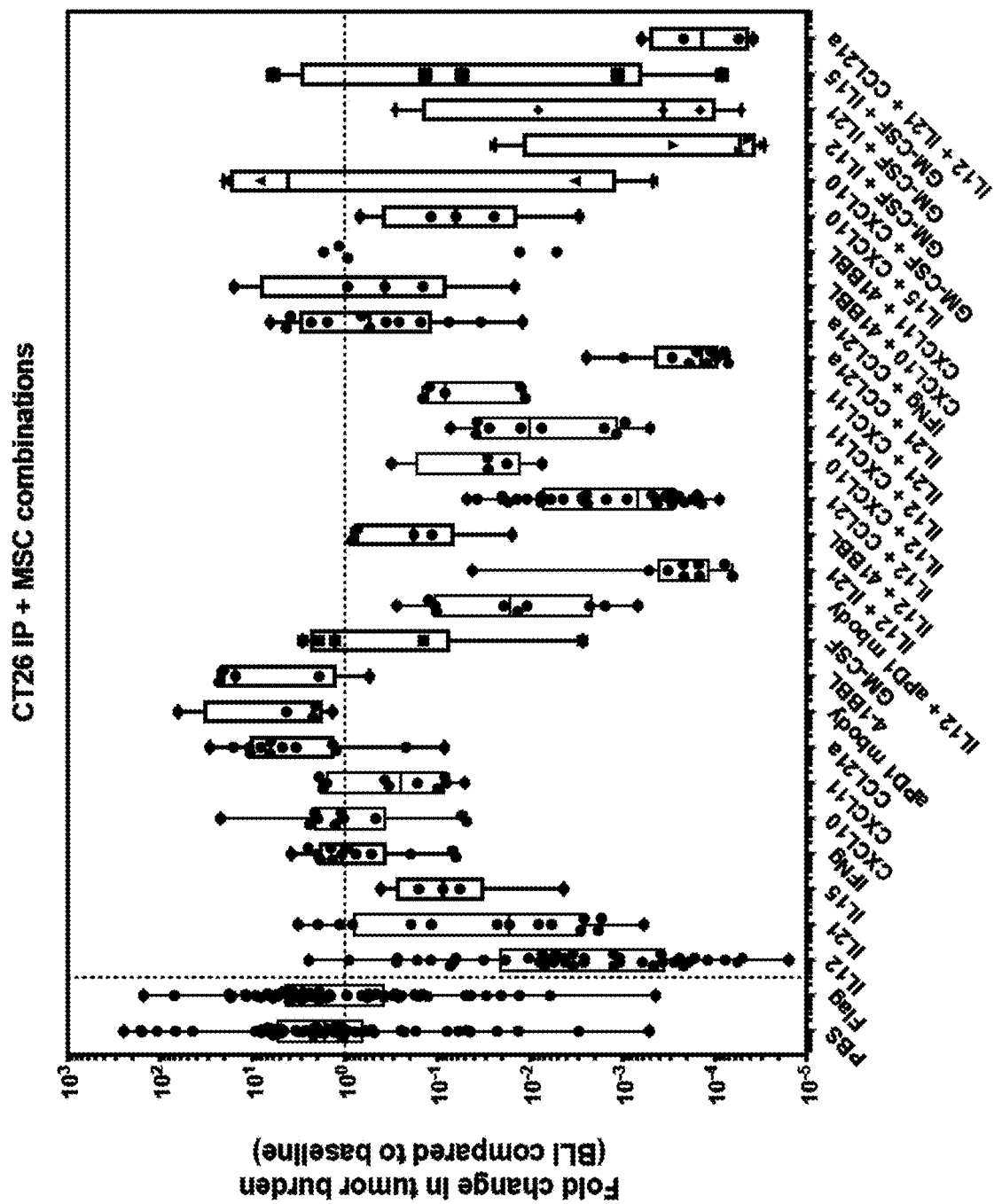
FIG. 51A shows MSCs engineered to express different effector molecules either alone or in combination and their efficacy in reducing CT26 tumor burden in an IP tumor model as assessed by BLI levels.

As shown in FIG. 51A, significant reductions in tumor burden were achieved with select effector-producing engineered-MSCs and select effector-producing engineered-MSCs in a CT26 syngeneic tumor model. Tumor burden fold change was calculated for each individual mouse by normalization of post-treatment BLI (day 10) vs pre-treatment BLI. All the cases where tumor burden fold change was lower than 1 (dotted line) represent tumor burden reduction. The top MSC-effectors that achieved significant reduction in tumor burden were: IL12, IL15, IL12+ anti-PD1(microbody), IL12+IL21, IL12+CCL21a, IL12+CXCL10, IL12+ CXCL11, IL21+CXCL11, IL21+CCL21a, IL15+CXCL10, GM-CSF+IL12, IL12+IL21+CCL21a.

Example 21: Engineered MSC Efficacy in B16F10 Tumor Model

In the following example, C57BL/6 mMSCs were engineered to express each of the various murine immune effectors shown in FIG. 51B using the lentiviral transduction method described in Example 6. Each MSC was engineered to express only a single agent. B16F10 tumor cells ($5\times10^4$ cells in 100 μl) modified to constitutively express luciferase enzyme (B16F10-Fluc-Puro Cat #:CL052, lot #: CL-IM150 Imanis Life Sciences) were injected into the peritoneal space of immunocompetent C57BL/6 female mice (age 6-8 weeks). One week after tumor implantation, tumor burden was measured by luciferase imaging (BLI) using an AMI imager. Mice were randomized into treatment groups and treated with intraperitoneally delivered mMSCs $1\times10^6$ expressing immune-modulatory cytokines or chemokines such as IL12p70. MSC-Flag-Myc and PBS were used as a negative control.

Figure 51B:
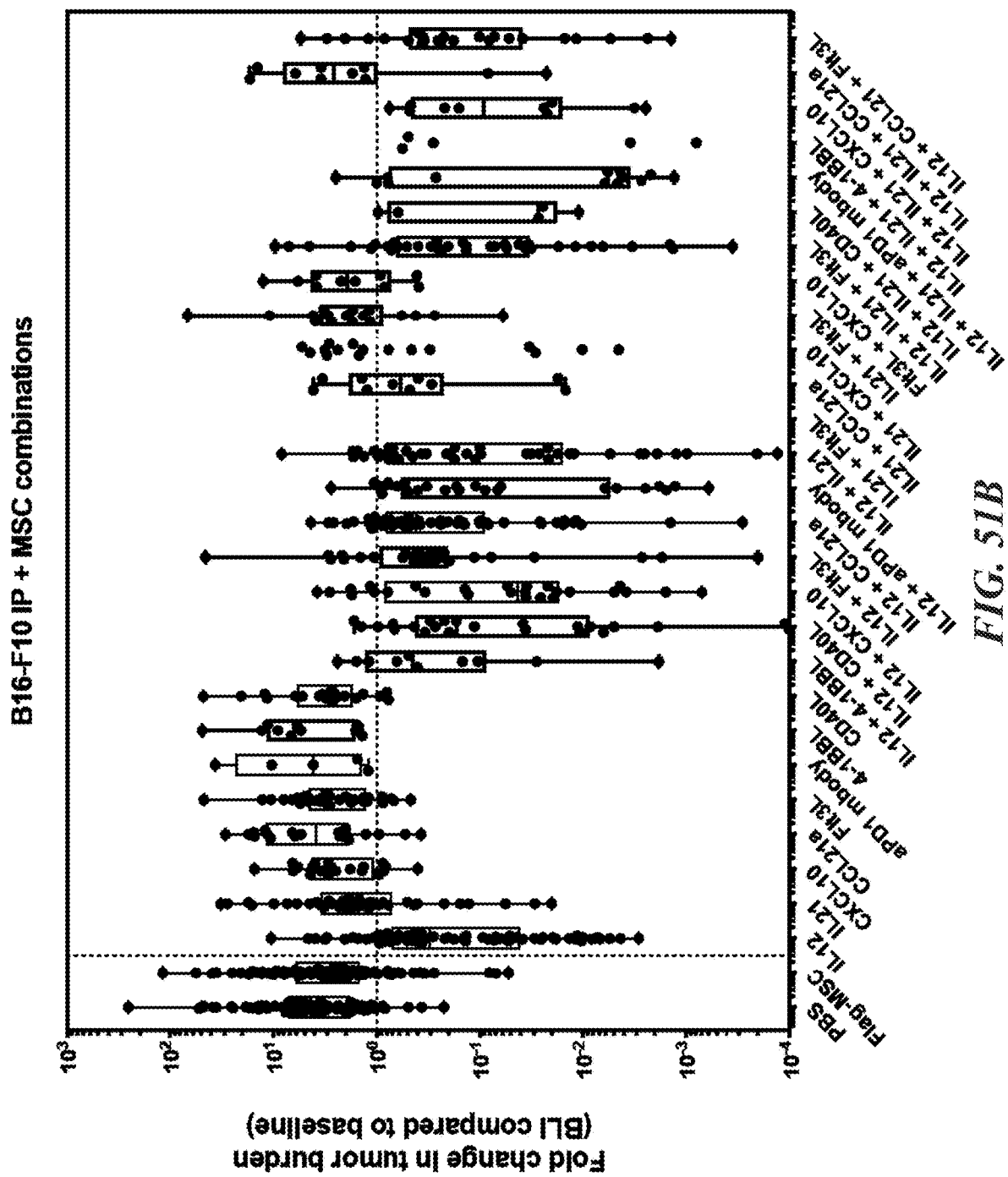
FIG. 51B shows MSCs engineered to express different effector molecules either alone or in combination and their efficacy in reducing B16F10 tumor burden in an IP tumor model as assessed by BLI levels.

As shown in FIG. 51B, significant reductions in tumor burden were achieved with select effector-producing engineered-MSCs and select effector-producing engineered-MSCs in a CT26 syngeneic tumor model. Selected effectors or combinations were achieving significant reduction in tumor burden: IL12, IL12+CD40L, IL12+CXCL10, IL12+ IL21, IL12+IL21+Flt3L, IL12+IL21+CXCL10, IL12+ CCL21a+Flt3L.

Example 22: IL12 Producing MSCs Reduce CT26 Tumor Burden in an IP Model

In the following example, balb/c mMSCs were engineered to express murine IL12p70 or murine IL21 (i.e., each MSC engineered to express only a single agent) using the lentiviral transduction method described in Example 6. CT26 tumor cells ($5\times10^4$ cells in 100 μl) modified to constitutively express luciferase enzyme (Cat no: CL043, Lot no: CL-IM147 Imanis Life Sciences) were injected into the peritoneal space of immunocompetent balb/c (age 6-8 weeks). One week after tumor implantation, tumor burden was measured by luciferase imaging (BLI) using an AMI imager. In addition, tumor weights were determined at the time of termination (day 17 post tumor implant). Mice were randomized into treatment groups and treated with intraperitoneally delivered mMSCs ($1\times10^6$ cells). MSC-Flag-Myc and PBS were used as a negative control. Experimental cohorts included: murine IL12-expressing murine MSCs, murine IL21-expressing murine MSCs, and combination treatment of murine IL12-expressing murine MSCs and murine IL21-expressing murine MSCs ($1\times10^6$ cells delivered for each in the combination).

Figure 52A:
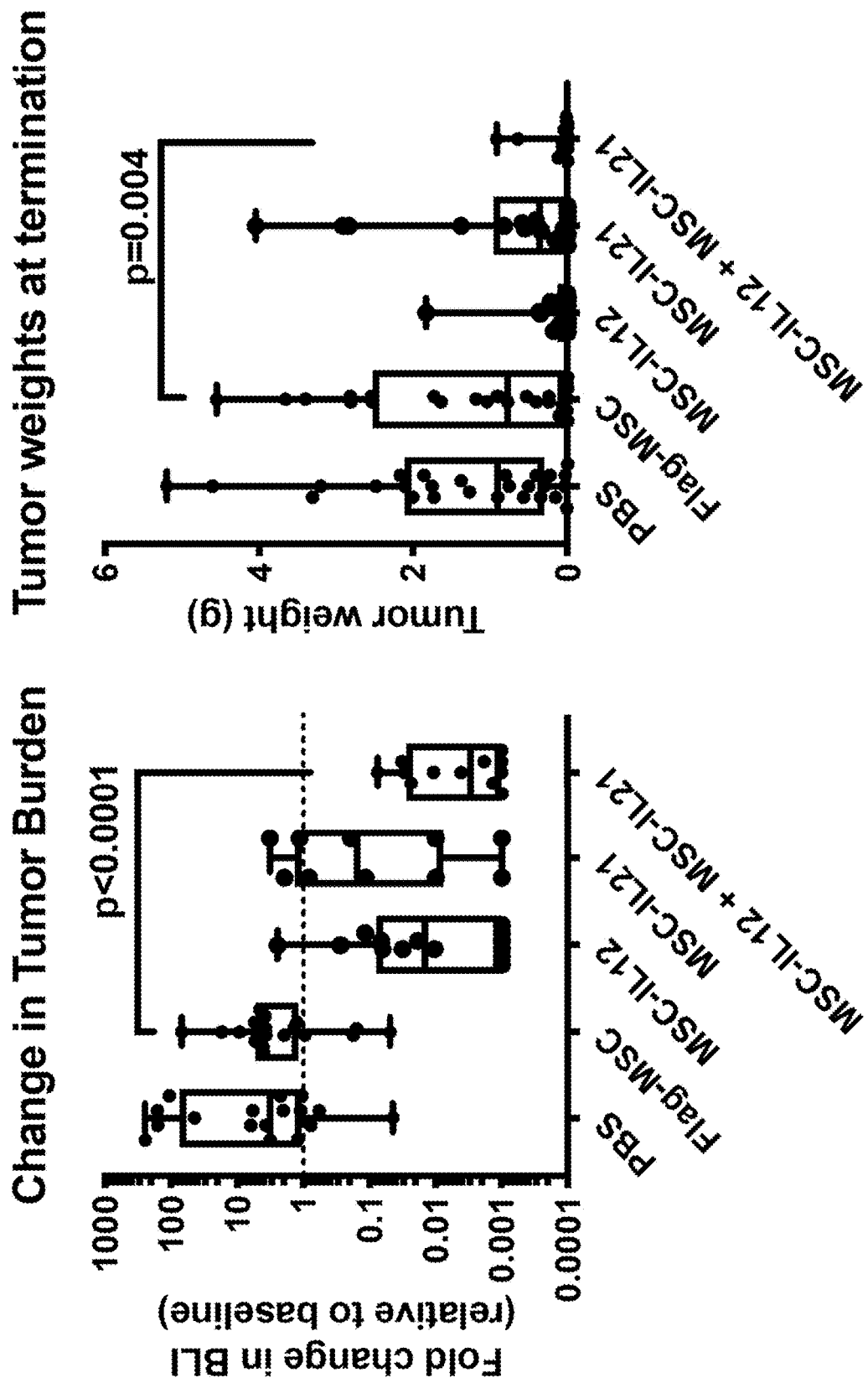
FIG. 52A shows efficacy of treatment using IL12p70-expressing MSCs, IL21-expressing MSCs, and the combination of IL12p70 and IL21-expressing MSCs as assessed by BLI for individual mice in each treatment, and the mean±SEM for each treatment group (left panel) and by tumor weight for individual mice in each treatment, and the mean±SEM for each treatment group (right panel) in a CT26 model.
Figure 52B:
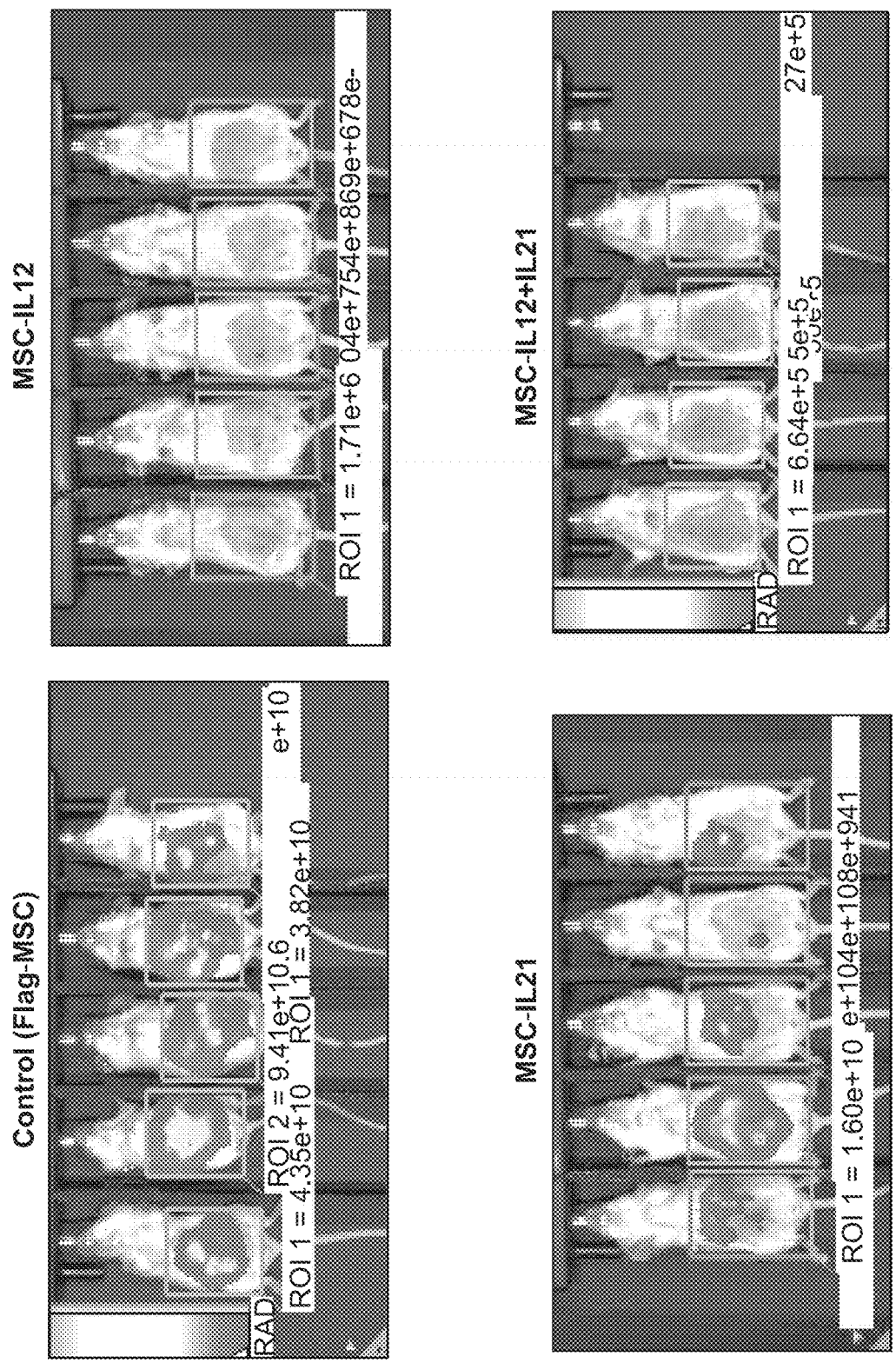
FIG. 52B shows efficacy of treatment using IL12p70-expressing MSCs, IL21-expressing MSCs, and the combination of IL12p70 and IL21-expressing MSCs in a CT26 model.

As shown in FIG. 52A and FIG. 52B, the groups receiving IL12p70-expressing MSCs, IL21-expressing MSCs, and the combination of IL12p70 and IL21-expressing MSCs led to reduction in tumor burdens as assessed by BLI (FIG. 52A left panel) and by tumor weight (FIG. 52A right panel) in a CT26 model, including a significant reduction in the combination treatment, relative to the controls. FIG. 52B demonstrates the BLI luciferase measurements of individual mice (results summarized in FIG. 52A left panel).

Figure 53A:
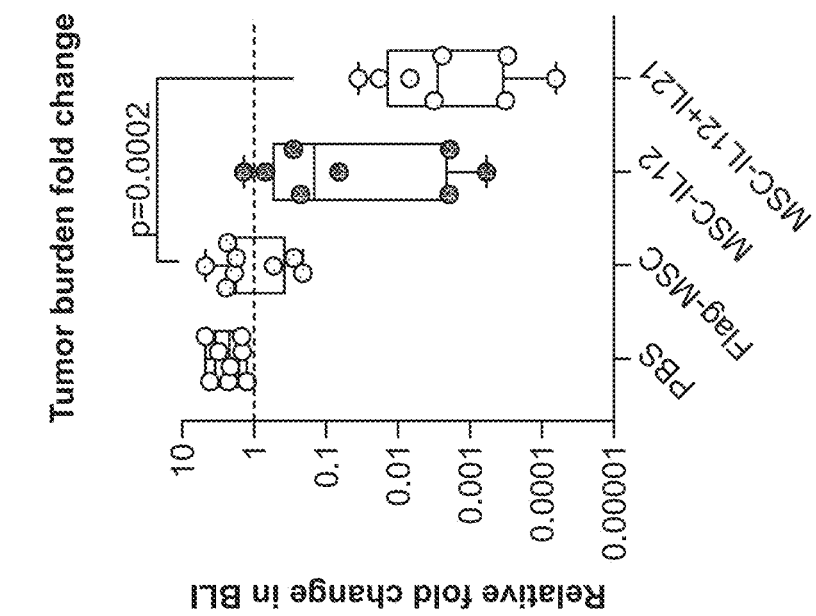
FIG. 53A shows efficacy of treatment using a lower dose of IL12p70-expressing MSCs, and the combination of IL12p70 and IL21-expressing MSCs as assessed by BLI; individual BLI measurements of mice—left panel; summary of BLI measurements for individual mice in each treatment, and the mean±SEM for each treatment group—right panel).
Figure 53A:
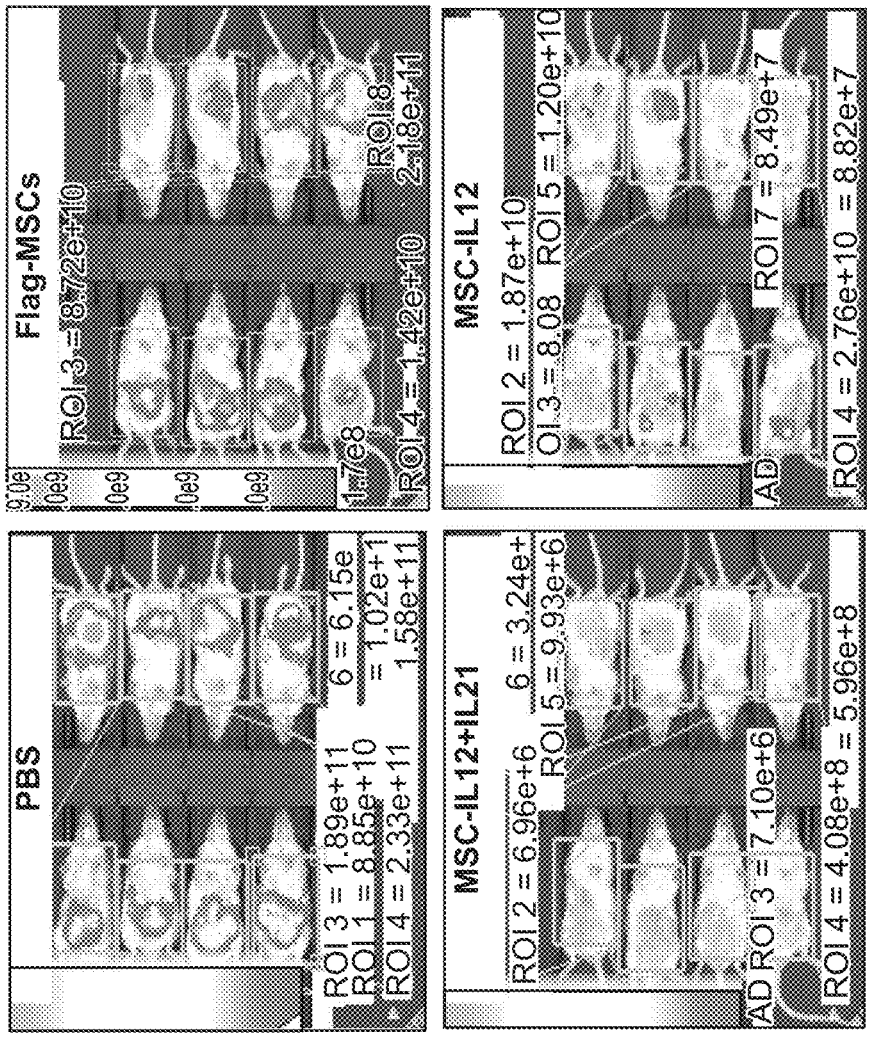
Figure 53B:
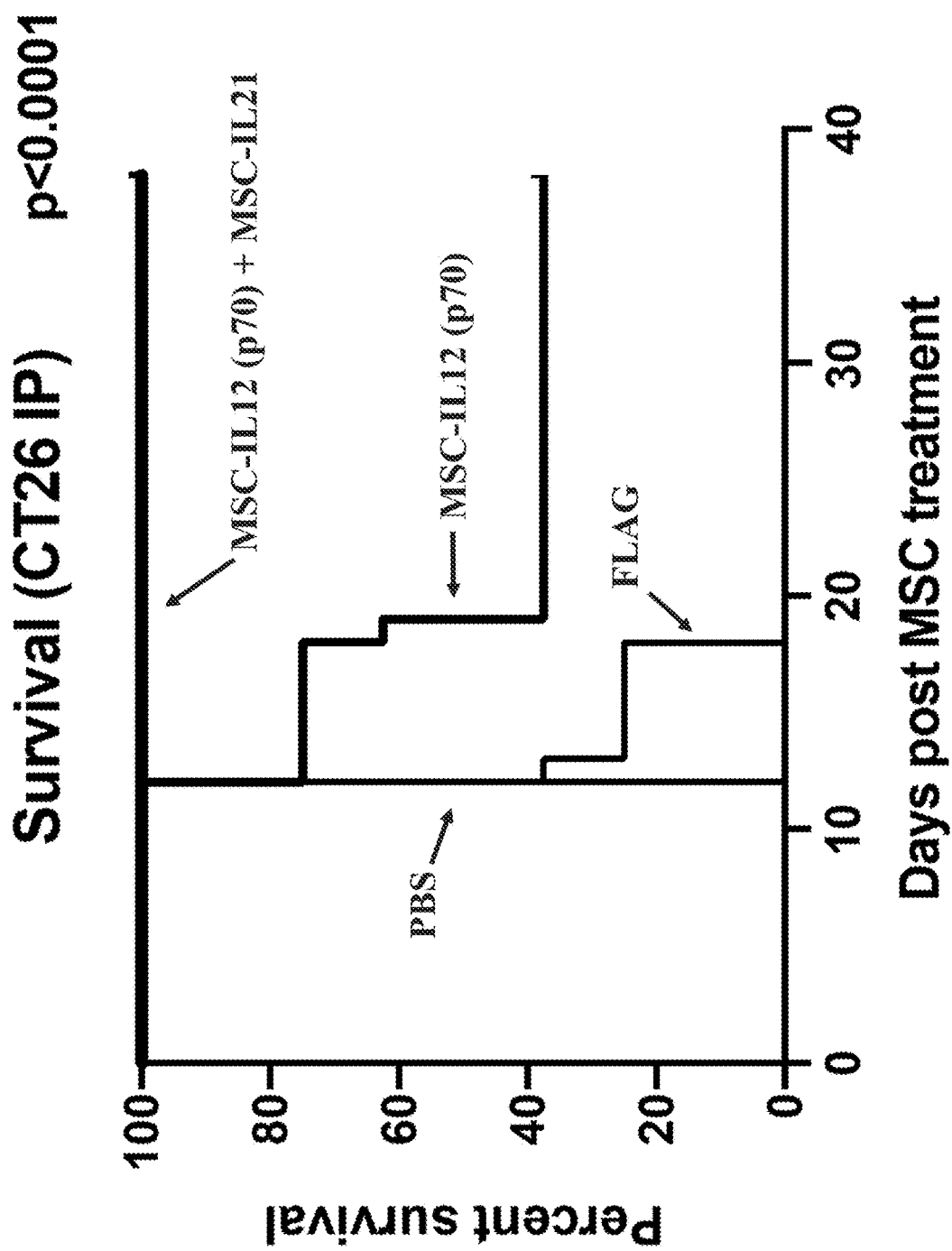
FIG. 53B shows efficacy of treatment using a lower dose of IL12p70-expressing MSCs, and the combination of IL12p70 and IL21-expressing MSCs.

The above experiment was repeated with the modification of delivering a lower dose of engineered mMSCs ($1\times10^5$ cells). As shown in FIG. 53A, the groups receiving IL12p70-expressing MSCs, and the combination of IL12p70 and IL21-expressing MSCs led to reduction in tumor burdens as assessed by BLI (FIG. 53A; individual BLI measurements of mice—left panel; summary of BLI measurements—right panel) in a CT26 model, including a significant reduction in the combination treatment, relative to the controls. Additionally, the combination treatment demonstrated increased efficacy relative to groups receiving IL12p70-expressing MSCs alone. As shown in FIG. 53B, treatment with $1\times10^5$ IL12p70 expressing MSCs in combination with $1\times10^5$ IL21 expressing MSCs led to tumor-free survival up to 40 days in all mice treated (n=8; median survival not reached). In contrast, treatment with $1\times10^5$ IL12p70 expressing MSCs alone only resulted in a 25% survival rate by day 40 (n=8; median survival 19 days). Control groups treated with PBS for FLAG-MSCs resulted in a 0% survival rate by day 40 (n=8 each; median survival 12 days each). Thus, IL21 expression by MSCs enhanced the efficacy of IL12p70 expressing MSCs.

Example 23: IL12 Producing MSCs Reduce B16F10 Tumor Burden in an IP Model

In the following example, C57BL/6 mMSCs were engineered to express murine IL12p70 or murine IL21 (i.e., each MSC engineered to express only a single agent) using the lentiviral transduction method described in Example 6. B16F10 tumor cells ($5\times10^4$ cells in 100 μl) modified to constitutively express luciferase enzyme (B16F10-Fluc-Puro Cat #:CL052, lot #: CL-IM150 Imanis Life Sciences) were injected into the peritoneal space of immunocompetent C57BL/6 (age 6-8 weeks). One week after tumor implantation, tumor burden was measured by luciferase imaging (BLI) using an AMI imager. In addition, tumor weights were determined at the time of termination (day 17 post tumor implant). Mice were randomized into treatment groups and treated with intraperitoneally delivered mMSCs ($1\times10^6$ cells). MSC-Flag-Myc and PBS were used as a negative control. Experimental cohorts included: murine IL12-expressing murine MSCs, murine IL21-expressing murine MSCs, and combination treatment of murine IL12-expressing murine MSCs and murine IL21-expressing murine MSCs ($1\times10^6$ cells delivered for each in the combination).

Figure 54:
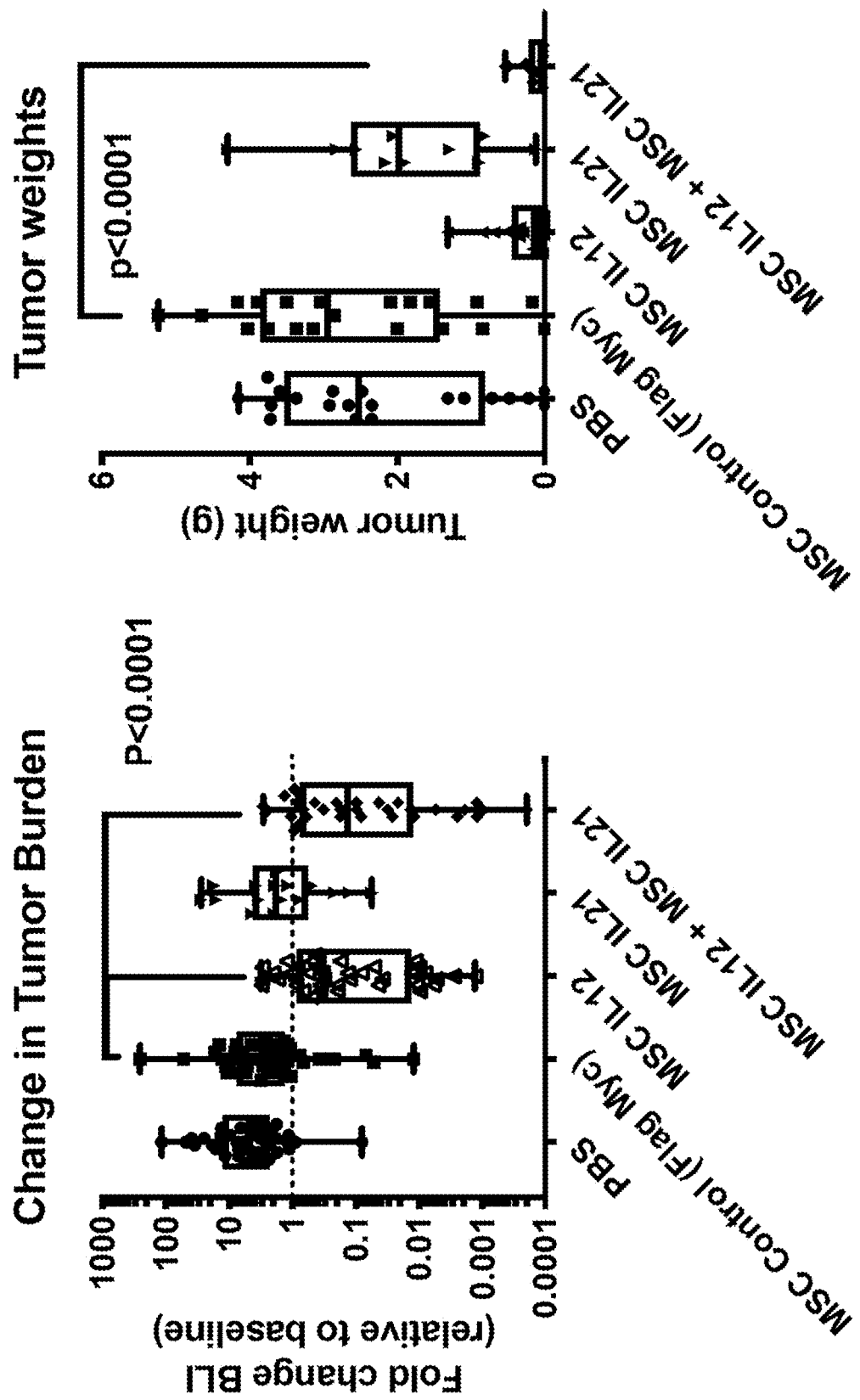
FIG. 54 shows efficacy of treatment using IL12p70-expressing MSCs, IL21-expressing MSCs, and the combination of IL12p70 and IL21-expressing MSCs as assessed by BLI for individual mice in each treatment, and the mean±SEM for each treatment group (left panel) and by tumor weight for individual mice in each treatment, and the mean±SEM for each treatment group (right panel) in a B16F10 model.
Figure 55:
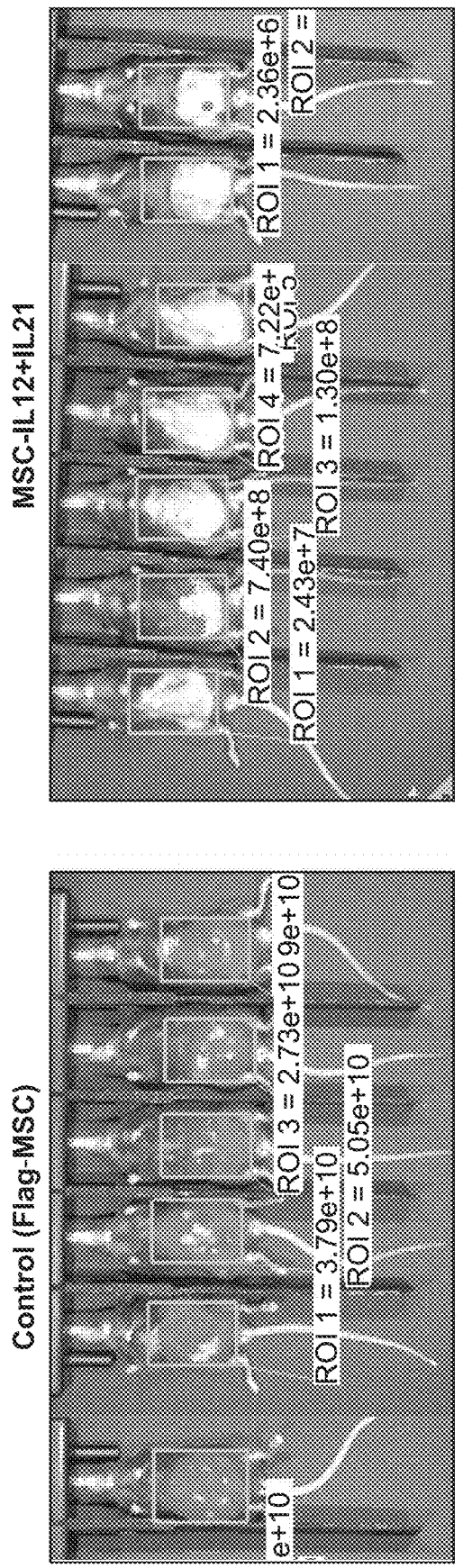
FIG. 55 demonstrates the BLI luciferase measurements of individual mice of following treatment using control FLAG-expressing MSCs (left panel) and the combination of IL12-expressing MSCs and IL21-expressing MSCs (right panel) in a B16F10 model.

As shown in FIG. 54 and FIG. 55, the groups receiving IL12p70-expressing MSCs, and the combination of IL12p70 and IL21-expressing MSCs led to reduction in tumor burdens as assessed by BLI (FIG. 54 left panel) and by tumor weight (FIG. 54 right panel) in a B16F10 model, including a significant reduction in the combination treatment, relative to the controls. Notably, IL21-expressing MSCs alone did not demonstrate a significant reduction in tumor burden or tumor weight. FIG. 55 demonstrates the BLI luciferase measurements of individual mice for the control FLAG-expressing MSCs and the combination of IL12-expressing MSCs and IL21-expressing MSCs (results summarized in FIG. 54 left panel).

Example 24: MSCs Producing IL12 and IL21 Prolong Tumor-Free Survival in a B16F10 IP Tumor Model and Survive Tumor Rechallenge In the following example, C57BL/6 mMSCs were engineered to express murine IL12 (p70) or murine IL21 (i.e., each MSC engineered to express only a single agent) using the lentiviral transduction method described in Example 6. B16F10 tumor cells ($5 \times 10^4$ cells in 100 µl) modified to constitutively express luciferase enzyme (B16F10-Fluc-Puro Cat #:CL052, lot #: CL-IM150 Imanis Life Sciences) were injected into the peritoneal space of immunocompetent C57BL/6 (age 6-8 weeks). Mice were randomized into treatment groups and treated with intraperitoneally delivered mMSCs ($1 \times 10^6$ cells). MSC-Flag-Myc and PBS were used as a negative control. Experimental cohorts included: murine IL12-expressing murine MSCs, murine IL21-expressing murine MSCs, and combination treatment of murine IL12-expressing murine MSCs and murine IL21-expressing murine MSCs ($1 \times 10^6$ cells delivered for each in the combination).

Figure 56:
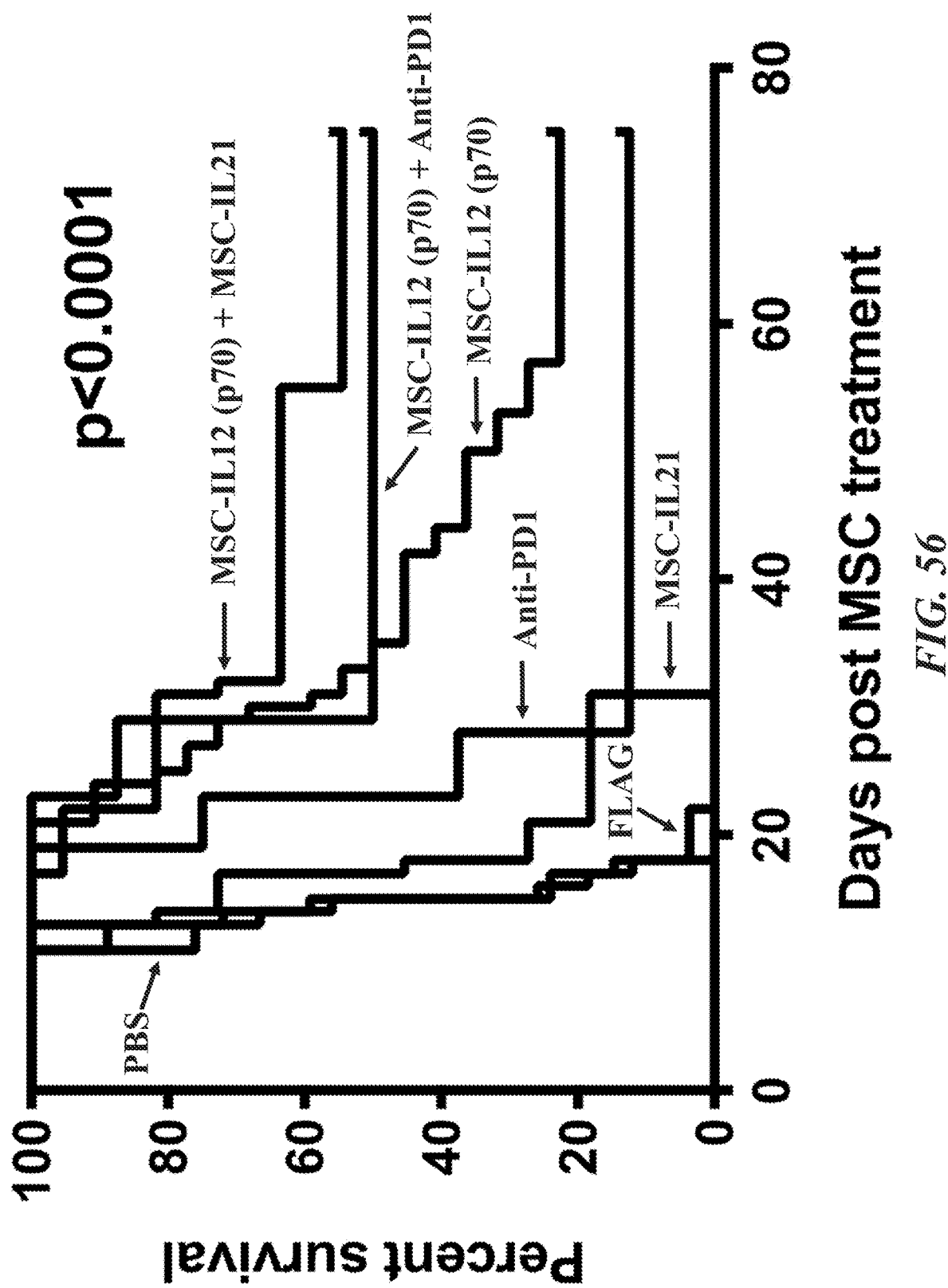
FIG. 56 shows survival curves of the treatment groups receiving IL12p70-expressing MSCs, IL21-expressing MSCs, the combination of IL12p70 and IL21-expressing MSCs, anti-PD1, or the combination of IL12p70 and anti-PD1.

As shown in FIG. 56, treatment with IL12p70 expressing MSCs led to prolonged survival (median survival 27 days post-treatment) relative to control treated mice (median survival of 8 days post-treatment for both PBS treated and FLAG-expressing MSCs). Treatment with IL12p70 expressing MSCs in combination with IL21 expressing MSCs led to prolonged survival (54.5% survival; median survival not reached) relative to treatment with IL12p70 expressing MSCs alone. Thus, IL21 expression by MSCs enhanced the efficacy of IL12p70 expressing MSCs.

Figure 57A:
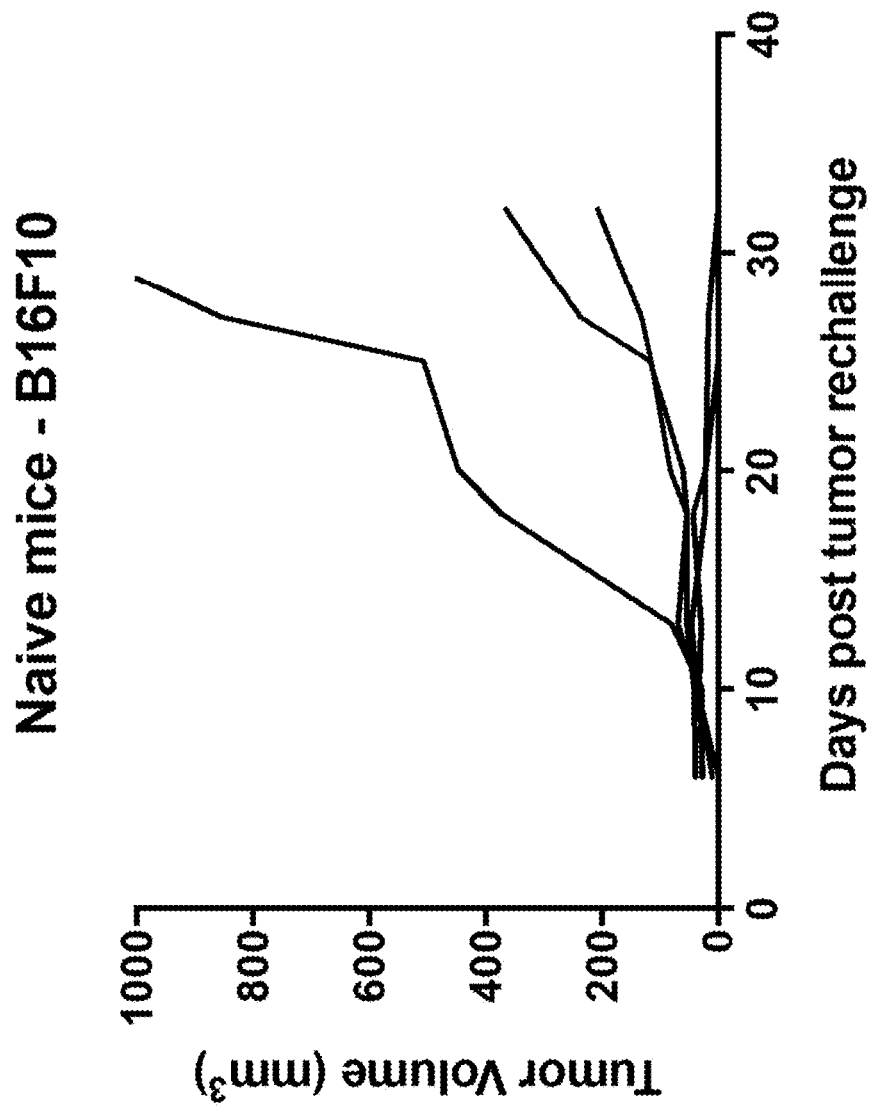
FIG. 57A shows survival curves of mice following tumor rechallenge.
Figure 57B:
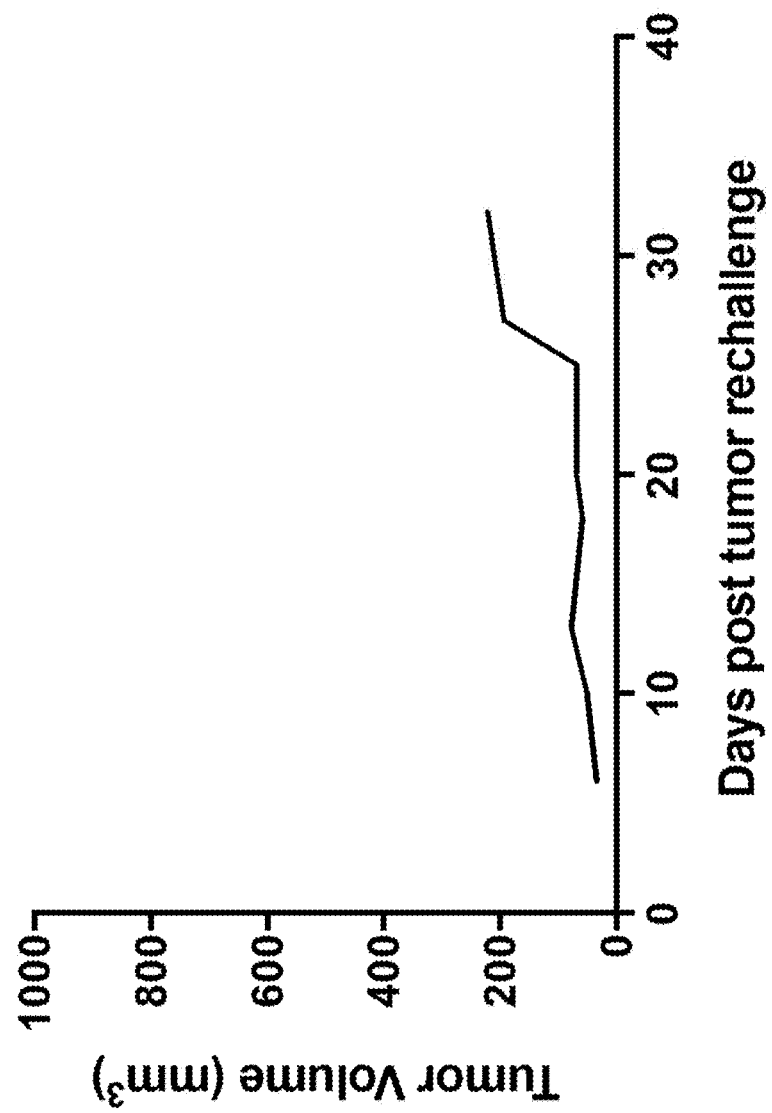
FIG. 57B shows survival curves of mice following tumor rechallenge.
Figure 57C:
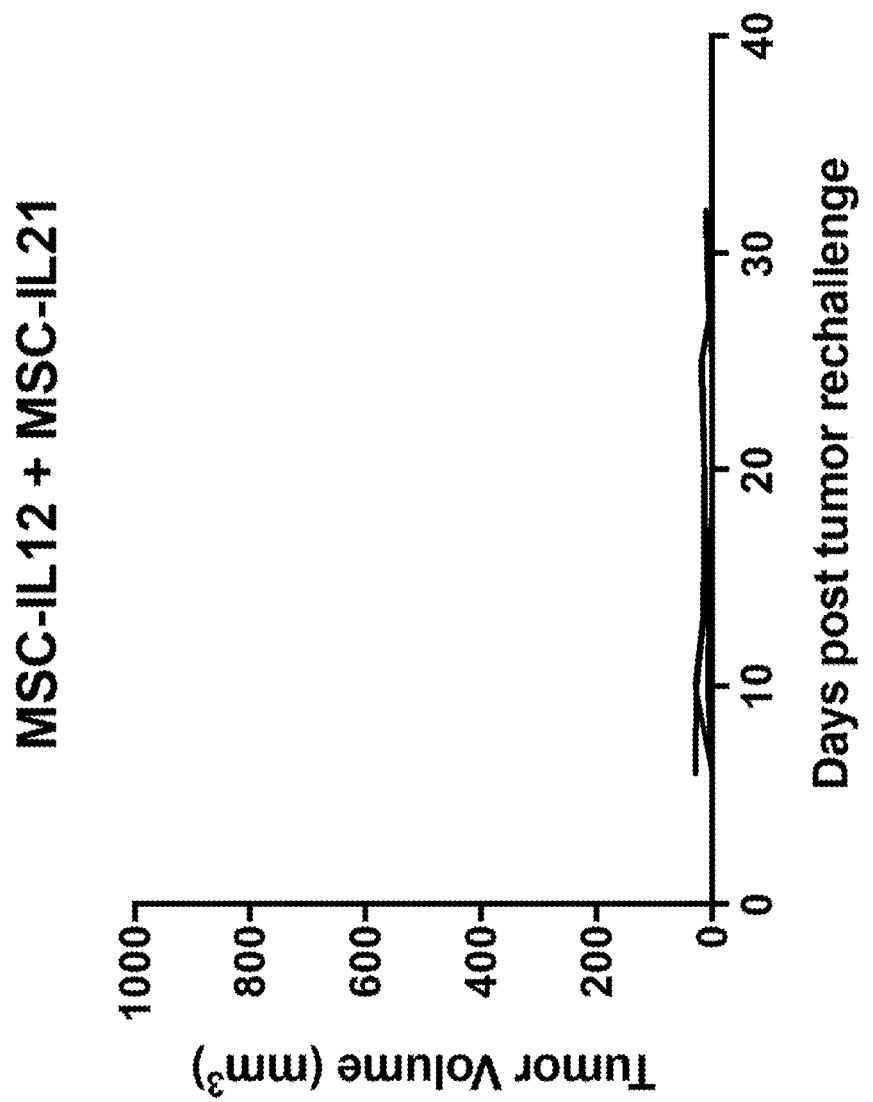
FIG. 57C shows survival curves of mice following tumor rechallenge.

Additionally, mice that were tumor-free for more than 90 days were subsequently re-challenged with B16-F10 tumor cells implanted in the flank ($1 \times 10^6$ cells). Naïve un-treated mice were implanted at the same time as controls. Subcutaneous tumor burden was measured by caliper. As shown in FIG. 57C, all mice (n=4) that previously received the combination treatment of IL12-expressing MSCs and IL21-expressing MSCs survived rejected the newly implanted tumor, indicating that the treatment resulted in achievement of anti-tumor immune memory. Mice that previously received the treatment of IL12-expressing MSCs alone had a 50% tumor-rejection rate (2 out of 4 mice; FIG. 57B). In contrast, tumor were established in 60% of naïve mice (3 out of 5 mice; FIG. 57A).

Example 25: MSCs Producing IL12 in Combination with Immune Checkpoint Therapy Prolong Survival in a B16F10 IP Tumor Model In the following example, C57BL/6 mMSCs were engineered to express murine IL12 (p70) using the lentiviral transduction method described in Example 6. B16F10 tumor cells ($5 \times 10^4$ cells in 100 µl) modified to constitutively express luciferase enzyme (B16F10-Fluc-Puro Cat #:CL052, lot #: CL-IM150 Imanis Life Sciences) were injected into the peritoneal space of immunocompetent C57BL/6 (age 6-8 weeks). Mice were randomized into treatment groups and treated with IP administration of anti-PD1 antibody (clone RMP1-14) at a dose of 200 mg/kg alone or in combination with low dose (1e5) of IL12-expressing murine MSCs.

As shown in FIG. 56, treatment with anti-PD1 alone resulted in a 12.5% survival rate and median survival of 23 days (FIG. 56 "Anti-PD1"; 1 out of 8 mice had long term tumor-free survival). In contrast, the combined treatment of anti-PD1 with IL12p70 expressing MSCs resulted in a 50% survival rate (FIG. 56 "MSC-IL12 (p70)+Anti-PD1"; 4 out of 8 mice had long term tumor-free survival; median survival not yet established). Thus, IL12 expression by MSCs enhanced the efficacy of anti-PD1 immune checkpoint therapy and convert a checkpoint refractory or resistant model (B16F10) into responsive.

Example 26: MSCs Producing Both IL12 and IL21 Reduce Tumor Burden in a CT26 IP Tumor Model In the following example, balb/c mMSCs were engineered to express murine IL12 (p70) and murine IL21 from a single lentiviral expression vector. The lentiviral expression vector used a 2A ribosome skipping elements to express both cytokines from a single transcript using the lentiviral transduction method described in Example 6. CT26 tumor cells ($1 \times 10^5$ cells in 100 µl) modified to constitutively express luciferase enzyme (Cat no: CL043, Lot no: CL-IM147 Imanis Life Sciences) were injected into the peritoneal space of immunocompetent female balb/c mice (age 6-8 weeks). One week after tumor implantation, tumor burden was measured by luciferase imaging (BLI) using an AMI imager. Mice were randomized into treatment groups and treated IP with different amounts of mMSCs ranging from $1 \times 10^4$ to $1 \times 10^6$ cells. MSC-Flag-Myc ($1 \times 10^6$ cells) and PBS were used as a negative control.

Figure 58A:
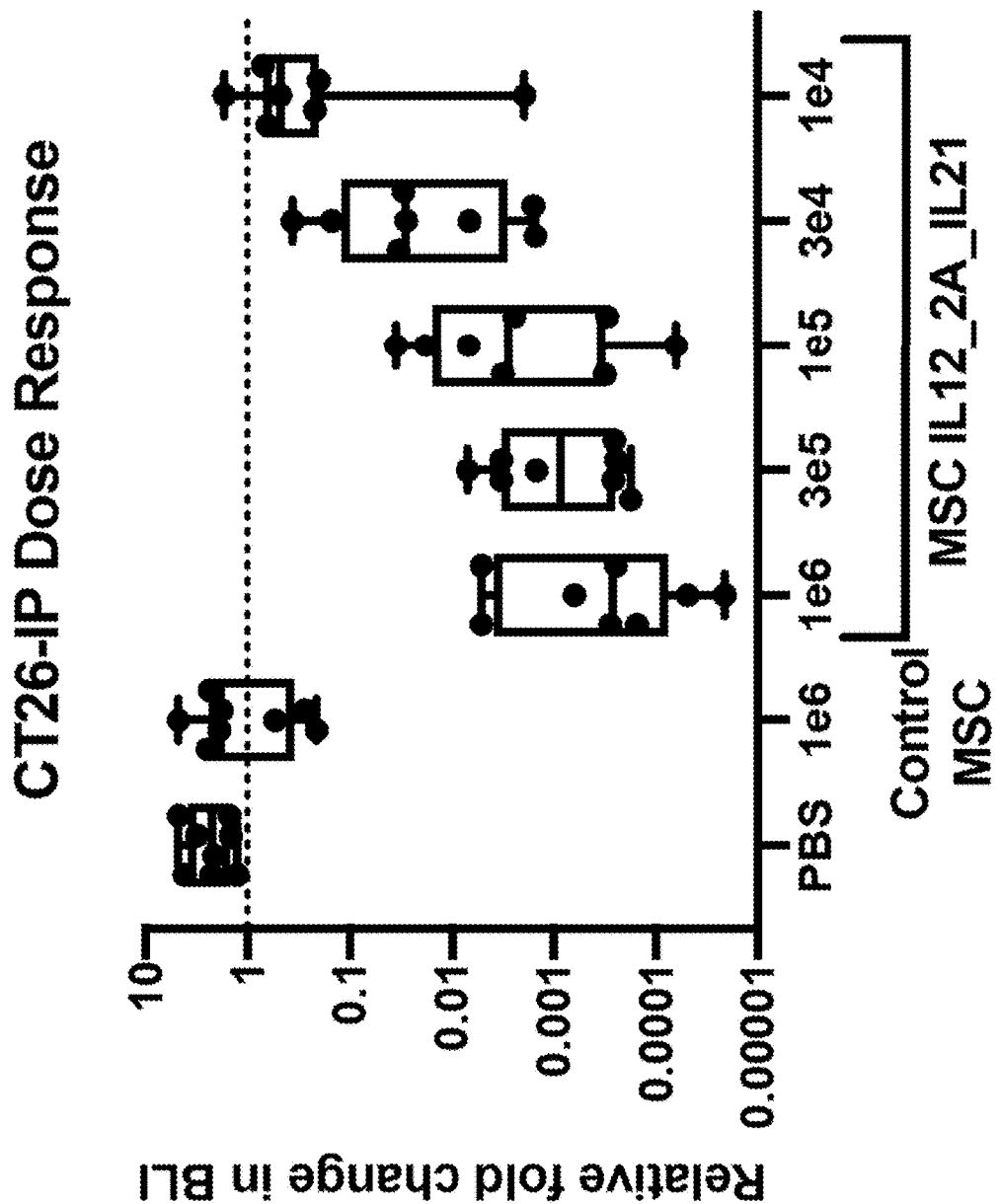
FIG. 58A shows dose-dependent efficacy of treatment using mMSCs engineered to express murine IL12 (p70) and murine IL21 from a single lentiviral expression vector in a CT26 tumor model.
Figure 58B:
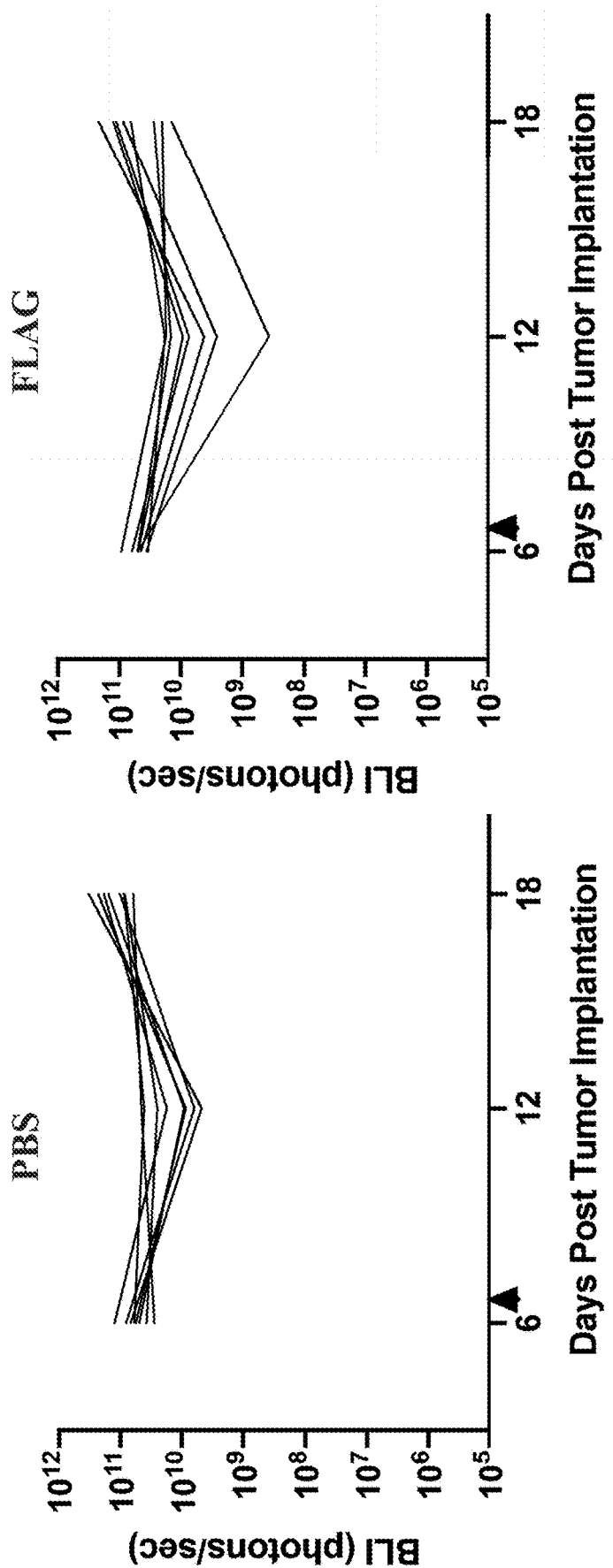
FIG. 58B shows dose-dependent efficacy of treatment using mMSCs engineered to express murine IL12 (p70) and murine IL21 from a single lentiviral expression vector in a CT26 tumor model.
Figure 58C:
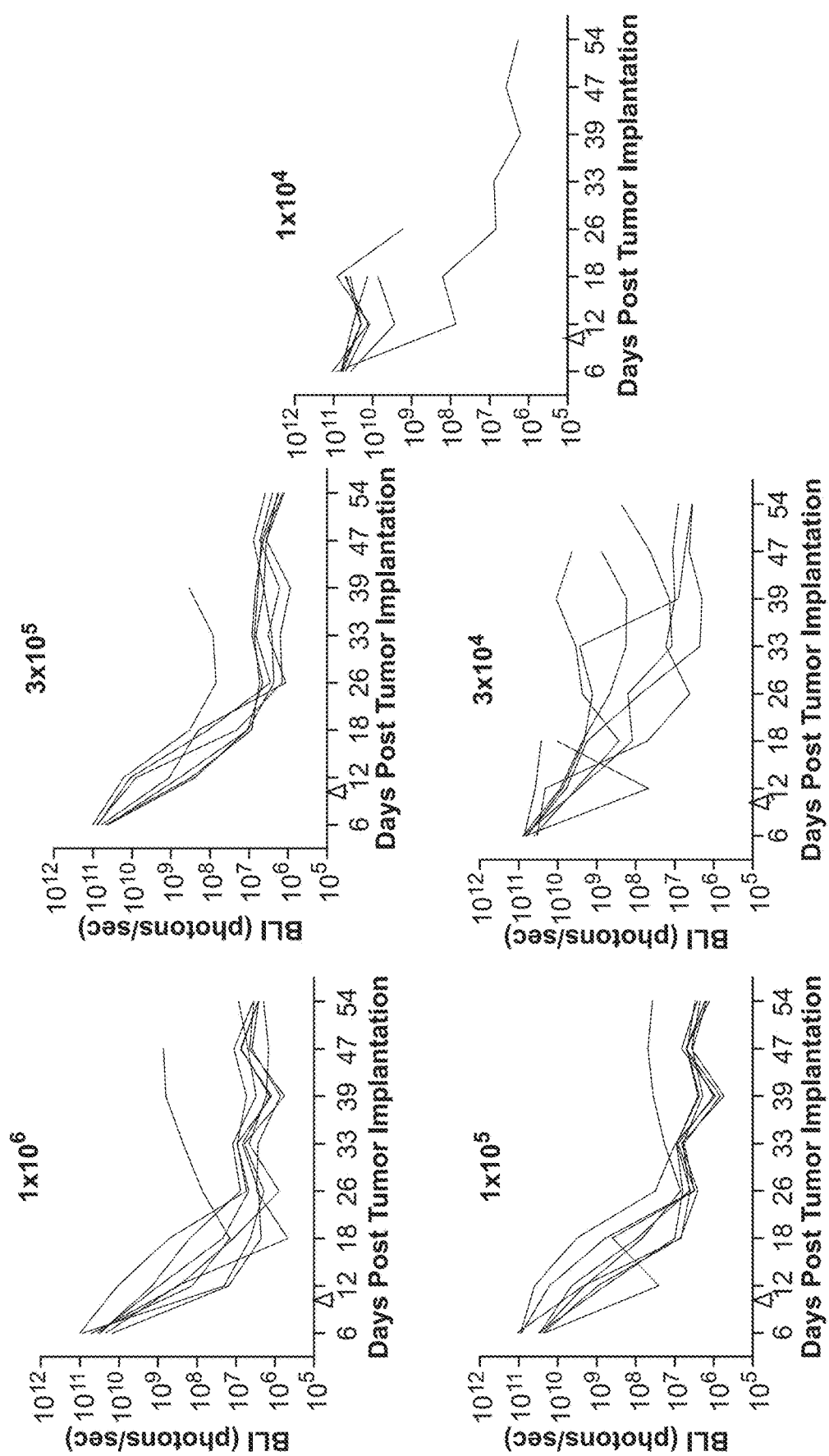
FIG. 58C shows dose-dependent efficacy of treatment using mMSCs engineered to express murine IL12 (p70) and murine IL21 from a single lentiviral expression vector in a CT26 tumor model.
Figure 58D:
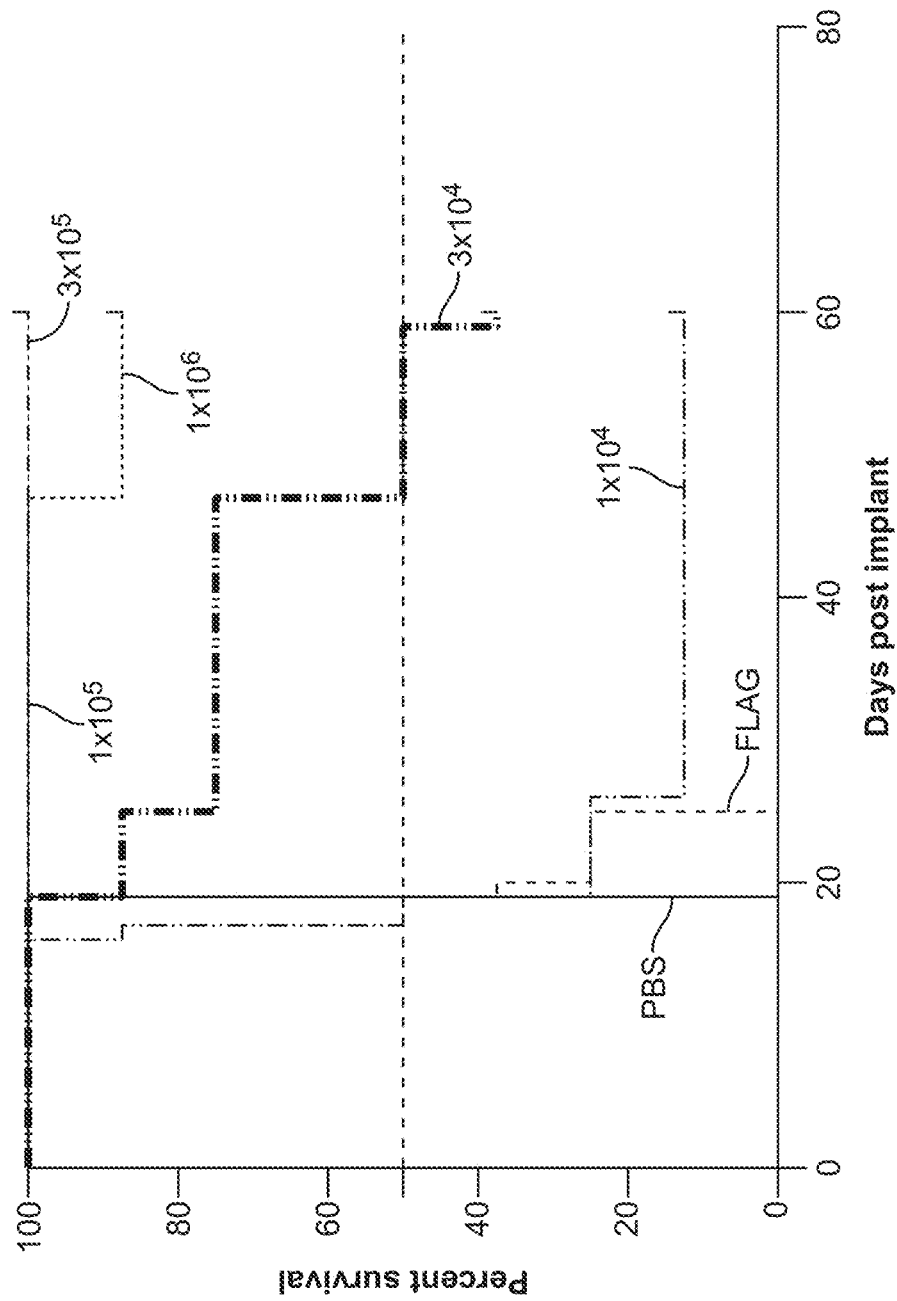
FIG. 58D shows dose-dependent efficacy of treatment using mMSCs engineered to express murine IL12 (p70) and murine IL21 from a single lentiviral expression vector in a CT26 tumor model.

As shown in FIG. 58A-C, anti-tumor activity was observed in a dose-dependent manner of MSCs expressing both IL12 and IL21, as assessed by BLI (FIG. 58A normalized day 17 vs day 7; FIG. 58B and FIG. 58C BLI over time for individual mice). No efficacy was observed in control FLAG or PBS mice (FIG. 58A and FIG. 58B). In contrast, minimal efficacy was observed at a dose of $1 \times 10^4$, with efficacy increasing at each increased dose (FIG. 58A and FIG. 58C). As shown in FIG. 58D, long term tumor-free survival up to 60 days post tumor implant was observed in a dose-dependent manner, with mice treated with $1 \times 10^6$ to $1 \times 10^5$ having significantly extended tumor-free survival (Median survival post-implant: PBS/FLAG—19 days; $1 \times 10^6$ to $1 \times 10^5$—not reached; $3 \times 10^4$—53 days; $1 \times 10^4$—18-19 days).

Example 27: MSCs Producing Both IL12 and IL21 Reduce Tumor Burden in a B16F10 IP Tumor Model In the following example, C57BL/6 mMSCs were engineered to express murine IL12 (p70) and murine IL21 from a single lentiviral expression vector. The lentiviral expression vector used a 2A ribosome skipping elements to express both cytokines from a single transcript using the lentiviral transduction method described in Example 6. B16F10 tumor cells ($5 \times 10^4$ cells in 100 µl) modified to constitutively express luciferase enzyme (B16F10-Fluc-Puro Cat #:CL052, lot #: CL-IM150 Imanis Life Sciences) were injected into the peritoneal space of immunocompetent C57BL/6 (age 6-8 weeks). One week after tumor implantation, tumor burden was measured by luciferase imaging (BLI) using an AMI imager. Mice were randomized into treatment groups and treated with different amounts of mMSCs ranging from $1\times10^5$ to $1\times10^7$ cells). MSC-Flag-Myc ($3\times10^6$ cells) and PBS were used as a negative control. Some groups were treated with multiple doses separated by 5 days (treatment on day 7, 12 and 17 post tumor-implant).

Figure 59A:
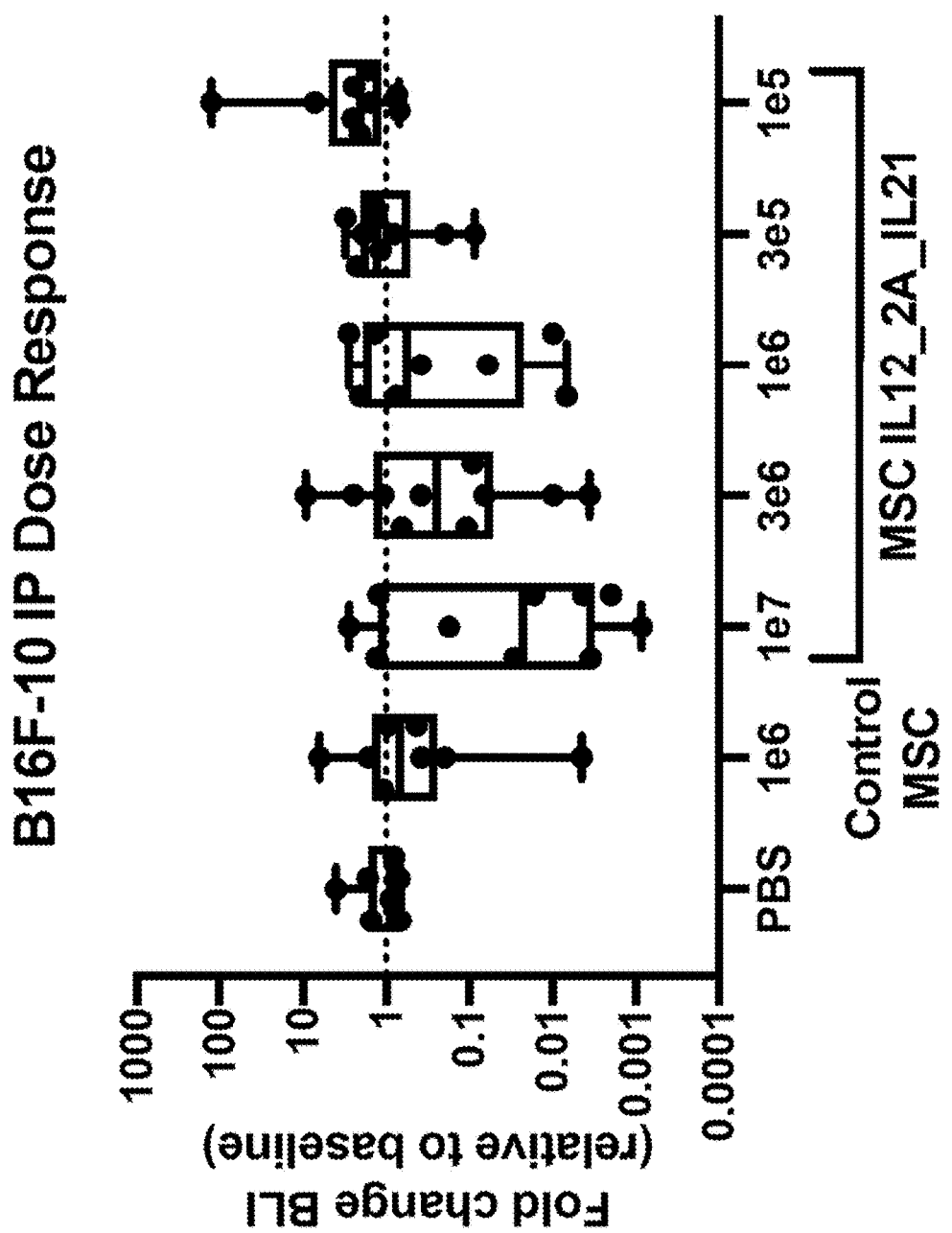
FIG. 59A shows dose-dependent efficacy of treatment using mMSCs engineered to express murine IL12 (p70) and murine IL21 from a single lentiviral expression vector in a B16F10 tumor model.
Figure 59B:
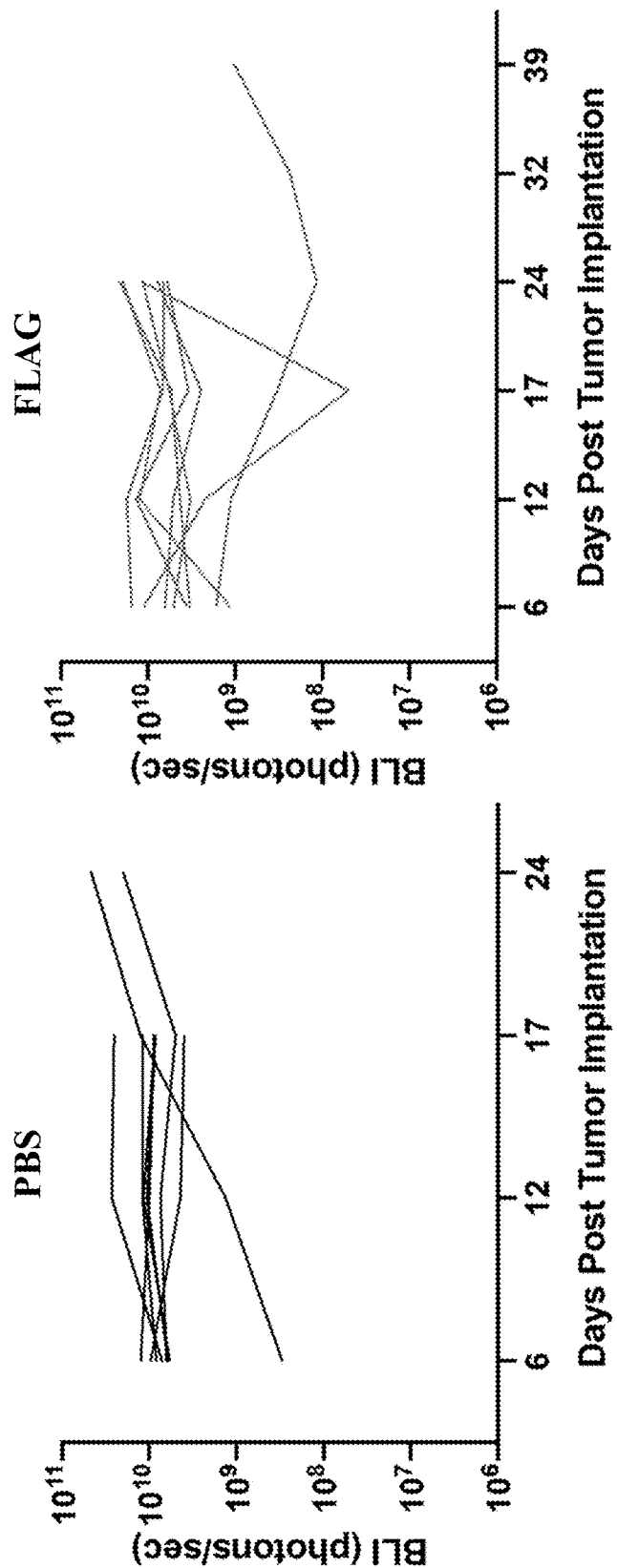
FIG. 59B shows efficacy of treatment using control FLAG mMSCs (right) or PBS (left) in a B16F10 tumor model.
Figure 59C:
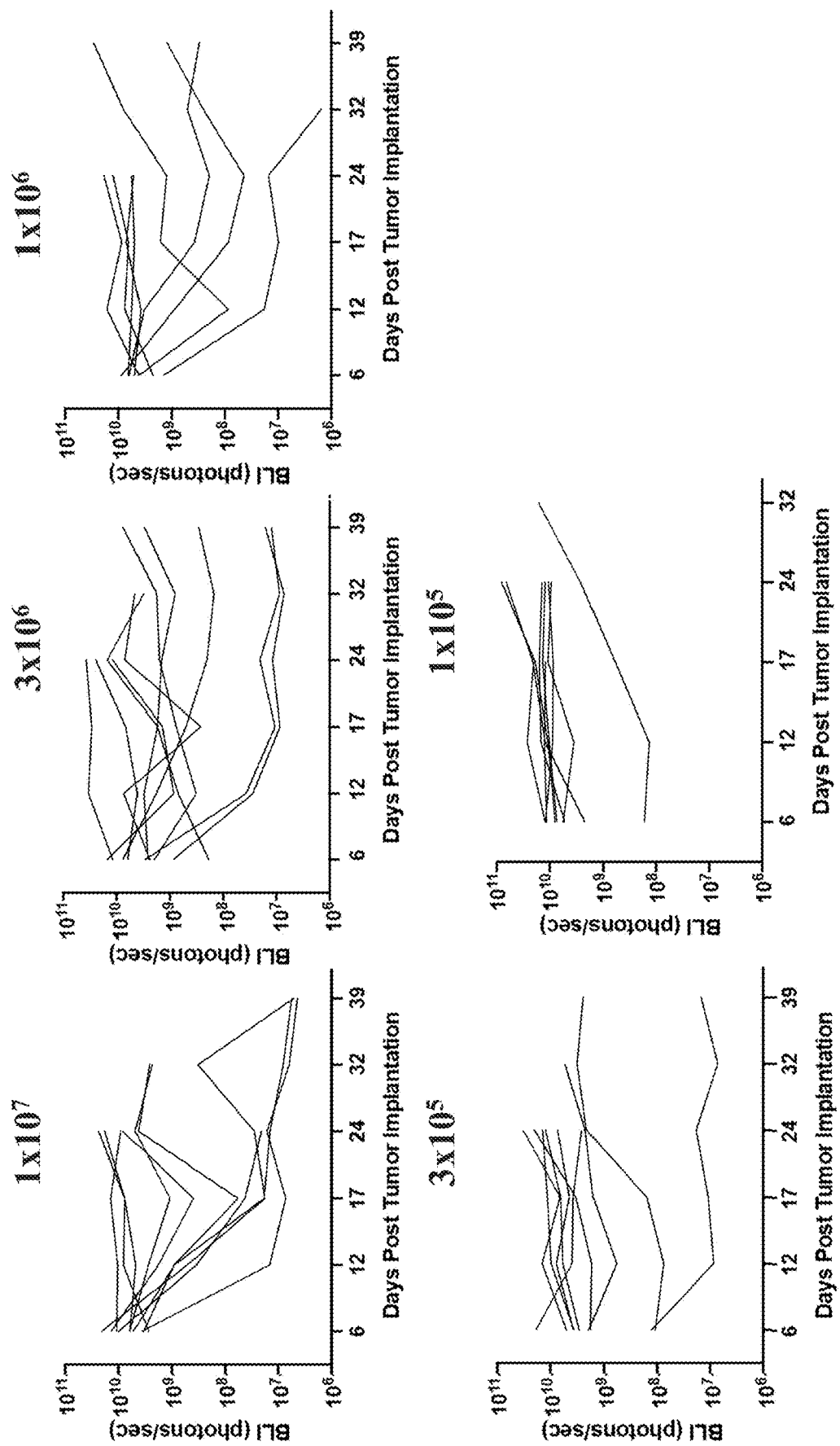
FIG. 59C shows dose-dependent efficacy of treatment using mMSCs engineered to express murine IL12 (p70) and murine IL21 from a single lentiviral expression vector in a B16F10 tumor model.
Figure 59D:
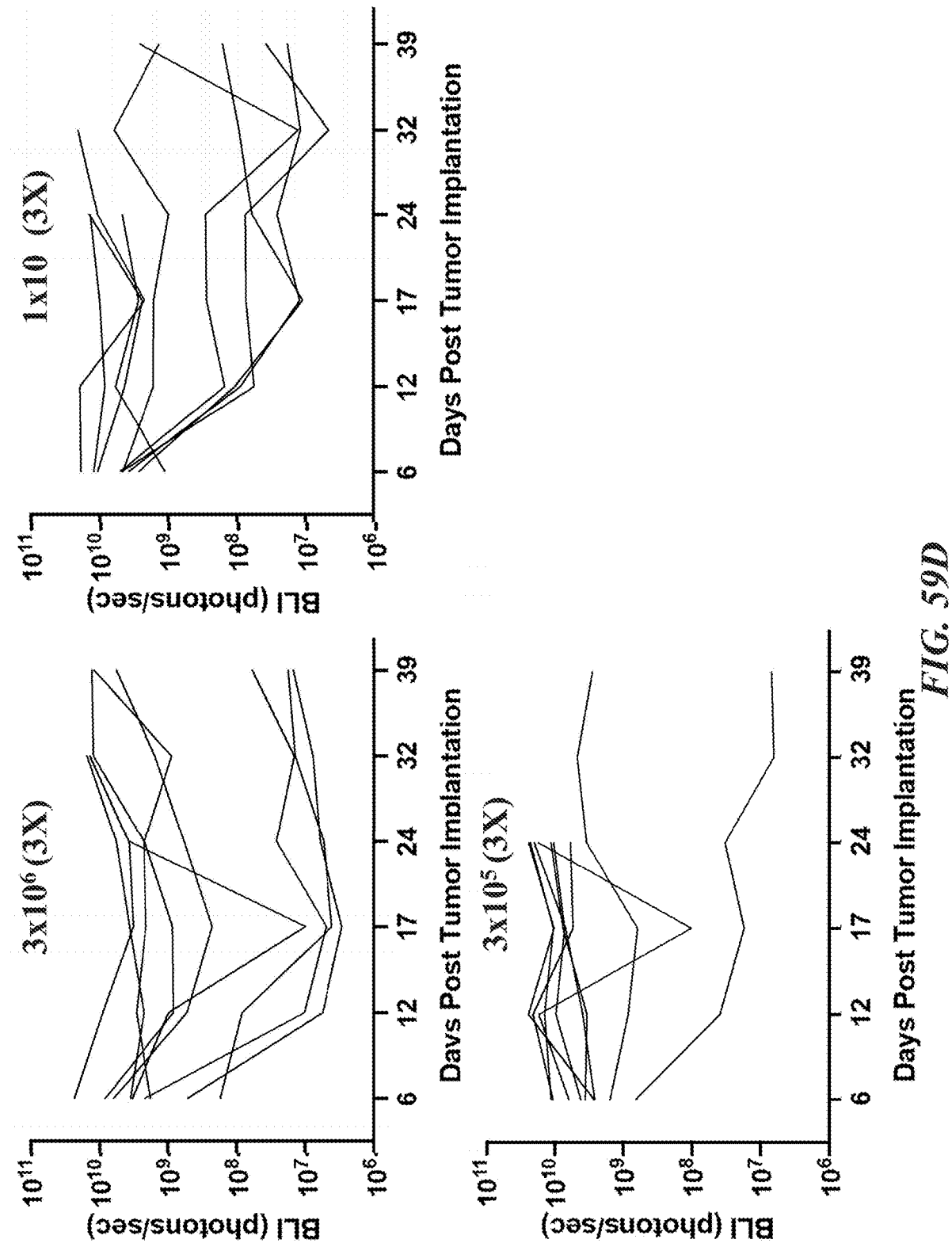
FIG. 59D shows dose-dependent efficacy of treatment using mMSCs engineered to express murine IL12 (p70) and murine IL21 from a single lentiviral expression vector in a B16F10 tumor model.
Figure 59E:
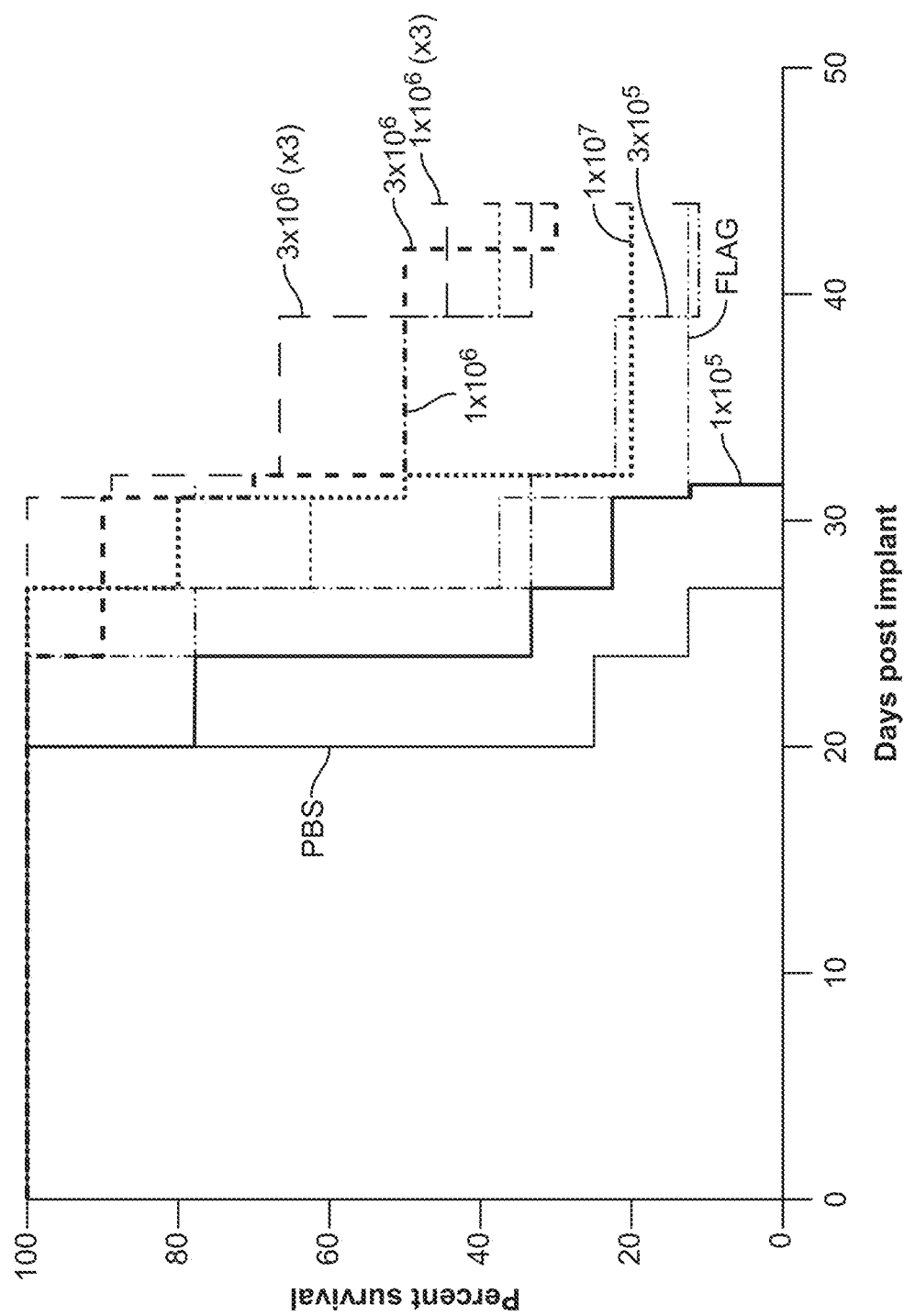
FIG. 59E shows dose-dependent efficacy of treatment using mMSCs engineered to express murine IL12 (p70) and murine IL21 from a single lentiviral expression vector in a B16F10 tumor model.

As shown in FIG. 59A-D, anti-tumor activity was observed in a dose-dependent manner of MSCs expressing both IL12 and IL21, as assessed by BLI (FIG. 59A normalized day 17 vs day 7; FIG. 59B-D BLI over time for individual mice). No efficacy was observed in control FLAG or PBS mice (FIG. 59A and FIG. 59B). No efficacy was also observed at doses of $1\times10^5$ or $3\times10^5$ cells (FIG. 59A and FIG. 59C). In contrast, minimal efficacy was observed at a dose of $1\times10^6$, with efficacy increasing at each increased dose (FIG. 59A and FIG. 59C). Efficacy was also observed following multiple administrations of higher doses (FIG. 59D). As shown in FIG. 59E, long term tumor-free survival was observed in a dose-dependent manner, and also observed following multiple administrations of higher doses (Median survival post-implant: PBS—20 days; FLAG ($\times3$)—27 days; $1\times10^7$—31.5 days; $3\times10^6$—36 days; $3\times10^6$ ($\times3$)—39 days; $1\times10^6$—33 days; $1\times10^6$ ($\times3$)—39 days; $3\times10^5$—27 days; $3\times10^5$ ($\times3$)—27 days [curve overlaps with $3\times10^5$ treatment]; $1\times10^5$—24 days).

Example 28: MSCs Producing Both IL12 and IL21 Reduce Tumor Burden in a MC-38 IP Tumor Model In the following example, C57BL/6 mMSCs were engineered to express murine IL12 (p70) and murine IL21 from a single lentiviral expression vector. The lentiviral expression vector used a 2A ribosome skipping elements to express both cytokines from a single transcript using the lentiviral transduction method described in Example 6. MC-38 tumor cells were transduced with fLUC-EGFP construct and sorted based on EGFP fluorescence, then $5\times10^5$ cells were injected into the peritoneal space of immunocompetent C57BL/6 (age 6-8 weeks). Nine days after tumor implantation, tumor burden was measured by luciferase imaging (BLI) using an AMI imager. Mice were randomized into treatment groups and treated with different amounts of mMSCs ranging from $3\times10^4$ to $1\times10^6$ cells. MSC-Flag-Myc and PBS were used as a negative control.

Figure 60A:
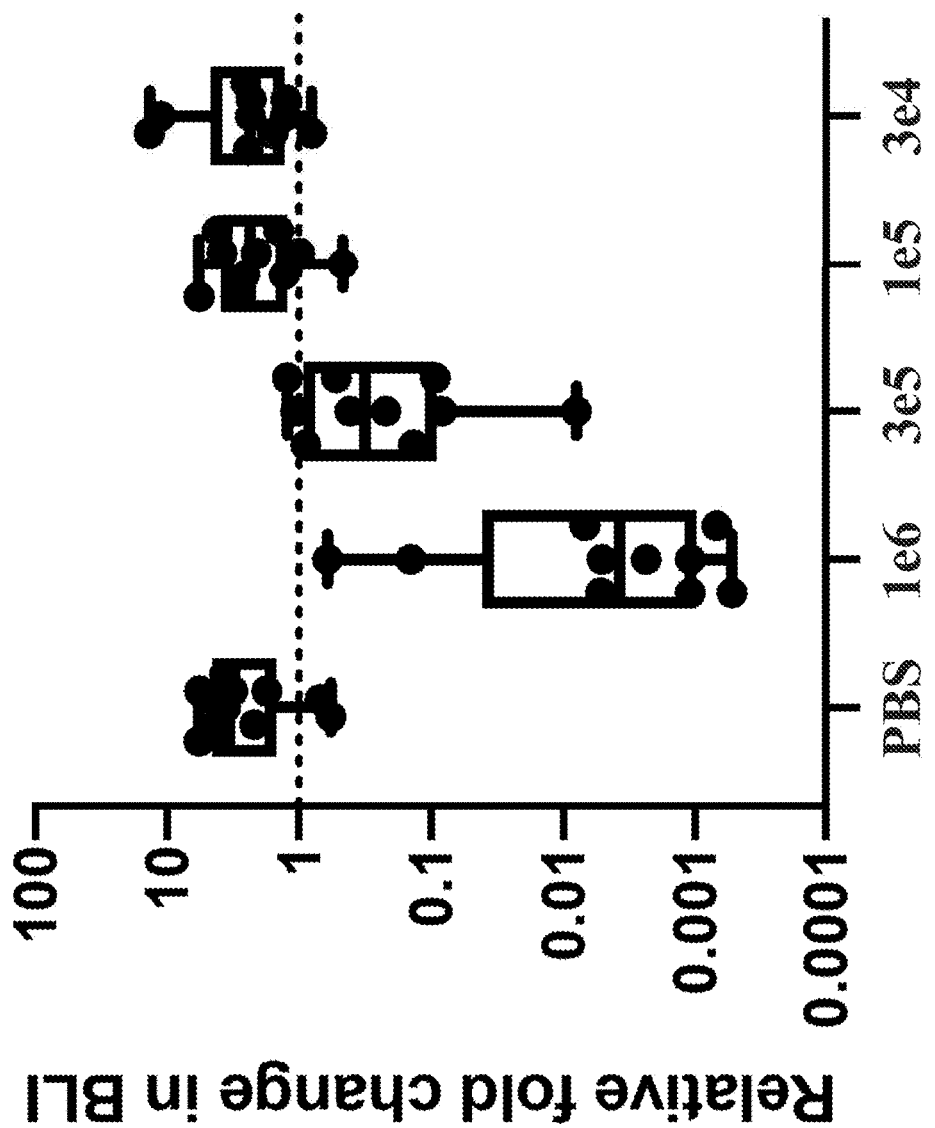
FIG. 60A shows dose-dependent efficacy of treatment using mMSCs engineered to express murine IL12 (p70) and murine IL21 from a single lentiviral expression vector in a MC-38 tumor model.
Figure 60B:
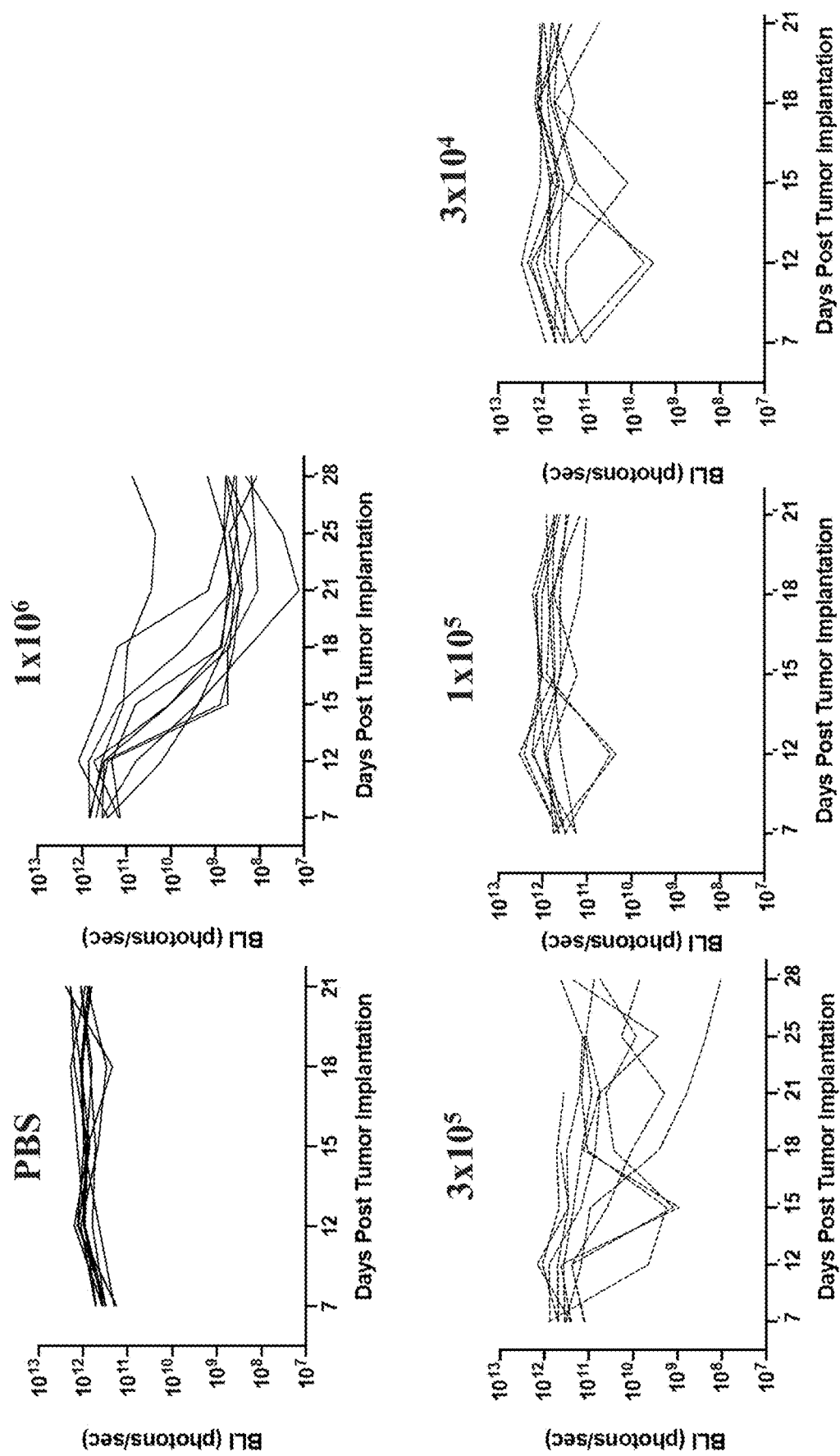
FIG. 60B shows dose-dependent efficacy of treatment using mMSCs engineered to express murine IL12 (p70) and murine IL21 from a single lentiviral expression vector in a MC-38 tumor model.
Figure 60C:
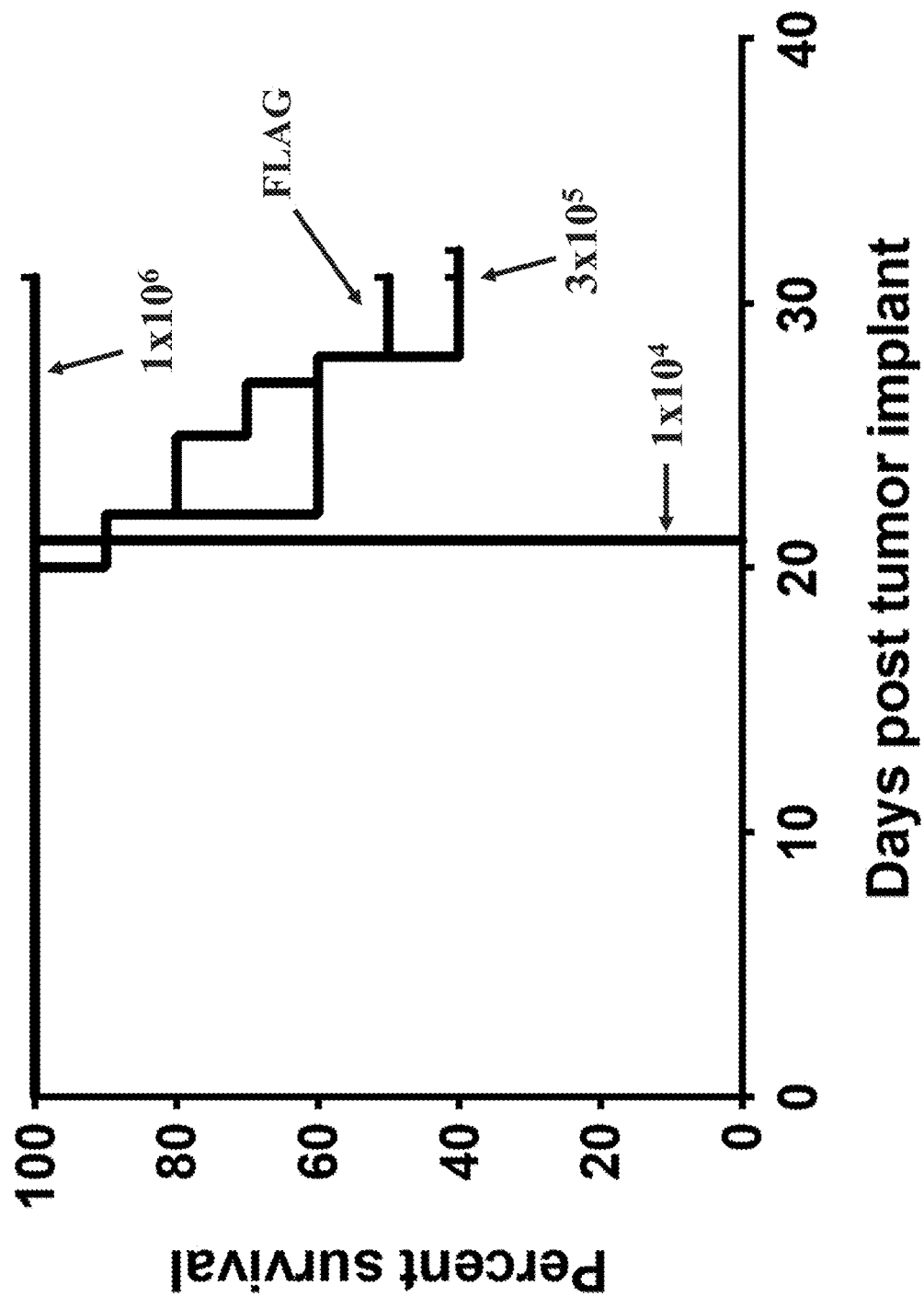
FIG. 60C shows dose-dependent efficacy of treatment using mMSCs engineered to express murine IL12 (p70) and murine IL21 from a single lentiviral expression vector in a MC-38 tumor model.

As shown in FIG. 60A and FIG. 60B, anti-tumor activity was observed in a dose-dependent manner of MSCs expressing both IL12 and IL21, as assessed by BLI (FIG. 60A normalized day 18 vs day 9; FIG. 60B BLI over time for individual mice). No efficacy was observed in control FLAG or PBS mice (FIG. 60A and FIG. 60B). No efficacy was also observed at doses of $1\times10^5$ or $3\times10^4$ cells (FIG. 60A and FIG. 60B). In contrast, minimal efficacy was observed at a dose of $3\times10^5$, with efficacy increasing at an increased dose of $1\times10^6$ cells (FIG. 60A and FIG. 60B). As shown in FIG. 60C, long term tumor-free survival was observed in a dose-dependent manner, with all mice treated with $1\times10^6$ cells surviving past at least day 30 (Median survival post-implant: PBS—21 days; FLAG—29 days; $1\times10^6$—not reached; $3\times10^5$—28 days; $1\times10^5$—21 days; $3\times10^4$—21 days [PBS, $1\times10^5$, and $3\times10^4$ overlap). Accordingly, mMSCs engineered to express murine IL12 (p70) and murine IL21 demonstrated efficacy in a MC-38 tumor model.

Example 29: Human MSCs Home to Tumors in an IP Model

In the following example, NSG mice were implanted with OVCAR8-fLUC cells IP. 14-21 days after tumor implantation, $1\times10^6$ human BM-MSCs engineered to express Nanoluc-EGFP were delivered IP. Mice were euthanized at 24 hours post injection of MSCs and peritoneal organs (stomach, kidney, liver, colon, spleen, pancreas, omentum/tumor, ovaries and Fallopian tubes) were imaged ex-vivo for Nano-Luc signaling (NanoGlo Substrate Kit, Vendor: Promega, Catalog No.: N1110). Human MSCs were imaged by EGFP fluorescence in tumor sections collected at 24 hours as well as 22 days post injection.

Figure 61A:
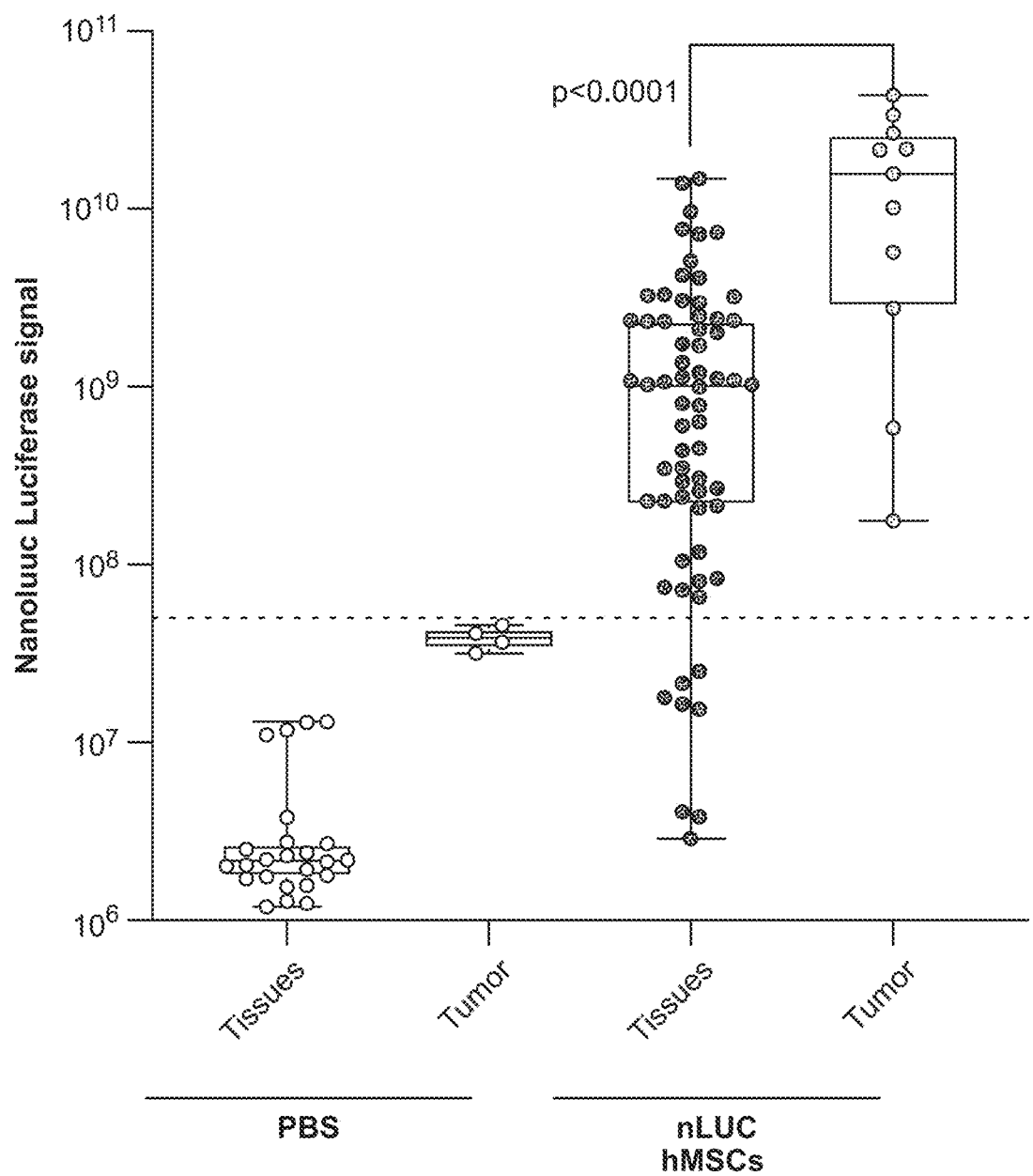
FIG. 61A shows preferential homing of human MSCs.
Figure 61B:
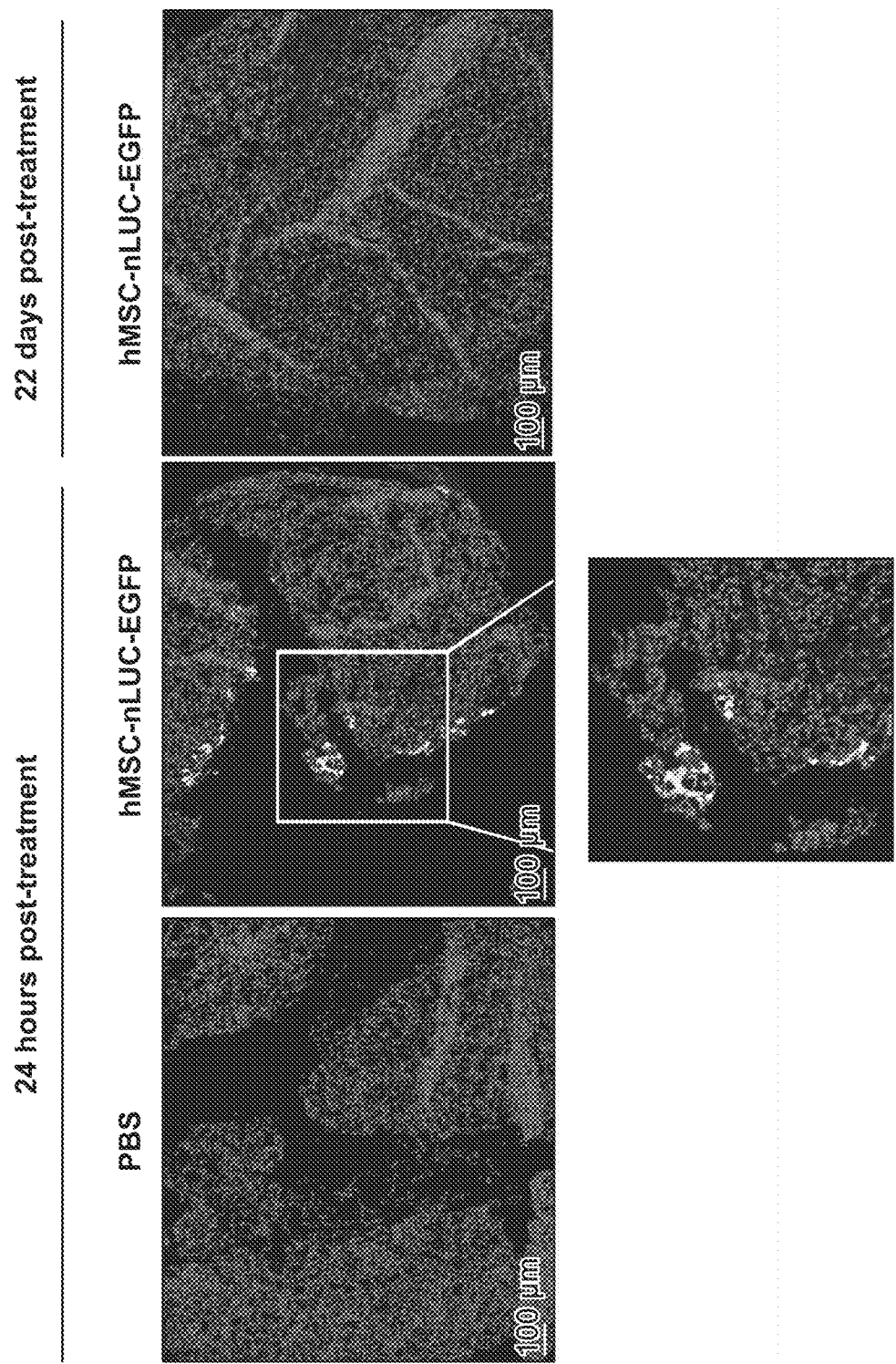
FIG. 61B shows preferential homing of human MSCs.

As shown in FIG. 61A and FIG. 61B, human MSC NanoLuc signal was preferentially enriched in the tumor compared to the other organs in the peritoneal cavity (FIG. 61A summarized luciferase quantification; FIG. 61B representative images of luciferase signal). Additionally, persistence of MSCs was lower than 22 days, with no cells being detected at the latest time point (FIG. 61B right most panel).

Example 30: Biodistribution and PK of Effector Cytokines

In the following example, biodistribution and PK of effector cytokines produced by engineered MSCs was assessed.

In a first experiment, NSG mice were implanted with $5\times10^6$ OVCAR8-fLUC tumor cells IP. 21-27 days after tumor implantation, mice were randomized based on tumor burden measured by BLI and treated with $1\times10^6$ hMSCs engineered to express human IL12 (p70) and human IL21 from a single lentiviral expression vector. The lentiviral expression vector used a 2A ribosome skipping elements to express both cytokines from a single transcript using the lentiviral transduction method described in Example 6. Mice were euthanized at 16-24 hours or 3, 4 and 7 days post MSC treatment and peritoneal fluid was collected via IP lavage by injecting 1 mL of PBS into the peritoneal space and collecting it. Serum was separated from whole blood after intracardiac puncture. ELISA (R&D systems) was used to determine the protein amount in each compartment (peritoneal fluid vs serum) for each time point and treatment type.

Figure 62A:
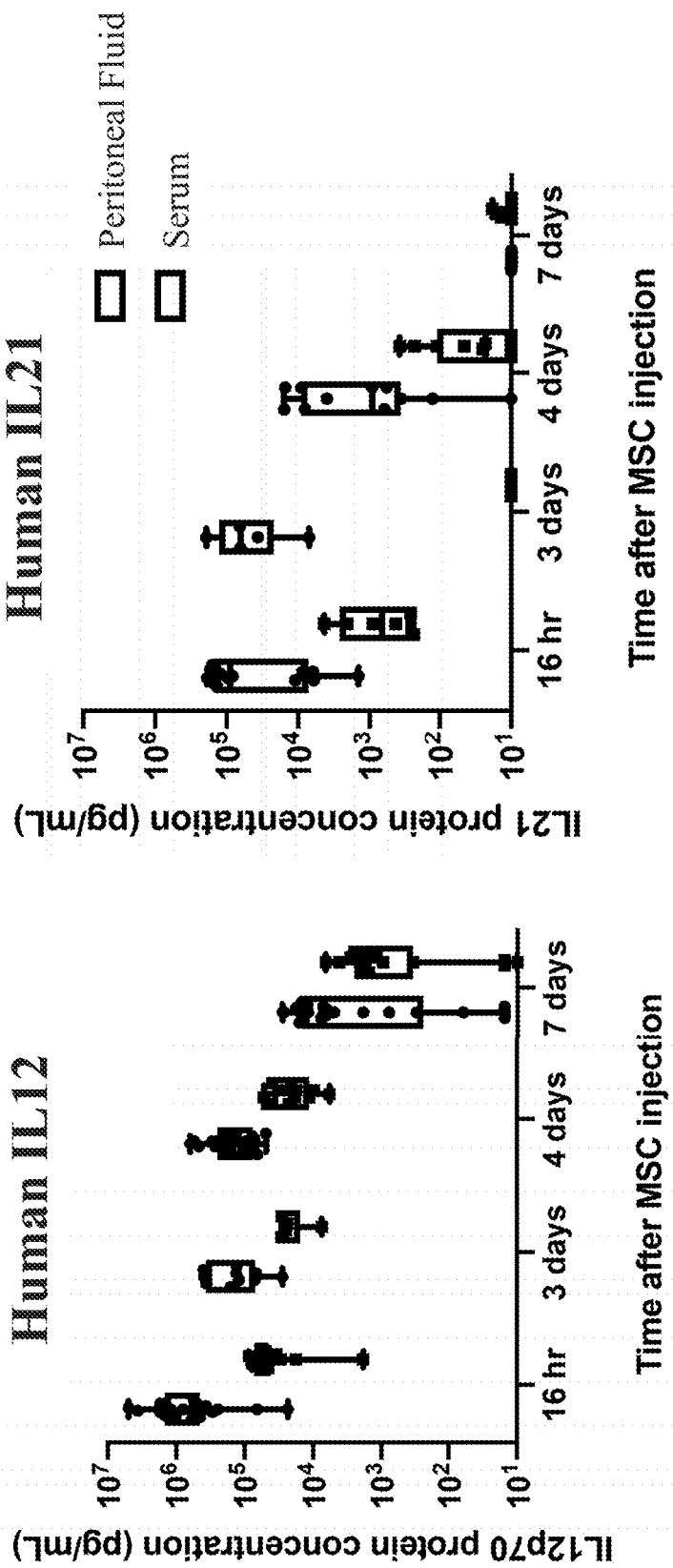
FIG. 62A shows production of human IL12 (left panel) and human IL21 (right panel) in the peritoneal fluid (left column for each respective time point) and serum (right column for each respective time point) in a OVCAR8 model for individual mice in each treatment, and the mean±SEM for each treatment group.

As shown in FIG. 62A, transient production of both human IL12 (left panel) and human IL21 (right panel) was observed in both the peritoneal fluid (left column for each respective time point) and serum (right column for each respective time point). At least a 10 fold increased protein abundance was observed in the peritoneal space (local) compared to systemic (serum), demonstrating localized delivery of cytokines by engineered MSCs.

In another experiment, balb/c mMSCs were engineered to express murine IL12p70 or murine IL21 (i.e., each MSC engineered to express only a single agent) using the lentiviral transduction method described in Example 6. CT26-fLUC tumor cells ($1\times10^5$ cells in 100 µl) were injected into the peritoneal space of immunocompetent balb/c (age 6-8 weeks). Murine IL12-expressing murine MSCs and murine IL21-expressing murine MSCs ($1\times10^6$ cells delivered for each in the combination) were delivered IP. Mice were euthanized at 24 or 72 hours post MSC treatment and peritoneal fluid was collected via IP lavage by injecting 1 mL of PBS into the peritoneal space and collecting it. Serum was separated from whole blood after intracardiac puncture. Luminex (Millipore) was used to determine the protein amount in each compartment (peritoneal fluid vs serum) for each time point and treatment type.

Figure 62B:
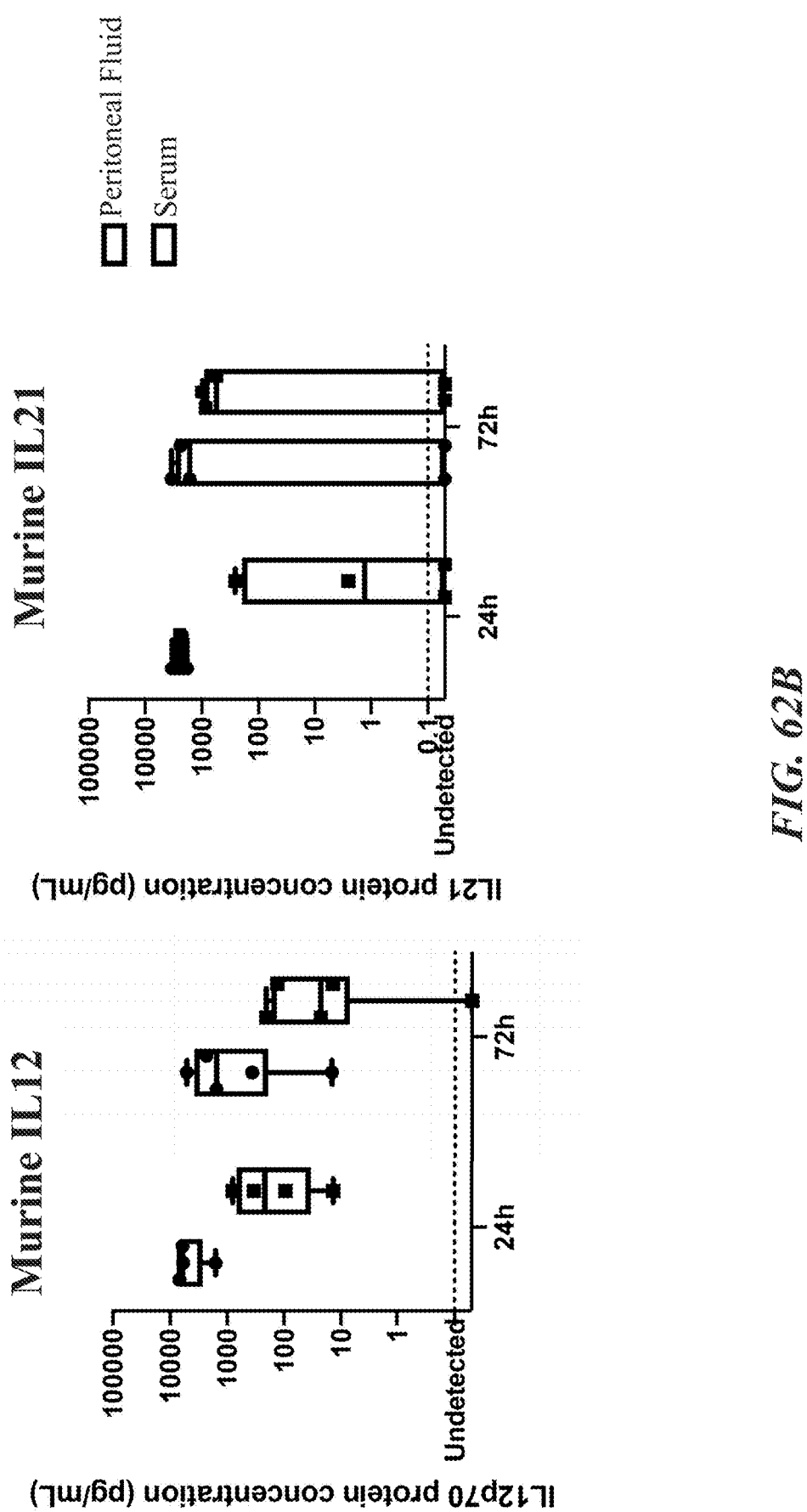
FIG. 62B shows transient production of murine IL12 (left panel) and murine IL21 (right panel) in the peritoneal fluid (left column for each respective time point) and serum (right column for each respective time point) in a CT26 model for individual mice in each treatment, and the mean±SEM for each treatment group.

As shown in FIG. 62B, transient production of both murine IL12 (left panel) and murine IL21 (right panel) was observed in both the peritoneal fluid (left column for each respective time point) and serum (right column for each respective time point). At least a 10 fold increased protein abundance was observed in the peritoneal space (local) compared to systemic (serum), demonstrating localized delivery of cytokines by engineered MSCs.

Example 31: Comparison of MSC Treatment and Recombinant Cytokine Treatment in a CT26 IP Tumor Model In the following example, balb/c mMSCs were engineered to express murine IL12 (p70) and murine IL21 from a single lentiviral expression vector. Balb/c mMSCs were also engineered to express either murine IL12 (p70) or murine IL21. The lentiviral expression vector used a 2A ribosome skipping elements to express both cytokines from a single transcript using the lentiviral transduction method described in Example 6. CT26 tumor cells ($1\times10^5$ cells in 100 µl) modified to constitutively express luciferase enzyme (Cat no: CL043, Lot no: CL-IM147 Imanis Life Sciences) were injected into the peritoneal space of immunocompetent female balb/c mice (age 6-8 weeks). One week after tumor implantation, tumor burden was measured by luciferase imaging (BLI) using an AMI imager. For MSC treated mice, mice were randomized into treatment groups and treated with intraperitoneally delivered mMSCs ($1\times10^6$ cells), receiving murine IL12-expressing murine MSCs, murine IL21-expressing murine MSCs, or murine IL12 and IL21-expressing murine MSCs, with MSC-Flag-Myc and PBS were used as a negative control. Additionally, treatment groups also included mice receiving a bolus dose of the respective recombinant cytokines at a dose of 4-times the amount produced by MSCs in vitro (measured by ELISA—recombinant IL12: 5 ug/mouse; Recombinant IL21: 0.4 ug/mouse). Tumor burden was measured by fLUC BLI across time points and mice were euthanized when reaching endpoint criteria due to tumor burden. Kaplan Meier survival curves were determined to calculate tumor-free survival.

Figure 63A:
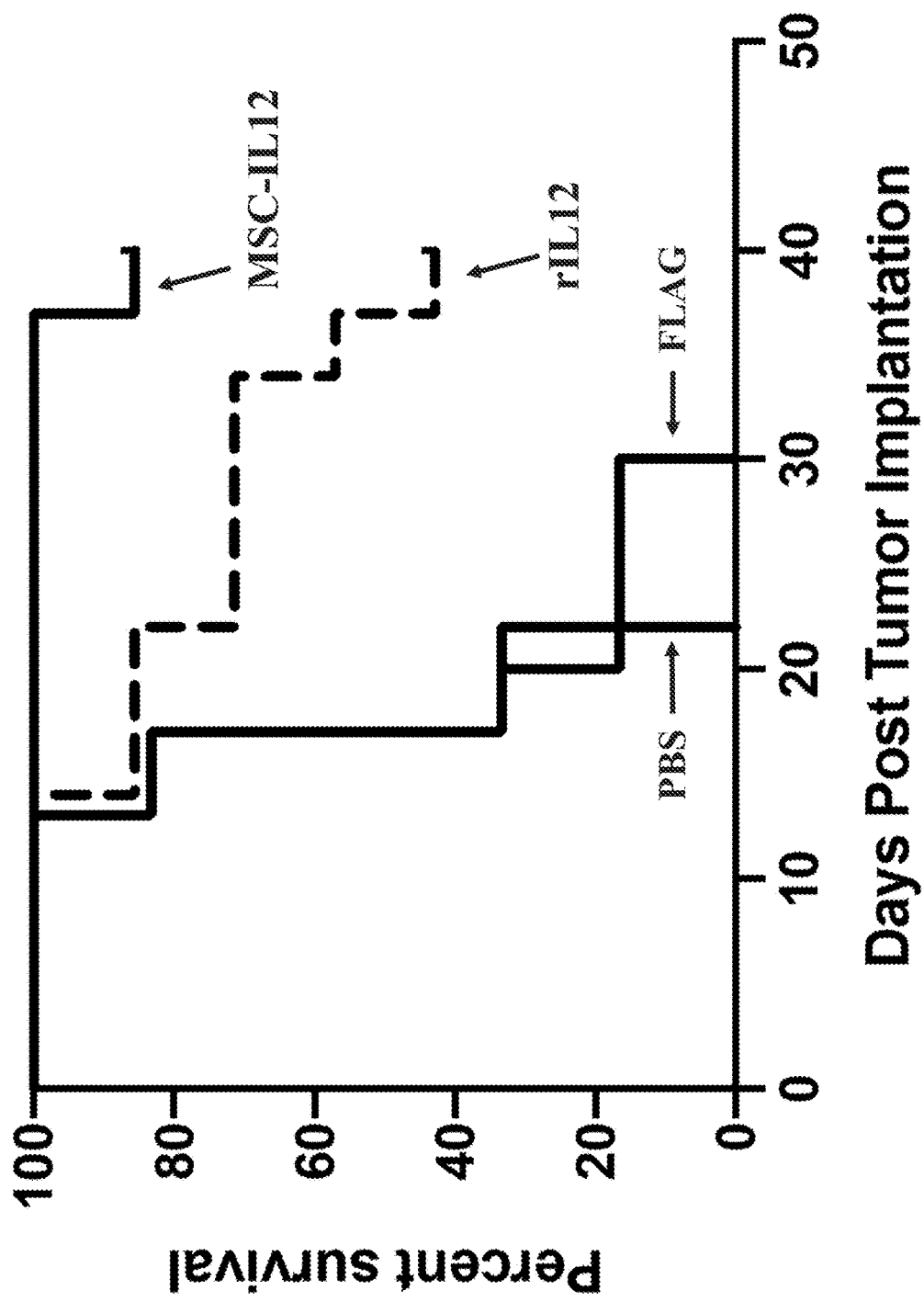
FIG. 63A shows efficacy of mice either treated with MSCs engineered to produce cytokines or treated with recombinant cytokine therapy in a CT26 model.
Figure 63B:
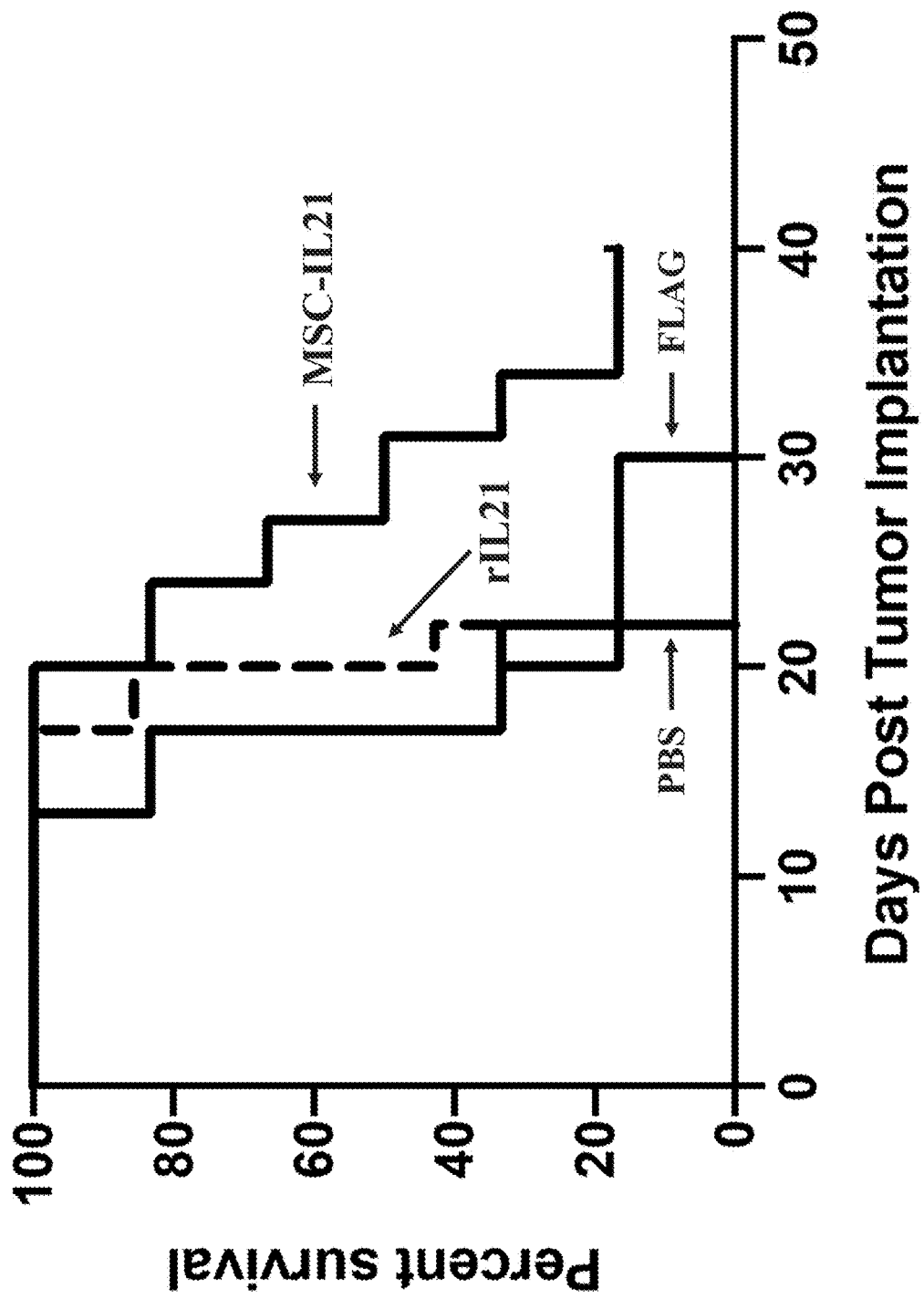
FIG. 63B shows efficacy of mice either treated with MSCs engineered to produce cytokines or treated with recombinant cytokine therapy in a CT26 model.
Figure 63C:
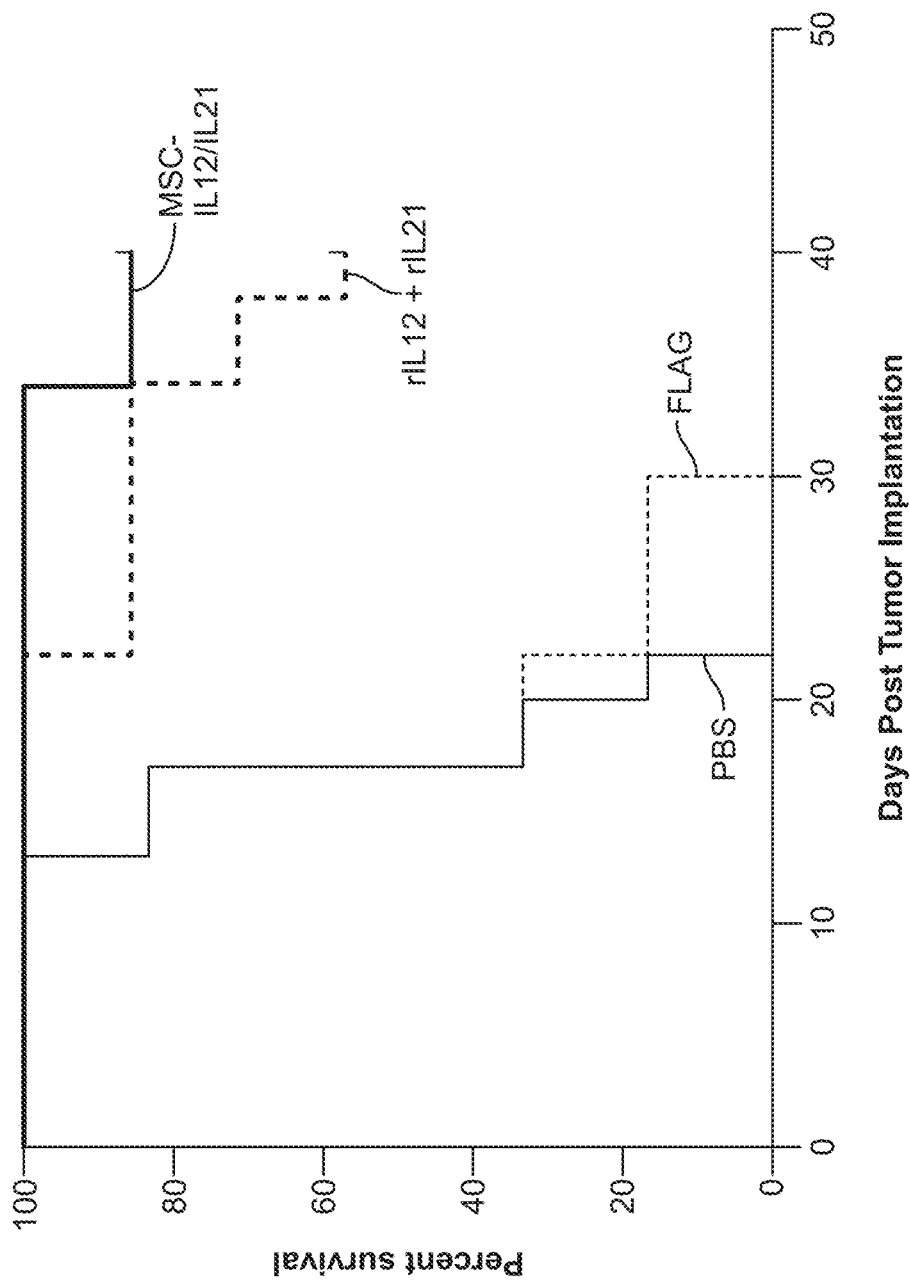
FIG. 63C shows efficacy of mice either treated with MSCs engineered to produce cytokines or treated with recombinant cytokine therapy in a CT26 model.
Figure 63D:
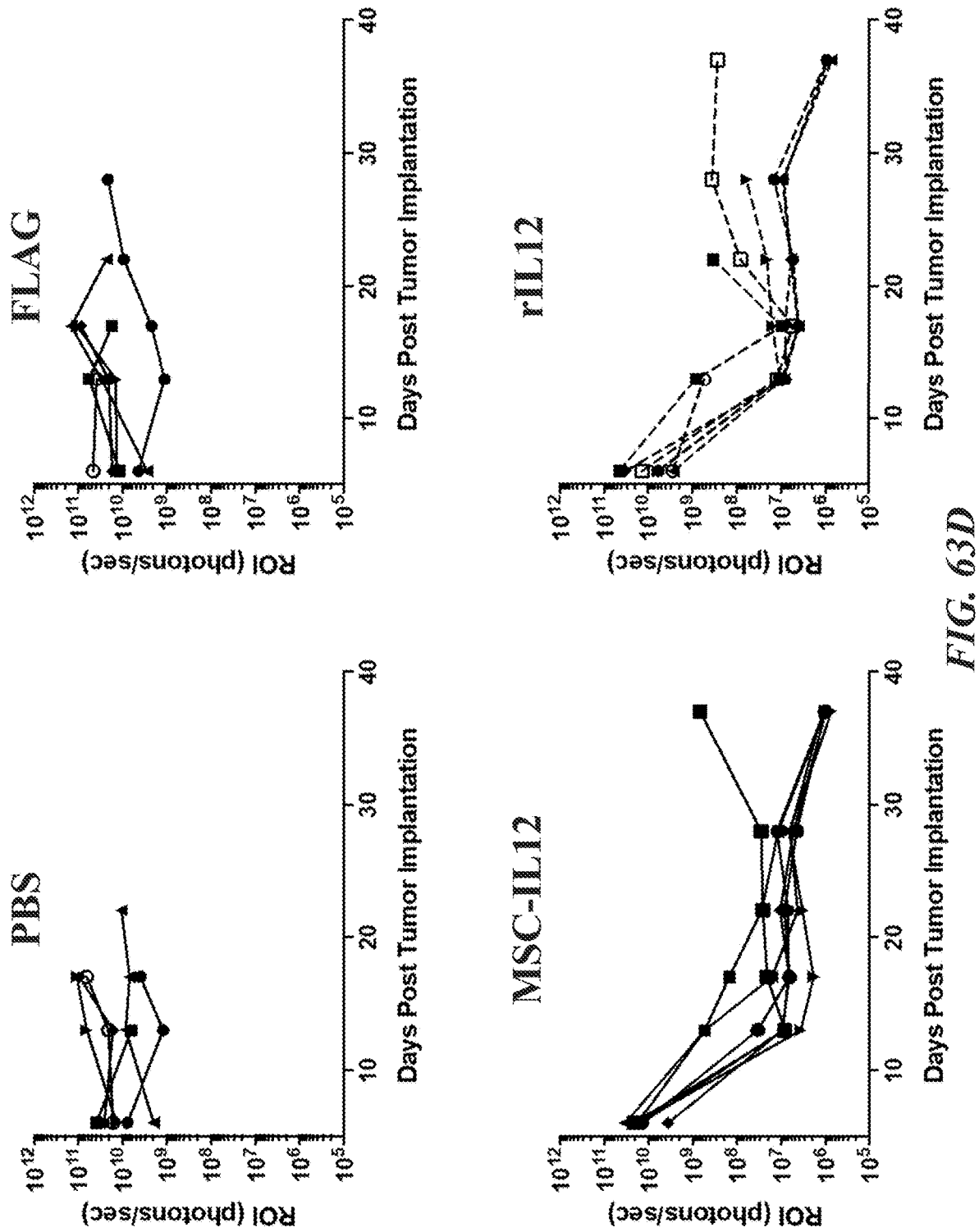
FIG. 63D shows efficacy of mice either treated with MSCs engineered to produce cytokines or treated with recombinant cytokine therapy in a CT26 model.
Figure 63E:
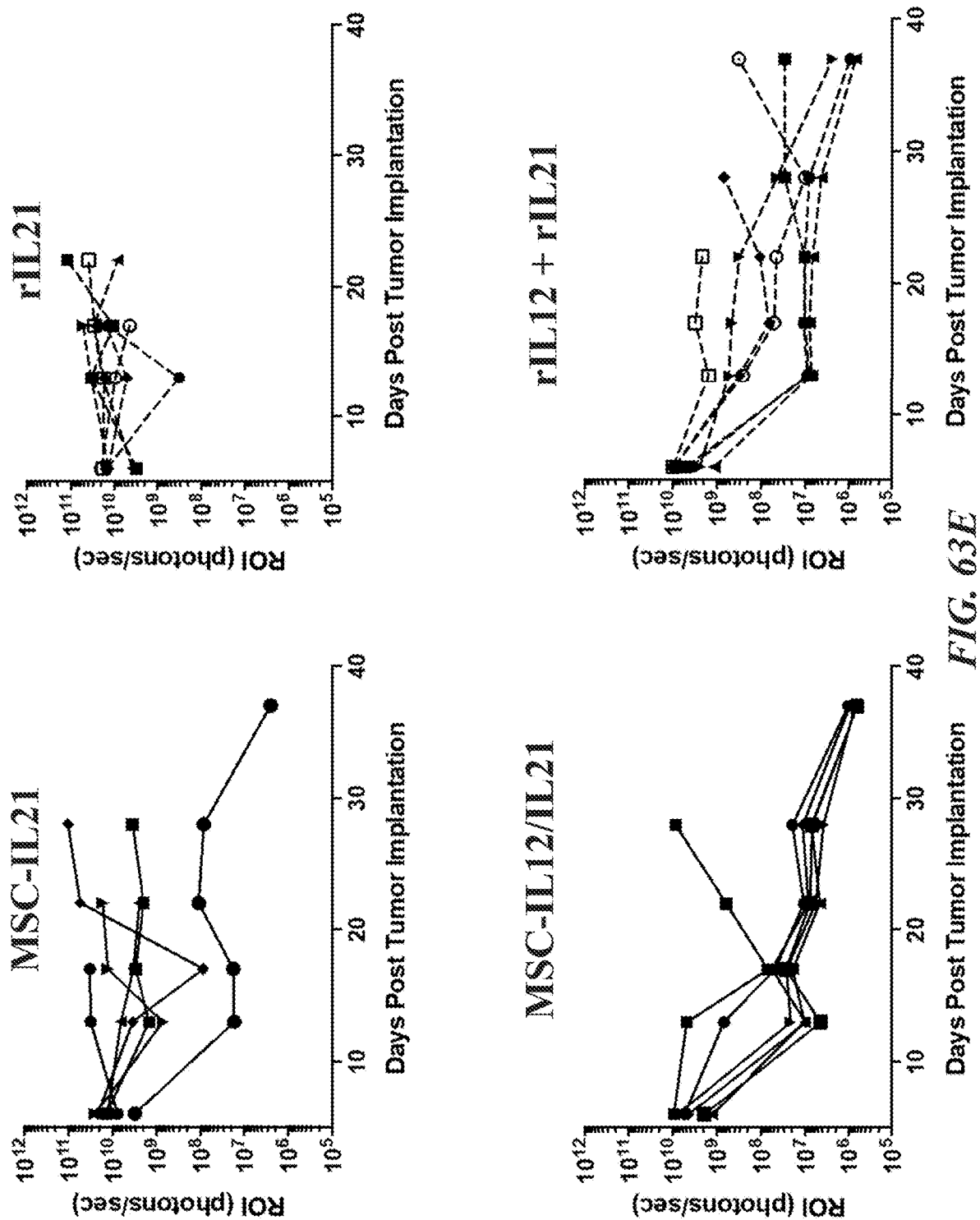
FIG. 63E shows efficacy of mice either treated with MSCs engineered to produce cytokines or treated with recombinant cytokine therapy in a CT26 model.

As shown in FIG. 63A-C, mice treated with MSCs engineered to produce cytokines outperformed recombinant cytokine therapy in terms of prolonged tumor-free survival, in all cases (FIG. 63A—MSC-IL12 vs rIL12; FIG. 63B—MSC-IL21 vs rIL21; FIG. 63C—MSC-IL12/IL21 vs rIL12+rIL21). Additionally, as shown in FIG. 63D-E, mice treated with MSCs engineered to produce cytokines outperformed recombinant cytokine therapy as assessed by tumor burden BLI), in all cases (FIG. 63D bottom row—MSC-IL12 vs rIL12; FIG. 63E top row—MSC-IL21 vs rIL21; FIG. 63E bottom row—MSC-IL12/IL21 vs rIL12+rIL21).

Example 32: Comparison of MSC Treatment and Recombinant Cytokine Treatment in a B16F10 IP Tumor Model In the following example, C57BL/6 mMSCs were engineered to express murine IL12 (p70) and murine IL21 from a single lentiviral expression vector. C57BL/6 mMSCs were also engineered to express either murine IL12 (p70) or murine IL21. The lentiviral expression vector used a 2A ribosome skipping elements to express both cytokines from a single transcript using the lentiviral transduction method described in Example 6. B16F10 tumor cells ($1\times10^5$ cells in 100 µl) modified to constitutively express luciferase enzyme (Cat no: CL043, Lot no: CL-IM147 Imanis Life Sciences) were injected into the peritoneal space of immunocompetent female balb/c mice (age 6-8 weeks). One week after tumor implantation, tumor burden was measured by luciferase imaging (BLI) using an AMI imager. For MSC treated mice, mice were randomized into treatment groups and treated with intraperitoneally delivered mMSCs ($3\times10^6$ cells) engineered to express both IL12 and IL21-expressing murine MSCs, with MSC-Flag-Myc and PBS were used as a negative control. Additionally, treatment groups also included mice receiving a bolus dose of the respective recombinant cytokines at a dose of 4-times the amount produced by MSCs in vitro (measured by ELISA—recombinant IL12: 3 ug/mouse; Recombinant IL21: 0.03 ug/mouse). Tumor burden was measured by tumor weight at day 7 post treatment and mice were euthanized when reaching endpoint criteria due to tumor burden. Kaplan Meier survival curves were determined to calculate tumor-free survival.

Figure 64A:
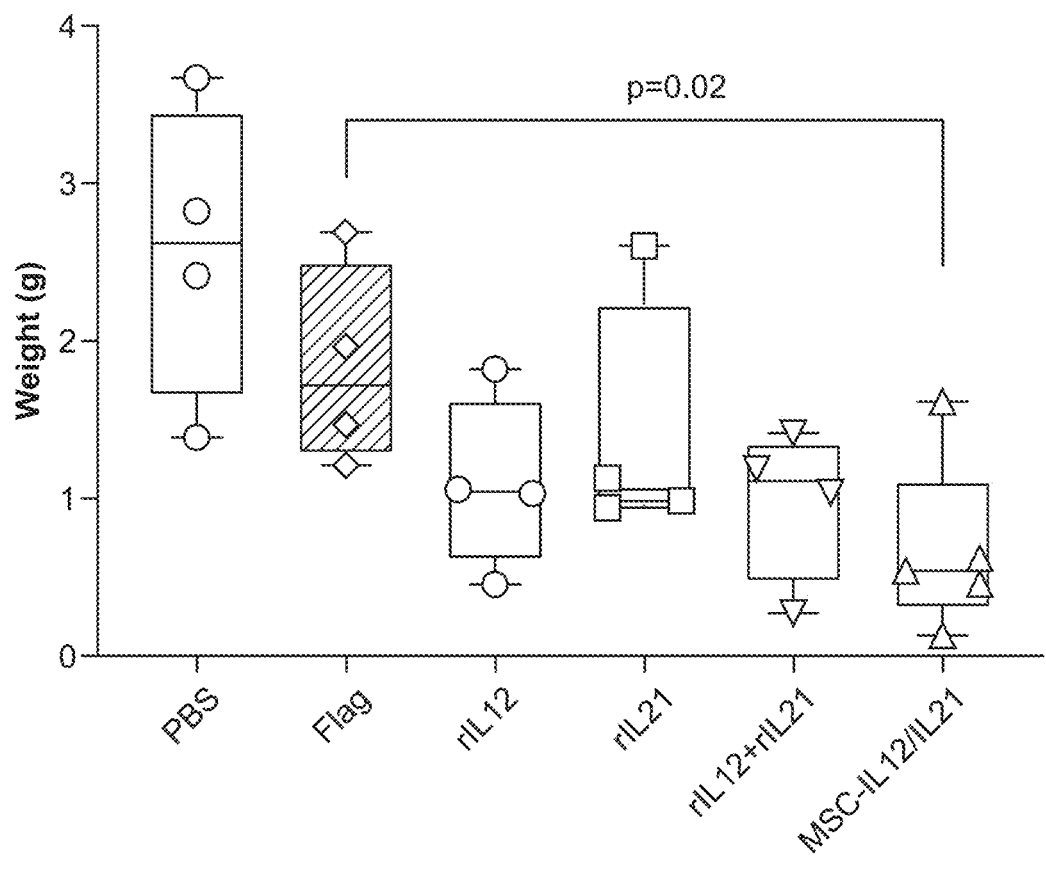
FIG. 64A shows efficacy of mice either treated with MSCs engineered to produce cytokines or treated with recombinant cytokine therapy in a B16F10 model.
Figure 64B:
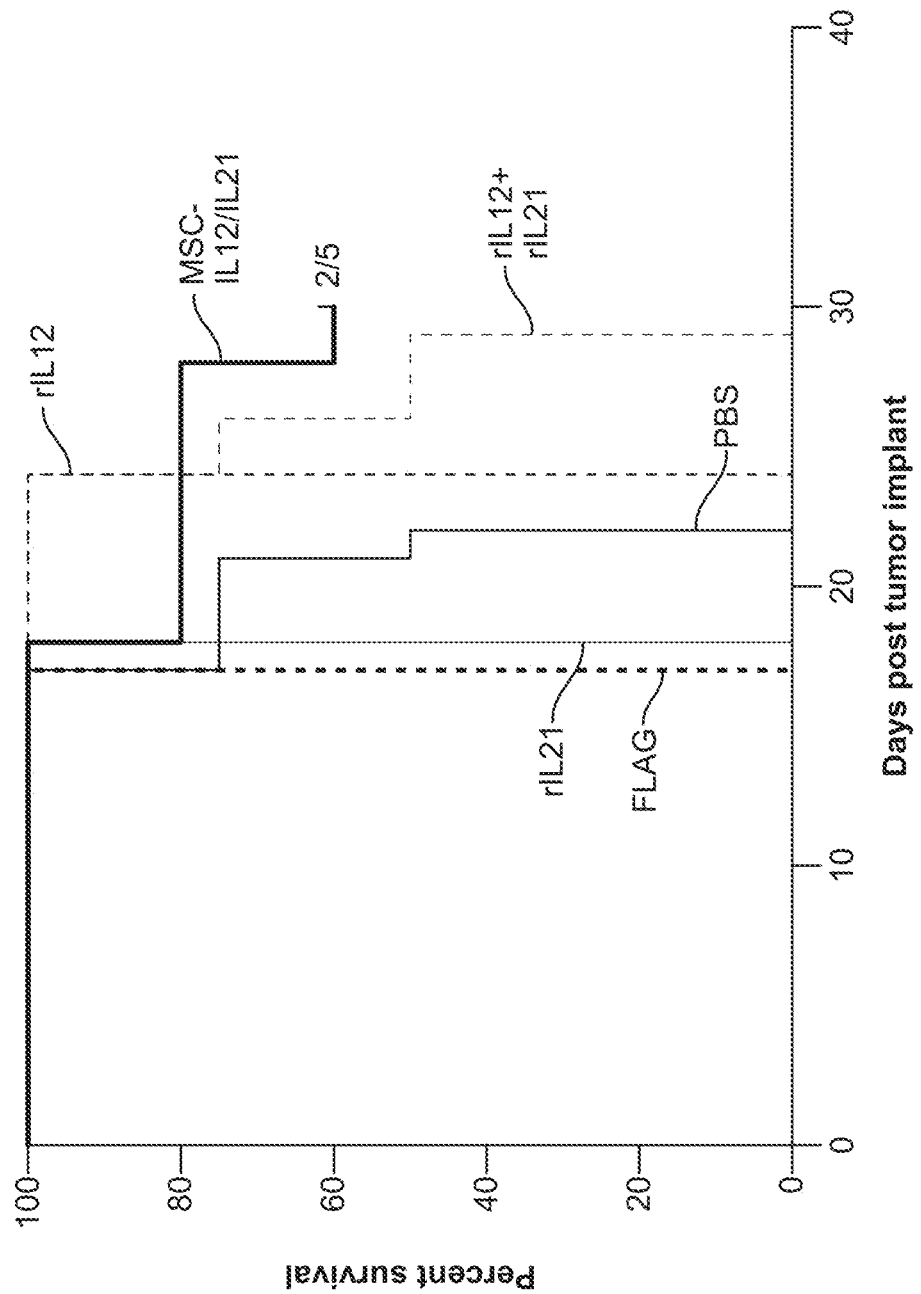
FIG. 64B shows efficacy of mice either treated with MSCs engineered to produce cytokines or treated with recombinant cytokine therapy in a B16F10 model.

As shown in FIG. 64A, mice treated with MSCs engineered to produce both IL12 and IL21 outperformed recombinant cytokine therapy as assessed by tumor weight. Additionally, as shown in FIG. 64B, mice treated with MSCs engineered to produce both IL12 and IL21 outperformed recombinant cytokine therapy as assessed by tumor-free prolonged survival.

Example 33: Immune Profile Following Treatment with MSCs Producing Both IL12 and IL21 in a CT26 IP Tumor Model In the following example, balb/c mMSCs were engineered to express murine IL12p70 or murine IL21 (i.e., each MSC engineered to express only a single agent) using the lentiviral transduction method described in Example 6. CT26 tumor cells ($1\times10^5$ cells) modified to constitutively express luciferase enzyme (Cat no: CL043, Lot no: CL-IM147 Imanis Life Sciences) were injected into the peritoneal space of immunocompetent balb/c (age 6-8 weeks). One week after tumor implantation, tumor burden was measured by luciferase imaging (BLI) using an AMI imager. Mice were randomized into treatment groups and treated with a intraperitoneally delivered combination treatment of murine IL12-expressing murine MSCs and murine IL21-expressing murine MSCs ($1\times10^6$ cells delivered for each in the combination), or MSC-Flag-Myc and PBS as a negative controls. Mice were euthanized and organs collected at 72 hours after treatment. Multicolor flow cytometry was used to characterize immune infiltrates in response to treatment.

As shown in FIG. 65A and FIG. 65B, T-cell subsets and activation markers (CD3, CD4, CD8, CD8/CD38+, CD8/IFNg+, CD8/Gzmb+, NK/Gzmb+ and ratio CD8:Tregs-FoxP3) were significantly increased in the peritoneal fluid after treatment with MSCs-IL12+MSCs IL21. Additionally, as shown in FIG. 65C, antigen-presenting cells such as dendritic cells (CD11c/MHC-II hi, CD86+, CD103+, CD11b+) were also significantly increased in peritoneal tumor-draining lymph nodes after treatment with MSC-IL12+MSC-IL21. Accordingly, combination treatment of murine IL12-expressing murine MSCs and murine IL21-expressing murine MSCs demonstrated an activated immune profile.

Example 34: Optimization of Signal Peptide Sequences

In the following example, effector molecules are modified to replace their native signal peptide sequence with an exogenous signal peptide sequence (see Table 5 for exemplary signal peptide sequences that are tested). Modified effector molecules are tested for functional improvements such as improved expression and maintained secretion, such as in particular environments (e.g., tumor microenvironments). Functional performance for the modified effector molecules is also tested in tumor models (e.g., improved ability to clear tumors, improved ability to clear tumors in different environments, or improved ability to clear different types of tumors).

Example 35: Enrichment of Engineered MSCs

In the following example, MSCs are engineered to express effector molecules within a population of cells that include unmodified cells, such as unmodified MSCs. The engineered MSCs are enriched within the population by contacting the engineered MSCs with a growth factor (such as the effector molecules described in Table 1) such that those engineered MSCs that are enriched are a sub-population of engineered MSCs that express a receptor or receptor ligand for the growth factor. The sub-population of engineered MSCs of interest are contacted with the growth factor in various manners:
1. In an autocrine manner by genetically engineering the MSCs themselves to express the factors.
2. In a paracrine manner by genetically engineering feeder or support cells to express the factors and supply those factors to the MSCs, or by using conditioned media containing the factors from the feeder or support cells (such as 293 Ts) engineered to express these factors.
3. In an endocrine manner, by injecting recombinant protein or nucleic acid versions of these factors into patients following MSC transplantation.
4. Via addition of soluble recombinant protein versions of these factors to the MSC culture conditions.
5. Via coating of the tissue culture plate/flask surfaces used for MSC propagation with recombinant versions of these factors.

REFERENCES

1. Kidd S, et al. (2009) Stem Cells 27(10):2614-2623.
2. Dembinski J L, et al. (2013) Cytotherapy 15(1):20-32.
3. Siegel R L, et al. (2016) C A Cancer J Clin 66(1):7-30.
4. Dizon D M J (2010) Gynecol Oncol 116(3).
5. Woo S R, et al. (2015) Trends Immunol 36(4):250-256.
6. Hamanishi J, et al. (2016) Int Immunol 28(7):339-348.
7. Li S, et al. (2012) Oncolytic Virother 1:1-21.
8. Koneru M, et al. (2015) J Transl Med 13:102.
9. Cruz C R, et al. (2010) Cytotherapy 12(6):743-749.
10. Li Y Q, et al. (2013) PLoS One 8(10):e76379.
11. Wiedemann G M, et al. (2016) Oncoimmunology 5(9): e1175794.
12. Squillaro T, et al. (2016) Cell Transplant 25(5):829-848.
13. Studeny M, et al. (2004) J Natl Cancer Inst 96(21):1593-1603.
14. Ling X, et al. (2010) Cancer Microenviron 3(1):83-95.
15. Schukur L, et al. (2015) Sci Transl Med 7β18):318ra201.
16. Howlader N N A, Krapcho M, Garshell J, Miller D, Altekruse S F, Kosary C L, Yu M, Ruhl J, Tatalovich Z, Mariotto A, Lewis D R, Chen H S, Feuer E J and Cronin K A. (2015).
17. Lengyel E (2010) Am J Pathol 177(3):1053-1064.
18. McGuire W P, et al. (1996) The New England journal of medicine 334(1):1-6.
19. McGuire W P, et al. (1989) Annals of internal medicine 111(4):273-279.
20. Adams S F & Benencia F (2015) Future Oncology 11(9):1293-1296.
21. Maude S L, et al. (2014) N Engl J Med 371(16):1507-1517.
22. Bargou R, et al. (2008) Science 321(5891):974-977.
23. Kershaw M H, et al. (2014) Clin Trans Immunol 3:e16.
24. Gilham D E, et al. (2012) Trends Mol Med 18(7):377-384.
25. Klinger M, et al. (2012) Blood 119(26):6226-6233.
26. Fu J, et al. (2015) Sci Transl Med 7(283):283ra252.
27. Moynihan K D, et al. (2016) Nat Med 22(12):1402-1410.
28. Mohammadi M, et al. (2016) Cancer Gene Ther 23(9): 285-286.
29. Wang D, et al. (2013) Cell Transplant 22(12):2267-2277.
30. Nowakowski A, et al. (2016) Stem Cells Int 2016: 4956063.
31. Sun Z, et al. (2014) J Hematol Oncol 7:14.
32. Ando M, et al. (2015) Stem Cell Reports 5(4):597-608.
33. Zhao Q, et al. (2015) Proc Natl Acad Sci USA 112(2): 530-535.
34. Xie C, et al. (2013) Br J Cancer 109(5):1198-1205.
35. Parker B S, et al. (2016) Nat Rev Cancer 16(3):131-144.
36. Roby K F, et al. (2000) Carcinogenesis 21(4):585-591.
37. Sharma A D, et al. (2015) J Vis Exp (95):e52242.
38. Waterman R S, et al. (2012) PLoS One 7(9):e45590.
39. Dubinett S M, et al. (2010) Cancer J 16(4):325-335.
40. Tang E D & Wang C Y (2015) PLoS One 10(3): e0120090.
41. Cieri N, et al. (2013) Blood 121(4):573-584.
42. Fitzgerald K A, et al. (2003) Nat Immunol 4(5):491-496.
43. Wong A S, et al. (2016) Proc Natl Acad Sci USA 113(9):2544-2549.
44. Wong A S, et al. (2015) Nat Biotechnol 33(9):952-961.
45. Nissim L, et al. (2014) Mol Cell 54(4):698-710.
46. Deng P, et al. (2016) Neural Regen Res 11(5):702-705.
47. Beegle J R, et al. (2016) Mol Ther Methods Clin Dev 3:16053.
48. Boutros C, et al. (2016) Nat Rev Clin Oncol 13(8):473-486.
49. Valsecchi M E (2015) New Engl J Med 373(13):1270-1270.
50. Pardoll D M (2012) Nat Rev Cancer 12(4):252-264.
51. Legat A, et al. (2013) Front Immunol 4:455.
52. Justus C R, et al. (2014) J Vis Exp (88).
53. Jedema I, et al. (2004) Blood 103(7):2677-2682.
54. Peng D, et al. (2015) Nature 527(7577):249-253.
55. Gitzinger M, et al. (2009) Proc Natl Acad Sci USA 106(26):10638-10643.
56. Clackson T, et al. (1998) Proc Natl Acad Sci USA 95(18):10437-10442.
57. Siuti P, et al. (2013) Nature Biotechnology 31(5):448-452.
58. Farzadfard F & Lu T K (2014) Science 346(6211): 1256272.
59. Perli S D, et al. (2016) Science 353(6304).
60. Roquet N, et al. (2016) Science 353(6297):aad8559.
61. Wong A S L, et al. (2016) Proceedings of the National Academy of Sciences.
62. Gardner T S, et al. (2000) Nature 403(6767):339-342.
63. Deans T L, et al. (2007) Cell 130(2):363-372.
64. Warren L, et al. (2010) Cell Stem Cell 7(5):618-630.
65. Yang B X, et al. (2015) Cell 163(1):230-245.
66. Kumar R M, et al. (2014) Nature 516(7529):56-61.
67. Zhang J, et al. (2016) Cell Stem Cell 19(1):66-80.
68. Cahan P, et al. (2014) Cell 158(4):903-915.
69. Doulatov S, et al. (2013) Cell Stem Cell 13(4):459-470.
70. Kim K, et al. (2011) Nat Biotechnol 29(12):1117-1119.
71. Chavez A, et al. (2016) Nat Methods 13(7):563-567.

72. Slomovic S & Collins J J (2015) Nat Methods 12(11): 1085-1090.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of treating a human subject having cancer, wherein the method comprises delivering to the subject an engineered human cell in an effective amount to induce an immune response, wherein the engineered human cell comprises:
  a) a promoter; and
  b) an exogenous polynucleotide sequence comprising an expression cassette described in a formula, oriented from 5' to 3', comprising

S1-E1-L-S2-E2 wherein
  S1 comprises a polynucleotide sequence encoding a first signal peptide,
  E1 comprises a polynucleotide sequence encoding a first effector molecule,
  L comprises a linker polynucleotide sequence,
  S2 comprises a polynucleotide sequence encoding a second signal peptide,
  E2 comprises a polynucleotide sequence encoding a second effector molecule, and
  wherein the promoter is operably linked to the expression cassette, the first signal peptide is operably linked to the first effector molecule, and the second signal peptide is operably linked to the second effector molecule,
  wherein the engineered human cell is selected from the group consisting of: a mesenchymal stem cell (MSC), natural killer (NK) cell, NKT cell, and macrophage, wherein
  (a) the first effector molecule comprises an IL12p70 fusion protein and the second effector molecule comprises CCL21a, IL7, IL15, IL21, Flt3L, an anti-PD1 antibody, CD40L, or a CXCL10-CXCL11 fusion protein,
  (b) the first effector molecule comprises CCL21a, IL7, IL15, IL21, Flt3L, an anti-PD1 antibody, CD40L, or a CXCL10-CXCL11 fusion protein and the second effector molecule comprises an IL12p70 fusion protein,
  (c) the first effector molecule comprises IL21 and the second effector molecule comprises CCL21a, IL7, IL15, IL18, an IL12p70 fusion protein, Flt3L, an anti-PD1 antibody, CD40L, or a CXCL10-CXCL11 fusion protein, or
  (d) the first effector molecule comprises CCL21a, IL7, IL15, IL18, an IL12p70 fusion protein, Flt3L, an anti-PD1 antibody, CD40L, or a CXCL10-CXCL11 fusion protein and the second effector molecule comprises IL21,
  wherein at least one of the first effector molecule and the second effector molecule does not comprise, nor is operably linked to, a transmembrane domain, and
  wherein the engineered human cell further comprises a chimeric antigen receptor (CAR) or exogenous polynucleotide sequence encoding the same.

2. The method of claim 1, wherein the promoter is operably linked to the expression cassette such that the polynucleotides are capable of being transcribed as a single polynucleotide comprising the formula S1-E1-L-S2-E2.

3. The method of claim 1, wherein the linker polynucleotide sequence is operably associated with the translation of the first effector molecule and the second effector molecule as separate polypeptides.

4. The method of claim 3, wherein the linker polynucleotide sequence encodes a 2A ribosome skipping tag or encodes an Internal Ribosome Entry Site (IRES), optionally wherein when the linker polynucleotide sequence encodes a 2A ribosome skipping tag, and the 2A ribosome skipping tag is selected from the group consisting of: P2A, T2A, E2A, and F2A.

5. The method of claim 1, wherein the linker polynucleotide sequence encodes a second promoter,
  wherein the promoter is operably linked to the expression cassette such that a first polynucleotide comprising the formula S1-E1 is capable of being transcribed, wherein the second promoter is operably linked to the expression cassette such that a second polynucleotide comprising the formula S2-E2 is capable of being transcribed, and wherein the first and the second polynucleotide are separate polynucleotides.

6. The method of claim 1, wherein the engineered human cell is a natural killer (NK) cell.

7. The method of claim 1, wherein the promoter comprises a constitutive promoter selected from the group consisting of: CMV, EFS, SFFV, SV40, MND, PGK, UbC, hEF1aV1, hCAGG, hEF1aV2, hACTb, heIF4A1, hGAPDH, hGRP78, hGRP94, hHSP70, hKINb, and hUBIb.

8. The method of claim 1, wherein the promoter comprises an inducible promoter selected from the group consisting of: minP, NFkB response element, CREB response element, NFAT response element, SRF response element 1, SRF response element 2, AP1 response element, TCF-LEF response element promoter fusion, Hypoxia responsive element, SMAD binding element, STAT3 binding site, inducer molecule responsive promoters, and tandem repeats thereof.

9. The method of claim 1, wherein:
the first signal peptide comprises a native signal peptide native to the first effector molecule; or
the second signal peptide comprises a native signal peptide native to the second effector molecule; or
the first signal peptide comprises a non-native signal peptide non-native to the first effector molecule; or
the second signal peptide comprises a non-native signal peptide non-native to the second effector molecule, respectively; or any combination thereof.

10. The method of claim 1, wherein the expression cassette further comprises following E2, an additional exogenous polynucleotide sequence comprising a formula, oriented from 5' to 3', comprising:
$(L-S-E)_x$
wherein
S comprises a polynucleotide sequence encoding a signal peptide,
E comprises a polynucleotide sequence encoding an additional effector molecule,
L comprises a linker polynucleotide sequence,
X=1 to 20
wherein the promoter is operably linked to the expression cassette, and wherein for each iteration for a given X, the corresponding signal peptide is operably linked to the respective effector molecule,
optionally wherein one or more of the additional effector molecules comprises a chimeric antigen receptor.

11. The method of claim 1, wherein the exogenous polynucleotide sequence comprises one or more viral vector polynucleotide sequences, and wherein the one or more viral vector polynucleotide sequences comprise lentiviral, retroviral, retrotransposon, or adenoviral polynucleotide sequences.

12. A method of reducing tumor volume in a human subject, the method comprising delivering to the subject having a tumor a composition comprising an engineered human cell comprising:
a) a promoter; and
b) an exogenous polynucleotide sequence comprising an expression cassette described in a formula, oriented from 5' to 3', comprising
S1-E1-L-S2-E2
wherein
S1 comprises a polynucleotide sequence encoding a first signal peptide,
E1 comprises a polynucleotide sequence encoding a first effector molecule,
L comprises a linker polynucleotide sequence,
S2 comprises a polynucleotide sequence encoding a second signal peptide,
E2 comprises a polynucleotide sequence encoding a second effector molecule, and
wherein the promoter is operably linked to the expression cassette, the first signal peptide is operably linked to the first effector molecule, and the second signal peptide is operably linked to the second effector molecule, and
wherein the engineered human cell is selected from the group consisting of: a mesenchymal stem cell (MSC), natural killer (NK) cell, NKT cell, and macrophage, wherein
(a) the first effector molecule comprises an IL12p70 fusion protein and the second effector molecule comprises CCL21a, IL7, IL15, IL21, Flt3L, an anti-PD1 antibody, CD40L, or a CXCL10-CXCL11 fusion protein,
(b) the first effector molecule comprises CCL21a, IL7, IL15, IL21, Flt3L, an anti-PD1 antibody, CD40L, or a CXCL10-CXCL11 fusion protein and the second effector molecule comprises an IL12p70 fusion protein,
(c) the first effector molecule comprises IL21 and the second effector molecule comprises CCL21a, IL7, IL15, IL18, an IL12p70 fusion protein, Flt3L, an anti-PD1 antibody, CD40L, or a CXCL10-CXCL11 fusion protein, or
(d) the first effector molecule comprises CCL21a, IL7, IL15, IL18, an IL12p70 fusion protein, Flt3L, an anti-PD1 antibody, CD40L, or a CXCL10-CXCL11 fusion protein and the second effector molecule comprises IL21, and
wherein at least one of the first effector molecule and the second effector molecule does not comprise, nor is operably linked to, a transmembrane domain, and
wherein the engineered human cell further comprises a chimeric antigen receptor (CAR) or exogenous polynucleotide sequence encoding the same.

13. A method of inducing an immune response in a human subject, the method comprising administering a therapeutically effective dose of an engineered human cell comprising:
a) a promoter; and
b) an exogenous polynucleotide sequence comprising an expression cassette described in a formula, oriented from 5' to 3', comprising

S1-E1-L-S2-E2 wherein
S1 comprises a polynucleotide sequence encoding a first signal peptide,
E1 comprises a polynucleotide sequence encoding a first effector molecule,
L comprises a linker polynucleotide sequence,
S2 comprises a polynucleotide sequence encoding a second signal peptide,
E2 comprises a polynucleotide sequence encoding a second effector molecule, and
wherein the promoter is operably linked to the expression cassette, the first signal peptide is operably linked to the first effector molecule, and the second signal peptide is operably linked to the second effector molecule, and
wherein the engineered human cell is selected from the group consisting of: a mesenchymal stem cell (MSC), natural killer (NK) cell, NKT cell, and macrophage, wherein
(a) the first effector molecule comprises an IL12p70 fusion protein and the second effector molecule comprises CCL21a, IL7, IL15, IL21, Flt3L, an anti-PD1 antibody, CD40L, or a CXCL10-CXCL11 fusion protein,
(b) the first effector molecule comprises CCL21a, IL7, IL15, IL21, Flt3L, an anti-PD1 antibody, CD40L, or a CXCL10-CXCL11 fusion protein and the second effector molecule comprises an IL12p70 fusion protein,
(c) the first effector molecule comprises IL21 and the second effector molecule comprises CCL21a, IL7, IL15, IL18, an IL12p70 fusion protein, Flt3L, an anti-PD1 antibody, CD40L, or a CXCL10-CXCL11 fusion protein, or
(d) the first effector molecule comprises CCL21a, IL7, IL15, IL18, an IL12p70 fusion protein, Flt3L, an anti-PD1 antibody, CD40L, or a CXCL10-CXCL11 fusion protein and the second effector molecule comprises IL21, and wherein at least one of the first effector molecule and the second effector molecule does not comprise, nor is operably linked to, a transmembrane domain, and wherein the engineered human cell further comprises a chimeric antigen receptor (CAR) or exogenous polynucleotide sequence encoding the same.

14. The method of claim 1, wherein the first effector molecule comprises an IL12p70 fusion protein and the second effector molecule comprises CCL21a, IL7, IL15, IL21, Flt3L, an anti-PD1 antibody, CD40L, or a CXCL10-CXCL11 fusion protein.

15. The method of claim 1, wherein the first effector molecule comprises CCL21a, IL7, IL15, IL21, Flt3L, an anti-PD1 antibody, CD40L, or the CXCL10-CXCL11 fusion protein and the second effector molecule comprises the IL12p70 fusion protein.

16. The method of claim 1, wherein the first effector molecule comprises IL21 and the second effector molecule comprises IL15.

17. The method of claim 13, wherein the first effector molecule comprises the IL12p70 fusion protein and the second effector molecule comprises CCL21a, IL7, IL15, IL21, Flt3L, an anti-PD1 antibody, CD40L, or a CXCL10-CXCL11 fusion protein.

18. The method of claim 13, wherein the first effector molecule comprises CCL21a, IL7, IL15, IL21, Flt3L, an anti-PD1 antibody, CD40L, or a CXCL10-CXCL11 fusion protein and the second effector molecule comprises the IL12p70 fusion protein.

19. The method of claim 13, wherein the first effector molecule comprises IL21 and the second effector molecule comprises IL15.

20. The method of claim 13, wherein the engineered human cell is a natural killer (NK) cell.

* * * * *

UNITED STATES PATENT AND TRADEMARK OFFICE
CERTIFICATE OF CORRECTION

| | |
|---|---|
| PATENT NO. | : 11,419,898 B2 |
| APPLICATION NO. | : 17/219569 |
| DATED | : August 23, 2022 |
| INVENTOR(S) | : Timothy Kuan-Ta Lu et al. |

It is certified that error appears in the above-identified patent and that said Letters Patent is hereby corrected as shown below:

On the Title Page

In Column 1, Item (60), under Related U.S. Application Data, Line 4, replace "62/474,109" with --62/747,109--.

Signed and Sealed this
Seventh Day of February, 2023

Katherine Kelly Vidal
*Director of the United States Patent and Trademark Office*

SEQUENCE LISTING

```
<160> NUMBER OF SEQ ID NOS: 145

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agagggtata taatggaagc tcgacttcca g                                    31

<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gggaatttcc ggggactttc cgggaatttc cgggggacttt ccgggaattt cc            52

<210> SEQ ID NO 3
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
caccagacag tgacgtcagc tgccagatcc catggccgtc atactgtgac gtctttcaga     60
caccccattg acgtcaatgg gagaa                                           85

<210> SEQ ID NO 4
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggaggaaaaa ctgtttcata cagaaggcgt ggaggaaaaa ctgtttcata cagaaggcgt     60
ggaggaaaaa ctgtttcata cagaaggcgt                                      90

<210> SEQ ID NO 5
<211> LENGTH: 115
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 5
aggatgtcca tattaggaca tctaggatgt ccatattagg acatctagga tgtccatatt    60
aggacatcta ggatgtccat attaggacat ctaggatgtc catattagga catct        115

<210> SEQ ID NO 6
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
agtatgtcca tattaggaca tctaccatgt ccatattagg acatctacta tgtccatatt    60
aggacatctt gtatgtccat attaggacat ctaaaatgtc catattagga catct        115

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgagtcagtg actcagtgag tcagtgactc agtgagtcag tgactcag                48

<210> SEQ ID NO 8
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
agatcaaagg gtttaagatc aaagggctta agatcaaagg gtataagatc aaagggccta    60
agatcaaagg gactaagatc aaagggttta agatcaaagg gcttaagatc aaagggccta   120

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtctagacgt ctagacgtct agacgtctag ac                                  32

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cagacacaga cacagacaca gaca                                           24
```

<210> SEQ ID NO 11
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggatccggta ctcgagatct gcgatctaag taagcttggc attccggtac tgttggtaaa    60
gccac                                                                65

<210> SEQ ID NO 12
<211> LENGTH: 588
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gttgacattg attattgact agttattaat agtaatcaat tacggggtca ttagttcata    60
gcccatatat ggagttccgc gttacataac ttacggtaaa tggcccgcct ggctgaccgc   120
ccaacgaccc ccgcccattg acgtcaataa tgacgtatgt tcccatagta acgccaatag   180
ggactttcca ttgacgtcaa tgggtggagt atttacggta aactgcccac ttggcagtac   240
atcaagtgta tcatatgcca agtacgcccc ctattgacgt caatgacggt aaatggcccg   300
cctggcatta tgcccagtac atgaccttat gggactttcc tacttggcag tacatctacg   360
tattagtcat cgctattacc atggtgatgc ggttttggca gtacatcaat gggcgtggat   420
agcggtttga ctcacgggga tttccaagtc tccaccccat tgacgtcaat gggagtttgt   480
tttggcacca aaatcaacgg gactttccaa aatgtcgtaa caactccgcc ccattgacgc   540
aaatgggcgg taggcgtgta cggtgggagg tctatataag cagagctc                588

<210> SEQ ID NO 13
<211> LENGTH: 1179
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
ggctccggtg cccgtcagtg gcagagcgc acatcgccca cagtcccga gaagttgggg     60 ggaggggtcg gcaattgaac cggtgcctag agaaggtggc gcggggtaaa ctgggaaagt   120
gatgccgtgt actggctccg ccttttttccc gagggtgggg gagaaccgta tataagtgca   180
gtagtcgccg tgaacgttct ttttcgcaac gggtttgccg ccagaacaca ggtaagtgcc   240
gtgtgtggtt cccgcgggcc tggcctcttt acggttatg gccttgcgt gccttgaatt    300 acttccacct ggctgcagta cgtgattctt gatcccgagc ttcgggttgg aagtgggtgg   360
gagagttcga ggccttgcgc ttaaggagcc ccttcgcctc gtgcttgagt tgaggcctgg   420
cctgggcgct ggggccgccg cgtgcgaatc tggtggcacc ttcgcgcctg tctcgctgct   480
ttcgataagt ctctagccat ttaaaatttt tgatgacctg ctgcgacgct tttttctgg   540 caagatagtc ttgtaaatgc gggccaagat ctgcacactg gtatttcggt ttttggggcc   600
gcgggcggcg acgggcccg tgcgtcccag cgcacatgtt cggcgaggcg gggcctgcga   660

```
gcgcgaccac cgagaatcgg acggggggtag tctcaagctg gccggcctgc tctggtgcct    720
gtcctcgcgc cgccgtgtat cgccccgccc cgggcggcaa ggctggcccg gtcggcacca    780
gttgcgtgag cggaaagatg gccgcttccc ggtcctgctg cagggagctc aaaatggagg    840
acgcggcgct cgggagagcg ggcgggtgag tcacccacac aaaggaaaag gccttttccg    900
tcctcagccg tcgcttcatg tgactccacg gagtaccggg cgccgtccag gcacctcgat    960
tagttctcga gcttttggag tacgtcgtct ttaggttggg gggaggggtt ttatgcgatg   1020
gagtttcccc acactgagtg ggtggagact gaagttaggc cagcttggca cttgatgtaa   1080
ttctccttgg aatttgccct ttttgagttt ggatcttggt tcattctcaa gcctcagaca   1140
gtggttcaaa gttttttttct tccatttcag gtgtcgtga                         1179
```

```
<210> SEQ ID NO 14
<211> LENGTH: 544
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
ggatctgcga tcgctccggt gcccgtcagt gggcagagcg cacatcgccc acagtccccg     60
agaagttggg gggaggggtc ggcaattgaa ccggtgccta gagaaggtgg cgcggggtaa    120
actgggaaag tgatgtcgtg tactggctcc gccttttcc cgagggtggg ggagaaccgt    180
atataagtgc agtagtcgcc gtgaacgttc ttttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctac                                                                 544
```

```
<210> SEQ ID NO 15
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
tttatttagt ctccagaaaa agggggggaat gaaagacccc acctgtaggt ttggcaagct     60
aggatcaagg ttaggaacag agagacagca gaatatgggc caaacaggat atctgtggta    120
agcagttcct gccccggctc agggccaaga acagttggaa cagcagaata tgggccaaac    180
aggatatctg tggtaagcag ttcctgcccc ggctcagggc caagaacaga tggtccccag    240
atgcggtccc gccctcagca gtttctagag aaccatcaga tgtttccagg gtgccccaag    300
gacctgaaat gaccctgtgc cttatttgaa ctaaccaatc agttcgcttc tcgcttctgt    360
tcgcgcgctt ctgctccccg agctcaataa aagagccca                           399
```

```
<210> SEQ ID NO 16
<211> LENGTH: 511
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 16

```
ggggttgggg ttgcgccttt tccaaggcag ccctgggttt gcgcagggac gcggctgctc    60
tgggcgtggt tccgggaaac gcagcggcgc cgaccctggg tctcgcacat tcttcacgtc   120
cgttcgcagc gtcacccgga tcttcgccgc taccctggg gccccccgg cgacgcttcc    180
tgctccgccc ctaagtcggg aaggttcctt gcggttcgcg gcgtgccgga cgtgacaaac   240
ggaagccgca cgtctcacta gtaccctcgc agacggacag cgccagggag caatggcagc   300
gcgccgaccg cgatgggctg tggccaatag cggctgctca gcggggcgcg ccgagagcag   360
cggccgggaa ggggcggtgc gggaggcggg gtgtggggcg gtagtgtggg ccctgttcct   420
gcccgcgcgg tgttccgcat tctgcaagcc tccggagcgc acgtcggcag tcggctccct   480
cgttgaccga atcaccgacc tctctcccca g                                  511
```

<210> SEQ ID NO 17
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gtaacgccat tttgcaaggc atggaaaaat accaaaccaa gaatagagaa gttcagatca    60
agggcgggta catgaaaata gctaacgttg ggccaaacag gatatctgcg gtgagcagtt   120
tcggccccgg cccggggcca agaacagatg gtcaccgcag tttcggcccc ggcccgaggc   180
caagaacaga tggtccccag atatggccca accctcagca gtttcttaag acccatcaga   240
tgtttccagg ctcccccaag gacctgaaat gaccctgcgc cttatttgaa ttaaccaatc   300
agcctgcttc tcgcttctgt tcgcgcgctt ctgcttcccg agtctatata aagagctcac   360
aaccctcac tcggcgcgcc agtcctccga cagactgagt cgcccggg               408
```

<210> SEQ ID NO 18
<211> LENGTH: 344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
ctgtggaatg tgtgtcagtt agggtgtgga aagtccccag gctccccagc aggcagaagt    60
atgcaaagca tgcatctcaa ttagtcagca accaggtgtg gaaagtcccc aggctcccca   120
gcaggcagaa gtatgcaaag catgcatctc aattagtcag caaccatagt cccgcccta   180
actccgccca tcccgcccct aactccgccc agttccgccc attctccgcc ccatggctga   240
ctaattttt ttatttatgc agaggccgag gccgcctctg cctctgagct attccagaag   300
tagtgaggag gcttttttgg aggcctaggc ttttgcaaaa agct                    344
```

<210> SEQ ID NO 19
<211> LENGTH: 1229
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
gcgccgggtt ttggcgcctc ccgcgggcgc cccctcctc acggcgagcg ctgccacgtc    60
agacgaaggg cgcaggagcg ttcctgatcc ttccgcccgg acgctcagga cagcggcccg   120
ctgctcataa gactcggcct tagaaccca gtatcagcag aaggacattt taggacggga   180
cttgggtgac tctagggcac tggttttctt tccagagagc ggaacaggcg aggaaaagta   240
gtcccttctc ggcgattctg cggagggatc tccgtggggc ggtgaacgcc gatgattata   300
taaggacgcg ccgggtgtgg cacagctagt tccgtcgcag ccgggatttg gtcgcggtt    360
cttgttttgtg gatcgctgtg atcgtcactt ggtgagttgc gggctgctgg gctggccggg   420
gctttcgtgg ccgccgggcc gctcggtggg acggaagcgt gtggagagac cgccaagggc   480
tgtagtctgg gtccgcgagc aaggttgccc tgaactgggg gttgggggga gcgcacaaaa   540
tggcggctgt tcccgagtct tgaatggaag acgcttgtaa ggcgggctgt gaggtcgttg   600
aaacaaggtg gggggcatgg tgggcggcaa gaacccaagg tcttgaggcc ttcgctaatg   660
cgggaaagct cttattcggg tgagatgggc tggggcacca tctggggacc ctgacgtgaa   720
gtttgtcact gactggagaa ctcgggtttg tcgtctggtt gcggggggcg cagttatgcg   780
gtgccgttgg gcagtgcacc cgtacctttg ggagcgcgcg cctcgtcgtg tcgtgacgtc   840
acccgttctg ttggcttata atgcaggtg gggccacctg ccggtaggtg tgcggtaggc   900
ttttctccgt cgcaggacgc agggttcggg cctagggtag gctctcctga atcgacaggc   960
gccggacctc tggtgagggg agggataagt gaggcgtcag tttctttggt cggttttatg  1020
tacctatctt cttaagtagc tgaagctccg gttttgaact atgcgctcgg ggttggcgag  1080
tgtgttttgt gaagtttttt aggcacccttt tgaaatgtaa tcatttgggt caatatgtaa  1140
ttttcagtgt tagactagta aagcttctgc aggtcgactc tagaaaattg tccgctaaat  1200
tctggccgtt tttggctttt ttgttagac                                    1229
```

<210> SEQ ID NO 20
<211> LENGTH: 1179
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
ggctccggtg cccgtcagtg ggcagagcgc acatcgccca cagtccccga gaagttgggg    60
ggagggggtcg gcaattgaac cggtgcctag agaaggtggc gcggggtaaa ctgggaaagt   120
gatgtcgtgt actggctccg cctttttccc gagggtgggg gagaaccgta tataagtgca   180
gtagtcgccg tgaacgttct ttttcgcaac gggtttgccg ccagaacaca ggtaagtgcc   240
gtgtgtggtt cccgcgggcc tggcctcttt acggttatg gccctttgcgt gccttgaatt   300
acttccacct ggctgcagta cgtgattctt gatcccgagc ttcgggttgg aagtgggtgg   360
gagagttcga ggccttgcgc ttaaggagcc ccttcgcctc gtgcttgagt tgaggcctgg   420
cctgggcgct gggccgccg cgtgcgaatc tggtggcacc ttcgcgcctg tctcgctgct   480
ttcgataagt ctctagccat ttaaaatttt tgatgacctg ctgcgacgct tttttttctgg   540
caagatagtc ttgtaaatgc gggccaagat ctgcacactg gtatttcggt ttttggggcc   600
gcgggcggcg acggggcccg tgcgtcccag cgcacatgtt cggcgaggcg gggcctgcga   660
```

```
gcgcggccac cgagaatcgg acggggggtag tctcaagctg gccggcctgc tctggtgcct    720
ggtctcgcgc cgccgtgtat cgccccgccc tgggcggcaa ggctggcccg gtcggcacca    780
gttgcgtgag cggaaagatg gccgcttccc ggccctgctg cagggagctc aaaatggagg    840
acgcggcgct cgggagagcg ggcgggtgag tcacccacac aaaggaaaag gccttttccg    900
tcctcagccg tcgcttcatg tgactccacg gagtaccggg cgccgtccag gcacctcgat    960
tagttctcga gcttttggag tacgtcgtct ttaggttggg gggagggggtt ttatgcgatg   1020 gagtttcccc acactgagtg ggtggagact gaagttaggc cagcttggca cttgatgtaa   1080
ttctccttgg aatttgccct ttttgagttt ggatcttggt tcattctcaa gcctcagaca   1140
gtggttcaaa gttttttttct tccatttcag gtgtcgtga                         1179
```

<210> SEQ ID NO 21
<211> LENGTH: 1718
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
actagttatt aatagtaatc aattacgggg tcattagttc atagcccata tatggagttc     60
cgcgttacat aacttacggt aaatggcccg cctggctgac cgcccaacga cccccgccca    120
ttgacgtcaa taatgacgta tgttcccata gtaacgccaa tagggacttt ccattgacgt    180
caatgggtgg agtatttacg gtaaactgcc cacttggcag tacatcaagt gtatcatatg    240
ccaagtacgc cccctattga cgtcaatgac ggtaaatggc ccgcctggca ttatgcccag    300
tacatgacct tatgggactt tcctacttgg cagtacatct acgtattagt catcgctatt    360
accatggtcg aggtgagccc cacgttctgc ttcactctcc ccatctcccc cccctcccca    420
cccccaattt tgtatttatt tattttttaa ttattttgtg cagcgatggg ggcggggggg    480 ggggggggc gcgcgccagg cggggcgggg cgggcgaggg ggcggggcgg ggcgaggcgg    540
agaggtgcgg cggcagccaa tcagagcggc gcgctccgaa agtttccttt tatggcgagg    600
cggcggcggc ggcggcccta taaaaagcga agcgcgcggc gggcggggag tcgctgcgac    660
gctgccttcg ccccgtgccc cgctccgccg ccgcctcgcg ccgcccgccc cggctctgac    720
tgaccgcgtt actcccacag gtgagcgggc gggacggccc ttctcctccg ggctgtaatt    780
agcgcttggt ttaatgacgg cttgtttctt ttctgtggct gcgtgaaagc cttgaggggc    840
tccgggaggg ccctttgtgc gggggggagcg gctcgggggg tgcgtgcgtg tgtgtgtgcg    900
tggggagcgc cgcgtgcggc tccgcgctgc ccggcggctg tgagcgctgc gggcgcggcg    960
cggggctttg tgcgctccgc agtgtgcgcg agggggagcgc ggccggggc ggtgccccgc   1020 ggtgcggggg gggctgcgag gggaacaaag gctgcgtgcg gggtgtgtgc gtggggggt   1080 gagcagggggg tgtgggcgcg tcggtcggc tgcaaccccc cctgcacccc cctccccgag   1140
ttgctgagca cggcccggct tcgggtgcgg ggctccgtac ggggcgtggc gcgggctcg   1200 ccgtgccggg cggggggtgg cggcaggtgg gggtgccggg cggggcgggg ccgcctcggg   1260
ccggggaggg ctcgggggag gggcgcggcg gcccccggag cgccggcggc tgtcgaggcg   1320
cggcgagccg cagccattgc ctttttatggt aatcgtgcga gagggcgcag ggacttcctt   1380
tgtcccaaat ctgtgcggag ccgaaatctg gaggcgccg ccgcacccc tctagcgggc   1440 gcggggcgaa gcggtgcggc gccggcagga aggaaatggg cggggagggc cttcgtgcgt   1500
```

```
cgccgcgccg ccgtcccctt ctccctctcc agcctcgggg ctgtccgcgg ggggacggct      1560
gccttcgggg gggacggggc agggcggggt tcggcttctg gcgtgtgacc ggcggctcta      1620
gagcctctgc taaccatgtt catgccttct tcttttcct acagctcctg ggcaacgtgc       1680
tggttattgt gctgtctcat cattttggca aagaattc                              1718

<210> SEQ ID NO 22
<211> LENGTH: 212
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gggcagagcg cacatcgccc acagtccccg agaagttggg gggaggggtc ggcaattgaa        60
ccggtgccta gagaaggtgg cgcggggtaa actgggaaag tgatgtcgtg tactggctcc       120
gcctttttcc cgagggtggg ggagaaccgt atataagtgc agtagtcgcc gtgaacgttc       180
tttttcgcaa cgggtttgcc gccagaacac ag                                    212

<210> SEQ ID NO 23
<211> LENGTH: 2379
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
ccactagttc catgtcctta tatggactca tctttgccta ttgcgacaca cactcaatga        60
acacctacta cgcgctgcaa agagccccgc aggcctgagg tgcccccacc tcaccactct       120
tcctattttt gtgtaaaaat ccagcttctt gtcaccacct ccaaggaggg ggaggaggag       180
gaaggcaggt tcctctaggc tgagccgaat gcccctctgt ggtcccacgc cactgatcgc       240
tgcatgccca ccacctgggt acacacagtc tgtgattccc ggagcagaac ggaccctgcc       300
cacccggtct tgtgtgctac tcagtggaca gacccaaggc aagaaagggt gacaaggaca       360
gggtcttccc aggctggctt tgagttccta gcaccgcccc gcccccaatc tctgtggca       420 catggagtct tggtccccag agtccccag cggcctccag atggtctggg agggcagttc        480
agctgtggct gcgcatagca gacatacaac ggacggtggg cccagaccca ggctgtgtag       540
acccagcccc ccgccccgc agtgcctagg tcacccacta cgccccagg cctggtcttg        600 gctgggcgtg actgttaccc tcaaaagcag gcagctccag ggtaaaaggt gccctgccct       660
gtagagccca ccttccttcc cagggctgcg gctgggtagg tttgtagcct tcatcacggg       720
ccacctccag ccactggacc gctggcccct gccctgtcct ggggagtgtg gtcctgcgac       780
ttctaagtgg ccgcaagcca cctgactccc caacaccac actctacctc tcaagcccag       840
gtctctccct agtgacccac ccagcacatt tagctagctg agcccacag ccagaggtcc        900 tcaggccctg ctttcagggc agttgctctg aagtcggcaa gggggagtga ctgcctggcc       960
actccatgcc ctccaagagc tccttctgca ggagcgtaca gaaccagggg ccctggcacc      1020
cgtgcagacc ctggcccacc ccacctgggc gctcagtgcc caagagatgt ccacacctag      1080
gatgtcccgc ggtgggtggg gggcccgaga cgggcagg ccggggcag gcctggccat         1140 gcggggccga accgggcact gcccagcgtg gggcgcgggg gccacggcgc gcgccccag       1200 cccccgggcc cagcacccca aggcggccaa cgccaaaact ctccctcctc ctcttcctca      1260
```

| | | |
|---|---|---|
| atctcgctct cgctctttt tttttcgca aaaggagggg agagggggta aaaaaatgct | 1320 |
| gcactgtgcg gcgaagccgg tgagtgagcg gcgcggggcc aatcagcgtg cgccgttccg | 1380 |
| aaagttgcct tttatggctc gagcggccgc ggcggcgccc tataaaaccc agcggcgcga | 1440 |
| cgcgccacca ccgccgagac cgcgtccgcc ccgcgagcac agagcctcgc ctttgccgat | 1500 |
| ccgccgcccg tccacacccg ccgccaggta agcccggcca gccgaccggg gcaggcggct | 1560 |
| cacgccccgg ccgcaggcgg ccgcggcccc ttcgcccgtg cagagccgcc gtctgggccg | 1620 |
| cagcggggg cgcatggggg gggaaccgga ccgccgtggg gggcgcggga aagcccctg | 1680 |
| ggcctccgga gatgggggac accccacgcc agttcggagg cgcgaggccg cgctcggag | 1740 |
| gcgcgctccg ggggtgccgc tctcggggcg ggggcaaccg gcggggtctt tgtctgagcc | 1800 |
| gggctcttgc caatgggat cgcagggtgg gcgcggcgga gcccccgcca ggcccggtgg | 1860 |
| gggctggggc gccattgcgc gtgcgcgctg gtcctttggg cgctaactgc gtgcgcgctg | 1920 |
| ggaattggcg ctaattgcgc gtgcgcgctg ggactcaagg cgctaactgc gcgtgcgttc | 1980 |
| tggggcccgg ggtgccgcgg cctgggctgg ggcgaaggcg ggctcggccg gaaggggtgg | 2040 |
| ggtcgccgcg gctcccggc gcttgcgcgc acttcctgcc cgagccgctg gccgcccgag | 2100 |
| ggtgtggccg ctgcgtgcgc gcgcgccgac ccggcgctgt ttgaaccggg cggaggcggg | 2160 |
| gctggcgccc ggttgggagg gggttggggc ctggcttcct gccgcgcgcc gcggggacgc | 2220 |
| ctccgaccag tgtttgcctt ttatggtaat aacgcggccg gcccggcttc ctttgtcccc | 2280 |
| aatctgggcg cgcgccggcg ccccctggcg gcctaaggac tcggcgcgcc ggaagtggcc | 2340 |
| agggcggggg cgacctcggc tcacagcgcg cccggctat | 2379 |

<210> SEQ ID NO 24
<211> LENGTH: 529
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

| | | |
|---|---|---|
| gttgatttcc ttcatccctg gcacacgtcc aggcagtgtc gaatccatct ctgctacagg | 60 |
| ggaaaacaaa taacatttga gtccagtgga gaccgggagc agaagtaaag ggaagtgata | 120 |
| accccagag cccggaagcc tctggaggct gagacctcgc ccccttgcg tgatagggcc | 180 |
| tacggagcca catgaccaag gcactgtcgc ctccgcacgt gtgagagtgc agggccccaa | 240 |
| gatggctgcc aggcctcgag gcctgactct tctatgtcac ttccgtaccg gcgagaaagg | 300 |
| cgggcccctcc agccaatgag gctgcggggc gggccttcac cttgataggc actcgagtta | 360 |
| tccaatggtg cctgcgggcc ggagcgacta ggaactaacg tcatgccgag ttgctgagcg | 420 |
| ccggcaggcg gggccggggc ggccaaacca atgcgatggc cggggcggag tcgggcgctc | 480 |
| tataagttgt cgataggcgg gcactccgcc ctagtttcta aggaccatg | 529 |

<210> SEQ ID NO 25
<211> LENGTH: 794
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

| | |
|---|---|
| agttccccaa ctttcccgcc tctcagcctt tgaaagaaag aaaggggagg gggcaggccg | 60 |
| cgtgcagtcg cgagcggtgc tgggctccgg ctccaattcc ccatctcagt cgctcccaaa | 120 |
| gtccttctgt ttcatccaag cgtgtaaggg tccccgtcct tgactcccta gtgtcctgct | 180 |
| gcccacagtc cagtcctggg aaccagcacc gatcacctcc catcgggcca atctcagtcc | 240 |
| cttcccccct acgtcggggc ccacacgctc ggtgcgtgcc cagttgaacc aggcggctgc | 300 |
| ggaaaaaaaa aagcggggag aaagtagggc ccggctacta gcggttttac gggcgcacgt | 360 |
| agctcaggcc tcaagacctt gggctgggac tggctgagcc tggcgggagg cggggtccga | 420 |
| gtcaccgcct gccgccgcgc ccccggtttc tataaattga gcccgcagcc tcccgcttcg | 480 |
| ctctctgctc ctcctgttcg acagtcagcc gcatcttctt ttgcgtcgcc aggtgaagac | 540 |
| gggcggagag aaacccggga ggctaggac ggcctgaagg cggcagggc gggcgcaggc | 600 |
| cggatgtgtt cgcgccgctg cggggtgggc ccggcggcc tccgcattgc aggggcgggc | 660 |
| ggaggacgtg atgcggcgcg ggctgggcat ggaggcctgg tggggaggg aggggaggc | 720 |
| gtgggtgtcg gccggggcca ctaggcgctc actgttctct ccctccgcgc agccgagcca | 780 |
| catcgctgag acac | 794 |

<210> SEQ ID NO 26
<211> LENGTH: 532
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

| | |
|---|---|
| agtgcggtta ccagcggaaa tgcctcgggg tcagaagtcg caggagagat agacagctgc | 60 |
| tgaaccaatg ggaccagcgg atgggcgga tgttatctac cattggtgaa cgttagaaac | 120 |
| gaatagcagc caatgaatca gctgggggg cggagcagtg acgtttattg cggaggggc | 180 |
| cgcttcgaat cggcggcggc cagcttggtg gcctgggcca atgaacggcc tccaacgagc | 240 |
| agggccttca ccaatcggcg gcctccacga cggggctggg ggagggtata taagccgagt | 300 |
| aggcgacggt gaggtcgacg ccggccaaga cagcacagac agattgacct attgggtgt | 360 |
| ttcgcgagtg tgagagggaa gcgccgcggc ctgtatttct agacctgccc ttcgcctggt | 420 |
| tcgtggcgcc ttgtgacccc gggcccctgc cgcctgcaag tcggaaattg cgctgtgctc | 480 |
| ctgtgctacg gcctgtggct ggactgcctg ctgctgccca actggctggc ac | 532 |

<210> SEQ ID NO 27
<211> LENGTH: 701
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

| | |
|---|---|
| tagtttcatc accaccgcca ccccccgcc ccccgccat ctgaaagggt tctaggggat | 60 |
| ttgcaacctc tctcgtgtgt ttcttctttc cgagaagcgc cgccacacga gaaagctggc | 120 |
| cgcgaaagtc gtgctggaat cacttccaac gaaacccag gcatagatgg gaaagggtga | 180 |
| agaacacgtt gccatggcta ccgtttcccc ggtcacggaa taaacgctct ctaggatccg | 240 |
| gaagtagttc cgccgcgacc tctctaaaag gatggatgtg ttctctgctt acattcattg | 300 |
| gacgttttcc cttagaggcc aaggccgccc aggcaaaggg gcggtcccac gcgtgagggg | 360 |

```
cccgcggagc catttgattg gagaaaagct gcaaaccctg accaatcgga aggagccacg     420
cttcgggcat cggtcaccgc acctggacag ctccgattgg tggacttccg ccccccctca     480
cgaatcctca ttgggtgccg tgggtgcgtg gtgcggcgcg attggtgggt tcatgtttcc     540
cgtcccccgc ccgcgagaag tggggggtgaa aagcggcccg acctgcttgg ggtgtagtgg    600
gcggaccgcg cggctggagg tgtgaggatc cgaacccagg ggtgggggt ggaggcggct      660 cctgcgatcg aagggggactt gagactcacc ggccgcacgt c                       701
```

<210> SEQ ID NO 28
<211> LENGTH: 465
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
gggccgccca ctccccttc ctctcagggt ccctgtcccc tccagtgaat cccagaagac      60
tctggagagt tctgagcagg gggcggcact ctggcctctg attggtccaa ggaaggctgg    120
ggggcaggac gggaggcgaa aaccctggaa tattcccgac ctggcagcct catcgagctc    180
ggtgattggc tcagaaggga aaaggcgggt ctccgtgacg acttataaaa gcccaggggc    240
aagcggtccg gataacggct agcctgagga gctgctgcga cagtccacta ccttttttcga   300 gagtgactcc cgttgtccca aggcttccca gagcgaacct gtgcggctgc aggcaccggc    360
gcgtcgagtt tccggcgtcc ggaaggaccg agctcttctc gcggatccag tgttccgttt    420
ccagccccca atctcagagc ggagccgaca gagagcaggg aaccc                    465
```

<210> SEQ ID NO 29
<211> LENGTH: 538
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
gccccaccc cgtccgcgtt acaaccggga ggcccgctgg gtcctgcacc gtcaccctcc      60
tccctgtgac cgcccacctg atacccaaac aactttctcg cccctccagt ccccagctcg    120
ccgagcgctt gcggggagcc acccagcctc agtttcccca gccccgggcg gggcgagggg    180
cgatgacgtc atgccggcgc gcggcattgt ggggcgggc gaggcggggc gccggggggga    240 gcaacactga gacgccattt tcggcggcgg gagcggcgca ggcggccgag cgggactggc    300
tgggtcggct gggctgctgg tgcgaggagc cgcggggctg tgctcggcgg ccaagggggac   360 agcgcgtggg tggccgagga tgctgcgggg cggtagctcc ggcgcccctc gctggtgact    420
gctgcgccgt gcctcacaca gccgaggcg gctcggcgca cagtcgctgc tccgcgctcg     480
cgcccggcgg cgctccaggt gctgacagcg cgagagagcg cggcctcagg agcaacac     538
```

<210> SEQ ID NO 30
<211> LENGTH: 1091
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
ttccagagct ttcgaggaag gtttcttcaa ctcaaattca tccgcctgat aattttctta      60
tattttccta aagaaggaag agaagcgcat agaggagaag ggaaataatt ttttaggagc     120
ctttcttacg gctatgagga atttggggct cagttgaaaa gcctaaactg cctctcggga     180
ggttgggcgc ggcgaactac tttcagcggc gcacggagac ggcgtctacg tgaggggtga     240
taagtgacgc aacactcgtt gcataaattt gcgctccgcc agcccggagc atttaggggc     300
ggttggcttt gttgggtgag cttgtttgtg tccctgtggg tggacgtggt tggtgattgg     360
caggatcctg gtatccgcta acaggtactg gcccacagcc gtaaagacct gcggggggcgt    420 gagagggggg aatgggtgag gtcaagctgg aggcttcttg gggttgggtg ggccgctgag     480
gggaggggag ggcgaggtga cgcgacaccc ggcctttctg ggagagtggg ccttgttgac     540 ctaaggggg cgaggggcagt tggcacgcgc acgcgccgac agaaactaac agacattaac     600
caacagcgat tccgtcgcgt ttacttggga ggaaggcgga aaagaggtag tttgtgtggc     660
ttctggaaac cctaaatttg gaatcccagt atgagaatgg tgtcccttct tgtgtttcaa     720
tgggattttt acttcgcgag tcttgtgggt ttggttttgt tttcagtttg cctaacaccg     780
tgcttaggtt tgaggcagat tggagttcgg tcggggagt ttgaatatcc ggaacagtta      840
gtggggaaag ctgtggacgc ttggtaagag agcgctctgg attttccgct gttgacgttg     900
aaaccttgaa tgacgaattt cgtattaagt gacttagcct tgtaaaattg aggggaggct     960
tgcggaatat taacgtattt aaggcatttt gaaggaatag ttgctaattt tgaagaatat    1020
taggtgtaaa agcaagaaat acaatgatcc tgaggtgaca cgcttatgtt ttactttaa    1080 actaggtcac c                                                          1091

<210> SEQ ID NO 31
<211> LENGTH: 66
<212> TYPE: DNA
<213> ORGANISM: Homo sapiens

<400> SEQUENCE: 31
atgtgtcacc agcagctcgt tatatcctgg tttagtttgg tgtttctcgc ttcacccctg      60
gtggca                                                                66

<210> SEQ ID NO 32
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
atgtgccatc agcaactcgt catctcctgg ttctcccttg tgttcctcgc ttccctctg      60 gtcgcc                                                                66

<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
atgcaactgc tgtcatgtat cgcactcatc ctggcgctgg ta                        42
```

<210> SEQ ID NO 34
<211> LENGTH: 60
<212> TYPE: DNA
<213> ORGANISM: Homo sapiens

<400> SEQUENCE: 34
atgtatcgga tgcaactttt gagctgcatc gcattgtctc tggcgctggt gacaaattcc    60

<210> SEQ ID NO 35
<211> LENGTH: 45
<212> TYPE: DNA
<213> ORGANISM: Homo sapiens

<400> SEQUENCE: 35
atgaatctct tgctcatact tacgtttgtc gctgctgccg ttgcg    45

<210> SEQ ID NO 36
<211> LENGTH: 51
<212> TYPE: DNA
<213> ORGANISM: Unknown
<220> FEATURE:
<223> OTHER INFORMATION: Description of Unknown:
      Gaussia Luciferase sequence

<400> SEQUENCE: 36
atgggcgtga aggtcttgtt tgcccttatc tgcatagctg ttgcggaggc g    51

<210> SEQ ID NO 37
<211> LENGTH: 72
<212> TYPE: DNA
<213> ORGANISM: Homo sapiens

<400> SEQUENCE: 37
atgccgatgg ggagccttca acctttggca acgctttatc ttctggggat gttggttgct    60
agttgccttg gg    72

<210> SEQ ID NO 38
<211> LENGTH: 63
<212> TYPE: DNA
<213> ORGANISM: Mus sp.

<400> SEQUENCE: 38
atggaaactg acacgttgtt gctgtgggta ttgctcttgt gggtcccagg atctacgggc    60
gac    63

<210> SEQ ID NO 39
<211> LENGTH: 66
<212> TYPE: DNA
<213> ORGANISM: Homo sapiens

<400> SEQUENCE: 39
atggatatga gggttcccgc ccagcttttg gggctgcttt tgttgtggct tcgaggggct    60
cggtgt    66

<210> SEQ ID NO 40
<211> LENGTH: 48
<212> TYPE: DNA
<213> ORGANISM: Unknown
<220> FEATURE:
<223> OTHER INFORMATION: Description of Unknown:
      VSV-G sequence

<400> SEQUENCE: 40

```
atgaagtgtc tgttgtacct ggcgtttctg ttcattggtg taaactgt           48
```

<210> SEQ ID NO 41
<211> LENGTH: 84
<212> TYPE: DNA
<213> ORGANISM: Homo sapiens

<400> SEQUENCE: 41

```
atgaatatca aaggaagtcc gtggaagggt agtctcctgc tgctcctcgt atctaacctt   60
ctcctttgtc aatccgtggc accc                                         84
```

<210> SEQ ID NO 42
<211> LENGTH: 54
<212> TYPE: DNA
<213> ORGANISM: Homo sapiens

<400> SEQUENCE: 42

```
atgaaatggg taacattcat atcacttctc tttctgttca gctctgcgta ttct       54
```

<210> SEQ ID NO 43
<211> LENGTH: 57
<212> TYPE: DNA
<213> ORGANISM: Homo sapiens

<400> SEQUENCE: 43

```
atgacaaggc ttactgtttt ggctctcctc gctggactct tggcttcctc ccgagca    57
```

<210> SEQ ID NO 44
<211> LENGTH: 51
<212> TYPE: DNA
<213> ORGANISM: Homo sapiens

<400> SEQUENCE: 44

```
atgagggctt ggattttttt tctgctctgc cttgccggtc gagccctggc g          51
```

<210> SEQ ID NO 45
<211> LENGTH: 48
<212> TYPE: DNA
<213> ORGANISM: Homo sapiens

<400> SEQUENCE: 45

```
atgcctcttc tgcttttgct tcctcttttg tgggcaggtg ccctcgca              48
```

<210> SEQ ID NO 46
<211> LENGTH: 87
<212> TYPE: DNA
<213> ORGANISM: Homo sapiens

<400> SEQUENCE: 46

```
atgaactctt tctcaacctc tgcgtttggt ccggtcgctt tctcccttgg gctcctgctt   60
gtcttgccag cagcgtttcc tgcgcca                                      87
```

<210> SEQ ID NO 47
<211> LENGTH: 60
<212> TYPE: DNA
<213> ORGANISM: Homo sapiens

<400> SEQUENCE: 47

```
atgacaagta aactggcggt agccttgctc gcggccttt tgatttccgc agccctttgt   60
```

<210> SEQ ID NO 48

<211> LENGTH: 69
<212> TYPE: DNA
<213> ORGANISM: Homo sapiens

<400> SEQUENCE: 48
atgaaggtaa gtgcagcgtt gctttgcctt ctcctcattg cagcgacctt tattcctcaa    60
gggctggcc                                                             69

<210> SEQ ID NO 49
<211> LENGTH: 78
<212> TYPE: DNA
<213> ORGANISM: Homo sapiens

<400> SEQUENCE: 49
atgggagcgg cagctagaac acttcgactt gcccttgggc tcttgctcct tgcaaccctc    60
cttagacctg ccgacgca                                                   78

<210> SEQ ID NO 50
<211> LENGTH: 63
<212> TYPE: DNA
<213> ORGANISM: Homo sapiens

<400> SEQUENCE: 50
atgtcaccgt tgttgcggag attgctgttg gccgcacttt tgcaactggc tcctgctcaa    60
gcc                                                                   63

<210> SEQ ID NO 51
<211> LENGTH: 63
<212> TYPE: DNA
<213> ORGANISM: Homo sapiens

<400> SEQUENCE: 51
atgaataacc tgctctgttg tgcgctcgtg ttcctggaca tttctataaa atggacaacg    60
caa                                                                   63

<210> SEQ ID NO 52
<211> LENGTH: 69
<212> TYPE: DNA
<213> ORGANISM: Homo sapiens

<400> SEQUENCE: 52
atgcaaatgt ctcctgccct tacctgtctc gtacttggtc ttgcgctcgt atttggagag    60
ggatcagcc                                                             69

<210> SEQ ID NO 53
<211> LENGTH: 102
<212> TYPE: DNA
<213> ORGANISM: Homo sapiens

<400> SEQUENCE: 53
atggcaaggg ctgcactcag tgctgccccg tctaatccca gattgcttcg agttgcattg    60
cttcttctgt tgctggttgc agctggtagg agagcagcgg gt                       102

<210> SEQ ID NO 54
<211> LENGTH: 63
<212> TYPE: DNA
<213> ORGANISM: Homo sapiens

<400> SEQUENCE: 54
atgaatgcaa aagtcgtggt cgtgctggtt ttggttctga cggcgttgtg tcttagtgat    60

```
ggg                                                                  63

<210> SEQ ID NO 55
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
atggaacgca ttgtgatctg cctgatggtc atcttcctgg gcaccttagt gcacaagtcg    60
agcagc                                                               66

<210> SEQ ID NO 56
<211> LENGTH: 1626
<212> TYPE: DNA
<213> ORGANISM: Homo sapiens

<400> SEQUENCE: 56
atgtgccatc agcagcttgt catatcttgg ttttcacttg tattcctggc cagcccttttg   60
gttgcgatct gggagctcaa gaaggatgtg tacgttgtag agctggactg gtaccccgat   120
gctcccggtg agatggtcgt tttgacatgt gacactccag aagaggacgg tattacgtgg   180
actctggacc agtcctccga agttcttggt tctggtaaga ctctgactat ccaggtgaaa   240
gaatttgggg atgcgggaca atacacatgc acaagggagg cgaggtgtt gtctcatagt   300
ttgctgcttc tccacaagaa agaggatgga atctggagca ccgacatact caaggatcaa   360
aaggaaccca aaaataagac atttctgcga tgtgaggcta agaactatag tggccgcttc   420
acttgttggt ggctgactac catcagcaca gatctcacgt tttcagtaaa aagtagtaga   480
ggttcaagtg atcctcaagg ggtaacgtgc ggtgctgcaa cactgtctgc tgaacgcgta   540
agaggagata taaggagta cgagtattcc gtagaatgcc aagaggacag tgcttgtcct   600
gcggccgagg agtctctccc aatagaagtg atggtggacg cggtgcataa actgaaatat   660
gagaactaca agcagttt ttttataaga gatatcatca gcccgatcc gccgaagaat   720
ttgcaactta accgcttaa aaactcacgc caggttgaag tatcctggga gtatccggat   780
acatggtcaa caccacacag ctattttttcc cttaccttct gtgtgcaggt ccaagggaag   840
agcaaaaggg agaagaagga cagggtattc actgataaaa cttccgcgac ggtcatctgc   900
cgaaaaaacg ctagtatatc tgtacgggcg caggataggg actatagttc ttcttggtct   960
gagtgggcct cagttccgtg ctctggggga ggaagtggag gagggtccgg cggtggaagc  1020
gggggagggga gtcgcaactt gccagtggct acaccagatc caggcatgtt ccatgtctg  1080
catcattccc agaatctcct gagagcggtg tcaaatatgc tccaaaaagc gagacaaaca  1140
ctggaattt accegtgtac cagtgaggag attgatcacg aggacataac caaggacaag  1200
acctcaactg tagaagcgtg tttgccgctg gagttgacta agaatgagtc ctgcctcaat  1260
tccagagaaa cttcattcat tactaacggc agttgtcttg catcccggaa aacgtccttt  1320
atgatggccc tttgccttag ttcaatttac gaggatctta aaatgtatca agtggagttt  1380
aaaaccatga atgctaaact tcttatggac cccaaacgac aaattttttct ggatcagaat  1440
atgcttgccg tgatagacga actcatgcag gcgcttaatt ttaactccga aacagttcca  1500
caaaatctat gccttgaaga acctgatttt tataaaacga agattaaact gtgtatcctg  1560
ctgcatgcct ttcgcatccg agctgtcaca atcgataggg ttatgtccta ccttaacgcg  1620
``` agctag 1626

<210> SEQ ID NO 57
<211> LENGTH: 1623
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
atgtgccatc agcaactcgt catctcctgg ttctcccttg tgttcctcgc ttccctctg      60
gtcgccattt gggaactgaa gaaggacgtc tacgtggtcg agctggattg gtacccggac   120
gcccctggag aaatggtcgt gctgacttgc gatacgccag aagaggacgg cataacctgg   180
accctggatc agagctccga ggtgctcgga agcggaaaga ccctgaccat tcaagtcaag   240
gagttcggcg acgcgggcca gtacacttgc cacaagggtg gcgaagtgct gtcccactcc   300
ctgctgctgc tgcacaagaa agaggatgga atctggtcca ctgacatcct caaggaccaa   360
aaagaaccga gaacaagac cttcctccgc tgcgaagcca gaactacag cggtcggttc   420
acctgttggt ggctgacgac aatctccacc gacctgactt tctccgtgaa gtcgtcacgg   480
ggatcaagcg atcctcaggg cgtgacctgt ggagccgcca ctctgtccgc cgagagagtc   540
aggggagaca caaggaata tgagtactcc gtggaatgcc aggaggacag cgcctgccct   600
gccgcggaag agtccctgcc tatcgaggtc atggtcgatg ccgtgcataa gctgaaatac   660
gagaactaca cttcctcctt ctttatccgc gacatcatca gcctgacccc cccaagaac   720
ttgcagctga agccactcaa gaactcccgc caagtggaag tgtcttggga atatccagac   780
acttggagca ccccgcactc atacttctcg ctcactttct gtgtgcaagt gcagggaaag   840
tccaaacggg agaagaaaga ccgggtgttc accgacaaaa cctccgccac tgtgatttgt   900
cggaagaacg cgtcaatcag cgtccgggcg caggatagat actactcgtc ctcctggagc   960
gaatgggcca gcgtgccttg ttccggtggc ggatcaggcg gaggttcagg aggaggctcc  1020
ggaggaggtt cccggaacct ccctgtggca accccgacc ctggaatgtt cccgtgccta  1080
caccactccc aaaacctcct gagggctgtg tcgaacatgt tgcagaaggc ccgccagacc  1140
cttgagttct accctgcac ctcggaagaa attgatcacg aggacatcac caaggacaag  1200
acctcgaccg tggaagcctg cctgccgctg gaactgacca gaacgaatc gtgtctgaac  1260
tcccgcgaga caagctttat cactaacggc agctgcctgg cgtcgagaaa gacctcattc  1320
atgatggcgc tctgtctttc ctcgatctac gaagatctga agatgtatca ggtcgagttc  1380
aagaccatga cgccaagct gctcatggac ccgaagcggc agatcttcct ggaccagaat  1440
atgctcgccg tgattgatga actgatgcag gccctgaatt tcaactccga gactgtgcct  1500
caaaagtcca gcctgaaaga accggacttc tacaagacca gatcaagct gtgcatcctg  1560
ttgcacgctt ccgcattcg agccgtgacc attgaccgcg tgatgtccta cctgaacgcc  1620
agt                                                                 1623
```

<210> SEQ ID NO 58
<211> LENGTH: 1635
<212> TYPE: DNA
<213> ORGANISM: Mus sp.

<400> SEQUENCE: 58

```
atgtgtccac agaagctgac aataagttgg tttgccattg tcctcctggt gagcccactc   60
```

```
atggcaatgt gggaactcga aaaggatgtc tacgtggtag aagtagattg gactccagac      120
gcgccagggg agacagtgaa tttgacatgt gacacaccag aagaagatga cattacatgg      180
acatctgacc aacgccatgg cgtaataggg agtgggaaaa cactcacgat cacagttaaa      240
gagttcttgg atgctggtca atatacttgc cataaaggcg gcgagacact cagccactca      300
catttgcttt tgcataaaaa agagaatggc atttggagca ctgaaatact taagaacttt      360
aagaacaaga catttctcaa gtgtgaggcc cctaattaca gcggcaggtt cacgtgctca      420
tggctggtcc agcgcaacat ggacctcaag tttaacataa aatcttcttc ctcttcacct      480
gactccagag ctgttacttg cggcatggct tctctgagcg cagaaaaagt aacgttggat      540
caaagagact acgaaaagta ctctgtttct tgtcaagagg atgttacgtg cccgacggcc      600
gaagaaacgc ttccaattga actcgcgttg gaagctcgcc aacaaaacaa gtatgaaaac      660
tacagtacaa gcttctttat acgggatata attaaacccg atcccccaa gaacttgcaa       720 atgaaaccac ttaagaacag ccaggtggaa gtttcctggg agtatccaga ctcatggagt      780
actcctcaca gctattttc tctgaaattc tttgtaagga tacaacggaa gaaagagaag       840
atgaaagaga ccgaggaggg ttgtaatcag aagggagcgt ttctcgtgga gaaaacgtct      900
accgaagtcc aatgtaaagg tggcaatgtg tgcgtccaag ctcaggatag atactataat      960
tcaagttgct ccaagtgggc ctgtgttcca tgccgcgttc ggagcggggg aggtagcgga     1020
ggaggtagtg ggggtgggtc aggaggaggg agtcgagtta tcccggtgtc aggccccgca     1080
cgctgcttga gccagagtcg caacctcctt aagacaacag atgacatggt gaaaacagca     1140
cgcgaaaagc ttaaacacta ctcttgtacg gcggaggata ttgatcacga ggatattacc     1200
cgagaccaaa ctagcacttt gaaaacctgt ctgccccttg aacttcataa aaatgagagc     1260
tgtctggcta cacgagagac gtcaagtacg actaggggca gctgtctccc gccgcaaaag     1320
acaagcctca tgatgacgct ctgtttgggt tccatttacg aggacttgaa atgtatcaa      1380 acggagttcc aggctataaa tgcggcgttg cagaaccata accatcaaca aattatactt     1440
gataaaggca tgttggtggc gattgatgaa ctcatgcaga gtctcaatca acacgggaa      1500 acgttgagac agaaaccccc agtcggtgaa gcggacccat atcgagtaaa aatgaagctc     1560
tgcattctgc ttcacgcatt cagcactaga gttgttacca tcaaccgggt aatgggatat     1620
ctctccagtg cgtag                                                      1635

<210> SEQ ID NO 59
<211> LENGTH: 465
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
atggaacgca ttgtgatctg cctgatggtc atcttcctgg caccttagt gcacaagtcg       60 agcagccagg gacaggacag gcacatgatt agaatgcgcc agctcatcga tatcgtggac     120
cagttgaaga actacgtgaa cgacctggtg cccgagttcc tgccggcccc cgaagatgtg     180
gaaaccaatt gcgaatggtc ggcattttcc tgctttcaaa aggcacagct caagtccgct     240
aacaccggga caacgaacg gatcatcaac gtgtccatca aaagctgaa gcggaagcct       300 ccctccacca acgccggacg gaggcagaag cataggctga cttgcccgtc atgcgactcc     360
tacgagaaga agccgccgaa ggagttcctg gagcggttca gtcgctcct gcaaaagatg      420
```
attcatcagc acctgtcctc ccggactcat gggtctgagg attca        465

<210> SEQ ID NO 60
<211> LENGTH: 2163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
atgtgccatc agcaactcgt catctcctgg ttctcccttg tgttcctcgc ttccctctg       60
gtcgccattt gggaactgaa gaaggacgtc tacgtggtcg agctggattg gtacccggac     120
gccctggag aaatggtcgt gctgacttgc gatacgccag aagaggacgg cataacctgg      180
accctggatc agagctccga ggtgctcgga agcggaaaga ccctgaccat tcaagtcaag     240
gagttcggcg acgcgggcca gtacacttgc cacaagggtg gcgaagtgct gtcccactcc     300
ctgctgctgc tgcacaagaa agaggatgga atctggtcca ctgacatcct caaggaccaa    360
aaagaaccga gaacaagac cttcctccgc tgcgaagcca gaactacag cggtcggttc       420
acctgttggt ggctgacgac aatctccacc gacctgactt tctccgtgaa gtcgtcacgg    480
ggatcaagcg atcctcaggg cgtgacctgt ggagccgcca ctctgtccgc cgagagagtc    540
aggggagaca caaggaata tgagtactcc gtggaatgcc aggaggacag cgcctgccct    600
gccgcggaag agtccctgcc tatcgaggtc atggtcgatg ccgtgcataa gctgaaatac  660
gagaactaca cttcctcctt ctttatccgc gacatcatca gcctgacccc cccaagaac   720
ttgcagctga gccactcaa gaactcccgc caagtggaag tgtcttggga atatccagac    780
acttggagca ccccgcactc atacttctcg ctcactttct gtgtgcaagt gcagggaaag   840
tccaaacggg agaagaaaga ccgggtgttc accgacaaaa cctccgccac tgtgatttgt    900
cggaagaacg cgtcaatcag cgtccgggcg caggatagat actactcgtc ctcctggagc    960
gaatgggcca gcgtgccttg ttccggtggc ggatcaggcg gaggttcagg aggaggctcc   1020
ggaggaggtt cccggaacct ccctgtggca cccccgacc ctggaatgtt cccgtgccta    1080
caccactccc aaaacctcct gagggctgtg tcgaacatgt tgcagaaggc ccgccagacc   1140
cttgagttct acccctgcac ctcggaagaa attgatcacg aggacatcac caaggacaag   1200
acctcgaccg tggaagcctg cctgccgctg gaactgacca gaacgaatc gtgtctgaac    1260
tcccgcgaga caagctttat cactaacggc agctgcctgg cgtcgagaaa gacctcattc   1320
atgatggcgc tctgtctttc ctcgatctac gaagatctga agatgtatca ggtcgagttc    1380
aagaccatga cgccaagct gctcatggac ccgaagcggc agatcttcct ggaccagaat    1440
atgctcgccg tgattgatga actgatgcag gccctgaatt tcaactccga gactgtgcct   1500
caaaagtcca gcctgaaga accggacttc tacaagacca agatcaagct gtgcatcctg    1560
ttgcacgctt tccgcattcg agccgtgacc attgaccgcg tgatgtccta cctgaacgcc   1620
agtagacgga aacgcggaag cggagagggc agagctcgc tgcttacatg cggggacgtg    1680
gaagagaacc ccgtccgat ggaacgcatt gtgatctgcc tgatggtcat cttcctgggc    1740
accttagtgc acaagtcgag cagccaggga caggacaggc acatgattag aatgcgccag   1800
ctcatcgata tcgtggacca gttgaagaac tacgtgaacg acctggtgcc cgagttcctg   1860
ccggcccccg aagatgtgga aaccaattgc gaatggtcgg catttcctg ctttcaaaag    1920
gcacagctca gtccgctaa caccgggaac aacgaacgga tcatcaacgt gtccatcaaa    1980

| | |
|---|---|
| aagctgaagc ggaagcctcc ctccaccaac gccggacgga ggcagaagca taggctgact | 2040 |
| tgcccgtcat gcgactccta cgagaagaag ccgccgaagg agttcctgga gcggttcaag | 2100 |
| tcgctcctgc aaaagatgat tcatcagcac ctgtcctccc ggactcatgg gtctgaggat | 2160 |
| tca | 2163 |

<210> SEQ ID NO 61
<211> LENGTH: 2103
<212> TYPE: DNA
<213> ORGANISM: Homo sapiens

<400> SEQUENCE: 61

| | |
|---|---|
| atgtgccatc agcagcttgt catatcttgg ttttcacttg tattcctggc cagcccttg | 60 |
| gttgcgatct gggagctcaa gaaggatgtg tacgttgtag agctggactg gtaccccgat | 120 |
| gctcccggtg agatggtcgt tttgacatgt gacactccag aagaggacgg tattacgtgg | 180 |
| actctggacc agtcctccga agttcttggt tctggtaaga ctctgactat ccaggtgaaa | 240 |
| gaatttgggg atgcgggaca atacacatgc cacaagggag gcgaggtgtt gtctcatagt | 300 |
| ttgctgcttc tccacaagaa agaggatgga atctggagca ccgacatact caaggatcaa | 360 |
| aaggaaccca aaataagac atttctgcga tgtgaggcta agaactatag tggccgcttc | 420 |
| acttgttggt ggctgactac catcagcaca gatctcacgt tttcagtaaa aagtagtaga | 480 |
| ggttcaagtg atcctcaagg ggtaacgtgc ggtgctgcaa cactgtctgc tgaacgcgta | 540 |
| agaggagata taaggagta cgagtattcc gtagaatgcc aagaggacag tgcttgtcct | 600 |
| gcggccgagg agtctctccc aatagaagtg atggtggacg cggtgcataa actgaaatat | 660 |
| gagaactaca caagcagttt ttttataaga gatatcatca agcccgatcc gccgaagaat | 720 |
| ttgcaactta aaccgcttaa aaactcacgc caggttgaag tatcctggga gtatcctgat | 780 |
| acatggtcaa caccacacag ctattttcc cttaccttct gtgtgcaggt ccaagggaag | 840 |
| agcaaaaggg agaagaagga cagggtattc actgataaaa cttccgcgac ggtcatctgc | 900 |
| cgaaaaaacg ctagtatatc tgtacgggcg caggataggt actatagttc ttcttggtct | 960 |
| gagtgggcct cagttccgtg ctctggggga ggaagtggag gagggtccgg cggtggaagc | 1020 |
| gggggaggga gtcgcaactt gccagtggct acaccagatc caggcatgtt tccatgtctg | 1080 |
| catcattccc agaatctcct gagagcggtg tcaaatatgc tccaaaaagc gagacaaaca | 1140 |
| ctggaatttt acccgtgtac cagtgaggag attgatcacg aggacataac caaggacaag | 1200 |
| acctcaactg tagaagcgtg tttgccgctg gagttgacta agaatgagtc ctgcctcaat | 1260 |
| tccagagaaa cttcattcat tactaacggc agttgtcttg catcccggaa aacgtccttt | 1320 |
| atgatggccc tttgccttag ttcaatttac gaggatctta aaatgtatca agtggagttt | 1380 |
| aaaaccatga atgctaaact tcttatggac cccaaacgac aaattttct ggatcagaat | 1440 |
| atgcttgccg tgatagacga actcatgcag gcgcttaatt ttaactccga aacagttcca | 1500 |
| caaaaatcta gccttgaaga acctgatttt tataaaacga agattaaact gtgtatcctg | 1560 |
| ctgcatgcct ttcgcatccg agctgtcaca atcgataggg ttatgtccta ccttaacgcg | 1620 |
| agccggcgca agaggggttc cggagaggga agggtagtc tgctcacctg cggcgatgtt | 1680 |
| gaagaaaatc ctggtcccat ggcgcaaagt ctggctcttt cactcctgat cctggtcttg | 1740 |
| gccttcggga ttccgaggac ccaaggaagt gatggtggcg cccaagattg ttgccttaaa | 1800 |
| tacagccagc ggaaaatacc cgcgaaagtg gtcaggagtt atagaaaaca ggagccttcc | 1860 |

```
ctgggttgta gtatccccgc catactttc ctcccgagaa acggagcca ggccgaactg    1920 tgcgctgacc ctaaggaact ttgggtgcaa caacttatgc aacacctgga taagacacct    1980
tctcctcaaa agccagctca gggctgccga aaagatagag gcgcctcaaa aaccggaaaa    2040
aagggcaaag gttctaaagg atgtaagcgg actgaacgct ctcaaacgcc taaagggccg    2100
tag                                                                  2103
```

<210> SEQ ID NO 62
<211> LENGTH: 2109
<212> TYPE: DNA
<213> ORGANISM: Mus sp.

<400> SEQUENCE: 62

```
atgtgtccac agaagctgac aataagttgg tttgccattg tcctcctggt gagcccactc      60
atggcaatgt gggaactcga aaaggatgtc tacgtggtag aagtagattg gactccagac     120
gcgccagggg agacagtgaa tttgacatgt gacacaccag aagaagatga cattacatgg     180
acatctgacc aacgccatgg cgtaataggg agtgggaaaa cactcacgat cacagttaaa     240
gagttcttgg atgctggtca atatacttgc cataaaggcg gcgagacact cagccactca     300
catttgcttt tgcataaaaa agagaatggc atttggagca ctgaaatact taagaacttt     360
aagaacaaga catttctcaa gtgtgaggcc ctaattaca gcggcaggtt cacgtgctca      420
tggctggtcc agcgcaacat ggaccctcaag tttaacataa aatcttcttc ctcttcacct     480
gactccagag ctgttacttg cggcatggct tctctgagcg cagaaaaagt aacgttggat     540
caaagagact acgaaaagta ctctgtttct tgtcaagagg atgttacgtg cccgacggcc     600
gaagaaacgc ttccaattga actcgcgttg gaagctcgcc aacaaaacaa gtatgaaaac     660
tacagtacaa gcttctttat acgggatata attaaacccg atccccccaa gaacttgcaa     720
atgaaaccac ttaagaacag ccaggtggaa gtttcctggg agtatccaga ctcatggagt     780
actcctcaca gctattttc tctgaaattc tttgtaagga tacaacggaa gaaagagaag     840
atgaaagaga ccgaggaggg ttgtaatcag aagggagcgt ttctcgtgga gaaaacgtct     900
accgaagtcc aatgtaaagg tggcaatgtg tgcgtccaag ctcaggatag atactataat     960
tcaagttgct ccaagtgggc ctgtgttcca tgccgcgttc ggagcggggg aggtagcgga    1020
ggaggtagtg ggggtgggtc aggaggaggg agtcgagtta tcccggtgtc aggccccgca    1080
cgctgcttga gccagagtcg caacctcctt aagacaacag atgacatggt gaaaacagca    1140
cgcgaaaagc ttaaacacta ctcttgtacg gcggaggata ttgatcacga ggatattacc    1200
cgagaccaaa ctagcacttt gaaaacctgt ctgccccttg aacttcataa aaatgagagc    1260
tgtctggcta cacgagagac gtcaagtacg actaggggca gctgtctccc gccgcaaaag    1320
acaagcctca tgatgacgct ctgtttgggt tccatttacg aggacttgaa aatgtatcaa    1380
acggagttcc aggctataaa tgcggcgttg cagaaccata accatcaaca aattatactt    1440
gataaaggca tgttggtggc gattgatgaa ctcatgcaga gtctcaatca caacggggaa    1500
acgttgagac agaaaccccc agtcggtgaa gcggacccat atcgagtaaa aatgaagctc    1560
tgcattctgc ttcacgcatt cagcactaga gttgttacca tcaaccgggt aatgggatat    1620
ctctccagtg cgcggcgcaa gaggggttcc ggagagggaa ggggtagtct gctcacctgc    1680
ggcgatgttg aagaaaatcc tggtcccatg gcgcaaatga tgacccttc cctgctgagt    1740 cttgtcctcg cgctctgcat cccgtggacg cagggggctg atgggggggg ccaagactgt    1800
tgcctgaagt attcacaaaa aaagataccg tactctattg tcagagggta caggaagcaa    1860
```

```
gaaccctcct tgggttgccc tataccagca attcttttct ccccacgcaa gcattccaaa    1920
ccagaactgt gtgcgaaccc cgaggagggt tgggtacaga acttgatgcg aaggcttgac    1980
cagcccccag cccctggcaa gcagtcacct gggtgcagaa aaacagagg tacttcaaag     2040 agcggcaaga aaggcaaagg gagtaaagga tgtaaaagaa cggagcagac ccagccttca    2100
cgaggctag                                                           2109
```

<210> SEQ ID NO 63
<211> LENGTH: 2109
<212> TYPE: DNA
<213> ORGANISM: Mus sp.

<400> SEQUENCE: 63

```
atggcgcaaa tgatgaccct ttccctgctg agtcttgtcc tcgcgctctg catcccgtgg     60
acgcaggggt ctgatggggg gggccaagac tgttgcctga agtattcaca aaaaaagata    120
ccgtactcta ttgtcagagg gtacaggaag caagaaccct ccttgggttg ccctatacca    180
gcaattcttt tctccccacg caagcattcc aaaccagaac tgtgtgcgaa ccccgaggag    240
ggttgggtac agaacttgat gcgaaggctt gaccagcccc cagcccctgg caagcagtca    300
cctgggtgca gaaaaacag aggtacttca agagcggca agaaaggcaa agggagtaaa      360
ggatgtaaaa gaacggagca gacccagcct tcacgaggcc ggcgcaagag gggttccgga    420
gagggaaggg gtagtctgct cacctgcggc gatgttgaag aaaatcctgg tcccatgtgt    480
ccacagaagc tgacaataag ttggtttgcc attgtcctcc tggtgagccc actcatggca    540
atgtgggaac tcgaaaagga tgtctacgtg gtagaagtag attggactcc agacgcgcca    600
ggggagacag tgaatttgac atgtgacaca ccagaagaag atgacattac atggacatct    660
gaccaacgcc atggcgtaat agggagtggg aaaacactca cgatcacagt taaagagttc    720
ttggatgctg tcaatatac ttgccataaa ggcggcgaga cactcagcca ctcacatttg     780
cttttgcata aaaagagaa tggcatttgg agcactgaaa tacttaagaa ctttaagaac     840
aagacatttc tcaagtgtga ggcccctaat tacagcggca ggttcacgtg ctcatggctg    900
gtccagcgca acatggacct caagtttaac ataaaatctt cttcctcttc acctgactcc    960
agagctgtta cttgcggcat ggcttctctg agcgcagaaa aagtaacgtt ggatcaaaga   1020
gactacgaaa agtactctgt tcttgtcaa gaggatgtta cgtgcccgac ggccgaagaa    1080
acgcttccaa ttgaactcgc gttggaagct cgccaacaaa acaagtatga aaactacagt   1140
acaagcttct ttatacggga tataattaaa cccgatcccc ccaagaactt gcaaatgaaa   1200
ccacttaaga acagccaggt ggaagtttcc tgggagtatc cagactcatg gagtactcct   1260
cacagctatt tttctctgaa attctttgta aggatacaac ggaagaaaga gaagatgaaa   1320
gagaccgagg agggttgtaa tcagaaggga gcgtttctcg tggagaaaac gtctaccgaa   1380
gtccaatgta aagtggcaa tgtgtgcgtc aagctcagg atagatacta taattcaagt    1440
tgctccaagt gggcctgtgt tccatgccgc gttcggagcg gggaggtag cggaggaggt    1500 agtgggggtg gtcaggagg agggagtcga gttatcccgg tgtcaggccc cgcacgctgc    1560
ttgagccaga gtcgcaacct ccttaagaca acagatgaca tggtgaaaac agcacgcgaa    1620
aagcttaaac actactcttg tacggcggag gatattgatc acgaggatat acccgagac     1680 caaactagca ctttgaaaac ctgtctgccc cttgaacttc ataaaaatga gagctgtctg    1740
gctacacgag agacgtcaag tacgactagg ggcagctgtc tcccgccgca aaagacaagc    1800
```

```
ctcatgatga cgctctgttt gggttccatt tacgaggact tgaaaatgta tcaaacggag      1860
ttccaggcta taaatgcggc gttgcagaac cataaccatc aacaaattat acttgataaa      1920
ggcatgttgg tggcgattga tgaactcatg cagagtctca atcacaacgg ggaaacgttg      1980
agacagaaac ccccagtcgg tgaagcggac ccatatcgag taaaaatgaa gctctgcatt      2040
ctgcttcacg cattcagcac tagagttgtt accatcaacc gggtaatggg atatctctcc      2100
agtgcgtag                                                              2109
```

<210> SEQ ID NO 64
<211> LENGTH: 465
<212> TYPE: DNA
<213> ORGANISM: Mus sp.

<400> SEQUENCE: 64

```
atgtttcatg tgtccttcag gtacatattt ggtatcccac cacttatatt ggtgctcttg       60
cctgtaacca gctctgaatg tcatataaaa gacaaggagg gcaaagcata cgagtccgta      120
ttgatgatct caatcgatga acttgacaag atgacaggga ccgattctaa ttgtccaaat      180
aacgagccaa acttctttcg gaaacacgtg tgtgatgata caaagaagc tgcttttctt       240 aacagagctg ccagaaaact caagcagttc ctcaagatga atatatccga ggaatttaac      300
gtgcatctcc tcacagtatc tcagggaact caaaccttg taaactgcac ttctaaggag       360
gagaagaatg tcaaagagca agagaaaaat gatgcatgtt ttttgaaacg gctgttgagg      420
gagatcaaaa catgctggaa taaaatcctc aagggctcaa tttag                      465
```

<210> SEQ ID NO 65
<211> LENGTH: 1428
<212> TYPE: DNA
<213> ORGANISM: Homo sapiens

<400> SEQUENCE: 65

```
atggaaacag acacattgct gctttgggta ttgttgctct gggtgcctgg atcaacagga       60
aactgggtaa acgtaatttc agatctgaag aagatcgagg accttattca atccatgcac      120
atcgatgcca ctctctacac cgaaagcgac gttcacccat cttgcaaggt gaccgctatg      180
aaatgtgaat tgttggaact tcaggtaatt tctctggaga gcggcgatgc ctcaatacat      240
gacaccgttg aaaatcttat catccttgct aatgattcac tctctagtaa tgggaacgta      300
acagagagcg ggtgtaagga gtgtgaagaa ctggaggaga aaacattaa ggaattttg        360 cagtcattcg tccatatagt gcaaatgttc ataaacactt ccagaagaaa gcgaggctct      420
ggggaggggc gaggctctct gctgacctgt ggggatgtag aagagaatcc aggtcccatg      480
gaccggctga ccagctcatt cctgcttctg attgtgccag cctacgtgct ctccatcaca      540
tgtcctcccc caatgagcgt cgagcatgct gacatctggg tgaagtcata ctccttgtac      600
agcagagaga gatacatttg taattccgga ttcaagcgca aggccggcac ctcctctctg      660
acagagtgcg tccttaacaa agcaaccaac gtagcacatt ggaccacacc atccttgaag      720
tgcatacgag aacctaaatc ttgcgataag actcatactt gtccaccttg ccagccccca      780
gaactgcttg gcggaccctc agtattttg ttcccaccaa agccaaaaga cactcatg         840 atatccagaa ctcctgaggt gacctgtgtc gttgtagacg tttcccacga agatcctgaa      900
gtaaaattca actggtacgt ggatggggtc gaagtccata acgccaagac taaaccaagg      960
gaggaacagt ataactctac ttaccgagta gtttctgtgt tgaccgtgct gcaccaggac     1020
tggttgaacg ggaaggagta caaatgcaag gtgagcaata agctctgcc cgcaccaatc     1080
```

| | | |
|---|---|---|
| gaaaagacaa tatctaaggc caaggggcag ccacgagagc cccaggtata cacactgcca | 1140 |
| ccctcacgcg atgaattgac taagaaccag gtttccctga cctgtcttgt aaaaggtttc | 1200 |
| taccccttccg acatagctgt tgagtgggaa agtaacgggc agccagagaa caattacaag | 1260 |
| acaactccac ccgttcttga tagcgatgga tcattttttc tgtattccaa actcactgtc | 1320 |
| gataaaagtc gctggcagca aggcaatgtt tttagctgct cagtcatgca cgaagcactg | 1380 |
| cataatcact acacacaaaa aagtttgtcc cttagccctg gtaagtag | 1428 |

<210> SEQ ID NO 66
<211> LENGTH: 1080
<212> TYPE: DNA
<213> ORGANISM: Homo sapiens

<400> SEQUENCE: 66

| | | |
|---|---|---|
| atgtactcaa tgcagttggc ctcctgtgta acattgacct tggtcctctt ggtcaacagc | 60 |
| aattggatcg atgtacgcta cgacttggag aagattgagt cccttataca gagtatacac | 120 |
| atagatacaa ccttgtatac tgacagtgac ttccatccca gctgtaaagt gactgcaatg | 180 |
| aactgttttt tgttggagtt gcaagtaatt ctgcatgaat acagcaacat gaccctcaat | 240 |
| gaaaccgtta ggaatgtcct ttatctcgca aattctactc tgagtagcaa taagaatgtt | 300 |
| gccgaaagcg gctgcaagga gtgcgaagaa ctggaggaaa aactttcac cgagtttctc | 360 |
| cagagtttca tcagaattgt ccaaatgttc attaatacaa gtagtggtgg tgggagcggg | 420 |
| ggtggaggca gtggggggagg tgggagcgga ggtggagggt ccggaggggg gagccttcaa | 480 |
| ggcactactt gtcctccacc cgtatccatc gagcacgccg atattcgagt taaaaattat | 540 |
| agtgttaata gcagagaacg atacgtctgc aactcagggt ttaagagaaa ggccggaact | 600 |
| tcaactctca tagaatgcgt gattaataag aatactaacg tcgcacattg gactactccc | 660 |
| agtctcaagt gcatacgcga tccatctctc gctcattact caccagtacc tacagtggtt | 720 |
| actcctaagg tgacctctca gcccgaatca ccatctccca gcgcaaaaga gcctgaggcc | 780 |
| ttttctccta aatcagacac tgctatgact acagaaacag ccataatgcc aggaagccgg | 840 |
| ctgacaccat ctcaaactac cagcgcaggc acaactggga ctggctccca caaaagctca | 900 |
| cgcgcaccaa gtctcgccgc aacaatgaca ttggagccta cagccagcac atctcttaga | 960 |
| atcacagaaa tttctccccca cagtagcaag atgaccaagg tggcaattag taccagcgtc | 1020 |
| cttcttgtag gagctggagt tgtgatggca ttttttggcat ggtatatcaa aagcaggtag | 1080 |

<210> SEQ ID NO 67
<211> LENGTH: 489
<212> TYPE: DNA
<213> ORGANISM: Mus sp.

<400> SEQUENCE: 67

| | | |
|---|---|---|
| atgaagatcc tcaagccata catgcgaaac actagtatta gctgttactt gtgttttctg | 60 |
| ctgaatagtc atttttttgac tgaagcagga atccatgtat ttatactcgg ttgtgtgtct | 120 |
| gtaggtctgc caaagactga ggctaattgg attgacgtgc gctatgatct tgaaaaaata | 180 |
| gagtccttga ttcaatcaat acacatcgat accactctct acaccgacag tgatttccat | 240 |
| ccttcctgca aggtaacagc tatgaattgc ttcctcctgg agctccaagt cattctccat | 300 |
| gagtactcca acatgacttt gaacgaaact gtaagaaacg tattgtatct ggctaatagc | 360 |
| accttgtcta gtaacaaaaa tgtggcagag agcggctgca aagaatgtga agaattggaa | 420 |

| | |
|---|---|
| gagaaaacat tacagagtt cctgcaatcc tttattcgca tcgtccaaat gtttatcaat | 480 |
| acctcttag | 489 |

<210> SEQ ID NO 68
<211> LENGTH: 438
<212> TYPE: DNA
<213> ORGANISM: Mus sp.

<400> SEQUENCE: 68

| | |
|---|---|
| atgtattcca tgcaacttgc cagttgtgta acccttactc tcgtcctgct cgttaattcc | 60 |
| gctggtgcta actggataga tgttcgatac gatctggaaa agattgagtc ccttatccaa | 120 |
| tccattcata tagataccac cctttatact gacagcgact tccatccttc ttgcaaggtg | 180 |
| accgctatga attgtttcct gctggaactc caagttattc tgcatgaata ctctaatatg | 240 |
| acacttaacg agaccgtaag aaatgttctc tatctcgcta atagtacttt gagctcaaat | 300 |
| aagaacgtgg ccgagtctgg gtgtaaggaa tgcgaagagc tggaagaaaa gacattcacc | 360 |
| gagtttctcc agtctttcat acggattgtg cagatgttta tcaacacatc agattacaaa | 420 |
| gacgacgatg ataagtag | 438 |

<210> SEQ ID NO 69
<211> LENGTH: 579
<212> TYPE: DNA
<213> ORGANISM: Mus sp.

<400> SEQUENCE: 69

| | |
|---|---|
| atggcagcca tgtctgagga ctcttgtgtg aactttaaag aaatgatgtt catagacaat | 60 |
| acactctact ttatacctga ggagaatgga gatttggaat ctgacaactt ggcaggctg | 120 |
| cattgcacta ccgcagttat ccgaaacatc aacgatcagg tactgtttgt tgataaaaga | 180 |
| caacctgtat tcgaggacat gaccgacata gatcagtctg cctcagagcc ccagactagg | 240 |
| cttatcatct atatgtacaa ggacagcgaa gtacgaggcc tggctgttac actctcagtc | 300 |
| aaagactcta agatgagcac cctgtcatgc aagaacaaaa ttatcagttt tgaggagatg | 360 |
| gacccacctg aaaacataga tgacattcag tcagacctca tttttttca aaagcgggta | 420 |
| ccaggacaca acaaaatgga atttgaatca tcactctacg aaggacattt ccttgcatgc | 480 |
| cagaaagagg atgacgcatt caaattgatc ctgaaaaaaa aggacgaaaa tggtgataaa | 540 |
| tcagtcatgt ttacattgac caatcttcac caaagttag | 579 |

<210> SEQ ID NO 70
<211> LENGTH: 579
<212> TYPE: DNA
<213> ORGANISM: Mus sp.

<400> SEQUENCE: 70

| | |
|---|---|
| atggctgcaa tgtctgaaga tagctgtgtc aactttaagg agatgatgtt cattgataat | 60 |
| actttgtact ttatacctga agaaaatgga gaccttgagt cagacaactt cgggagactg | 120 |
| cactgcacaa ctgccgttat ccgaaacata aatgatcaag tattgttcgt ggacaaaaga | 180 |
| caaccagtct ttgaggatat gacagacatc gaccaatccg catctgaacc tcagactagg | 240 |
| ctgatcatct atatgtacgc cgactccgaa gtaagaggcc ttgctgtgac acttagtgtt | 300 |
| aaggatagta agatgagcac actgtcctgt aagaataaga ttatatcttt tgaagagatg | 360 |
| gacctcccg agaacataga tgacatccag agcgacttga tcttctttca gaagcgagtg | 420 |
| ccaggccata caagatgga atttgaatca tctctcttatg aaggccattt cctcgcatgt | 480 |

```
caaaaggagg acgatgcctt caagctcatt ctgaaaaaaa aagacgagaa cggtgataag    540
agcgtgatgt tcactctgac aaatctgcac cagtcatag                           579
```

<210> SEQ ID NO 71
<211> LENGTH: 534
<212> TYPE: DNA
<213> ORGANISM: Homo sapiens

<400> SEQUENCE: 71

```
atgtatcgca tgcaactcct gtcctgcatt gctctgagct tggctttggt aaccaactca     60
tacttcggga aactggagag taaactctcc gtaatcagga tcttaatga ccaagtattg    120 tttattgacc agggcaaccg cccgttgttc gaggatatga ctgattctga ctgtcgggat    180
aacgctccga gaactatctt tatcatttca atgtacaagg acagccaacc gcggggtatg    240
gctgtgacaa tcagtgtcaa atgtgagaag atttccacgc tgtcctgcga aacaagata    300 atttctttca aagaaatgaa ccccctgac aatataaagg atacaaagag tgatatcatc    360
ttctttcaga ggtccgtgcc cggccacgat aataagatgc aatttgaaag ttcatcttat    420
gaggggtact ttttggcatg cgagaaagaa agggatctct tcaagttgat cctgaagaag    480
gaggacgaat gggcgaccg ctccatcatg ttcacagtcc agaacgagga ctag            534
```

<210> SEQ ID NO 72
<211> LENGTH: 534
<212> TYPE: DNA
<213> ORGANISM: Homo sapiens

<400> SEQUENCE: 72

```
atgtaccgca tgcagctcct gagttgtatt gccctttccc tcgctctcgt taccaattct     60
tacttcggta agcttgcctc taaactctct gttattagga acttgaacga ccaagtcctt    120
ttcatagacc aagggaacag accactgttt gaagatatga cggatagcga ttgccgagat    180 aatgcccta ggacgatttt tatcattagt atgtatgcgg actctcaacc gagggggatg     240
gccgttacta taagtgtgaa atgcgagaaa atatcaacgc tcagttgtga gaacaaaatc    300
ataagtttca aggagatgaa tccacctgat aacatcaaag cactaagtc tgatattata    360 tttttccaac gaagtgttcc gggacacgat aacaaaatgc aatttgagag ctcctcatac    420
gagggctact tcctcgcgtg tgagaaagaa agggatttgt ttaagcttat cctcaagaaa    480
gaggacgagt gggggatcg gagcataatg tttaccgtac agaatgagga ctag            534
```

<210> SEQ ID NO 73
<211> LENGTH: 441
<212> TYPE: DNA
<213> ORGANISM: Mus sp.

<400> SEQUENCE: 73

```
atggagcgga cactcgtgtg tcttgtcgta attttctcg ggacagtcgc acacaagtcc      60
tcaccccagg gtcctgatcg ccttctcata cgcctccgac atttgatcga cattgtagag    120
cagctcaaaa tttacgagaa tgacctcgat cccgagcttt tgagtgctcc ccaagacgtt    180
aagggtcatt gcgagcacgc agcttttgct tgcttccaga aggccaagtt gaaaccaagc    240
aaccctggta ataataagac tttcatcatc gacttggtcg cccaactccg aaggaggctg    300
cctgcccggc gcgaggaaa aaaacaaaag catatttgcaa agtgtccttc atgtgattca    360
tacgaaaagc ggactcccaa agagttcttg gaaaggttga atggcttct tcagaagatg    420
```

```
attcatcaac atttgtcata g                                          441

<210> SEQ ID NO 74
<211> LENGTH: 564
<212> TYPE: DNA
<213> ORGANISM: Homo sapiens

<400> SEQUENCE: 74
atgaccaaca aatgcctttt gcaaattgcc ctgcttttgt gttttagcac taccgcattg    60
agcatgtcat ataacctcct cggcttcctt cagagatcat caaactttca gtgtcagaaa   120 ctgcttggc aacttaatgg caggctcgaa tattgtctga agatcggat gaatttcgac     180 attccagaag aaataaaaca gcttcaacaa ttccagaaag aggacgccgc cctgactatt   240
tacgagatgc tccagaatat cttcgccatt ttccggcagg acagctcatc cacggggtgg   300
aatgagacta ttgtagaaaa tcttctggct aatgtgtacc atcaaattaa tcacctcaaa   360
acggtgcttg aggaaaaact tgaaaaggaa gatttcacac ggggcaagtt gatgtcctcc   420
ctgcacctta acgatacta cggcaggatt cttcattact tgaaggctaa ggagtatagc    480
cattgcgcgt ggacaattgt acgggtagaa atactgcgaa acttttattt catcaaccgg   540
ctcactggat accttagaaa ttag                                          564

<210> SEQ ID NO 75
<211> LENGTH: 549
<212> TYPE: DNA
<213> ORGANISM: Mus sp.

<400> SEQUENCE: 75
atgaacaatc ggtggatact ccacgccgca tttctcctct gctttagcac gacggccctg    60
tccatcaact acaaacagct tcagttgcag gagcggacta cataaggaa gtgccaggaa   120 ctgctggaac agcttaatgg taaaattaat cttacatacc gagctgactt caaaattcct   180
atggaaatga ccgagaagat gcagaaatcc tacacggcat cgccatcca ggaaatgctc    240 cagaacgtat ttctcgtgtt ccgcaataat ttctcttcta cgggttggaa cgaaaccatt   300
gttgttagac tgcttgacga actgcatcag caaaccgtgt tccttaaaac cgtgcttgag   360
gagaagcagg aggagcgcct gacttgggag atgtctagta ccgcacttca cttgaaatcc   420
tactactggc gcgttcagcg gtatctgaag ctgatgaagt ataactcata cgcctggatg   480
gtagtgcgcg cagagatctt cagaaacttt cttatcatcc ggcgactgac ccgaaacttt   540
cagaattag                                                           549

<210> SEQ ID NO 76
<211> LENGTH: 501
<212> TYPE: DNA
<213> ORGANISM: Homo sapiens

<400> SEQUENCE: 76
atgaagtaca ctagctatat attggccttc cagctttgca tcgtattggg tagcctcgga    60
tgctattgcc aagacccgta tgtcaaagaa gccgaaaatc tcaaaaagta tttcaatgcc   120
ggacactcag acgtcgcgga taacggtaca ctgtttcttg gcatcctgaa aaattggaag   180
gaagagagtg acagaaaaat aatgcagtca caaatagtgt ccttttactt taagctgttc    240
aaaaatttca aggatgacca agtatccag aagagtgttg aaactatcaa agaggacatg    300
aatgtgaaat tctttaacag taataagaag aagcgcgatg acttcgagaa actcactaat   360
tacagcgtaa cggatcttaa cgtccaacgc aaggcaatcc acgagcttat acaggtaatg   420
```

| | |
|---|---:|
| gctgagctta gtcccgcagc caagacaggg aagagaaaaa ggtctcaaat gcttttcgg | 480 |
| ggccggcgag cttcacaata g | 501 |

<210> SEQ ID NO 77
<211> LENGTH: 468
<212> TYPE: DNA
<213> ORGANISM: Mus sp.

<400> SEQUENCE: 77

| | |
|---|---:|
| atgaacgcta cgcattgcat cctcgcactc caattgttcc tcatggctgt gtcagggtgt | 60 |
| tactgtcacg gtactgtcat agaaagcctc gaatccctga ataactattt taacagtagc | 120 |
| ggtatagatg tagaagaaaa gtctctcttt cttgacatct ggaggaattg gcaaaaggat | 180 |
| ggagacatga agattctcca atctcagatt atatcatttt acttgaggct ttttgaggtt | 240 |
| ctgaaggata accaggcgat cagcaataat atcagcgtaa ttgaatctca ccttattaca | 300 |
| acatttttct caaattccaa ggcaaagaaa gatgctttca tgtctatcgc gaaatttgag | 360 |
| gtgaacaatc ctcaggtaca aaggcaagcc tttaacgagc tgattagagt tgtacatcag | 420 |
| ttgttgcccg aaagtagtct tagaaaacgc aaacggagcc gatgctag | 468 |

<210> SEQ ID NO 78
<211> LENGTH: 570
<212> TYPE: DNA
<213> ORGANISM: Mus sp.

<400> SEQUENCE: 78

| | |
|---|---:|
| atggcaaggt tgtgcgcttt tctcatggta ctggctgtgc tctcctattg gcctacttgt | 60 |
| tctctgggat gcgacttgcc acagacccac aatctgcgga ataagagggc tctgactctg | 120 |
| ctggtgcaaa tgagacggct ctctccactt agctgtttga agatagaaa ggatttcggg | 180 |
| ttcccccagg agaaggtgga tgcccagcag atcaagaagg cacaggctat ccccgtcctt | 240 |
| tccgagctga cccagcaaat tttgaacatc tttacaagta aggatagttc agctgcatgg | 300 |
| aataccacac ttttggattc tttttgtaac gatctgcatc agcagctgaa cgatctccag | 360 |
| ggatgcctga tgcagcaagt cggcgtgcaa gaatttccac tcacccagga ggacgctctg | 420 |
| ctcgcagtgc gaaagtattt tcaccgaatt accgtgtacc tccgggagaa aaagcattca | 480 |
| ccctgcgctt gggaagtagt cagggccgaa gtatggagag cccttagtag ctccgctaat | 540 |
| gtactgggcc ggttgcggga agagaaatag | 570 |

<210> SEQ ID NO 79
<211> LENGTH: 405
<212> TYPE: DNA
<213> ORGANISM: Homo sapiens

<400> SEQUENCE: 79

| | |
|---|---:|
| atggcgcaaa gtctggctct ttcactcctg atcctggtct ggccttcgg gattccgagg | 60 |
| acccaaggaa gtgatggtgg cgcccaagat tgttgcctta atacagcca gcggaaaata | 120 |
| cccgcgaaag tggtcaggag ttatagaaaa caggagcctt ccctggggttg tagtatcccc | 180 |
| gccatacttt tcctccgag aaaacggagc caggccgaac tgtgcgctga ccctaaggaa | 240 |
| ctttgggtgc aacaacttat gcaacacctg ataagacac cttctcctca aaagccagct | 300 |
| cagggctgcc gaaagatag aggcgcctca aaaaccggaa aaagggcaa aggttctaaa | 360 |
| ggatgtaagc ggactgaacg ctctcaaacg cctaaagggc cgtag | 405 |

<210> SEQ ID NO 80
<211> LENGTH: 402
<212> TYPE: DNA
<213> ORGANISM: Mus sp.

<400> SEQUENCE: 80

| atggcgcaaa tgatgaccct tccctgctg agtcttgtcc tcgcgctctg catcccgtgg | 60 |
| acgcaggggt ctgatggggg gggccaagac tgttgcctga agtattcaca aaaaaagata | 120 |
| ccgtactcta ttgtcagagg gtacaggaag caagaaccct ccttgggttg ccctatacca | 180 |
| gcaattcttt tctccccacg caagcattcc aaaccagaac tgtgtgcgaa ccccgaggag | 240 |
| ggttgggtac agaacttgat gcgaaggctt gaccagcccc cagcccctgg caagcagtca | 300 |
| cctgggtgca gaaaaaacag aggtacttca agagcggca agaaaggcaa agggagtaaa | 360 |
| ggatgtaaaa gaacggagca gacccagcct tcacgaggct ag | 402 |

<210> SEQ ID NO 81
<211> LENGTH: 309
<212> TYPE: DNA
<213> ORGANISM: Homo sapiens

<400> SEQUENCE: 81

| atggcgcaaa gtctggctct ttcactcctg atcctggtct tggccttcgg gattccgagg | 60 |
| acccaaggaa gtgatggtgg cgcccaagat tgttgcctta aatacagcca gcggaaaata | 120 |
| cccgcgaaag tggtcaggag ttatagaaaa caggagcctt ccctgggttg tagtatcccc | 180 |
| gccatacttt tcctcccgag aaaacggagc caggccgaac tgtgcgctga ccctaaggaa | 240 |
| ctttgggtgc aacaacttat gcaacacctg ataagacac cttctcctca aaagccagct | 300 |
| cagggctag | 309 |

<210> SEQ ID NO 82
<211> LENGTH: 309
<212> TYPE: DNA
<213> ORGANISM: Mus sp.

<400> SEQUENCE: 82

| atggcgcaaa tgatgaccct tccctgctg agtcttgtcc tcgcgctctg catcccgtgg | 60 |
| acgcaggggt ctgatggggg gggccaagac tgttgcctga agtattcaca aaaaaagata | 120 |
| ccgtactcta ttgtcagagg gtacaggaag caagaaccct ccttgggttg ccctatacca | 180 |
| gcaattcttt tctccccacg caagcattcc aaaccagaac tgtgtgcgaa ccccgaggag | 240 |
| ggttgggtac agaacttgat gcgaaggctt gaccagcccc cagcccctgg caagcagtca | 300 |
| cctgggtag | 309 |

<210> SEQ ID NO 83
<211> LENGTH: 327
<212> TYPE: DNA
<213> ORGANISM: Mus sp.

<400> SEQUENCE: 83

| atggcacccc gcgtcacacc cttgcttgct tttctctgc ttgtcctctg gaccttcccc | 60 |
| gctcctaccc ttggaggagc caatgatgcc gaggattgct gcctgagtgt tacacaaagg | 120 |
| ccaataccag ggaatatagt gaaggcattc cggtatctgc tcaatgaaga tgggtgcaga | 180 |
| gtccccgcag ttgtctttac aacattgcga ggttaccagc tttgtgctcc cccagaccag | 240 |
| ccttgggtag atcgcattat tcgccggttg aagaagagct cagcaaagaa taagggcaat | 300 |

| | |
|---|---|
| tccacacgga gaagccccgt ctcctag | 327 |

<210> SEQ ID NO 84
<211> LENGTH: 381
<212> TYPE: DNA
<213> ORGANISM: Mus sp.

<400> SEQUENCE: 84

| | |
|---|---|
| atgaaatcag cagtccttttt cttgctcggg attattttc tggaacaatg tggagtgagg | 60 |
| ggaacactcg taataagaaa cgctcggtgc tcatgcatat caacatcacg gggcactatc | 120 |
| cactacaaat ccctgaagga tctgaagcag ttcgccccaa gccctaactg taacaagacc | 180 |
| gaaattatcg caactctcaa aaatggagat cagacttgtc ttgacccaga ttcagcaaat | 240 |
| gtcaagaagc tgatgaaaga gtgggaaaag aagatttcac aaaaaaaaaa gcaaaaacgc | 300 |
| ggcaagaaac atcaaaagaa catgaaaaac aggaaaccta agactcccca gtcaaggaga | 360 |
| agatcccgca agacaaccta g | 381 |

<210> SEQ ID NO 85
<211> LENGTH: 303
<212> TYPE: DNA
<213> ORGANISM: Mus sp.

<400> SEQUENCE: 85

| | |
|---|---|
| atgaacagaa aagttaccgc tatagcactt gctgccataa tatgggccac cgcagctcaa | 60 |
| gggttcctga tgttcaagca gggccgatgc ctctgcattg ccctggaat gaaggccgtg | 120 |
| aaaatggccg aaatagaaaa agctagtgtc atataccccct ctaacggttg cgataaagtc | 180 |
| gaggttatag tcacaatgaa agctcataaa cgccaacgct gcctcgaccc ccggtctaag | 240 |
| caggctaggc tcataatgca agcaatcgag aagaaaaact ttcttagacg gcaaaacatg | 300 |
| tag | 303 |

<210> SEQ ID NO 86
<211> LENGTH: 297
<212> TYPE: DNA
<213> ORGANISM: Mus sp.

<400> SEQUENCE: 86

| | |
|---|---|
| atgaacccat ctgccgccgt tatttctgt ctgatactcc ttgggctgag tggcacacaa | 60 |
| ggcataccc tcgcccgcac agtccggtgt aattgtatac atattgacga cggccctgtt | 120 |
| agaatgcggg ccatcggtaa gctggagatt ataccagcaa gccttagttg tcccagggtt | 180 |
| gaaatcatag caactatgaa aaaaaacgac gaacaaagat gtttgaatcc cgagagcaag | 240 |
| acaatcaaaa accttatgaa agcatttagt caaaaacgct ctaaacgcgc tccatag | 297 |

<210> SEQ ID NO 87
<211> LENGTH: 297
<212> TYPE: DNA
<213> ORGANISM: Homo sapiens

<400> SEQUENCE: 87

| | |
|---|---|
| atgaatcaga cggcaatcct tatatgctgc cttatattcc ttactctctc agggatacaa | 60 |
| ggggtaccac tttctcggac tgttcgctgc acttgcattt caatatctaa ccaacctgta | 120 |
| aatccgcgga gcctggaaaa attggagatt ataccctgctt ctcaattctg ccctcgggtg | 180 |
| gaaatcatcg ccactatgaa gaagaagggc gagaaaaggt gtctgaatcc agagtcaaag | 240 |

```
gcaatcaaaa acctgctgaa agcggtgtca aggaacggt  ccaagagatc accctag       297
```

<210> SEQ ID NO 88
<211> LENGTH: 534
<212> TYPE: DNA
<213> ORGANISM: Mus sp.

<400> SEQUENCE: 88

```
atgaacagga aagtaacagc cattgcattg gctgccatca tctgggccac cgcagcacag    60
ggttttctga tgtttaagca agggcgctgt ctctgtatag gcccaggcat gaaggccgtg   120
aagatggcag agattgagaa ggcatctgtg atttatcctt ctaacgggtg cgataaagtc   180
gaagttattg tgacaatgaa ggcacacaaa cgccaacggt gtttggaccc acgatctaaa   240
caggcaagat tgattatgca agccatcgag aaaaagaact ttctccgaag gcaaaatatg   300
atcccttttgg ctcggacagt gcggtgtaac tgtattcaca tcgacgatgg gccagtacgg   360
atgagagcaa taggaaagct cgaaatcata cccgcctcat tgtcttgtcc cagggtggaa   420
ataatcgcca ctatgaaaaa gaacgatgaa cagaggtgtc tcaacccaga gagtaagact   480
atcaagaacc ttatgaaggc attcagtcag aagaggtcaa agcgagcacc atag          534
```

<210> SEQ ID NO 89
<211> LENGTH: 345
<212> TYPE: DNA
<213> ORGANISM: Homo sapiens

<400> SEQUENCE: 89

```
atgagacttc tcatattggc gcttctcggg atatgttctc ttacggcata catagttgag    60
ggggtgggat ctgaggttag cgataaacga acttgtgtta gtcttacaac acagaggctt   120
ccagtctcca ggataaaaac atatacgata actgagggat ctctcagagc ggtcatcttc   180
ataacgaaga ggggcctgaa ggtctgtgct gacccacaag cgacttgggt aagggacgtt   240
gtgcggagca tggacaggaa gagcaatact cgcaacaaca tgatccaaac caaacctacg   300
ggcacccaac agtcaaccaa tactgcggta acattgacgg ggtag                    345
```

<210> SEQ ID NO 90
<211> LENGTH: 345
<212> TYPE: DNA
<213> ORGANISM: Mus sp.

<400> SEQUENCE: 90

```
atgcgcctcc ttctgctgac ttttctgggt gtatgttgcc tgacaccctg ggtcgtagaa    60
ggagtaggaa ccgaggttct ggaagagtcc tcatgtgtaa acttgcagac acaacgactc   120
cccgtccaaa aaatcaagac ctatataatc tgggaggggg caatgcgggc cgtcattttc   180
gtgactaaac gaggtctcaa aatctgcgcc gaccccgagg ctaagtgggt gaaggcagcc   240
attaagaccg tggatgggag agccagcacc agaaagaaca tggccgaaac agtacctact   300
ggcgcacagc ggtcaacctc aactgctata accttgacag gatag                   345
```

<210> SEQ ID NO 91
<211> LENGTH: 513
<212> TYPE: DNA
<213> ORGANISM: Unknown
<220> FEATURE:
<223> OTHER INFORMATION: Description of Unknown:
      m_sCD40L #1 sequence

<400> SEQUENCE: 91

```
atggagactg acactctgct tctgtgggtg ttgctgctgt gggtgcctgg cagtacaggc    60
gatatgcaac gaggtgacga ggaccctcaa atcgccgccc atgtagtctc tgaagctaat   120
agcaacgctg catccgtctt gcagtgggca agaaaggct  actatactat gaagtccaac   180
ttggtaatgc ttgaaaacgg caagcagttg actgtcaaga gagagggact ttattacgtc   240
tatacccaag tcacattctg tagcaatcga gaaccctcct cacagaggcc ttttatagtg   300
ggactctggc ttaaaccaag tagcggctct gagcgcatac tgttgaaagc cgcaaacaca   360
cacagctctt cccaactctg cgagcagcaa tccgtgcatc tcggtggagt atttgagctt   420
caagccggtg cctcagtgtt tgtgaacgtc actgaggcct cccaggtcat acatcgagtt   480
gggttcagct ccttcggctt gctcaagctc tag                                 513
```

<210> SEQ ID NO 92
<211> LENGTH: 588
<212> TYPE: DNA
<213> ORGANISM: Unknown
<220> FEATURE:
<223> OTHER INFORMATION: Description of Unknown:
    m_sCD40L #2 sequence

<400> SEQUENCE: 92

```
atggaaactg atacattgct gctctgggtt ttgctgctct gggtgcctgg gagtacaggc    60
gacatgagga ggcagttcga ggatctcgtt aaggatatta cccttaataa ggaggagaag   120
aaagaaaact cttttgagat gcaacgaggg gacgaagatc ctcagatcgc tgctcacgtg   180
gtctctgaag ctaacagcaa cgccgcttct gtcctccagt gggccaagaa aggttattac   240
accatgaaat caaaccttgt aatgcttgaa acgggaaac  agcttacagt gaagagggaa   300
ggtctttact acgtctatac ccaggtaacc ttctgctcaa acagagaacc atcaagccag   360
aggccattca tagtggggct ctggctcaaa ccttccagtg gcagcgagag aatcttgttg   420
aaagctgcta atacacatag tagtagccag cttttgcgagc aacagtcagt ccacctcggg   480
ggggtgtttg agttgcaagc aggggcctca gtattcgtga atgtcactga ggcttcccag   540
gtaattcaca gggtaggctt tagttcattc ggtttgctga agctttag                588
```

<210> SEQ ID NO 93
<211> LENGTH: 849
<212> TYPE: DNA
<213> ORGANISM: Unknown
<220> FEATURE:
<223> OTHER INFORMATION: Description of Unknown:
    m_sCD40L #3 sequence

<400> SEQUENCE: 93

```
atgcgaagaa tgcagcttct gctccttatt gctctgagtc tcgcccttgt caccaactcc    60
ggggacagaa tgaaacaaat cgaggacaaa attgaagaaa tactgagtaa atatatcac   120 atcgaaaacg aaattgcacg cattaagaaa ttgattggcg aacgcaccag tggcggctct   180
ggtggcaccg gaggttcagg cgggaccggg ggctctgaca aagtcgaaga ggaggttaac   240
cttcatgagg actttgtgtt catcaagaag ctgaaacggt gcaataaagg agaaggttct   300
ttgagcctcc ttaattgcga agagatgcga cgacagttcg aggatctggt taaggacatt   360
acacttaata aggaagagaa aaaggagaac tctttcgaaa tgcagcgcgg cgatgaagat   420
ccccagatag ccgcccatgt cgtctctgag gccaactcta acgcagcatc cgtcctccag   480
tgggctaaga aaggatatta tactatgaaa agcaatttgg tcatgctcga aaacggtaaa   540
cagctcactg ttaagagaga aggcctctat tacgtatata ctcaagtaac tttctgttct   600
```

| | |
|---|---:|
| aatagggaac cctcctctca aagaccttt atcgtaggac tctggttgaa accaagtagc | 660 |
| ggtagtgaaa ggattctgct caaagcagct aatactcact ccagcagtca actgtgcgaa | 720 |
| caacaaagcg ttcacctcgg gggcgtcttt gaacttcagg caggtgccag tgttttcgtc | 780 |
| aacgtaacag aagcatccca ggtaattcat cgagtagggt tttctagctt tggtttgctg | 840 |
| aagctgtag | 849 |

<210> SEQ ID NO 94
<211> LENGTH: 2160
<212> TYPE: DNA
<213> ORGANISM: Unknown
<220> FEATURE:
<223> OTHER INFORMATION: Description of Unknown:
    anti-CD40_FGK4.5 sequence

<400> SEQUENCE: 94

| | |
|---|---:|
| atggaaactg atcgcctgtt gctctgggta cttcttctgt gggtgcctgg gtccactggt | 60 |
| gacactgtac ttacacaatc acccgctttg ccgtttctc ctggtgaacg ggtcacaatt | 120 |
| agttgccgag cttccgattc tgtatctact cttatgcatt ggtatcaaca aaaacctggt | 180 |
| cagcagccaa aattgctcat ttatcttgct agtcacttgg agtccggcgt acctgctcga | 240 |
| ttcagcggta gtgggtctgg cacagatttc actttgacca tagatcccgt ggaggccgat | 300 |
| gacactgcaa cctactattg ccagcaatcc tggaacgacc cttggacttt cggcggcggc | 360 |
| accaagctgg aactcaagcg agcagatgct gccccaaccg ttagtatatt cccacccttca | 420 |
| accgaacaac tcgccacagg aggcgctagt gtcgtgtgtc ttatgaacaa tttctatccca | 480 |
| cgagacatta gcgtcaagtg gaaaattgat gggacagaaa ggcgagatgg agttttggat | 540 |
| tcagtaacag accaggattc aaaggattct acctatagca tgagctccac cttgagcctg | 600 |
| accaaagctg attatgaatc tcataacctg tatacttgtg aagtggtgca taagacttct | 660 |
| agctcaccag tggttaaatc ttttaaccgc aacgaatgtc ggcgcaagag gggttccgga | 720 |
| gagggaaggg gtagtctgct cacctgcggc gatgttgaag aaaatcctgg tcccatggac | 780 |
| attcggctct ctttggtatt cctggtactt tttataaagg gggtgcaatg tgaagtccag | 840 |
| ctcgtggaaa gcggtggggg cctggttcag cccggtcgca gccttaaact tagttgcgca | 900 |
| gcatccggat ttacattttc tgactataac atggcctggg ttcgacaggc acccaaaaaa | 960 |
| gggctggagt gggtcgcaac tatcatatac gatggttccc ggacatacta tagagattca | 1020 |
| gtgaaggggc gctttacaat aagcagggac aatgctaagt ctaccttgta tcttcagatg | 1080 |
| gactccctga ggagcgaaga tacagcaaca tattattgtg ctacaaaccg ctggttgctg | 1140 |
| cttcattatt tcgactactg gggtcagggc gtcatggtaa ctgtatcaag cgccgagacc | 1200 |
| acagccccttt ctgtatatcc attggcacca ggtactgctc tgaaatccaa ctcaatggta | 1260 |
| acccttggat gtctggttaa gggttatttt cccgagcccg tcacagttac ttggaactct | 1320 |
| ggggcccttt ctagcggagt ccatacccttt cccgccgttt gcagagtgg tctgtacacc | 1380 |
| cttacctcaa gcgtcacagt tccatctagc acatggagct cccaggcagt aacttgtaat | 1440 |
| gtggcccatc cagcctcctc aactaaggta gataaaaaga tcgttcccag agaatgcaat | 1500 |
| ccatgtggat gcaccgggtc tgaggtcagc agtgtgttca ttttcccacc caagactaaa | 1560 |
| gatgtattga ctattactct tacacccaaa gtaacctgcg tggtggttga tattagtcaa | 1620 |
| aatgatcccg aggtacggtt ctcttggttt atcgacgacg tcgaagtaca tacagctcag | 1680 |
| acacacgctc ccgagaaaca aagcaattcc actcttagga gcgtgtccga gttgccaatc | 1740 |

```
gtacataggg attggcttaa tggcaagacc tttaagtgta aggtcaattc agggcattc      1800 cccgcaccaa tagagaagag tataagcaaa cccgagggga cacccagagg tccacaggtc    1860
tatacaatgg ctcccccaa ggaagagatg acccaaagtc aagtctcaat tacatgtatg     1920
gtgaagggct tttatccacc cgacatatac actgagtgga agatgaatgg acagccccaa    1980
gagaattata aaacactcc ccctaccatg acaccgacg gtcctatttt tctttatagt       2040
aaattgaacg tgaaaagga gacctggcaa caaggcaaca ctttcacctg ctccgttctt     2100
cacgagggcc tgcataatca tcataccgaa aagtctctca gtcattctcc aggtaagtag    2160
```

<210> SEQ ID NO 95
<211> LENGTH: 528
<212> TYPE: DNA
<213> ORGANISM: Homo sapiens

<400> SEQUENCE: 95

```
atggaaacag tacgttgct gttgtgggta cttctccttt gggtccctgg cagcacaggg      60
gacgagaata gtttcgaaat gcagaagggc gaccagaacc cacagatcgc ggctcacgtt    120
atatcagaag caagtagtaa gaccacttcc gtacttcagt gggctgaaaa aggatattac    180
accatgtcca acaatctcgt gacactggag aacggtaaac aacttacggt gaaacgacag    240
ggcctctatt acatctacgc tcaggtgaca ttctgctcaa ataggagggc ttctagtcaa    300
gcgcccttca tcgccagcct gtgcctcaaa tctcccggcc ggttcgaacg aatcctgttg    360
cgagcggcca atacccatag ctcagctaaa ccttgcggcc agcagagtat tcatcttggt    420
ggtgtgtttg aacttcagcc gggagcatct gtgttcgtca acgtaacgga ccctagccaa    480
gtgtctcatg ggacaggttt tacatccttc ggactcctca agttgtag                 528
```

<210> SEQ ID NO 96
<211> LENGTH: 540
<212> TYPE: DNA
<213> ORGANISM: Homo sapiens

<400> SEQUENCE: 96

```
atgacagttc tcgcgccagc ttggagtccc accacatact tgcttttgct tctgcttctg    60
tcctctggcc tgagtgggac ccaagattgt tcctttcaac attccccaat tagttctgat   120
tttgcagtga agattagaga gctctcagac tatctgctgc aagattatcc tgtcacagtc    180
gcttcaaacc tgcaagacga agagctctgc ggtgccttgt ggcggttggt cttggctcaa    240
agatggatgg agagactgaa aaccgtagca ggcagcaaga tgcagggtct cctggaaagg    300
gtgaacacgg aaatccattt tgtgaccaag tgcgcgttcc agccccacc gagttgtctc    360 cggtttgttc aaacgaatat atcccggttg ctccaggaaa cctcagaaca actggtggct    420
ttgaaaccct ggatcacaag acaaaaacttt agtcggtgcc tcgaactcca gtgccaacca   480
gattcttcta cacttccccc cccgtggtcc ccgcgcccgt tggaagcaac ggccccatag    540
```

<210> SEQ ID NO 97
<211> LENGTH: 876
<212> TYPE: DNA
<213> ORGANISM: Homo sapiens

<400> SEQUENCE: 97

```
atggcctgga gtcctctgtt tctgactctt ataactcact gtgccggcag ttgggctata    60
ccccctcatg tacagaagtc tgtaaacaac gacatgattg taaccgacaa taatggcgca   120
```

```
gtgaaattcc cacaactgtg taagttctgt gatgtacggt ttagtacatg cgacaatcaa    180
aaaagctgta tgtctaactg ctctattaca tccatatgtg aaaaacctca ggaggtgtgt    240
gttgccgttt ggcgaaaaaa tgatgagaat atcacactgg agacagtatg tcatgaccct    300
aaactgccat accatgattt catactggag gacgccgcca gtcctaagtg cattatgaaa    360
gagaaaaaga aacccggtga acattctttt atgtgctctt gtagctctga cgagtgtaac    420
gacaacatta tattcagcga ggagtacaat acaagcaacc ccgatatacc acctcacgta    480
caaaaaagtg tcaacaacga tatgattgtt accgacaata acggagctgt taagtttcct    540
cagttgtgca agttctgcga tgtacgattc tctacctgcg acaaccaaaa gtcatgtatg    600
tctaactgtt ccataacctc catctgcgag aagccccagg aagtctgcgt cgccgtgtgg    660
cggaaaaacg acgagaatat cactcttgaa accgtttgtc atgatcctaa actgccctat    720
cacgacttta ttctggaaga tgctgcttcc cctaagtgta tcatgaaaga aaagaagaaa    780
cctggggaga cattctttat gtgttcatgc tcctccgatg agtgtaacga caatatcatc    840
ttctctgagg aatacaacac ttctaaccct gattag                              876

<210> SEQ ID NO 98
<211> LENGTH: 2178
<212> TYPE: DNA
<213> ORGANISM: Homo sapiens

<400> SEQUENCE: 98
atggcctggt cccctctttt tctgaccctc atcacacact gtgcaggctc atgggctgag     60
accgtcttga cccagtcccc aggaactttg tctctgtctc ctggtgaaag agctaccctt    120
agttgtcgag cctctcagtc ccttggttct agctatctcg cttggtacca gcaaaagcca    180
ggccaggccc cacgactgct gatctacgga gcatcttcac gggctcccgg cattcccgat    240
cgattttccg gatctggtag tggtacagat ttcacactga ccatatctcg cctggagccc    300
gaggactttg ctgtttatta ttgtcagcag tacgccgatt ctcctatcac ttttggacag    360
ggaacccgcc tggagattaa gcgcacagta gcagctccat ccgtctttat ctttccacca    420
tcagatgaac agctcaagag tgggaccgca agtgtagtat gcctgctgaa caattttac    480 cctagagagg ccaaagtgca gtggaaggtg gataacgccc tccagagtgg caatagtcaa    540
gaaagtgtta ctgagcaaga tagtaaggac tctacatact tttgagttc tacttgacc    600 ctgtcaaaag cagattatga aaaacataag gtgtatgcat gtgaagttac acaccaaggg    660
ttgtcctctc cagttacaaa atcttttaat agaggagagt gccgccgcaa acgcggtagt    720
ggagaaggtc gaggctcact cttgacctgt ggcgacgtgg aagaaaatcc cggtcctatg    780
gattggactt ggagggtatt tgtcttttg gcagtaacac ctggagctca cccccaagta    840
cagctcgtcc aatctggtgc cgaggttaaa aagcctggaa gttcagtgaa ggtctcttgc    900
aaggcatctg gatacacctt tcatctaac gtcatatcct gggtacggca agcccagga    960 cagggacttg agtggatggg aggggtcatc cccatcgtgg acattgctaa ttacgctcag   1020
cgattcaaag gcgggttac tataactgcc gacgagtcta cctcaactac ctacatggag   1080
ttgtcctctc tccgctccga ggacactgct gtatattact gtgccagcac tctcgggttg   1140
gtgttggatg ccatggacta ttggggacaa ggaaccctgg tgacagttag ctccgcaagc   1200
actaaaggcc cttctgtttt tccccttggca ccttgtagta ggtctacctc tgagtctaca   1260
gcagcacttg gatgcttggt taaggactat tttcccgagc cagttacagt ctcttggaac   1320
agtggtgccc tcacaagtgg ggttcatacc ttccccgcag tcctccagag tagtggcctt   1380
```

| | |
|---|---|
| tacagcctct catcagttgt gactgttcct agttcatcac tcggtactaa gacatataca | 1440 |
| tgtaacgtag accacaagcc aagcaacaca aaagtagaca aacgagtcga atctaagtat | 1500 |
| ggacccctt gtccctcctg tcctgctccc gagttccttg ggggcccttc cgtgttcttg | 1560 |
| tttcctccca agcccaagga taccctcatg atctcacgaa ccccagaggt aacatgtgtg | 1620 |
| gttgttgacg taagtcagga agatcccgaa gtgcaattta attggtacgt ggatggcgtc | 1680 |
| gaagtccata acgctaaaac aaaaccccga gaggaacaat tcaattccac atatcgggtg | 1740 |
| gtgagtgtat tgaccgttct tcaccaagat tggctgaacg gcaaggagta aagtgtaaa | 1800 |
| gtaagcaaca aaggtctgcc aagtagcata gaaaaaacaa tatctaaagc taagggccaa | 1860 |
| ccaagggaac cacaagtata tacattgccc ccctctcagg aagagatgac aaagaatcaa | 1920 |
| gttagcctga cctgtttggt aaaggggttc tatccctcag atatagcagt cgagtgggaa | 1980 |
| tctaacggcc agcccgagaa taattataaa acaacccccc ctgtgttgga ctcagacggc | 2040 |
| agcttctttc tctattcacg gctcactgtt gataagtccc gatggcagga ggggaatgtt | 2100 |
| ttcagctgta gcgtgatgca cgaagctctc cacaaccact atacacagaa aagtttgtct | 2160 |
| ttgtcccttg gaaaatag | 2178 |

<210> SEQ ID NO 99
<211> LENGTH: 1062
<212> TYPE: DNA
<213> ORGANISM: Homo sapiens

<400> SEQUENCE: 99

| | |
|---|---|
| atgagtacat cctttccaga gctggatctg gagaattttg agtatgacga cagtgccgaa | 60 |
| gcctgctacc tcggggacat agtcgcattc gggacaatct ttttgtctgt attttacgcc | 120 |
| ctggtgttta catttggcct ggttggaaat ctgttggtcg tactcgctct caccaattcc | 180 |
| cgaaaaccca aaagtataac agacatatac ctgttgaatc tggcactgag tgaccttttg | 240 |
| ttcgtcgcca ccctt ccttt ttggacacac taccttatca gtcacgaggg gcttcataat | 300 |
| gctatgtgca agctcactac tgccttcttc tttatcggat tcttcggggg tatctttttt | 360 |
| atcacagtta ttagcattga ccgatacctt gccatagtgc tcgcagccaa ctcaatgaac | 420 |
| aaccgcaccg tgcagcatgg agtgactatt tccttgggtg tgtgggccgc tgctatactt | 480 |
| gtcgccagcc ctcaattcat gtttaccaaa aggaaagaca atgagtgcct cggagattac | 540 |
| cctgaggtgt tgcaagaaat gtggcctgta cttcgaaata gcgaagtgaa tatactcggc | 600 |
| tttgctcttc ctctgctcat catgtcattc tgttattttc gaataatcca acattgttc | 660 |
| agctgtaaga accgaaagaa agcccgcgcc gtacgcctga ttctgctcgt tgtgttcgcc | 720 |
| tttttctgt tttggactcc ttacaacata atgatattcc tggagactct caaattctat | 780 |
| aactttttc cctcctgtga tatgaaaagg gaccttagat tggctctcag tgtcactgaa | 840 |
| acagtagcct ttagccattg ttgtctcaac cctttcatat atgcatttgc aggggaaaag | 900 |
| ttccggcggt atctcggaca tttgtatcgg aagtgcttgg ccgtgttgtg tggtcatcct | 960 |
| gtccataccg gattctctcc tgagagtcaa cggagccgcc aagattcaat cctgtccagt | 1020 |
| ttcactcact atacttcaga gggggatggc agccttctgc tc | 1062 |

<210> SEQ ID NO 100
<211> LENGTH: 1458
<212> TYPE: DNA
<213> ORGANISM: Unknown
<220> FEATURE:

<223> OTHER INFORMATION: Description of Unknown:
      Kynureinase #1 sequence

<400> SEQUENCE: 100

```
atggagaccg acactttgtt gctgtgggta cttttgttgt gggtcccagg atctaccggg      60
gatatggaac cctctcctct tgaactgcca gtagacgccg tgcgccgcat tgcagccgag     120
ttgaattgcg atccaacaga tgaacgcgtt gccctgaggc tcgacgaaga ggataaattg     180
tcacatttca ggaactgctt ttacattcca aagatgaggg atcttccatc catagatctt     240
agcctcgtgt ccgaggatga cgatgccata tattttcttg gaacagtct tgggttgcag      300
ccaaaaatgg tacggacata tctcgaagag gagctgaca aatgggctaa atgggtgct      360
tacggccacg acgtgggaaa acgccctgg atagttggcg acgaatctat cgtgagtctt      420
atgaaagata tagttggagc acatgagaaa gaaattgcac tgatgaatgc cttactatc      480
aatctgcatc tcctcttgct ttcattcttt aagcccactc ctaaacgcca caaatactt      540
ttggaagcaa aagcctttcc aagcgaccac tacgctattg agtcacaaat acaactccat     600
ggacttgatg tggaaaagtc tatgcggatg gtaaaaccac gcgaaggcga ggagacccct     660
cgaatggagg acatacttga ggtcatcgaa gaagaaggag atagtatagc agttatcctt     720
ttcagcgggc tgcacttcta cacaggtcaa ctctttaaca ttccagctat tactaaggca     780
ggccacgcta aaggatgctt cgtgggcttt gaccttgcac acgcagtagg aaacgtagag     840
ctccgcttgc acgattgggg cgttgatttc gcctgctggt gttcatataa gtatcttaac     900
tcaggagctg gtgggttggc aggcgcattc gtacacgaga acacgctca taccgtaaag     960
cctgcactgg tagggtggtt cggacacgat ctctctaccc gcttcaatat ggataataaa    1020
ctccagctta tacctggcgc caatggattc aggatctcaa atcctcctat tttgctcgtt    1080
tgcagtttgc acgcatctct tgaggtgttc cagcaggcta ccatgactgc actccgccgg    1140
aagtcaatcc ttttgaccgg atacttggag tatatgctga acattatca ctcaaaagat    1200
aacactgaga ataagggccc catagtaaac attatcactc catctcgggc tgaagagcgc    1260
ggctgccaac tcacattgac tttttccatt cccaagaagt cagtgttcaa agagttggag    1320
aaacggggg ttgtatgtga taagcgggag ccagatggaa tccgcgttgc cccagtcccc     1380
ctctataatt cttttcacga tgtatacaag tttattagac tgctgacaag tatcttggac    1440
tcatctgagc gatcttag                                                  1458
```

<210> SEQ ID NO 101
<211> LENGTH: 1395
<212> TYPE: DNA
<213> ORGANISM: Unknown
<220> FEATURE:
<223> OTHER INFORMATION: Description of Unknown:
      Kynureinase #2 sequence

<400> SEQUENCE: 101

```
atggaaccct ctcctcttga actgccagta gacgccgtgc gccgcattgc agccgagttg      60
aattgcgatc caacagatga acgcgttgcc ctgaggctcg acgaagagga taaattgtca     120
catttcagga actgctttta cattccaaag atgagggat tccatccat agatcttagc       180
ctcgtgtccg aggatgacga tgccatatat tttcttggga cagtcttgg gttgcagcca     240
aaaatggtac ggacatatct cgaagaggag ctgacaaat gggctaaaat gggtgcttac     300
ggccacgacg tgggaaaacg cccctggata gttggcgacg aatctatcgt gagtcttatg     360
aaagatatag ttggagcaca tgagaaagaa attgcactga tgaatgccct tactatcaat     420
```

```
ctgcatctcc tcttgctttc attctttaag cccactccta aacgccacaa aatactttg      480 gaagcaaaag cctttccaag cgaccactac gctattgagt cacaaataca actccatgga      540
cttgatgtgg aaaagtctat gcggatggta aaaccacgcg aaggcgagga gacccttcga      600
atggaggaca tacttgaggt catcgaagaa gaaggagata gtatagcagt tatccttttc      660
agcgggctgc acttctacac aggtcaactc tttaacattc cagctattac taaggcaggc      720
cacgctaaag gatgcttcgt gggctttgac cttcacacg cagtaggaaa cgtagagctc       780
cgcttgcacg attggggcgt tgatttcgcc tgctggtgtt catataagta tcttaactca      840
ggagctggtg gttggcagg cgcattcgta cacgagaaac acgctcatac cgtaaagcct       900
gcactggtag ggtggttcgg acacgatctc tctacccgct tcaatatgga taataaactc      960
cagcttatac ctggcgccaa tggattcagg atctcaaatc ctcctatttt gctcgtttgc     1020
agtttgcacg catctcttga ggtgttccag caggctacca tgactgcact ccgccggaag     1080
tcaatccttt tgaccggata cttggagtat atgctgaaac attatcactc aaaagataac     1140
actgagaata agggccccat agtaaacatt atcactccat ctcgggctga agagcgcggc     1200
tgccaactca cattgacttt ttccattccc aagaagtcag tgttcaaaga gttggagaaa     1260
cggggggttg tatgtgataa gcgggagcca gatggaatcc gcgttgcccc agtccccctc     1320
tataattctt ttcacgatgt atacaagttt attagactgc tgacaagtat cttggactca     1380
tctgagcgat cttag                                                      1395
```

<210> SEQ ID NO 102
<211> LENGTH: 573
<212> TYPE: DNA
<213> ORGANISM: Unknown
<220> FEATURE:
<223> OTHER INFORMATION: Description of Unknown:
      VEGF sequence

<400> SEQUENCE: 102

```
atgaatttct tgctgagctg ggtgcattgg acactcgcat tgttgctgta cttgcaccat       60
gccaagtggt cccaggctgc acccactact gagggcgagc aaaagtctca tgaggtgatt      120
aaatttatgg acgtttacca acgatcatac tgtcggccaa tcgaaaccct cgtagatata      180
ttccaggagt acccagacga gatcgaatac attttcaagc cctcatgtgt cccattgatg      240
cgatgtgctg ggtgctgtaa cgacgaagca cttgaatgtg tccccacctc cgagagtaac      300
atcacaatgc aaataatgag aatcaagccc caccaatccc aacatatcgg tgaaatgtca      360
ttccttcagc attcccgctg cgagtgccgg cctaagaagg accgcaccaa accagagaac      420
cattgtgaac cctgttctga gagacggaag cacttgttcg tacaggaccc tcaaacatgc      480
aagtgcagct gtaagaatac cgactcacgg tgtaaagcta ggcaactgga gcttaatgaa      540
aggacctgcc gatgcgataa acccaggagg taa                                   573
```

<210> SEQ ID NO 103
<211> LENGTH: 426
<212> TYPE: DNA
<213> ORGANISM: Unknown
<220> FEATURE:
<223> OTHER INFORMATION: Description of Unknown:
      GM-CSF sequence

<400> SEQUENCE: 103

```
atgtggttgc agaatttgct cttcctgggg attgtggtct acagcctctc cgcacctacc       60
```

-continued

| | |
|---|---|
| cgctctccta tcacagttac aagaccctgg aaacatgtgg aggccattaa agaagcattg | 120 |
| aatttgttgg acgatatgcc cgtcaccctg aatgaagaag tagaagttgt ttctaatgag | 180 |
| ttcagcttta aaaaattgac ctgtgtgcag acacggctta aaattttga acagggactt | 240 |
| agaggaaact ttactaagct gaaggggca cttaacatga cagcttctta ttatcagacc | 300 |
| tattgtcctc caacacctga aaccgactgt gaaacacagg taaccactta cgccgatttt | 360 |
| attgattctt tgaaaacatt cctcaccgat ataccatttg agtgtaagaa gccaggccaa | 420 |
| aagtag | 426 |

<210> SEQ ID NO 104
<211> LENGTH: 822
<212> TYPE: DNA
<213> ORGANISM: Unknown
<220> FEATURE:
<223> OTHER INFORMATION: Description of Unknown:
    Anti-PD1 sequence

<400> SEQUENCE: 104

| | |
|---|---|
| atggaaactg acacacttct tctgtgggtc ttgctcctgt gggtcccagg ctctactggt | 60 |
| gacagtcctg ataggccatg gaacccacct acctttagtc cagccttgct cgtcgtaacc | 120 |
| gaagggaca cgctacatt cacctgctct tttagcaata cttctgagag ttttcatgta | 180 |
| gtctggcatc gggagagtcc atccggacaa acagatactt tggccgcttt tccagaggat | 240 |
| aggtctcaac ctgggcaaga cgcaaggttt cgagtcacac agcttcctaa cgggagagat | 300 |
| tttcacatgt ctgtagttcg ggcacgccga aatgattctg cacatatgt ttgcggtgtg | 360 |
| atctcacttg ctccaaagat tcaaataaag gagagccttc gcgccgagtt gcgggtgact | 420 |
| gagcgggagc ccaagtcctg cgacaaaacc catacttgtc caccctgtgg cggcgggtca | 480 |
| tccggtggcg ggtctggggg gcaaccaaga gagccacagg tatatactct ccccccagc | 540 |
| agagaagaaa tgacaaaaaa ccaagtgtcc ctgacatgtc tggttaaagg atttatccc | 600 |
| agtgacattg ctgtagaatg ggaatccaat ggtcaacccg agaataacta caaaaccact | 660 |
| cctccagtat tggacagtga cggttccttc ttcctctatt ccaaacttac agtggataaa | 720 |
| tcccgctggc agcagggaa tgtattcagc tgtagtgtca tgcacgaagc tcttcataac | 780 |
| cattatacac agaaatctct ttccctgagc ccaggtaaat ag | 822 |

<210> SEQ ID NO 105
<211> LENGTH: 1116
<212> TYPE: DNA
<213> ORGANISM: Mus sp.

<400> SEQUENCE: 105

| | |
|---|---|
| atggagactg atacactttt gctctgggtt ttgctcttgt gggtaccagg gtctactgga | 60 |
| gatgcacaaa ctcctgcatt caacaagcct aaggtagagc ttcatgtcca tttggacgga | 120 |
| gccataaaac tgaaaccat actctatttc ggcaagaaac ggggtatagc acttcccgct | 180 |
| gataccgtgg aagagttgag aaatatcatt ggcatggaca aacctcttag cctgcctggc | 240 |
| tttcttgcaa agttcgacta ctatatgcca gttatagcag ggtgtagaga agcaataaag | 300 |
| cgaatcgcct atgagttcgt tgagatgaag gctaaagaag gagttgttta cgtggaagtc | 360 |
| cggtactcac ctcatctgct tgctaatagc aaggtggacc caatgccatg gaatcaaact | 420 |
| gaaggtgatg taacccctga cgatgtggtc gatttggtca atcaaggtct ccaagaaggc | 480 |
| gagcaggctt tcggcattaa ggtaagaagt atattgtgct gtatgcgaca tcaaccttca | 540 |

```
tggtccctgg aggtcctcga attgtgcaaa aagtacaatc aaaaaacagt ggtcgcaatg       600
gatctcgctg gagatgagac catagaaggt tcctctcttt tccccggtca tgtcgaagca       660
tatgaagggg ctgtcaaaaa tggtatccac cgcaccgtcc acgcagggga agtagggtcc       720
ccagaagtag tcagggaagc cgttgacatt ttgaaaacag aaagagtcgg gcatggctac       780
catacaatag aggacgaagc cttgtacaat cgacttttga agaaaatat gcacttcgag        840 gtctgtccct ggagttcata tctcaccgga gcatgggacc ccaaaacaac ccacgccgtc       900
gtacgcttca agaatgataa ggcaaactac agtttgaata cagatgatcc actgatattc       960
aagtcaacac ttgacactga ctaccagatg acaaaaaaag atatgggttt caccgaagaa      1020
gagttcaaga gattgaacat taacgcagca aaaagctcct tcctgccaga ggaagagaaa      1080
aaagaattgc ttgaaaggtt gtatcgagaa taccaa                                1116

<210> SEQ ID NO 106
<211> LENGTH: 1056
<212> TYPE: DNA
<213> ORGANISM: Mus sp.

<400> SEQUENCE: 106
atggcacaaa ctccagcttt taataagccc aaagtggaac ttcatgttca tctggatggg        60
gcaattaagc ccgaaactat attgtacttt ggcaaaaaga ggggtattgc cctgccagca       120
gataccgttg aggagcttcg caacatcatt gggatgacaa gcccctctc tctgccaggt       180 tttctcgcta aattcgatta ttatatgcct gttattgctg gttgccggga ggccatcaag       240
aggatagcct acgagtttgt tgagatgaag gccaaagagg gcgtggtgta cgtagaggtc       300
agatacagcc ctcacctgct tgccaacagc aaggtggacc caatgccctg aaccaaacc       360 gagggggatg tcactcccga cgacgttgta gacctcgtaa atcagggcct tcaagagggc       420
gagcaggcat ttggcataaa agtccggtct atactctgct gtatgaggca ccaacccctcc      480 tggtctttgg aggtacttga gttgtgtaag aaatacaatc aaaagactgt agtcgccatg       540
gatcttgcag gcgatgaaac catcgagggt agctccttgt tccctggaca tgttgaagcc       600
tacgaggggg ccgtaaaaaa tgggatacac aggactgtcc acgctggtga agtcggaagc       660
ccagaggtgg taagggaggc agttgacata ctcaagacag agcgggttgg acacggatac       720
cacacaattg aggacgaggc cctgtataac cgcctcctca agagaacat gcattttgag       780 gtgtgtcctt ggtccagcta cctgactggt gcttgggacc ctaaaacaac tcacgccgtg       840
gtccggttca gaacgataa agccaattac tctttgaata ccgacgaccc cctcatattc       900
aaatcaacat tggataccga ctaccaaatg accaaaaagg atatggggtt tactgaagag       960
gagttcaaga ggctcaacat aaatgccgct aaatcctcct ttctccccga ggaagaaaaa      1020
aaagaactcc ttgagcggct gtataggag tatcaa                                 1056

<210> SEQ ID NO 107
<211> LENGTH: 966
<212> TYPE: DNA
<213> ORGANISM: Mus sp.

<400> SEQUENCE: 107
atggaaacag atacactctt gctctgggta ctgcttctgt gggtccccgg ctctactggg        60
gatgaagatg atgtaactac tacagaagaa ctcgctcccg ctcttgtccc cccacccaag       120
ggtacctgcg ccggttggat ggctggcatc ccaggcacatc caggtcacaa cggtacccccc     180 ggaagagatg gtcgggatgg aactcccggc gagaagggcg aaaaagggga tgcagggctt       240
```

```
ctgggaccta aaggtgaaac aggggacgtt ggaatgactg gtgcagaagg gcctcgcggc    300
tttcctggca cccctgggag gaaaggagag cccggagagc tccagagaac tgaacctcgg    360
cctgcactca ctataactac ttcccctaat cttgggaccc gcgagaacaa cgccgatcag    420
gttacacctg taagccatat cgggtgcccc aatactaccc agcaagggag tcccgtgttc    480
gcaaagcttt tggctaaaaa ccaagcatcc ctgtgtaaca ctactcttaa ttggcattca    540
caagacggtg ctggtagctc ttatcttttct caggggctgc ggtacgaaga agataagaag    600
gaattggttg tggattctcc aggactctat tatgtctttc tcgaattgaa gctcagtccc    660
accttcacaa acactggaca caaagtccag ggctgggtaa gtctggtact ccaagcaaag    720
ccccaggttg acgatttcga caatttggca ctcaccgtag agcttttccc atgctccatg    780
gaaaataaac ttgttgatcg gtcatggtca cagctcttgc tgcttaaggc agggcatcgc    840
ctctcagtgg gtctgagagc ttatttgcat ggtgcacaag atgcttacag ggattgggaa    900
ttgtcctacc caaacactac aagtttcggg ttgttccttg tcaaacctga taacccatgg    960
gagtag                                                               966

<210> SEQ ID NO 108
<211> LENGTH: 900
<212> TYPE: DNA
<213> ORGANISM: Mus sp.

<400> SEQUENCE: 108
atggaaactg atacactcct cctgtgggtc cttcttttgt gggtgcccgg atcaaccggc     60
gatggctgga tggcaggcat cccaggacac ccaggacaca acggtactcc aggtcgagac    120
ggtcgggatg ggactcctgg ggagaaaggc gagaagggg acgctggttt gctcggtcct    180 aaggggaaa ccggggatgt aggaatgaca ggggctgaag ggcctcgggg atttcctggg    240
acaccaggca ggaagggtga accagggagg ccctccagc gcaccgagcc acggccagct    300
ctgaccataa caacaagtcc aaacctgggc acacgcgaaa acaatgctga ccaggtgact    360
cctgtaagtc acatcggatg ccctaacact acacaacagg gctctcctgt atttgcaaag    420
cttctcgcaa aaaatcaagc atcactttgt aatacaaccc tgaactggca ttctcaggac    480
ggagcagggt cctcttattt gtctcaaggg ctccgctacg aagaagataa aaaggaattg    540
gttgttgaca gtccaggttt gtattatgtg ttttggaac ttaagctgtc accaaccttc    600
actaacaccg ccacaaggt ccaaggctgg gttagtcttg ttttgcaagc caaacctcaa    660
gtggatgatt ttgacaatct ggctttgact gttgagcttt ttccatgcag tatggagaat    720
aaactggttg atcggtcatg gtcacagctc cttctgctca aggccggaca taggctgagt    780
gtgggacttc gggcctactt gcacggcgcc caggacgcat accgagactg gaactcagc    840 taccctaaca caacttcttt tgggttgttc cttgtcaaac ccgataatcc ttgggaatag    900

<210> SEQ ID NO 109
<211> LENGTH: 870
<212> TYPE: DNA
<213> ORGANISM: Mus sp.

<400> SEQUENCE: 109
atggagactg atactttgct cctgtgggtt cttctcctgt gggttcctgg ttccacaggg     60
gatatgcatg tcaatggcaa ggtagcactc gtgactgggg ctgcacaggg tatcgggaaa    120
gcttttgccg aggccctgtt gctgcatggc gccaaggtcg ctttggtaga ttggaacttg    180
```

| | |
|---|---|
| gaggctggag ttaaatgcaa agctgcactc gacgaacaat ttgagcctca aaaaaccctc | 240 |
| tttgtgcagt gtgacgttgc tgaccaaaag caactcaggg acacattcag gaaggtcgta | 300 |
| gaccatttcg gacgcctcga tatactcgtt aataatgccg gggtaaacaa cgaaaagaac | 360 |
| tgggaacaaa cattgcaaat caacctggta agtgtcatta gcggaactta tctgggtctt | 420 |
| gattatatga gcaagcagaa cggggggcgag gcgggatca ttatcaacat gtcaagtctt | 480 |
| gccggattga tgccagttgc tcagcagcct gtttactgtg ccagcaagca cggtattatt | 540 |
| gggtttaccc ggagtgccgc catggccgca aatcttatga agagtggggt aagactgaat | 600 |
| gttatctgcc caggtttcgt agataccca atcctggaga gcatcgagaa ggaggaaaat | 660 |
| atgggacaat acattgaata taaagatcaa atcaaggcta tgatgaagtt ctacggggtt | 720 |
| ctgcatccat ccacaattgc caacgggctc attaatctga ttgaggacga cgccttgaac | 780 |
| ggagctataa tgaaaatcac agcttccaaa ggcattcact ccaagatta tgatatatca | 840 |
| cccttgcttg tcaaggctcc tctgacaagt | 870 |

<210> SEQ ID NO 110
<211> LENGTH: 807
<212> TYPE: DNA
<213> ORGANISM: Mus sp.

<400> SEQUENCE: 110

| | |
|---|---|
| atgcatgtca atggcaaggt agcactcgtg actggggctg cacagggtat cgggaaagct | 60 |
| tttgccgagg ccctgttgct gcatggcgcc aaggtcgctt tggtagattg aacttggag | 120 |
| gctggagtta aatgcaaagc tgcactcgac gaacaatttg agcctcaaaa acccctcttt | 180 |
| gtgcagtgtg acgttgctga ccaaaagcaa ctcaggaca cattcaggaa ggtcgtagac | 240 |
| catttcggac gcctcgatat actcgttaat aatgccgggg taaacaacga aaagaactgg | 300 |
| gaacaaacat gcaaatcaa cctggtaagt gtcattagcg gaacttatct gggtcttgat | 360 |
| tatatgagca agcagaacgg gggcgaggc gggatcatta tcaacatgtc aagtcttgcc | 420 |
| ggattgatgc cagttgctca gcagcctgtt tactgtgcca gcaagcacgg tattattggg | 480 |
| tttacccgga gtgccgccat ggccgcaaat cttatgaaga gtggggtaag actgaatgtt | 540 |
| atctgcccag gtttcgtaga taccccaatc ctggagagca tcgagaagga ggaaaatatg | 600 |
| ggacaataca ttgaatataa agatcaaatc aaggctatga tgaagttcta cggggttctg | 660 |
| catccatcca caattgccaa cgggctcatt aatctgattg aggacgacgc cttgaacgga | 720 |
| gctataatga aaatcacagc ttccaaaggc attcacttcc aagattatga tatatcaccc | 780 |
| ttgcttgtca aggctcctct gacaagt | 807 |

<210> SEQ ID NO 111
<211> LENGTH: 6029
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 111

| | |
|---|---|
| acgcgtgtag tcttatgcaa tactcttgta gtcttgcaac atggtaacga tgagttagca | 60 |
| acatgcctta caaggagaga aaagcaccg tgcatgccga ttggtggaag taaggtggta | 120 |
| cgatcgtgcc ttattaggaa ggcaacagac gggtctgaca tggattggac gaaccactga | 180 |
| attgccgcat tgcagagata ttgtatttaa gtgcctagct cgatacaata aacgggtctc | 240 |

```
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agacccttt  agtcagtgtg aaaatctct  agcagtggcg    420 cccgaacagg gacctgaaag cgaaagggaa accagagctc tctcgacgca ggactcggct    480
tgctgaagcg cgcacggcaa gaggcgaggg gcggcgactg gtgagtacgc caaaaatttt    540
gactagcgga ggctagaagg agagagatgg gtgcgagagc gtcagtatta agcggggggag   600 aattagatcg cgatgggaaa aaattcggtt aaggccaggg ggaagaaaaa aatataaatt    660
aaaacatata gtatgggcaa gcaggagct  agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata aagtagtaaa aattgaacca ttaggagtag    1020
cacccaccaa ggcaaagaga agagtggtgc agagagaaaa aagagcagtg ggaataggag    1080
ctttgttcct tgggttcttg ggagcagcag gaagcactat gggcgcagcc tcaatgacgc    1140
tgacggtaca ggccagacaa ttattgtctg gtatagtgca gcagcagaac aatttgctga    1200
gggctattga ggcgcaacag catctgttgc aactcacagt ctggggcatc aagcagctcc    1260
aggcaagaat cctggctgtg gaaagatacc taaaggatca acagctcctg gggatttggg    1320
gttgctctgg aaaactcatt tgcaccactg ctgtgccttg gaatgctagt tggagtaata    1380
aatctctgga acagattgga atcacgcac  ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620 agttttgct  gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcggtt    1800 aactttttaaa agaaaagggg ggattggggg gtacagtgca ggggaaagaa tagtagacat    1860
aatagcaaca gacatacaaa ctaaagaatt acaaaaacaa attacaaaaa tcaaaatttt    1920
atctcgacat ggtggcgacc ggtagcgcta gcggatcgat aagcttgata tcgcctgcag    1980
ccgaattcct tgacttggga tccgcgtcaa gtggagcaag gcaggtggac agtcctgcag    2040
gcatgcgtga ctgactgagg ccgcgactct agtttaaact gcgtgactga ctctagaaga    2100
tccggcagtg cggccgcgtc gacaatcaac ctctggatta caaaatttgt gaaagattga    2160
ctggtattct taactatgtt gctccttta  cgctatgtgg atacgctgct ttaatgcctt    2220
tgtatcatgc tattgcttcc cgtatggctt tcattttctc ctccttgtat aaatcctggt    2280
tgctgtctct ttatgaggag ttgtggcccg ttgtcaggca acgtggcgtg gtgtgcactg    2340
tgtttgctga cgcaacccc  actggttggg gcattgccac cacctgtcag ctcctttccg    2400
ggactttcgc tttcccctc  cctattgcca cggcggaact catcgccgcc tgccttgccc    2460
gctgctggac agggggctcgg ctgttgggca ctgacaattc cgtggtgttg tcggggaaat    2520
catcgtcctt tccttggctg ctcgcctgtg ttgccacctg gattctgcgc gggacgtcct    2580
tctgctacgt cccttcggcc ctcaatccag cggaccttcc ttcccgcggc ctgctgccgg    2640
```

```
ctctgcggcc tcttccgcgt cttcgccttc gccctcagac gagtcggatc tcccttgggg    2700
ccgcctcccc gcctggtacc tttaagacca atgacttaca aggcagctgt agatcttagc    2760
cacttttaa aagaaaaggg gggactggaa gggctaattc actcccaacg aaaataagat     2820
ctgcttttg cttgtactgg gtctctctgg ttagaccaga tctgagcctg ggagctctct     2880
ggctaactag ggaacccact gcttaagcct caataaagct tgccttgagt gcttcaagta    2940
gtgtgtgccc gtctgttgtg tgactctggt aactagagat ccctcagacc cttttagtca    3000
gtgtggaaaa tctctagcag tagtagttca tgtcatctta ttattcagta tttataactt    3060
gcaaagaaat gaatatcaga gagtgagagg aacttgttta ttgcagctta taatggttac    3120
aaataaagca atagcatcac aaatttcaca aataaagcat tttttcact gcattctagt     3180
tgtggtttgt ccaaactcat caatgtatct tatcatgtct ggctctagct atcccgcccc    3240
taactccgcc cagttccgcc cattctccgc cccatggctg actaattttt tttatttatg    3300
cagaggccga ggccgcctcg gcctctgagc tattccagaa gtagtgagga ggcttttttg    3360
gaggcctaga cttttgcaga gacggcccaa attcgtaatc atggtcatag ctgtttcctg    3420
tgtgaaattg ttatccgctc acaattccac acaacatacg agccgaagc ataaagtgta     3480
aagcctgggg tgcctaatga gtgagctaac tcacattaat tgcgttgcgc tcactgcccg    3540
ctttccagtc gggaaacctg tcgtgccagc tgcattaatg aatcggccaa cgcgcgggga    3600
gaggcggttt gcgtattggg cgctcttccg cttcctcgct cactgactcg ctgcgctcgg    3660
tcgttcggct gcggcgagcg gtatcagctc actcaaaggc ggtaatacgg ttatccacag    3720
aatcaggga taacgcagga aagaacatgt gagcaaaagg ccagcaaaag gccaggaacc     3780
gtaaaaaggc cgcgttgctg gcgtttttcc ataggctccg ccccctgac gagcatcaca     3840
aaaatcgacg ctcaagtcag aggtggcgaa acccgacagg actataaaga taccaggcgt    3900
ttccccctgg aagctccctc gtgcgctctc ctgttccgac cctgccgctt accggatacc    3960
tgtccgcctt tctcccttcg ggaagcgtgg cgctttctca gctcacgc tgtaggtatc      4020
tcagttcggt gtaggtcgtt cgctccaagc tgggctgtgt gcacgaaccc ccgttcagc     4080
ccgaccgctg cgccttatcc ggtaactatc gtcttgagtc aacccggta agacacgact     4140
tatcgccact ggcagcagcc actggtaaca ggattagcag agcgaggtat gtaggcggtg    4200
ctacagagtt cttgaagtgg tggcctaact acggctacac tagaaggaca gtatttggta    4260
tctgcgctct gctgaagcca gttaccttcg gaaaagagt tggtagctct tgatccggca     4320
aacaaaccac cgctggtagc ggtggttttt tgtttgcaa gcagcagatt acgcgcagaa     4380
aaaaaggatc tcaagaagat cctttgatct tttctacggg gtctgacgct cagtggaacg    4440
aaaactcacg ttaagggatt ttggtcatga gattatcaaa aaggatcttc acctagatcc    4500
ttttaaatta aaaatgaagt tttaaatcaa tctaaagtat atatgagtaa acttggtctg    4560
acagttacca atgcttaatc agtgaggcac ctatctcagc gatctgtcta tttcgttcat    4620
ccatagttgc ctgactcccc gtcgtgtaga taactacgat acgggagggc ttaccatctg    4680
gccccagtgc tgcaatgata ccgcgagacc cacgctcacc ggctccagat ttatcagcaa    4740
taaaccagcc agccggaagg gccgagcgca gaagtggtcc tgcaacttta tccgcctcca    4800
tccagtctat taattgttgc cgggaagcta gagtaagtag ttcgccagtt aatagtttgc    4860
gcaacgttgt tgccattgct acaggcatcg tggtgtcacg ctcgtcgttt ggtatggctt    4920
cattcagctc cggttcccaa cgatcaaggc gagttacatg atccccatg ttgtgcaaaa     4980
```

```
aagcggttag ctccttcggt cctccgatcg ttgtcagaag taagttggcc gcagtgttat    5040
cactcatggt tatggcagca ctgcataatt ctcttactgt catgccatcc gtaagatgct    5100
tttctgtgac tggtgagtac tcaaccaagt cattctgaga atagtgtatg cggcgaccga    5160
gttgctcttg cccggcgtca atacgggata ataccgcgcc acatagcaga actttaaaag    5220
tgctcatcat tggaaaacgt tcttcggggc gaaaactctc aaggatctta ccgctgttga    5280
gatccagttc gatgtaaccc actcgtgcac ccaactgatc ttcagcatct tttactttca    5340
ccagcgtttc tgggtgagca aaaacaggaa ggcaaaatgc cgcaaaaaag ggaataaggg    5400
cgacacggaa atgttgaata ctcatactct ccttttttca atattattga agcatttatc    5460
agggttattg tctcatgagc ggatacatat ttgaatgtat ttagaaaaat aaacaaatag    5520
gggttccgcg cacatttccc cgaaaagtgc cacctgacgt ctaagaaacc attattatca    5580
tgacattaac ctataaaaat aggcgtatca cgaggccctt tcgtctcgcg cgtttcggtg    5640
atgacggtga aaacctctga cacatgcagc tcccggagac ggtcacagct tgtctgtaag    5700
cggatgccgg gagcagacaa gcccgtcagg gcgcgtcagc gggtgttggc gggtgtcggg    5760
gctggcttaa ctatgcggca tcagagcaga ttgtactgag agtgcaccat atgcggtgtg    5820
aaataccgca cagatgcgta aggagaaaat accgcatcag cgccattcg ccattcaggc    5880 tgcgcaactg ttgggaaggg cgatcggtgc gggcctcttc gctattacgc cagctggcga    5940 aaggggatg tgctgcaagg cgattaagtt gggtaacgcc agggttttcc cagtcacgac    6000
gttgtaaaac gacggccagt gccaagctg                                      6029
```

<210> SEQ ID NO 112
<211> LENGTH: 22
<212> TYPE: PRT
<213> ORGANISM: Homo sapiens

<400> SEQUENCE: 112

Met Cys His Gln Gln Leu Val Ile Ser Trp Phe Ser Leu Val Phe Leu
1               5                   10                  15

Ala Ser Pro Leu Val Ala
            20

<210> SEQ ID NO 113
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Met Gln Leu Leu Ser Cys Ile Ala Leu Ile Leu Ala Leu Val
1               5                   10

<210> SEQ ID NO 114
<211> LENGTH: 20
<212> TYPE: PRT
<213> ORGANISM: Homo sapiens

<400> SEQUENCE: 114

Met Tyr Arg Met Gln Leu Leu Ser Cys Ile Ala Leu Ser Leu Ala Leu
1               5                   10                  15

Val Thr Asn Ser
            20

```
<210> SEQ ID NO 115
<211> LENGTH: 15
<212> TYPE: PRT
<213> ORGANISM: Homo sapiens

<400> SEQUENCE: 115

Met Asn Leu Leu Leu Ile Leu Thr Phe Val Ala Ala Val Ala
1               5                   10                  15

<210> SEQ ID NO 116
<211> LENGTH: 17
<212> TYPE: PRT
<213> ORGANISM: Unknown
<220> FEATURE:
<223> OTHER INFORMATION: Description of Unknown:
      Gaussia Luciferase sequence

<400> SEQUENCE: 116

Met Gly Val Lys Val Leu Phe Ala Leu Ile Cys Ile Ala Val Ala Glu
1               5                   10                  15
Ala

<210> SEQ ID NO 117
<211> LENGTH: 24
<212> TYPE: PRT
<213> ORGANISM: Homo sapiens

<400> SEQUENCE: 117

Met Pro Met Gly Ser Leu Gln Pro Leu Ala Thr Leu Tyr Leu Leu Gly
1               5                   10                  15
Met Leu Val Ala Ser Cys Leu Gly
            20

<210> SEQ ID NO 118
<211> LENGTH: 21
<212> TYPE: PRT
<213> ORGANISM: Mus sp.

<400> SEQUENCE: 118

Met Glu Thr Asp Thr Leu Leu Leu Trp Val Leu Leu Leu Trp Val Pro
1               5                   10                  15
Gly Ser Thr Gly Asp
            20

<210> SEQ ID NO 119
<211> LENGTH: 22
<212> TYPE: PRT
<213> ORGANISM: Homo sapiens

<400> SEQUENCE: 119

Met Asp Met Arg Val Pro Ala Gln Leu Leu Gly Leu Leu Leu Leu Trp
1               5                   10                  15
Leu Arg Gly Ala Arg Cys
            20

<210> SEQ ID NO 120
<211> LENGTH: 16
<212> TYPE: PRT
<213> ORGANISM: Unknown
<220> FEATURE:
<223> OTHER INFORMATION: Description of Unknown:
      VSV-G sequence

<400> SEQUENCE: 120
```

Met Lys Cys Leu Leu Tyr Leu Ala Phe Leu Phe Ile Gly Val Asn Cys
1               5                   10                  15

<210> SEQ ID NO 121
<211> LENGTH: 28
<212> TYPE: PRT
<213> ORGANISM: Homo sapiens

<400> SEQUENCE: 121

Met Asn Ile Lys Gly Ser Pro Trp Lys Gly Ser Leu Leu Leu Leu
1               5                   10                  15

Val Ser Asn Leu Leu Cys Gln Ser Val Ala Pro
            20                  25

<210> SEQ ID NO 122
<211> LENGTH: 18
<212> TYPE: PRT
<213> ORGANISM: Homo sapiens

<400> SEQUENCE: 122

Met Lys Trp Val Thr Phe Ile Ser Leu Leu Phe Leu Phe Ser Ser Ala
1               5                   10                  15

Tyr Ser

<210> SEQ ID NO 123
<211> LENGTH: 19
<212> TYPE: PRT
<213> ORGANISM: Homo sapiens

<400> SEQUENCE: 123

Met Thr Arg Leu Thr Val Leu Ala Leu Leu Ala Gly Leu Leu Ala Ser
1               5                   10                  15

Ser Arg Ala

<210> SEQ ID NO 124
<211> LENGTH: 17
<212> TYPE: PRT
<213> ORGANISM: Homo sapiens

<400> SEQUENCE: 124

Met Arg Ala Trp Ile Phe Phe Leu Leu Cys Leu Ala Gly Arg Ala Leu
1               5                   10                  15

Ala

<210> SEQ ID NO 125
<211> LENGTH: 16
<212> TYPE: PRT
<213> ORGANISM: Homo sapiens

<400> SEQUENCE: 125

Met Pro Leu Leu Leu Leu Leu Pro Leu Leu Trp Ala Gly Ala Leu Ala
1               5                   10                  15

<210> SEQ ID NO 126
<211> LENGTH: 29
<212> TYPE: PRT
<213> ORGANISM: Homo sapiens

<400> SEQUENCE: 126

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro 20              25

<210> SEQ ID NO 127
<211> LENGTH: 20
<212> TYPE: PRT
<213> ORGANISM: Homo sapiens

<400> SEQUENCE: 127

Met Thr Ser Lys Leu Ala Val Ala Leu Leu Ala Ala Phe Leu Ile Ser
1               5                   10                  15

Ala Ala Leu Cys
            20

<210> SEQ ID NO 128
<211> LENGTH: 23
<212> TYPE: PRT
<213> ORGANISM: Homo sapiens

<400> SEQUENCE: 128

Met Lys Val Ser Ala Ala Leu Leu Cys Leu Leu Leu Ile Ala Ala Thr
1               5                   10                  15

Phe Ile Pro Gln Gly Leu Ala
            20

<210> SEQ ID NO 129
<211> LENGTH: 26
<212> TYPE: PRT
<213> ORGANISM: Homo sapiens

<400> SEQUENCE: 129

Met Gly Ala Ala Ala Arg Thr Leu Arg Leu Ala Leu Gly Leu Leu Leu
1               5                   10                  15

Leu Ala Thr Leu Leu Arg Pro Ala Asp Ala
            20                  25

<210> SEQ ID NO 130
<211> LENGTH: 21
<212> TYPE: PRT
<213> ORGANISM: Homo sapiens

<400> SEQUENCE: 130

Met Ser Pro Leu Leu Arg Arg Leu Leu Leu Ala Ala Leu Leu Gln Leu
1               5                   10                  15

Ala Pro Ala Gln Ala
            20

<210> SEQ ID NO 131
<211> LENGTH: 21
<212> TYPE: PRT
<213> ORGANISM: Homo sapiens

<400> SEQUENCE: 131

Met Asn Asn Leu Leu Cys Cys Ala Leu Val Phe Leu Asp Ile Ser Ile
1               5                   10                  15

Lys Trp Thr Thr Gln
            20

<210> SEQ ID NO 132
<211> LENGTH: 23
<212> TYPE: PRT
<213> ORGANISM: Homo sapiens

<400> SEQUENCE: 132

Met Gln Met Ser Pro Ala Leu Thr Cys Leu Val Leu Gly Leu Ala Leu
1               5                   10                  15

Val Phe Gly Glu Gly Ser Ala
            20

<210> SEQ ID NO 133
<211> LENGTH: 34
<212> TYPE: PRT
<213> ORGANISM: Homo sapiens

<400> SEQUENCE: 133

Met Ala Arg Ala Ala Leu Ser Ala Ala Pro Ser Asn Pro Arg Leu Leu
1               5                   10                  15

Arg Val Ala Leu Leu Leu Leu Leu Val Ala Ala Gly Arg Arg Ala
            20                  25                  30

Ala Gly

<210> SEQ ID NO 134
<211> LENGTH: 21
<212> TYPE: PRT
<213> ORGANISM: Homo sapiens

<400> SEQUENCE: 134

Met Asn Ala Lys Val Val Val Leu Val Leu Val Leu Thr Ala Leu
1               5                   10                  15

Cys Leu Ser Asp Gly
            20

<210> SEQ ID NO 135
<211> LENGTH: 22
<212> TYPE: PRT
<213> ORGANISM: Homo sapiens

<400> SEQUENCE: 135

Met Glu Arg Ile Val Ile Cys Leu Met Val Ile Phe Leu Gly Thr Leu
1               5                   10                  15

Val His Lys Ser Ser Ser
            20

<210> SEQ ID NO 136
<211> LENGTH: 1557
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
atttgggaac tgaagaagga cgtctacgtg gtcgagctgg attggtaccc ggacgcccct      60
ggagaaatgg tcgtgctgac ttgcgatacg ccagaagagg acggcataac ctggaccctg     120
gatcagagct ccgaggtgct cggaagcgga aagaccctga ccattcaagt caaggagttc     180
ggcgacgcgg gccagtacac ttgccacaag ggtggcgaag tgctgtccca ctccctgctg     240
ctgctgcaca agaaagagga tggaatctgg tccactgaca tcctcaagga ccaaaaagaa     300
ccgaagaaca gaccttcct ccgctgcgaa gccaagaact acagcggtcg gttcacctgt      360
tggtggctga cgacaatctc caccgacctg actttctccg tgaagtcgtc acggggatca     420
agcgatcctc agggcgtgac ctgtggagcc gccactctgt ccgccgagag agtcaggga     480 gacaacaagg aatatgagta ctccgtggaa tgccaggagg acagcgcctg ccctgccgcg     540

```
gaagagtccc tgcctatcga ggtcatggtc gatgccgtgc ataagctgaa atacgagaac    600
tacacttcct ccttctttat ccgcgacatc atcaagcctg accccccaa gaacttgcag     660 ctgaagccac tcaagaactc ccgccaagtg aagtgtctt gggaatatcc agacacttgg    720
agcaccccgc actcatactt ctcgctcact ttctgtgtgc aagtgcaggg aaagtccaaa    780
cgggagaaga aagaccgggt gttcaccgac aaaacctccg ccactgtgat tgtcggaag     840 aacgcgtcaa tcagcgtccg ggcgcaggat agatactact cgtcctcctg gagcgaatgg    900
gccagcgtgc cttgttccgg tggcggatca ggcggaggtt caggaggagg ctccggagga    960
ggttcccgga acctccctgt ggcaacccc gaccctggaa tgttcccgtg cctacaccac    1020
tcccaaaacc tcctgagggc tgtgtcgaac atgttgcaga aggcccgcca gaccttgag    1080 ttctacccct gcacctcgga agaaattgat cacgaggaca tcaccaagga caagacctcg    1140
accgtggaag cctgcctgcc gctggaactg accaagaacg aatcgtgtct gaactcccgc    1200
gagacaagct ttatcactaa cggcagctgc ctggcgtcga aaagacctc attcatgatg    1260 gcgctctgtc tttcctcgat ctacgaagat ctgaagatgt atcaggtcga gttcaagacc    1320
atgaacgcca agctgctcat ggacccgaag cggcagatct tcctggacca gaatatgctc    1380
gccgtgattg atgaactgat gcaggccctg aatttcaact ccgagactgt gcctcaaaag    1440
tccagcctgg aagaaccgga cttctacaag accaagatca agctgtgcat cctgttgcac    1500
gctttccgca ttcgagccgt gaccattgac cgcgtgatgt cctacctgaa cgccagt      1557
```

<210> SEQ ID NO 137
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175
```

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Ser Gly Gly Gly Ser Gly Gly Gly Ser Gly Gly Gly
305                 310                 315                 320

Gly Ser Arg Asn Leu Pro Val Ala Thr Pro Asp Pro Gly Met Phe Pro
                325                 330                 335

Cys Leu His His Ser Gln Asn Leu Leu Arg Ala Val Ser Asn Met Leu
            340                 345                 350

Gln Lys Ala Arg Gln Thr Leu Glu Phe Tyr Pro Cys Thr Ser Glu Glu
        355                 360                 365

Ile Asp His Glu Asp Ile Thr Lys Asp Lys Thr Ser Thr Val Glu Ala
    370                 375                 380

Cys Leu Pro Leu Glu Leu Thr Lys Asn Glu Ser Cys Leu Asn Ser Arg
385                 390                 395                 400

Glu Thr Ser Phe Ile Thr Asn Gly Ser Cys Leu Ala Ser Arg Lys Thr
                405                 410                 415

Ser Phe Met Met Ala Leu Cys Leu Ser Ser Ile Tyr Glu Asp Leu Lys
            420                 425                 430

Met Tyr Gln Val Glu Phe Lys Thr Met Asn Ala Lys Leu Leu Met Asp
        435                 440                 445

Pro Lys Arg Gln Ile Phe Leu Asp Gln Asn Met Leu Ala Val Ile Asp
    450                 455                 460

Glu Leu Met Gln Ala Leu Asn Phe Asn Ser Glu Thr Val Pro Gln Lys
465                 470                 475                 480

Ser Ser Leu Glu Glu Pro Asp Phe Tyr Lys Thr Lys Ile Lys Leu Cys
                485                 490                 495

Ile Leu Leu His Ala Phe Arg Ile Arg Ala Val Thr Ile Asp Arg Val
            500                 505                 510

Met Ser Tyr Leu Asn Ala Ser
        515

<210> SEQ ID NO 138
<211> LENGTH: 541
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Met Cys His Gln Gln Leu Val Ile Ser Trp Phe Ser Leu Val Phe Leu
1               5                   10                  15

```
Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Ser Gly Gly Gly Ser
                325                 330                 335

Gly Gly Gly Ser Gly Gly Ser Arg Asn Leu Pro Val Ala Thr Pro
            340                 345                 350

Asp Pro Gly Met Phe Pro Cys Leu His His Ser Gln Asn Leu Leu Arg
        355                 360                 365

Ala Val Ser Asn Met Leu Gln Lys Ala Arg Gln Thr Leu Glu Phe Tyr
    370                 375                 380

Pro Cys Thr Ser Glu Glu Ile Asp His Glu Asp Ile Thr Lys Asp Lys
385                 390                 395                 400

Thr Ser Thr Val Glu Ala Cys Leu Pro Leu Glu Leu Thr Lys Asn Glu
                405                 410                 415

Ser Cys Leu Asn Ser Arg Glu Thr Ser Phe Ile Thr Asn Gly Ser Cys
            420                 425                 430
```

```
Leu Ala Ser Arg Lys Thr Ser Phe Met Met Ala Leu Cys Leu Ser Ser
            435                 440                 445

Ile Tyr Glu Asp Leu Lys Met Tyr Gln Val Glu Phe Lys Thr Met Asn
    450                 455                 460

Ala Lys Leu Leu Met Asp Pro Lys Arg Gln Ile Phe Leu Asp Gln Asn
465                 470                 475                 480

Met Leu Ala Val Ile Asp Glu Leu Met Gln Ala Leu Asn Phe Asn Ser
                485                 490                 495

Glu Thr Val Pro Gln Lys Ser Ser Leu Glu Pro Asp Phe Tyr Lys
                500                 505                 510

Thr Lys Ile Lys Leu Cys Ile Leu Leu His Ala Phe Arg Ile Arg Ala
            515                 520                 525

Val Thr Ile Asp Arg Val Met Ser Tyr Leu Asn Ala Ser
            530                 535                 540

<210> SEQ ID NO 139
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
agacggaaac gcggaagcgg agagggcaga ggctcgctgc ttacatgcgg ggacgtggaa      60
gagaaccccg gtccg                                                       75

<210> SEQ ID NO 140
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Arg Arg Lys Arg Gly Ser Gly Glu Gly Arg Gly Ser Leu Leu Thr Cys
1               5                   10                  15

Gly Asp Val Glu Glu Asn Pro Gly Pro
            20                  25

<210> SEQ ID NO 141
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
cagggacagg acaggcacat gattagaatg cgccagctca tcgatatcgt ggaccagttg      60
aagaactacg tgaacgacct ggtgcccgag ttcctgccgg cccccgaaga gtgtggaaacc    120 aattgcgaat ggtcggcatt ttcctgcttt caaaaggcac agctcaagtc cgctaacacc    180
gggaacaacg aacggatcat caacgtgtcc atcaaaaagc tgaagcggaa gcctcccctcc   240 accaacgccg acggaggca gaagcatagg ctgacttgcc cgtcatgcga ctcctacgag     300
aagaagccgc cgaaggagtt cctggagcgg ttcaagtcgc tcctgcaaaa gatgattcat    360
cagcacctgt cctcccggac tcatgggtct gaggattca                           399
```

```
<210> SEQ ID NO 142
<211> LENGTH: 133
<212> TYPE: PRT
<213> ORGANISM: Homo sapiens

<400> SEQUENCE: 142

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 143
<211> LENGTH: 155
<212> TYPE: PRT
<213> ORGANISM: Homo sapiens

<400> SEQUENCE: 143

Met Glu Arg Ile Val Ile Cys Leu Met Val Ile Phe Leu Gly Thr Leu
1               5                   10                  15

Val His Lys Ser Ser Ser Gln Gly Gln Asp Arg His Met Ile Arg Met
            20                  25                  30

Arg Gln Leu Ile Asp Ile Val Asp Gln Leu Lys Asn Tyr Val Asn Asp
        35                  40                  45

Leu Val Pro Glu Phe Leu Pro Ala Pro Glu Asp Val Glu Thr Asn Cys
    50                  55                  60

Glu Trp Ser Ala Phe Ser Cys Phe Gln Lys Ala Gln Leu Lys Ser Ala
65                  70                  75                  80

Asn Thr Gly Asn Asn Glu Arg Ile Ile Asn Val Ser Ile Lys Lys Leu
                85                  90                  95

Lys Arg Lys Pro Pro Ser Thr Asn Ala Gly Arg Arg Gln Lys His Arg
            100                 105                 110

Leu Thr Cys Pro Ser Cys Asp Ser Tyr Glu Lys Lys Pro Pro Lys Glu
        115                 120                 125

Phe Leu Glu Arg Phe Lys Ser Leu Leu Gln Lys Met Ile His Gln His
    130                 135                 140

Leu Ser Ser Arg Thr His Gly Ser Glu Asp Ser
145                 150                 155

<210> SEQ ID NO 144
<211> LENGTH: 2598
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 144

| | |
|---|---|
| gtaacgccat tttgcaaggc atggaaaaat accaaaccaa gaatagagaa gttcagatca | 60 |
| agggcgggta catgaaaata gctaacgttg ggccaaacag gatatctgcg gtgagcagtt | 120 |
| tcggccccgg cccggggcca agaacagatg gtcaccgcag tttcggcccc ggcccgaggc | 180 |
| caagaacaga tggtcccag atatggccca accctcagca gtttcttaag acccatcaga | 240 |
| tgtttccagg ctcccccaag gacctgaaat gaccctgcgc cttatttgaa ttaaccaatc | 300 |
| agcctgcttc tcgcttctgt tcgcgcgctt ctgcttcccg agctctataa aagagctcac | 360 |
| aaccccctcac tcggcgcgcc agtcctccga cagactgagt cgcccggggg atccgcggaa | 420 |
| ttcgccgcca ccatgtgcca tcagcaactc gtcatctcct ggttctccct tgtgttcctc | 480 |
| gcttcccctc tggtcgccat tgggaactg aagaaggacg tctacgtggt cgagctggat | 540 |
| tggtacccgg acgcccctgg agaaatggtc gtgctgactt gcgatacgcc agaagaggac | 600 |
| ggcataacct ggaccctgga tcagagctcc gaggtgctcg gaagcggaaa gaccctgacc | 660 |
| attcaagtca aggagttcgg cgacgcgggc cagtacactt gccacaaggg tggcgaagtg | 720 |
| ctgtcccact ccctgctgct gctgcacaag aaagaggatg gaatctggtc cactgacatc | 780 |
| ctcaaggacc aaaaagaacc gaagaacaag accttcctcc gctgcgaagc caagaactac | 840 |
| agcggtcggt tcacctgttg gtggctgacg acaatctcca ccgacctgac tttctccgtg | 900 |
| aagtcgtcac ggggatcaag cgatcctcag ggcgtgacct gtggagccgc cactctgtcc | 960 |
| gccgagagag tcaggggaga caacaaggaa tatgagtact ccgtggaatg ccaggaggac | 1020 |
| agcgcctgcc ctgccgcgga agagtccctg cctatcgagg tcatggtcga tgccgtgcat | 1080 |
| aagctgaaat acgagaacta cacttcctcc ttctttatcc gcgacatcat caagcctgac | 1140 |
| ccccccaaga acttgcagct gaagccactc aagaactccc gccaagtgga agtgtcttgg | 1200 |
| gaatatccag acacttggag cacccccgcac tcatacttct cgctcacttt ctgtgtgcaa | 1260 |
| gtgcagggaa agtccaaacg ggagaagaaa gaccgggtgt tcaccgacaa aacctccgcc | 1320 |
| actgtgattt gtcggaagaa cgcgtcaatc agcgtccggg cgcaggatag atactactcg | 1380 |
| tcctcctgga gcgaatgggc cagcgtgcct tgttccggtg gcggatcagg cggaggttca | 1440 |
| ggaggaggct ccggaggagg ttcccggaac ctccctgtgg caaccccga ccctggaatg | 1500 |
| ttcccgtgcc tacaccactc ccaaaacctc ctgagggctg tgtcgaacat gttgcagaag | 1560 |
| gcccgccaga cccttgagtt ctaccccctgc acctcggaag aaattgatca cgaggacatc | 1620 |
| accaaggaca agacctcgac cgtggaagcc tgcctgccgc tggaactgac caagaacgaa | 1680 |
| tcgtgtctga actcccgcga gacaagcttt atcactaacg gcagctgcct ggcgtcgaga | 1740 |
| aagacctcat tcatgatggc gctctgtctt tcctcgatct acgaagatct gaagatgtat | 1800 |
| caggtcgagt tcaagaccat gaacgccaag ctgctcatgg acccgaagcg gcagatcttc | 1860 |
| ctggaccaga atatgctcgc cgtgattgat gaactgatgc aggccctgaa tttcaactcc | 1920 |
| gagactgtgc ctcaaaagtc cagcctggaa gaaccggact tctacaagac caagatcaag | 1980 |
| ctgtgcatcc tgttgcacgc tttccgcatt cgagccgtga ccattgaccg cgtgatgtcc | 2040 |
| tacctgaacg ccagtagacg gaaacgcgga agcggagagg gcagaggctc gctgcttaca | 2100 |
| tgcggggacg tggaagagaa ccccggtccg atggaacgca ttgtgatctg cctgatggtc | 2160 |
| atcttcctgg gcaccttagt gcacaagtcg agcagccagg acaggacag gcacatgatt | 2220 |
| agaatgcgcc agctcatcga tatcgtggac cagttgaaga actacgtgaa cgacctggtg | 2280 |

```
cccgagttcc tgccggcccc cgaagatgtg gaaaccaatt gcgaatggtc ggcattttcc    2340
tgctttcaaa aggcacagct caagtccgct aacaccggga caacgaacg gatcatcaac    2400 gtgtccatca aaaagctgaa gcggaagcct ccctccacca acgccggacg gaggcagaag    2460
cataggctga cttgcccgtc atgcgactcc tacgagaaga agccgccgaa ggagttcctg    2520
gagcggttca gtcgctcct gcaaaagatg attcatcagc acctgtcctc ccggactcat    2580
gggtctgagg attcatga                                                  2598
```

<210> SEQ ID NO 145
<211> LENGTH: 7213
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 145

```
tgactcctgc gcagtccaaa aaaaaggct ccaaaaggag cctttaattg tatcggtggg     60
cccttagaaa aactcatcga gcatcaaatg aaactgcaat ttattcatat caggattatc   120
aataccatat ttttgaaaaa gccgtttctg taatgaagga gaaaactcac cgaggcagtt   180
ccataggatg gcaagatcct ggtatcggtc tgcgattccg actcgtccaa catcaataca   240
acctattaat ttccctcgt caaaataag gttatcaagt gagaaatcac catgagtgac    300
gactgaatcc ggtgagaatg gcaaaagctt atgcatttct ttccagactt gttcaacagg   360
ccagccatta cgctcgtcat caaaatcact cgcatcaacc aaaccgttat tcattcgtga   420
ttgcgcctga gcgagacgaa atacgcgatc gctgttaaaa ggacaattac aaacaggaat   480
cgaatgcaac cggcgcagga acactgccag cgcatcaaca atattttcac ctgaatcagg   540
atattcttct aatacctgga atgctgtttt cccggggatc gcagtggtga gtaaccatgc   600
atcatcagga gtacggataa aatgcttgat ggtcggaaga ggcataaatt ccgtcagcca   660
gtttagtctg accatctcat ctgtaacatc attggcaacg ctacctttgc catgtttcag   720
aaacaactct ggcgcatcgg gcttcccata caatcgatag attgtcgcac ctgattgccc   780
gacattatcg cgagcccatt tatacccata taaatcagca tccatgttgg aatttaatcg   840
cggcctcgag caagacgttt cccgttgaat atggctcata acaccccttg tattactgtt   900
tatgtaagca gacagttta ttgttcatga tgatatattt ttatcttgtg caatgtaaca   960
tcagagattt tgagacacaa cgtggtttaa acaaatagtc aaaagcctcc ggcgactagt  1020
cggggtcatt agttcatagc ccatatatgg agttccgcgt tacataactt acggtaaatg  1080
gcccgcctgg ctgaccgccc aacgaccccc gcccattgac gtcaataatg acgtatgttc  1140
ccatagtaac gccaataggg actttccatt gacgtcaatg ggtggagtat ttacggtaaa  1200
ctgcccactt ggcagtacat caagtgtatc atatgccaag tacgccccct attgacgtca  1260
atgacggtaa atggcccgcc tggcattatg cccagtacat gaccttatgg actttccta   1320 cttggcagta catctacgta ttagtcatcg ctattaccat ggtgatgcgg ttttggcagt  1380
acatcaatgg gcgtggatag cggtttgact cacggggatt ccaagtctc cacccccattg  1440 acgtcaatgg gagtttgttt tggcaccaaa atcaacggga ctttccaaaa tgtcgtaaca  1500
actccgcccc attgacgcaa atgggcggta ggcgtgtacg gtgggaggtc tatataagca  1560
gagctggttt agtgaaccgg gtctctctgg ttagaccaga tttgagcctg ggagctctct  1620
ggctaactag ggaacccact gcttaagcct caataaagct tgccttgagt gcttcaagta  1680
```

```
gtgtgtgccc gtctgttgtg tgactctggt aactagagat ccctcagacc cttttagtca   1740
gtgtggaaaa tctctagcag tggcgcccga acagggacct gaaagcgaaa gggaaaccag   1800
aggagctctc tcgacgcagg actcggcttg ctgaagcgcg cacggcaaga ggcgaggggc   1860
ggcgactgca gagtacgcca aaattttgac tagcggaggc tagaaggaga gagatgggtg   1920
cgagagcgtc agtattaagc gggggaaaat agcggccgcc acaatttaa aagaaaaggg    1980
gggattgggg ggtacagtgc aggggaaaga atagtagaca taatagcaac agacatacaa   2040
actaaagaat tacaaaaaca aattacaaaa attcaaattt tcgggggatc cgtaacgcca   2100
ttttgcaagg catggaaaaa taccaaacca agaatagaga agttcagatc aagggcgggt   2160
acatgaaaat agctaacgtt gggccaaaca ggatatctgc ggtgagcagt ttcggccccg   2220
gcccggggcc aagaacagat ggtcaccgca gtttcggccc cggcccgagg ccaagaacag   2280
atggtcccca gatatggccc aaccctcagc agtttcttaa gacccatcag atgtttccag   2340
gctcccccaa ggacctgaaa tgaccctgcg ccttatttga attaaccaat cagcctgctt   2400
ctcgcttctg ttcgcgcgct tctgcttccc gagctctata aaagagctca caaccccctca  2460
ctcggcgcgc cagtcctccg acagactgag tcgcccgggg gatccgcgga attcgccgcc   2520
accatgtgcc atcagcaact cgtcatctcc tggttctccc ttgtgttcct cgcttcccct   2580
ctggtcgcca tttgggaact gaagaaggac gtctacgtgg tcgagctgga ttggtacccg   2640
gacgcccctg gagaaatggt cgtgctgact tgcgatacgc agaagagga cggcataacc     2700
tggaccctgg atcagagctc cgaggtgctc ggaagcggaa agaccctgac cattcaagtc   2760
aaggagttcg gcgacgcggg ccagtacact tgccacaagg gtggcgaagt gctgtcccac   2820
tccctgctgc tgctgcacaa gaaagaggat ggaatctggt ccactgacat cctcaaggac   2880
caaaaagaac cgaagaacaa gaccttcctc cgctgcgaag ccaagaacta cagcggtcgg   2940
ttcacctgtt ggtggctgac gacaatctcc accgacctga cttctctccgt gaagtcgtca   3000
cggggatcaa gcgatcctca gggcgtgacc tgtggagccg ccactctgtc cgccgagaga   3060
gtcaggggag acaacaagga atatgagtac tccgtggaat gccaggagga cagcgcctgc   3120
cctgccgcgg aagagtccct gcctatcgag gtcatggtcg atgccgtgca taagctgaaa   3180
tacgagaact acactccctc cttctttatc cgcgacatca tcaagcctga cccccccaag   3240
aacttgcagc tgaagccact caagaactcc cgccaagtgg aagtgtcttg ggaatatcca   3300
gacacttgga gcaccccgca ctcatacttc tcgctcactt tctgtgtgca agtgcaggga   3360
aagtccaaac gggagaagaa agaccgggtg ttcaccgaca aaacctccgc cactgtgatt   3420
tgtcggaaga acgcgtcaat cagcgtccgg gcgcaggata gatactactc gtcctcctgg   3480
agcgaatggg ccagcgtgcc ttgttccggt ggcggatcag gcggaggttc aggaggaggc   3540
tccggaggag gttccggaa cctccctgtg gcaaccccgg accctggaat gttcccgtgc   3600
ctacaccact cccaaaacct cctgagggct gtgtcgaaca tgttgcagaa ggcccgccag   3660
acccttgagt tctaccctg cacctcggaa gaaattgatc acgaggacat caccaaggac   3720
aagacctcga ccgtggaagc ctgcctgccg ctggaactga ccaagaacga atcgtgtctg   3780
aactcccgcg agacaagctt tatcactaac ggcagctgcc tggcgtcgag aaagacctca   3840
ttcatgatgg cgctctgtct ttcctcgatc tacgaagatc tgaagatgta tcaggtcgag   3900
ttcaagacca tgaacgccaa gctgctcatg gacccgaagc ggcagatctt cctggaccag   3960
aatatgctcg ccgtgattga tgaactgatg caggccctga atttcaactc cgagactgtg   4020
```

```
cctcaaaagt ccagcctgga agaaccggac ttctacaaga ccaagatcaa gctgtgcatc      4080
ctgttgcacg ctttccgcat tcgagccgtg accattgacc gcgtgatgtc ctacctgaac      4140
gccagtagac ggaaacgcgg aagcggagag ggcagaggct cgctgcttac atgcggggac      4200
gtggaagaga accccggtcc gatggaacgc attgtgatct gcctgatggt catcttcctg      4260
ggcaccttag tgcacaagtc gagcagccag ggacaggaca ggcacatgat tagaatgcgc      4320
cagctcatcg atatcgtgga ccagttgaag aactacgtga acgacctggt gcccgagttc      4380
ctgccggccc ccgaagatgt ggaaaccaat tgcgaatggt cggcattttc ctgcttt caa      4440 aaggcacagc tcaagtccgc taacaccggg aacaacgaac ggatcatcaa cgtgtccatc      4500
aaaaagctga agcggaagcc tccctccacc aacgccggac ggaggcagaa gcataggctg      4560
acttgcccgt catgcgactc ctacgagaag aagccgccga aggagttcct ggagcggttc      4620
aagtcgctcc tgcaaaagat gattcatcag cacctgtcct cccggactca tgggtctgag      4680
gattcatgag gttagtcgac aatcaacctc tggattacaa aatttgtgaa agattgactg      4740
gtattcttaa ctatgttgct ccttttacgc tatgtggata cgctgcttta atgcctttgt      4800
atcatgctat tgcttcccgt atggctttca ttttctcctc cttgtataaa tcctggttgc      4860
tgtctcttta tgaggagttg tggcccgttg tcaggcaacg tggcgtggtg tgcactgtgt      4920
ttgctgacgc aacccccact ggttggggca ttgccaccac ctgtcagctc ctttccggga      4980 cttt cgcttt cccccct ccct attgccacgc cggaactcat cgccgcctgc cttgcccgct      5040
gctggacagg ggctcggctg ttgggcactg acaattccgt ggtgttgtcg gggaaatcat      5100 cgtccttttcc ttggctgctc gcctgtgttg ccacctggat tctgcgcggg acgtccttct      5160
gctacgtccc ttcggccctc aatccagcgg accttccttc ccgcggcctg ctgccggctc      5220
tgcggcctct tccgcgtctt cgccttcgcc ctcagacgag tcggatctcc ctttgggccg      5280
cctccccgct tagtactggt acctttaaga ccaatgactt acaaggcagc tgtagatctt      5340
agccactttt taaagaaaaa ggggggactg aagggctaa ttcactccca acgaagacaa      5400
gattccggaa tttatttgtg aaatttgtga tgctattgct ttatttgtaa accggtgcag      5460 ctgcttt ttg cctgtactgg gtctctctgg ttagaccaga tctgagcctg ggagctctct      5520
ggctaactag ggaacccact gcttaagcct caataaagct tgccttgagt gcttcaagta      5580
gtgtgtgccc gtctgttgtg tgactctggt aactagagat ccctcagacc cttttagtca      5640
gtgtggaaaa tctctagcat ctagagtatg caaagcatgc atctcaatta gtcagcaacc      5700
aggtgtggaa agtccccagg ctccccagca ggcagaagta tgcaaagcat gcatctcaat      5760
tagtcagcaa ccatagtccc gcccctaact ccgcccatcc cgcccctaac tccgcccagt      5820
tccgcccatt ctccgcccca tggctgacta attttttttta tttatgcaga ggccgaggcc      5880
gcctcggcct ctgagctatt ccagaagtag tgaggaggct ttttt tggagg cctaggctag      5940 agatcataat cagccatacc acatttgtag aggttttact tgctttaaaa aacctcccac      6000
acctccccct gaacctgaaa cataaaatga atgcaattgt tgttgttaac ttgttt attg      6060 cagcttataa tggttacaaa taaagcaata gcatcacaaa tttcacaaat aaagcatttt      6120
tttcactgca ttctagttgt ggtttgtcca aactcatcaa tgtatcttat catgtctgct      6180
agccgggctt ttttttctta ggccttcttc cgcttcctcg ctcactgact cgctgcgctc      6240
ggtcgttcgg ctgcggcgag cggtatcagc tcactcaaag gcggtaatac ggttatccac      6300
agaatcaggg gataacgcag gaaagaacat gtgagcaaaa ggccagcaaa aggccaggaa      6360
ccgtaaaaag gccgcgttgc tggcgttttt ccataggctc cgcccccctg acgagcatca      6420
```

```
caaaaatcga cgctcaagtc agaggtggcg aaacccgaca ggactataaa gataccaggc    6480
gtttccccct ggaagctccc tcgtgcgctc tcctgttccg accctgccgc ttaccggata    6540
cctgtccgcc tttctcccct cgggaagcgt ggcgctttct catagctcac gctgtaggta    6600
tctcagttcg gtgtaggtcg ttcgctccaa gctgggctgt gtgcacgaac cccccgttca    6660
gcccgaccgc tgcgccttat ccggtaacta tcgtcttgag tccaacccgg taagacacga    6720
cttatcgcca ctggcagcag ccactggtaa caggattagc agagcgaggt atgtaggcgg    6780
tgctacagag ttcttgaagt ggtggcctaa ctacggctac actagaagaa cagtatttgg    6840
tatctgcgct ctgctgaagc cagttacctt cggaaaaaga gttggtagct cttgatccgg    6900
caaacaaacc accgctggta gcggtggttt ttttgtttgc aagcagcaga ttacgcgcag    6960
aaaaaaagga tctcaagaag atcctttgat cttttctacg gggtctgacg ctcagtggaa    7020
cgaaaactca cgttaaggga ttttggtcat gagattatca aaaaggatct tcacctagat    7080 cctttaaat  taaaaatgaa gttttaaatc aatctaaagt atatatgagt aaacttggtc     7140
tgacagttac caatgcttaa tcagtgaggc acctatctca gcgatctgtc tatttcgttc    7200
atccatagtt gcc                                                        7213
```